US012643945B2

(12) United States Patent (10) Patent No.: US 12,643,945 B2
Scales et al. (45) Date of Patent: Jun. 2, 2026

(54) APOLIPOPROTEIN L1-SPECIFIC ANTIBODIES AND METHODS OF USE

(71) Applicant: Genentech Inc., South San Francisco, CA (US)

(72) Inventors: Suzanna Jane Scales, South San Francisco, CA (US); Nidhi Gupta, Redwood City, CA (US); Andrew Scott Peterson, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 875 days.

(21) Appl. No.: 17/846,744

(22) Filed: Jun. 22, 2022

(65) Prior Publication Data

US 2023/0071609 A1 Mar. 9, 2023

Related U.S. Application Data

(63) Continuation of application No. PCT/US2020/066377, filed on Dec. 21, 2020.

(60) Provisional application No. 62/953,097, filed on Dec. 23, 2019.

(51) Int. Cl.
*C07K 16/28* (2006.01)
*G01N 33/68* (2006.01)

(52) U.S. Cl.
CPC ......... *C07K 16/28* (2013.01); *G01N 33/6872* (2013.01); *C07K 2317/24* (2013.01); *C07K 2317/54* (2013.01); *C07K 2317/55* (2013.01); *C07K 2317/565* (2013.01); *C07K 2317/622* (2013.01)

(58) Field of Classification Search
CPC ........ C07K 2317/565; C07K 2317/622; C07K 2317/55; C07K 2317/54
See application file for complete search history.

(56) References Cited

FOREIGN PATENT DOCUMENTS

| | | |
|---|---|---|
| CN | 107782904 A | 3/2018 |
| RU | 2215747 C2 | 11/2003 |
| WO | 9916459 A1 | 4/1999 |
| WO | 2004012757 A2 | 2/2004 |
| WO | 2014078213 A2 | 5/2014 |
| WO | WO-2016077369 A1 * | 5/2016 .............. A61P 13/12 |

OTHER PUBLICATIONS

Al Qaraghuli et al (2020, Nature Scientific Reports 10:13969) (Year: 2020).*
Rabia, et al (2018, Biochemical Engineering Journal 137:365-374) (Year: 2018).*
Tiller et al (2017, J. Biol. Chem. (2017) 292(40) 16638-16652) (Year: 2017).*
Tsuji et al (2022, J Virol 96:e00071-22) (Year: 2022).*
Chun, Justin et al., "Recruitment of APOL1 kidney disease risk variants to lipid droplets attenuates cell toxicity", PNAS, vol. 16, No. 9, pp. 3712-3721, Feb. 26, 2019.
Gupta, Nidhi et al., "Domain-Specific Antibodies Reveal Differences in the Membrane Topologies of Apolipoprotin L1 in Serum and Podocytes", JASN 31: 2065-2082, 2020.
PCT International Search Report and Written Opinion from PCT/US2020/066377, mailed on Jul. 13, 2021, 19 pages.
Weckerle, Allison et al., "Characterization of circulating APOL 1 protein complexes in African Americans", Journal of Lipid Research, vol. 57, Issue 1, pp. 120-130, 2016.

* cited by examiner

*Primary Examiner* — Gregory S Emch
*Assistant Examiner* — Ashley H. Gao

(57) ABSTRACT

This disclosure provides anti-apolipoprotein L1 (APOL1) antibodies, including anti-APOL1 antibodies that distinguish the G0 and G1 forms from the G2 form of APOL1, distinguish APOL1 found on podocytes from that found on HDL particles in serum, and distinguish APOL1 from apolipoproteins L2, L3, L4 and L6 (APOL2, APOL3, APOL4 and APOL6), and methods of using the same.

20 Claims, 77 Drawing Sheets

Specification includes a Sequence Listing.

3.7D6 (PFD)

3.3A8 (MAD)

3.5H9 (MAD)

3.1C1 (SRA-ID)

3.2D4 (Multi-domain)

3.3F7 (Conformational)

3.5B10 (FACS-ve)

Proteintech

Sigma

Epitomics gD-Tag

- PFD
- MAD
- SRA-ID / Linker
- Multi-domain
- Conformational
- FACS-negative

61

376
398
364

313
333

172     235
305

EXTRACELLULAR

INTRACELLULAR 150     172     235     260     305
313

111

103

130

61

203

333     398

376

364

HDL CORE

61

203

172

305

235     313

333     376     398

364

HDL CORE

Figure 10A
Figure 10B
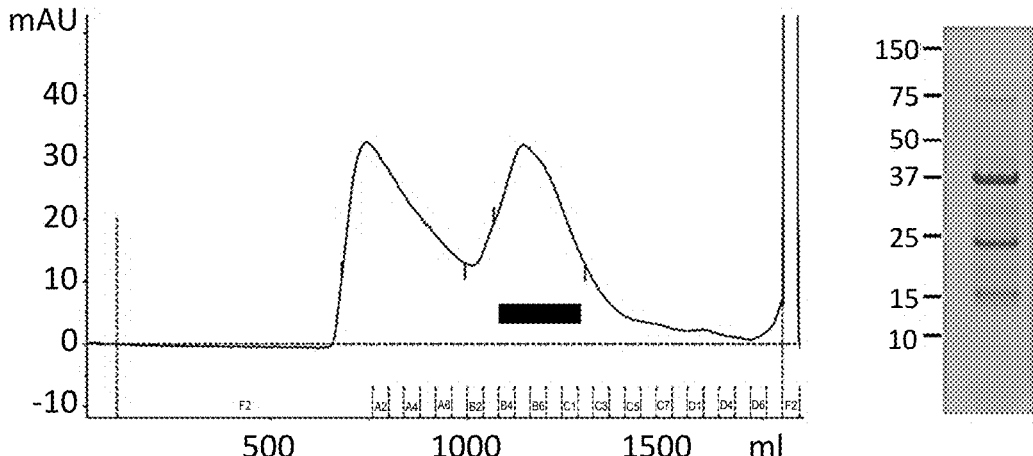
Figure 10C
Figure 10D
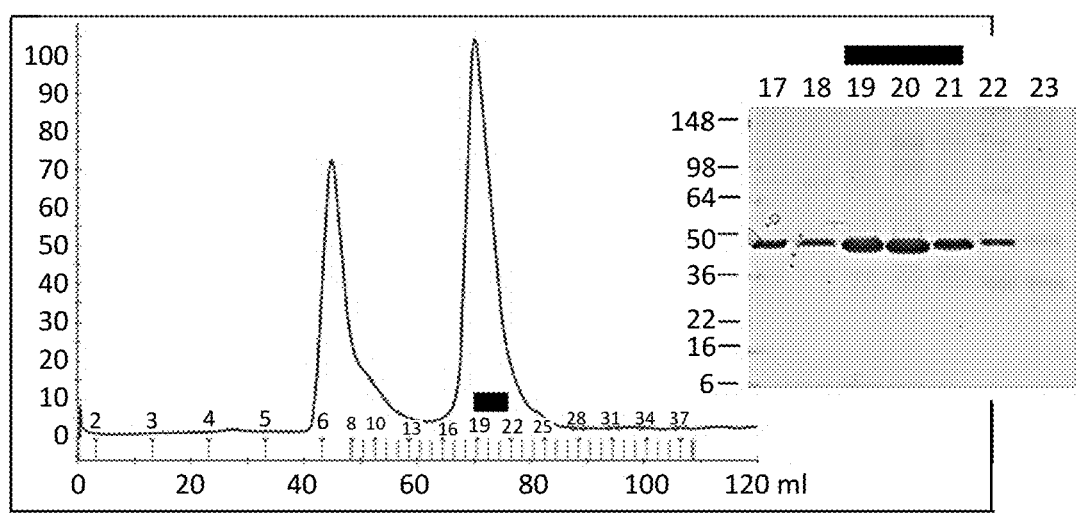

gD-i*APOL1*-GIP-CHO

| gRNA # | gRNA pair |
|--------|-----------|
| 89401 | L2, R3 |
| 89402 | L2, R4 |
| 90109 | L1, R2 |
| 90110 | L1, R4 |
| 90111 | L2, R2 |

FIG. 20E
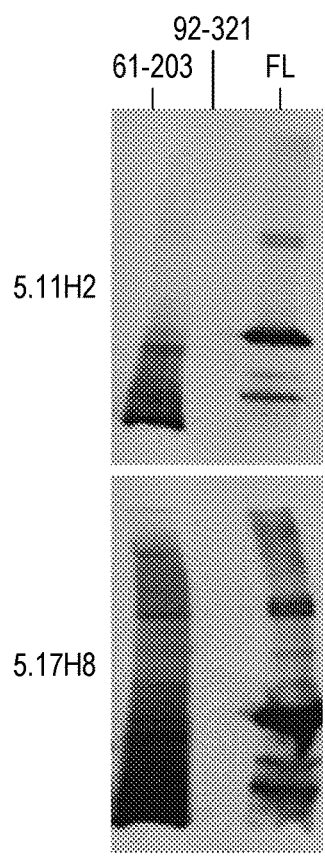
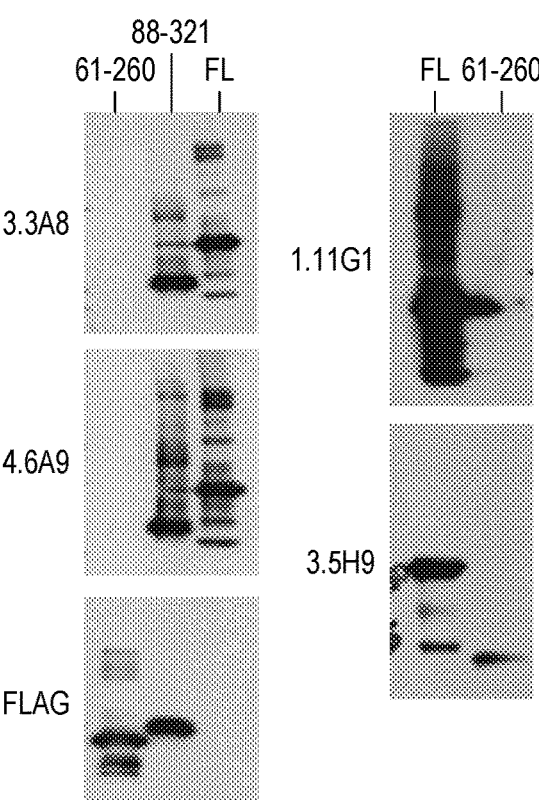

Figure 21B
Figure 21C
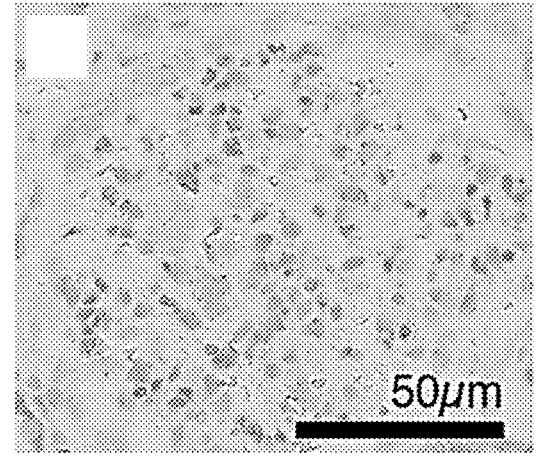
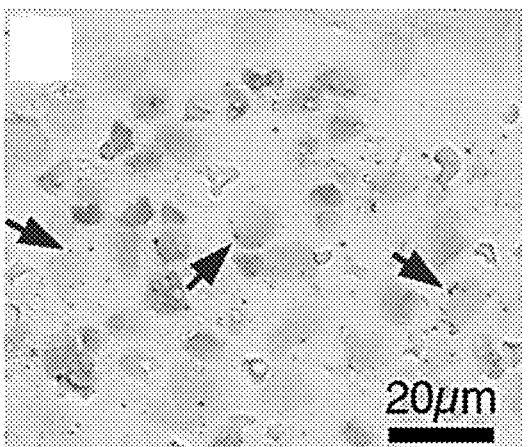
Figure 21D
Figure 21E
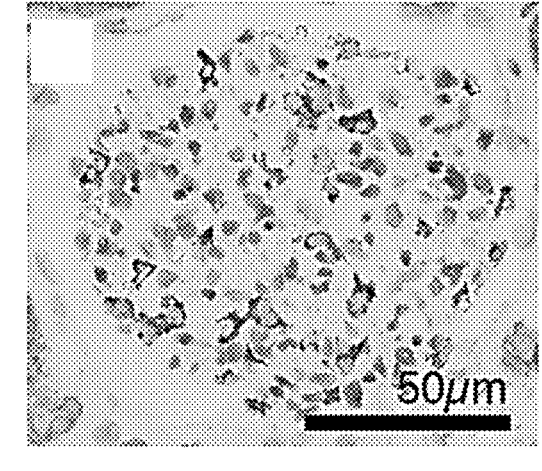
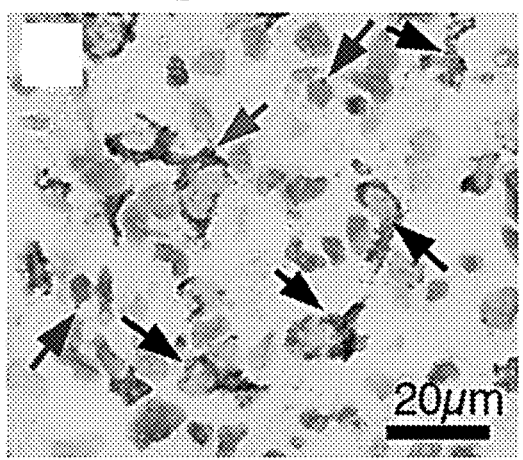
Figure 21F
Figure 22G
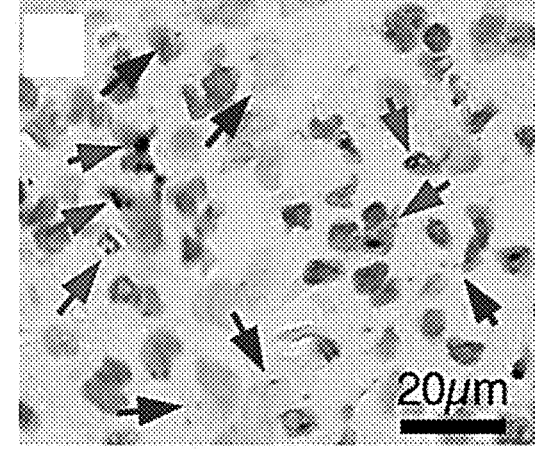
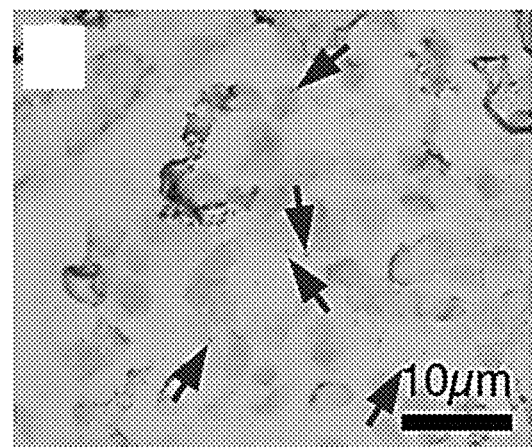

ApoL1 5.17D12          ApoL1 5.17D12          Isotype Control

Alexa488

Figure 39A    Figure 39B
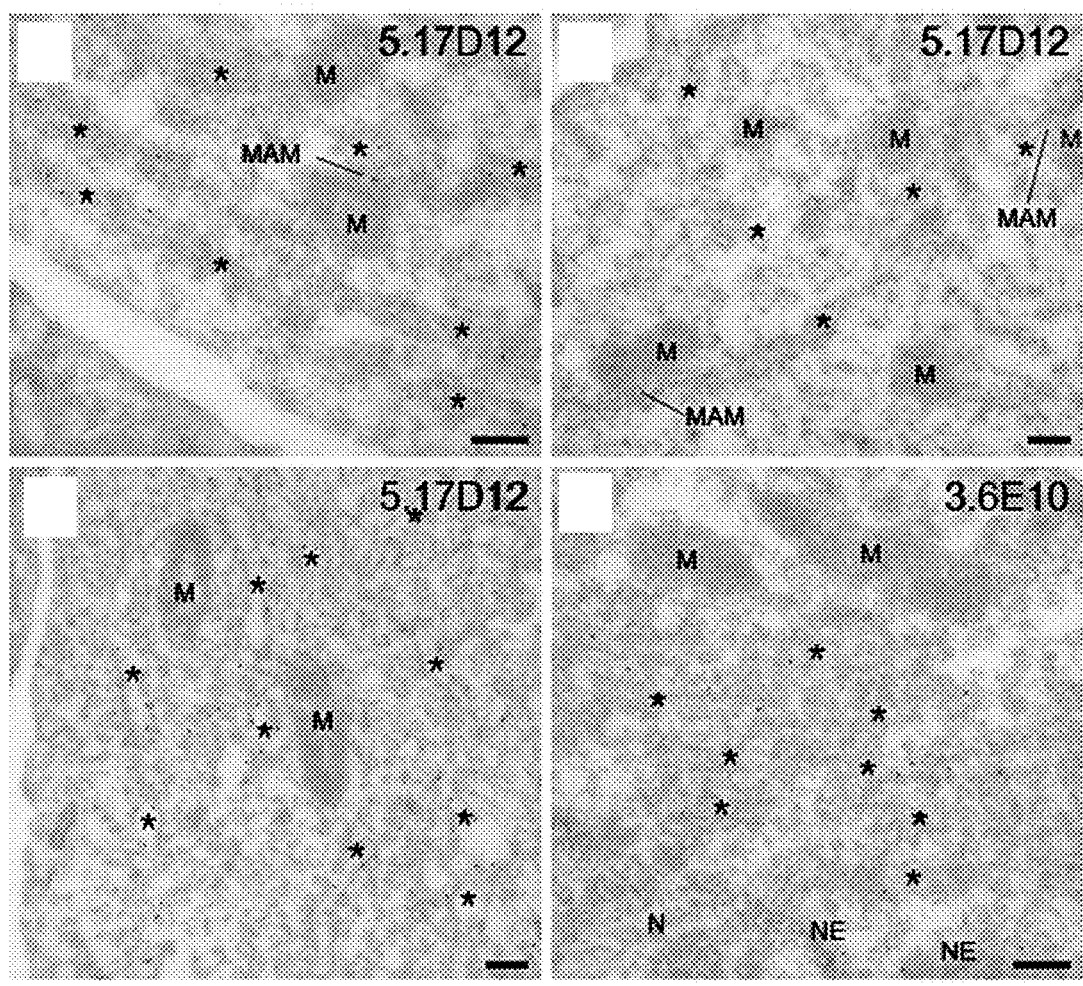
Figure 39C    Figure 39D
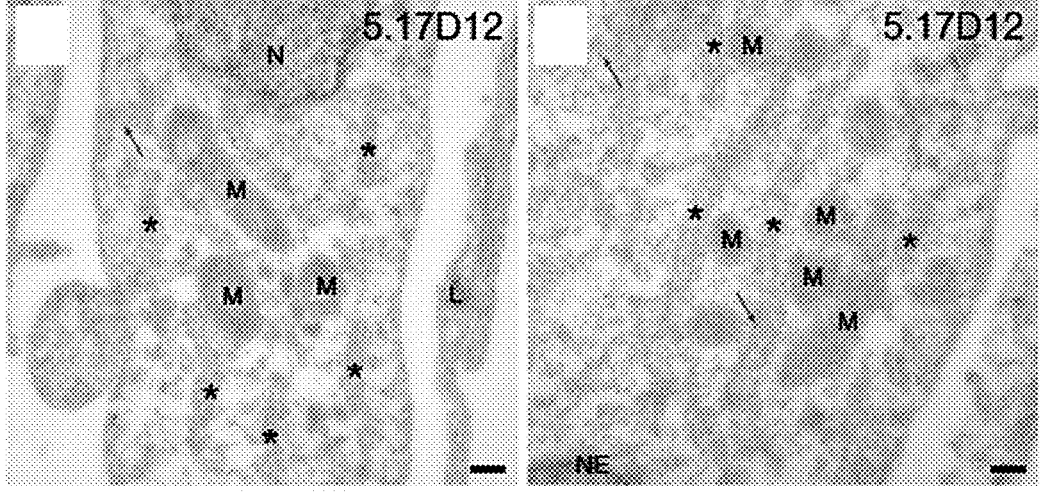
Figure 39E    Figure 39F

Figure 40B
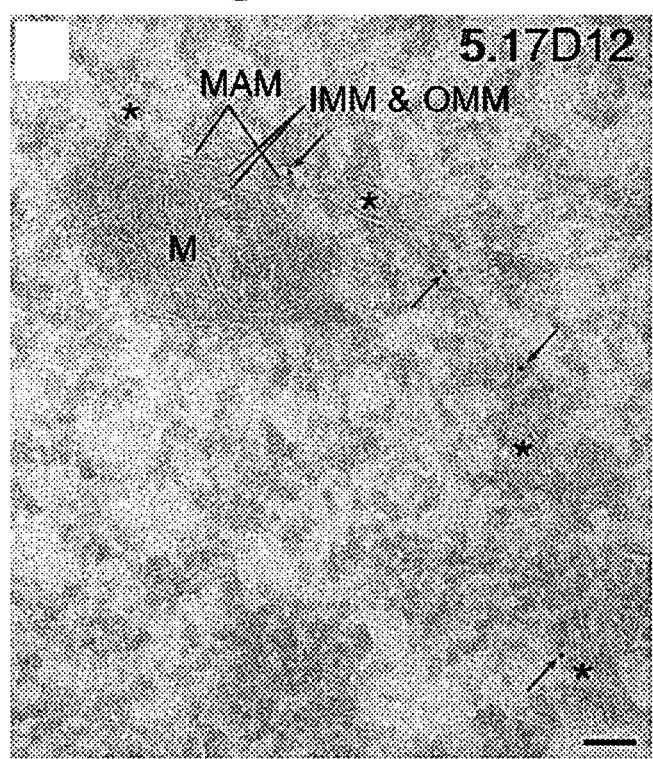
Figure 40C          # Figure 40D
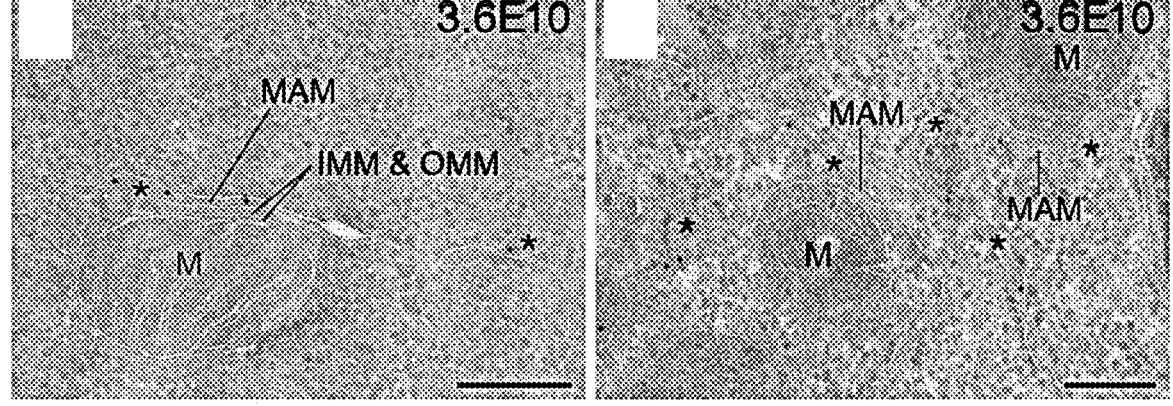

APOL1 4.17A5    Calnexin (ER)    Merge

APOL1 4.17A5    PDI (ER)    Merge + DAPI

3.6D12 (APOL1&2 )

IP:        WB:

Lysate   3.6D12    5.17H8

Media    3.6D12    5.17H8

Input
lysate    none     3.6D12

IP:        WB:

none   3.1C7 & 3.7D6

APOL WT     EEA1     LAMP1     Merge

APOL.vB3     LAMP1     EEA1     Merge

SEQUENCE LISTING

<160> NUMBER OF SEQ ID NOS: 220

<210> SEQ ID NO 1
<211> LENGTH: 398
<212> TYPE: PRT
<213> ORGANISM: Homo sapiens
<220> FEATURE:
<221> NAME/KEY: misc_feature
<222> LOCATION: (1)..(398)
<223> OTHER INFORMATION: Human APOL1 (with leader sequence)  G0 form EMR
      variant Accession no. NP003652

<400> SEQUENCE: 1

Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
            20                  25                  30

Arg Val Gln Gln Asn Val Pro Ser Gly Thr Asp Thr Gly Asp Pro Gln
        35                  40                  45

Ser Lys Pro Leu Gly Asp Trp Ala Ala Gly Thr Met Asp Pro Glu Ser
    50                  55                  60

Ser Ile Phe Ile Glu Asp Ala Ile Lys Tyr Phe Lys Glu Lys Val Ser
65                  70                  75                  80

Thr Gln Asn Leu Leu Leu Leu Leu Thr Asp Asn Glu Ala Trp Asn Gly
                85                  90                  95

Phe Val Ala Ala Ala Glu Leu Pro Arg Asn Glu Ala Asp Glu Leu Arg
            100                 105                 110

Lys Ala Leu Asp Asn Leu Ala Arg Gln Met Ile Met Lys Asp Lys Asn
        115                 120                 125

Trp His Asp Lys Gly Gln Gln Tyr Arg Asn Trp Phe Leu Lys Glu Phe
    130                 135                 140

Pro Arg Leu Lys Ser Glu Leu Glu Asp Asn Ile Arg Arg Leu Arg Ala
145                 150                 155                 160

Leu Ala Asp Gly Val Gln Lys Val His Lys Gly Thr Thr Ile Ala Asn
                165                 170                 175

Val Val Ser Gly Ser Leu Ser Ile Ser Ser Gly Ile Leu Thr Leu Val
                180                 185                 190

```
Gly Met Gly Leu Ala Pro Phe Thr Glu Gly Gly Ser Leu Val Leu Leu
    195                 200                 205

Glu Pro Gly Met Glu Leu Gly Ile Thr Ala Ala Leu Thr Gly Ile Thr
    210                 215                 220

Ser Ser Thr Met Asp Tyr Gly Lys Lys Trp Trp Thr Gln Ala Gln Ala
225                 230                 235                 240

His Asp Leu Val Ile Lys Ser Leu Asp Lys Leu Lys Glu Val Arg Glu
                245                 250                 255

Phe Leu Gly Glu Asn Ile Ser Asn Phe Leu Ser Leu Ala Gly Asn Thr
                260                 265                 270

Tyr Gln Leu Thr Arg Gly Ile Gly Lys Asp Ile Arg Ala Leu Arg Arg
                275                 280                 285

Ala Arg Ala Asn Leu Gln Ser Val Pro His Ala Ser Ala Ser Arg Pro
    290                 295                 300

Arg Val Thr Glu Pro Ile Ser Ala Glu Ser Gly Glu Gln Val Glu Arg
305                 310                 315                 320

Val Asn Glu Pro Ser Ile Leu Glu Met Ser Arg Gly Val Lys Leu Thr
                325                 330                 335

Asp Val Ala Pro Val Ser Phe Phe Leu Val Leu Asp Val Val Tyr Leu
                340                 345                 350

Val Tyr Glu Ser Lys His Leu His Glu Gly Ala Lys Ser Glu Thr Ala
    355                 360                 365

Glu Glu Leu Lys Lys Val Ala Gln Glu Leu Glu Glu Lys Leu Asn Ile
    370                 375                 380

Leu Asn Asn Asn Tyr Lys Ile Leu Gln Ala Asp Gln Glu Leu
385                 390                 395
```

```
<210> SEQ ID NO 2
<211> LENGTH: 370
<212> TYPE: PRT
<213> ORGANISM: Homo sapiens
<220> FEATURE:
<221> NAME/KEY: misc_feature
<222> LOCATION: (1)..(370)
<223> OTHER INFORMATION: Human APOL1 without leader sequence  G0 form
      EMR variant NP003652

<400> SEQUENCE: 2
```

```
Glu Ala Gly Ala Arg Val Gln Gln Asn Val Pro Ser Gly Thr Asp Thr
1               5                   10                  15

Gly Asp Pro Gln Ser Lys Pro Leu Gly Asp Trp Ala Ala Gly Thr Met
                20                  25                  30

Asp Pro Glu Ser Ser Ile Phe Ile Glu Asp Ala Ile Lys Tyr Phe Lys
                35                  40                  45

Glu Lys Val Ser Thr Gln Asn Leu Leu Leu Leu Thr Asp Asn Glu
    50                  55                  60

Ala Trp Asn Gly Phe Val Ala Ala Ala Glu Leu Pro Arg Asn Glu Ala
65                  70                  75                  80

Asp Glu Leu Arg Lys Ala Leu Asp Asn Leu Ala Arg Gln Met Ile Met
                85                  90                  95

Lys Asp Lys Asn Trp His Asp Lys Gly Gln Gln Tyr Arg Asn Trp Phe
                100                 105                 110

Leu Lys Glu Phe Pro Arg Leu Lys Ser Glu Leu Glu Asp Asn Ile Arg
                115                 120                 125

Arg Leu Arg Ala Leu Ala Asp Gly Val Gln Lys Val His Lys Gly Thr
    130                 135                 140
```

```
Thr Ile Ala Asn Val Val Ser Gly Ser Leu Ser Ile Ser Ser Gly Ile
145                 150                 155                 160

Leu Thr Leu Val Gly Met Gly Leu Ala Pro Phe Thr Glu Gly Gly Ser
                165                 170                 175

Leu Val Leu Leu Glu Pro Gly Met Glu Leu Gly Ile Thr Ala Ala Leu
            180                 185                 190

Thr Gly Ile Thr Ser Ser Thr Met Asp Tyr Gly Lys Lys Trp Trp Thr
            195                 200                 205

Gln Ala Gln Ala His Asp Leu Val Ile Lys Ser Leu Asp Lys Leu Lys
        210                 215                 220

Glu Val Arg Glu Phe Leu Gly Glu Asn Ile Ser Asn Phe Leu Ser Leu
225                 230                 235                 240

Ala Gly Asn Thr Tyr Gln Leu Thr Arg Gly Ile Gly Lys Asp Ile Arg
                245                 250                 255

Ala Leu Arg Arg Ala Arg Ala Asn Leu Gln Ser Val Pro His Ala Ser
            260                 265                 270

Ala Ser Arg Pro Arg Val Thr Glu Pro Ile Ser Ala Glu Ser Gly Glu
            275                 280                 285

Gln Val Glu Arg Val Asn Glu Pro Ser Ile Leu Glu Met Ser Arg Gly
        290                 295                 300

Val Lys Leu Thr Asp Val Ala Pro Val Ser Phe Phe Leu Val Leu Asp
305                 310                 315                 320

Val Val Tyr Leu Val Tyr Glu Ser Lys His Leu His Glu Gly Ala Lys
                325                 330                 335

Ser Glu Thr Ala Glu Glu Leu Lys Lys Val Ala Gln Glu Leu Glu Glu
            340                 345                 350

Lys Leu Asn Ile Leu Asn Asn Asn Tyr Lys Ile Leu Gln Ala Asp Gln
            355                 360                 365

Glu Leu
    370
```

```
<210> SEQ ID NO 3
<211> LENGTH: 5
<212> TYPE: PRT
<213> ORGANISM: Artificial Sequence
<220> FEATURE:
<223> OTHER INFORMATION: Synthetic: 3.6D12 VH CDR1

<400> SEQUENCE: 3

Arg Cys Ala Met Ser
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic: 3.6D12 VH CDR2

<400> SEQUENCE: 4

Ala Ile Ser Arg Asp Ser Thr Tyr Thr Tyr Tyr Ser Asp Ser Val Lys
1               5                   10                  15

Gly

<210> SEQ ID NO 5
<211> LENGTH: 12
<212> TYPE: PRT
<213> ORGANISM: Artificial Sequence
<220> FEATURE:
```

<223> OTHER INFORMATION: Synthetic: 3.6D12 VH CDR3

<400> SEQUENCE: 5

Gln Ile Asp Asp Tyr Tyr Val Asp Ala Leu Asp Tyr
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic: 3.6D12 VL CDR1

<400> SEQUENCE: 6

Arg Ala Ser Lys Ile Ile Ser Lys Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Synthetic: 3.6D12 VL CDR2

<400> SEQUENCE: 7

Ser Gly Phe Thr Leu Gln Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic: 3.6D12 VL CDR3

<400> SEQUENCE: 8

Gln Gln His Asn Glu Tyr Pro Leu Thr
1               5

<210> SEQ ID NO 9
<211> LENGTH: 117
<212> TYPE: PRT
<213> ORGANISM: Artificial Sequence
<220> FEATURE:
<223> OTHER INFORMATION: Synthetic: 3.6D12 VH

<400> SEQUENCE: 9

Glu Val Met Leu Val Glu Ser Gly Gly Gly Leu Val Arg Pro Gly Gly
1               5                   10                  15

Ser Leu Lys Leu Ser Cys Thr Ala Ser Gly Phe Thr Phe Ser Arg Cys
            20                  25                  30

Ala Met Ser Trp Val Arg Gln Thr Pro Glu Lys Arg Leu Glu Trp Val
            35                  40                  45

Ser Ala Ile Ser Arg Asp Ser Thr Tyr Thr Tyr Tyr Ser Asp Ser Val
        50                  55                  60

Lys Gly Arg Phe Thr Val Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Gln Ile Asp Asp Tyr Tyr Val Asp Ala Leu Asp Tyr Trp Gly
            100                 105                 110

Gln Gly Thr Ser Val
            115

<210> SEQ ID NO 10
<211> LENGTH: 100
<212> TYPE: PRT
<213> ORGANISM: Artificial Sequence
<220> FEATURE:
<223> OTHER INFORMATION: Synthetic: 3.6D12 VL

<400> SEQUENCE: 10

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ile Ile Ser Lys Tyr
                20                  25                  30

Leu Ala Trp Tyr Gln Glu Lys Pro Gly Lys Thr Ile Lys Leu Leu Ile
            35                  40                  45

Tyr Ser Gly Phe Thr Leu Gln Ser Gly Ile Pro Ser Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Leu
                85                  90                  95

Thr Phe Gly Ala
            100

<210> SEQ ID NO 11
<211> LENGTH: 470
<212> TYPE: PRT
<213> ORGANISM: Artificial Sequence
<220> FEATURE:
<223> OTHER INFORMATION: Synthetic: 3.6D12 HC LALAPG mIgG2a

<400> SEQUENCE: 11

Met Gly Trp Ser Cys Ile Ile Leu Phe Leu Val Ala Thr Ala Thr Gly
1               5                   10                  15

Ala Tyr Ala Glu Val Met Leu Val Glu Ser Gly Gly Gly Leu Val Arg
                20                  25                  30

Pro Gly Gly Ser Leu Lys Leu Ser Cys Thr Ala Ser Gly Phe Thr Phe
            35                  40                  45

Ser Arg Cys Ala Met Ser Trp Val Arg Gln Thr Pro Glu Lys Arg Leu
        50                  55                  60

Glu Trp Val Ser Ala Ile Ser Arg Asp Ser Thr Tyr Thr Tyr Tyr Ser
65                  70                  75                  80

Asp Ser Val Lys Gly Arg Phe Thr Val Ser Arg Asp Asn Ala Lys Asn
                85                  90                  95

Thr Leu Tyr Leu Gln Met Ser Ser Leu Arg Ser Glu Asp Thr Ala Met
                100                 105                 110

Tyr Tyr Cys Ala Arg Gln Ile Asp Asp Tyr Tyr Val Asp Ala Leu Asp
            115                 120                 125

Tyr Trp Gly Gln Gly Thr Ser Val Thr Val Ser Ser Ala Ser Thr Lys
        130                 135                 140

Gly Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
                180                 185                 190

Phe Pro Ala Val Leu Gln Ser Asp Leu Tyr Thr Leu Ser Ser Ser Val

```
            195                 200                 205
Thr Val Thr Ser Ser Thr Trp Pro Ser Gln Ser Ile Thr Cys Asn Val
    210                 215                 220

Ala His Pro Ala Ser Ser Thr Lys Val Asp Lys Lys Ile Glu Pro Arg
225                 230                 235                 240

Gly Pro Thr Ile Lys Pro Cys Pro Pro Cys Lys Cys Pro Ala Pro Asn
                245                 250                 255

Ala Ala Gly Gly Pro Ser Val Phe Ile Phe Pro Pro Lys Ile Lys Asp
                260                 265                 270

Val Leu Met Ile Ser Leu Ser Pro Ile Val Thr Cys Val Val Val Asp
                275                 280                 285

Val Ser Glu Asp Asp Pro Asp Val Gln Ile Ser Trp Phe Val Asn Asn
    290                 295                 300

Val Glu Val His Thr Ala Gln Thr Gln Thr His Arg Glu Asp Tyr Asn
305                 310                 315                 320

Ser Thr Leu Arg Val Val Ser Ala Leu Pro Ile Gln His Gln Asp Trp
                325                 330                 335

Met Ser Gly Lys Glu Phe Lys Cys Lys Val Asn Asn Lys Asp Leu Gly
                340                 345                 350

Ala Pro Ile Glu Arg Thr Ile Ser Lys Pro Lys Gly Ser Val Arg Ala
                355                 360                 365

Pro Gln Val Tyr Val Leu Pro Pro Glu Glu Glu Met Thr Lys Lys
    370                 375                 380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                405                 410                 415

Thr Glu Pro Val Leu Asp Ser Asp Gly Ser Tyr Phe Met Tyr Ser Lys
                420                 425                 430

Leu Arg Val Glu Lys Lys Asn Trp Val Glu Arg Asn Ser Tyr Ser Cys
                435                 440                 445

Ser Val Val His Glu Gly Leu His Asn His His Thr Thr Lys Ser Phe
    450                 455                 460

Ser Arg Thr Pro Gly Lys
465                 470

<210> SEQ ID NO 12
<211> LENGTH: 233
<212> TYPE: PRT
<213> ORGANISM: Artificial Sequence
<220> FEATURE:
<223> OTHER INFORMATION: Synthetic: 3.6D12 LC LALAPG mIgG2a

<400> SEQUENCE: 12

Met Gly Trp Ser Cys Ile Ile Leu Phe Leu Val Ala Thr Ala Thr Gly
1               5                   10                  15

Val His Ser Asp Val Gln Ile Thr Gln Ser Pro Ser Tyr Leu Ala Ala
                20                  25                  30

Ser Pro Gly Glu Thr Ile Thr Ile Asn Cys Arg Ala Ser Lys Ile Ile
        35                  40                  45

Ser Lys Tyr Leu Ala Trp Tyr Gln Glu Lys Pro Gly Lys Thr Ile Lys
    50                  55                  60

Leu Leu Ile Tyr Ser Gly Phe Thr Leu Gln Ser Gly Ile Pro Ser Arg
65                  70                  75                  80

Phe Ser Gly Ser Gly Ser Gly Thr Asp Phe Thr Leu Thr Ile Ser Ser
```

-continued

```
                 85                  90                  95

Leu Glu Pro Glu Asp Phe Ala Met Tyr Tyr Cys Gln Gln His Asn Glu
            100                 105                 110

Tyr Pro Leu Thr Phe Gly Ala Gly Thr Lys Leu Glu Ile Lys Arg Ala
            115                 120                 125

Asp Ala Ala Pro Thr Val Ser Ile Phe Pro Pro Ser Ser Glu Gln Leu
            130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
                180                 185                 190

Ser Met Ser Ser Thr Leu Thr Leu Thr Lys Asp Glu Tyr Glu Arg His
                195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230

<210> SEQ ID NO 13
<211> LENGTH: 5
<212> TYPE: PRT
<213> ORGANISM: Artificial Sequence
<220> FEATURE:
<223> OTHER INFORMATION: Synthetic: 3.3B6 VH CDR1

<400> SEQUENCE: 13

Ser His Trp Met Gln
1               5

<210> SEQ ID NO 14
<211> LENGTH: 17
<212> TYPE: PRT
<213> ORGANISM: Artificial Sequence
<220> FEATURE:
<223> OTHER INFORMATION: Synthetic: 3.3B6 VH CDR2

<400> SEQUENCE: 14

Ala Ile Tyr Pro Gly Asp Gly Asp Thr Lys Phe Thr Gln Lys Phe Lys
1               5                   10                  15

Asp

<210> SEQ ID NO 15
<211> LENGTH: 9
<212> TYPE: PRT
<213> ORGANISM: Artificial Sequence
<220> FEATURE:
<223> OTHER INFORMATION: Synthetic: 3.3B6 VH CDR3

<400> SEQUENCE: 15

Asn Leu Tyr Gly Tyr Tyr Phe Asp Tyr
1               5

<210> SEQ ID NO 16
<211> LENGTH: 14
<212> TYPE: PRT
<213> ORGANISM: Artificial Sequence
<220> FEATURE:
<223> OTHER INFORMATION: Synthetic: 3.3B6 VL CDR1

<400> SEQUENCE: 16
```

```
Arg Ser Ser Thr Gly Ala Val Thr Ser Gly Asn Phe Ala Asn
1               5                   10
```

<210> SEQ ID NO 17
<211> LENGTH: 7
<212> TYPE: PRT
<213> ORGANISM: Artificial Sequence
<220> FEATURE:
<223> OTHER INFORMATION: Synthetic: 3.3B6 VL CDR2

<400> SEQUENCE: 17

```
Gly Ala Asp Asn Arg Ala Pro
1               5
```

<210> SEQ ID NO 18
<211> LENGTH: 9
<212> TYPE: PRT
<213> ORGANISM: Artificial Sequence
<220> FEATURE:
<223> OTHER INFORMATION: Synthetic: 3.3B6 VL CDR3

<400> SEQUENCE: 18

```
Ala Leu Trp Tyr Ser Asp His Trp Val
1               5
```

<210> SEQ ID NO 19
<211> LENGTH: 115
<212> TYPE: PRT
<213> ORGANISM: Artificial Sequence
<220> FEATURE:
<223> OTHER INFORMATION: Synthetic: 3.3B6 VH

<400> SEQUENCE: 19

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser His
            20                  25                  30

Trp Met Gln Trp Leu Lys Gln Arg Pro Gly Gln Gly Leu Glu Trp Ile
        35                  40                  45

Gly Ala Ile Tyr Pro Gly Asp Gly Asp Thr Lys Phe Thr Gln Lys Phe
    50                  55                  60

Lys Asp Lys Ala Thr Leu Thr Ala Asp Lys Ser Ser Thr Thr Ala Tyr
65                  70                  75                  80

Met Gln Leu Ser Ser Leu Ala Ser Glu Asp Ser Ala Val Tyr Tyr Cys
                85                  90                  95

Ala Arg Glu Asn Leu Tyr Gly Tyr Tyr Phe Asp Tyr Trp Gly Gln Gly
            100                 105                 110

Thr Thr Leu
        115
```

<210> SEQ ID NO 20
<211> LENGTH: 102
<212> TYPE: PRT
<213> ORGANISM: Artificial Sequence
<220> FEATURE:
<223> OTHER INFORMATION: Synthetic: 3.3B6 VL

<400> SEQUENCE: 20

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Ser Gly
            20                  25                  30
```

```
Asn Phe Ala Asn Trp Val Gln Glu Lys Pro Asp His Leu Phe Thr Gly
        35                  40                  45

Leu Ile Gly Gly Ala Asp Asn Arg Ala Pro Gly Val Pro Ala Arg Phe
        50                  55                  60

Ser Gly Ser Leu Ile Gly Asp Lys Ala Ala Leu Ile Ile Thr Gly Ala
65                  70                  75                  80

Gln Thr Glu Asp Glu Ala Ile Tyr Phe Cys Ala Leu Trp Tyr Ser Asp
                85                  90                  95

His Trp Val Phe Gly Gly
                100

<210> SEQ ID NO 21
<211> LENGTH: 468
<212> TYPE: PRT
<213> ORGANISM: Artificial Sequence
<220> FEATURE:
<223> OTHER INFORMATION: Synthetic: 3.3B6 HC LALAPG mIgG2a

<400> SEQUENCE: 21

Met Gly Trp Ser Cys Ile Ile Leu Phe Leu Val Ala Thr Ala Thr Gly
1                5                  10                  15

Ala Tyr Ala Gln Val Gln Leu Gln Gln Ser Gly Ala Glu Leu Ala Arg
                20                  25                  30

Pro Gly Ala Ser Val Lys Leu Ser Cys Lys Ala Ser Gly Tyr Thr Phe
        35                  40                  45

Thr Ser His Trp Met Gln Trp Leu Lys Gln Arg Pro Gly Gln Gly Leu
        50                  55                  60

Glu Trp Ile Gly Ala Ile Tyr Pro Gly Asp Gly Asp Thr Lys Phe Thr
65                  70                  75                  80

Gln Lys Phe Lys Asp Lys Ala Thr Leu Thr Ala Asp Lys Ser Ser Thr
                85                  90                  95

Thr Ala Tyr Met Gln Leu Ser Ser Leu Ala Ser Glu Asp Ser Ala Val
                100                 105                 110

Tyr Tyr Cys Ala Arg Glu Asn Leu Tyr Gly Tyr Tyr Phe Asp Tyr Trp
                115                 120                 125

Gly Gln Gly Thr Thr Leu Thr Val Ser Ser Ala Ser Thr Lys Gly Pro
        130                 135                 140

Ser Val Tyr Pro Leu Ala Pro Val Cys Gly Asp Thr Thr Gly Ser Ser
145                 150                 155                 160

Val Thr Leu Gly Cys Leu Val Lys Gly Tyr Phe Pro Glu Pro Val Thr
                165                 170                 175

Leu Thr Trp Asn Ser Gly Ser Leu Ser Ser Gly Val His Thr Phe Pro
                180                 185                 190

Ala Val Leu Gln Ser Asp Leu Tyr Thr Leu Ser Ser Ser Val Thr Val
                195                 200                 205

Thr Ser Ser Thr Trp Pro Ser Gln Ser Ile Thr Cys Asn Val Ala His
        210                 215                 220

Pro Ala Ser Ser Thr Lys Val Asp Lys Lys Ile Glu Pro Arg Gly Pro
225                 230                 235                 240

Thr Ile Lys Pro Cys Pro Pro Cys Lys Cys Pro Ala Pro Asn Ala Ala
                245                 250                 255

Gly Gly Pro Ser Val Phe Ile Phe Pro Pro Lys Ile Lys Asp Val Leu
                260                 265                 270

Met Ile Ser Leu Ser Pro Ile Val Thr Cys Val Val Val Asp Val Ser
        275                 280                 285
```

```
Glu Asp Asp Pro Asp Val Gln Ile Ser Trp Phe Val Asn Asn Val Glu
    290             295             300

Val His Thr Ala Gln Thr Gln Thr His Arg Glu Asp Tyr Asn Ser Thr
305             310             315             320

Leu Arg Val Val Ser Ala Leu Pro Ile Gln His Gln Asp Trp Met Ser
                325             330             335

Gly Lys Glu Phe Lys Cys Lys Val Asn Asn Lys Asp Leu Gly Ala Pro
            340             345             350

Ile Glu Arg Thr Ile Ser Lys Pro Lys Gly Ser Val Arg Ala Pro Gln
            355             360             365

Val Tyr Val Leu Pro Pro Pro Glu Glu Glu Met Thr Lys Lys Gln Val
    370             375             380

Thr Leu Thr Cys Met Val Thr Asp Phe Met Pro Glu Asp Ile Tyr Val
385             390             395             400

Glu Trp Thr Asn Asn Gly Lys Thr Glu Leu Asn Tyr Lys Asn Thr Glu
            405             410             415

Pro Val Leu Asp Ser Asp Gly Ser Tyr Phe Met Tyr Ser Lys Leu Arg
            420             425             430

Val Glu Lys Lys Asn Trp Val Glu Arg Asn Ser Tyr Ser Cys Ser Val
            435             440             445

Val His Glu Gly Leu His Asn His His Thr Thr Lys Ser Phe Ser Arg
    450             455             460

Thr Pro Gly Lys
465
```

```
<210> SEQ ID NO 22
<211> LENGTH: 233
<212> TYPE: PRT
<213> ORGANISM: Artificial Sequence
<220> FEATURE:
<223> OTHER INFORMATION: Synthetic: 3.3B6 LC LALAPG mIgG2a

<400> SEQUENCE: 22

Met Gly Trp Ser Cys Ile Ile Leu Phe Leu Val Ala Thr Ala Thr Gly
1               5               10              15

Val His Ser Gln Ala Val Val Thr Gln Glu Ser Ala Leu Thr Thr Ser
            20              25              30

Pro Gly Glu Thr Val Thr Leu Thr Cys Arg Ser Ser Thr Gly Ala Val
        35              40              45

Thr Ser Gly Asn Phe Ala Asn Trp Val Gln Glu Lys Pro Asp His Leu
    50              55              60

Phe Thr Gly Leu Ile Gly Gly Ala Asp Asn Arg Ala Pro Gly Val Pro
65              70              75              80

Ala Arg Phe Ser Gly Ser Leu Ile Gly Asp Lys Ala Ala Leu Ile Ile
            85              90              95

Thr Gly Ala Gln Thr Glu Asp Glu Ala Ile Tyr Phe Cys Ala Leu Trp
            100             105             110

Tyr Ser Asp His Trp Val Phe Gly Gly Gly Thr Lys Leu Thr Val Leu
        115             120             125

Gly Gln Pro Lys Ser Thr Pro Thr Leu Thr Val Phe Pro Pro Ser Ser
    130             135             140

Glu Glu Leu Lys Glu Asn Lys Ala Thr Leu Val Cys Leu Ile Ser Asn
145             150             155             160

Phe Ser Pro Ser Gly Val Thr Val Ala Trp Lys Ala Asn Gly Thr Pro
            165             170             175
```

```
Ile Thr Gln Gly Val Asp Thr Ser Asn Pro Thr Lys Glu Gly Asn Lys
            180                     185                     190

Phe Met Ala Ser Ser Phe Leu His Leu Thr Ser Asp Gln Trp Arg Ser
        195                     200                     205

His Asn Ser Phe Thr Cys Gln Val Thr His Glu Gly Asp Thr Val Glu
    210                     215                     220

Lys Ser Leu Ser Arg Ala Asp Cys Leu
225                     230
```

```
<210> SEQ ID NO 23
<211> LENGTH: 5
<212> TYPE: PRT
<213> ORGANISM: Artificial Sequence
<220> FEATURE:
<223> OTHER INFORMATION: Synthetic: 3.7D6 VH CDR1

<400> SEQUENCE: 23

Asn Tyr Gly Val Asn
1               5
```

```
<210> SEQ ID NO 24
<211> LENGTH: 17
<212> TYPE: PRT
<213> ORGANISM: Artificial Sequence
<220> FEATURE:
<223> OTHER INFORMATION: Synthetic: 3.7D6 VH CDR2

<400> SEQUENCE: 24

Trp Ile Asn Thr Asn Thr Gly Gln Thr Thr Tyr Ala Glu Glu Phe Arg
1               5                   10                  15

Gly
```

```
<210> SEQ ID NO 25
<211> LENGTH: 12
<212> TYPE: PRT
<213> ORGANISM: Artificial Sequence
<220> FEATURE:
<223> OTHER INFORMATION: Synthetic: 3.7D6 VH CDR3

<400> SEQUENCE: 25

Leu Ile Tyr Asp Gly Asp Tyr Ile Ser Ser Asp Phe
1               5                   10
```

```
<210> SEQ ID NO 26
<211> LENGTH: 11
<212> TYPE: PRT
<213> ORGANISM: Artificial Sequence
<220> FEATURE:
<223> OTHER INFORMATION: Synthetic: 3.7D6 VL CDR1

<400> SEQUENCE: 26

Gly Ala Ser Glu Asn Ile Tyr Gly Ala Leu Asn
1               5                   10
```

```
<210> SEQ ID NO 27
<211> LENGTH: 7
<212> TYPE: PRT
<213> ORGANISM: Artificial Sequence
<220> FEATURE:
<223> OTHER INFORMATION: Synthetic: 3.7D6 VL CDR2

<400> SEQUENCE: 27

Gly Ala Thr Asn Leu Ala Asp
1               5
```

```
<210> SEQ ID NO 28
<211> LENGTH: 9
<212> TYPE: PRT
<213> ORGANISM: Artificial Sequence
<220> FEATURE:
<223> OTHER INFORMATION: Synthetic: 3.7D6 VL CDR3

<400> SEQUENCE: 28

Gln Asn Ala Leu Ser Met Pro Tyr Thr
1               5

<210> SEQ ID NO 29
<211> LENGTH: 117
<212> TYPE: PRT
<213> ORGANISM: Artificial Sequence
<220> FEATURE:
<223> OTHER INFORMATION: Synthetic: 3.7D6 VH

<400> SEQUENCE: 29

Gln Ile Gln Leu Val Gln Ser Gly Pro Asp Leu Lys Lys Pro Gly Glu
1               5                   10                  15

Thr Val Lys Ile Ser Cys Arg Thr Ser Gly Tyr Ala Phe Thr Asn Tyr
            20                  25                  30

Gly Val Asn Trp Val Lys Gln Ala Pro Gly Lys Gly Leu Lys Trp Met
        35                  40                  45

Gly Trp Ile Asn Thr Asn Thr Gly Gln Thr Thr Tyr Ala Glu Glu Phe
    50                  55                  60

Arg Gly Arg Phe Ala Ile Ser Leu Glu Thr Ser Ala Ser Thr Ala Phe
65                  70                  75                  80

Leu Thr Ile Ser Asn Leu Lys Asn Glu Asp Ser Ala Thr Tyr Phe Cys
                85                  90                  95

Ala Arg Leu Ile Tyr Asp Gly Asp Tyr Ile Ser Ser Asp Phe Trp Gly
            100                 105                 110

Gln Gly Thr Thr Leu
        115

<210> SEQ ID NO 30
<211> LENGTH: 100
<212> TYPE: PRT
<213> ORGANISM: Artificial Sequence
<220> FEATURE:
<223> OTHER INFORMATION: Synthetic: 3.7D6 VL

<400> SEQUENCE: 30

Asp Ile Gln Met Thr Gln Ser Pro Asp Ser Leu Ser Ala Ser Val Gly
1               5                   10                  15

Glu Thr Val Thr Ile Thr Cys Gly Ala Ser Glu Asn Ile Tyr Gly Ala
            20                  25                  30

Leu Asn Trp Tyr Gln Arg Lys Gln Gly Lys Ser Pro Gln Leu Leu Ile
        35                  40                  45

Tyr Gly Ala Thr Asn Leu Ala Asp Gly Met Ser Ser Arg Phe Ser Gly
    50                  55                  60

Ser Arg Ser Gly Arg Gln Tyr Ser Leu Lys Ile Ser Ser Leu His Pro
65                  70                  75                  80

Asp Asp Val Ala Thr Tyr Tyr Cys Gln Asn Ala Leu Ser Met Pro Tyr
                85                  90                  95

Thr Phe Gly Gly
            100
```

<210> SEQ ID NO 31
<211> LENGTH: 470
<212> TYPE: PRT
<213> ORGANISM: Artificial Sequence
<220> FEATURE:
<223> OTHER INFORMATION: Synthetic: 3.7D6 HC LALAPG mIgG2a

<400> SEQUENCE: 31

```
Met Gly Trp Ser Cys Ile Ile Leu Phe Leu Val Ala Thr Ala Thr Gly
1               5                   10                  15

Ala Tyr Ala Gln Ile Gln Leu Val Gln Ser Gly Pro Asp Leu Lys Lys
                20                  25                  30

Pro Gly Glu Thr Val Lys Ile Ser Cys Arg Thr Ser Gly Tyr Ala Phe
            35                  40                  45

Thr Asn Tyr Gly Val Asn Trp Val Lys Gln Ala Pro Gly Lys Gly Leu
        50                  55                  60

Lys Trp Met Gly Trp Ile Asn Thr Asn Thr Gly Gln Thr Thr Tyr Ala
65                  70                  75                  80

Glu Glu Phe Arg Gly Arg Phe Ala Ile Ser Leu Glu Thr Ser Ala Ser
                85                  90                  95

Thr Ala Phe Leu Thr Ile Ser Asn Leu Lys Asn Glu Asp Ser Ala Thr
            100                 105                 110

Tyr Phe Cys Ala Arg Leu Ile Tyr Asp Gly Asp Tyr Ile Ser Ser Asp
            115                 120                 125

Phe Trp Gly Gln Gly Thr Thr Leu Thr Val Ser Ser Ala Ser Thr Lys
        130                 135                 140

Gly Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
            195                 200                 205

Thr Val Thr Ser Ser Thr Trp Pro Ser Gln Ser Ile Thr Cys Asn Val
        210                 215                 220

Ala His Pro Ala Ser Ser Thr Lys Val Asp Lys Lys Ile Glu Pro Arg
225                 230                 235                 240

Gly Pro Thr Ile Lys Pro Cys Pro Pro Cys Lys Cys Pro Ala Pro Asn
                245                 250                 255

Ala Ala Gly Gly Pro Ser Val Phe Ile Phe Pro Pro Lys Ile Lys Asp
            260                 265                 270

Val Leu Met Ile Ser Leu Ser Pro Ile Val Thr Cys Val Val Val Asp
            275                 280                 285

Val Ser Glu Asp Asp Pro Asp Val Gln Ile Ser Trp Phe Val Asn Asn
        290                 295                 300

Val Glu Val His Thr Ala Gln Thr Gln Thr His Arg Glu Asp Tyr Asn
305                 310                 315                 320

Ser Thr Leu Arg Val Val Ser Ala Leu Pro Ile Gln His Gln Asp Trp
                325                 330                 335

Met Ser Gly Lys Glu Phe Lys Cys Lys Val Asn Asn Lys Asp Leu Gly
            340                 345                 350

Ala Pro Ile Glu Arg Thr Ile Ser Lys Pro Lys Gly Ser Val Arg Ala
            355                 360                 365
```

```
Pro Gln Val Tyr Val Leu Pro Pro Glu Glu Glu Met Thr Lys Lys
    370                 375         380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                405                 410                 415

Thr Glu Pro Val Leu Asp Ser Asp Gly Ser Tyr Phe Met Tyr Ser Lys
                420                 425                 430

Leu Arg Val Glu Lys Lys Asn Trp Val Glu Arg Asn Ser Tyr Ser Cys
                435                 440                 445

Ser Val Val His Glu Gly Leu His Asn His His Thr Thr Lys Ser Phe
    450                 455                 460

Ser Arg Thr Pro Gly Lys
465                 470
```

```
<210> SEQ ID NO 32
<211> LENGTH: 233
<212> TYPE: PRT
<213> ORGANISM: Artificial Sequence
<220> FEATURE:
<223> OTHER INFORMATION: Synthetic: 3.7D6 LC LALAPG mIgG2a

<400> SEQUENCE: 32
```

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Asp Ser Leu Ser Ala
                20                  25                  30

Ser Val Gly Glu Thr Val Thr Ile Thr Cys Gly Ala Ser Glu Asn Ile
            35                  40                  45

Tyr Gly Ala Leu Asn Trp Tyr Gln Arg Lys Gln Gly Lys Ser Pro Gln
    50                  55                  60

Leu Leu Ile Tyr Gly Ala Thr Asn Leu Ala Asp Gly Met Ser Ser Arg
65                  70                  75                  80

Phe Ser Gly Ser Arg Ser Gly Arg Gln Tyr Ser Leu Lys Ile Ser Ser
                85                  90                  95

Leu His Pro Asp Asp Val Ala Thr Tyr Tyr Cys Gln Asn Ala Leu Ser
            100                 105                 110

Met Pro Tyr Thr Phe Gly Gly Gly Thr Lys Leu Glu Ile Lys Arg Ala
    115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
                180                 185                 190

Ser Met Ser Ser Thr Leu Thr Leu Thr Lys Asp Glu Tyr Glu Arg His
            195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230
```

```
<210> SEQ ID NO 33
<211> LENGTH: 5
```

<212> TYPE: PRT
<213> ORGANISM: Artificial Sequence
<220> FEATURE:
<223> OTHER INFORMATION: Synthetic: 3.3A8 VH CDR1

<400> SEQUENCE: 33

Asn Tyr Glu Ile His
1               5

<210> SEQ ID NO 34
<211> LENGTH: 17
<212> TYPE: PRT
<213> ORGANISM: Artificial Sequence
<220> FEATURE:
<223> OTHER INFORMATION: Synthetic: 3.3A8 VH CDR2

<400> SEQUENCE: 34

Ala Ile His Pro Gly Asn Gly Val Thr Ala Tyr Asn Gln Met Phe Lys
1               5                   10                  15

Gly

<210> SEQ ID NO 35
<211> LENGTH: 4
<212> TYPE: PRT
<213> ORGANISM: Artificial Sequence
<220> FEATURE:
<223> OTHER INFORMATION: Synthetic: 3.3A8 VH CDR3

<400> SEQUENCE: 35

Asn Phe Asp Tyr
1

<210> SEQ ID NO 36
<211> LENGTH: 16
<212> TYPE: PRT
<213> ORGANISM: Artificial Sequence
<220> FEATURE:
<223> OTHER INFORMATION: Synthetic: 3.3A8 VL CDR1

<400> SEQUENCE: 36

Arg Ser Ser Gln Ser Leu Thr Asn Ser Tyr Gly Ile Thr Tyr Leu Ser
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Synthetic: 3.3A8 VL CDR2

<400> SEQUENCE: 37

Glu Ile Ser Asn Arg Phe Ser
1               5

<210> SEQ ID NO 38
<211> LENGTH: 9
<212> TYPE: PRT
<213> ORGANISM: Artificial Sequence
<220> FEATURE:
<223> OTHER INFORMATION: Synthetic: 3.3A8 VL CDR3

<400> SEQUENCE: 38

Leu Gln Gly Thr His Gln Pro Phe Thr
1               5

<210> SEQ ID NO 39

```
<211> LENGTH: 109
<212> TYPE: PRT
<213> ORGANISM: Artificial Sequence
<220> FEATURE:
<223> OTHER INFORMATION: Synthetic: 3.3A8 VH

<400> SEQUENCE: 39

Gln Val Gln Phe Gln Gln Ser Gly Ala Glu Leu Val Arg Pro Gly Ala
1               5                   10                  15

Ser Val Lys Val Thr Cys Lys Ala Leu Gly Tyr Thr Phe Ser Asn Tyr
                20                  25                  30

Glu Ile His Trp Val Arg Gln Pro Pro Val His Gly Leu Glu Trp Ile
            35                  40                  45

Gly Ala Ile His Pro Gly Asn Gly Val Thr Ala Tyr Asn Gln Met Phe
        50                  55                  60

Lys Gly Arg Ala Thr Leu Ala Ala Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Thr Glu Asn Phe Asp Tyr Trp Gly Gln Gly Thr Ala Leu
            100                 105

<210> SEQ ID NO 40
<211> LENGTH: 105
<212> TYPE: PRT
<213> ORGANISM: Artificial Sequence
<220> FEATURE:
<223> OTHER INFORMATION: Synthetic: 3.3A8 VL

<400> SEQUENCE: 40

Asp Val Val Val Thr Gln Thr Pro Leu Ser Leu Pro Val Ser Phe Gly
1               5                   10                  15

Asp Gln Val Ser Ile Ser Cys Arg Ser Ser Gln Ser Leu Thr Asn Ser
                20                  25                  30

Tyr Gly Ile Thr Tyr Leu Ser Trp Phe Leu Leu Lys Pro Gly Gln Ser
            35                  40                  45

Pro Gln Leu Leu Ile Tyr Glu Ile Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Thr Ile Lys Pro Glu Asp Leu Gly Val Tyr Phe Cys Leu Gln Gly
                85                  90                  95

Thr His Gln Pro Phe Thr Phe Gly Ala
            100                 105

<210> SEQ ID NO 41
<211> LENGTH: 462
<212> TYPE: PRT
<213> ORGANISM: Artificial Sequence
<220> FEATURE:
<223> OTHER INFORMATION: Synthetic: 3.3A8 HC LALAPG mIgG2a

<400> SEQUENCE: 41

Met Gly Trp Ser Cys Ile Ile Leu Phe Leu Val Ala Thr Ala Thr Gly
1               5                   10                  15

Ala Tyr Ala Gln Val Gln Phe Gln Gln Ser Gly Ala Glu Leu Val Arg
                20                  25                  30

Pro Gly Ala Ser Val Lys Val Thr Cys Lys Ala Leu Gly Tyr Thr Phe
            35                  40                  45
```

-continued

```
Ser Asn Tyr Glu Ile His Trp Val Arg Gln Pro Pro Val His Gly Leu
    50              55                  60

Glu Trp Ile Gly Ala Ile His Pro Gly Asn Gly Val Thr Ala Tyr Asn
65              70                  75                  80

Gln Met Phe Lys Gly Arg Ala Thr Leu Ala Ala Asp Lys Ser Ser Ser
                85                  90                  95

Thr Ala Tyr Met Glu Leu Ser Ser Leu Thr Ser Glu Asp Ser Ala Val
                100                 105                 110

Tyr Tyr Cys Thr Glu Asn Phe Asp Tyr Trp Gly Gln Gly Thr Ala Leu
            115                 120                 125

Thr Val Ser Ser Ala Ser Thr Lys Gly Pro Ser Val Tyr Pro Leu Ala
    130                 135                 140

Pro Val Cys Gly Asp Thr Thr Gly Ser Ser Val Thr Leu Gly Cys Leu
145                 150                 155                 160

Val Lys Gly Tyr Phe Pro Glu Pro Val Thr Leu Thr Trp Asn Ser Gly
                165                 170                 175

Ser Leu Ser Ser Gly Val His Thr Phe Pro Ala Val Leu Gln Ser Asp
            180                 185                 190

Leu Tyr Thr Leu Ser Ser Ser Val Thr Val Thr Ser Ser Thr Trp Pro
        195                 200                 205

Ser Gln Ser Ile Thr Cys Asn Val Ala His Pro Ala Ser Ser Thr Lys
    210                 215                 220

Val Asp Lys Lys Ile Glu Pro Arg Gly Pro Thr Ile Lys Pro Cys Pro
225                 230                 235                 240

Pro Cys Lys Cys Pro Ala Pro Asn Ala Ala Gly Gly Pro Ser Val Phe
                245                 250                 255

Ile Phe Pro Pro Lys Ile Lys Asp Val Leu Met Ile Ser Leu Ser Pro
            260                 265                 270

Ile Val Thr Cys Val Val Val Asp Val Ser Glu Asp Asp Pro Asp Val
            275                 280                 285

Gln Ile Ser Trp Phe Val Asn Asn Val Glu Val His Thr Ala Gln Thr
    290                 295                 300

Gln Thr His Arg Glu Asp Tyr Asn Ser Thr Leu Arg Val Val Ser Ala
305                 310                 315                 320

Leu Pro Ile Gln His Gln Asp Trp Met Ser Gly Lys Glu Phe Lys Cys
                325                 330                 335

Lys Val Asn Asn Lys Asp Leu Gly Ala Pro Ile Glu Arg Thr Ile Ser
                340                 345                 350

Lys Pro Lys Gly Ser Val Arg Ala Pro Gln Val Tyr Val Leu Pro Pro
            355                 360                 365

Pro Glu Glu Glu Met Thr Lys Lys Gln Val Thr Leu Thr Cys Met Val
    370                 375                 380

Thr Asp Phe Met Pro Glu Asp Ile Tyr Val Glu Trp Thr Asn Asn Gly
385                 390                 395                 400

Lys Thr Glu Leu Asn Tyr Lys Asn Thr Glu Pro Val Leu Asp Ser Asp
                405                 410                 415

Gly Ser Tyr Phe Met Tyr Ser Lys Leu Arg Val Glu Lys Lys Asn Trp
                420                 425                 430

Val Glu Arg Asn Ser Tyr Ser Cys Ser Val Val His Glu Gly Leu His
            435                 440                 445

Asn His His Thr Thr Lys Ser Phe Ser Arg Thr Pro Gly Lys
    450                 455                 460
```

-continued

```
<210> SEQ ID NO 42
<211> LENGTH: 238
<212> TYPE: PRT
<213> ORGANISM: Artificial Sequence
<220> FEATURE:
<223> OTHER INFORMATION: Synthetic: 3.3A8 LC LALAPG mIgG2a

<400> SEQUENCE: 42

Met Gly Trp Ser Cys Ile Ile Leu Phe Leu Val Ala Thr Ala Thr Gly
1               5                   10                  15

Val His Ser Asp Val Val Val Thr Gln Thr Pro Leu Ser Leu Pro Val
                20                  25                  30

Ser Phe Gly Asp Gln Val Ser Ile Ser Cys Arg Ser Ser Gln Ser Leu
            35                  40                  45

Thr Asn Ser Tyr Gly Ile Thr Tyr Leu Ser Trp Phe Leu Leu Lys Pro
        50                  55                  60

Gly Gln Ser Pro Gln Leu Leu Ile Tyr Glu Ile Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Thr Ile Lys Pro Glu Asp Leu Gly Val Tyr Phe Cys
            100                 105                 110

Leu Gln Gly Thr His Gln Pro Phe Thr Phe Gly Ala Gly Thr Lys Leu
        115                 120                 125

Glu Ile Lys Arg Ala Asp Ala Ala Pro Thr Val Ser Ile Phe Pro Pro
        130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
            195                 200                 205

Glu Tyr Glu Arg His Asn Ser Tyr Thr Cys Glu Ala Thr His Lys Thr
        210                 215                 220

Ser Thr Ser Pro Ile Val Lys Ser Phe Asn Arg Asn Glu Cys
225                 230                 235

<210> SEQ ID NO 43
<211> LENGTH: 5
<212> TYPE: PRT
<213> ORGANISM: Artificial Sequence
<220> FEATURE:
<223> OTHER INFORMATION: Synthetic: 3.2C11 VH CDR1

<400> SEQUENCE: 43

Asp Tyr Glu Ile His
1               5

<210> SEQ ID NO 44
<211> LENGTH: 17
<212> TYPE: PRT
<213> ORGANISM: Artificial Sequence
<220> FEATURE:
<223> OTHER INFORMATION: Synthetic: 3.2C11 VH CDR2

<400> SEQUENCE: 44

Gly Ile His Pro Gly Asn Gly Gly Thr Ala Tyr Asn Pro Lys Phe Lys
1               5                   10                  15
```

-continued

Gly

<210> SEQ ID NO 45
<211> LENGTH: 4
<212> TYPE: PRT
<213> ORGANISM: Artificial Sequence
<220> FEATURE:
<223> OTHER INFORMATION: Synthetic: 3.2C11 VH CDR3

<400> SEQUENCE: 45

Trp Val Asp Tyr
1

<210> SEQ ID NO 46
<211> LENGTH: 16
<212> TYPE: PRT
<213> ORGANISM: Artificial Sequence
<220> FEATURE:
<223> OTHER INFORMATION: Synthetic: 3.2C11 VL CDR1

<400> SEQUENCE: 46

Arg Ser Ser Gln Ser Leu Val Asn Arg His Gly Ile Thr Tyr Leu Ser
1               5                   10                  15

<210> SEQ ID NO 47
<211> LENGTH: 7
<212> TYPE: PRT
<213> ORGANISM: Artificial Sequence
<220> FEATURE:
<223> OTHER INFORMATION: Synthetic: 3.2C11 VL CDR2

<400> SEQUENCE: 47

Glu Ile Ser Asn Arg Phe Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic: 3.2C11 VL CDR3

<400> SEQUENCE: 48

Phe Gln Gly Thr His Gln Pro Phe Thr
1               5

<210> SEQ ID NO 49
<211> LENGTH: 109
<212> TYPE: PRT
<213> ORGANISM: Artificial Sequence
<220> FEATURE:
<223> OTHER INFORMATION: Synthetic: 3.2C11 VH

<400> SEQUENCE: 49

Gln Val Gln Leu Gln Gln Ser Gly Ala Glu Leu Val Arg Pro Gly Ala
1               5                   10                  15

Ser Val Lys Leu Ser Cys Lys Ala Leu Gly Tyr Thr Phe Thr Asp Tyr
                20                  25                  30

Glu Ile His Trp Val Lys Gln Thr Pro Val His Gly Leu Glu Trp Ile
        35                  40                  45

Gly Gly Ile His Pro Gly Asn Gly Gly Thr Ala Tyr Asn Pro Lys Phe
    50                  55                  60

Lys Gly Lys Ala Thr Leu Thr Ala Asp Thr Ser Ser Ser Thr Ala Ser
65                  70                  75                  80

-continued

```
Met Glu Leu Ser Ser Leu Thr Ser Glu Asp Ser Ala Val Tyr Tyr Cys
                85                  90                  95

Thr Asp Trp Val Asp Tyr Trp Gly Gln Gly Thr Thr Leu
            100                 105

<210> SEQ ID NO 50
<211> LENGTH: 105
<212> TYPE: PRT
<213> ORGANISM: Artificial Sequence
<220> FEATURE:
<223> OTHER INFORMATION: Synthetic: 3.2C11 VL

<400> SEQUENCE: 50

Asp Val Val Val Thr Gln Thr Pro Leu Ser Leu Pro Val Asn Phe Gly
1               5                   10                  15

Asp Gln Val Ser Ile Ser Cys Arg Ser Ser Gln Ser Leu Val Asn Arg
            20                  25                  30

His Gly Ile Thr Tyr Leu Ser Trp Tyr Leu His Lys Pro Gly Gln Ser
        35                  40                  45

Pro Gln Leu Leu Ile Tyr Glu Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Thr Ile Lys Pro Glu Asp Leu Gly Met Tyr Tyr Cys Phe Gln Gly
                85                  90                  95

Thr His Gln Pro Phe Thr Phe Gly Gly
            100                 105

<210> SEQ ID NO 51
<211> LENGTH: 462
<212> TYPE: PRT
<213> ORGANISM: Artificial Sequence
<220> FEATURE:
<223> OTHER INFORMATION: Synthetic: 3.2C11 HC LALAPG mIgG2a

<400> SEQUENCE: 51

Met Gly Trp Ser Cys Ile Ile Leu Phe Leu Val Ala Thr Ala Thr Gly
1               5                   10                  15

Val His Ser Gln Val Gln Leu Gln Gln Ser Gly Ala Glu Leu Val Arg
            20                  25                  30

Pro Gly Ala Ser Val Lys Leu Ser Cys Lys Ala Leu Gly Tyr Thr Phe
        35                  40                  45

Thr Asp Tyr Glu Ile His Trp Val Lys Gln Thr Pro Val His Gly Leu
    50                  55                  60

Glu Trp Ile Gly Gly Ile His Pro Gly Asn Gly Gly Thr Ala Tyr Asn
65                  70                  75                  80

Pro Lys Phe Lys Gly Lys Ala Thr Leu Thr Ala Asp Thr Ser Ser Ser
                85                  90                  95

Thr Ala Ser Met Glu Leu Ser Ser Leu Thr Ser Glu Asp Ser Ala Val
            100                 105                 110

Tyr Tyr Cys Thr Asp Trp Val Asp Tyr Trp Gly Gln Gly Thr Thr Leu
        115                 120                 125

Thr Val Ser Ser Ala Lys Thr Thr Ala Pro Ser Val Tyr Pro Leu Ala
    130                 135                 140

Pro Val Cys Gly Asp Thr Thr Gly Ser Ser Val Thr Leu Gly Cys Leu
145                 150                 155                 160

Val Lys Gly Tyr Phe Pro Glu Pro Val Thr Leu Thr Trp Asn Ser Gly
```

```
              165             170             175
Ser Leu Ser Ser Gly Val His Thr Phe Pro Ala Val Leu Gln Ser Asp
          180             185             190

Leu Tyr Thr Leu Ser Ser Ser Val Thr Val Thr Ser Ser Thr Trp Pro
          195             200             205

Ser Gln Ser Ile Thr Cys Asn Val Ala His Pro Ala Ser Ser Thr Lys
          210             215             220

Val Asp Lys Lys Ile Glu Pro Arg Gly Pro Thr Ile Lys Pro Cys Pro
225             230             235             240

Pro Cys Lys Cys Pro Ala Pro Asn Ala Ala Gly Gly Pro Ser Val Phe
              245             250             255

Ile Phe Pro Pro Lys Ile Lys Asp Val Leu Met Ile Ser Leu Ser Pro
              260             265             270

Ile Val Thr Cys Val Val Val Asp Val Ser Glu Asp Asp Pro Asp Val
              275             280             285

Gln Ile Ser Trp Phe Val Asn Asn Val Glu Val His Thr Ala Gln Thr
          290             295             300

Gln Thr His Arg Glu Asp Tyr Asn Ser Thr Leu Arg Val Val Ser Ala
305             310             315             320

Leu Pro Ile Gln His Gln Asp Trp Met Ser Gly Lys Glu Phe Lys Cys
              325             330             335

Lys Val Asn Asn Lys Asp Leu Gly Ala Pro Ile Glu Arg Thr Ile Ser
              340             345             350

Lys Pro Lys Gly Ser Val Arg Ala Pro Gln Val Tyr Val Leu Pro Pro
              355             360             365

Pro Glu Glu Glu Met Thr Lys Lys Gln Val Thr Leu Thr Cys Met Val
          370             375             380

Thr Asp Phe Met Pro Glu Asp Ile Tyr Val Glu Trp Thr Asn Asn Gly
385             390             395             400

Lys Thr Glu Leu Asn Tyr Lys Asn Thr Glu Pro Val Leu Asp Ser Asp
              405             410             415

Gly Ser Tyr Phe Met Tyr Ser Lys Leu Arg Val Glu Lys Lys Asn Trp
              420             425             430

Val Glu Arg Asn Ser Tyr Ser Cys Ser Val Val His Glu Gly Leu His
          435             440             445

Asn His His Thr Thr Lys Ser Phe Ser Arg Thr Pro Gly Lys
    450             455             460
```

<210> SEQ ID NO 52
<211> LENGTH: 238
<212> TYPE: PRT
<213> ORGANISM: Artificial Sequence
<220> FEATURE:
<223> OTHER INFORMATION: Synthetic: 3.2C11 LC LALAPG mIgG2a

<400> SEQUENCE: 52

```
Met Gly Trp Ser Cys Ile Ile Leu Phe Leu Val Ala Thr Ala Thr Gly
1               5               10              15

Val His Ser Asp Val Val Val Thr Gln Thr Pro Leu Ser Leu Pro Val
              20              25              30

Asn Phe Gly Asp Gln Val Ser Ile Ser Cys Arg Ser Ser Gln Ser Leu
          35              40              45

Val Asn Arg His Gly Ile Thr Tyr Leu Ser Trp Tyr Leu His Lys Pro
    50              55              60

Gly Gln Ser Pro Gln Leu Leu Ile Tyr Glu Ile Ser Asn Arg Phe Ser
```

-continued

```
65                70                75                80

Gly Val Pro Asp Arg Phe Ser Gly Ser Gly Ser Gly Thr Asp Phe Thr
                85                90                95

Leu Lys Ile Ser Thr Ile Lys Pro Glu Asp Leu Gly Met Tyr Tyr Cys
                100               105               110

Phe Gln Gly Thr His Gln Pro Phe Thr Phe Gly Gly Gly Thr Lys Leu
                115               120               125

Glu Ile Lys Arg Ala Asp Ala Ala Pro Thr Val Ser Ile Phe Pro Pro
          130               135               140

Ser Ser Glu Gln Leu Thr Ser Gly Gly Ala Ser Val Val Cys Phe Leu
145               150               155               160

Asn Asn Phe Tyr Pro Lys Asp Ile Asn Val Lys Trp Lys Ile Asp Gly
                165               170               175

Ser Glu Arg Gln Asn Gly Val Leu Asn Ser Trp Thr Asp Gln Asp Ser
                180               185               190

Lys Asp Ser Thr Tyr Ser Met Ser Ser Thr Leu Thr Leu Thr Lys Asp
                195               200               205

Glu Tyr Glu Arg His Asn Ser Tyr Thr Cys Glu Ala Thr His Lys Thr
          210               215               220

Ser Thr Ser Pro Ile Val Lys Ser Phe Asn Arg Asn Glu Cys
225               230               235
```

```
<210> SEQ ID NO 53
<211> LENGTH: 5
<212> TYPE: PRT
<213> ORGANISM: Artificial Sequence
<220> FEATURE:
<223> OTHER INFORMATION: Synthetic: 3.1C1 VH CDR1

<400> SEQUENCE: 53

Asn Tyr Phe Ile His
1               5

<210> SEQ ID NO 54
<211> LENGTH: 17
<212> TYPE: PRT
<213> ORGANISM: Artificial Sequence
<220> FEATURE:
<223> OTHER INFORMATION: Synthetic: 3.1C1 VH CDR2

<400> SEQUENCE: 54

Trp Ile Asn Pro Gly Asn Leu Asn Thr Lys Tyr Thr Glu Glu Phe Lys
1               5               10               15

Gly

<210> SEQ ID NO 55
<211> LENGTH: 6
<212> TYPE: PRT
<213> ORGANISM: Artificial Sequence
<220> FEATURE:
<223> OTHER INFORMATION: Synthetic: 3.1C1 VH CDR3

<400> SEQUENCE: 55

Gly Asn Pro Phe Val Tyr
1               5

<210> SEQ ID NO 56
<211> LENGTH: 17
<212> TYPE: PRT
<213> ORGANISM: Artificial Sequence
<220> FEATURE:
```

-continued

<223> OTHER INFORMATION: Synthetic: 3.1C1 VL CDR1

<400> SEQUENCE: 56

Lys Ser Ser Gln Ser Leu Leu Asn Ser Gly Asn Gln Lys Lys Tyr Leu
1               5                   10                  15

Thr

<210> SEQ ID NO 57
<211> LENGTH: 7
<212> TYPE: PRT
<213> ORGANISM: Artificial Sequence
<220> FEATURE:
<223> OTHER INFORMATION: Synthetic: 3.1C1 VL CDR2

<400> SEQUENCE: 57

Trp Thr Ser Thr Arg Asp Ser
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic: 3.1C1 VL CDR3

<400> SEQUENCE: 58

Gln Asn Asp Tyr Ser Tyr Pro Leu Thr
1               5

<210> SEQ ID NO 59
<211> LENGTH: 111
<212> TYPE: PRT
<213> ORGANISM: Artificial Sequence
<220> FEATURE:
<223> OTHER INFORMATION: Synthetic: 3.1C1 VH

<400> SEQUENCE: 59

Gln Val Gln Leu Gln Gln Ser Gly Pro Glu Leu Val Lys Pro Gly Ala
1               5                   10                  15

Ser Val Arg Ile Ser Cys Lys Ala Ser Gly Tyr Thr Phe Thr Asn Tyr
                20                  25                  30

Phe Ile His Trp Val Lys Gln Arg Pro Gly Gln Gly Leu Glu Trp Ile
            35                  40                  45

Gly Trp Ile Asn Pro Gly Asn Leu Asn Thr Lys Tyr Thr Glu Glu Phe
        50                  55                  60

Lys Gly Lys Ala Thr Leu Thr Ala Asp Lys Ser Ser Ser Thr Ala Tyr
65                  70                  75                  80

Ile Gln Leu Asn Ser Leu Thr Ser Glu Asp Ser Ala Val Tyr Phe Cys
                85                  90                  95

Val Asn Gly Asn Pro Phe Val Tyr Trp Gly Gln Gly Thr Leu Val
                100                 105                 110

<210> SEQ ID NO 60
<211> LENGTH: 106
<212> TYPE: PRT
<213> ORGANISM: Artificial Sequence
<220> FEATURE:
<223> OTHER INFORMATION: Synthetic: 3.1C1 VL

<400> SEQUENCE: 60

Asp Ile Val Met Thr Gln Ser Pro Ser Ser Leu Thr Val Ile Ala Gly
1               5                   10                  15

Glu Lys Val Thr Leu Asn Cys Lys Ser Ser Gln Ser Leu Leu Asn Ser
                20                  25                  30

Gly Asn Gln Lys Lys Tyr Leu Thr Trp Leu Gln Gln Lys Pro Gly Gln
            35                  40                  45

Pro Pro Lys Leu Leu Ile Tyr Trp Thr Ser Thr Arg Asp Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala
            100                 105

<210> SEQ ID NO 61
<211> LENGTH: 464
<212> TYPE: PRT
<213> ORGANISM: Artificial Sequence
<220> FEATURE:
<223> OTHER INFORMATION: Synthetic: 3.1C1 HC LALAPG mIgG2a

<400> SEQUENCE: 61

Met Gly Trp Ser Cys Ile Ile Leu Phe Leu Val Ala Thr Ala Thr Gly
1                   5                   10                  15

Ala Tyr Ala Gln Val Gln Leu Gln Gln Ser Gly Pro Glu Leu Val Lys
                20                  25                  30

Pro Gly Ala Ser Val Arg Ile Ser Cys Lys Ala Ser Gly Tyr Thr Phe
            35                  40                  45

Thr Asn Tyr Phe Ile His Trp Val Lys Gln Arg Pro Gly Gln Gly Leu
        50                  55                  60

Glu Trp Ile Gly Trp Ile Asn Pro Gly Asn Leu Asn Thr Lys Tyr Thr
65                  70                  75                  80

Glu Glu Phe Lys Gly Lys Ala Thr Leu Thr Ala Asp Lys Ser Ser Ser
                85                  90                  95

Thr Ala Tyr Ile Gln Leu Asn Ser Leu Thr Ser Glu Asp Ser Ala Val
                100                 105                 110

Tyr Phe Cys Val Asn Gly Asn Pro Phe Val Tyr Trp Gly Gln Gly Thr
            115                 120                 125

Leu Val Thr Val Ser Ala Ala Ser Thr Lys Gly Pro Ser Val Tyr Pro
        130                 135                 140

Leu Ala Pro Val Cys Gly Asp Thr Thr Gly Ser Ser Val Thr Leu Gly
145                 150                 155                 160

Cys Leu Val Lys Gly Tyr Phe Pro Glu Pro Val Thr Leu Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Thr Ser Ser Thr
            195                 200                 205

Trp Pro Ser Gln Ser Ile Thr Cys Asn Val Ala His Pro Ala Ser Ser
        210                 215                 220

Thr Lys Val Asp Lys Lys Ile Glu Pro Arg Gly Pro Thr Ile Lys Pro
225                 230                 235                 240

Cys Pro Pro Cys Lys Cys Pro Ala Pro Asn Ala Ala Gly Gly Pro Ser
                245                 250                 255

Val Phe Ile Phe Pro Pro Lys Ile Lys Asp Val Leu Met Ile Ser Leu
            260                 265                 270

```
Ser Pro Ile Val Thr Cys Val Val Val Asp Val Ser Glu Asp Asp Pro
    275             280             285

Asp Val Gln Ile Ser Trp Phe Val Asn Asn Val Glu Val His Thr Ala
    290             295             300

Gln Thr Gln Thr His Arg Glu Asp Tyr Asn Ser Thr Leu Arg Val Val
305             310             315             320

Ser Ala Leu Pro Ile Gln His Gln Asp Trp Met Ser Gly Lys Glu Phe
            325             330             335

Lys Cys Lys Val Asn Asn Lys Asp Leu Gly Ala Pro Ile Glu Arg Thr
            340             345             350

Ile Ser Lys Pro Lys Gly Ser Val Arg Ala Pro Gln Val Tyr Val Leu
            355             360             365

Pro Pro Pro Glu Glu Glu Met Thr Lys Lys Gln Val Thr Leu Thr Cys
    370             375             380

Met Val Thr Asp Phe Met Pro Glu Asp Ile Tyr Val Glu Trp Thr Asn
385             390             395             400

Asn Gly Lys Thr Glu Leu Asn Tyr Lys Asn Thr Glu Pro Val Leu Asp
            405             410             415

Ser Asp Gly Ser Tyr Phe Met Tyr Ser Lys Leu Arg Val Glu Lys Lys
            420             425             430

Asn Trp Val Glu Arg Asn Ser Tyr Ser Cys Ser Val Val His Glu Gly
            435             440             445

Leu His Asn His His Thr Thr Lys Ser Phe Ser Arg Thr Pro Gly Lys
    450             455             460
```

<210> SEQ ID NO 62
<211> LENGTH: 239
<212> TYPE: PRT
<213> ORGANISM: Artificial Sequence
<220> FEATURE:
<223> OTHER INFORMATION: Synthetic: 3.1C1 LC LALAPG mIgG2a

<400> SEQUENCE: 62

```
Met Gly Trp Ser Cys Ile Ile Leu Phe Leu Val Ala Thr Ala Thr Gly
1               5               10              15

Val His Ser Asp Ile Val Met Thr Gln Ser Pro Ser Ser Leu Thr Val
            20              25              30

Ile Ala Gly Glu Lys Val Thr Leu Asn Cys Lys Ser Ser Gln Ser Leu
            35              40              45

Leu Asn Ser Gly Asn Gln Lys Lys Tyr Leu Thr Trp Leu Gln Gln Lys
    50              55              60

Pro Gly Gln Pro Pro Lys Leu Leu Ile Tyr Trp Thr Ser Thr Arg Asp
65              70              75              80

Ser Gly Val Pro Asp Arg Phe Thr Gly Ser Gly Ser Gly Thr Asp Phe
            85              90              95

Thr Leu Thr Ile Ser Ser Val Gln Ala Glu Asp Leu Ala Val Tyr Tyr
            100             105             110

Cys Gln Asn Asp Tyr Ser Tyr Pro Leu Thr Phe Gly Ala Gly Thr Lys
            115             120             125

Leu Glu Ile Lys Arg Ala Asp Ala Ala Pro Thr Val Ser Ile Phe Pro
    130             135             140

Pro Ser Ser Glu Gln Leu Thr Ser Gly Gly Ala Ser Val Val Cys Phe
145             150             155             160

Leu Asn Asn Phe Tyr Pro Lys Asp Ile Asn Val Lys Trp Lys Ile Asp
            165             170             175
```

-continued

```
Gly Ser Glu Arg Gln Asn Gly Val Leu Asn Ser Trp Thr Asp Gln Asp
            180             185             190

Ser Lys Asp Ser Thr Tyr Ser Met Ser Ser Thr Leu Thr Leu Thr Lys
        195             200             205

Asp Glu Tyr Glu Arg His Asn Ser Tyr Thr Cys Glu Ala Thr His Lys
    210             215             220

Thr Ser Thr Ser Pro Ile Val Lys Ser Phe Asn Arg Asn Glu Cys
225             230             235
```

<210> SEQ ID NO 63
<211> LENGTH: 5
<212> TYPE: PRT
<213> ORGANISM: Artificial Sequence
<220> FEATURE:
<223> OTHER INFORMATION: Synthetic: 3.1C7 VH CDR1

<400> SEQUENCE: 63

```
Ser Tyr Trp Met His
1               5
```

<210> SEQ ID NO 64
<211> LENGTH: 17
<212> TYPE: PRT
<213> ORGANISM: Artificial Sequence
<220> FEATURE:
<223> OTHER INFORMATION: Synthetic: 3.1C7 VH CDR2

<400> SEQUENCE: 64

```
Ala Ile Tyr Pro Gly Lys Ser Asp Ile Lys Tyr Asn Gln Lys Phe Lys
1               5                   10                  15

Asp
```

<210> SEQ ID NO 65
<211> LENGTH: 6
<212> TYPE: PRT
<213> ORGANISM: Artificial Sequence
<220> FEATURE:
<223> OTHER INFORMATION: Synthetic: 3.1C7 VH CDR3

<400> SEQUENCE: 65

```
Ser Ile Pro Phe Val Tyr
1               5
```

<210> SEQ ID NO 66
<211> LENGTH: 17
<212> TYPE: PRT
<213> ORGANISM: Artificial Sequence
<220> FEATURE:
<223> OTHER INFORMATION: Synthetic: 3.1C7 VL CDR1

<400> SEQUENCE: 66

```
Lys Ser Ser Gln Ser Leu Leu Asn Ser Glu Asn Gln Lys Lys Tyr Leu
1               5                   10                  15

Thr
```

<210> SEQ ID NO 67
<211> LENGTH: 7
<212> TYPE: PRT
<213> ORGANISM: Artificial Sequence
<220> FEATURE:
<223> OTHER INFORMATION: Synthetic: 3.1C7 VL CDR2

<400> SEQUENCE: 67

```
Trp Thr Ser Thr Arg Tyr Ser
```

```
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic: 3.1C7 VL CDR3

<400> SEQUENCE: 68

Gln Asn Asp Tyr Ser Tyr Pro Leu Thr
1               5

<210> SEQ ID NO 69
<211> LENGTH: 111
<212> TYPE: PRT
<213> ORGANISM: Artificial Sequence
<220> FEATURE:
<223> OTHER INFORMATION: Synthetic: 3.1C7 VH

<400> SEQUENCE: 69

Glu Val Gln Leu Gln Gln Ser Gly Thr Val Leu Ser Arg Pro Gly Ala
1               5                   10                  15

Ser Val Lys Met Ser Cys Lys Ala Ser Gly Tyr Thr Met Thr Ser Tyr
            20                  25                  30

Trp Met His Trp Ile Lys Gln Arg Pro Gly Gln Gly Leu Glu Trp Ile
        35                  40                  45

Gly Ala Ile Tyr Pro Gly Lys Ser Asp Ile Lys Tyr Asn Gln Lys Phe
    50                  55                  60

Lys Asp Lys Ala Lys Leu Thr Ala Val Thr Ala Thr Ser Thr Ala Tyr
65                  70                  75                  80

Met Glu Ile Asn Ser Leu Thr Asn Glu Asp Ser Ala Val Tyr Tyr Cys
                85                  90                  95

Thr Asn Ser Ile Pro Phe Val Tyr Trp Gly Gln Gly Thr Leu Ile
            100                 105                 110

<210> SEQ ID NO 70
<211> LENGTH: 106
<212> TYPE: PRT
<213> ORGANISM: Artificial Sequence
<220> FEATURE:
<223> OTHER INFORMATION: Synthetic: 3.1C7 VL

<400> SEQUENCE: 70

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Glu Asn Gln Lys Lys Tyr Leu Thr Trp Phe Gln Gln Lys Pro Gly Gln
        35                  40                  45

Pro Pro Lys Leu Leu Ile Tyr Trp Thr Ser Thr Arg Tyr Ser Gly Ile
    50                  55                  60

Pro Asp Arg Phe Thr Gly Ser Gly Ser Gly Thr Val Phe Thr Leu Thr
65                  70                  75                  80

Ile Ser Ser Val Gln Ala Asp Asp Leu Ala Val Tyr Tyr Cys Gln Asn
                85                  90                  95

Asp Tyr Ser Tyr Pro Leu Thr Phe Gly Gly
            100                 105

<210> SEQ ID NO 71
```

<211> LENGTH: 464
<212> TYPE: PRT
<213> ORGANISM: Artificial Sequence
<220> FEATURE:
<223> OTHER INFORMATION: Synthetic: 3.1C7 HC LALAPG mIgG2a

<400> SEQUENCE: 71

```
Met Gly Trp Ser Cys Ile Ile Leu Phe Leu Val Ala Thr Ala Thr Gly
1               5                   10                  15

Ala Tyr Ala Glu Val Gln Leu Gln Gln Ser Gly Thr Val Leu Ser Arg
            20                  25                  30

Pro Gly Ala Ser Val Lys Met Ser Cys Lys Ala Ser Gly Tyr Thr Met
        35                  40                  45

Thr Ser Tyr Trp Met His Trp Ile Lys Gln Arg Pro Gly Gln Gly Leu
    50                  55                  60

Glu Trp Ile Gly Ala Ile Tyr Pro Gly Lys Ser Asp Ile Lys Tyr Asn
65                  70                  75                  80

Gln Lys Phe Lys Asp Lys Ala Lys Leu Thr Ala Val Thr Ala Thr Ser
            85                  90                  95

Thr Ala Tyr Met Glu Ile Asn Ser Leu Thr Asn Glu Asp Ser Ala Val
            100                 105                 110

Tyr Tyr Cys Thr Asn Ser Ile Pro Phe Val Tyr Trp Gly Gln Gly Thr
            115                 120                 125

Leu Ile Thr Val Ser Ala Ala Ser Thr Lys Gly Pro Ser Val Tyr Pro
    130                 135                 140

Leu Ala Pro Val Cys Gly Asp Thr Thr Gly Ser Ser Val Thr Leu Gly
145                 150                 155                 160

Cys Leu Val Lys Gly Tyr Phe Pro Glu Pro Val Thr Leu Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Thr Ser Ser Thr
            195                 200                 205

Trp Pro Ser Gln Ser Ile Thr Cys Asn Val Ala His Pro Ala Ser Ser
    210                 215                 220

Thr Lys Val Asp Lys Lys Ile Glu Pro Arg Gly Pro Thr Ile Lys Pro
225                 230                 235                 240

Cys Pro Pro Cys Lys Cys Pro Ala Pro Asn Ala Ala Gly Gly Pro Ser
                245                 250                 255

Val Phe Ile Phe Pro Pro Lys Ile Lys Asp Val Leu Met Ile Ser Leu
                260                 265                 270

Ser Pro Ile Val Thr Cys Val Val Val Asp Val Ser Glu Asp Asp Pro
            275                 280                 285

Asp Val Gln Ile Ser Trp Phe Val Asn Asn Val Glu Val His Thr Ala
    290                 295                 300

Gln Thr Gln Thr His Arg Glu Asp Tyr Asn Ser Thr Leu Arg Val Val
305                 310                 315                 320

Ser Ala Leu Pro Ile Gln His Gln Asp Trp Met Ser Gly Lys Glu Phe
            325                 330                 335

Lys Cys Lys Val Asn Asn Lys Asp Leu Gly Ala Pro Ile Glu Arg Thr
            340                 345                 350

Ile Ser Lys Pro Lys Gly Ser Val Arg Ala Pro Gln Val Tyr Val Leu
            355                 360                 365

Pro Pro Pro Glu Glu Glu Met Thr Lys Lys Gln Val Thr Leu Thr Cys
    370                 375                 380
```

```
Met Val Thr Asp Phe Met Pro Glu Asp Ile Tyr Val Glu Trp Thr Asn
385                 390                 395                 400

Asn Gly Lys Thr Glu Leu Asn Tyr Lys Asn Thr Glu Pro Val Leu Asp
                405                 410                 415

Ser Asp Gly Ser Tyr Phe Met Tyr Ser Lys Leu Arg Val Glu Lys Lys
                420                 425                 430

Asn Trp Val Glu Arg Asn Ser Tyr Ser Cys Ser Val Val His Glu Gly
                435                 440                 445

Leu His Asn His His Thr Thr Lys Ser Phe Ser Arg Thr Pro Gly Lys
            450                 455                 460
```

<210> SEQ ID NO 72
<211> LENGTH: 239
<212> TYPE: PRT
<213> ORGANISM: Artificial Sequence
<220> FEATURE:
<223> OTHER INFORMATION: Synthetic: 3.1C7 LC mIgG2a

<400> SEQUENCE: 72

```
Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
                20                  25                  30

Thr Ala Gly Glu Lys Val Thr Met Ser Cys Lys Ser Ser Gln Ser Leu
            35                  40                  45

Leu Asn Ser Glu Asn Gln Lys Lys Tyr Leu Thr Trp Phe Gln Gln Lys
        50                  55                  60

Pro Gly Gln Pro Pro Lys Leu Leu Ile Tyr Trp Thr Ser Thr Arg Tyr
65                  70                  75                  80

Ser Gly Ile Pro Asp Arg Phe Thr Gly Ser Gly Ser Gly Thr Val Phe
                85                  90                  95

Thr Leu Thr Ile Ser Ser Val Gln Ala Asp Asp Leu Ala Val Tyr Tyr
            100                 105                 110

Cys Gln Asn Asp Tyr Ser Tyr Pro Leu Thr Phe Gly Gly Gly Thr Lys
            115                 120                 125

Leu Glu Ile Lys Arg Ala Asp Ala Ala Pro Thr Val Ser Ile Phe Pro
        130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
                180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
        210                 215                 220

Thr Ser Thr Ser Pro Ile Val Lys Ser Phe Asn Arg Asn Glu Cys
225                 230                 235
```

<210> SEQ ID NO 73
<211> LENGTH: 6
<212> TYPE: PRT
<213> ORGANISM: Artificial Sequence
<220> FEATURE:
<223> OTHER INFORMATION: Synthetic: 3.4G10 VH CDR1

-continued

<400> SEQUENCE: 73

Ser Gly Glu Ser Trp His
1               5

<210> SEQ ID NO 74
<211> LENGTH: 16
<212> TYPE: PRT
<213> ORGANISM: Artificial Sequence
<220> FEATURE:
<223> OTHER INFORMATION: Synthetic: 3.4G10 VH CDR2

<400> SEQUENCE: 74

Phe Ile His Tyr Ser Gly Ser Ala Asn Tyr Asn Pro Ser Leu Lys Ser
1               5                   10                  15

<210> SEQ ID NO 75
<211> LENGTH: 12
<212> TYPE: PRT
<213> ORGANISM: Artificial Sequence
<220> FEATURE:
<223> OTHER INFORMATION: Synthetic: 3.4G10 VH CDR3

<400> SEQUENCE: 75

Ser Val Tyr Asn Tyr Asp Gly Ala Trp Phe Pro Tyr
1               5                   10

<210> SEQ ID NO 76
<211> LENGTH: 12
<212> TYPE: PRT
<213> ORGANISM: Artificial Sequence
<220> FEATURE:
<223> OTHER INFORMATION: Synthetic: 3.4G10 VL CDR1

<400> SEQUENCE: 76

Ser Ala Ser Ser Ser Val Ser Ser Ser Tyr Leu Asn
1               5                   10

<210> SEQ ID NO 77
<211> LENGTH: 7
<212> TYPE: PRT
<213> ORGANISM: Artificial Sequence
<220> FEATURE:
<223> OTHER INFORMATION: Synthetic: 3.4G10 VL CDR2

<400> SEQUENCE: 77

Arg Thr Ser Asn Leu Ala Ser
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic: 3.4G10 VL CDR3

<400> SEQUENCE: 78

His Gln Trp Ser Ala Tyr Pro Pro Thr
1               5

<210> SEQ ID NO 79
<211> LENGTH: 117
<212> TYPE: PRT
<213> ORGANISM: Artificial Sequence
<220> FEATURE:
<223> OTHER INFORMATION: Synthetic: 3.4G10 VH

<400> SEQUENCE: 79

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
                20                  25                  30

Glu Ser Trp His Trp Ile Arg His Phe Pro Gly Asn Glu Leu Glu Trp
            35                  40                  45

Met Gly Phe Ile His Tyr Ser Gly Ser Ala Asn Tyr Asn Pro Ser Leu
        50                  55                  60

Lys Ser Arg Ile Ser Ile Thr Arg Asp Thr Ser Lys Asn Gln Phe Phe
65                  70                  75                  80

Leu Gln Leu Leu Ser Val Thr Thr Asp Asp Thr Ala Thr Tyr Tyr Cys
                85                  90                  95

Ala Arg Ser Val Tyr Asn Tyr Asp Gly Ala Trp Phe Pro Tyr Trp Gly
            100                 105                 110

Gln Gly Thr Leu Val
        115

<210> SEQ ID NO 80
<211> LENGTH: 101
<212> TYPE: PRT
<213> ORGANISM: Artificial Sequence
<220> FEATURE:
<223> OTHER INFORMATION: Synthetic: 3.4G10 VL

<400> SEQUENCE: 80

Gln Ile Val Leu Thr Gln Ser Pro Val Ile Met Ser Ala Ser Pro Gly
1               5                   10                  15

Glu Arg Val Thr Leu Thr Cys Ser Ala Ser Ser Ser Val Ser Ser Ser
                20                  25                  30

Tyr Leu Asn Trp Tyr Gln Leu Lys Pro Gly Ser Ser Pro Lys Val Trp
            35                  40                  45

Ile Tyr Arg Thr Ser Asn Leu Ala Ser Gly Val Pro Ala Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ala Tyr Pro
                85                  90                  95

Pro Thr Phe Gly Gly
            100

<210> SEQ ID NO 81
<211> LENGTH: 470
<212> TYPE: PRT
<213> ORGANISM: Artificial Sequence
<220> FEATURE:
<223> OTHER INFORMATION: Synthetic: 3.4G10 HC LALAPG mIgG2a

<400> SEQUENCE: 81

Met Gly Trp Ser Cys Ile Ile Leu Phe Leu Val Ala Thr Ala Thr Gly
1               5                   10                  15

Ala Tyr Ala Asp Val Gln Leu Gln Glu Ser Gly Pro Asp Leu Val Lys
                20                  25                  30

Pro Ser Gln Ser Leu Ser Leu Thr Cys Thr Val Thr Gly Tyr Ser Ile
            35                  40                  45

Thr Ser Gly Glu Ser Trp His Trp Ile Arg His Phe Pro Gly Asn Glu
        50                  55                  60

Leu Glu Trp Met Gly Phe Ile His Tyr Ser Gly Ser Ala Asn Tyr Asn

-continued

```
65              70              75              80

Pro Ser Leu Lys Ser Arg Ile Ser Ile Thr Arg Asp Thr Ser Lys Asn
                85              90              95

Gln Phe Phe Leu Gln Leu Leu Ser Val Thr Thr Asp Asp Thr Ala Thr
            100             105             110

Tyr Tyr Cys Ala Arg Ser Val Tyr Asn Tyr Asp Gly Ala Trp Phe Pro
            115             120             125

Tyr Trp Gly Gln Gly Thr Leu Val Thr Val Ser Ala Ala Ser Thr Lys
    130             135             140

Gly Pro Ser Val Tyr Pro Leu Ala Pro Val Cys Gly Asp Thr Thr Gly
145             150             155             160

Ser Ser Val Thr Leu Gly Cys Leu Val Lys Gly Tyr Phe Pro Glu Pro
            165             170             175

Val Thr Leu Thr Trp Asn Ser Gly Ser Leu Ser Ser Gly Val His Thr
            180             185             190

Phe Pro Ala Val Leu Gln Ser Asp Leu Tyr Thr Leu Ser Ser Ser Val
            195             200             205

Thr Val Thr Ser Ser Thr Trp Pro Ser Gln Ser Ile Thr Cys Asn Val
    210             215             220

Ala His Pro Ala Ser Ser Thr Lys Val Asp Lys Lys Ile Glu Pro Arg
225             230             235             240

Gly Pro Thr Ile Lys Pro Cys Pro Pro Cys Lys Cys Pro Ala Pro Asn
            245             250             255

Ala Ala Gly Gly Pro Ser Val Phe Ile Phe Pro Pro Lys Ile Lys Asp
            260             265             270

Val Leu Met Ile Ser Leu Ser Pro Ile Val Thr Cys Val Val Val Asp
    275             280             285

Val Ser Glu Asp Asp Pro Asp Val Gln Ile Ser Trp Phe Val Asn Asn
    290             295             300

Val Glu Val His Thr Ala Gln Thr Gln Thr His Arg Glu Asp Tyr Asn
305             310             315             320

Ser Thr Leu Arg Val Val Ser Ala Leu Pro Ile Gln His Gln Asp Trp
            325             330             335

Met Ser Gly Lys Glu Phe Lys Cys Lys Val Asn Asn Lys Asp Leu Gly
            340             345             350

Ala Pro Ile Glu Arg Thr Ile Ser Lys Pro Lys Gly Ser Val Arg Ala
            355             360             365

Pro Gln Val Tyr Val Leu Pro Pro Pro Glu Glu Glu Met Thr Lys Lys
    370             375             380

Gln Val Thr Leu Thr Cys Met Val Thr Asp Phe Met Pro Glu Asp Ile
385             390             395             400

Tyr Val Glu Trp Thr Asn Asn Gly Lys Thr Glu Leu Asn Tyr Lys Asn
            405             410             415

Thr Glu Pro Val Leu Asp Ser Asp Gly Ser Tyr Phe Met Tyr Ser Lys
            420             425             430

Leu Arg Val Glu Lys Lys Asn Trp Val Glu Arg Asn Ser Tyr Ser Cys
            435             440             445

Ser Val Val His Glu Gly Leu His Asn His His Thr Thr Lys Ser Phe
    450             455             460

Ser Arg Thr Pro Gly Lys
465             470
```

<210> SEQ ID NO 82

-continued

<211> LENGTH: 234
<212> TYPE: PRT
<213> ORGANISM: Artificial Sequence
<220> FEATURE:
<223> OTHER INFORMATION: Synthetic: 3.4G10 LC LALAPG mIgG2a

<400> SEQUENCE: 82

```
Met Gly Trp Ser Cys Ile Ile Leu Phe Leu Val Ala Thr Ala Thr Gly
1               5                   10                  15

Val His Ser Gln Ile Val Leu Thr Gln Ser Pro Val Ile Met Ser Ala
            20                  25                  30

Ser Pro Gly Glu Arg Val Thr Leu Thr Cys Ser Ala Ser Ser Ser Val
        35                  40                  45

Ser Ser Ser Tyr Leu Asn Trp Tyr Gln Leu Lys Pro Gly Ser Ser Pro
    50                  55                  60

Lys Val Trp Ile Tyr Arg Thr Ser Asn Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Ser Met Glu Ala Glu Asp Ala Ala Ser Tyr Phe Cys His Gln Trp Ser
            100                 105                 110

Ala Tyr Pro Pro Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230
```

<210> SEQ ID NO 83
<211> LENGTH: 5
<212> TYPE: PRT
<213> ORGANISM: Artificial Sequence
<220> FEATURE:
<223> OTHER INFORMATION: Synthetic: 3.6E10 VH CDR1

<400> SEQUENCE: 83

```
Ser Tyr Tyr Leu His
1               5
```

<210> SEQ ID NO 84
<211> LENGTH: 17
<212> TYPE: PRT
<213> ORGANISM: Artificial Sequence
<220> FEATURE:
<223> OTHER INFORMATION: Synthetic: 3.6E10 VH CDR2

<400> SEQUENCE: 84

```
Tyr Ile Asn Pro Asn Thr Gly Tyr Thr Glu Tyr Thr Gln Asn Phe Lys
1               5                   10                  15
```

Asp

<210> SEQ ID NO 85
<211> LENGTH: 6
<212> TYPE: PRT
<213> ORGANISM: Artificial Sequence
<220> FEATURE:
<223> OTHER INFORMATION: Synthetic: 3.6E10 VH CDR3

<400> SEQUENCE: 85

Gly Asn Pro Phe Val Tyr
1               5

<210> SEQ ID NO 86
<211> LENGTH: 17
<212> TYPE: PRT
<213> ORGANISM: Artificial Sequence
<220> FEATURE:
<223> OTHER INFORMATION: Synthetic: 3.6E10 VL CDR1

<400> SEQUENCE: 86

Arg Ser Ser Gln Ser Leu Leu Asn Ser Gly Asn Gln Lys Asn Tyr Leu
1               5                   10                  15

Thr

<210> SEQ ID NO 87
<211> LENGTH: 7
<212> TYPE: PRT
<213> ORGANISM: Artificial Sequence
<220> FEATURE:
<223> OTHER INFORMATION: Synthetic: 3.6E10 VL CDR2

<400> SEQUENCE: 87

Trp Thr Ser Thr Arg Tyr Ser
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic: 3.6E10 VL CDR3

<400> SEQUENCE: 88

Gln Asn Asp Tyr Ser Tyr Pro Leu Thr
1               5

<210> SEQ ID NO 89
<211> LENGTH: 111
<212> TYPE: PRT
<213> ORGANISM: Artificial Sequence
<220> FEATURE:
<223> OTHER INFORMATION: Synthetic: 3.6E10 VH

<400> SEQUENCE: 89

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Ile Phe Thr Ser Tyr
            20                  25                  30

Tyr Leu His Trp Val Lys Gln Arg Pro Gly Gln Gly Leu Glu Trp Ile
        35                  40                  45

Gly Tyr Ile Asn Pro Asn Thr Gly Tyr Thr Glu Tyr Thr Gln Asn Phe
    50                  55                  60

Lys Asp Arg Ala Thr Leu Thr Ala Asp Lys Ser Ser Ser Thr Ala Tyr

-continued

```
65              70              75              80

Met Gln Leu Thr Ser Leu Thr Ser Glu Asp Ser Ala Val Tyr Phe Cys
                85              90              95

Val Asn Gly Asn Pro Phe Val Tyr Trp Gly Gln Gly Thr Leu Val
                100             105             110
```

<210> SEQ ID NO 90
<211> LENGTH: 106
<212> TYPE: PRT
<213> ORGANISM: Artificial Sequence
<220> FEATURE:
<223> OTHER INFORMATION: Synthetic: 3.6E10 VL

<400> SEQUENCE: 90

```
Asp Ile Val Met Thr Gln Ser Pro Ser Ser Leu Thr Val Thr Thr Gly
1               5               10              15

Glu Lys Val Thr Met Thr Cys Arg Ser Ser Gln Ser Leu Leu Asn Ser
                20              25              30

Gly Asn Gln Lys Asn Tyr Leu Thr Trp Phe Gln Gln Lys Pro Gly Gln
        35              40              45

Pro Pro Lys Leu Leu Ile Tyr Trp Thr Ser Thr Arg Tyr Ser Gly Val
        50              55              60

Pro Asp Arg Phe Thr Gly Ser Gly Ser Gly Thr Asp Phe Thr Leu Thr
65              70              75              80

Ile Ser Ser Val Gln Ala Glu Asp Leu Ala Val Tyr Tyr Cys Gln Asn
                85              90              95

Asp Tyr Ser Tyr Pro Leu Thr Phe Gly Ala
                100             105
```

<210> SEQ ID NO 91
<211> LENGTH: 464
<212> TYPE: PRT
<213> ORGANISM: Artificial Sequence
<220> FEATURE:
<223> OTHER INFORMATION: Synthetic: 3.6E10 HC LALAPG mIgG2a

<400> SEQUENCE: 91

```
Met Gly Trp Ser Cys Ile Ile Leu Phe Leu Val Ala Thr Ala Thr Gly
1               5               10              15

Ala Tyr Ala Gln Val Gln Leu Gln Gln Ser Gly Ala Glu Leu Ala Lys
                20              25              30

Pro Gly Ala Ser Val Lys Met Ser Cys Lys Ala Ser Gly Tyr Ile Phe
        35              40              45

Thr Ser Tyr Tyr Leu His Trp Val Lys Gln Arg Pro Gly Gln Gly Leu
        50              55              60

Glu Trp Ile Gly Tyr Ile Asn Pro Asn Thr Gly Tyr Thr Glu Tyr Thr
65              70              75              80

Gln Asn Phe Lys Asp Arg Ala Thr Leu Thr Ala Asp Lys Ser Ser Ser
                85              90              95

Thr Ala Tyr Met Gln Leu Thr Ser Leu Thr Ser Glu Asp Ser Ala Val
                100             105             110

Tyr Phe Cys Val Asn Gly Asn Pro Phe Val Tyr Trp Gly Gln Gly Thr
        115             120             125

Leu Val Thr Val Ser Ala Ala Ser Thr Lys Gly Pro Ser Val Tyr Pro
        130             135             140

Leu Ala Pro Val Cys Gly Asp Thr Thr Gly Ser Ser Val Thr Leu Gly
145             150             155             160
```

-continued

```
Cys Leu Val Lys Gly Tyr Phe Pro Glu Pro Val Thr Leu Thr Trp Asn
                165                 170                 175

Ser Gly Ser Leu Ser Ser Gly Val His Thr Phe Pro Ala Val Leu Gln
            180                 185                 190

Ser Asp Leu Tyr Thr Leu Ser Ser Ser Val Thr Val Thr Ser Ser Thr
            195                 200                 205

Trp Pro Ser Gln Ser Ile Thr Cys Asn Val Ala His Pro Ala Ser Ser
    210                 215                 220

Thr Lys Val Asp Lys Lys Ile Glu Pro Arg Gly Pro Thr Ile Lys Pro
225                 230                 235                 240

Cys Pro Pro Cys Lys Cys Pro Ala Pro Asn Ala Ala Gly Gly Pro Ser
                245                 250                 255

Val Phe Ile Phe Pro Pro Lys Ile Lys Asp Val Leu Met Ile Ser Leu
                260                 265                 270

Ser Pro Ile Val Thr Cys Val Val Val Asp Val Ser Glu Asp Asp Pro
            275                 280                 285

Asp Val Gln Ile Ser Trp Phe Val Asn Asn Val Glu Val His Thr Ala
    290                 295                 300

Gln Thr Gln Thr His Arg Glu Asp Tyr Asn Ser Thr Leu Arg Val Val
305                 310                 315                 320

Ser Ala Leu Pro Ile Gln His Gln Asp Trp Met Ser Gly Lys Glu Phe
                325                 330                 335

Lys Cys Lys Val Asn Asn Lys Asp Leu Gly Ala Pro Ile Glu Arg Thr
                340                 345                 350

Ile Ser Lys Pro Lys Gly Ser Val Arg Ala Pro Gln Val Tyr Val Leu
            355                 360                 365

Pro Pro Pro Glu Glu Glu Met Thr Lys Lys Gln Val Thr Leu Thr Cys
    370                 375                 380

Met Val Thr Asp Phe Met Pro Glu Asp Ile Tyr Val Glu Trp Thr Asn
385                 390                 395                 400

Asn Gly Lys Thr Glu Leu Asn Tyr Lys Asn Thr Glu Pro Val Leu Asp
                405                 410                 415

Ser Asp Gly Ser Tyr Phe Met Tyr Ser Lys Leu Arg Val Glu Lys Lys
                420                 425                 430

Asn Trp Val Glu Arg Asn Ser Tyr Ser Cys Ser Val Val His Glu Gly
            435                 440                 445

Leu His Asn His His Thr Thr Lys Ser Phe Ser Arg Thr Pro Gly Lys
    450                 455                 460
```

<210> SEQ ID NO 92
<211> LENGTH: 239
<212> TYPE: PRT
<213> ORGANISM: Artificial Sequence
<220> FEATURE:
<223> OTHER INFORMATION: Synthetic: 3.6E10 LC LALAPG mIgG2a

<400> SEQUENCE: 92

```
Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Thr Val
            20                  25                  30

Thr Thr Gly Glu Lys Val Thr Met Thr Cys Arg Ser Ser Gln Ser Leu
            35                  40                  45

Leu Asn Ser Gly Asn Gln Lys Asn Tyr Leu Thr Trp Phe Gln Gln Lys
    50                  55                  60
```

-continued

```
Pro Gly Gln Pro Pro Lys Leu Leu Ile Tyr Trp Thr Ser Thr Arg Tyr
65              70              75              80

Ser Gly Val Pro Asp Arg Phe Thr Gly Ser Gly Ser Gly Thr Asp Phe
                85              90              95

Thr Leu Thr Ile Ser Ser Val Gln Ala Glu Asp Leu Ala Val Tyr Tyr
            100             105             110

Cys Gln Asn Asp Tyr Ser Tyr Pro Leu Thr Phe Gly Ala Gly Thr Lys
        115             120             125

Leu Glu Ile Lys Arg Ala Asp Ala Ala Pro Thr Val Ser Ile Phe Pro
        130             135             140

Pro Ser Ser Glu Gln Leu Thr Ser Gly Gly Ala Ser Val Val Cys Phe
145             150             155             160

Leu Asn Asn Phe Tyr Pro Lys Asp Ile Asn Val Lys Trp Lys Ile Asp
            165             170             175

Gly Ser Glu Arg Gln Asn Gly Val Leu Asn Ser Trp Thr Asp Gln Asp
            180             185             190

Ser Lys Asp Ser Thr Tyr Ser Met Ser Ser Thr Leu Thr Leu Thr Lys
        195             200             205

Asp Glu Tyr Glu Arg His Asn Ser Tyr Thr Cys Glu Ala Thr His Lys
    210             215             220

Thr Ser Thr Ser Pro Ile Val Lys Ser Phe Asn Arg Asn Glu Cys
225             230             235
```

```
<210> SEQ ID NO 93
<211> LENGTH: 5
<212> TYPE: PRT
<213> ORGANISM: Artificial Sequence
<220> FEATURE:
<223> OTHER INFORMATION: Synthetic: 3.3F7 VH CDR1

<400> SEQUENCE: 93

Thr Tyr Gly Val His
1               5

<210> SEQ ID NO 94
<211> LENGTH: 16
<212> TYPE: PRT
<213> ORGANISM: Artificial Sequence
<220> FEATURE:
<223> OTHER INFORMATION: Synthetic: 3.3F7 VH CDR2

<400> SEQUENCE: 94

Val Ile Trp Arg Gly Gly Asn Thr Asp Tyr Asn Ala Ala Phe Met Ser
1               5                   10                  15

<210> SEQ ID NO 95
<211> LENGTH: 11
<212> TYPE: PRT
<213> ORGANISM: Artificial Sequence
<220> FEATURE:
<223> OTHER INFORMATION: Synthetic: 3.3F7 VH CDR3

<400> SEQUENCE: 95

Ser Ser Tyr Gly Tyr His Tyr Thr Met Asp Tyr
1               5                   10

<210> SEQ ID NO 96
<211> LENGTH: 11
<212> TYPE: PRT
<213> ORGANISM: Artificial Sequence
<220> FEATURE:
<223> OTHER INFORMATION: Synthetic: 3.3F7 VL CDR1
```

<400> SEQUENCE: 96

Lys Ala Ser Gln Asn Val Gly Thr Ala Val Ala
1               5                   10

<210> SEQ ID NO 97
<211> LENGTH: 7
<212> TYPE: PRT
<213> ORGANISM: Artificial Sequence
<220> FEATURE:
<223> OTHER INFORMATION: Synthetic: 3.3F7 VL CDR2

<400> SEQUENCE: 97

Trp Ala Ser Thr Arg His Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic: 3.3F7 VL CDR3

<400> SEQUENCE: 98

Gln Arg Tyr Asn Asn Phe Pro Phe Thr
1               5

<210> SEQ ID NO 99
<211> LENGTH: 115
<212> TYPE: PRT
<213> ORGANISM: Artificial Sequence
<220> FEATURE:
<223> OTHER INFORMATION: Synthetic: 3.3F7 VH

<400> SEQUENCE: 99

Gln Val Gln Leu Lys Gln Ser Gly Pro Ser Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Val His Trp Val Arg Gln Ser Pro Gly Lys Gly Leu Glu Trp Leu
        35                  40                  45

Gly Val Ile Trp Arg Gly Gly Asn Thr Asp Tyr Asn Ala Ala Phe Met
    50                  55                  60

Ser Arg Leu Ser Ile Thr Lys Asp Asn Ser Gln Ser Gln Val Phe Phe
65                  70                  75                  80

Lys Met Asn Ser Leu Gln Ala Asp Asp Thr Ala Ile Tyr Tyr Cys Ala
                85                  90                  95

Lys Ser Ser Tyr Gly Tyr His Tyr Thr Met Asp Tyr Trp Gly His Gly
            100                 105                 110

Thr Ser Val
        115

<210> SEQ ID NO 100
<211> LENGTH: 100
<212> TYPE: PRT
<213> ORGANISM: Artificial Sequence
<220> FEATURE:
<223> OTHER INFORMATION: Synthetic: 3.3F7 VL

<400> SEQUENCE: 100

Asp Ile Val Val Thr Gln Ser His Arg Phe Met Ser Thr Ser Val Gly
1               5                   10                  15

```
Asp Arg Val Ile Ile Thr Cys Lys Ala Ser Gln Asn Val Gly Thr Ala
            20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Arg Tyr Asn Asn Phe Pro Phe
                85                  90                  95

Thr Phe Gly Ser
            100
```

```
<210> SEQ ID NO 101
<211> LENGTH: 468
<212> TYPE: PRT
<213> ORGANISM: Artificial Sequence
<220> FEATURE:
<223> OTHER INFORMATION: Synthetic: 3.3F7 HC LALAPG mIgG2a

<400> SEQUENCE: 101
```

```
Met Gly Trp Ser Cys Ile Ile Leu Phe Leu Val Ala Thr Ala Thr Gly
1               5                   10                  15

Ala Tyr Ala Gln Val Gln Leu Lys Gln Ser Gly Pro Ser Leu Val Gln
            20                  25                  30

Pro Ser Gln Ser Leu Ser Ile Thr Cys Thr Val Ser Gly Phe Ser Leu
            35                  40                  45

Thr Thr Tyr Gly Val His Trp Val Arg Gln Ser Pro Gly Lys Gly Leu
    50                  55                  60

Glu Trp Leu Gly Val Ile Trp Arg Gly Gly Asn Thr Asp Tyr Asn Ala
65                  70                  75                  80

Ala Phe Met Ser Arg Leu Ser Ile Thr Lys Asp Asn Ser Gln Ser Gln
                85                  90                  95

Val Phe Phe Lys Met Asn Ser Leu Gln Ala Asp Asp Thr Ala Ile Tyr
            100                 105                 110

Tyr Cys Ala Lys Ser Ser Tyr Gly Tyr His Tyr Thr Met Asp Tyr Trp
            115                 120                 125

Gly His Gly Thr Ser Val Thr Val Ser Ser Ala Ser Thr Lys Gly Pro
    130                 135                 140

Ser Val Tyr Pro Leu Ala Pro Val Cys Gly Asp Thr Thr Gly Ser Ser
145                 150                 155                 160

Val Thr Leu Gly Cys Leu Val Lys Gly Tyr Phe Pro Glu Pro Val Thr
                165                 170                 175

Leu Thr Trp Asn Ser Gly Ser Leu Ser Ser Gly Val His Thr Phe Pro
                180                 185                 190

Ala Val Leu Gln Ser Asp Leu Tyr Thr Leu Ser Ser Ser Val Thr Val
            195                 200                 205

Thr Ser Ser Thr Trp Pro Ser Gln Ser Ile Thr Cys Asn Val Ala His
    210                 215                 220

Pro Ala Ser Ser Thr Lys Val Asp Lys Lys Ile Glu Pro Arg Gly Pro
225                 230                 235                 240

Thr Ile Lys Pro Cys Pro Pro Cys Lys Cys Pro Ala Pro Asn Ala Ala
                245                 250                 255

Gly Gly Pro Ser Val Phe Ile Phe Pro Pro Lys Ile Lys Asp Val Leu
            260                 265                 270
```

```
Met Ile Ser Leu Ser Pro Ile Val Thr Cys Val Val Val Asp Val Ser
        275                 280                 285

Glu Asp Asp Pro Asp Val Gln Ile Ser Trp Phe Val Asn Asn Val Glu
        290                 295                 300

Val His Thr Ala Gln Thr Gln Thr His Arg Glu Asp Tyr Asn Ser Thr
305                 310                 315                 320

Leu Arg Val Val Ser Ala Leu Pro Ile Gln His Gln Asp Trp Met Ser
                325                 330                 335

Gly Lys Glu Phe Lys Cys Lys Val Asn Asn Lys Asp Leu Gly Ala Pro
                340                 345                 350

Ile Glu Arg Thr Ile Ser Lys Pro Lys Gly Ser Val Arg Ala Pro Gln
                355                 360                 365

Val Tyr Val Leu Pro Pro Pro Glu Glu Glu Met Thr Lys Lys Gln Val
        370                 375                 380

Thr Leu Thr Cys Met Val Thr Asp Phe Met Pro Glu Asp Ile Tyr Val
385                 390                 395                 400

Glu Trp Thr Asn Asn Gly Lys Thr Glu Leu Asn Tyr Lys Asn Thr Glu
                405                 410                 415

Pro Val Leu Asp Ser Asp Gly Ser Tyr Phe Met Tyr Ser Lys Leu Arg
                420                 425                 430

Val Glu Lys Lys Asn Trp Val Glu Arg Asn Ser Tyr Ser Cys Ser Val
                435                 440                 445

Val His Glu Gly Leu His Asn His His Thr Thr Lys Ser Phe Ser Arg
        450                 455                 460

Thr Pro Gly Lys
465

<210> SEQ ID NO 102
<211> LENGTH: 233
<212> TYPE: PRT
<213> ORGANISM: Artificial Sequence
<220> FEATURE:
<223> OTHER INFORMATION: Synthetic: 3.3F7 LC LALAPG mIgG2a

<400> SEQUENCE: 102

Met Gly Trp Ser Cys Ile Ile Leu Phe Leu Val Ala Thr Ala Thr Gly
1               5                   10                  15

Val His Ser Asp Ile Val Val Thr Gln Ser His Arg Phe Met Ser Thr
                20                  25                  30

Ser Val Gly Asp Arg Val Ile Ile Thr Cys Lys Ala Ser Gln Asn Val
                35                  40                  45

Gly Thr Ala Val Ala Trp Tyr Gln Gln Lys Pro Gly Gln Ser Pro Lys
        50                  55                  60

Leu Leu Ile Tyr Trp Ala Ser Thr Arg His Thr Gly Val Pro Asp Arg
65                  70                  75                  80

Phe Thr Gly Ser Gly Ser Gly Thr Asp Phe Thr Leu Thr Ile Ser Asn
                85                  90                  95

Val Gln Ser Glu Asp Leu Ala Asp Tyr Phe Cys Gln Arg Tyr Asn Asn
                100                 105                 110

Phe Pro Phe Thr Phe Gly Ser Gly Thr Lys Leu Glu Ile Lys Arg Ala
        115                 120                 125

Asp Ala Ala Pro Thr Val Ser Ile Phe Pro Pro Ser Ser Glu Gln Leu
        130                 135                 140

Thr Ser Gly Gly Ala Ser Val Val Cys Phe Leu Asn Asn Phe Tyr Pro
145                 150                 155                 160
```

-continued

```
Lys Asp Ile Asn Val Lys Trp Lys Ile Asp Gly Ser Glu Arg Gln Asn
            165             170                 175

Gly Val Leu Asn Ser Trp Thr Asp Gln Asp Ser Lys Asp Ser Thr Tyr
            180             185                 190

Ser Met Ser Ser Thr Leu Thr Leu Thr Lys Asp Glu Tyr Glu Arg His
        195             200                 205

Asn Ser Tyr Thr Cys Glu Ala Thr His Lys Thr Ser Thr Ser Pro Ile
    210             215                 220

Val Lys Ser Phe Asn Arg Asn Glu Cys
225             230
```

<210> SEQ ID NO 103
<211> LENGTH: 5
<212> TYPE: PRT
<213> ORGANISM: Artificial Sequence
<220> FEATURE:
<223> OTHER INFORMATION: Synthetic: 4.17A5 VH CDR1

<400> SEQUENCE: 103

```
Asn Ser Trp Ile Asn
1               5
```

<210> SEQ ID NO 104
<211> LENGTH: 17
<212> TYPE: PRT
<213> ORGANISM: Artificial Sequence
<220> FEATURE:
<223> OTHER INFORMATION: Synthetic: 4.17A5 VH CDR2

<400> SEQUENCE: 104

```
Arg Ile Tyr Pro Gly Asp Gly Asp Thr Lys Tyr Asn Gly Lys Phe Lys
1               5                   10                  15

Gly
```

<210> SEQ ID NO 105
<211> LENGTH: 14
<212> TYPE: PRT
<213> ORGANISM: Artificial Sequence
<220> FEATURE:
<223> OTHER INFORMATION: Synthetic: 4.17A5 VH CDR3

<400> SEQUENCE: 105

```
Phe Pro Phe Gly Lys Tyr Glu Gly Pro Gly Ala Met Asp Tyr
1               5                   10
```

<210> SEQ ID NO 106
<211> LENGTH: 11
<212> TYPE: PRT
<213> ORGANISM: Artificial Sequence
<220> FEATURE:
<223> OTHER INFORMATION: Synthetic: 4.17A5 VL CDR1

<400> SEQUENCE: 106

```
Arg Ala Ser Gln Asp Ile Ser Ser Tyr Leu Asn
1               5                   10
```

<210> SEQ ID NO 107
<211> LENGTH: 7
<212> TYPE: PRT
<213> ORGANISM: Artificial Sequence
<220> FEATURE:
<223> OTHER INFORMATION: Synthetic: 4.17A5 VL CDR2

<400> SEQUENCE: 107

-continued

```
Tyr Thr Ser Arg Leu His Ser
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic: 4.17A5 VL CDR3

<400> SEQUENCE: 108

Gln Gln Gly Asn Thr Leu Pro Tyr Thr
1               5

<210> SEQ ID NO 109
<211> LENGTH: 119
<212> TYPE: PRT
<213> ORGANISM: Artificial Sequence
<220> FEATURE:
<223> OTHER INFORMATION: Synthetic: 4.17A5 VH

<400> SEQUENCE: 109

Gln Val Gln Leu Gln Gln Ser Gly Pro Glu Leu Leu Lys Pro Gly Ala
1               5                   10                  15

Ser Val Lys Ile Ser Cys Lys Gly Ser Gly Tyr Ala Phe Ser Asn Ser
            20                  25                  30

Trp Ile Asn Trp Val Lys Leu Arg Pro Gly Gln Gly Leu Glu Trp Ile
            35                  40                  45

Gly Arg Ile Tyr Pro Gly Asp Gly Asp Thr Lys Tyr Asn Gly Lys Phe
        50                  55                  60

Lys Gly Lys Ala Thr Leu Thr Ala Asp Lys Ser Ser Ser Thr Ala His
65                  70                  75                  80

Met Gln Leu Arg Ser Leu Thr Ser Val Asp Ser Ala Val Tyr Phe Cys
                85                  90                  95

Ala Arg Phe Pro Phe Gly Lys Tyr Glu Gly Pro Gly Ala Met Asp Tyr
                100                 105                 110

Trp Gly Gln Gly Thr Ser Val
        115

<210> SEQ ID NO 110
<211> LENGTH: 100
<212> TYPE: PRT
<213> ORGANISM: Artificial Sequence
<220> FEATURE:
<223> OTHER INFORMATION: Synthetic: 4.17A5 VL

<400> SEQUENCE: 110

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Ser Tyr
            20                  25                  30

Leu Asn Trp Tyr Gln Gln Lys Pro Asp Gly Thr Ile Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly
```

-continued

```
            100

<210> SEQ ID NO 111
<211> LENGTH: 472
<212> TYPE: PRT
<213> ORGANISM: Artificial Sequence
<220> FEATURE:
<223> OTHER INFORMATION: Synthetic: 4.17A5 HC  LALAPG mIgG2a

<400> SEQUENCE: 111

Met Gly Trp Ser Cys Ile Ile Leu Phe Leu Val Ala Thr Ala Thr Gly
1               5                   10                  15

Val His Ser Gln Val Gln Leu Gln Gln Ser Gly Pro Glu Leu Leu Lys
            20                  25                  30

Pro Gly Ala Ser Val Lys Ile Ser Cys Lys Gly Ser Gly Tyr Ala Phe
        35                  40                  45

Ser Asn Ser Trp Ile Asn Trp Val Lys Leu Arg Pro Gly Gln Gly Leu
    50                  55                  60

Glu Trp Ile Gly Arg Ile Tyr Pro Gly Asp Gly Asp Thr Lys Tyr Asn
65                  70                  75                  80

Gly Lys Phe Lys Gly Lys Ala Thr Leu Thr Ala Asp Lys Ser Ser Ser
                85                  90                  95

Thr Ala His Met Gln Leu Arg Ser Leu Thr Ser Val Asp Ser Ala Val
            100                 105                 110

Tyr Phe Cys Ala Arg Phe Pro Phe Gly Lys Tyr Glu Gly Pro Gly Ala
            115                 120                 125

Met Asp Tyr Trp Gly Gln Gly Thr Ser Val Thr Val Ser Ser Ala Lys
    130                 135                 140

Thr Thr Ala Pro Ser Val Tyr Pro Leu Ala Pro Val Cys Gly Asp Thr
145                 150                 155                 160

Thr Gly Ser Ser Val Thr Leu Gly Cys Leu Val Lys Gly Tyr Phe Pro
                165                 170                 175

Glu Pro Val Thr Leu Thr Trp Asn Ser Gly Ser Leu Ser Ser Gly Val
            180                 185                 190

His Thr Phe Pro Ala Val Leu Gln Ser Asp Leu Tyr Thr Leu Ser Ser
            195                 200                 205

Ser Val Thr Val Thr Ser Ser Thr Trp Pro Ser Gln Ser Ile Thr Cys
    210                 215                 220

Asn Val Ala His Pro Ala Ser Ser Thr Lys Val Asp Lys Lys Ile Glu
225                 230                 235                 240

Pro Arg Gly Pro Thr Ile Lys Pro Cys Pro Pro Cys Lys Cys Pro Ala
                245                 250                 255

Pro Asn Ala Ala Gly Gly Pro Ser Val Phe Ile Phe Pro Pro Lys Ile
            260                 265                 270

Lys Asp Val Leu Met Ile Ser Leu Ser Pro Ile Val Thr Cys Val Val
            275                 280                 285

Val Asp Val Ser Glu Asp Asp Pro Asp Val Gln Ile Ser Trp Phe Val
    290                 295                 300

Asn Asn Val Glu Val His Thr Ala Gln Thr Gln Thr His Arg Glu Asp
305                 310                 315                 320

Tyr Asn Ser Thr Leu Arg Val Val Ser Ala Leu Pro Ile Gln His Gln
            325                 330                 335

Asp Trp Met Ser Gly Lys Glu Phe Lys Cys Lys Val Asn Asn Lys Asp
            340                 345                 350

Leu Gly Ala Pro Ile Glu Arg Thr Ile Ser Lys Pro Lys Gly Ser Val
```

-continued

```
            355                 360                 365

Arg Ala Pro Gln Val Tyr Val Leu Pro Pro Glu Glu Glu Met Thr
    370                 375                 380

Lys Lys Gln Val Thr Leu Thr Cys Met Val Thr Asp Phe Met Pro Glu
385                 390                 395                 400

Asp Ile Tyr Val Glu Trp Thr Asn Asn Gly Lys Thr Glu Leu Asn Tyr
                405                 410                 415

Lys Asn Thr Glu Pro Val Leu Asp Ser Asp Gly Ser Tyr Phe Met Tyr
                420                 425                 430

Ser Lys Leu Arg Val Glu Lys Lys Asn Trp Val Glu Arg Asn Ser Tyr
                435                 440                 445

Ser Cys Ser Val Val His Glu Gly Leu His Asn His His Thr Thr Lys
    450                 455                 460

Ser Phe Ser Arg Thr Pro Gly Lys
465                 470
```

<210> SEQ ID NO 112
<211> LENGTH: 233
<212> TYPE: PRT
<213> ORGANISM: Artificial Sequence
<220> FEATURE:
<223> OTHER INFORMATION: Synthetic: 4.17A5 LC LALAPG mIgG2a

<400> SEQUENCE: 112

```
Met Gly Trp Ser Cys Ile Ile Leu Phe Leu Val Ala Thr Ala Thr Gly
1                   5                   10                  15

Val His Ser Asp Ile Gln Met Thr Gln Thr Thr Ser Ser Leu Ser Ala
                20                  25                  30

Ser Leu Gly Asp Arg Val Thr Ile Ser Cys Arg Ala Ser Gln Asp Ile
            35                  40                  45

Ser Ser Tyr Leu Asn Trp Tyr Gln Gln Lys Pro Asp Gly Thr Ile Lys
    50                  55                  60

Leu Leu Ile Tyr Tyr Thr Ser Arg Leu His Ser Gly Val Pro Ser Arg
65                  70                  75                  80

Phe Ser Gly Ser Gly Ser Gly Thr Asp Phe Ser Leu Thr Ile Ser Asn
                85                  90                  95

Leu Glu Gln Glu Asp Ile Ala Thr Tyr Phe Cys Gln Gln Gly Asn Thr
            100                 105                 110

Leu Pro Tyr Thr Phe Gly Gly Gly Thr Lys Leu Glu Ile Lys Arg Ala
        115                 120                 125

Asp Ala Ala Pro Thr Val Ser Ile Phe Pro Pro Ser Ser Glu Gln Leu
    130                 135                 140

Thr Ser Gly Gly Ala Ser Val Val Cys Phe Leu Asn Asn Phe Tyr Pro
145                 150                 155                 160

Lys Asp Ile Asn Val Lys Trp Lys Ile Asp Gly Ser Glu Arg Gln Asn
                165                 170                 175

Gly Val Leu Asn Ser Trp Thr Asp Gln Asp Ser Lys Asp Ser Thr Tyr
            180                 185                 190

Ser Met Ser Ser Thr Leu Thr Leu Thr Lys Asp Glu Tyr Glu Arg His
        195                 200                 205

Asn Ser Tyr Thr Cys Glu Ala Thr His Lys Thr Ser Thr Ser Pro Ile
    210                 215                 220

Val Lys Ser Phe Asn Arg Asn Glu Cys
225                 230
```

-continued

```
<210> SEQ ID NO 113
<211> LENGTH: 5
<212> TYPE: PRT
<213> ORGANISM: Artificial Sequence
<220> FEATURE:
<223> OTHER INFORMATION: Synthetic: 4.2C4 VH CDR1

<400> SEQUENCE: 113

Asp Tyr Val Ile Ser
1               5

<210> SEQ ID NO 114
<211> LENGTH: 17
<212> TYPE: PRT
<213> ORGANISM: Artificial Sequence
<220> FEATURE:
<223> OTHER INFORMATION: Synthetic: 4.2C4 VH CDR2

<400> SEQUENCE: 114

Glu Met Phe Pro Gly Ser Gly Thr Thr Tyr Tyr Thr Glu Lys Phe Arg
1               5                   10                  15

Gly

<210> SEQ ID NO 115
<211> LENGTH: 6
<212> TYPE: PRT
<213> ORGANISM: Artificial Sequence
<220> FEATURE:
<223> OTHER INFORMATION: Synthetic: 4.2C4 VH CDR3

<400> SEQUENCE: 115

Gly Thr Thr Ala Asp Tyr
1               5

<210> SEQ ID NO 116
<211> LENGTH: 10
<212> TYPE: PRT
<213> ORGANISM: Artificial Sequence
<220> FEATURE:
<223> OTHER INFORMATION: Synthetic: 4.2C4 VL  CDR1

<400> SEQUENCE: 116

Arg Ala Ser Ser Ser Val Asn Tyr Met Tyr
1               5                   10

<210> SEQ ID NO 117
<211> LENGTH: 7
<212> TYPE: PRT
<213> ORGANISM: Artificial Sequence
<220> FEATURE:
<223> OTHER INFORMATION: Synthetic: 4.2C4 VL CDR2

<400> SEQUENCE: 117

Tyr Thr Ser Asn Leu Ala Pro
1               5

<210> SEQ ID NO 118
<211> LENGTH: 9
<212> TYPE: PRT
<213> ORGANISM: Artificial Sequence
<220> FEATURE:
<223> OTHER INFORMATION: Synthetic: 4.2C4 VL CDR3

<400> SEQUENCE: 118

Gln Gln Phe Thr Ser Ser Pro Tyr Thr
1               5
```

-continued

<210> SEQ ID NO 119
<211> LENGTH: 111
<212> TYPE: PRT
<213> ORGANISM: Artificial Sequence
<220> FEATURE:
<223> OTHER INFORMATION: Synthetic: 4.2C4 VH

<400> SEQUENCE: 119

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Met Phe Pro Gly Ser Gly Thr Thr Tyr Tyr Thr Glu Lys Phe
    50                  55                  60

Arg Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Thr Thr Ala Asp Tyr Trp Gly Gln Gly Thr Thr Leu
            100                 105                 110

<210> SEQ ID NO 120
<211> LENGTH: 99
<212> TYPE: PRT
<213> ORGANISM: Artificial Sequence
<220> FEATURE:
<223> OTHER INFORMATION: Synthetic: 4.2C4 VL

<400> SEQUENCE: 120

Glu Asn Val Leu Thr Gln Ser Pro Ala Ile Met Ser Ala Ser Leu Gly
1               5                   10                  15

Glu Lys Val Thr Met Ser Cys Arg Ala Ser Ser Ser Val Asn Tyr Met
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Tyr Thr
                85                  90                  95

Phe Gly Gly

<210> SEQ ID NO 121
<211> LENGTH: 464
<212> TYPE: PRT
<213> ORGANISM: Artificial Sequence
<220> FEATURE:
<223> OTHER INFORMATION: Synthetic: 4.2C4 HC  LALAPG mIgG2a

<400> SEQUENCE: 121

Met Gly Trp Ser Cys Ile Ile Leu Phe Leu Val Ala Thr Ala Thr Gly
1               5                   10                  15

Val His Ser Gln Val Gln Leu Gln Gln Ser Gly Pro Glu Leu Val Lys
            20                  25                  30

Pro Gly Ala Ser Val Lys Met Ser Cys Lys Ala Ser Gly Tyr Thr Phe
            35                  40                  45

```
Thr Asp Tyr Val Ile Ser Trp Val Lys Gln Arg Thr Gly Gln Gly Leu
    50              55              60

Glu Trp Ile Gly Glu Met Phe Pro Gly Ser Gly Thr Thr Tyr Tyr Thr
65              70              75              80

Glu Lys Phe Arg Gly Lys Ala Thr Leu Thr Ala Asp Lys Ser Ser Asn
                85              90              95

Thr Ala Tyr Met Gln Leu Ser Ser Leu Thr Ser Glu Asp Ser Ala Val
            100             105             110

Tyr Phe Cys Ala Arg Gly Thr Thr Ala Asp Tyr Trp Gly Gln Gly Thr
        115             120             125

Thr Leu Thr Val Ser Ser Ala Lys Thr Thr Ala Pro Ser Val Tyr Pro
    130             135             140

Leu Ala Pro Val Cys Gly Asp Thr Thr Gly Ser Ser Val Thr Leu Gly
145             150             155             160

Cys Leu Val Lys Gly Tyr Phe Pro Glu Pro Val Thr Leu Thr Trp Asn
                165             170             175

Ser Gly Ser Leu Ser Ser Gly Val His Thr Phe Pro Ala Val Leu Gln
            180             185             190

Ser Asp Leu Tyr Thr Leu Ser Ser Ser Val Thr Val Thr Ser Ser Thr
        195             200             205

Trp Pro Ser Gln Ser Ile Thr Cys Asn Val Ala His Pro Ala Ser Ser
    210             215             220

Thr Lys Val Asp Lys Lys Ile Glu Pro Arg Gly Pro Thr Ile Lys Pro
225             230             235             240

Cys Pro Pro Cys Lys Cys Pro Ala Pro Asn Ala Ala Gly Gly Pro Ser
                245             250             255

Val Phe Ile Phe Pro Pro Lys Ile Lys Asp Val Leu Met Ile Ser Leu
            260             265             270

Ser Pro Ile Val Thr Cys Val Val Val Asp Val Ser Glu Asp Asp Pro
        275             280             285

Asp Val Gln Ile Ser Trp Phe Val Asn Asn Val Glu Val His Thr Ala
    290             295             300

Gln Thr Gln Thr His Arg Glu Asp Tyr Asn Ser Thr Leu Arg Val Val
305             310             315             320

Ser Ala Leu Pro Ile Gln His Gln Asp Trp Met Ser Gly Lys Glu Phe
            325             330             335

Lys Cys Lys Val Asn Asn Lys Asp Leu Gly Ala Pro Ile Glu Arg Thr
            340             345             350

Ile Ser Lys Pro Lys Gly Ser Val Arg Ala Pro Gln Val Tyr Val Leu
        355             360             365

Pro Pro Pro Glu Glu Glu Met Thr Lys Lys Gln Val Thr Leu Thr Cys
    370             375             380

Met Val Thr Asp Phe Met Pro Glu Asp Ile Tyr Val Glu Trp Thr Asn
385             390             395             400

Asn Gly Lys Thr Glu Leu Asn Tyr Lys Asn Thr Glu Pro Val Leu Asp
            405             410             415

Ser Asp Gly Ser Tyr Phe Met Tyr Ser Lys Leu Arg Val Glu Lys Lys
            420             425             430

Asn Trp Val Glu Arg Asn Ser Tyr Ser Cys Ser Val Val His Glu Gly
        435             440             445

Leu His Asn His His Thr Thr Lys Ser Phe Ser Arg Thr Pro Gly Lys
    450             455             460
```

<210> SEQ ID NO 122
<211> LENGTH: 232
<212> TYPE: PRT
<213> ORGANISM: Artificial Sequence
<220> FEATURE:
<223> OTHER INFORMATION: Synthetic: 4.2C4 LC LALAPG mIgG2a

<400> SEQUENCE: 122

Met Gly Trp Ser Cys Ile Ile Leu Phe Leu Val Ala Thr Ala Thr Gly
1               5                   10                  15

Val His Ser Glu Asn Val Leu Thr Gln Ser Pro Ala Ile Met Ser Ala
            20                  25                  30

Ser Leu Gly Glu Lys Val Thr Met Ser Cys Arg Ala Ser Ser Ser Val
        35                  40                  45

Asn Tyr Met Tyr Trp Tyr Gln Gln Lys Ser Asp Ala Ser Pro Lys Leu
    50                  55                  60

Trp Ile Tyr Tyr Thr Ser Asn Leu Ala Pro Gly Val Pro Ala Arg Phe
65                  70                  75                  80

Ser Gly Ser Gly Ser Gly Asn Ser Tyr Ser Leu Thr Ile Ser Ser Met
                85                  90                  95

Glu Gly Glu Asp Ala Ala Thr Tyr Tyr Cys Gln Gln Phe Thr Ser Ser
            100                 105                 110

Pro Tyr Thr Phe Gly Gly Gly Thr Lys Leu Glu Ile Lys Arg Ala Asp
        115                 120                 125

Ala Ala Pro Thr Val Ser Ile Phe Pro Pro Ser Ser Glu Gln Leu Thr
    130                 135                 140

Ser Gly Gly Ala Ser Val Val Cys Phe Leu Asn Asn Phe Tyr Pro Lys
145                 150                 155                 160

Asp Ile Asn Val Lys Trp Lys Ile Asp Gly Ser Glu Arg Gln Asn Gly
                165                 170                 175

Val Leu Asn Ser Trp Thr Asp Gln Asp Ser Lys Asp Ser Thr Tyr Ser
            180                 185                 190

Met Ser Ser Thr Leu Thr Leu Thr Lys Asp Glu Tyr Glu Arg His Asn
        195                 200                 205

Ser Tyr Thr Cys Glu Ala Thr His Lys Thr Ser Thr Ser Pro Ile Val
    210                 215                 220

Lys Ser Phe Asn Arg Asn Glu Cys
225                 230

<210> SEQ ID NO 123
<211> LENGTH: 5
<212> TYPE: PRT
<213> ORGANISM: Artificial Sequence
<220> FEATURE:
<223> OTHER INFORMATION: Synthetic: 4.12E5 VH CDR1

<400> SEQUENCE: 123

Gly Tyr Phe Met His
1               5

<210> SEQ ID NO 124
<211> LENGTH: 17
<212> TYPE: PRT
<213> ORGANISM: Artificial Sequence
<220> FEATURE:
<223> OTHER INFORMATION: Synthetic: 4.12E5 VH CDR2

<400> SEQUENCE: 124

Tyr Ile Ser Cys Tyr Asn Gly Ala Ser Val Tyr Asn Gln Arg Phe Lys

-continued

```
1               5               10              15

Gly

<210> SEQ ID NO 125
<211> LENGTH: 12
<212> TYPE: PRT
<213> ORGANISM: Artificial Sequence
<220> FEATURE:
<223> OTHER INFORMATION: Synthetic: 4.12E5 VH CDR3

<400> SEQUENCE: 125

Asp Val Leu Arg Tyr Pro Arg Tyr Ala Val Asp Tyr
1               5               10

<210> SEQ ID NO 126
<211> LENGTH: 16
<212> TYPE: PRT
<213> ORGANISM: Artificial Sequence
<220> FEATURE:
<223> OTHER INFORMATION: Synthetic: 4.12E5 VL CDR1

<400> SEQUENCE: 126

Lys Ser Ser Gln Ser Leu Leu Asp Ser Asp Gly Lys Thr Tyr Leu Asn
1               5               10              15

<210> SEQ ID NO 127
<211> LENGTH: 7
<212> TYPE: PRT
<213> ORGANISM: Artificial Sequence
<220> FEATURE:
<223> OTHER INFORMATION: Synthetic: 4.12E5 VL CDR2

<400> SEQUENCE: 127

Leu Val Ser Asn Leu Asp Ser
1               5

<210> SEQ ID NO 128
<211> LENGTH: 9
<212> TYPE: PRT
<213> ORGANISM: Artificial Sequence
<220> FEATURE:
<223> OTHER INFORMATION: Synthetic: 4.12E5 VL CDR3

<400> SEQUENCE: 128

Trp Gln Gly Ser His Phe Pro Phe Thr
1               5

<210> SEQ ID NO 129
<211> LENGTH: 117
<212> TYPE: PRT
<213> ORGANISM: Artificial Sequence
<220> FEATURE:
<223> OTHER INFORMATION: Synthetic: 4.12E5 VH

<400> SEQUENCE: 129

Glu Val Gln Leu Gln Gln Ser Gly Pro Glu Leu Val Lys Thr Gly Ala
1               5               10              15

Ser Val Lys Ile Ser Cys Lys Ala Ser Gly Tyr Ser Phe Thr Gly Tyr
            20              25              30

Phe Met His Trp Val Lys Gln Ser His Gly Lys Ser Leu Glu Trp Ile
            35              40              45

Gly Tyr Ile Ser Cys Tyr Asn Gly Ala Ser Val Tyr Asn Gln Arg Phe
    50              55              60

Lys Gly Lys Ala Thr Phe Thr Ile Asp Thr Ser Ser Ser Thr Ala Tyr
```

```
65              70              75              80

Met Gln Phe Asn Ser Leu Thr Ser Glu Asp Ser Ala Val Tyr Tyr Cys
                85              90              95

Ala Arg Asp Val Leu Arg Tyr Pro Arg Tyr Ala Val Asp Tyr Trp Gly
            100             105             110

Gln Gly Thr Ser Val
        115

<210> SEQ ID NO 130
<211> LENGTH: 105
<212> TYPE: PRT
<213> ORGANISM: Artificial Sequence
<220> FEATURE:
<223> OTHER INFORMATION: Synthetic: 4.12E5 VL

<400> SEQUENCE: 130

Asp Val Val Met Thr Gln Thr Pro Leu Thr Leu Ser Val Thr Ile Gly
1               5               10              15

Gln Pro Ala Ser Ile Ser Cys Lys Ser Ser Gln Ser Leu Leu Asp Ser
                20              25              30

Asp Gly Lys Thr Tyr Leu Asn Trp Leu Leu Gln Arg Pro Gly Gln Ser
            35              40              45

Pro Lys Arg Leu Ile Tyr Leu Val Ser Asn Leu Asp Ser Gly Val Pro
        50              55              60

Ala Arg Phe Thr Gly Ser Gly Ser Gly Thr Asp Phe Thr Leu Lys Ile
65              70              75              80

Ser Arg Val Glu Ala Glu Asp Leu Gly Val Tyr Tyr Cys Trp Gln Gly
                85              90              95

Ser His Phe Pro Phe Thr Phe Gly Ser
            100             105

<210> SEQ ID NO 131
<211> LENGTH: 470
<212> TYPE: PRT
<213> ORGANISM: Artificial Sequence
<220> FEATURE:
<223> OTHER INFORMATION: Synthetic: 4.12E5 HC LALAPG mIgG2a

<400> SEQUENCE: 131

Met Gly Trp Ser Cys Ile Ile Leu Phe Leu Val Ala Thr Ala Thr Gly
1               5               10              15

Val His Ser Glu Val Gln Leu Gln Gln Ser Gly Pro Glu Leu Val Lys
                20              25              30

Thr Gly Ala Ser Val Lys Ile Ser Cys Lys Ala Ser Gly Tyr Ser Phe
            35              40              45

Thr Gly Tyr Phe Met His Trp Val Lys Gln Ser His Gly Lys Ser Leu
        50              55              60

Glu Trp Ile Gly Tyr Ile Ser Cys Tyr Asn Gly Ala Ser Val Tyr Asn
65              70              75              80

Gln Arg Phe Lys Gly Lys Ala Thr Phe Thr Ile Asp Thr Ser Ser Ser
                85              90              95

Thr Ala Tyr Met Gln Phe Asn Ser Leu Thr Ser Glu Asp Ser Ala Val
            100             105             110

Tyr Tyr Cys Ala Arg Asp Val Leu Arg Tyr Pro Arg Tyr Ala Val Asp
        115             120             125

Tyr Trp Gly Gln Gly Thr Ser Val Thr Val Ser Ser Ala Lys Thr Thr
    130             135             140
```

-continued

```
Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
                180                 185                 190

Phe Pro Ala Val Leu Gln Ser Asp Leu Tyr Thr Leu Ser Ser Ser Val
                195                 200                 205

Thr Val Thr Ser Ser Thr Trp Pro Ser Gln Ser Ile Thr Cys Asn Val
                210                 215                 220

Ala His Pro Ala Ser Ser Thr Lys Val Asp Lys Lys Ile Glu Pro Arg
225                 230                 235                 240

Gly Pro Thr Ile Lys Pro Cys Pro Pro Cys Lys Cys Pro Ala Pro Asn
                245                 250                 255

Ala Ala Gly Gly Pro Ser Val Phe Ile Phe Pro Pro Lys Ile Lys Asp
                260                 265                 270

Val Leu Met Ile Ser Leu Ser Pro Ile Val Thr Cys Val Val Val Asp
                275                 280                 285

Val Ser Glu Asp Asp Pro Asp Val Gln Ile Ser Trp Phe Val Asn Asn
        290                 295                 300

Val Glu Val His Thr Ala Gln Thr Gln Thr His Arg Glu Asp Tyr Asn
305                 310                 315                 320

Ser Thr Leu Arg Val Val Ser Ala Leu Pro Ile Gln His Gln Asp Trp
                325                 330                 335

Met Ser Gly Lys Glu Phe Lys Cys Lys Val Asn Asn Lys Asp Leu Gly
                340                 345                 350

Ala Pro Ile Glu Arg Thr Ile Ser Lys Pro Lys Gly Ser Val Arg Ala
                355                 360                 365

Pro Gln Val Tyr Val Leu Pro Pro Pro Glu Glu Glu Met Thr Lys Lys
        370                 375                 380

Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                405                 410                 415

Thr Glu Pro Val Leu Asp Ser Asp Gly Ser Tyr Phe Met Tyr Ser Lys
                420                 425                 430

Leu Arg Val Glu Lys Lys Asn Trp Val Glu Arg Asn Ser Tyr Ser Cys
                435                 440                 445

Ser Val Val His Glu Gly Leu His Asn His His Thr Thr Lys Ser Phe
        450                 455                 460

Ser Arg Thr Pro Gly Lys
465                 470

<210> SEQ ID NO 132
<211> LENGTH: 238
<212> TYPE: PRT
<213> ORGANISM: Artificial Sequence
<220> FEATURE:
<223> OTHER INFORMATION: Synthetic: 4.12E5 LC LALAPG mIgG2a

<400> SEQUENCE: 132

Met Gly Trp Ser Cys Ile Ile Leu Phe Leu Val Ala Thr Ala Thr Gly
1               5                   10                  15

Val His Ser Asp Val Val Met Thr Gln Thr Pro Leu Thr Leu Ser Val
                20                  25                  30
```

-continued

```
Thr Ile Gly Gln Pro Ala Ser Ile Ser Cys Lys Ser Ser Gln Ser Leu
        35                  40                  45

Leu Asp Ser Asp Gly Lys Thr Tyr Leu Asn Trp Leu Leu Gln Arg Pro
    50                  55                  60

Gly Gln Ser Pro Lys Arg Leu Ile Tyr Leu Val Ser Asn Leu Asp Ser
65                  70                  75                  80

Gly Val Pro Ala Arg Phe Thr Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Trp Gln Gly Ser His Phe Pro Phe Thr Phe Gly Ser Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
            195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

```
<210> SEQ ID NO 133
<211> LENGTH: 5
<212> TYPE: PRT
<213> ORGANISM: Artificial Sequence
<220> FEATURE:
<223> OTHER INFORMATION: Synthetic: 4.11A10 VH CDR1

<400> SEQUENCE: 133

Gly Tyr Phe Met His
1               5
```

```
<210> SEQ ID NO 134
<211> LENGTH: 17
<212> TYPE: PRT
<213> ORGANISM: Artificial Sequence
<220> FEATURE:
<223> OTHER INFORMATION: Synthetic: 4.11A10 VH CDR2

<400> SEQUENCE: 134

Tyr Ile Ser Cys Tyr Asn Gly Val Ser Val Tyr Asn Gln Arg Phe Lys
1               5                   10                  15

Gly
```

```
<210> SEQ ID NO 135
<211> LENGTH: 12
<212> TYPE: PRT
<213> ORGANISM: Artificial Sequence
<220> FEATURE:
<223> OTHER INFORMATION: Synthetic: 4.11A10 VH CDR3

<400> SEQUENCE: 135

Asp Val Leu Arg Tyr Pro Arg Tyr Ala Val Asp Tyr
1               5                   10
```

<210> SEQ ID NO 136
<211> LENGTH: 16
<212> TYPE: PRT
<213> ORGANISM: Artificial Sequence
<220> FEATURE:
<223> OTHER INFORMATION: Synthetic: 4.11A10 VL CDR1

<400> SEQUENCE: 136

Lys Ser Ser Gln Ser Leu Leu Asp Ser Asp Gly Lys Thr Tyr Leu Asn
1               5                   10                  15

<210> SEQ ID NO 137
<211> LENGTH: 7
<212> TYPE: PRT
<213> ORGANISM: Artificial Sequence
<220> FEATURE:
<223> OTHER INFORMATION: Synthetic: 4.11A10 VL CDR2

<400> SEQUENCE: 137

Leu Val Ser Asn Leu Asp Ser
1               5

<210> SEQ ID NO 138
<211> LENGTH: 9
<212> TYPE: PRT
<213> ORGANISM: Artificial Sequence
<220> FEATURE:
<223> OTHER INFORMATION: Synthetic: 4.11A10 VL CDR3

<400> SEQUENCE: 138

Trp Gln Gly Ser His Phe Pro Phe Thr
1               5

<210> SEQ ID NO 139
<211> LENGTH: 117
<212> TYPE: PRT
<213> ORGANISM: Artificial Sequence
<220> FEATURE:
<223> OTHER INFORMATION: Synthetic: 4.11A10 VH

<400> SEQUENCE: 139

Glu Val Gln Leu Gln Gln Ser Gly Pro Glu Leu Val Lys Thr Gly Ala
1               5                   10                  15

Ser Val Lys Ile Ser Cys Lys Ala Ser Gly Tyr Ser Phe Thr Gly Tyr
                20                  25                  30

Phe Met His Trp Val Lys Gln Ser His Gly Lys Ser Leu Glu Trp Ile
            35                  40                  45

Gly Tyr Ile Ser Cys Tyr Asn Gly Val Ser Val Tyr Asn Gln Arg Phe
        50                  55                  60

Lys Gly Lys Ala Thr Phe Thr Ile Asp Thr Ser Ser Ser Thr Ala Tyr
65                  70                  75                  80

Met Gln Phe Asn Ser Leu Thr Ser Glu Asp Ser Ala Val Tyr Tyr Cys
                85                  90                  95

Ala Arg Asp Val Leu Arg Tyr Pro Arg Tyr Ala Val Asp Tyr Trp Gly
            100                 105                 110

Gln Gly Thr Ser Val
        115

<210> SEQ ID NO 140
<211> LENGTH: 105
<212> TYPE: PRT
<213> ORGANISM: Artificial Sequence

```
<220> FEATURE:
<223> OTHER INFORMATION: Synthetic: 4.11A10 VL

<400> SEQUENCE: 140

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Asn Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ser His Phe Pro Phe Thr Phe Gly Ser
            100                 105

<210> SEQ ID NO 141
<211> LENGTH: 470
<212> TYPE: PRT
<213> ORGANISM: Artificial Sequence
<220> FEATURE:
<223> OTHER INFORMATION: Synthetic: 4.11A10 HC LALAPG mIgG2a

<400> SEQUENCE: 141

Met Gly Trp Ser Cys Ile Ile Leu Phe Leu Val Ala Thr Ala Thr Gly
1               5                   10                  15

Val His Ser Glu Val Gln Leu Gln Gln Ser Gly Pro Glu Leu Val Lys
            20                  25                  30

Thr Gly Ala Ser Val Lys Ile Ser Cys Lys Ala Ser Gly Tyr Ser Phe
        35                  40                  45

Thr Gly Tyr Phe Met His Trp Val Lys Gln Ser His Gly Lys Ser Leu
    50                  55                  60

Glu Trp Ile Gly Tyr Ile Ser Cys Tyr Asn Gly Val Ser Val Tyr Asn
65                  70                  75                  80

Gln Arg Phe Lys Gly Lys Ala Thr Phe Thr Ile Asp Thr Ser Ser Ser
                85                  90                  95

Thr Ala Tyr Met Gln Phe Asn Ser Leu Thr Ser Glu Asp Ser Ala Val
            100                 105                 110

Tyr Tyr Cys Ala Arg Asp Val Leu Arg Tyr Pro Arg Tyr Ala Val Asp
        115                 120                 125

Tyr Trp Gly Gln Gly Thr Ser Val Thr Val Ser Ser Ala Lys Thr Thr
    130                 135                 140

Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
            195                 200                 205

Thr Val Thr Ser Ser Thr Trp Pro Ser Gln Ser Ile Thr Cys Asn Val
    210                 215                 220

Ala His Pro Ala Ser Ser Thr Lys Val Asp Lys Lys Ile Glu Pro Arg
```

-continued

```
225               230               235               240

Gly Pro Thr Ile Lys Pro Cys Pro Pro Cys Lys Cys Pro Ala Pro Asn
                245               250               255

Ala Ala Gly Gly Pro Ser Val Phe Ile Phe Pro Pro Lys Ile Lys Asp
                260               265               270

Val Leu Met Ile Ser Leu Ser Pro Ile Val Thr Cys Val Val Val Asp
                275               280               285

Val Ser Glu Asp Asp Pro Asp Val Gln Ile Ser Trp Phe Val Asn Asn
        290               295               300

Val Glu Val His Thr Ala Gln Thr Gln Thr His Arg Glu Asp Tyr Asn
305               310               315               320

Ser Thr Leu Arg Val Val Ser Ala Leu Pro Ile Gln His Gln Asp Trp
                325               330               335

Met Ser Gly Lys Glu Phe Lys Cys Lys Val Asn Asn Lys Asp Leu Gly
                340               345               350

Ala Pro Ile Glu Arg Thr Ile Ser Lys Pro Lys Gly Ser Val Arg Ala
                355               360               365

Pro Gln Val Tyr Val Leu Pro Pro Glu Glu Glu Met Thr Lys Lys
        370               375               380

Gln Val Thr Leu Thr Cys Met Val Thr Asp Phe Met Pro Glu Asp Ile
385               390               395               400

Tyr Val Glu Trp Thr Asn Asn Gly Lys Thr Glu Leu Asn Tyr Lys Asn
                405               410               415

Thr Glu Pro Val Leu Asp Ser Asp Gly Ser Tyr Phe Met Tyr Ser Lys
                420               425               430

Leu Arg Val Glu Lys Lys Asn Trp Val Glu Arg Asn Ser Tyr Ser Cys
                435               440               445

Ser Val Val His Glu Gly Leu His Asn His His Thr Thr Lys Ser Phe
        450               455               460

Ser Arg Thr Pro Gly Lys
465               470
```

<210> SEQ ID NO 142
<211> LENGTH: 238
<212> TYPE: PRT
<213> ORGANISM: Artificial Sequence
<220> FEATURE:
<223> OTHER INFORMATION: Synthetic: 4.11A10 LC LALAPG mIgG2a

<400> SEQUENCE: 142

```
Met Gly Trp Ser Cys Ile Ile Leu Phe Leu Val Ala Thr Ala Thr Gly
1               5               10               15

Val His Ser Asp Val Val Met Thr Gln Thr Pro Leu Thr Leu Ser Val
                20               25               30

Thr Ile Gly Gln Pro Ala Ser Ile Ser Cys Lys Ser Ser Gln Ser Leu
                35               40               45

Leu Asp Ser Asp Gly Lys Thr Tyr Leu Asn Trp Leu Leu Gln Arg Pro
        50               55               60

Gly Gln Ser Pro Lys Arg Leu Ile Tyr Leu Val Ser Asn Leu Asp Ser
65               70               75               80

Gly Val Pro Asp Arg Phe Thr Gly Ser Gly Ser Gly Thr Asp Phe Thr
                85               90               95

Leu Lys Ile Ser Arg Val Glu Ala Glu Asp Leu Gly Val Tyr Tyr Cys
                100               105               110

Trp Gln Gly Ser His Phe Pro Phe Thr Phe Gly Ser Gly Thr Lys Leu
```

-continued

```
        115                 120                 125
Glu Ile Lys Arg Ala Asp Ala Ala Pro Thr Val Ser Ile Phe Pro Pro
   130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
            195                 200                 205

Glu Tyr Glu Arg His Asn Ser Tyr Thr Cys Glu Ala Thr His Lys Thr
   210                 215                 220

Ser Thr Ser Pro Ile Val Lys Ser Phe Asn Arg Asn Glu Cys
225                 230                 235
```

```
<210> SEQ ID NO 143
<211> LENGTH: 5
<212> TYPE: PRT
<213> ORGANISM: Artificial Sequence
<220> FEATURE:
<223> OTHER INFORMATION: Synthetic: 4.11H11 VH CDR1

<400> SEQUENCE: 143

Val Tyr Thr Met Asn
1               5

<210> SEQ ID NO 144
<211> LENGTH: 17
<212> TYPE: PRT
<213> ORGANISM: Artificial Sequence
<220> FEATURE:
<223> OTHER INFORMATION: Synthetic: 4.11H11 VH CDR2

<400> SEQUENCE: 144

Leu Ile Asn Pro Tyr Asn Gly Gly Thr Ile Tyr Asn Arg Lys Phe Lys
1               5                   10                  15

Gly

<210> SEQ ID NO 145
<211> LENGTH: 12
<212> TYPE: PRT
<213> ORGANISM: Artificial Sequence
<220> FEATURE:
<223> OTHER INFORMATION: Synthetic: 4.11H11 VH CDR3

<400> SEQUENCE: 145

Gly Ala Leu Tyr Arg Tyr Glu Gly Ala Met Asp Tyr
1               5                   10

<210> SEQ ID NO 146
<211> LENGTH: 10
<212> TYPE: PRT
<213> ORGANISM: Artificial Sequence
<220> FEATURE:
<223> OTHER INFORMATION: Synthetic: 4.11H11 VL CDR1

<400> SEQUENCE: 146

Arg Ala Ser Ser Ser Val Ile Tyr Val His
1               5                   10

<210> SEQ ID NO 147
```

```
<211> LENGTH: 7
<212> TYPE: PRT
<213> ORGANISM: Artificial Sequence
<220> FEATURE:
<223> OTHER INFORMATION: Synthetic: 4.11H11 VL CDR2

<400> SEQUENCE: 147

Ala Thr Ser Asn Leu Ala Ser
1               5

<210> SEQ ID NO 148
<211> LENGTH: 9
<212> TYPE: PRT
<213> ORGANISM: Artificial Sequence
<220> FEATURE:
<223> OTHER INFORMATION: Synthetic: 4.11H11 VL CDR3

<400> SEQUENCE: 148

Gln Gln Trp Ser Ser Asn Pro Leu Thr
1               5

<210> SEQ ID NO 149
<211> LENGTH: 118
<212> TYPE: PRT
<213> ORGANISM: Artificial Sequence
<220> FEATURE:
<223> OTHER INFORMATION: Synthetic: 4.11H11 VH

<400> SEQUENCE: 149

Glu Val Gln Val Gln Gln Ser Gly Pro Glu Leu Val Lys Pro Gly Ala
1               5                   10                  15

Ser Met Lys Ile Ser Cys Lys Ala Ser Gly Tyr Ser Phe Ile Val Tyr
            20                  25                  30

Thr Met Asn Trp Val Lys Gln Ser His Gly Lys Asn Leu Glu Trp Ile
        35                  40                  45

Gly Leu Ile Asn Pro Tyr Asn Gly Gly Thr Ile Tyr Asn Arg Lys Phe
    50                  55                  60

Lys Gly Lys Ala Thr Leu Thr Val Asp Lys Ser Ser Ser Thr Ala Tyr
65                  70                  75                  80

Leu Glu Leu Leu Ser Leu Thr Ser Glu Asp Ser Ala Val Tyr Tyr Cys
                85                  90                  95

Ala Arg Gly Ala Leu Tyr Arg Tyr Glu Gly Ala Met Asp Tyr Trp Gly
            100                 105                 110

Gln Gly Thr Ser Val Ile
        115

<210> SEQ ID NO 150
<211> LENGTH: 99
<212> TYPE: PRT
<213> ORGANISM: Artificial Sequence
<220> FEATURE:
<223> OTHER INFORMATION: Synthetic: 4.11H11 VL

<400> SEQUENCE: 150

Gln Ile Val Leu Ser Gln Phe Pro Ala Ile Leu Ser Ala Ser Pro Gly
1               5                   10                  15

Glu Lys Val Thr Met Thr Cys Arg Ala Ser Ser Ser Val Ile Tyr Val
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60
```

-continued

```
Gly Ser Gly Thr Ser His Ser Leu Thr Ile Ser Arg Leu Glu Ala Glu
65                  70                  75                  80

Asp Thr Ala Thr Tyr Tyr Cys Gln Gln Trp Ser Ser Asn Pro Leu Thr
                85                  90                  95

Phe Gly Ala

<210> SEQ ID NO 151
<211> LENGTH: 470
<212> TYPE: PRT
<213> ORGANISM: Artificial Sequence
<220> FEATURE:
<223> OTHER INFORMATION: Synthetic: 4.11H11 HC LALAPG mIgG2a

<400> SEQUENCE: 151

Met Gly Trp Ser Cys Ile Ile Leu Phe Leu Val Ala Thr Ala Thr Gly
1               5                   10                  15

Val His Ser Glu Val Gln Val Gln Gln Ser Gly Pro Glu Leu Val Lys
                20                  25                  30

Pro Gly Ala Ser Met Lys Ile Ser Cys Lys Ala Ser Gly Tyr Ser Phe
                35                  40                  45

Ile Val Tyr Thr Met Asn Trp Val Lys Gln Ser His Gly Lys Asn Leu
            50                  55                  60

Glu Trp Ile Gly Leu Ile Asn Pro Tyr Asn Gly Gly Thr Ile Tyr Asn
65                  70                  75                  80

Arg Lys Phe Lys Gly Lys Ala Thr Leu Thr Val Asp Lys Ser Ser Ser
                85                  90                  95

Thr Ala Tyr Leu Glu Leu Leu Ser Leu Thr Ser Glu Asp Ser Ala Val
                100                 105                 110

Tyr Tyr Cys Ala Arg Gly Ala Leu Tyr Arg Tyr Glu Gly Ala Met Asp
            115                 120                 125

Tyr Trp Gly Gln Gly Thr Ser Val Ile Val Ser Ser Ala Lys Thr Thr
    130                 135                 140

Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
                180                 185                 190

Phe Pro Ala Val Leu Gln Ser Asp Leu Tyr Thr Leu Ser Ser Ser Val
            195                 200                 205

Thr Val Thr Ser Ser Thr Trp Pro Ser Gln Ser Ile Thr Cys Asn Val
    210                 215                 220

Ala His Pro Ala Ser Ser Thr Lys Val Asp Lys Lys Ile Glu Pro Arg
225                 230                 235                 240

Gly Pro Thr Ile Lys Pro Cys Pro Pro Cys Lys Cys Pro Ala Pro Asn
                245                 250                 255

Ala Ala Gly Gly Pro Ser Val Phe Ile Phe Pro Pro Lys Ile Lys Asp
                260                 265                 270

Val Leu Met Ile Ser Leu Ser Pro Ile Val Thr Cys Val Val Val Asp
            275                 280                 285

Val Ser Glu Asp Asp Pro Asp Val Gln Ile Ser Trp Phe Val Asn Asn
    290                 295                 300

Val Glu Val His Thr Ala Gln Thr Gln Thr His Arg Glu Asp Tyr Asn
305                 310                 315                 320
```

-continued

```
Ser Thr Leu Arg Val Val Ser Ala Leu Pro Ile Gln His Gln Asp Trp
            325             330             335

Met Ser Gly Lys Glu Phe Lys Cys Lys Val Asn Asn Lys Asp Leu Gly
            340             345             350

Ala Pro Ile Glu Arg Thr Ile Ser Lys Pro Lys Gly Ser Val Arg Ala
            355             360             365

Pro Gln Val Tyr Val Leu Pro Pro Glu Glu Glu Met Thr Lys Lys
    370             375             380

Gln Val Thr Leu Thr Cys Met Val Thr Asp Phe Met Pro Glu Asp Ile
385             390             395             400

Tyr Val Glu Trp Thr Asn Asn Gly Lys Thr Glu Leu Asn Tyr Lys Asn
            405             410             415

Thr Glu Pro Val Leu Asp Ser Asp Gly Ser Tyr Phe Met Tyr Ser Lys
            420             425             430

Leu Arg Val Glu Lys Lys Asn Trp Val Glu Arg Asn Ser Tyr Ser Cys
            435             440             445

Ser Val Val His Glu Gly Leu His Asn His His Thr Thr Lys Ser Phe
    450             455             460

Ser Arg Thr Pro Gly Lys
465             470
```

```
<210> SEQ ID NO 152
<211> LENGTH: 232
<212> TYPE: PRT
<213> ORGANISM: Artificial Sequence
<220> FEATURE:
<223> OTHER INFORMATION: Synthetic: 4.11H11 LC LALAPG mIgG2a

<400> SEQUENCE: 152
```

```
Met Gly Trp Ser Cys Ile Ile Leu Phe Leu Val Ala Thr Ala Thr Gly
1               5               10              15

Val His Ser Gln Ile Val Leu Ser Gln Phe Pro Ala Ile Leu Ser Ala
            20              25              30

Ser Pro Gly Glu Lys Val Thr Met Thr Cys Arg Ala Ser Ser Ser Val
            35              40              45

Ile Tyr Val His Trp Tyr Gln Gln Lys Pro Gly Ser Ser Pro Lys Pro
    50              55              60

Trp Ile Tyr Ala Thr Ser Asn Leu Ala Ser Gly Val Pro Ala Arg Phe
65              70              75              80

Ser Gly Ser Gly Ser Gly Thr Ser His Ser Leu Thr Ile Ser Arg Leu
            85              90              95

Glu Ala Glu Asp Thr Ala Thr Tyr Tyr Cys Gln Gln Trp Ser Ser Asn
            100             105             110

Pro Leu Thr Phe Gly Ala Gly Thr Lys Leu Glu Ile Lys Arg Ala Asp
            115             120             125

Ala Ala Pro Thr Val Ser Ile Phe Pro Pro Ser Ser Glu Gln Leu Thr
    130             135             140

Ser Gly Gly Ala Ser Val Val Cys Phe Leu Asn Asn Phe Tyr Pro Lys
145             150             155             160

Asp Ile Asn Val Lys Trp Lys Ile Asp Gly Ser Glu Arg Gln Asn Gly
            165             170             175

Val Leu Asn Ser Trp Thr Asp Gln Asp Ser Lys Asp Ser Thr Tyr Ser
            180             185             190

Met Ser Ser Thr Leu Thr Leu Thr Lys Asp Glu Tyr Glu Arg His Asn
            195             200             205
```

```
Ser Tyr Thr Cys Glu Ala Thr His Lys Thr Ser Thr Ser Pro Ile Val
    210                 215                 220

Lys Ser Phe Asn Arg Asn Glu Cys
225                 230

<210> SEQ ID NO 153
<211> LENGTH: 5
<212> TYPE: PRT
<213> ORGANISM: Artificial Sequence
<220> FEATURE:
<223> OTHER INFORMATION: Synthetic: 4.29C4 VH CDR1

<400> SEQUENCE: 153

Asn Tyr Trp Met Asn
1               5

<210> SEQ ID NO 154
<211> LENGTH: 17
<212> TYPE: PRT
<213> ORGANISM: Artificial Sequence
<220> FEATURE:
<223> OTHER INFORMATION: Synthetic: 4.29C4 VH CDR2

<400> SEQUENCE: 154

Met Ile His Pro Ser Asp Ser Glu Ser Arg Leu Ser Gln Arg Phe Lys
1               5                   10                  15

Asp

<210> SEQ ID NO 155
<211> LENGTH: 3
<212> TYPE: PRT
<213> ORGANISM: Artificial Sequence
<220> FEATURE:
<223> OTHER INFORMATION: Synthetic: 4.29C4 VH CDR3

<400> SEQUENCE: 155

Leu Asp Tyr
1

<210> SEQ ID NO 156
<211> LENGTH: 17
<212> TYPE: PRT
<213> ORGANISM: Artificial Sequence
<220> FEATURE:
<223> OTHER INFORMATION: Synthetic: 4.29C4 VL CDR1

<400> SEQUENCE: 156

Lys Ser Ser Gln Ser Leu Leu Lys Ser Ser Asn Gln Lys Asn Tyr Leu
1               5                   10                  15

Ala

<210> SEQ ID NO 157
<211> LENGTH: 7
<212> TYPE: PRT
<213> ORGANISM: Artificial Sequence
<220> FEATURE:
<223> OTHER INFORMATION: Synthetic: 4.29C4 VL CDR2

<400> SEQUENCE: 157

Phe Ala Ser Thr Arg Glu Ser
1               5

<210> SEQ ID NO 158
<211> LENGTH: 9
<212> TYPE: PRT
```

-continued

```
<213> ORGANISM: Artificial Sequence
<220> FEATURE:
<223> OTHER INFORMATION: Synthetic: 4.29C4 VL CDR3

<400> SEQUENCE: 158

Gln Gln His Tyr Ser Ala Pro Leu Thr
1               5

<210> SEQ ID NO 159
<211> LENGTH: 108
<212> TYPE: PRT
<213> ORGANISM: Artificial Sequence
<220> FEATURE:
<223> OTHER INFORMATION: Synthetic: 4.29C4 VH

<400> SEQUENCE: 159

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Ser Phe Ala Asn Tyr
            20                  25                  30

Trp Met Asn Trp Val Lys Gln Arg Pro Gly Gln Gly Leu Glu Trp Ile
        35                  40                  45

Gly Met Ile His Pro Ser Asp Ser Glu Ser Arg Leu Ser Gln Arg Phe
    50                  55                  60

Lys Asp Lys Ala Thr Leu Thr Val Asp Lys Ser Ser Ser Thr Ala Tyr
65                  70                  75                  80

Met Gln Leu Asn Ser Pro Thr Ser Glu Asp Ser Ala Val Tyr Tyr Cys
                85                  90                  95

Ala Arg Leu Asp Tyr Trp Gly Gln Gly Thr Ser Val
            100                 105

<210> SEQ ID NO 160
<211> LENGTH: 106
<212> TYPE: PRT
<213> ORGANISM: Artificial Sequence
<220> FEATURE:
<223> OTHER INFORMATION: Synthetic: 4.29C4 VL

<400> SEQUENCE: 160

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Lys Ser
            20                  25                  30

Ser Asn Gln Lys Asn Tyr Leu Ala Trp Tyr Gln Gln Lys Pro Gly Gln
        35                  40                  45

Ser Pro Lys Leu Leu Val Phe Phe Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Phe Cys Gln Gln
                85                  90                  95

His Tyr Ser Ala Pro Leu Thr Phe Gly Ala
            100                 105

<210> SEQ ID NO 161
<211> LENGTH: 461
<212> TYPE: PRT
<213> ORGANISM: Artificial Sequence
<220> FEATURE:
<223> OTHER INFORMATION: Synthetic: 4.29C4 HC  LALAPG mIgG2a
```

```
<400> SEQUENCE: 161

Met Gly Trp Ser Cys Ile Ile Leu Phe Leu Val Ala Thr Ala Thr Gly
1               5                   10                  15

Val His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Ser Phe
        35                  40                  45

Ala Asn Tyr Trp Met Asn Trp Val Lys Gln Arg Pro Gly Gln Gly Leu
    50                  55                  60

Glu Trp Ile Gly Met Ile His Pro Ser Asp Ser Glu Ser Arg Leu Ser
65                  70                  75                  80

Gln Arg Phe Lys Asp Lys Ala Thr Leu Thr Val Asp Lys Ser Ser Ser
            85                  90                  95

Thr Ala Tyr Met Gln Leu Asn Ser Pro Thr Ser Glu Asp Ser Ala Val
            100                 105                 110

Tyr Tyr Cys Ala Arg Leu Asp Tyr Trp Gly Gln Gly Thr Ser Val Thr
        115                 120                 125

Val Ser Ser Ala Lys Thr Thr Ala Pro Ser Val Tyr Pro Leu Ala Pro
    130                 135                 140

Val Cys Gly Asp Thr Thr Gly Ser Ser Val Thr Leu Gly Cys Leu Val
145                 150                 155                 160

Lys Gly Tyr Phe Pro Glu Pro Val Thr Leu Thr Trp Asn Ser Gly Ser
            165                 170                 175

Leu Ser Ser Gly Val His Thr Phe Pro Ala Val Leu Gln Ser Asp Leu
            180                 185                 190

Tyr Thr Leu Ser Ser Ser Val Thr Val Thr Ser Ser Thr Trp Pro Ser
        195                 200                 205

Gln Ser Ile Thr Cys Asn Val Ala His Pro Ala Ser Ser Thr Lys Val
    210                 215                 220

Asp Lys Lys Ile Glu Pro Arg Gly Pro Thr Ile Lys Pro Cys Pro Pro
225                 230                 235                 240

Cys Lys Cys Pro Ala Pro Asn Ala Ala Gly Gly Pro Ser Val Phe Ile
            245                 250                 255

Phe Pro Pro Lys Ile Lys Asp Val Leu Met Ile Ser Leu Ser Pro Ile
            260                 265                 270

Val Thr Cys Val Val Val Asp Val Ser Glu Asp Asp Pro Asp Val Gln
        275                 280                 285

Ile Ser Trp Phe Val Asn Asn Val Glu Val His Thr Ala Gln Thr Gln
    290                 295                 300

Thr His Arg Glu Asp Tyr Asn Ser Thr Leu Arg Val Val Ser Ala Leu
305                 310                 315                 320

Pro Ile Gln His Gln Asp Trp Met Ser Gly Lys Glu Phe Lys Cys Lys
            325                 330                 335

Val Asn Asn Lys Asp Leu Gly Ala Pro Ile Glu Arg Thr Ile Ser Lys
            340                 345                 350

Pro Lys Gly Ser Val Arg Ala Pro Gln Val Tyr Val Leu Pro Pro Pro
        355                 360                 365

Glu Glu Glu Met Thr Lys Lys Gln Val Thr Leu Thr Cys Met Val Thr
    370                 375                 380

Asp Phe Met Pro Glu Asp Ile Tyr Val Glu Trp Thr Asn Asn Gly Lys
385                 390                 395                 400

Thr Glu Leu Asn Tyr Lys Asn Thr Glu Pro Val Leu Asp Ser Asp Gly
            405                 410                 415
```

-continued

Ser Tyr Phe Met Tyr Ser Lys Leu Arg Val Glu Lys Lys Asn Trp Val
              420                   425                   430

Glu Arg Asn Ser Tyr Ser Cys Ser Val Val His Glu Gly Leu His Asn
          435                   440                   445

His His Thr Thr Lys Ser Phe Ser Arg Thr Pro Gly Lys
      450                   455                   460

<210> SEQ ID NO 162
<211> LENGTH: 239
<212> TYPE: PRT
<213> ORGANISM: Artificial Sequence
<220> FEATURE:
<223> OTHER INFORMATION: Synthetic: 4.29C4 LC LALAPG mIgG2a

<400> SEQUENCE: 162

Met Gly Trp Ser Cys Ile Ile Leu Phe Leu Val Ala Thr Ala Thr Gly
1               5                   10                  15

Val His Ser Asp Ile Val Met Thr Gln Ser Pro Ser Ser Leu Ala Met
              20                  25                  30

Ser Val Gly Gln Lys Val Thr Met Ser Cys Lys Ser Ser Gln Ser Leu
          35                  40                  45

Leu Lys Ser Ser Asn Gln Lys Asn Tyr Leu Ala Trp Tyr Gln Gln Lys
      50                  55                  60

Pro Gly Gln Ser Pro Lys Leu Leu Val Phe Phe Ala Ser Thr Arg Glu
65                  70                  75                  80

Ser Gly Val Pro Asp Arg Phe Ile Gly Ser Gly Ser Gly Thr Asp Phe
              85                  90                  95

Thr Leu Thr Ile Ser Ser Val Gln Ala Glu Asp Leu Ala Asp Tyr Phe
              100                 105                 110

Cys Gln Gln His Tyr Ser Ala Pro Leu Thr Phe Gly Ala Gly Thr Lys
          115                 120                 125

Leu Glu Ile Lys Arg Ala Asp Ala Ala Pro Thr Val Ser Ile Phe Pro
      130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
              165                 170                 175

Gly Ser Glu Arg Gln Asn Gly Val Leu Asn Ser Trp Thr Asp Gln Asp
          180                 185                 190

Ser Lys Asp Ser Thr Tyr Ser Met Ser Ser Thr Leu Thr Leu Thr Lys
          195                 200                 205

Asp Glu Tyr Glu Arg His Asn Ser Tyr Thr Cys Glu Ala Thr His Lys
      210                 215                 220

Thr Ser Thr Ser Pro Ile Val Lys Ser Phe Asn Arg Asn Glu Cys
225                 230                 235

<210> SEQ ID NO 163
<211> LENGTH: 6
<212> TYPE: PRT
<213> ORGANISM: Artificial Sequence
<220> FEATURE:
<223> OTHER INFORMATION: Synthetic: 5.17D12 VH CDR1

<400> SEQUENCE: 163

Ser Asn Tyr Tyr Met Cys
1               5

-continued

```
<210> SEQ ID NO 164
<211> LENGTH: 17
<212> TYPE: PRT
<213> ORGANISM: Artificial Sequence
<220> FEATURE:
<223> OTHER INFORMATION: Synthetic: 5.17D12 VH CDR2

<400> SEQUENCE: 164

Cys Val Tyr Val Gly Ser Gly Gly Ser Thr Tyr Tyr Ala Ser Trp Ala
1               5                   10                  15

Lys

<210> SEQ ID NO 165
<211> LENGTH: 8
<212> TYPE: PRT
<213> ORGANISM: Artificial Sequence
<220> FEATURE:
<223> OTHER INFORMATION: Synthetic: 5.17D12 VH CDR3

<400> SEQUENCE: 165

Asp Leu Ser Tyr Ala Gly Asp Leu
1               5

<210> SEQ ID NO 166
<211> LENGTH: 11
<212> TYPE: PRT
<213> ORGANISM: Artificial Sequence
<220> FEATURE:
<223> OTHER INFORMATION: Synthetic: 5.17D12 VL CDR1

<400> SEQUENCE: 166

Gln Ala Ser Glu Ser Ile Ser Ser Tyr Leu Ala
1               5                   10

<210> SEQ ID NO 167
<211> LENGTH: 7
<212> TYPE: PRT
<213> ORGANISM: Artificial Sequence
<220> FEATURE:
<223> OTHER INFORMATION: Synthetic: 5.17D12 VL CDR2

<400> SEQUENCE: 167

Gly Ala Ser Asn Leu Ala Ser
1               5

<210> SEQ ID NO 168
<211> LENGTH: 12
<212> TYPE: PRT
<213> ORGANISM: Artificial Sequence
<220> FEATURE:
<223> OTHER INFORMATION: Synthetic: 5.17D12 VL CDR3

<400> SEQUENCE: 168

Gln Ser Ala Tyr Tyr Ser Asn Ser Gly Gly His Ala
1               5                   10

<210> SEQ ID NO 169
<211> LENGTH: 117
<212> TYPE: PRT
<213> ORGANISM: Artificial Sequence
<220> FEATURE:
<223> OTHER INFORMATION: Synthetic: 5.17D12 VH

<400> SEQUENCE: 169

Gln Ser Leu Glu Glu Ser Gly Gly Asp Leu Val Lys Pro Gly Ala Ser
1               5                   10                  15
```

```
Leu Thr Leu Thr Cys Thr Ala Ser Gly Phe Ser Phe Ser Ser Asn Tyr
            20                  25                  30

Tyr Met Cys Trp Val Arg Gln Ala Pro Gly Lys Gly Leu Glu Trp Ile
            35                  40                  45

Ala Cys Val Tyr Val Gly Ser Gly Gly Ser Thr Tyr Tyr Ala Ser Trp
            50                  55                  60

Ala Lys Gly Arg Phe Thr Phe Ser Lys Thr Ser Ser Thr Thr Trp Thr
65                  70                  75                  80

Leu Gln Met Thr Ser Leu Thr Ala Ala Asp Thr Ala Thr Tyr Phe Cys
                85                  90                  95

Ala Arg Asp Leu Ser Tyr Ala Gly Asp Leu Trp Gly Pro Gly Thr Leu
            100                 105                 110

Val Thr Val Ser Ser
            115

<210> SEQ ID NO 170
<211> LENGTH: 110
<212> TYPE: PRT
<213> ORGANISM: Artificial Sequence
<220> FEATURE:
<223> OTHER INFORMATION: Synthetic: 5.17D12 VL

<400> SEQUENCE: 170

Asp Pro Val Met Thr Gln Thr Pro Ala Ser Val Ser Glu Pro Val Gly
1               5                   10                  15

Gly Thr Val Thr Ile Asn Cys Gln Ala Ser Glu Ser Ile Ser Ser Tyr
            20                  25                  30

Leu Ala Trp Tyr Gln Gln Lys Pro Gly Gln Pro Pro Lys Leu Leu Ile
            35                  40                  45

Tyr Gly Ala Ser Asn Leu Ala Ser Gly Val Pro Ser Arg Phe Lys Gly
            50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys Gln Ser Ala Tyr Tyr Ser Asn Ser
                85                  90                  95

Gly Gly His Ala Phe Gly Gly Gly Thr Glu Val Val Val Lys
            100                 105                 110

<210> SEQ ID NO 171
<211> LENGTH: 459
<212> TYPE: PRT
<213> ORGANISM: Artificial Sequence
<220> FEATURE:
<223> OTHER INFORMATION: Synthetic: 5.17D12 HC

<400> SEQUENCE: 171

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
            20                  25                  30

Gly Ala Ser Leu Thr Leu Thr Cys Thr Ala Ser Gly Phe Ser Phe Ser
            35                  40                  45

Ser Asn Tyr Tyr Met Cys Trp Val Arg Gln Ala Pro Gly Lys Gly Leu
            50                  55                  60

Glu Trp Ile Ala Cys Val Tyr Val Gly Ser Gly Gly Ser Thr Tyr Tyr
65                  70                  75                  80

Ala Ser Trp Ala Lys Gly Arg Phe Thr Phe Ser Lys Thr Ser Ser Thr
                85                  90                  95
```

-continued

```
Thr Trp Thr Leu Gln Met Thr Ser Leu Thr Ala Ala Asp Thr Ala Thr
            100                 105                 110

Tyr Phe Cys Ala Arg Asp Leu Ser Tyr Ala Gly Asp Leu Trp Gly Pro
            115                 120                 125

Gly Thr Leu Val Thr Val Ser Ser Gly Gln Pro Lys Ala Pro Ser Val
        130                 135                 140

Phe Pro Leu Ala Pro Cys Cys Gly Asp Thr Pro Ser Ser Thr Val Thr
145                 150                 155                 160

Leu Gly Cys Leu Val Lys Gly Tyr Leu Pro Glu Pro Val Thr Val Thr
                165                 170                 175

Trp Asn Ser Gly Thr Leu Thr Asn Gly Val Arg Thr Phe Pro Ser Val
            180                 185                 190

Arg Gln Ser Ser Gly Leu Tyr Ser Leu Ser Ser Val Val Ser Val Thr
            195                 200                 205

Ser Ser Ser Gln Pro Val Thr Cys Asn Val Ala His Pro Ala Thr Asn
        210                 215                 220

Thr Lys Val Asp Lys Thr Val Ala Pro Ser Thr Cys Ser Lys Pro Thr
225                 230                 235                 240

Cys Pro Pro Pro Glu Leu Leu Gly Gly Pro Ser Val Phe Ile Phe Pro
                245                 250                 255

Pro Lys Pro Lys Asp Thr Leu Met Ile Ser Arg Thr Pro Glu Val Thr
            260                 265                 270

Cys Val Val Val Asp Val Ser Gln Asp Asp Pro Glu Val Gln Phe Thr
            275                 280                 285

Trp Tyr Ile Asn Asn Glu Gln Val Arg Thr Ala Arg Pro Pro Leu Arg
        290                 295                 300

Glu Gln Gln Phe Asn Ser Thr Ile Arg Val Val Ser Thr Leu Pro Ile
305                 310                 315                 320

Ala His Gln Asp Trp Leu Arg Gly Lys Glu Phe Lys Cys Lys Val His
                325                 330                 335

Asn Lys Ala Leu Pro Ala Pro Ile Glu Lys Thr Ile Ser Lys Ala Arg
            340                 345                 350

Gly Gln Pro Leu Glu Pro Lys Val Tyr Thr Met Gly Pro Pro Arg Glu
            355                 360                 365

Glu Leu Ser Ser Arg Ser Val Ser Leu Thr Cys Met Ile Asn Gly Phe
        370                 375                 380

Tyr Pro Ser Asp Ile Ser Val Glu Trp Glu Lys Asn Gly Lys Ala Glu
385                 390                 395                 400

Asp Asn Tyr Lys Thr Thr Pro Ala Val Leu Asp Ser Asp Gly Ser Tyr
                405                 410                 415

Phe Leu Tyr Asn Lys Leu Ser Val Pro Thr Ser Glu Trp Gln Arg Gly
            420                 425                 430

Asp Val Phe Thr Cys Ser Val Met His Glu Ala Leu His Asn His Tyr
            435                 440                 445

Thr Gln Lys Ser Ile Ser Arg Ser Pro Gly Lys
        450                 455
```

<210> SEQ ID NO 172
<211> LENGTH: 236
<212> TYPE: PRT
<213> ORGANISM: Artificial Sequence
<220> FEATURE:
<223> OTHER INFORMATION: Synthetic: 5.17D12 LC

<400> SEQUENCE: 172

```
Met Asp Met Arg Ala Pro Thr Gln Leu Leu Gly Leu Leu Leu Leu Trp
1               5                   10                  15

Leu Pro Gly Val Ile Cys Asp Pro Val Met Thr Gln Thr Pro Ala Ser
            20                  25                  30

Val Ser Glu Pro Val Gly Gly Thr Val Thr Ile Asn Cys Gln Ala Ser
        35                  40                  45

Glu Ser Ile Ser Ser Tyr Leu Ala Trp Tyr Gln Gln Lys Pro Gly Gln
    50                  55                  60

Pro Pro Lys Leu Leu Ile Tyr Gly Ala Ser Asn Leu Ala Ser Gly Val
65                  70                  75                  80

Pro Ser Arg Phe Lys Gly Ser Gly Ser Gly Thr Glu Tyr Thr Leu Thr
                85                  90                  95

Ile Ser Asp Leu Glu Cys Asp Asp Ala Ala Thr Tyr Tyr Cys Gln Ser
            100                 105                 110

Ala Tyr Tyr Ser Asn Ser Gly Gly His Ala Phe Gly Gly Gly Thr Glu
            115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
            165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
            195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235
```

```
<210> SEQ ID NO 173
<211> LENGTH: 5
<212> TYPE: PRT
<213> ORGANISM: Artificial Sequence
<220> FEATURE:
<223> OTHER INFORMATION: Synthetic: 5.17H8 VH CDR1

<400> SEQUENCE: 173

Ser Tyr Ala Met Gly
1               5
```

```
<210> SEQ ID NO 174
<211> LENGTH: 14
<212> TYPE: PRT
<213> ORGANISM: Artificial Sequence
<220> FEATURE:
<223> OTHER INFORMATION: Synthetic: 5.17H8 VH CDR2

<400> SEQUENCE: 174

Ile Ile Ser Ser Ser Gly Ser Thr His Tyr Ala Ser Trp Ala
1               5                   10
```

```
<210> SEQ ID NO 175
<211> LENGTH: 15
<212> TYPE: PRT
<213> ORGANISM: Artificial Sequence
<220> FEATURE:
<223> OTHER INFORMATION: Synthetic: 5.17H8 VH CDR3
```

<400> SEQUENCE: 175

Ala Arg Ala Gly Ser Thr Tyr Tyr Thr Gly Tyr Tyr Phe Asn Leu
1               5                   10                  15

<210> SEQ ID NO 176
<211> LENGTH: 11
<212> TYPE: PRT
<213> ORGANISM: Artificial Sequence
<220> FEATURE:
<223> OTHER INFORMATION: Synthetic: 5.17H8 VL CDR1

<400> SEQUENCE: 176

Gln Ala Ser Glu Ser Ile Tyr Ser Asn Leu Ala
1               5                   10

<210> SEQ ID NO 177
<211> LENGTH: 7
<212> TYPE: PRT
<213> ORGANISM: Artificial Sequence
<220> FEATURE:
<223> OTHER INFORMATION: Synthetic: 5.17H8 VL CDR2

<400> SEQUENCE: 177

Gly Ala Ser Thr Leu Glu Ser
1               5

<210> SEQ ID NO 178
<211> LENGTH: 13
<212> TYPE: PRT
<213> ORGANISM: Artificial Sequence
<220> FEATURE:
<223> OTHER INFORMATION: Synthetic: 5.17H8 VL CDR3

<400> SEQUENCE: 178

Gln Ser Gly Tyr Tyr Gly Ile Ser Ala Ile Asn Asn Ala
1               5                   10

<210> SEQ ID NO 179
<211> LENGTH: 120
<212> TYPE: PRT
<213> ORGANISM: Artificial Sequence
<220> FEATURE:
<223> OTHER INFORMATION: Synthetic: 5.17H8 VH

<400> SEQUENCE: 179

Gln Ser Leu Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Ala
                20                  25                  30

Met Gly Trp Val Arg Gln Ala Pro Gly Lys Gly Leu Glu Trp Ile Gly
            35                  40                  45

Ile Ile Ser Ser Ser Gly Ser Thr His Tyr Ala Ser Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Ala Arg
                85                  90                  95

Ala Gly Ser Thr Tyr Tyr Thr Gly Tyr Tyr Phe Asn Leu Trp Gly Gln
            100                 105                 110

Gly Thr Leu Val Thr Val Ser Ser
        115                 120

```
<210> SEQ ID NO 180
<211> LENGTH: 111
<212> TYPE: PRT
<213> ORGANISM: Artificial Sequence
<220> FEATURE:
<223> OTHER INFORMATION: Synthetic: 5.17H8 VL

<400> SEQUENCE: 180

Ala Ile Glu Met Thr Gln Thr Ala Ser Pro Val Ser Ala Ala Val Gly
1               5                   10                  15

Gly Thr Val Thr Ile Asn Cys Gln Ala Ser Glu Ser Ile Tyr Ser Asn
            20                  25                  30

Leu Ala Trp Tyr Gln Gln Lys Pro Gly Gln Arg Pro Lys Leu Leu Ile
        35                  40                  45

Tyr Gly Ala Ser Thr Leu Glu Ser Gly Val Pro Ser Arg Phe Lys Gly
    50                  55                  60

Ser Gly Ser Gly Thr Glu Tyr Thr Leu Thr Ile Ser Asp Leu Glu Cys
65                  70                  75                  80

Asp Asp Ala Ala Thr Tyr Tyr Cys Gln Ser Gly Tyr Tyr Gly Ile Ser
                85                  90                  95

Ala Ile Asn Asn Ala Phe Gly Gly Gly Thr Glu Val Val Val Lys
            100                 105                 110

<210> SEQ ID NO 181
<211> LENGTH: 462
<212> TYPE: PRT
<213> ORGANISM: Artificial Sequence
<220> FEATURE:
<223> OTHER INFORMATION: Synthetic: 5.17H8 HC

<400> SEQUENCE: 181

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Thr Pro Leu Thr Leu Thr Cys Thr Val Ser Gly Ile Asp Leu Ser
        35                  40                  45

Ser Tyr Ala Met Gly Trp Val Arg Gln Ala Pro Gly Lys Gly Leu Glu
    50                  55                  60

Trp Ile Gly Ile Ile Ser Ser Ser Gly Ser Thr His Tyr Ala Ser Trp
65                  70                  75                  80

Ala Lys Gly Arg Phe Thr Ile Ser Lys Thr Ser Thr Thr Val Asp Leu
                85                  90                  95

Lys Ile Thr Ser Pro Thr Thr Glu Asp Thr Ala Thr Tyr Phe Cys Ala
            100                 105                 110

Arg Ala Arg Ala Gly Ser Thr Tyr Tyr Thr Gly Tyr Tyr Phe Asn Leu
            115                 120                 125

Trp Gly Gln Gly Thr Leu Val Thr Val Ser Ser Gly Gln Pro Lys Ala
    130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175

Thr Val Thr Trp Asn Ser Gly Thr Leu Thr Asn Gly Val Arg Thr Phe
            180                 185                 190

Pro Ser Val Arg Gln Ser Ser Gly Leu Tyr Ser Leu Ser Ser Val Val
            195                 200                 205
```

-continued

```
Ser Val Thr Ser Ser Ser Gln Pro Val Thr Cys Asn Val Ala His Pro
    210             215             220

Ala Thr Asn Thr Lys Val Asp Lys Thr Val Ala Pro Ser Thr Cys Ser
225             230             235             240

Lys Pro Thr Cys Pro Pro Pro Glu Leu Leu Gly Gly Pro Ser Val Phe
            245             250             255

Ile Phe Pro Pro Lys Pro Lys Asp Thr Leu Met Ile Ser Arg Thr Pro
            260             265             270

Glu Val Thr Cys Val Val Val Asp Val Ser Gln Asp Asp Pro Glu Val
        275             280             285

Gln Phe Thr Trp Tyr Ile Asn Asn Glu Gln Val Arg Thr Ala Arg Pro
    290             295             300

Pro Leu Arg Glu Gln Gln Phe Asn Ser Thr Ile Arg Val Val Ser Thr
305             310             315             320

Leu Pro Ile Ala His Gln Asp Trp Leu Arg Gly Lys Glu Phe Lys Cys
            325             330             335

Lys Val His Asn Lys Ala Leu Pro Ala Pro Ile Glu Lys Thr Ile Ser
            340             345             350

Lys Ala Arg Gly Gln Pro Leu Glu Pro Lys Val Tyr Thr Met Gly Pro
            355             360             365

Pro Arg Glu Glu Leu Ser Ser Arg Ser Val Ser Leu Thr Cys Met Ile
    370             375             380

Asn Gly Phe Tyr Pro Ser Asp Ile Ser Val Glu Trp Glu Lys Asn Gly
385             390             395             400

Lys Ala Glu Asp Asn Tyr Lys Thr Thr Pro Ala Val Leu Asp Ser Asp
            405             410             415

Gly Ser Tyr Phe Leu Tyr Asn Lys Leu Ser Val Pro Thr Ser Glu Trp
            420             425             430

Gln Arg Gly Asp Val Phe Thr Cys Ser Val Met His Glu Ala Leu His
            435             440             445

Asn His Tyr Thr Gln Lys Ser Ile Ser Arg Ser Pro Gly Lys
    450             455             460
```

<210> SEQ ID NO 182
<211> LENGTH: 237
<212> TYPE: PRT
<213> ORGANISM: Artificial Sequence
<220> FEATURE:
<223> OTHER INFORMATION: Synthetic: 5.17H8 LC

<400> SEQUENCE: 182

```
Met Asp Met Arg Ala Pro Thr Gln Leu Leu Gly Leu Leu Leu Leu Trp
1               5               10              15

Leu Pro Gly Val Thr Phe Ala Ile Glu Met Thr Gln Thr Ala Ser Pro
            20              25              30

Val Ser Ala Ala Val Gly Gly Thr Val Thr Ile Asn Cys Gln Ala Ser
        35              40              45

Glu Ser Ile Tyr Ser Asn Leu Ala Trp Tyr Gln Gln Lys Pro Gly Gln
    50              55              60

Arg Pro Lys Leu Leu Ile Tyr Gly Ala Ser Thr Leu Glu Ser Gly Val
65              70              75              80

Pro Ser Arg Phe Lys Gly Ser Gly Ser Gly Thr Glu Tyr Thr Leu Thr
            85              90              95

Ile Ser Asp Leu Glu Cys Asp Asp Ala Ala Thr Tyr Tyr Cys Gln Ser
            100             105             110
```

```
Gly Tyr Tyr Gly Ile Ser Ala Ile Asn Asn Ala Phe Gly Gly Gly Thr
        115                 120                 125

Glu Val Val Val Lys Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
                180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235
```

```
<210> SEQ ID NO 183
<211> LENGTH: 6
<212> TYPE: PRT
<213> ORGANISM: Artificial Sequence
<220> FEATURE:
<223> OTHER INFORMATION: Synthetic: 5.11H2 VH CDR1

<400> SEQUENCE: 183

Tyr Asn Tyr Trp Ile Tyr
1               5
```

```
<210> SEQ ID NO 184
<211> LENGTH: 17
<212> TYPE: PRT
<213> ORGANISM: Artificial Sequence
<220> FEATURE:
<223> OTHER INFORMATION: Synthetic: 5.11H2 VH CDR2

<400> SEQUENCE: 184

Cys Ile Asn Thr Gly Asn Ser Gly Ile Thr Asn Tyr Ala Asn Trp Ala
1               5                   10                  15

Lys
```

```
<210> SEQ ID NO 185
<211> LENGTH: 11
<212> TYPE: PRT
<213> ORGANISM: Artificial Sequence
<220> FEATURE:
<223> OTHER INFORMATION: Synthetic: 5.11H2 VH CDR3

<400> SEQUENCE: 185

Gly Gly Ile Asn Ser Gly Asp Tyr Met Asn Leu
1               5                   10
```

```
<210> SEQ ID NO 186
<211> LENGTH: 11
<212> TYPE: PRT
<213> ORGANISM: Artificial Sequence
<220> FEATURE:
<223> OTHER INFORMATION: Synthetic: 5.11H2 VL CDR1

<400> SEQUENCE: 186

Gln Ala Ser Glu Asn Ile Tyr Arg Leu Leu Ala
1               5                   10
```

```
<210> SEQ ID NO 187
<211> LENGTH: 7
<212> TYPE: PRT
<213> ORGANISM: Artificial Sequence
<220> FEATURE:
<223> OTHER INFORMATION: Synthetic: 5.11H2 VL CDR2

<400> SEQUENCE: 187

Asp Ala Ser Thr Leu Ala Ser
1               5

<210> SEQ ID NO 188
<211> LENGTH: 12
<212> TYPE: PRT
<213> ORGANISM: Artificial Sequence
<220> FEATURE:
<223> OTHER INFORMATION: Synthetic: 5.11H2 VL CDR3

<400> SEQUENCE: 188

Gln Gln Ala Tyr Ser Asn Ser Asn Ile Asp Asn Tyr
1               5                   10

<210> SEQ ID NO 189
<211> LENGTH: 120
<212> TYPE: PRT
<213> ORGANISM: Artificial Sequence
<220> FEATURE:
<223> OTHER INFORMATION: Synthetic: 5.11H2 VH

<400> SEQUENCE: 189

Gln Ser Leu Glu Glu Ser Gly Gly Asp Leu Val Lys Pro Gly Ala Ser
1               5                   10                  15

Leu Thr Leu Thr Cys Thr Ala Ser Gly Phe Ser Phe Ser Tyr Asn Tyr
                20                  25                  30

Trp Ile Tyr Trp Val Arg Gln Ala Pro Gly Lys Gly Leu Glu Trp Ile
        35                  40                  45

Gly Cys Ile Asn Thr Gly Asn Ser Gly Ile Thr Asn Tyr Ala Asn Trp
    50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Gly Gly Ile Asn Ser Gly Asp Tyr Met Asn Leu Trp Gly Pro
            100                 105                 110

Gly Thr Leu Val Thr Val Ser Ser
        115                 120

<210> SEQ ID NO 190
<211> LENGTH: 110
<212> TYPE: PRT
<213> ORGANISM: Artificial Sequence
<220> FEATURE:
<223> OTHER INFORMATION: Synthetic: 5.11H2 VL

<400> SEQUENCE: 190

Ala Tyr Asp Met Thr Gln Thr Pro Ala Ser Val Glu Val Ala Val Gly
1               5                   10                  15

Gly Thr Val Thr Ile Lys Cys Gln Ala Ser Glu Asn Ile Tyr Arg Leu
                20                  25                  30

Leu Ala Trp Tyr Gln Gln Lys Pro Gly Gln Ala Pro Lys Leu Leu Ile
        35                  40                  45
```

```
Tyr Asp Ala Ser Thr Leu Ala Ser Gly Val Pro Ser Arg Phe Ser Gly
    50                  55                  60

Ser Gly Ser Gly Thr Gln Phe Thr Leu Thr Val Ser Gly Val Gln Cys
65                  70                  75                  80

Asp Asp Ala Ala Thr Tyr Tyr Cys Gln Gln Ala Tyr Ser Asn Ser Asn
                85                  90                  95

Ile Asp Asn Tyr Phe Gly Gly Gly Thr Glu Val Val Val Lys
                100                 105                 110

<210> SEQ ID NO 191
<211> LENGTH: 462
<212> TYPE: PRT
<213> ORGANISM: Artificial Sequence
<220> FEATURE:
<223> OTHER INFORMATION: Synthetic: 5.11H2 HC

<400> SEQUENCE: 191

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Asp Leu Val Lys Pro
                20                  25                  30

Gly Ala Ser Leu Thr Leu Thr Cys Thr Ala Ser Gly Phe Ser Phe Ser
        35                  40                  45

Tyr Asn Tyr Trp Ile Tyr Trp Val Arg Gln Ala Pro Gly Lys Gly Leu
    50                  55                  60

Glu Trp Ile Gly Cys Ile Asn Thr Gly Asn Ser Gly Ile Thr Asn Tyr
65                  70                  75                  80

Ala Asn Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
                100                 105                 110

Tyr Phe Cys Ala Arg Gly Gly Ile Asn Ser Gly Asp Tyr Met Asn Leu
        115                 120                 125

Trp Gly Pro Gly Thr Leu Val Thr Val Ser Ser Gly Gln Pro Lys Ala
    130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175

Thr Val Thr Trp Asn Ser Gly Thr Leu Thr Asn Gly Val Arg Thr Phe
                180                 185                 190

Pro Ser Val Arg Gln Ser Ser Gly Leu Tyr Ser Leu Ser Ser Val Val
        195                 200                 205

Ser Val Thr Ser Ser Ser Gln Pro Val Thr Cys Asn Val Ala His Pro
    210                 215                 220

Ala Thr Asn Thr Lys Val Asp Lys Thr Val Ala Pro Ser Thr Cys Ser
225                 230                 235                 240

Lys Pro Thr Cys Pro Pro Pro Glu Leu Leu Gly Gly Pro Ser Val Phe
                245                 250                 255

Ile Phe Pro Pro Lys Pro Lys Asp Thr Leu Met Ile Ser Arg Thr Pro
                260                 265                 270

Glu Val Thr Cys Val Val Val Asp Val Ser Gln Asp Asp Pro Glu Val
        275                 280                 285

Gln Phe Thr Trp Tyr Ile Asn Asn Glu Gln Val Arg Thr Ala Arg Pro
    290                 295                 300
```

-continued

```
Pro Leu Arg Glu Gln Gln Phe Asn Ser Thr Ile Arg Val Val Ser Thr
305             310             315             320

Leu Pro Ile Ala His Gln Asp Trp Leu Arg Gly Lys Glu Phe Lys Cys
            325             330             335

Lys Val His Asn Lys Ala Leu Pro Ala Pro Ile Glu Lys Thr Ile Ser
            340             345             350

Lys Ala Arg Gly Gln Pro Leu Glu Pro Lys Val Tyr Thr Met Gly Pro
            355             360             365

Pro Arg Glu Glu Leu Ser Ser Arg Ser Val Ser Leu Thr Cys Met Ile
            370             375             380

Asn Gly Phe Tyr Pro Ser Asp Ile Ser Val Glu Trp Glu Lys Asn Gly
385             390             395             400

Lys Ala Glu Asp Asn Tyr Lys Thr Thr Pro Ala Val Leu Asp Ser Asp
            405             410             415

Gly Ser Tyr Phe Leu Tyr Asn Lys Leu Ser Val Pro Thr Ser Glu Trp
            420             425             430

Gln Arg Gly Asp Val Phe Thr Cys Ser Val Met His Glu Ala Leu His
            435             440             445

Asn His Tyr Thr Gln Lys Ser Ile Ser Arg Ser Pro Gly Lys
    450             455             460
```

```
<210> SEQ ID NO 192
<211> LENGTH: 236
<212> TYPE: PRT
<213> ORGANISM: Artificial Sequence
<220> FEATURE:
<223> OTHER INFORMATION: Synthetic: 5.11H2 LC

<400> SEQUENCE: 192

Met Asp Met Arg Ala Pro Thr Gln Leu Leu Gly Leu Leu Leu Leu Trp
1               5               10              15

Leu Pro Gly Ala Arg Cys Ala Tyr Asp Met Thr Gln Thr Pro Ala Ser
            20              25              30

Val Glu Val Ala Val Gly Gly Thr Val Thr Ile Lys Cys Gln Ala Ser
            35              40              45

Glu Asn Ile Tyr Arg Leu Leu Ala Trp Tyr Gln Gln Lys Pro Gly Gln
    50              55              60

Ala Pro Lys Leu Leu Ile Tyr Asp Ala Ser Thr Leu Ala Ser Gly Val
65              70              75              80

Pro Ser Arg Phe Ser Gly Ser Gly Ser Gly Thr Gln Phe Thr Leu Thr
            85              90              95

Val Ser Gly Val Gln Cys Asp Asp Ala Ala Thr Tyr Tyr Cys Gln Gln
            100             105             110

Ala Tyr Ser Asn Ser Asn Ile Asp Asn Tyr Phe Gly Gly Gly Thr Glu
            115             120             125

Val Val Val Lys Gly Asp Pro Val Ala Pro Thr Val Leu Ile Phe Pro
            130             135             140

Pro Ala Ala Asp Gln Val Ala Thr Gly Thr Val Thr Ile Val Cys Val
145             150             155             160

Ala Asn Lys Tyr Phe Pro Asp Val Thr Val Thr Trp Glu Val Asp Gly
            165             170             175

Thr Thr Gln Thr Thr Gly Ile Glu Asn Ser Lys Thr Pro Gln Asn Ser
            180             185             190

Ala Asp Cys Thr Tyr Asn Leu Ser Ser Thr Leu Thr Leu Thr Ser Thr
            195             200             205
```

-continued

```
Gln Tyr Asn Ser His Lys Glu Tyr Thr Cys Lys Val Thr Gln Gly Thr
    210               215               220

Thr Ser Val Val Gln Ser Phe Asn Arg Gly Asp Cys
225               230               235

<210> SEQ ID NO 193
<211> LENGTH: 5
<212> TYPE: PRT
<213> ORGANISM: Artificial Sequence
<220> FEATURE:
<223> OTHER INFORMATION: Synthetic: 5.14D6 VH CDR1

<400> SEQUENCE: 193

Ser Lys Thr Ile Thr
1               5

<210> SEQ ID NO 194
<211> LENGTH: 14
<212> TYPE: PRT
<213> ORGANISM: Artificial Sequence
<220> FEATURE:
<223> OTHER INFORMATION: Synthetic: 5.14D6 VH CDR2

<400> SEQUENCE: 194

Phe Ile Asn Thr Asp Gly Arg Ala Tyr Tyr Ala Ser Trp Ala
1               5               10

<210> SEQ ID NO 195
<211> LENGTH: 3
<212> TYPE: PRT
<213> ORGANISM: Artificial Sequence
<220> FEATURE:
<223> OTHER INFORMATION: Synthetic: 5.14D6 VH CDR3

<400> SEQUENCE: 195

Thr Asn Leu
1

<210> SEQ ID NO 196
<211> LENGTH: 13
<212> TYPE: PRT
<213> ORGANISM: Artificial Sequence
<220> FEATURE:
<223> OTHER INFORMATION: Synthetic: 5.14D6 VL CDR1

<400> SEQUENCE: 196

Gln Ala Ser Gln Ser Val Tyr Lys Asn Asn Tyr Leu Ala
1               5               10

<210> SEQ ID NO 197
<211> LENGTH: 7
<212> TYPE: PRT
<213> ORGANISM: Artificial Sequence
<220> FEATURE:
<223> OTHER INFORMATION: Synthetic: 5.14D6 VL CDR2

<400> SEQUENCE: 197

Ser Val Ser Thr Leu Asp Ser
1               5

<210> SEQ ID NO 198
<211> LENGTH: 13
<212> TYPE: PRT
<213> ORGANISM: Artificial Sequence
<220> FEATURE:
<223> OTHER INFORMATION: Synthetic: 5.14D6 VL CDR3
```

-continued

<400> SEQUENCE: 198

Leu Gly Ser Tyr Asp Cys Ser Ser Ala Asp Cys Ala Ala
1               5                   10

<210> SEQ ID NO 199
<211> LENGTH: 108
<212> TYPE: PRT
<213> ORGANISM: Artificial Sequence
<220> FEATURE:
<223> OTHER INFORMATION: Synthetic: 5.14D6 VH

<400> SEQUENCE: 199

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Lys Thr
            20                  25                  30

Ile Thr Trp Val Arg Gln Ala Pro Gly Lys Gly Leu Glu Trp Ile Gly
        35                  40                  45

Phe Ile Asn Thr Asp Gly Arg Ala Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Gly Arg Thr Asn
                85                  90                  95

Leu Trp Gly Gln Gly Thr Leu Val Thr Val Ser Ser
            100                 105

<210> SEQ ID NO 200
<211> LENGTH: 113
<212> TYPE: PRT
<213> ORGANISM: Artificial Sequence
<220> FEATURE:
<223> OTHER INFORMATION: Synthetic: 5.14D6 VL

<400> SEQUENCE: 200

Ala Gln Val Leu Thr Gln Thr Ser Ser Pro Val Ser Ala Ala Val Gly
1               5                   10                  15

Ser Thr Val Thr Ile Asn Cys Gln Ala Ser Gln Ser Val Tyr Lys Asn
            20                  25                  30

Asn Tyr Leu Ala Trp Phe Gln Gln Lys Pro Gly Gln Pro Pro Lys Arg
        35                  40                  45

Leu Ile Tyr Ser Val Ser Thr Leu Asp Ser Gly Val Pro Ser Arg Phe
    50                  55                  60

Ser Gly Ser Gly Ser Gly Thr Gln Phe Thr Leu Thr Ile Ser Asp Val
65                  70                  75                  80

Gln Cys Asp Asp Ala Ala Thr Tyr Tyr Cys Leu Gly Ser Tyr Asp Cys
                85                  90                  95

Ser Ser Ala Asp Cys Ala Ala Phe Gly Gly Gly Thr Glu Val Val Val
            100                 105                 110

Lys

<210> SEQ ID NO 201
<211> LENGTH: 450
<212> TYPE: PRT
<213> ORGANISM: Artificial Sequence
<220> FEATURE:
<223> OTHER INFORMATION: Synthetic: 5.14D6 HC

<400> SEQUENCE: 201

-continued

```
Met Glu Thr Gly Leu Arg Trp Leu Leu Leu Val Ala Val Leu Lys Gly
1               5               10              15

Val Gln Cys Gln Ser Val Glu Glu Ser Gly Gly Arg Leu Val Thr Pro
            20              25              30

Gly Thr Pro Leu Thr Leu Thr Cys Thr Val Ser Gly Phe Ser Leu Ser
            35              40              45

Ser Lys Thr Ile Thr Trp Val Arg Gln Ala Pro Gly Lys Gly Leu Glu
        50              55              60

Trp Ile Gly Phe Ile Asn Thr Asp Gly Arg Ala Tyr Tyr Ala Ser Trp
65              70              75              80

Ala Lys Gly Arg Phe Thr Ile Ser Lys Thr Ser Thr Thr Val Asp Leu
                85              90              95

Lys Ile Thr Ser Pro Thr Thr Glu Asp Thr Ala Thr Tyr Phe Cys Gly
            100             105             110

Arg Thr Asn Leu Trp Gly Gln Gly Thr Leu Val Thr Val Ser Ser Gly
            115             120             125

Gln Pro Lys Ala Pro Ser Val Phe Pro Leu Ala Pro Cys Cys Gly Asp
    130             135             140

Thr Pro Ser Ser Thr Val Thr Leu Gly Cys Leu Val Lys Gly Tyr Leu
145             150             155             160

Pro Glu Pro Val Thr Val Thr Trp Asn Ser Gly Thr Leu Thr Asn Gly
            165             170             175

Val Arg Thr Phe Pro Ser Val Arg Gln Ser Ser Gly Leu Tyr Ser Leu
            180             185             190

Ser Ser Val Val Ser Val Thr Ser Ser Ser Gln Pro Val Thr Cys Asn
    195             200             205

Val Ala His Pro Ala Thr Asn Thr Lys Val Asp Lys Thr Val Ala Pro
    210             215             220

Ser Thr Cys Ser Lys Pro Thr Cys Pro Pro Pro Glu Leu Leu Gly Gly
225             230             235             240

Pro Ser Val Phe Ile Phe Pro Pro Lys Pro Lys Asp Thr Leu Met Ile
            245             250             255

Ser Arg Thr Pro Glu Val Thr Cys Val Val Val Asp Val Ser Gln Asp
            260             265             270

Asp Pro Glu Val Gln Phe Thr Trp Tyr Ile Asn Asn Glu Gln Val Arg
    275             280             285

Thr Ala Arg Pro Pro Leu Arg Glu Gln Gln Phe Asn Ser Thr Ile Arg
    290             295             300

Val Val Ser Thr Leu Pro Ile Ala His Gln Asp Trp Leu Arg Gly Lys
305             310             315             320

Glu Phe Lys Cys Lys Val His Asn Lys Ala Leu Pro Ala Pro Ile Glu
            325             330             335

Lys Thr Ile Ser Lys Ala Arg Gly Gln Pro Leu Glu Pro Lys Val Tyr
            340             345             350

Thr Met Gly Pro Pro Arg Glu Glu Leu Ser Ser Arg Ser Val Ser Leu
            355             360             365

Thr Cys Met Ile Asn Gly Phe Tyr Pro Ser Asp Ile Ser Val Glu Trp
    370             375             380

Glu Lys Asn Gly Lys Ala Glu Asp Asn Tyr Lys Thr Thr Pro Ala Val
385             390             395             400

Leu Asp Ser Asp Gly Ser Tyr Phe Leu Tyr Asn Lys Leu Ser Val Pro
            405             410             415

Thr Ser Glu Trp Gln Arg Gly Asp Val Phe Thr Cys Ser Val Met His
```

```
              420               425               430
Glu Ala Leu His Asn His Tyr Thr Gln Lys Ser Ile Ser Arg Ser Pro
        435               440               445

Gly Lys
    450

<210> SEQ ID NO 202
<211> LENGTH: 239
<212> TYPE: PRT
<213> ORGANISM: Artificial Sequence
<220> FEATURE:
<223> OTHER INFORMATION: Synthetic: 5.14D6 LC

<400> SEQUENCE: 202

Met Asp Met Arg Ala Pro Thr Gln Leu Leu Gly Leu Leu Leu Leu Trp
1               5               10              15

Leu Pro Gly Ala Thr Phe Ala Gln Val Leu Thr Gln Thr Ser Ser Pro
            20              25              30

Val Ser Ala Ala Val Gly Ser Thr Val Thr Ile Asn Cys Gln Ala Ser
        35              40              45

Gln Ser Val Tyr Lys Asn Asn Tyr Leu Ala Trp Phe Gln Gln Lys Pro
    50              55              60

Gly Gln Pro Pro Lys Arg Leu Ile Tyr Ser Val Ser Thr Leu Asp Ser
65              70              75              80

Gly Val Pro Ser Arg Phe Ser Gly Ser Gly Ser Gly Thr Gln Phe Thr
            85              90              95

Leu Thr Ile Ser Asp Val Gln Cys Asp Asp Ala Ala Thr Tyr Tyr Cys
            100             105             110

Leu Gly Ser Tyr Asp Cys Ser Ser Ala Asp Cys Ala Ala Phe Gly Gly
        115             120             125

Gly Thr Glu Val Val Val Lys Gly Asp Pro Val Ala Pro Thr Val Leu
    130             135             140

Ile Phe Pro Pro Ala Ala Asp Gln Val Ala Thr Gly Thr Val Thr Ile
145             150             155             160

Val Cys Val Ala Asn Lys Tyr Phe Pro Asp Val Thr Val Thr Trp Glu
            165             170             175

Val Asp Gly Thr Thr Gln Thr Thr Gly Ile Glu Asn Ser Lys Thr Pro
            180             185             190

Gln Asn Ser Ala Asp Cys Thr Tyr Asn Leu Ser Ser Thr Leu Thr Leu
    195             200             205

Thr Ser Thr Gln Tyr Asn Ser His Lys Glu Tyr Thr Cys Lys Val Thr
    210             215             220

Gln Gly Thr Thr Ser Val Val Gln Ser Phe Asn Arg Gly Asp Cys
225             230             235

<210> SEQ ID NO 203
<211> LENGTH: 5
<212> TYPE: PRT
<213> ORGANISM: Artificial Sequence
<220> FEATURE:
<223> OTHER INFORMATION: Synthetic: 3.7F5 VH CDR1

<400> SEQUENCE: 203

Asp Tyr Asn Val Phe
1               5

<210> SEQ ID NO 204
<211> LENGTH: 17
```

```
<212> TYPE: PRT
<213> ORGANISM: Artificial Sequence
<220> FEATURE:
<223> OTHER INFORMATION: Synthetic: 3.7F5 VH CDR2

<400> SEQUENCE: 204

Tyr Ile Asp Pro Tyr Asn Gly Ala Thr Ser Tyr Asn Gln Lys Phe Lys
1               5                   10                  15

Asp

<210> SEQ ID NO 205
<211> LENGTH: 9
<212> TYPE: PRT
<213> ORGANISM: Artificial Sequence
<220> FEATURE:
<223> OTHER INFORMATION: Synthetic: 3.7F5 VH CDR3

<400> SEQUENCE: 205

Gly Thr Val Arg Ala Phe Phe Asp Ser
1               5

<210> SEQ ID NO 206
<211> LENGTH: 17
<212> TYPE: PRT
<213> ORGANISM: Artificial Sequence
<220> FEATURE:
<223> OTHER INFORMATION: Synthetic: 3.7F5  VL CDR1

<400> SEQUENCE: 206

Lys Ser Ser Gln Ser Leu Leu Tyr Arg Asn Asp Gln Ile Asn Tyr Leu
1               5                   10                  15

Ala

<210> SEQ ID NO 207
<211> LENGTH: 7
<212> TYPE: PRT
<213> ORGANISM: Artificial Sequence
<220> FEATURE:
<223> OTHER INFORMATION: Synthetic: 3.7F5 VL CDR2

<400> SEQUENCE: 207

Trp Ala Ser Thr Arg Glu Ser
1               5

<210> SEQ ID NO 208
<211> LENGTH: 9
<212> TYPE: PRT
<213> ORGANISM: Artificial Sequence
<220> FEATURE:
<223> OTHER INFORMATION: Synthetic: 3.7F5 VL CDR3

<400> SEQUENCE: 208

Gln Gln Tyr Tyr Ser Tyr Pro Pro Thr
1               5

<210> SEQ ID NO 209
<211> LENGTH: 114
<212> TYPE: PRT
<213> ORGANISM: Artificial Sequence
<220> FEATURE:
<223> OTHER INFORMATION: Synthetic: 3.7F5 VH

<400> SEQUENCE: 209

Glu Ile His Leu Gln Gln Ser Gly Pro Glu Val Val Gln Pro Gly Ala
1               5                   10                  15
```

```
Ser Leu Lys Val Ser Cys Lys Ala Ser Asp Tyr Ser Phe Thr Asp Tyr
            20                  25                  30

Asn Val Phe Trp Val Lys Gln Ser His Gly Lys Ser Leu Glu Trp Ile
            35                  40                  45

Ala Tyr Ile Asp Pro Tyr Asn Gly Ala Thr Ser Tyr Asn Gln Lys Phe
            50                  55                  60

Lys Asp Lys Ala Thr Leu Thr Val Asp Lys Ser Ser Ser Thr Ala Phe
65                  70                  75                  80

Met Tyr Leu Asn Ser Leu Thr Ser Glu Asp Ser Ala Val Tyr Tyr Cys
                    85                  90                  95

Ala Arg Gly Thr Val Arg Ala Phe Phe Asp Ser Trp Gly Gln Gly Thr
            100                 105                 110

Thr Leu

<210> SEQ ID NO 210
<211> LENGTH: 106
<212> TYPE: PRT
<213> ORGANISM: Artificial Sequence
<220> FEATURE:
<223> OTHER INFORMATION: Synthetic: 3.7F5 VL

<400> SEQUENCE: 210

Asp Ile Val Met Ser Gln Ser Pro Ser Ser Leu Val Val Ser Val Gly
1                   5                   10                  15

Glu Lys Val Ser Leu Ser Cys Lys Ser Ser Gln Ser Leu Leu Tyr Arg
            20                  25                  30

Asn Asp Gln Ile Asn Tyr Leu Ala Trp Tyr Gln Gln Lys Pro Gly Gln
            35                  40                  45

Ser Pro Lys Leu Leu Ile Phe Trp Ala Ser Thr Arg Glu Ser Gly Val
            50                  55                  60

Pro Val Arg Phe Thr Gly Ser Gly Ser Gly Thr Asp Phe Thr Leu Asn
65                  70                  75                  80

Ile Asn Thr Val Lys Ala Glu Asp Leu Ala Val Tyr Tyr Cys Gln Gln
                    85                  90                  95

Tyr Tyr Ser Tyr Pro Pro Thr Phe Gly Thr
            100                 105

<210> SEQ ID NO 211
<211> LENGTH: 467
<212> TYPE: PRT
<213> ORGANISM: Artificial Sequence
<220> FEATURE:
<223> OTHER INFORMATION: Synthetic: 3.7F5 HC LALAPG mIgG2a

<400> SEQUENCE: 211

Met Gly Trp Ser Cys Ile Ile Leu Phe Leu Val Ala Thr Ala Thr Gly
1                   5                   10                  15

Ala Tyr Ala Glu Ile His Leu Gln Gln Ser Gly Pro Glu Val Val Gln
            20                  25                  30

Pro Gly Ala Ser Leu Lys Val Ser Cys Lys Ala Ser Asp Tyr Ser Phe
            35                  40                  45

Thr Asp Tyr Asn Val Phe Trp Val Lys Gln Ser His Gly Lys Ser Leu
            50                  55                  60

Glu Trp Ile Ala Tyr Ile Asp Pro Tyr Asn Gly Ala Thr Ser Tyr Asn
65                  70                  75                  80

Gln Lys Phe Lys Asp Lys Ala Thr Leu Thr Val Asp Lys Ser Ser Ser
                    85                  90                  95
```

-continued

```
Thr Ala Phe Met Tyr Leu Asn Ser Leu Thr Ser Glu Asp Ser Ala Val
            100                 105                 110

Tyr Tyr Cys Ala Arg Gly Thr Val Arg Ala Phe Phe Asp Ser Trp Gly
            115                 120                 125

Gln Gly Thr Thr Leu Thr Val Ser Ser Ala Ser Thr Lys Gly Pro Ser
    130                 135                 140

Val Tyr Pro Leu Ala Pro Val Cys Gly Asp Thr Thr Gly Ser Ser Val
145                 150                 155                 160

Thr Leu Gly Cys Leu Val Lys Gly Tyr Phe Pro Glu Pro Val Thr Leu
            165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Thr
            195                 200                 205

Ser Ser Thr Trp Pro Ser Gln Ser Ile Thr Cys Asn Val Ala His Pro
    210                 215                 220

Ala Ser Ser Thr Lys Val Asp Lys Lys Ile Glu Pro Arg Gly Pro Thr
225                 230                 235                 240

Ile Lys Pro Cys Pro Pro Cys Lys Cys Pro Ala Pro Asn Ala Ala Gly
            245                 250                 255

Gly Pro Ser Val Phe Ile Phe Pro Pro Lys Ile Lys Asp Val Leu Met
            260                 265                 270

Ile Ser Leu Ser Pro Ile Val Thr Cys Val Val Val Asp Val Ser Glu
            275                 280                 285

Asp Asp Pro Asp Val Gln Ile Ser Trp Phe Val Asn Asn Val Glu Val
    290                 295                 300

His Thr Ala Gln Thr Gln Thr His Arg Glu Asp Tyr Asn Ser Thr Leu
305                 310                 315                 320

Arg Val Val Ser Ala Leu Pro Ile Gln His Gln Asp Trp Met Ser Gly
            325                 330                 335

Lys Glu Phe Lys Cys Lys Val Asn Asn Lys Asp Leu Gly Ala Pro Ile
            340                 345                 350

Glu Arg Thr Ile Ser Lys Pro Lys Gly Ser Val Arg Ala Pro Gln Val
            355                 360                 365

Tyr Val Leu Pro Pro Pro Glu Glu Glu Met Thr Lys Lys Gln Val Thr
    370                 375                 380

Leu Thr Cys Met Val Thr Asp Phe Met Pro Glu Asp Ile Tyr Val Glu
385                 390                 395                 400

Trp Thr Asn Asn Gly Lys Thr Glu Leu Asn Tyr Lys Asn Thr Glu Pro
            405                 410                 415

Val Leu Asp Ser Asp Gly Ser Tyr Phe Met Tyr Ser Lys Leu Arg Val
            420                 425                 430

Glu Lys Lys Asn Trp Val Glu Arg Asn Ser Tyr Ser Cys Ser Val Val
            435                 440                 445

His Glu Gly Leu His Asn His His Thr Thr Lys Ser Phe Ser Arg Thr
    450                 455                 460

Pro Gly Lys
465
```

<210> SEQ ID NO 212
<211> LENGTH: 239
<212> TYPE: PRT
<213> ORGANISM: Artificial Sequence
<220> FEATURE:
<223> OTHER INFORMATION: Synthetic: 3.7F5 LC LALAPG mIgG2a

<400> SEQUENCE: 212

```
Met Gly Trp Ser Cys Ile Ile Leu Phe Leu Val Ala Thr Ala Thr Gly
1               5                   10                  15

Val His Ser Asp Ile Val Met Ser Gln Ser Pro Ser Ser Leu Val Val
                20                  25                  30

Ser Val Gly Glu Lys Val Ser Leu Ser Cys Lys Ser Ser Gln Ser Leu
            35                  40                  45

Leu Tyr Arg Asn Asp Gln Ile Asn Tyr Leu Ala Trp Tyr Gln Gln Lys
        50                  55                  60

Pro Gly Gln Ser Pro Lys Leu Leu Ile Phe Trp Ala Ser Thr Arg Glu
65                  70                  75                  80

Ser Gly Val Pro Val Arg Phe Thr Gly Ser Gly Ser Gly Thr Asp Phe
                85                  90                  95

Thr Leu Asn Ile Asn Thr Val Lys Ala Glu Asp Leu Ala Val Tyr Tyr
            100                 105                 110

Cys Gln Gln Tyr Tyr Ser Tyr Pro Pro Thr Phe Gly Thr Gly Thr Lys
            115                 120                 125

Leu Glu Ile Lys Arg Ala Asp Ala Ala Pro Thr Val Ser Ile Phe Pro
        130                 135                 140

Pro Ser Ser Glu Gln Leu Thr Ser Gly Gly Ala Ser Val Val Cys Phe
145                 150                 155                 160

Leu Asn Asn Phe Tyr Pro Lys Asp Ile Asn Val Lys Trp Lys Ile Asp
                165                 170                 175

Gly Ser Glu Arg Gln Asn Gly Val Leu Asn Ser Trp Thr Asp Gln Asp
            180                 185                 190

Ser Lys Asp Ser Thr Tyr Ser Met Ser Ser Thr Leu Thr Leu Thr Lys
            195                 200                 205

Asp Glu Tyr Glu Arg His Asn Ser Tyr Thr Cys Glu Ala Thr His Lys
        210                 215                 220

Thr Ser Thr Ser Pro Ile Val Lys Ser Phe Asn Arg Asn Glu Cys
225                 230                 235
```

<210> SEQ ID NO 213
<211> LENGTH: 370
<212> TYPE: PRT
<213> ORGANISM: Homo sapiens
<220> FEATURE:
<221> NAME/KEY: misc_feature
<222> LOCATION: (1)..(370)
<223> OTHER INFORMATION: Human APOL1 KIK isotype G0 form (no signal
      sequence)

<400> SEQUENCE: 213

```
Glu Ala Gly Ala Arg Val Gln Gln Asn Val Pro Ser Gly Thr Asp Thr
1               5                   10                  15

Gly Asp Pro Gln Ser Lys Pro Leu Gly Asp Trp Ala Ala Gly Thr Met
                20                  25                  30

Asp Pro Glu Ser Ser Ile Phe Ile Glu Asp Ala Ile Lys Tyr Phe Lys
            35                  40                  45

Glu Lys Val Ser Thr Gln Asn Leu Leu Leu Leu Leu Thr Asp Asn Glu
        50                  55                  60

Ala Trp Asn Gly Phe Val Ala Ala Ala Glu Leu Pro Arg Asn Glu Ala
65                  70                  75                  80

Asp Glu Leu Arg Lys Ala Leu Asp Asn Leu Ala Arg Gln Met Ile Met
                85                  90                  95
```

```
Lys Asp Lys Asn Trp His Asp Lys Gly Gln Gln Tyr Arg Asn Trp Phe
            100             105             110

Leu Lys Glu Phe Pro Arg Leu Lys Ser Lys Leu Glu Asp Asn Ile Arg
        115             120             125

Arg Leu Arg Ala Leu Ala Asp Gly Val Gln Lys Val His Lys Gly Thr
    130             135             140

Thr Ile Ala Asn Val Val Ser Gly Ser Leu Ser Ile Ser Ser Gly Ile
145             150             155             160

Leu Thr Leu Val Gly Met Gly Leu Ala Pro Phe Thr Glu Gly Gly Ser
            165             170             175

Leu Val Leu Leu Glu Pro Gly Met Glu Leu Gly Ile Thr Ala Ala Leu
        180             185             190

Thr Gly Ile Thr Ser Ser Thr Ile Asp Tyr Gly Lys Lys Trp Trp Thr
        195             200             205

Gln Ala Gln Ala His Asp Leu Val Ile Lys Ser Leu Asp Lys Leu Lys
    210             215             220

Glu Val Lys Glu Phe Leu Gly Glu Asn Ile Ser Asn Phe Leu Ser Leu
225             230             235             240

Ala Gly Asn Thr Tyr Gln Leu Thr Arg Gly Ile Gly Lys Asp Ile Arg
            245             250             255

Ala Leu Arg Arg Ala Arg Ala Asn Leu Gln Ser Val Pro His Ala Ser
        260             265             270

Ala Ser Arg Pro Arg Val Thr Glu Pro Ile Ser Ala Glu Ser Gly Glu
        275             280             285

Gln Val Glu Arg Val Asn Glu Pro Ser Ile Leu Glu Met Ser Arg Gly
    290             295             300

Val Lys Leu Thr Asp Val Ala Pro Val Ser Phe Phe Leu Val Leu Asp
305             310             315             320

Val Val Tyr Leu Val Tyr Glu Ser Lys His Leu His Glu Gly Ala Lys
            325             330             335

Ser Glu Thr Ala Glu Glu Leu Lys Lys Val Ala Gln Glu Leu Glu Glu
        340             345             350

Lys Leu Asn Ile Leu Asn Asn Asn Tyr Lys Ile Leu Gln Ala Asp Gln
        355             360             365

Glu Leu
    370
```

```
<210> SEQ ID NO 214
<211> LENGTH: 370
<212> TYPE: PRT
<213> ORGANISM: Homo sapiens
<220> FEATURE:
<221> NAME/KEY: misc_feature
<222> LOCATION: (1)..(370)
<223> OTHER INFORMATION: Human APOL1 EIK isotype G0 form (no signal
      sequence)

<400> SEQUENCE: 214
```

```
Glu Ala Gly Ala Arg Val Gln Gln Asn Val Pro Ser Gly Thr Asp Thr
1               5               10              15

Gly Asp Pro Gln Ser Lys Pro Leu Gly Asp Trp Ala Ala Gly Thr Met
            20              25              30

Asp Pro Glu Ser Ser Ile Phe Ile Glu Asp Ala Ile Lys Tyr Phe Lys
        35              40              45

Glu Lys Val Ser Thr Gln Asn Leu Leu Leu Leu Leu Thr Asp Asn Glu
    50              55              60
```

-continued

```
Ala Trp Asn Gly Phe Val Ala Ala Ala Glu Leu Pro Arg Asn Glu Ala
65                  70                  75                  80

Asp Glu Leu Arg Lys Ala Leu Asp Asn Leu Ala Arg Gln Met Ile Met
                85                  90                  95

Lys Asp Lys Asn Trp His Asp Lys Gly Gln Gln Tyr Arg Asn Trp Phe
            100                 105                 110

Leu Lys Glu Phe Pro Arg Leu Lys Ser Glu Leu Glu Asp Asn Ile Arg
        115                 120                 125

Arg Leu Arg Ala Leu Ala Asp Gly Val Gln Lys Val His Lys Gly Thr
    130                 135                 140

Thr Ile Ala Asn Val Val Ser Gly Ser Leu Ser Ile Ser Ser Gly Ile
145                 150                 155                 160

Leu Thr Leu Val Gly Met Gly Leu Ala Pro Phe Thr Glu Gly Gly Ser
                165                 170                 175

Leu Val Leu Leu Glu Pro Gly Met Glu Leu Gly Ile Thr Ala Ala Leu
                180                 185                 190

Thr Gly Ile Thr Ser Ser Thr Ile Asp Tyr Gly Lys Lys Trp Trp Thr
            195                 200                 205

Gln Ala Gln Ala His Asp Leu Val Ile Lys Ser Leu Asp Lys Leu Lys
    210                 215                 220

Glu Val Lys Glu Phe Leu Gly Glu Asn Ile Ser Asn Phe Leu Ser Leu
225                 230                 235                 240

Ala Gly Asn Thr Tyr Gln Leu Thr Arg Gly Ile Gly Lys Asp Ile Arg
                245                 250                 255

Ala Leu Arg Arg Ala Arg Ala Asn Leu Gln Ser Val Pro His Ala Ser
            260                 265                 270

Ala Ser Arg Pro Arg Val Thr Glu Pro Ile Ser Ala Glu Ser Gly Glu
            275                 280                 285

Gln Val Glu Arg Val Asn Glu Pro Ser Ile Leu Glu Met Ser Arg Gly
    290                 295                 300

Val Lys Leu Thr Asp Val Ala Pro Val Ser Phe Phe Leu Val Leu Asp
305                 310                 315                 320

Val Val Tyr Leu Val Tyr Glu Ser Lys His Leu His Glu Gly Ala Lys
                325                 330                 335

Ser Glu Thr Ala Glu Glu Leu Lys Lys Val Ala Gln Glu Leu Glu Glu
            340                 345                 350

Lys Leu Asn Ile Leu Asn Asn Asn Tyr Lys Ile Leu Gln Ala Asp Gln
            355                 360                 365

Glu Leu
    370
```

```
<210> SEQ ID NO 215
<211> LENGTH: 370
<212> TYPE: PRT
<213> ORGANISM: Homo sapiens
<220> FEATURE:
<221> NAME/KEY: misc_feature
<222> LOCATION: (1)..(370)
<223> OTHER INFORMATION: Human APOL1 G1 variant of EMR isotype (no
      signal sequence)

<400> SEQUENCE: 215

Glu Ala Gly Ala Arg Val Gln Gln Asn Val Pro Ser Gly Thr Asp Thr
1               5                   10                  15

Gly Asp Pro Gln Ser Lys Pro Leu Gly Asp Trp Ala Ala Gly Thr Met
            20                  25                  30
```

```
Asp Pro Glu Ser Ser Ile Phe Ile Glu Asp Ala Ile Lys Tyr Phe Lys
        35                  40                  45

Glu Lys Val Ser Thr Gln Asn Leu Leu Leu Leu Leu Thr Asp Asn Glu
    50                  55                  60

Ala Trp Asn Gly Phe Val Ala Ala Ala Glu Leu Pro Arg Asn Glu Ala
65                  70                  75                  80

Asp Glu Leu Arg Lys Ala Leu Asp Asn Leu Ala Arg Gln Met Ile Met
                85                  90                  95

Lys Asp Lys Asn Trp His Asp Lys Gly Gln Gln Tyr Arg Asn Trp Phe
                100                 105                 110

Leu Lys Glu Phe Pro Arg Leu Lys Ser Glu Leu Glu Asp Asn Ile Arg
        115                 120                 125

Arg Leu Arg Ala Leu Ala Asp Gly Val Gln Lys Val His Lys Gly Thr
    130                 135                 140

Thr Ile Ala Asn Val Val Ser Gly Ser Leu Ser Ile Ser Ser Gly Ile
145                 150                 155                 160

Leu Thr Leu Val Gly Met Gly Leu Ala Pro Phe Thr Glu Gly Gly Ser
                165                 170                 175

Leu Val Leu Leu Glu Pro Gly Met Glu Leu Gly Ile Thr Ala Ala Leu
                180                 185                 190

Thr Gly Ile Thr Ser Ser Thr Met Asp Tyr Gly Lys Lys Trp Trp Thr
            195                 200                 205

Gln Ala Gln Ala His Asp Leu Val Ile Lys Ser Leu Asp Lys Leu Lys
    210                 215                 220

Glu Val Arg Glu Phe Leu Gly Glu Asn Ile Ser Asn Phe Leu Ser Leu
225                 230                 235                 240

Ala Gly Asn Thr Tyr Gln Leu Thr Arg Gly Ile Gly Lys Asp Ile Arg
                245                 250                 255

Ala Leu Arg Arg Ala Arg Ala Asn Leu Gln Ser Val Pro His Ala Ser
                260                 265                 270

Ala Ser Arg Pro Arg Val Thr Glu Pro Ile Ser Ala Glu Ser Gly Glu
        275                 280                 285

Gln Val Glu Arg Val Asn Glu Pro Ser Ile Leu Glu Met Ser Arg Gly
    290                 295                 300

Val Lys Leu Thr Asp Val Ala Pro Val Gly Phe Phe Leu Val Leu Asp
305                 310                 315                 320

Val Val Tyr Leu Val Tyr Glu Ser Lys His Leu His Glu Gly Ala Lys
                325                 330                 335

Ser Glu Thr Ala Glu Glu Leu Lys Lys Val Ala Gln Glu Leu Glu Glu
            340                 345                 350

Lys Leu Asn Met Leu Asn Asn Asn Tyr Lys Ile Leu Gln Ala Asp Gln
        355                 360                 365

Glu Leu
    370
```

<210> SEQ ID NO 216
<211> LENGTH: 368
<212> TYPE: PRT
<213> ORGANISM: Homo sapiens
<220> FEATURE:
<221> NAME/KEY: misc_feature
<222> LOCATION: (1)..(368)
<223> OTHER INFORMATION: Human APOL1 G2 variant of EMR isotype (no
      signal sequence)

<400> SEQUENCE: 216

```
Glu Ala Gly Ala Arg Val Gln Gln Asn Val Pro Ser Gly Thr Asp Thr
1               5                   10                  15

Gly Asp Pro Gln Ser Lys Pro Leu Gly Asp Trp Ala Ala Gly Thr Met
            20                  25                  30

Asp Pro Glu Ser Ser Ile Phe Ile Glu Asp Ala Ile Lys Tyr Phe Lys
            35                  40                  45

Glu Lys Val Ser Thr Gln Asn Leu Leu Leu Leu Leu Thr Asp Asn Glu
    50                  55                  60

Ala Trp Asn Gly Phe Val Ala Ala Ala Glu Leu Pro Arg Asn Glu Ala
65                  70                  75                  80

Asp Glu Leu Arg Lys Ala Leu Asp Asn Leu Ala Arg Gln Met Ile Met
                85                  90                  95

Lys Asp Lys Asn Trp His Asp Lys Gly Gln Gln Tyr Arg Asn Trp Phe
            100                 105                 110

Leu Lys Glu Phe Pro Arg Leu Lys Ser Glu Leu Glu Asp Asn Ile Arg
            115                 120                 125

Arg Leu Arg Ala Leu Ala Asp Gly Val Gln Lys Val His Lys Gly Thr
    130                 135                 140

Thr Ile Ala Asn Val Val Ser Gly Ser Leu Ser Ile Ser Ser Gly Ile
145                 150                 155                 160

Leu Thr Leu Val Gly Met Gly Leu Ala Pro Phe Thr Glu Gly Gly Ser
            165                 170                 175

Leu Val Leu Leu Glu Pro Gly Met Glu Leu Gly Ile Thr Ala Ala Leu
            180                 185                 190

Thr Gly Ile Thr Ser Ser Thr Met Asp Tyr Gly Lys Lys Trp Trp Thr
            195                 200                 205

Gln Ala Gln Ala His Asp Leu Val Ile Lys Ser Leu Asp Lys Leu Lys
    210                 215                 220

Glu Val Arg Glu Phe Leu Gly Glu Asn Ile Ser Asn Phe Leu Ser Leu
225                 230                 235                 240

Ala Gly Asn Thr Tyr Gln Leu Thr Arg Gly Ile Gly Lys Asp Ile Arg
            245                 250                 255

Ala Leu Arg Arg Ala Arg Ala Asn Leu Gln Ser Val Pro His Ala Ser
            260                 265                 270

Ala Ser Arg Pro Arg Val Thr Glu Pro Ile Ser Ala Glu Ser Gly Glu
            275                 280                 285

Gln Val Glu Arg Val Asn Glu Pro Ser Ile Leu Glu Met Ser Arg Gly
    290                 295                 300

Val Lys Leu Thr Asp Val Ala Pro Val Ser Phe Phe Leu Val Leu Asp
305                 310                 315                 320

Val Val Tyr Leu Val Tyr Glu Ser Lys His Leu His Glu Gly Ala Lys
            325                 330                 335

Ser Glu Thr Ala Glu Glu Leu Lys Lys Val Ala Gln Glu Leu Glu Glu
            340                 345                 350

Lys Leu Asn Ile Leu Asn Asn Lys Ile Leu Gln Ala Asp Gln Glu Leu
            355                 360                 365
```

```
<210> SEQ ID NO 217
<211> LENGTH: 41
<212> TYPE: PRT
<213> ORGANISM: Artificial Sequence
<220> FEATURE:
<223> OTHER INFORMATION: Synthetic: vA (v1)

<400> SEQUENCE: 217
```

-continued

```
Met Glu Gly Ala Ala Leu Leu Arg Val Ser Val Leu Cys Ile Trp Met
1               5                   10                  15

Ser Ala Leu Phe Leu Gly Val Gly Val Arg Ala Glu Glu Ala Gly Ala
            20                  25                  30

Arg Val Gln Gln Asn Val Pro Ser Gly
        35                  40
```

<210> SEQ ID NO 218
<211> LENGTH: 57
<212> TYPE: PRT
<213> ORGANISM: Artificial Sequence
<220> FEATURE:
<223> OTHER INFORMATION: Synthetic: vB1 (v2)

<400> SEQUENCE: 218

```
Met Arg Phe Lys Ser His Thr Val Glu Leu Arg Arg Pro Cys Ser Asp
1               5                   10                  15

Met Glu Gly Ala Ala Leu Leu Arg Val Ser Val Leu Cys Ile Trp Met
            20                  25                  30

Ser Ala Leu Phe Leu Gly Val Gly Val Arg Ala Glu Glu Ala Gly Ala
        35                  40                  45

Arg Val Gln Gln Asn Val Pro Ser Gly
    50                  55
```

<210> SEQ ID NO 219
<211> LENGTH: 39
<212> TYPE: PRT
<213> ORGANISM: Artificial Sequence
<220> FEATURE:
<223> OTHER INFORMATION: Synthetic: vB3 (v2-3)

<400> SEQUENCE: 219

```
Met Arg Phe Lys Ser His Thr Val Glu Leu Arg Arg Pro Cys Ser Asp
1               5                   10                  15

Met Glu Gly Ala Ala Leu Leu Arg Val Ser Val Leu Cys Ile Trp Val
            20                  25                  30

Gln Gln Asn Val Pro Ser Gly
        35
```

<210> SEQ ID NO 220
<211> LENGTH: 23
<212> TYPE: PRT
<213> ORGANISM: Artificial Sequence
<220> FEATURE:
<223> OTHER INFORMATION: Synthetic: vC (v4)

<400> SEQUENCE: 220

```
Met Glu Gly Ala Ala Leu Leu Arg Val Ser Val Leu Cys Ile Trp Val
1               5                   10                  15

Gln Gln Asn Val Pro Ser Gly
            20
```

APOLIPOPROTEIN L1-SPECIFIC ANTIBODIES AND METHODS OF USE

CROSS-REFERENCE TO RELATED APPLICATIONS

This application is a continuation of International Patent Application No. PCT/US2020/066377, filed Dec. 21, 2020, which claims the benefit of priority of U.S. Provisional Patent Application No. 62/953,097, filed Dec. 23, 2019, the contents of which are incorporated herein by reference in their entireties.

SEQUENCE LISTING

This application contains a Sequence Listing in computer readable form entitled "01164-0003-00PCT_ST25", created Jun. 3, 2022, having a size of 219000 Bytes, which is incorporated by reference herein.

FIELD

The present disclosure provides anti-apolipoprotein L1 (APOL1) antibodies, including anti-APOL1 antibodies that may distinguish the G0 and G1 forms from the G2 form of APOL1, distinguish APOL1 found on podocytes from that found on HDL particles in serum, and/or distinguish APOL1 from apolipoproteins L2 and L3 (APOL2 and APOL3). The disclosure also provides, inter alia, methods of using the antibodies, methods of making the antibodies, and nucleic acids encoding the antibodies.

BACKGROUND

Antibodies that specifically bind to APOL1 may be useful in various detection methods, for example, associated with assessing APOL1 on kidney podocyte cells and distinguishing it from other related proteins such as APOL2 and APOL3, distinguishing among particular variants of APOL1, and determining the expression of APOL1 on podocytes vs. at other locations such as in serum HDL particles. For example, two variants of APOL1, termed G1 and G2 (with wild-type APOL1 designated G0), are risk factors for renal disease, particularly in African Americans as compared to European Americans. Evidence supports that expression of APOL1 in kidney podocytes, rather than circulating APOL1, is likely responsible for kidney disease. Thus, for various detection methods, it may be helpful to use specific antibodies that recognize APOL1 localized on podocytes, and that may also be able to distinguish different forms of APOL1.

Localization of endogenous APOL1 has not been conclusively established, however, because most published antibodies cross-react with APOL2. For example, previous immunolocalization studies utilized commercially available antibodies that we demonstrate in the Examples below cross-react with APOL2. APOL2 is at least as abundant in kidneys and podocytes as APOL1. Most studies also used overexpressed APOL1, which may not traffic normally, and the antibodies they used were not characterized for cross-reactivity with related APOL family members. Those antibodies reportedly stained endogenous APOL1 in podocytes, endothelial cells and proximal tubules of human kidneys. But as we found that the antibodies used in those earlier experiments also recognize APOL2, one cannot be certain from them whether APOL1 is truly expressed at all of these purported locations. As described in the Examples below, we have generated antibodies that specifically bind APOL1 that are sensitive enough to detect endogenous podocyte APOL1, and some of which are able to distinguish APOL1 from APOL2 and other apolipoprotein family members such as APOL3, APOL4, and APOL6. In some aspects, these antibodies may be used in detecting APOL1 localized on podocytes, which can be used in detection methods such as immunofluorescence microscopy and immunohistochemistry.

Antibodies herein were also generated to different regions of the APOL1 molecule, which allow for information about portions of APOL1 that are exposed on podocytes but that are, for example, buried in APOL1 found in serum HDL particles. Such antibodies may be useful, for example, in distinguishing APOL1 found on cells such as podocytes, endothelial cells and hepatocytes from APOL1 found in serum such as on HDL particles. In addition, such antibodies may allow for targeting of other molecules such as drugs specifically to APOL1-expressing cells such as podocyte cells, endothelial cells and hepatocytes.

SUMMARY

The disclosure herein relates to certain anti-apolipoprotein L1 antibodies. Exemplary embodiments include an isolated antibody that specifically binds to apolipoprotein L1 (APOL1), wherein the antibody comprises:

(a) a heavy chain variable region (VH) comprising a CDR-H1 comprising the amino acid sequence of SEQ ID NO: 3, a CDR-H2 comprising the amino acid sequence of SEQ ID NO: 4, and a CDR-H3 comprising the amino acid sequence of SEQ ID NO: 5; and a light chain variable region (VL) comprising a CDR-L1 comprising the amino acid sequence of SEQ ID NO: 6, a CDR-L2 comprising the amino acid sequence of SEQ ID NO: 7, and a CDR-L3 comprising the amino acid sequence of SEQ ID NO: 8;

(b) a heavy chain variable region (VH) comprising a CDR-H1 comprising the amino acid sequence of SEQ ID NO: 13, a CDR-H2 comprising the amino acid sequence of SEQ ID NO: 14, and a CDR-H3 comprising the amino acid sequence of SEQ ID NO: 15; and a light chain variable region (VL) comprising a CDR-L1 comprising the amino acid sequence of SEQ ID NO: 16, a CDR-L2 comprising the amino acid sequence of SEQ ID NO: 17, and a CDR-L3 comprising the amino acid sequence of SEQ ID NO: 18;

(c) a heavy chain variable region (VH) comprising a CDR-H1 comprising the amino acid sequence of SEQ ID NO: 23, a CDR-H2 comprising the amino acid sequence of SEQ ID NO: 24, and a CDR-H3 comprising the amino acid sequence of SEQ ID NO: 25; and a light chain variable region (VL) comprising a CDR-L1 comprising the amino acid sequence of SEQ ID NO: 26, a CDR-L2 comprising the amino acid sequence of SEQ ID NO: 27, and a CDR-L3 comprising the amino acid sequence of SEQ ID NO: 28;

(d) a heavy chain variable region (VH) comprising a CDR-H1 comprising the amino acid sequence of SEQ ID NO: 33, a CDR-H2 comprising the amino acid sequence of SEQ ID NO: 34, and a CDR-H3 comprising the amino acid sequence of SEQ ID NO: 35; and a light chain variable region (VL) comprising a CDR-L1 comprising the amino acid sequence of SEQ ID NO: 36, a CDR-L2 comprising the amino acid sequence of SEQ ID NO: 37, and a CDR-L3 comprising the amino acid sequence of SEQ ID NO: 38;

(e) a heavy chain variable region (VH) comprising a CDR-H1 comprising the amino acid sequence of SEQ ID NO: 43, a CDR-H2 comprising the amino acid sequence of SEQ ID NO: 44, and a CDR-H3 comprising the amino acid sequence of SEQ ID NO: 45; and a light chain variable region (VL) comprising a CDR-L1 comprising the amino acid sequence of SEQ ID NO: 46, a CDR-L2 comprising the amino acid sequence of SEQ ID NO: 47, and a CDR-L3 comprising the amino acid sequence of SEQ ID NO: 48;

(f) a heavy chain variable region (VH) comprising a CDR-H1 comprising the amino acid sequence of SEQ ID NO: 53, a CDR-H2 comprising the amino acid sequence of SEQ ID NO: 54, and a CDR-H3 comprising the amino acid sequence of SEQ ID NO: 55; and a light chain variable region (VL) comprising a CDR-L1 comprising the amino acid sequence of SEQ ID NO: 56, a CDR-L2 comprising the amino acid sequence of SEQ ID NO: 57, and a CDR-L3 comprising the amino acid sequence of SEQ ID NO: 58;

(g) a heavy chain variable region (VH) comprising a CDR-H1 comprising the amino acid sequence of SEQ ID NO: 63, a CDR-H2 comprising the amino acid sequence of SEQ ID NO: 64, and a CDR-H3 comprising the amino acid sequence of SEQ ID NO: 65; and a light chain variable region (VL) comprising a CDR-L1 comprising the amino acid sequence of SEQ ID NO: 66, a CDR-L2 comprising the amino acid sequence of SEQ ID NO: 67, and a CDR-L3 comprising the amino acid sequence of SEQ ID NO: 68;

(h) a heavy chain variable region (VH) comprising a CDR-H1 comprising the amino acid sequence of SEQ ID NO: 73, a CDR-H2 comprising the amino acid sequence of SEQ ID NO: 74, and a CDR-H3 comprising the amino acid sequence of SEQ ID NO: 75; and a light chain variable region (VL) comprising a CDR-L1 comprising the amino acid sequence of SEQ ID NO: 76, a CDR-L2 comprising the amino acid sequence of SEQ ID NO: 77, and a CDR-L3 comprising the amino acid sequence of SEQ ID NO: 78;

(i) heavy chain variable region (VH) comprising a CDR-H1 comprising the amino acid sequence of SEQ ID NO: 83, a CDR-H2 comprising the amino acid sequence of SEQ ID NO: 84, and a CDR-H3 comprising the amino acid sequence of SEQ ID NO: 85; and a light chain variable region (VL) comprising a CDR-L1 comprising the amino acid sequence of SEQ ID NO: 86, a CDR-L2 comprising the amino acid sequence of SEQ ID NO: 87, and a CDR-L3 comprising the amino acid sequence of SEQ ID NO: 88;

(j) a heavy chain variable region (VH) comprising a CDR-H1 comprising the amino acid sequence of SEQ ID NO: 93, a CDR-H2 comprising the amino acid sequence of SEQ ID NO: 94, and a CDR-H3 comprising the amino acid sequence of SEQ ID NO: 95; and a light chain variable region (VL) comprising a CDR-L1 comprising the amino acid sequence of SEQ ID NO: 96, a CDR-L2 comprising the amino acid sequence of SEQ ID NO: 97, and a CDR-L3 comprising the amino acid sequence of SEQ ID NO: 98;

(k) a heavy chain variable region (VH) comprising a CDR-H1 comprising the amino acid sequence of SEQ ID NO: 103, a CDR-H2 comprising the amino acid sequence of SEQ ID NO: 104, and a CDR-H3 comprising the amino acid sequence of SEQ ID NO: 105; and a light chain variable region (VL) comprising a CDR-L1 comprising the amino acid sequence of SEQ ID NO: 106, a CDR-L2 comprising the amino acid sequence of SEQ ID NO: 107, and a CDR-L3 comprising the amino acid sequence of SEQ ID NO: 108;

(l) a heavy chain variable region (VH) comprising a CDR-H1 comprising the amino acid sequence of SEQ ID NO: 113, a CDR-H2 comprising the amino acid sequence of SEQ ID NO: 114, and a CDR-H3 comprising the amino acid sequence of SEQ ID NO: 115; and a light chain variable region (VL) comprising a CDR-L1 comprising the amino acid sequence of SEQ ID NO: 116, a CDR-L2 comprising the amino acid sequence of SEQ ID NO: 117, and a CDR-L3 comprising the amino acid sequence of SEQ ID NO: 118;

(m) a heavy chain variable region (VH) comprising a CDR-H1 comprising the amino acid sequence of SEQ ID NO: 123, a CDR-H2 comprising the amino acid sequence of SEQ ID NO: 124, and a CDR-H3 comprising the amino acid sequence of SEQ ID NO: 125; and a light chain variable region (VL) comprising a CDR-L1 comprising the amino acid sequence of SEQ ID NO: 126, a CDR-L2 comprising the amino acid sequence of SEQ ID NO: 127, and a CDR-L3 comprising the amino acid sequence of SEQ ID NO: 128;

(n) a heavy chain variable region (VH) comprising a CDR-H1 comprising the amino acid sequence of SEQ ID NO: 133, a CDR-H2 comprising the amino acid sequence of SEQ ID NO: 134, and a CDR-H3 comprising the amino acid sequence of SEQ ID NO: 135; and a light chain variable region (VL) comprising a CDR-L1 comprising the amino acid sequence of SEQ ID NO: 136, a CDR-L2 comprising the amino acid sequence of SEQ ID NO: 137, and a CDR-L3 comprising the amino acid sequence of SEQ ID NO: 138;

(o) a heavy chain variable region (VH) comprising a CDR-H1 comprising the amino acid sequence of SEQ ID NO: 143, a CDR-H2 comprising the amino acid sequence of SEQ ID NO: 144, and a CDR-H3 comprising the amino acid sequence of SEQ ID NO: 145; and a light chain variable region (VL) comprising a CDR-L1 comprising the amino acid sequence of SEQ ID NO: 146, a CDR-L2 comprising the amino acid sequence of SEQ ID NO: 147, and a CDR-L3 comprising the amino acid sequence of SEQ ID NO: 148;

(p) a heavy chain variable region (VH) comprising a CDR-H1 comprising the amino acid sequence of SEQ ID NO: 153, a CDR-H2 comprising the amino acid sequence of SEQ ID NO: 154, and a CDR-H3 comprising the amino acid sequence of SEQ ID NO: 155; and a light chain variable region (VL) comprising a CDR-L1 comprising the amino acid sequence of SEQ ID NO: 156, a CDR-L2 comprising the amino acid sequence of SEQ ID NO: 157, and a CDR-L3 comprising the amino acid sequence of SEQ ID NO: 158;

(q) a heavy chain variable region (VH) comprising a CDR-H1 comprising the amino acid sequence of SEQ ID NO: 163, a CDR-H2 comprising the amino acid sequence of SEQ ID NO: 164, and a CDR-H3 comprising the amino acid sequence of SEQ ID NO: 165; and a light chain variable region (VL) comprising a CDR-L1 comprising the amino acid sequence of SEQ ID NO: 166, a CDR-L2 comprising the amino acid sequence of SEQ ID NO: 167, and a CDR-L3 comprising the amino acid sequence of SEQ ID NO: 168;

(r) a heavy chain variable region (VH) comprising a CDR-H1 comprising the amino acid sequence of SEQ ID NO: 173, a CDR-H2 comprising the amino acid sequence of SEQ ID NO: 174, and a CDR-H3 comprising the amino acid sequence of SEQ ID NO: 175; and a light chain variable region (VL) comprising a CDR-L1 comprising the amino acid sequence of SEQ ID NO: 176, a CDR-L2 comprising the amino acid sequence of SEQ ID NO: 177, and a CDR-L3 comprising the amino acid sequence of SEQ ID NO: 178;

(s) a heavy chain variable region (VH) comprising a CDR-H1 comprising the amino acid sequence of SEQ ID NO: 183, a CDR-H2 comprising the amino acid sequence of SEQ ID NO: 184, and a CDR-H3 comprising the amino acid sequence of SEQ ID NO: 185; and a light chain variable region (VL) comprising a CDR-L1 comprising the amino acid sequence of SEQ ID NO: 186, a CDR-L2 comprising the amino acid sequence of SEQ ID NO: 187, and a CDR-L3 comprising the amino acid sequence of SEQ ID NO: 188;

(t) a heavy chain variable region (VH) comprising a CDR-H1 comprising the amino acid sequence of SEQ ID NO: 193, a CDR-H2 comprising the amino acid sequence of SEQ ID NO: 194, and a CDR-H3 comprising the amino acid sequence of SEQ ID NO: 195; and a light chain variable region (VL) comprising a CDR-L1 comprising the amino acid sequence of SEQ ID NO: 196, a CDR-L2 comprising the amino acid sequence of SEQ ID NO: 197, and a CDR-L3 comprising the amino acid sequence of SEQ ID NO: 198; or (u) a heavy chain variable region (VH) comprising a CDR-H1 comprising the amino acid sequence of SEQ ID NO: 203, a CDR-H2 comprising the amino acid sequence of SEQ ID NO: 204, and a CDR-H3 comprising the amino acid sequence of SEQ ID NO: 205; and a light chain variable region (VL) comprising a CDR-L1 comprising the amino acid sequence of SEQ ID NO: 206, a CDR-L2 comprising the amino acid sequence of SEQ ID NO: 207, and a CDR-L3 comprising the amino acid sequence of SEQ ID NO: 208.

In some embodiments, the antibody comprises:

the CDRs of embodiment (a) above and further comprises a VH that is at least 90%, at least 95%, at least 97%, or at least 99% identical to the amino acid sequence of SEQ ID NO: 9 and/or a VL that is at least 90%, at least 95%, at least 97%, or at least 99% identical to the amino acid sequence of SEQ ID NO: 10;

the CDRs of embodiment (b) above and further comprises a VH that is at least 90%, at least 95%, at least 97%, or at least 99% identical to the amino acid sequence of SEQ ID NO: 19 and/or a VL that is at least 90%, at least 95%, at least 97%, or at least 99% identical to the amino acid sequence of SEQ ID NO: 20;

the CDRs of embodiment (c) above and further comprises a VH that is at least 90%, at least 95%, at least 97%, or at least 99% identical to the amino acid sequence of SEQ ID NO: 29 and/or a VL that is at least 90%, at least 95%, at least 97%, or at least 99% identical to the amino acid sequence of SEQ ID NO: 30;

the CDRs of embodiment (d) above and further comprises a VH that is at least 90%, at least 95%, at least 97%, or at least 99% identical to the amino acid sequence of SEQ ID NO: 39 and/or a VL that is at least 90%, at least 95%, at least 97%, or at least 99% identical to the amino acid sequence of SEQ ID NO: 40;

the CDRs of embodiment (e) above and further comprises a VH that is at least 90%, at least 95%, at least 97%, or at least 99% identical to the amino acid sequence of SEQ ID NO: 49 and/or a VL that is at least 90%, at least 95%, at least 97%, or at least 99% identical to the amino acid sequence of SEQ ID NO: 50;

the CDRs of embodiment (f) above and further comprises a VH that is at least 90%, at least 95%, at least 97%, or at least 99% identical to the amino acid sequence of SEQ ID NO: 59 and/or a VL that is at least 90%, at least 95%, at least 97%, or at least 99% identical to the amino acid sequence of SEQ ID NO: 60;

the CDRs of embodiment (g) above and further comprises a VH that is at least 90%, at least 95%, at least 97%, or at least 99% identical to the amino acid sequence of SEQ ID NO: 69 and/or a VL that is at least 90%, at least 95%, at least 97%, or at least 99% identical to the amino acid sequence of SEQ ID NO: 70;

the CDRs of embodiment (h) above and further comprises a VH that is at least 90%, at least 95%, at least 97%, or at least 99% identical to the amino acid sequence of SEQ ID NO: 79 and/or a VL that is at least 90%, at least 95%, at least 97%, or at least 99% identical to the amino acid sequence of SEQ ID NO: 80;

the CDRs of embodiment (i) above and further comprises a VH that is at least 90%, at least 95%, at least 97%, or at least 99% identical to the amino acid sequence of SEQ ID NO: 89 and/or a VL that is at least 90%, at least 95%, at least 97%, or at least 99% identical to the amino acid sequence of SEQ ID NO: 90;

the CDRs of embodiment (j) above and further comprises a VH that is at least 90%, at least 95%, at least 97%, or at least 99% identical to the amino acid sequence of SEQ ID NO: 99 and/or a VL that is at least 90%, at least 95%, at least 97%, or at least 99% identical to the amino acid sequence of SEQ ID NO: 100;

the CDRs of embodiment (k) above and further comprises a VH that is at least 90%, at least 95%, at least 97%, or at least 99% identical to the amino acid sequence of SEQ ID NO: 109 and/or a VL that is at least 90%, at least 95%, at least 97%, or at least 99% identical to the amino acid sequence of SEQ ID NO: 110;

the CDRs of embodiment (1) above and further comprises a VH that is at least 90%, at least 95%, at least 97%, or at least 99% identical to the amino acid sequence of SEQ ID NO: 119 and/or a VL that is at least 90%, at least 95%, at least 97%, or at least 99% identical to the amino acid sequence of SEQ ID NO: 120;

the CDRs of embodiment 1(m) and further comprises a VH that is at least 90%, at least 95%, at least 97%, or at least 99% identical to the amino acid sequence of SEQ ID NO: 129 and/or a VL that is at least 90%, at least 95%, at least 97%, or at least 99% identical to the amino acid sequence of SEQ ID NO: 130;

the CDRs of embodiment (n) above and further comprises a VH that is at least 90%, at least 95%, at least 97%, or at least 99% identical to the amino acid sequence of SEQ ID NO: 139 and/or a VL that is at least 90%, at least 95%, at least 97%, or at least 99% identical to the amino acid sequence of SEQ ID NO: 140;

the CDRs of embodiment (o) above and further comprises a VH that is at least 90%, at least 95%, at least 97%, or at least 99% identical to the amino acid sequence of SEQ ID NO: 149 and/or a VL that is at least 90%, at least 95%, at least 97%, or at least 99% identical to the amino acid sequence of SEQ ID NO: 150;

the CDRs of embodiment (p) above and further comprises a VH that is at least 90%, at least 95%, at least 97%, or at least 99% identical to the amino acid sequence of SEQ ID NO: 159 and/or a VL that is at least 90%, at least 95%, at least 97%, or at least 99% identical to the amino acid sequence of SEQ ID NO: 160;

the CDRs of embodiment (q) above and further comprises a VH that is at least 90%, at least 95%, at least 97%, or at least 99% identical to the amino acid sequence of SEQ ID NO: 169 and/or a VL that is at least 90%, at least 95%, at least 97%, or at least 99% identical to the amino acid sequence of SEQ ID NO: 170;

the CDRs of embodiment (r) above and further comprises a VH that is at least 90%, at least 95%, at least 97%, or at least 99% identical to the amino acid sequence of SEQ ID NO: 179 and/or a VL that is at least 90%, at least 95%, at least 97%, or at least 99% identical to the amino acid sequence of SEQ ID NO: 180;

the CDRs of embodiment (s) above and further comprises a VH that is at least 90%, at least 95%, at least 97%, or at least 99% identical to the amino acid sequence of SEQ ID NO: 189 and/or a VL that is at least 90%, at least 95%, at least 97%, or at least 99% identical to the amino acid sequence of SEQ ID NO: 190;

the CDRs of embodiment (t) above and further comprises a VH that is at least 90%, at least 95%, at least 97%, or at least 99% identical to the amino acid sequence of SEQ ID NO: 199 and/or a VL that is at least 90%, at least 95%, at least 97%, or at least 99% identical to the amino acid sequence of SEQ ID NO: 200; or the CDRs of embodiment (u) above and further comprises a VH that is at least 90%, at least 95%, at least 97%, or at least 99% identical to the amino acid sequence of SEQ ID NO: 209 and/or a VL that is at least 90%, at least 95%, at least 97%, or at least 99% identical to the amino acid sequence of SEQ ID NO: 210.

In some embodiments, as described above, the antibody comprises: the CDRs of embodiment (a) and further comprises a VH comprising the amino acid sequence of SEQ ID NO: 9;

the CDRs of embodiment (b) and further comprises a VH comprising the amino acid sequence of SEQ ID NO: 19;

the CDRs of embodiment (c) and further comprises a VH comprising the amino acid sequence of SEQ ID NO: 29;

the CDRs of embodiment (d) and further comprises a VH comprising the amino acid sequence of SEQ ID NO: 39;

the CDRs of embodiment (e) and further comprises a VH comprising the amino acid sequence of SEQ ID NO: 49;

the CDRs of embodiment (f) and further comprises a VH comprising the amino acid sequence of SEQ ID NO: 59;

the CDRs of embodiment (g) and further comprises a VH comprising the amino acid sequence of SEQ ID NO: 69;

the CDRs of embodiment (h) and further comprises a VH comprising the amino acid sequence of SEQ ID NO: 79;

the CDRs of embodiment (i) and further comprises a VH comprising the amino acid sequence of SEQ ID NO: 89;

the CDRs of embodiment 1(j) and further comprises a VH comprising the amino acid sequence of SEQ ID NO: 99;

the CDRs of embodiment (k) and further comprises a VH comprising the amino acid sequence of SEQ ID NO: 109;

the CDRs of embodiment (1) and further comprises a VH comprising the amino acid sequence of SEQ ID NO: 119;

the CDRs of embodiment (m) and further comprises a VH comprising the amino acid sequence of SEQ ID NO: 129;

the CDRs of embodiment (n) and further comprises a VH comprising the amino acid sequence of SEQ ID NO: 139;

the CDRs of embodiment (o) and further comprises a VH comprising the amino acid sequence of SEQ ID NO: 149;

the CDRs of embodiment (p) and further comprises a VH comprising the amino acid sequence of SEQ ID NO: 159;

the CDRs of embodiment (q) and further comprises a VH comprising the amino acid sequence of SEQ ID NO: 169;

the CDRs of embodiment (r) and further comprises a VH comprising the amino acid sequence of SEQ ID NO: 179;

the CDRs of embodiment (s) and further comprises a VH comprising the amino acid sequence of SEQ ID NO: 189;

the CDRs of embodiment (t) and further comprises a VH comprising the amino acid sequence of SEQ ID NO: 199; or the CDRs of embodiment (u) and further comprises a VH comprising the amino acid sequence of SEQ ID NO: 209.

In some cases, the antibody comprises: the CDRs of embodiment (a) and further comprises a VL comprising the amino acid sequence of SEQ ID NO: 10;

the CDRs of embodiment (b) and further comprises a VL comprising the amino acid sequence of SEQ ID NO: 20;

the CDRs of embodiment (c) and further comprises a VL comprising the amino acid sequence of SEQ ID NO: 30;

the CDRs of embodiment (d) and further comprises a VL comprising the amino acid sequence of SEQ ID NO: 40;

the CDRs of embodiment (e) and further comprises a VL comprising the amino acid sequence of SEQ ID NO: 50;

the CDRs of embodiment (f) and further comprises a VL comprising the amino acid sequence of SEQ ID NO: 60;

the CDRs of embodiment (g) and further comprises a VL comprising the amino acid sequence of SEQ ID NO: 70;

the CDRs of embodiment (h) and further comprises a VL comprising the amino acid sequence of SEQ ID NO: 80;

the CDRs of embodiment (i) and further comprises a VL comprising the amino acid sequence of SEQ ID NO: 90;

the CDRs of embodiment (j) and further comprises a VL comprising the amino acid sequence of SEQ ID NO: 100;

the CDRs of embodiment (k) and further comprises a VL comprising the amino acid sequence of SEQ ID NO: 110;

the CDRs of embodiment (1) and further comprises a VL comprising the amino acid sequence of SEQ ID NO: 120;

the CDRs of embodiment (m) and further comprises a VL comprising the amino acid sequence of SEQ ID NO: 130;

the CDRs of embodiment (n) and further comprises a VL comprising the amino acid sequence of SEQ ID NO: 140;

the CDRs of embodiment (o) and further comprises a VL comprising the amino acid sequence of SEQ ID NO: 150;

the CDRs of embodiment (p) and further comprises a VL comprising the amino acid sequence of SEQ ID NO: 160;

the CDRs of embodiment (q) and further comprises a VL comprising the amino acid sequence of SEQ ID NO: 170;

the CDRs of embodiment (r) and further comprises a VL comprising the amino acid sequence of SEQ ID NO: 180;

the CDRs of embodiment (s) and further comprises a VL comprising the amino acid sequence of SEQ ID NO: 190;

the CDRs of embodiment (t) and further comprises a VL comprising the amino acid sequence of SEQ ID NO: 200; or the CDRs of embodiment (u) and further comprises a VL comprising the amino acid sequence of SEQ ID NO: 210.

In some aspects, the antibody comprises:

a VH comprising the amino acid sequence of SEQ ID NO: 9 and a VL comprising the amino acid sequence of SEQ ID NO: 10;

a VH comprising the amino acid sequence of SEQ ID NO: 19 and a VL comprising the amino acid sequence of SEQ ID NO: 20;

a VH comprising the amino acid sequence of SEQ ID NO: 29 and a VL comprising the amino acid sequence of SEQ ID NO: 30;

a VH comprising the amino acid sequence of SEQ ID NO: 39 and a VL comprising the amino acid sequence of SEQ ID NO: 40;

a VH comprising the amino acid sequence of SEQ ID NO: 49 and a VL comprising the amino acid sequence of SEQ ID NO: 50;

a VH comprising the amino acid sequence of SEQ ID NO: 59 and a VL comprising the amino acid sequence of SEQ ID NO: 60;

a VH comprising the amino acid sequence of SEQ ID NO: 69 and a VL comprising the amino acid sequence of SEQ ID NO: 70;

a VH comprising the amino acid sequence of SEQ ID NO: 79 and a VL comprising the amino acid sequence of SEQ ID NO: 80;

a VH comprising the amino acid sequence of SEQ ID NO: 89 and a VL comprising the amino acid sequence of SEQ ID NO: 90;

a VH comprising the amino acid sequence of SEQ ID NO: 99 and a VL comprising the amino acid sequence of SEQ ID NO: 100;

a VH comprising the amino acid sequence of SEQ ID NO: 109 and a VL comprising the amino acid sequence of SEQ ID NO: 110;

a VH comprising the amino acid sequence of SEQ ID NO: 119 and a VL comprising the amino acid sequence of SEQ ID NO: 120;

a VH comprising the amino acid sequence of SEQ ID NO: 129 and a VL comprising the amino acid sequence of SEQ ID NO: 130;

a VH comprising the amino acid sequence of SEQ ID NO: 139 and a VL comprising the amino acid sequence of SEQ ID NO: 140;

a VH comprising the amino acid sequence of SEQ ID NO: 149 and a VL comprising the amino acid sequence of SEQ ID NO: 150;

a VH comprising the amino acid sequence of SEQ ID NO: 159 and a VL comprising the amino acid sequence of SEQ ID NO: 160;

a VH comprising the amino acid sequence of SEQ ID NO: 169 and a VL comprising the amino acid sequence of SEQ ID NO: 170;

a VH comprising the amino acid sequence of SEQ ID NO: 179 and a VL comprising the amino acid sequence of SEQ ID NO: 180;

a VH comprising the amino acid sequence of SEQ ID NO: 189 and a VL comprising the amino acid sequence of SEQ ID NO: 190;

a VH comprising the amino acid sequence of SEQ ID NO: 199 and a VL comprising the amino acid sequence of SEQ ID NO: 200; or a VH comprising the amino acid sequence of SEQ ID NO: 209 and a VL comprising the amino acid sequence of SEQ ID NO: 210.

In some cases, the antibody comprises the CDRs of embodiment (a) and further comprises a heavy chain (HC) comprising an amino acid sequence at least 90%, at least 95%, at least 97%, or at least 99% identical to the amino acid sequence of SEQ ID NO: 11 and a light chain (LC) comprising an amino acid sequence at least 90%, at least 95%, at least 97%, or at least 99% identical to the SEQ ID NO: 12;

the CDRs of embodiment (b) and further comprises a heavy chain (HC) comprising an amino acid sequence at least 90%, at least 95%, at least 97%, or at least 99% identical to the amino acid sequence of SEQ ID NO: 21 and a light chain (LC) comprising an amino acid sequence at least 90%, at least 95%, at least 97%, or at least 99% identical to the amino acid sequence of SEQ ID NO: 22;

the CDRs of embodiment (c) and further comprises a heavy chain (HC) comprising an amino acid sequence at least 90%, at least 95%, at least 97%, or at least 99% identical to the amino acid sequence of SEQ ID NO: 31 and a light chain (LC) comprising an amino acid sequence at least 90%, at least 95%, at least 97%, or at least 99% identical to the amino acid sequence of SEQ ID NO: 32;

the CDRs of embodiment (d) and further comprises a heavy chain (HC) comprising an amino acid sequence at least 90%, at least 95%, at least 97%, or at least 99% identical to the amino acid sequence of SEQ ID NO: 41 and a light chain (LC) comprising an amino acid sequence at least 90%, at least 95%, at least 97%, or at least 99% identical to the amino acid sequence of SEQ ID NO: 42;

the CDRs of embodiment (e) and further comprises a heavy chain (HC) comprising an the amino acid sequence of SEQ ID NO: 51 and a light chain (LC) comprising an amino acid sequence at least 90%, at least 95%, at least 97%, or at least 99% identical to the amino acid sequence of SEQ ID NO: 52;

the CDRs of embodiment (f) and further comprises a heavy chain (HC) comprising an amino acid sequence at least 90%, at least 95%, at least 97%, or at least 99% identical to the amino acid sequence of SEQ ID NO: 61 and a light chain (LC) comprising an amino acid sequence at least 90%, at least 95%, at least 97%, or at least 99% identical to the amino acid sequence of SEQ ID NO: 62;

the CDRs of embodiment (g) and further comprises a heavy chain (HC) comprising an amino acid sequence at least 90%, at least 95%, at least 97%, or at least 99% identical to the amino acid sequence of SEQ ID NO: 71 and a light chain (LC) comprising an amino acid sequence at least 90%, at least 95%, at least 97%, or at least 99% identical to the amino acid sequence of SEQ ID NO: 72;

the CDRs of embodiment (h) and further comprises a heavy chain (HC) comprising an amino acid sequence at least 90%, at least 95%, at least 97%, or at least 99% identical to the amino acid sequence of SEQ ID NO: 81 and a light chain (LC) comprising an amino acid sequence at least 90%, at least 95%, at least 97%, or at least 99% identical to the amino acid sequence of SEQ ID NO: 82;

the CDRs of embodiment (i) and further comprises a heavy chain (HC) comprising an amino acid sequence at least 90%, at least 95%, at least 97%, or at least 99% identical to the amino acid sequence of SEQ ID NO: 91 and a light chain (LC) comprising an amino acid sequence at least 90%, at least 95%, at least 97%, or at least 99% identical to the amino acid sequence of SEQ ID NO: 92;

the CDRs of embodiment (j) and further comprises a heavy chain (HC) comprising an amino acid sequence at least 90%, at least 95%, at least 97%, or at least 99% identical to the amino acid sequence of SEQ ID NO: 101 and a light chain (LC) comprising an amino acid sequence at least 90%, at least 95%, at least 97%, or at least 99% identical to the amino acid sequence of SEQ ID NO: 102;

the CDRs of embodiment (k) and further comprises a heavy chain (HC) comprising an amino acid sequence at least 90%, at least 95%, at least 97%, or at least 99% identical to the amino acid sequence of SEQ ID NO: 111 and a light chain (LC) comprising an amino acid sequence at least 90%, at least 95%, at least 97%, or at least 99% identical to the amino acid sequence of SEQ ID NO: 112;

the CDRs of embodiment (1) and further comprises a heavy chain (HC) comprising an the amino acid sequence of SEQ ID NO: 121 and a light chain (LC) comprising an amino acid sequence at least 90%, at least 95%, at least 97%, or at least 99% identical to the amino acid sequence of SEQ ID NO: 122;

the CDRs of embodiment (m) and further comprises a heavy chain (HC) comprising an amino acid sequence at least 90%, at least 95%, at least 97%, or at least 99% identical to the amino acid sequence of SEQ ID NO: 131 and a light chain (LC) comprising an amino acid sequence at least 90%, at least 95%, at least 97%, or at least 99% identical to the amino acid sequence of SEQ ID NO: 132;

the CDRs of embodiment (n) and further comprises a heavy chain (HC) comprising an amino acid sequence at least 90%, at least 95%, at least 97%, or at least 99% identical to the amino acid sequence of SEQ ID NO: 141 and a light chain (LC) comprising an amino acid sequence at least 90%, at least 95%, at least 97%, or at least 99% identical to the amino acid sequence of SEQ ID NO: 142;

the CDRs of embodiment (o) and further comprises a heavy chain (HC) comprising an amino acid sequence at least 90%, at least 95%, at least 97%, or at least 99% identical to the amino acid sequence of SEQ ID NO: 151 and a light chain (LC) comprising an amino acid sequence at least 90%, at least 95%, at least 97%, or at least 99% identical to the amino acid sequence of SEQ ID NO: 152;

the CDRs of embodiment (p) and further comprises a heavy chain (HC) comprising an amino acid sequence at least 90%, at least 95%, at least 97%, or at least 99% identical to the amino acid sequence of SEQ ID NO: 161 and a light chain (LC) comprising an amino acid sequence at least 90%, at least 95%, at least 97%, or at least 99% identical to the amino acid sequence of SEQ ID NO: 162;

the CDRs of embodiment (q) and further comprises a heavy chain (HC) comprising an amino acid sequence at least 90%, at least 95%, at least 97%, or at least 99% identical to the amino acid sequence of SEQ ID NO: 171 and a light chain (LC) comprising an amino acid sequence at least 90%, at least 95%, at least 97%, or at least 99% identical to the amino acid sequence of SEQ ID NO: 172;

the CDRs of embodiment (r) and further comprises a heavy chain (HC) comprising an amino acid sequence at least 90%, at least 95%, at least 97%, or at least 99% identical to the amino acid sequence of SEQ ID NO: 181 and a light chain (LC) comprising an the amino acid sequence of SEQ ID NO: 182;

the CDRs of embodiment (s) and further comprises a heavy chain (HC) comprising an amino acid sequence at least 90%, at least 95%, at least 97%, or at least 99% identical to the amino acid sequence of SEQ ID NO: 191 and a light chain (LC) comprising an amino acid sequence at least 90%, at least 95%, at least 97%, or at least 99% identical to the amino acid sequence of SEQ ID NO: 192;

the CDRs of embodiment (t) and further comprises a heavy chain (HC) comprising an amino acid sequence at least 90%, at least 95%, at least 97%, or at least 99% identical to the amino acid sequence of SEQ ID NO: 201 and a light chain (LC) comprising an amino acid sequence at least 90%, at least 95%, at least 97%, or at least 99% identical to the amino acid sequence of SEQ ID NO: 202; or the CDRs of embodiment (u) and further comprises a heavy chain (HC) comprising an amino acid sequence at least 90%, at least 95%, at least 97%, or at least 99% identical to the amino acid sequence of SEQ ID NO: 211 and a light chain (LC) comprising an amino acid sequence at least 90%, at least 95%, at least 97%, or at least 99% identical to the amino acid sequence of SEQ ID NO: 212.

In some embodiments, the antibody comprises:

a heavy chain (HC) comprising the amino acid sequence of SEQ ID NO: 11 and a light chain (LC) comprising the amino acid sequence of SEQ ID NO: 12;

a heavy chain (HC) comprising the amino acid sequence of SEQ ID NO: 21 and a light chain (LC) comprising the amino acid sequence of SEQ ID NO: 22;

a heavy chain (HC) comprising the amino acid sequence of SEQ ID NO: 31 and a light chain (LC) comprising the amino acid sequence of SEQ ID NO: 32;

a heavy chain (HC) comprising the amino acid sequence of SEQ ID NO: 41 and a light chain (LC) comprising the amino acid sequence of SEQ ID NO: 42;

a heavy chain (HC) comprising the amino acid sequence of SEQ ID NO: 51 and a light chain (LC) comprising the amino acid sequence of SEQ ID NO: 52;

a heavy chain (HC) comprising the amino acid sequence of SEQ ID NO: 61 and a light chain (LC) comprising the amino acid sequence of SEQ ID NO: 62;

a heavy chain (HC) comprising the amino acid sequence of SEQ ID NO: 71 and a light chain (LC) comprising the amino acid sequence of SEQ ID NO: 72;

a heavy chain (HC) comprising the amino acid sequence of SEQ ID NO: 81 and a light chain (LC) comprising the amino acid sequence of SEQ ID NO: 82;

a heavy chain (HC) comprising the amino acid sequence of SEQ ID NO: 91 and a light chain (LC) comprising the amino acid sequence of SEQ ID NO: 92;

a heavy chain (HC) comprising the amino acid sequence of SEQ ID NO: 101 and a light chain (LC) comprising the amino acid sequence of SEQ ID NO: 102;

a heavy chain (HC) comprising the amino acid sequence of SEQ ID NO: 111 and a light chain (LC) comprising the amino acid sequence of SEQ ID NO: 112;

a heavy chain (HC) comprising the amino acid sequence of SEQ ID NO: 121 and a light chain (LC) comprising the amino acid sequence of SEQ ID NO: 122;

a heavy chain (HC) comprising the amino acid sequence of SEQ ID NO: 131 and a light chain (LC) comprising the amino acid sequence of SEQ ID NO: 132;

a heavy chain (HC) comprising the amino acid sequence of SEQ ID NO: 141 and a light chain (LC) comprising the amino acid sequence of SEQ ID NO: 142;

a heavy chain (HC) comprising the amino acid sequence of SEQ ID NO: 151 and a light chain (LC) comprising the amino acid sequence of SEQ ID NO: 152;

a heavy chain (HC) comprising the amino acid sequence of SEQ ID NO: 161 and a light chain (LC) comprising the amino acid sequence of SEQ ID NO: 162;

a heavy chain (HC) comprising the amino acid sequence of SEQ ID NO: 171 and a light chain (LC) comprising the amino acid sequence of SEQ ID NO: 172;

a heavy chain (HC) comprising the amino acid sequence of SEQ ID NO: 181 and a light chain (LC) comprising the amino acid sequence of SEQ ID NO: 182;

a heavy chain (HC) comprising the amino acid sequence of SEQ ID NO: 191 and a light chain (LC) comprising the amino acid sequence of SEQ ID NO: 192;

a heavy chain (HC) comprising the amino acid sequence of SEQ ID NO: 201 and a light chain (LC) comprising the amino acid sequence of SEQ ID NO: 202; or a heavy chain (HC) comprising the amino acid sequence of SEQ ID NO: 211 and a light chain (LC) comprising the amino acid sequence of SEQ ID NO: 212.

The disclosure also includes an isolated antibody that specifically binds to apolipoprotein L1 (APOL1), wherein the antibody: specifically binds to a region of APOL1 corresponding to amino acids 61-103 of APOL1 G0 (SEQ ID NO: 2); and/or specifically binds to a region of APOL1 corresponding to amino acids 111-150 of APOL1 G0 (SEQ ID NO: 2); and further wherein the antibody preferentially recognizes APOL1 expressed on podocytes over APOL1 found in serum. In some such cases, the antibody comprises:

(a) a heavy chain variable region (VH) comprising a CDR-H1 comprising the amino acid sequence of SEQ ID NO: 173, a CDR-H2 comprising the amino acid sequence of SEQ ID NO: 174, and a CDR-H3 comprising the amino acid sequence of SEQ ID NO: 175; and a light chain variable region (VL) comprising a CDR-L1 comprising the amino acid sequence of SEQ ID NO: 176, a CDR-L2 comprising the amino acid sequence of SEQ ID NO: 177, and a CDR-L3 comprising the amino acid sequence of SEQ ID NO: 178; or (b) a heavy chain variable region (VH) comprising a CDR-H1 comprising the amino acid sequence of SEQ ID NO: 183, a CDR-H2 comprising the amino acid sequence of SEQ ID NO: 184, and a CDR-H3 comprising the amino acid sequence of SEQ ID NO: 185; and a light chain variable region (VL) comprising a CDR-L1 comprising the amino acid sequence of SEQ ID NO: 186, a CDR-L2 comprising the amino acid sequence of SEQ ID NO: 187, and a CDR-L3 comprising the amino acid sequence of SEQ ID NO: 188.

Embodiments herein also include an isolated antibody that specifically binds to apolipoprotein L1 (APOL1), wherein the antibody: specifically binds to a region of APOL1 corresponding to amino acids 103-111 of APOL1 G0 (SEQ ID NO: 2); specifically binds to a region of APOL1 corresponding to amino acids 150-172 of APOL1 G0 (SEQ ID NO: 2); specifically binds to a region of APOL1 corresponding to amino acids 314-333 of APOL1 G0 (SEQ ID NO: 2); and/or specifically binds to a region of APOL1 corresponding to amino acids 376-398 of APOL1 G0 (SEQ ID NO: 2); and further wherein the antibody recognizes both APOL1 expressed on podocytes and APOL1 found in serum. In some such cases, the antibody comprises:

(a) a heavy chain variable region (VH) comprising a CDR-H1 comprising the amino acid sequence of SEQ ID NO: 3, a CDR-H2 comprising the amino acid sequence of SEQ ID NO: 4, and a CDR-H3 comprising the amino acid sequence of SEQ ID NO: 5; and a light chain variable region (VL) comprising a CDR-L1 comprising the amino acid sequence of SEQ ID NO: 6, a CDR-L2 comprising the amino acid sequence of SEQ ID NO: 7, and a CDR-L3 comprising the amino acid sequence of SEQ ID NO: 8;

(b) a heavy chain variable region (VH) comprising a CDR-H1 comprising the amino acid sequence of SEQ ID NO: 53, a CDR-H2 comprising the amino acid sequence of SEQ ID NO: 54, and a CDR-H3 comprising the amino acid sequence of SEQ ID NO: 55; and a light chain variable region (VL) comprising a CDR-L1 comprising the amino acid sequence of SEQ ID NO: 56, a CDR-L2 comprising the amino acid sequence of SEQ ID NO: 57, and a CDR-L3 comprising the amino acid sequence of SEQ ID NO: 58;

(c) a heavy chain variable region (VH) comprising a CDR-H1 comprising the amino acid sequence of SEQ ID NO: 63, a CDR-H2 comprising the amino acid sequence of SEQ ID NO: 64, and a CDR-H3 comprising the amino acid sequence of SEQ ID NO: 65; and a light chain variable region (VL) comprising a CDR-L1 comprising the amino acid sequence of SEQ ID NO: 66, a CDR-L2 comprising the amino acid sequence of SEQ ID NO: 67, and a CDR-L3 comprising the amino acid sequence of SEQ ID NO: 68;

(d) a heavy chain variable region (VH) comprising a CDR-H1 comprising the amino acid sequence of SEQ ID NO: 83, a CDR-H2 comprising the amino acid sequence of SEQ ID NO: 84, and a CDR-H3 comprising the amino acid sequence of SEQ ID NO: 85; and a light chain variable region (VL) comprising a CDR-L1 comprising the amino acid sequence of SEQ ID NO: 86, a CDR-L2 comprising the amino acid sequence of SEQ ID NO: 87, and a CDR-L3 comprising the amino acid sequence of SEQ ID NO: 88;

(e) a heavy chain variable region (VH) comprising a CDR-H1 comprising the amino acid sequence of SEQ ID NO: 73, a CDR-H2 comprising the amino acid sequence of SEQ ID NO: 74, and a CDR-H3 comprising the amino acid sequence of SEQ ID NO: 75; and a light chain variable region (VL) comprising a CDR-L1 comprising the amino acid sequence of SEQ ID NO: 76, a CDR-L2 comprising the amino acid sequence of SEQ ID NO: 77, and a CDR-L3 comprising the amino acid sequence of SEQ ID NO: 78;

(f) a heavy chain variable region (VH) comprising a CDR-H1 comprising the amino acid sequence of SEQ ID NO: 133, a CDR-H2 comprising the amino acid sequence of SEQ ID NO: 134, and a CDR-H3 comprising the amino acid sequence of SEQ ID NO: 135; and a light chain variable region (VL) comprising a CDR-L1 comprising the amino acid sequence of SEQ ID NO: 136, a CDR-L2 comprising the amino acid sequence of SEQ ID NO: 137, and a CDR-L3 comprising the amino acid sequence of SEQ ID NO: 138;

(g) a heavy chain variable region (VH) comprising a CDR-H1 comprising the amino acid sequence of SEQ ID NO: 143, a CDR-H2 comprising the amino acid sequence of SEQ ID NO: 144, and a CDR-H3 comprising the amino acid sequence of SEQ ID NO: 145; and a light chain variable region (VL) comprising a CDR-L1 comprising the amino acid sequence of SEQ ID NO: 146, a CDR-L2 comprising the amino acid sequence of SEQ ID NO: 147, and a CDR-L3 comprising the amino acid sequence of SEQ ID NO: 148; or (h) a heavy chain variable region (VH) comprising a CDR-H1 comprising the amino acid sequence of SEQ ID NO: 123, a CDR-H2 comprising the amino acid sequence of SEQ ID NO: 124, and a CDR-H3 comprising the amino acid sequence of SEQ ID NO: 125; and a light chain variable region (VL) comprising a CDR-L1 comprising the amino acid sequence of SEQ ID NO: 126, a CDR-L2 comprising the amino acid sequence of SEQ ID NO: 127, and a CDR-L3 comprising the amino acid sequence of SEQ ID NO: 128.

Embodiments herein also include isolated antibody that specifically binds to apolipoprotein L1 (APOL1), wherein the antibody: specifically binds to a region of APOL1 corresponding to amino acids 260-314 of APOL1 G0 (SEQ ID NO: 2); and further wherein the antibody preferentially recognizes APOL1 found in serum over APOL1 expressed on podocytes. In some such cases, the antibody comprises:

(a) a heavy chain variable region (VH) comprising a CDR-H1 comprising the amino acid sequence of SEQ ID NO: 33, a CDR-H2 comprising the amino acid sequence of SEQ ID NO: 34, and a CDR-H3 comprising the amino acid sequence of SEQ ID NO: 35; and a light chain variable region (VL) comprising a CDR-L1 comprising the amino acid sequence of SEQ ID NO: 36, a CDR-L2 comprising the amino acid sequence of SEQ ID NO: 37, and a CDR-L3 comprising the amino acid sequence of SEQ ID NO: 38; or (b) a heavy chain variable region (VH) comprising a CDR-H1 comprising the amino acid sequence of SEQ ID NO: 43, a CDR-H2 comprising the amino acid sequence of SEQ ID NO: 44, and a CDR-H3 comprising the amino acid sequence of SEQ ID NO: 45; and a light chain variable region (VL) comprising a CDR-L1 comprising the amino acid sequence of SEQ ID NO: 46, a CDR-L2 comprising the amino acid sequence of SEQ ID NO: 47, and a CDR-L3 comprising the amino acid sequence of SEQ ID NO: 48.

This disclosure further includes an isolated antibody that specifically binds to apolipoprotein L1 (APOL1), wherein the antibody preferentially binds to the G0 and G1 forms of APOL1 over the G2 form of APOL1. In some such cases, the antibody comprises:

(a) a heavy chain variable region (VH) comprising a CDR-H1 comprising the amino acid sequence of SEQ ID NO: 143, a CDR-H2 comprising the amino acid sequence of SEQ ID NO: 144, and a CDR-H3 comprising the amino acid sequence of SEQ ID NO: 145; and a light chain variable region (VL) comprising a CDR-L1 comprising the amino acid sequence of SEQ ID NO: 146, a CDR-L2 comprising the amino acid sequence of SEQ ID NO: 147, and a CDR-L3 comprising the amino acid sequence of SEQ ID NO: 148;

(b) a heavy chain variable region (VH) comprising a CDR-H1 comprising the amino acid sequence of SEQ ID NO: 123, a CDR-H2 comprising the amino acid sequence of SEQ ID NO: 124, and a CDR-H3 comprising the amino acid sequence of SEQ ID NO: 125; and a light chain variable region (VL) comprising a CDR-L1 comprising the amino acid sequence of SEQ ID NO: 126, a CDR-L2 comprising the amino acid sequence of SEQ ID NO: 127, and a CDR-L3 comprising the amino acid sequence of SEQ ID NO: 128; or (c) a heavy chain variable region (VH) comprising a CDR-H1 comprising the amino acid sequence of SEQ ID NO: 133, a CDR-H2 comprising the amino acid sequence of SEQ ID NO: 134, and a CDR-H3 comprising the amino acid sequence of SEQ ID NO: 135; and a light chain variable region (VL) comprising a CDR-L1 comprising the amino acid sequence of SEQ ID NO: 136, a CDR-L2 comprising the amino acid sequence of SEQ ID NO: 137, and a CDR-L3 comprising the amino acid sequence of SEQ ID NO: 138;

The present disclosure also includes an isolated antibody that specifically binds to apolipoprotein L1 (APOL1) and that (a) does not significantly bind to apolipoprotein L2 or L3 (APOL2 or APOL3), and/or (b) does not significantly bind to apolipoprotein L2 or L6 (APOL2 or APOL6), wherein the antibody comprises:

(a) a heavy chain variable region (VH) comprising a CDR-H1 comprising the amino acid sequence of SEQ ID NO: 163, a CDR-H2 comprising the amino acid sequence of SEQ ID NO: 164, and a CDR-H3 comprising the amino acid sequence of SEQ ID NO: 165; and a light chain variable region (VL) comprising a CDR-L1 comprising the amino acid sequence of SEQ ID NO: 166, a CDR-L2 comprising the amino acid sequence of SEQ ID NO: 167, and a CDR-L3 comprising the amino acid sequence of SEQ ID NO: 168;

(b) a heavy chain variable region (VH) comprising a CDR-H1 comprising the amino acid sequence of SEQ ID NO: 103, a CDR-H2 comprising the amino acid sequence of SEQ ID NO: 104, and a CDR-H3 comprising the amino acid sequence of SEQ ID NO: 105; and a light chain variable region (VL) comprising a CDR-L1 comprising the amino acid sequence of SEQ ID NO: 106, a CDR-L2 comprising the amino acid sequence of SEQ ID NO: 107, and a CDR-L3 comprising the amino acid sequence of SEQ ID NO: 108; or (c) a heavy chain variable region (VH) comprising a CDR-H1 comprising the amino acid sequence of SEQ ID NO: 23, a CDR-H2 comprising the amino acid sequence of SEQ ID NO: 24, and a CDR-H3 comprising the amino acid sequence of SEQ ID NO: 25; and a light chain variable region (VL) comprising a CDR-L1 comprising the amino acid sequence of SEQ ID NO: 26, a CDR-L2 comprising the amino acid sequence of SEQ ID NO: 27, and a CDR-L3 comprising the amino acid sequence of SEQ ID NO: 28.

In any of the above embodiments, the antibody can be optionally humanized or chimeric. The antibody may also be an IgG antibody, such as an IgG1, IgG2, IgG3, or IgG4. In some embodiments, the antibody is a full length antibody. In other embodiments, the antibody is an antibody fragment, such as an Fv, single-chain Fv (scFv), Fab, Fab', or (Fab')$_2$. In some embodiments, the antibody can be a bispecific or multispecific antibody or can be conjugated covalently or noncovalently to at least one other molecule. In some embodiments, the antibody is conjugated covalently or noncovalently to at least one other molecule, wherein the at least one other molecule comprises a detection label and/or a pharmaceutical agent. In some embodiments, the antibody specifically binds to a polypeptide comprising the amino acid sequence of SEQ ID NO: 2, SEQ ID NO: 213, and/or SEQ ID NO: 214.

The present disclosure also includes an isolated nucleic acid encoding an antibody described herein. The disclosure also encompasses an isolated vector comprising one or more nucleic acids encoding the heavy chain and the light chain of an antibody herein. The present disclosure also encompasses an isolated host cell comprising a nucleic acid or a set of nucleic acids encoding an antibody herein. Furthermore, the disclosure contemplates methods of producing an antibody that binds to APOL1 comprising culturing a host cell comprising a nucleic acid or set of nucleic acids encoding an antibody herein under conditions suitable for the expression of the antibody. In some cases, the method further comprises recovering the antibody from the host cell. The present disclosure also includes an antibody produced by those methods.

The disclosure herein also encompasses methods of detecting apolipoprotein L1 (APOL1) in a sample, comprising, for example, providing a sample comprising at least one of APOL1, APOL2, APOL3, APOL4, or APOL6; contacting the sample with an anti-APOL1 antibody according to the disclosure; and detecting the presence of the APOL1 protein in the sample based on recognition of the protein by the anti-APOL1 antibody. Optionally, the sample comprises human kidney cells, human podocyte cells, human endothelial cells, or optionally wherein the sample is a human serum or blood sample.

The present application further discloses methods of distinguishing endogenous apolipoprotein L1 (APOL1) from apolipoprotein L2 (APOL2), apolipoprotein L3 (APOL3), apolipoprotein L4 (APOL4), and apolipoprotein L6 (APOL6) comprising: providing a sample that may contain at least one of APOL1, APOL2, APOL3, APOL4, and APOL6, contacting the sample with an anti-APOL1 antibody, and detecting binding of the antibody to the sample, wherein the antibody is specifically binds to APOL1 but does not significantly bind to one or more of APOL2, APOL3, APOL4, and APOL6. In some such cases, the antibody comprises the VH CDR1, CDR2, and CDR3 and the VL CDR1, CDR2, and CDR3 of antibody 5.17D12, such as comprising SEQ ID Nos: 163-168. In some cases, the methods further comprise contacting the sample with an anti-APOL1 antibody that is capable of distinguishing the G0 and G1 forms of APOL1 from the G2 form, such as an antibody comprising the VH CDR1, CDR2, and CDR3 and the VL CDR1, CDR2, and CDR3 of antibody 4.11A10 (comprising SEQ ID Nos: 133-138), 4.12E5 (comprising SEQ ID Nos: 123-128), or 4.11H11 (comprising SEQ ID Nos: 143-148).

In some embodiments, the disclosure provides methods of distinguishing apolipoprotein L1 (APOL1) G0 and G1 forms from APOL1 G2 form, comprising providing a sample that may contain at least one of the G0, G1, and G2 forms, contacting the sample with an anti-APOL1 antibody according to the disclosure, and detecting binding of the antibody to the sample, wherein the antibody preferentially binds to the G0 and G1 forms of APOL1 over the G2 form of APOL1. In some cases, the sample comprises human kidney cells, human podocyte cells, or human endothelial cells.

The present disclosure also contemplates methods of specifically detecting podocyte cells expressing apolipoprotein L1 (APOL1), comprising providing a sample comprising podocyte cells, contacting the sample with an anti-APOL1 antibody herein, and detecting binding of the antibody to the sample, wherein the antibody (a) preferentially binds to APOL1 found on podocyte cells over APOL1 found in serum, (b) the antibody does not significantly bind to APOL2, and/or (c) the antibody does not significantly bind to APOL6. In some cases, the methods comprise at least one of: (a) contacting the sample with a control antibody that recognizes APOL1 found on both podocytes and serum and/or that recognizes APOL1 found in serum (e.g. in HDL particles), and/or (b) contacting the sample with an anti-APOL1 antibody that is capable of distinguishing the G0 and G1 forms of APOL1 from the G2 form.

BRIEF DESCRIPTION OF THE FIGURES

FIGS. 1A1-E show schematic representations of full length (FIG. 1A) and truncated iAPOL1 constructs (FIGS. 1-B-1E) used to domain-map the antibodies on CHO cells: Signal sequence (ss), Pore Forming Domain (PFD, black), Membrane Addressing Domain (MAD, spotty), Serum Resistance Associated-Interacting domain (SRA-ID, hatched) are indicated, with the intervening linker domain (L) shown as a white rectangle. Wild type full length (aa 28-398) native APOL1-G0 (FIG. 1A; iAPOL1-CHO; construct a, with its native signal sequence (ss, white)), and G0 (FIG. 1B; aa 61-398; construct b), with an N-terminal anti-gD epitope tag (gD) (which includes its own efficient signal sequence for secretion) as a positive control, and a C-terminal GPI anchor to ensure membrane attachment (both grey in constructs b-e; FIGS. 1B-1E) were created (gD-iAPOL1-GPI-CHO), since it had not yet been established whether APOL1 was a cell surface protein. Truncation mutants (FIGS. 1C-1E; constructs c-e) are shown: gD-PFD-MAD-GPI (FIG. 1C; construct c), gD-MAD-SRA-ID-GPI (FIG. 1D; construct d), and gD-SRA-/D-GPI (FIG. 1E; construct e). All constructs (FIG. 1A-1E) were stably expressed in CHO cells under a doxycycline-inducible promoter. Amino acid numbers indicate the domain boundaries as defined by Pays et al (see Example 1, reference 1). The MAD alone was predicted to be unstable, hence it was expressed jointly with the PFD or SRA-ID. Our mapping constructs b and c (FIGS. 1B-1C) started at amino acid 61 since our immunogen started at aa 61.

FIG. 1F provides examples of flow cytometry results leading to domain mapping. Stably transfected live (not fixed or permeabilized) CHO cells expressing the gD-iAPOL1-GPI constructs indicated in FIGS. 1A-1E after induction with 5 µg/ml dox for 48 h, showing differential antibody binding at 5 µg/ml. Antibodies binding to cells expressing PFD-MAD, but not to MAD-SRA-ID, were marked as having PFD epitopes (aa 61-235); those binding MAD-SRA-ID but not SRA-ID (i.e., epitopes between aa 238 and 305) were termed MAD binders, and those binding both MAD-SRA-ID and SRA-ID were called SRA-ID binders (aa 305-398), although this also includes the linker domain (aa 306-338). White histograms are Alexa488 anti-mouse or anti-rabbit secondaries only; grey histograms are the anti-APOL1 signals. A representative histogram for each category is shown: 3.7D6 for PFD; 3.3A8 for C-terminus of MAD, 3.5H9 for N-terminus of MAD; 3.1C1 for SRA-ID; 3.2D4 for multi-domain; 3.3F7 for conformational and 3.5B10 for FACS-negative (FACS-ve). The prefix 3 in the name of the antibodies denotes murine monoclonals from Method #3 (as shown in Example 1 below); other antibodies (not illustrated here) starting with the number 4 are murine monoclonals derived from mice additionally boosted with SRA-ID protein; and prefix 5-named antibodies are rabbit monoclonals from Method #5 (Table 2A; and Example 2). The commercial rabbit polyclonal from Proteintech (11486-2-AP, raised specifically to the PFD, aa 1-238) is a PFD binder, which was used to validate our methodology. The Sigma polyclonal (HPA018885, raised to aa 263-387) and the Epitomics rabbit monoclonal (EPR2907(2), raised to an undisclosed peptide) are SRA-ID binders. Successful APOL1 surface expression of each construct was confirmed with the anti-gD epitope tag (gD-tag) antibody (to Herpes Simplex Virus glycoprotein D).

FIG. 1G shows a pie chart summarizing the results of the gross domain mapping of all 170 antibodies. PFD: 81 (48% of 170); MAD: 10 (6%); SRA-ID: 38 (22%); Multi-domain: 4 (2%); Conformational: 17 (10%); FACS-negative: 20 (12%).

FIG. 2A shows flow cytometry of live (not fixed or permeabilized) stably transfected CHO cells with doxycycline induced (5 µg/ml for 48 h) full-length native untagged (and non-GPI anchored) WT iAPOL1-G0 (construct a in FIG. 1A) with all 170 antibodies at 5 µg/ml. Each dot represents an individual antibody. 88% of antibodies recognize full length APOL1 on the CHO cell surface. The dashed line indicates the cutoff for positive binders. No antibodies stained uninduced iAPOL1-CHO cells (data not shown), indicating lack of background staining on CHO cells.

FIG. 2B shows that native APOL1 has a similar surface conformation to GPI-anchored APOL1. Flow cytometry of live native full length iAPOL1-G0 (construct a in FIG. 1A; y-axis) versus gD-iAPOL1-GPI (construct b in FIG. 1A; x-axis) expressing CHO cells (both induced with 5 µg/ml doxycycline for 24 h) with all 170 antibodies at 5 µg/ml. Each triangle represents the MFI of an individual antibody by FACS on both constructs, with antibody 3.3A8 drawn in white instead of black and denoted in the graph by an arrow. Almost all the antibodies bound with similar intensity to both forms of APOL1, indicating that APOL1 is stably expressed on the cell surface and that the GPI anchor, somewhat unexpectedly, has little effect on its surface accessibility.

FIG. 2C is the same as FIG. 2A except with full length native iAPOL1-G0, G1 or G2 expressing CHO cells and the 38 SRA-ID antibodies only. All the FACS-positive antibodies cross-reacted with APOL1-G1 (closed squares), but 7 antibodies did not recognize APOL1 G2 (open triangles: 4.11A10, 4.11H11, 4.12E5, 4.1H8, 4.9F7, 3.2B5 and 3.1C4).

Figure 2A:
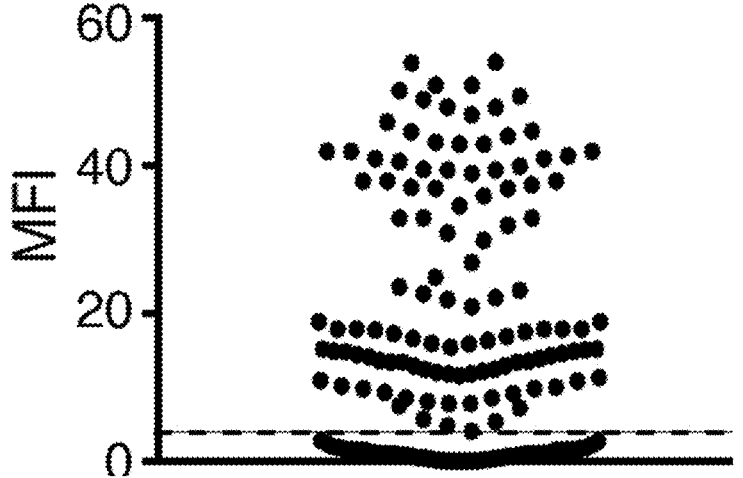
FIGS. 2A-D show native APOL1-G0 binding and G1/G2 recognition of the anti-APOL1 antibodies.
Figure 2B:
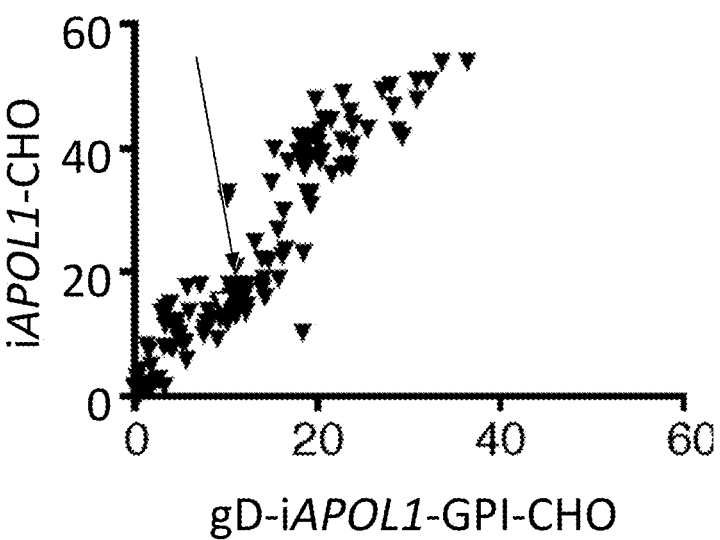
Figure 2C:
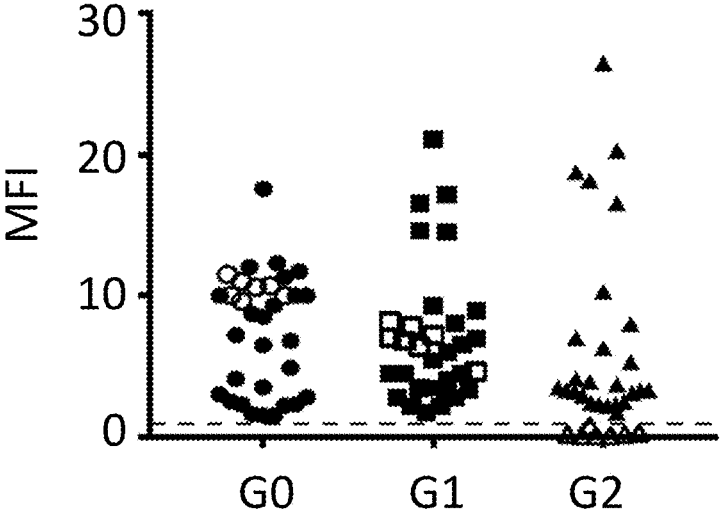
Figure 2D:
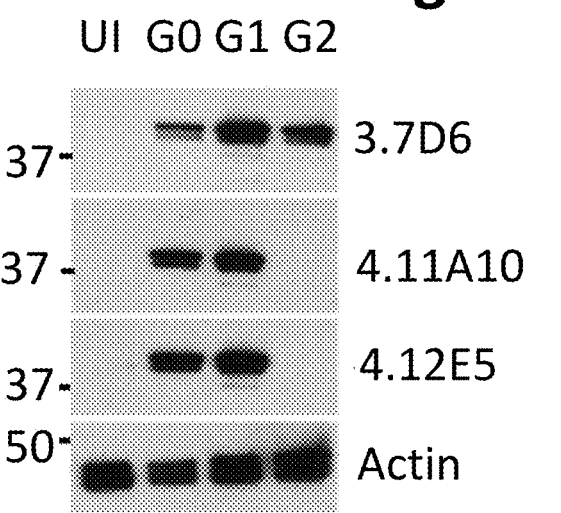

FIG. 2D shows a Western blot of lysates from CHO cells expressing iAPOL1-G0, G1 or G2 confirms the lack of recognition of APOL-G2 by antibodies 4.11A10 and 4.12E5 at 2.5 µg/ml (data not shown for the other antibodies), showing that their inability to recognize G2 is not restricted to the cell surface setting. The positive control antibody 3.7D6 (2.5 µg/ml) recognizes all three variants.

Figure 3A:
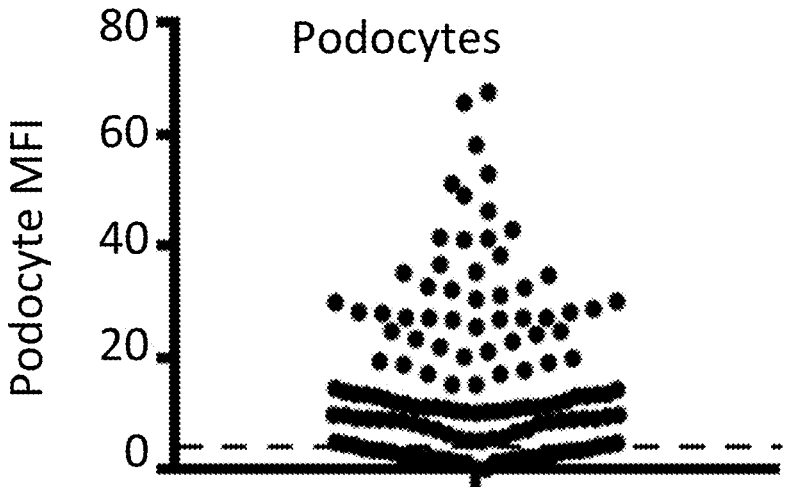

FIGS. 3A-3G show that endogenous APOL1 is present on cell surface of podocytes. FIG. 3A shows flow cytometry of wild-type (WT) podocytes, induced with 100 ng/ml IFNγ with all 170 anti-APOL1 antibodies (5 µg/ml), each dot representing an individual antibody. As in iAPOL1-CHO cells, most antibodies could recognize cell surface-bound endogenous APOL1 in WT podocytes.

Figure 3B:
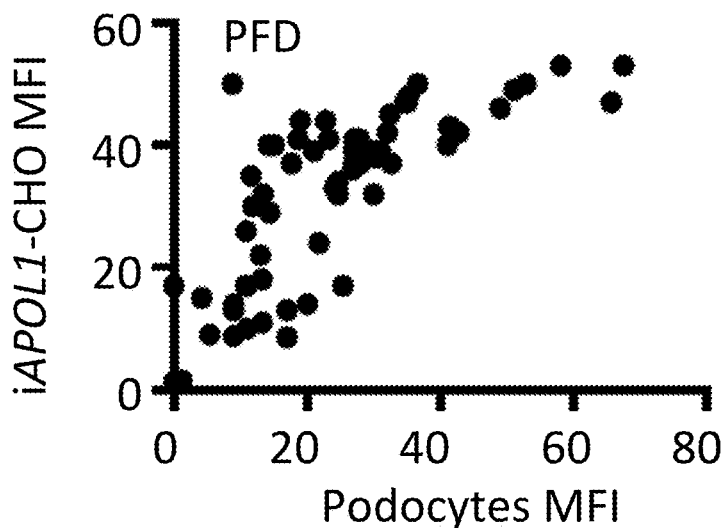
Figure 3C:
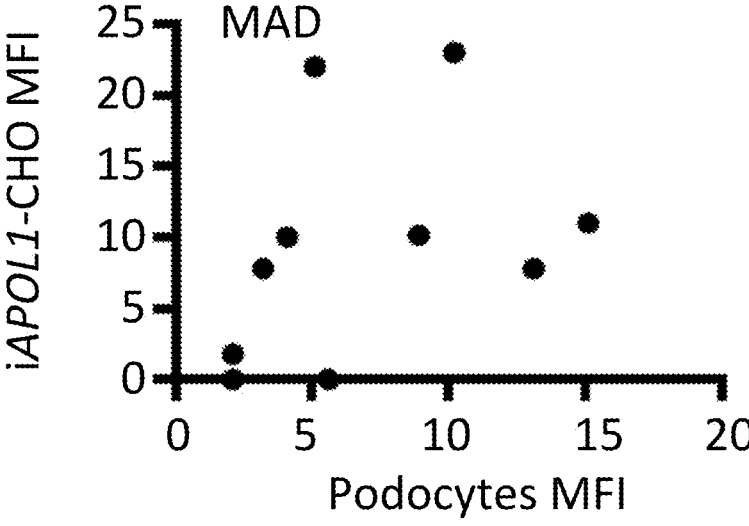
Figure 3D:
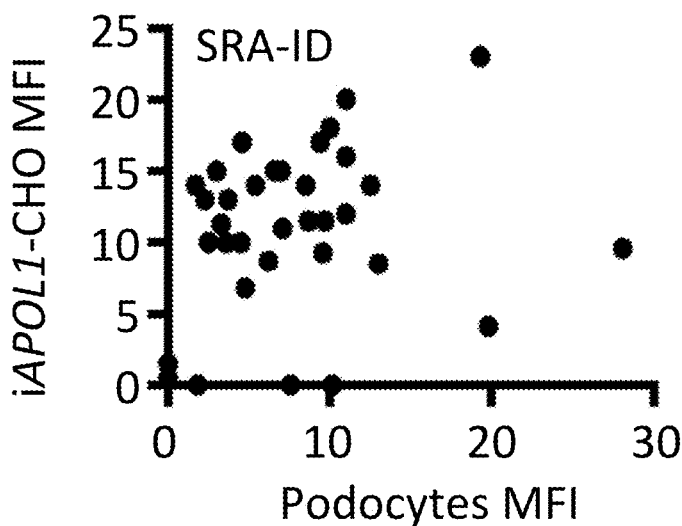

FIGS. 3B-3D show correlation plots of antibody binding between endogenous podocyte APOL1 (x-axis) and induced iAPOL1-CHO cells (y-Axis), using the MFI data from FIG. 3A and FIG. 2A, respectively. Each dot represents an individual antibody to the PFD (FIG. 3B), MAD (FIG. 3C) or SRA-ID (FIG. 3D). While the podocytes expressed lower levels of APOL1 than the iAPOL1-CHO cells (compare FIGS. 3E, 3F and 3G below), the relative signals for each antibody showed similar trends, with the exception that the MAD and SRA-ID signals were noticeably lower on podocytes than on CHO cells.

Figure 3E:
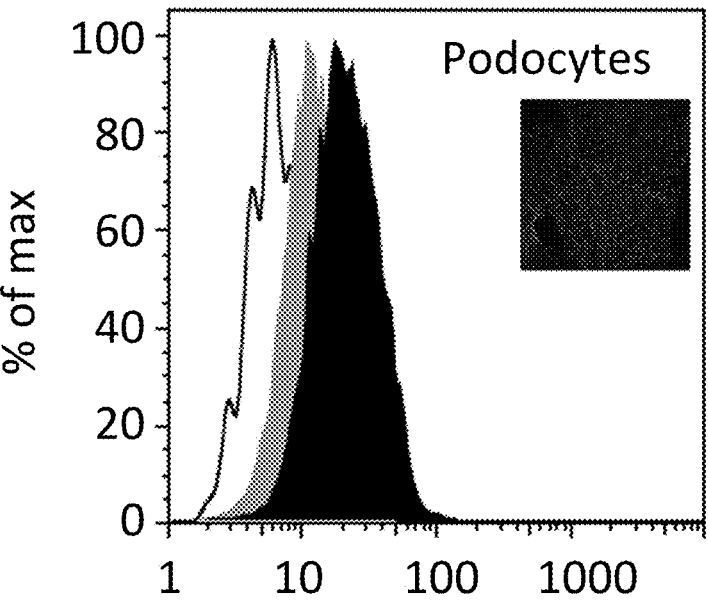

FIG. 3E shows flow cytometry of podocytes with (black) or without (grey) 24 hour (h) induction with 100 ng/ml IFNγ with 5 µg/ml anti-APOL1 PFD antibody 3.7D6. White is Alexa488 anti-mouse secondary antibody alone. Endogenous APOL1 is detectable on the surface of podocytes and the shift increases after IFNγ upregulation. Inset shows immunofluorescence of surface APOL1 on unpermeabilized WT IFNγ-induced podocytes.

Figure 3F:
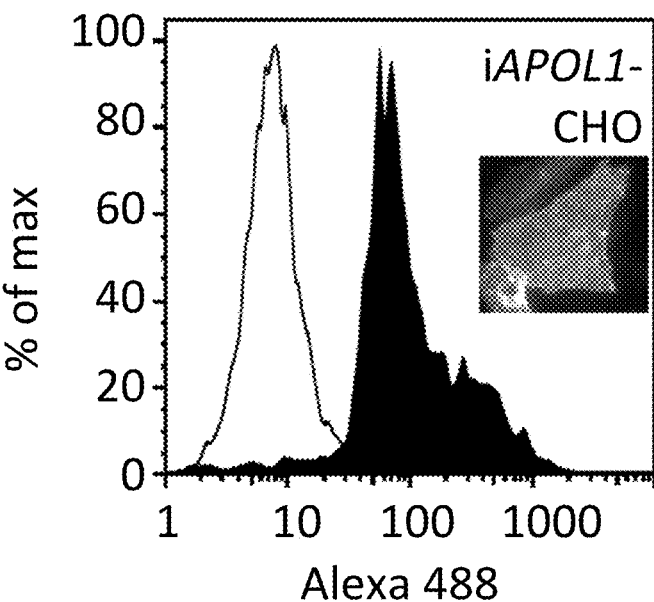

FIG. 3F is as in FIG. 3E except with iAPOL1-CHO cells after 24 h doxycycline induction at 5 ug/ml (but no IFNγ). Insets show surface APOL1 staining with antibody 3.7D6 by immunofluorescence on non-permeabilized iAPOL1-CHO cells.

Figure 3G:
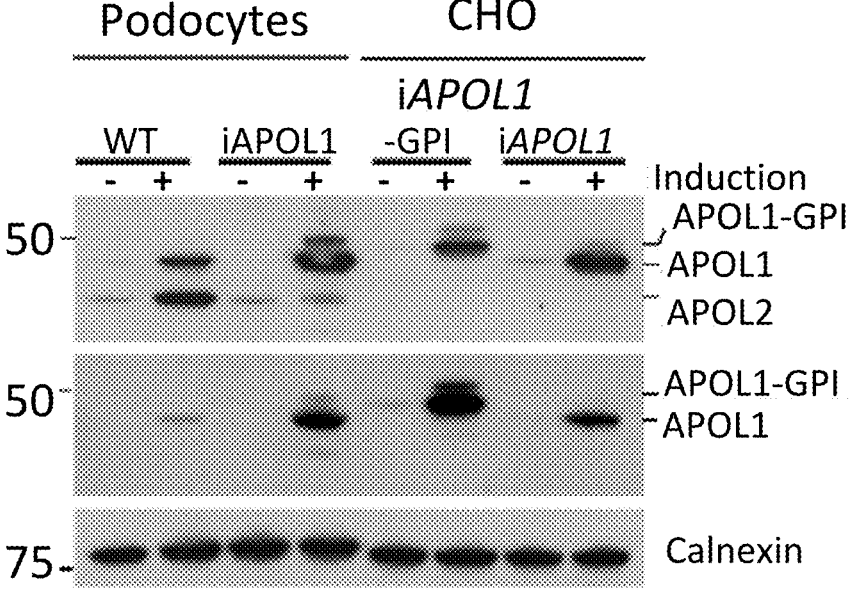

FIG. 3G shows a Western blot of WT podocytes and iAPOL1 cell lines. 6 lysates (from left to right) of WT-podocytes uninduced (−) or induced (+) with IFNg (100 ng/ml for 48 h); iAPOL1-G0-podocytes (explained later) ±10 ng/ml doxycycline for 48 h; gD-iAPOL1-CHO-GPI (construct b in FIG. 1A); and full length iAPOL1-CHO (construct a), both ±5 µg/ml doxycycline-induction for 48 h. Upper blot was probed with 0.44 µg/ml Proteintech anti-APOL1 polyclonal (which also recognizes APOL2; (See Example 2), which was then stripped and reprobed with 0.05 µg/ml rabbit 3.1C1/3.7D6 in-house antibodies (middle) and calnexin loading control (lower); the APOL1 signal is weaker due to reprobing, but APOL2 is absent. The 36 kDa APOL2 band in podocytes is only seen with the Proteintech antibody, and is upregulated by IFNg but not dox. There is higher expression of iAPOL1 (41 kDa) in the stable cell lines than in podocytes. The GPI anchor in gD-iAPOL1-GPI-CHO (aa 61-398, predicted 40.5 kDa including 2.6 kDa from the 25 aa gD tag) is presumably intact since the band runs higher than that of iAPOL1-CHO (aa 28-398, predicted 41.1 kDa) despite encoding a smaller protein.

Figures 4A, 4B, 4C:
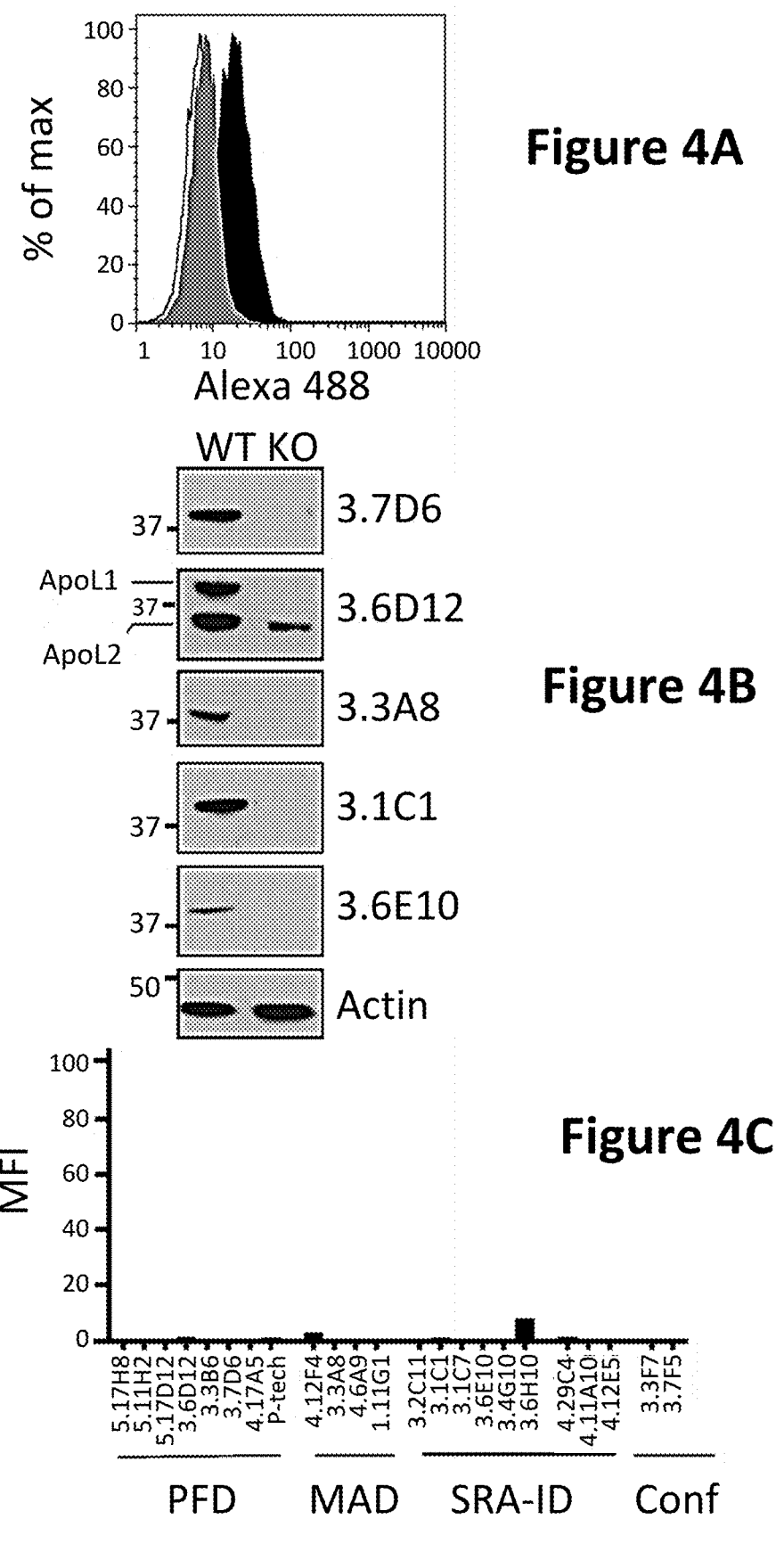

FIGS. 4A-4C shows confirmation that the surface signal in podocytes is APOL1. FIG. 4A shows characterization of the best APOL1 KO podocyte clone. FACS with PFD antibody 3.7D6 on the fastest growing APOL1 KO podocyte clone 89401-3 (grey) versus WT podocytes (black), both treated with 100 ng/ml IFNγ for 24 h. The APOL1 KO clone shows similar anti-APOL1 3.7D6 signal to the Alexa488 anti-mouse secondary antibody alone (white), indicating successful knockout of APOL1.

FIG. 4B shows confirmation of complete APOL1 knockout in clone 89401-3 (6 µg lysate per lane on 4-12% Bis-Tris gels) with various domain-specific antibodies: 3.7D6 and 3.6D12 (PFD); 3.3A8 (MAD); 3.1C1 and 3.6E10 (SRA-ID) all show loss of APOL1. Antibody 3.6D12 cross-reacts with APOL2 (Example 2 below) and shows that, as intended, APOL2 is not deleted in APOL1 KO podocytes, although there does appear to be some reduction in APOL2 level in this particular clone.

Figures 6A, 6B, 6C:
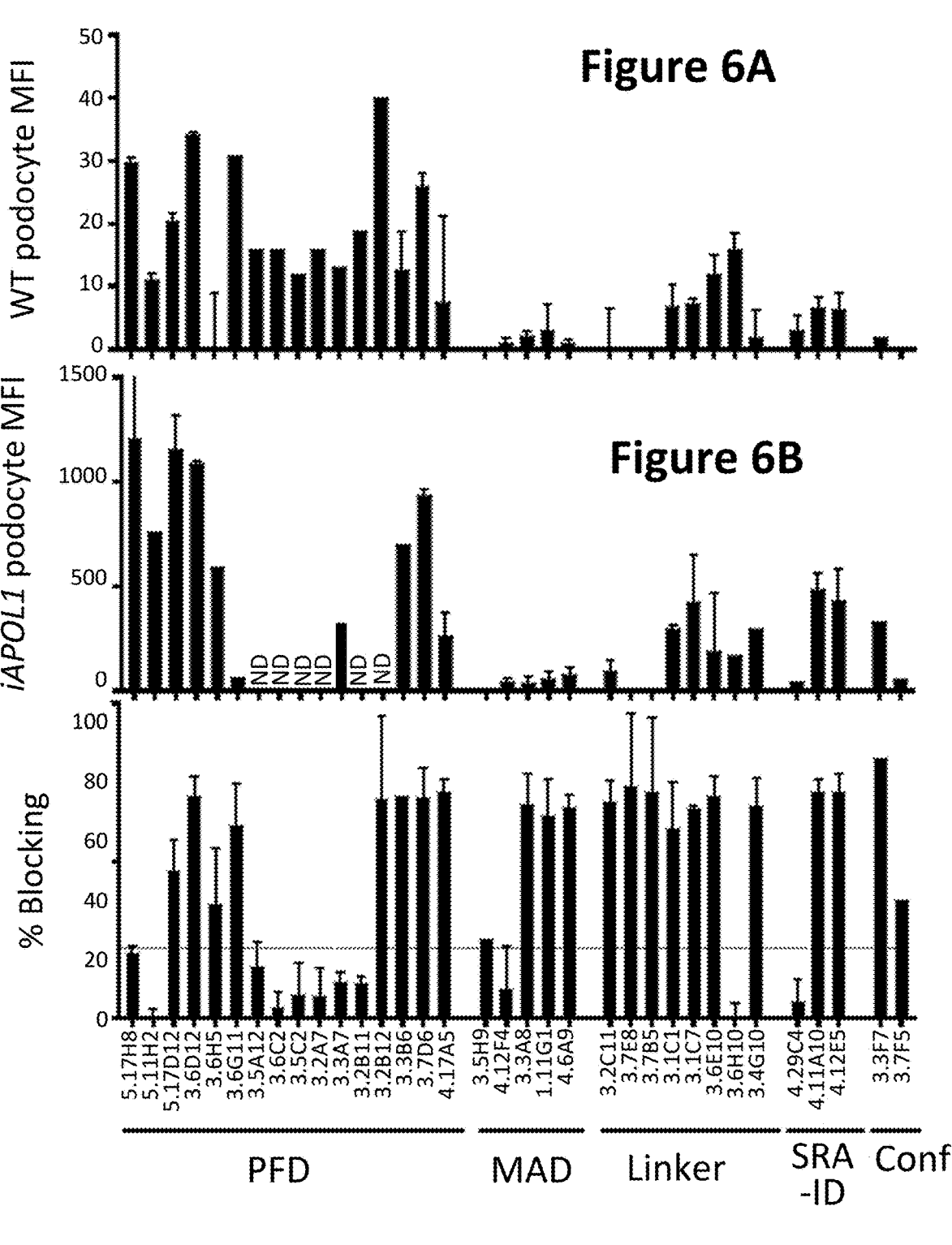

FIG. 4C shows Specificity of the FACS shifts on podocytes. Flow cytometry on APOL1 KO clone 89401-3 shows complete loss of signal with almost all the anti-APOL1 antibodies tested. Mean fluorescence intensity data is plotted from a single representative experiment of at least 3 independent experiments performed. The few small signals were not from the antibodies classified as FACS-negative on CHO cells, but rather represent a low level of non-specific background binding, since the signals for these antibodies on WT podocytes was much higher (FIGS. 6A-C). P-tech is the Proteintech polyclonal anti-APOL1.

FIGS. 5A-5E show that the majority of antibodies recognize circulating APOL1.

Figure 5A:
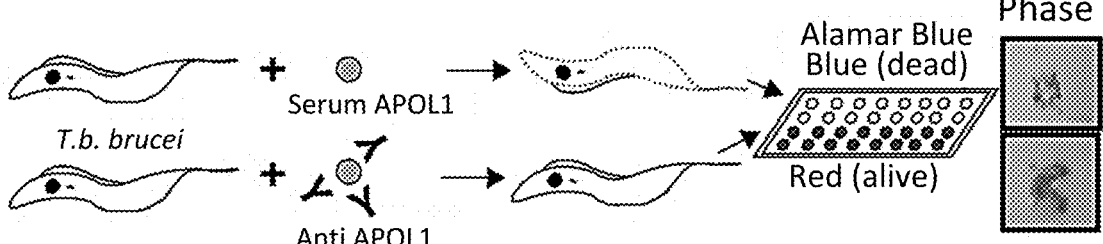

FIG. 5A shows a schematic of our anti-APOL1 trypanolysis blocking assay. Trypanosomes (SRA-negative *T. brucei brucei*) incubated in 96-well plates with Normal Human Serum (NETS) naturally containing APOL1 die and do not alter the blue color of the Alamar Blue viability reagent. If the anti-APOL1 antibodies ("Y") block APOL1 activity, the trypanosomes survive and the Alamar Blue turns red in proportion to the level of metabolic activity of the live trypanosomes. Representative phase contrast images for dead (upper) and live (lower) trypanosomes are shown on the right.

Figure 5B:
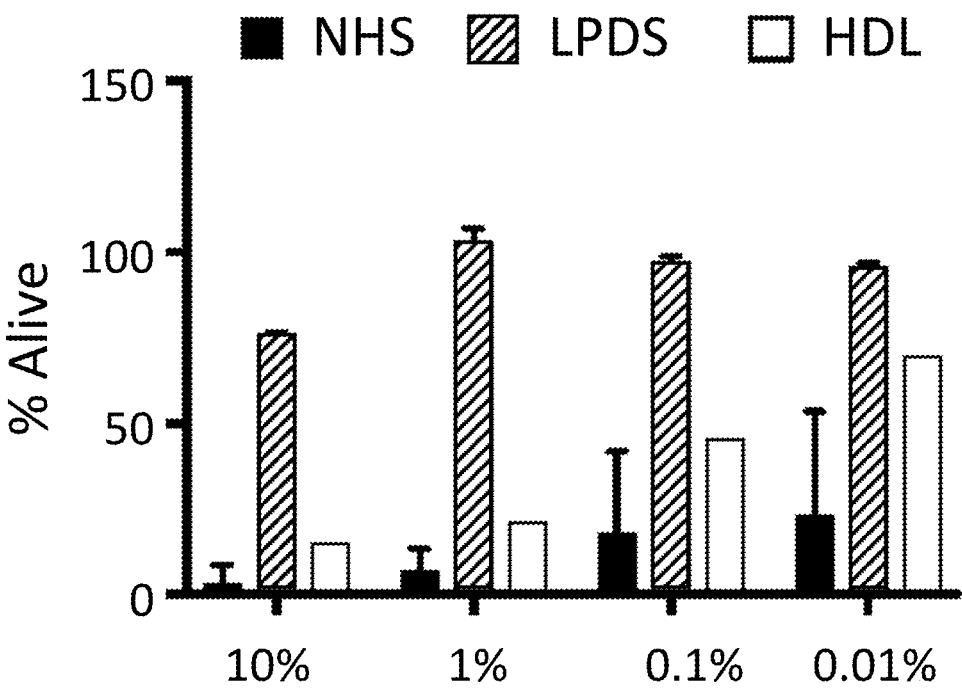

FIG. 5B shows titration of NETS (black), purified High Density Lipoprotein (HDL; white) and Lipoprotein-deficient NHS (LPDS; grey) for trypanolytic activity. The percentage of live trypanosomes, assessed using the Alamar Blue viability assay, is plotted as a function of dilution. Data plotted are means and S.D. from n=6 experiments for NETS and n=2 for LPDS. Data shows less lytic activity in LPDS compared to NETS and HDL. There was day-to-day variability in the efficiency of trypanosome killing below 1% NETS, which could be due to the source of NETS or loss of activity due to APOL1 degradation when not properly stored at −80° C.

Figure 5C:
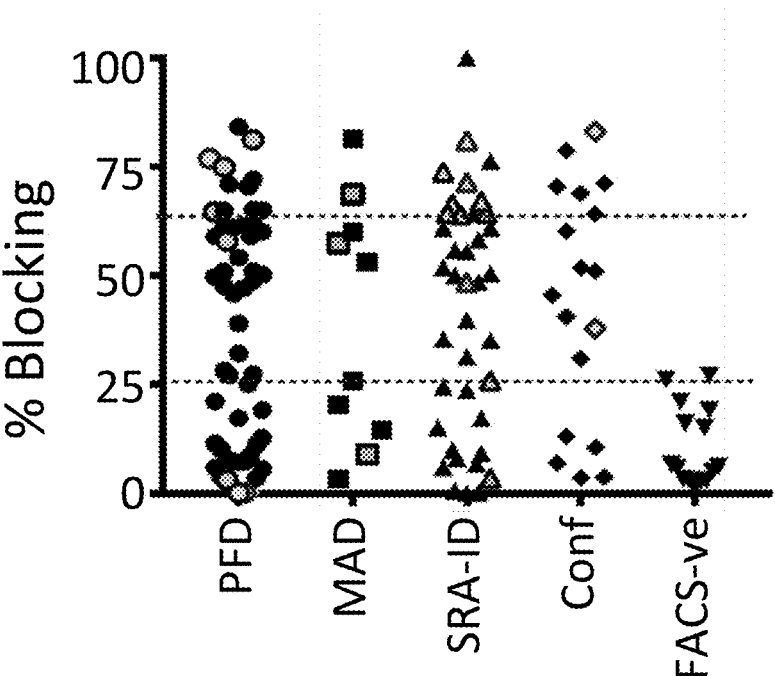

FIG. 5C shows blocking of serum-associated APOL1-mediated trypanolytic activity in the presence of 1 µg/ml anti-APOL1 antibodies is plotted. Antibodies are grouped according to their domain recognition as determined in FIG. 1C. The percentage of blocking is calculated by normalizing to no antibody control (NETS only). Each symbol represents the average of 2 independent experiments for a given antibody. Antibodies used in the immunoprecipitation assay in FIG. 5D and FIGS. 17A-C) are plotted in grey. Note that all experiments were performed with 1 and 10 µg/ml antibodies in parallel, but only the 1 µg/ml data is shown due to higher stringency. The dashed line at 25% indicates the cutoff limit for blockers; the line at 60% indicates the cutoff for "strong" blockers.

Figure 5D:
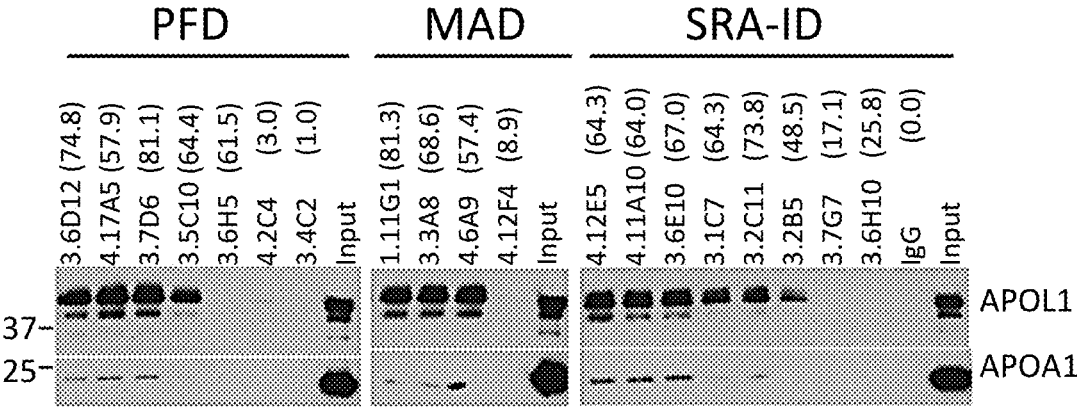

FIG. 5D shows immunoprecipitation of APOL1 from NHS. A subset of the cloned anti-APOL1 antibodies to each domain (selected for a range of blocking activities (see FIG. 5C) were conjugated to Dynabeads and incubated with NHS. Immunoprecipitates were western blotted with rabbit anti-APOL1 (Proteintech, upper) or rabbit anti-APOA1

Figure 17A:
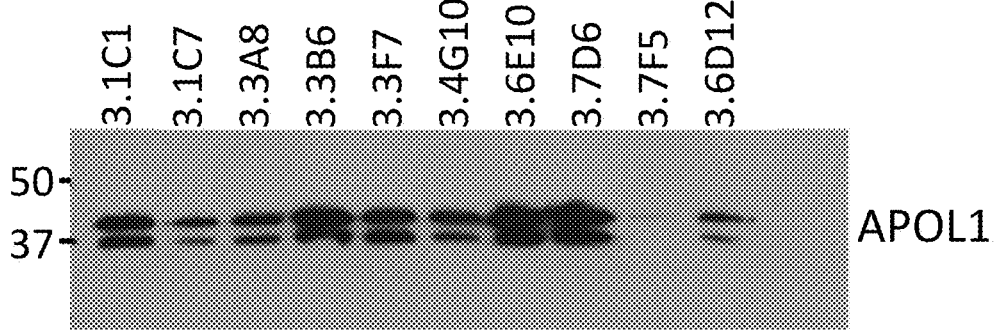
Figure 17B:
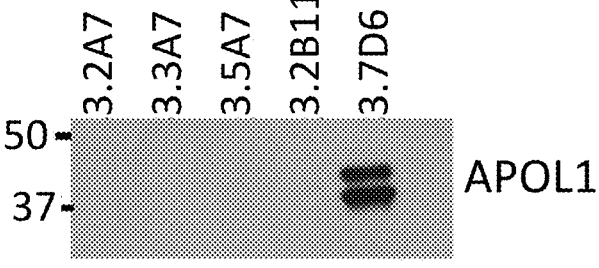
Figure 17C:
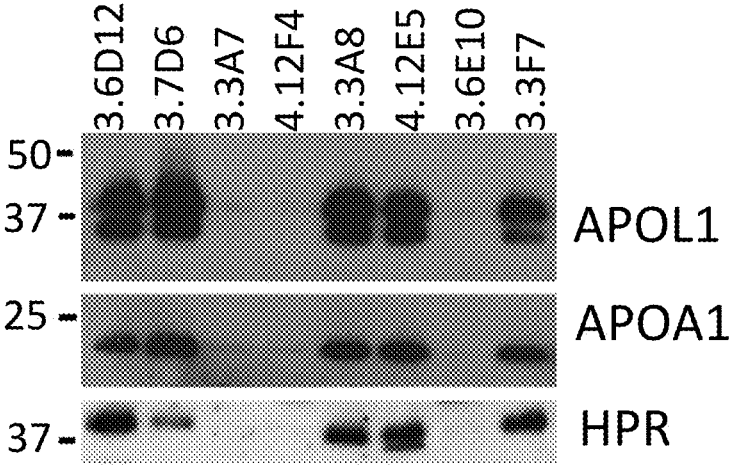

(Rockland, lower) on 4-12% Bis-Tris gels. The strong blockers pulled down large quantities of APOL1, the weak blockers pulled down little or no APOL1 and the non-blockers pulled down no APOL1. Grey numbers in parentheses indicate % blocking activity as plotted in FIG. 5C. Since APOL1 is only present in HDL3b (Ref. 50 of Example 1), which comprises only ~5% HDL particles (Ref. 51 of Example 1), only a fraction of total APOA1 is co-immunoprecipitated by the best anti-APOL1 antibodies, as expected. Another experiment including some of the other antibodies, as well as HPR pull-down, are shown in FIGS. 17A-C.

Figure 5E:
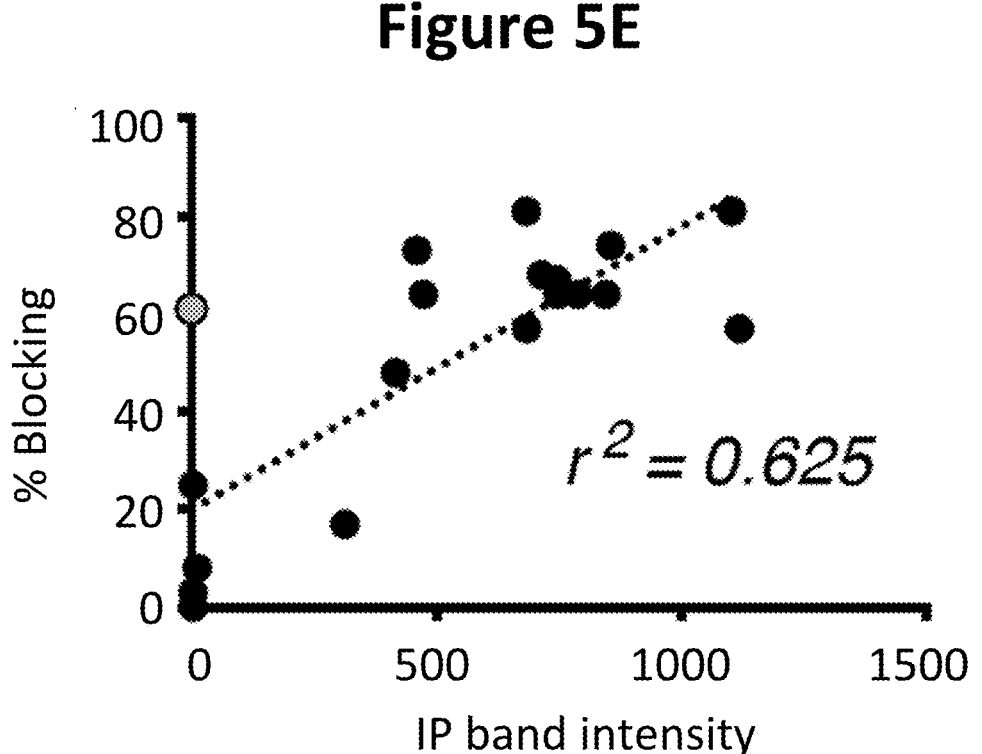

FIG. 5E shows a correlation plot of trypanolytic blockade versus serum APOL1 recognition. The intensity of the immunoprecipitated APOL1 bands (average of 2-3 blots) is plotted on the x-axis versus percentage of blocking of trypanolysis (y-axis) for each of the antibodies in FIG. 5D. With the exception of one antibody (3.6H5, shown in grey), the blockers all recognized APOL1 by immunoprecipitation, correlating reasonably well with band intensity (Spearman's rho coefficient of 0.625; (0.75 excluding 3.6H5)).

FIGS. 6A-6C show that APOL1 conformation differs between circulating and cell surface APOL1. Flow cytometry on WT podocytes, induced with 100 ng/ml IFNγ for 48 h (FIG. 6A), and flow cytometry iAPOL1-G0 podocytes induced for 24 h with 10 ng/ml dox (FIG. 6B) show similar binding patterns with all individual antibodies. The y-axis denotes mean fluorescence intensity (MFI); note the lower scale for WT than inducible podocytes. The means and SDs of 3 independent experiments are plotted for cloned antibodies (in bold font) and 1-2 experiments for hybridoma purified antibodies. ND indicates 'not determined' due to lack of (non-cloned) antibody availability.

FIG. 6C shows blockade of serum APOL1-mediated trypanosomal lysis plotted as a surrogate for serum APOL1 binding. The y-axis represents % blocking activity (mean and SD of 3 independent experiments, each normalized to no antibody control). Non-blockers fall below the dashed line (≤25% blocking). The antibodies are listed in tentative binding order (N to C-terminus) along the length of APOL1, with the exception of the conformational antibodies (Conf), which we could not map since they only recognize full length APOL1 (see FIGS. 7A-B and FIGS. 19A-B and 20A-E).

Figures 7A, 7B:
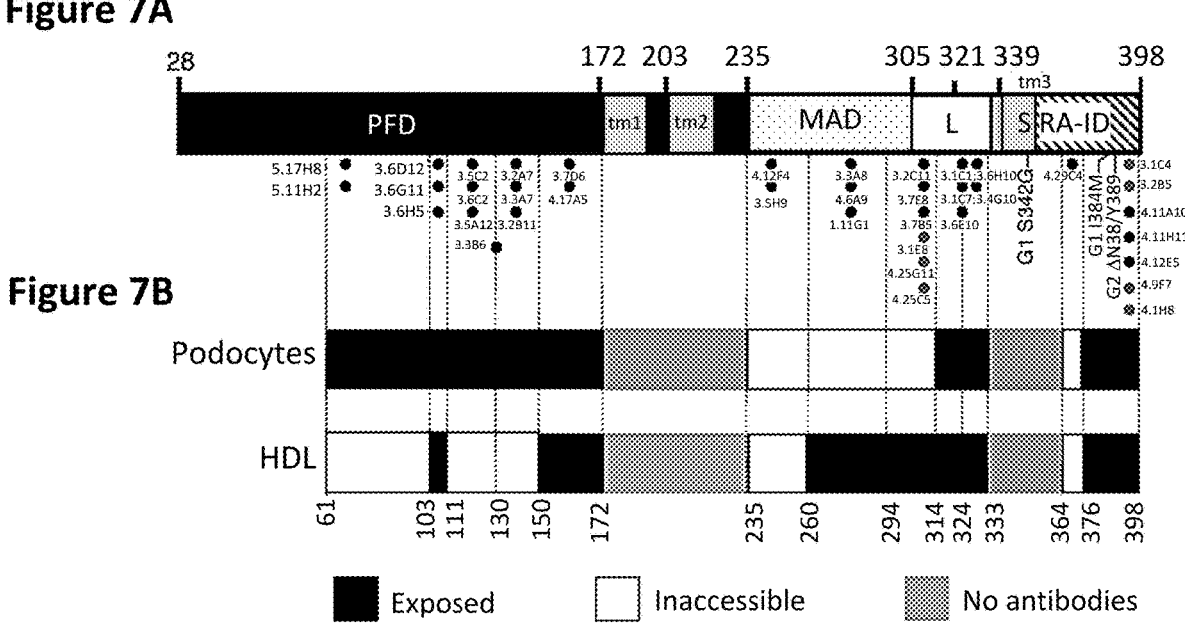

FIGS. 7A-7B show epitope mapping of anti APOL1 antibodies and model for APOL1 topologies. FIG. 7A shows schematic representation (drawn to scale) of domain mapping results of individual cloned antibodies is shown on APOL1-G0 with the three predicted transmembrane (tm) domains (Thomson et al; ref. 22 in Example 1) as grey squares; L, linker between MAD and SRA-ID. Dotted vertical lines indicate the boundaries of the epitopes that the various antibodies mapped to with aa numbers at the bottom (see FIGS. 19A-B and 20A-E). The dots below indicate the number of antibodies that mapped to that region. The positions of the G1 and G2 variants are indicated respectively.

FIG. 7B Predicted exposure of APOL1 epitopes in podocytes (top) and serum APOL/HDL (bottom). Black bars indicate exposed regions, white bars non-accessible regions and grey represents regions to which we obtained no antibodies (mainly the transmembrane domains and surrounding residues). Dotted vertical lines and numbers indicate the positions of the exposed/non-exposed boundaries determined by epitope mapping.

Figure 8A:
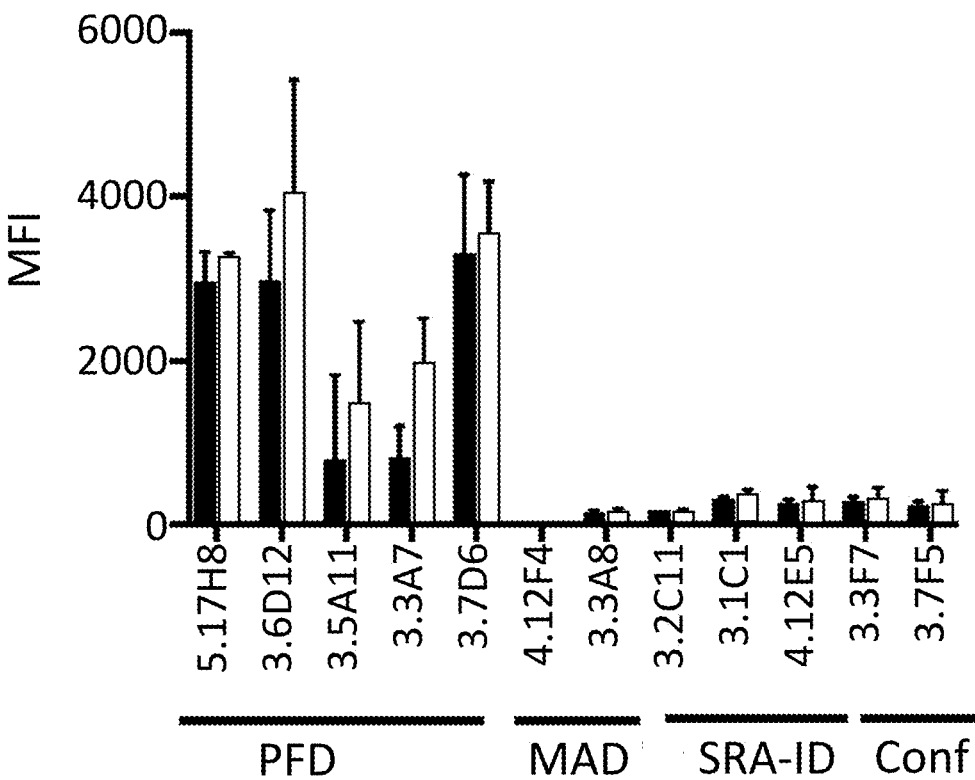
Figure 8B:
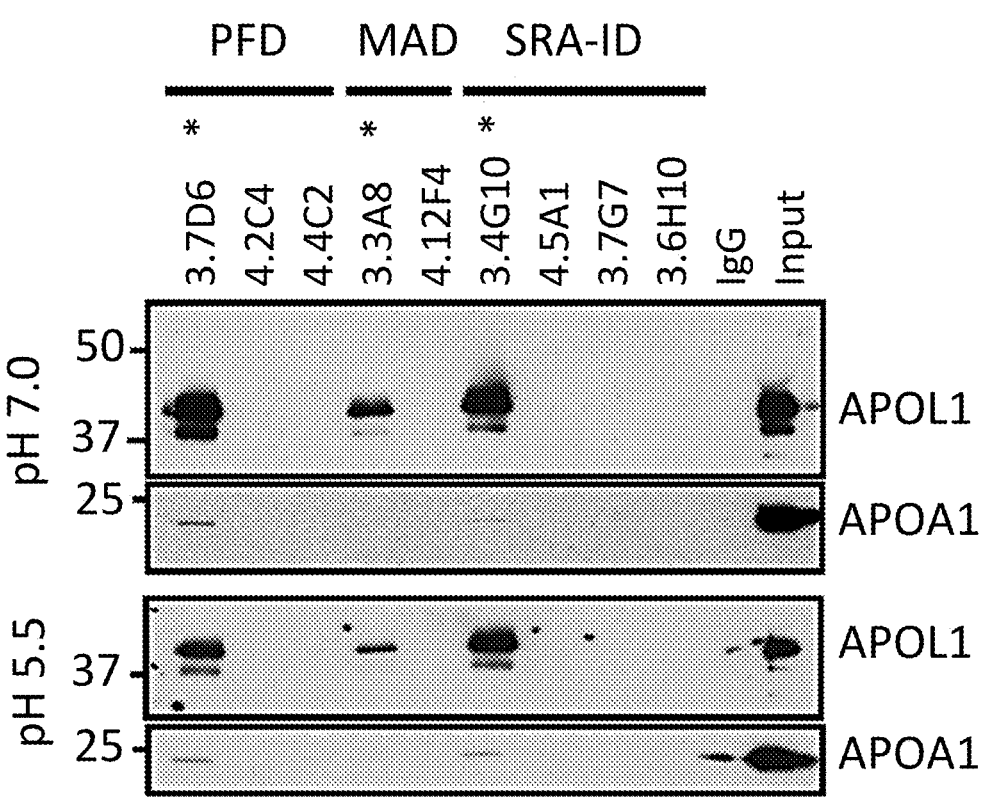

FIGS. 8A-8B show that low pH does not detectably affect APOL1 topology. FIG. 8A shows flow cytometry on iAPOL1 podocytes treated with 10 ng/ml doxycycline for 24 h. Mean fluorescence intensities of live cells incubated with primary antibody in the presence of PBS at pH 7.0 (black) or pH 5.5 (grey) at 4° C. after subtraction of secondary antibody alone background. There was no detectable difference in binding of any of the antibodies to the three different domains at low pH. This experiment was performed on a different flow cytometer than the other figures, hence the higher MFI readings. Means and standard deviations of duplicates from two independent experiments are plotted.

FIG. 8B shows immunoprecipitation of serum APOL1 at low and neutral pH. Serum APOL1 was immunoprecipitated using Dynabeads conjugated with anti-APOL1 antibodies and run on a 4-12% Bis-Tris gel. The resulting blots were immunolabeled with 3.1C1/3.7D6 for APOL1, revealing APOL1 was pulled down in both pH conditions only by blocking antibodies (asterisks) along with APOA1; the weak or non-blockers did not become binders at pH 5.5.

Figures 9A, 9B, 9C:
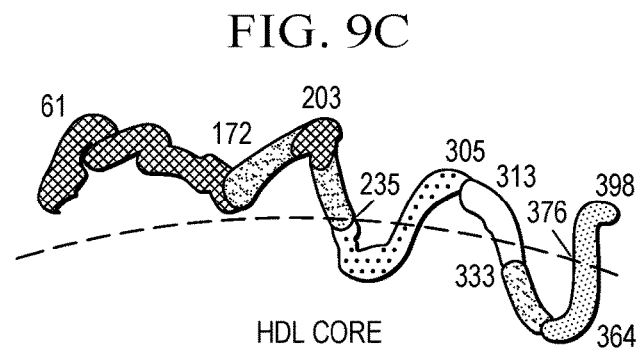

FIGS. 9A-9C show models for APOL1 topology. FIG. 9A shows a cell-based model for APOL1 topology based on the assumption that at least the first of the two transmembrane domains is correct (they are numbered according to the DAS and SPLIT server predictions, Table 2B below). In FIG. 9A, the number of predicted transmembrane domains in APOL1 varies from 1 to 4 according to the program used (Table 2B), although all agree on the first transmembrane being from aa ~177-196. Our data are not fully consistent with any of the transmembrane predictions, unless the two PFD transmembrane domains (between 175 and 224) are real, and the third one (~338-353) is a loop rather than a complete transmembrane pass. No antibodies were obtained to any of these predicted hydrophobic regions, possibly because they were buried in the antigen. The cell surface bilayer is depicted as dashed lines and the numbers denote the aa positions, as in FIG. 7. The exposure of both the N- and C-termini of APOL1 would normally predict an even number of transmembrane domains, but the clear exposure of the linker domain (aa 314-333) in between renders two or four transmembrane domains impossible. Likewise, three transmembrane domains with the $2^{nd}$ (less strongly predicted one) being a "half-spanning loop" similarly fail to account for the linker exposure and the fact that the MAD is exposed on CHO cells. Thus, the SRA-ID transmembrane domain (tm3) is expected to be a half-spanning loop. However, some portions of APOL1 may be buried by other proteins or are simply in an inaccessible orientation rather than embedded in lipids. Numbers indicate the transmembrane domains predicted by the DAS and SPLIT servers (Table 2B). The pore forming domain is completely exposed up to the first transmembrane domain, and the MAD is likely extracellular but obscured by a hypothetical antibody-blocking protein (shaded oval) that is expressed in podocytes and other human cell lines but not CHO cells in order to account for the fact that the MAD is inaccessible in human and exposed in CHO. The end of the linker is exposed, but the third transmembrane and first half of the SRA-ID are inaccessible, with only the C-terminus of the SRA-ID (including the G1 I384M and G2 mutations) exposed. FIGS. 9B-9C show models for APOL1 topology in serum based on the assumption that our trypanolytic assay mainly measured HDL-associated APOL1 activity (as shown in FIG. 5D), although the regions depicted as buried in the HDL membrane could theoretically be bound by other serum proteins, such as IgM in TLF2, instead. The model in FIG. 9B assumes the predicted transmembrane domains are buried in the HDL particle, while the model in FIG. 9C does not make this assumption and just shows the results of the trypanosome blocking.

Figure 10E:
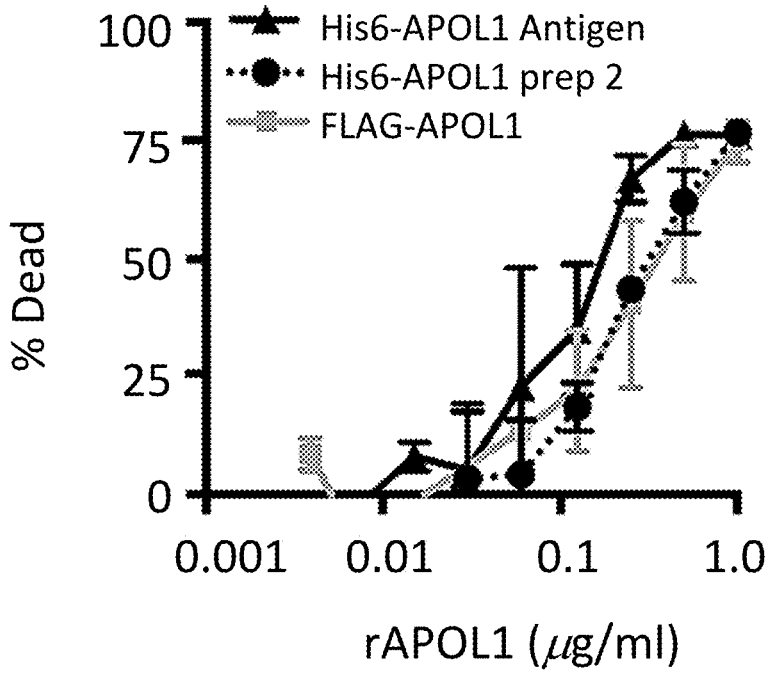

FIGS. 10A-10F show that the APOL1 immunogen is functional. FIG. 10A shows S200 column purification of $his_6$-APOL1 antigen. NiNTA-purified $his_6$-APOL1 was fractionated on a large 5200 column in the presence of 0.1% DDM. The main peak at 1142 ml corresponds to full length monomer. Fractions B4-C1 (black rectangle) were pooled for characterization and immunization.

FIG. 10B shows SDS-PAGE gel of final pooled fractions B4-C1 of $his_6$-APOL1 antigen. Samples were boiled in reducing sample buffer and run on a Bolt 4-20% Bis-Tris PLUS gel in Bis-Tris SDS buffer, followed by Coomassie Blue staining. The major 37 kDa band represents full length $his_6$-APOL1, with cleavage products at 24 and 16 kDa.

FIG. 10C shows 5200 column purification of FLAG-APOL1 used for trypanolytic assays. FLAG-APOL1 was purified with an anti-FLAG antibody column was fractionated on an S200 column in the presence of 0.026% DDM. The main peak at 70 ml corresponds to full length monomer and the black rectangle denotes fractions 19-21 that were pooled for use in trypanolysis assays.

FIG. 10D shows Coomassie Blue stained 4-20% Tris-Glycine SDS-PAGE gel of the 5200 fractions in FIG. 10C, showing one major band corresponding to full length protein. Fractions 19-21 (black rectangle) were pooled for use. Molecular weight markers were See Blue Plus 2 (Invitrogen LC5625), so APOL1 appears at around 41 kDa on this gel.

FIG. 10E shows that recombinant APOL1 (rAPOL1) is active at killing trypanosomes. Three different preps, all formulated in buffer containing 0.026% DDM, were compared for trypanolytic activity. Dilution series of initial $His_6$-APOL1 antigen prep (from FIG. 10A; black solid line), a subsequent (improved, less degraded) $His_6$-APOL1 prep, used for trypanolysis assays (black dotted line) and FLAG-APOL1 (from FIGS. 10C-D; grey solid line) incubated with *Trypanosoma brucei brucei* show similar dose-dependent lytic activity of the recombinant protein in the Alamar Blue assay. The y-axis denotes the percentage of dead trypanosomes calculated as in FIG. 5.

Figure 10F:
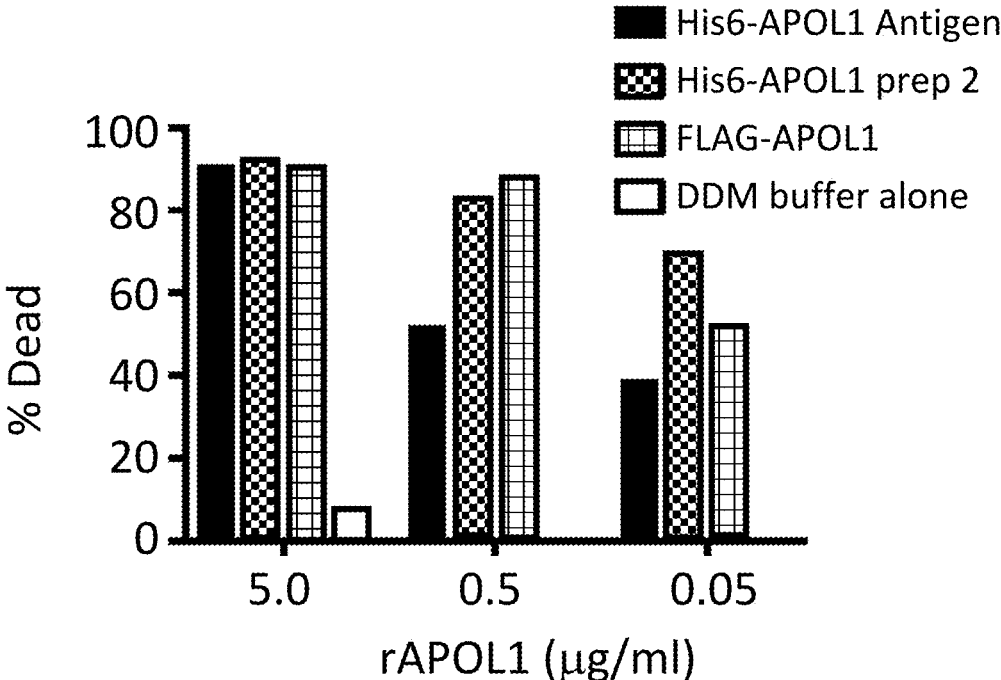

FIG. 10F shows that trypanosome lysis is due to recombinant APOL1 and not DDM, since equivalent volumes of DDM buffer alone (white) do not result in trypanosome death.

Figure 11:
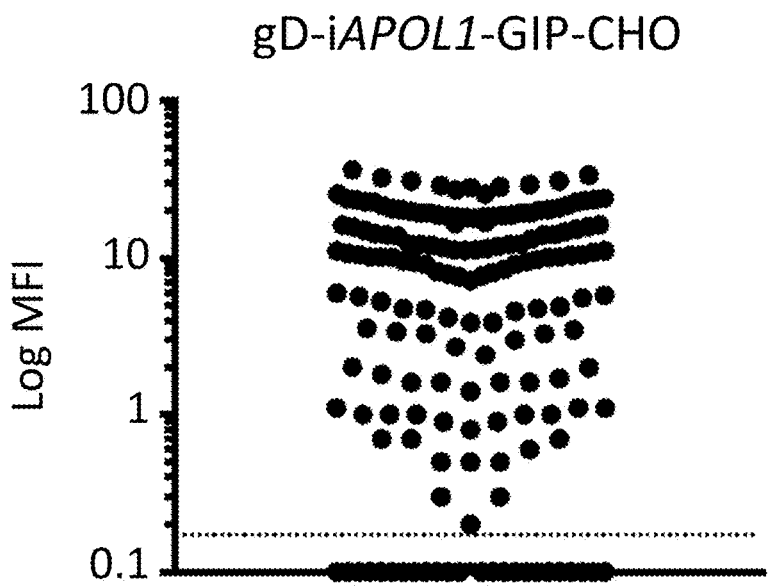

FIG. 11 shows antibody recognition of APOL1 on gD-iAPOL1-GPI-expressing CHO cells. Flow cytometry with all 170 antibodies on full length gD-APOL1-G0-GPI (construct b in FIG. 1A). The y-axis denotes the Mean Fluorescence Intensity (MFI, log scale). Each dot represents an individual antibody. The 150 FACS-positive antibodies (88%) are above the dotted line and the 20 negative antibodies (12%) are below the dotted line.

Figure 12A:
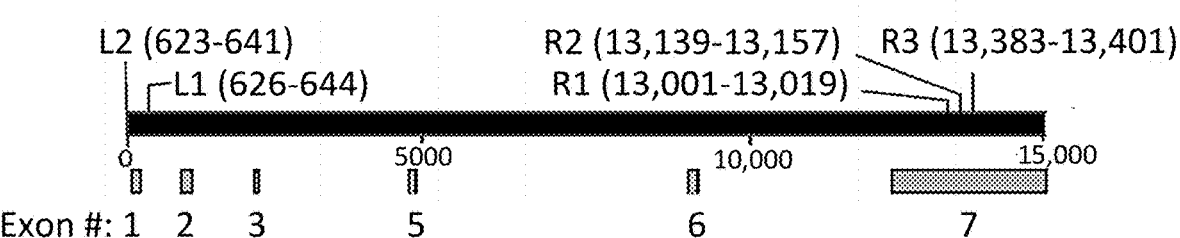

FIGS. 12A-12D show CRISPR/Cas9-mediated APOL1 KO strategy and characterization of clones. FIG. 12A shows schematic representation of the paired guide RNA locations targeting exon 1 and exon 7 on the whole APOL1 genomic locus to attempt APOL1 knockout by homologous recombination. The guide positions in nucleotides are indicated in parentheses. L is left, R is right.

Figures 12B, 12C:
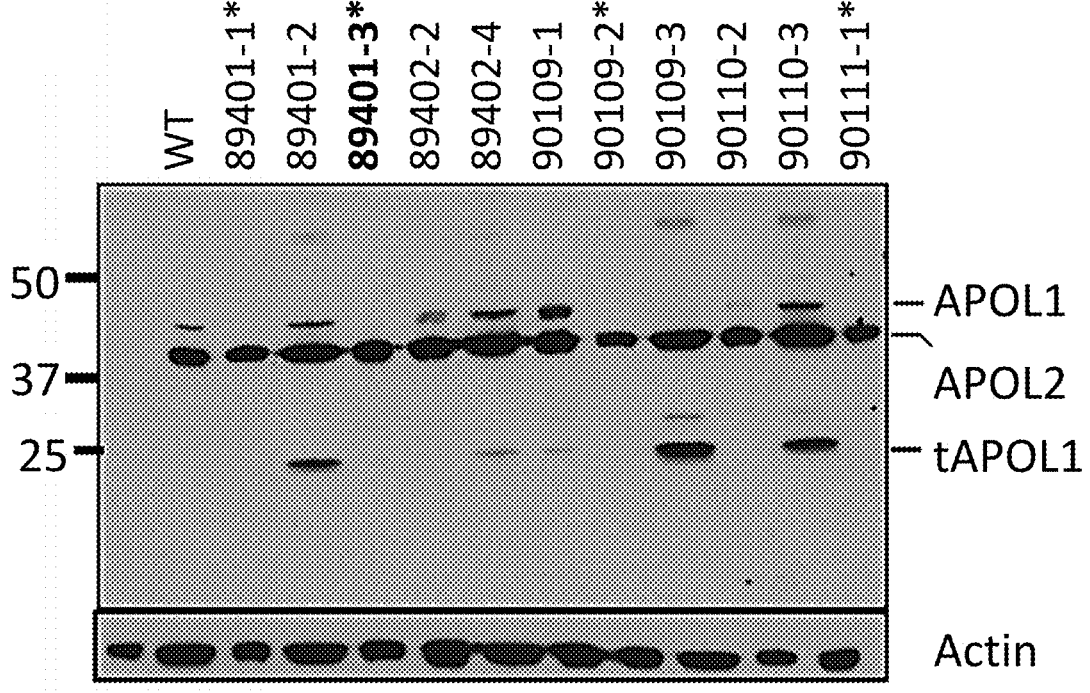

FIG. 12B shows the gRNA pairs used per transfection, each pair indicated by a number. Cell lines are named after their respective gRNA pairs.

FIG. 12C shows a Western blot of all single cell clones, obtained from individual transfections, with Proteintech polyclonal anti-APOL1. Asterisks indicate clones that showed complete loss of APOL1 (89401-1, 89401-3, 90109-2 and 90111-1; genomic data not shown), while two clones retained full length APOL1 (89402-2 and 90110-2). Five clones were rejected due to expression a truncated form of APOL1 (tAPOL1), with or without full length APOL1. As intended, none of the clones were knocked out for APOL2, although further western analysis suggested one allele might be lost in 89401-3 (see FIGS. 4B and 22). Actin served as a loading control.

Figure 12D:
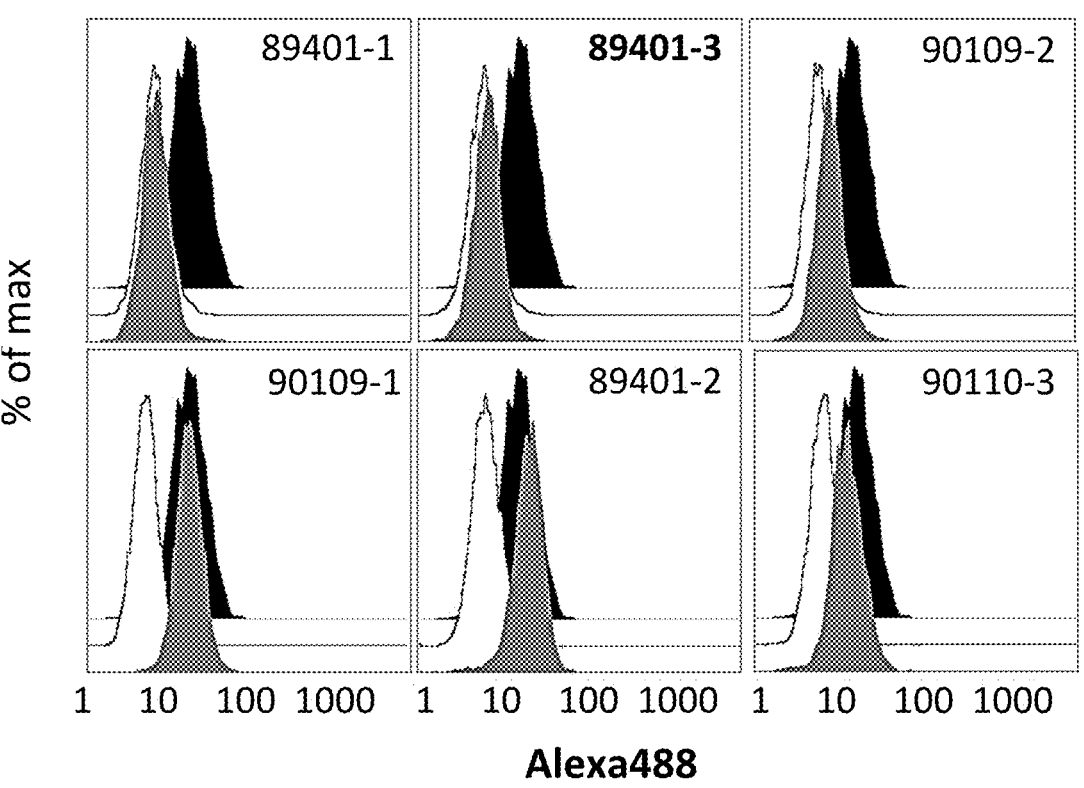

FIG. 12D shows flow cytometry with antibody 3.7D6 of selected single cell APOL1 KO podocyte clones show loss (i.e., successful knockout; top row) or presence (failed knockout; bottom row) of APOL1 on the surface (grey histograms) as compared to parental WT podocytes (black histograms); white histograms are Alexa488 anti-mouse secondary antibody alone. Clone 89401-3 (bold) was selected for further studies due to more similar morphology and growth rate to the parental cells.

Figure 13A:
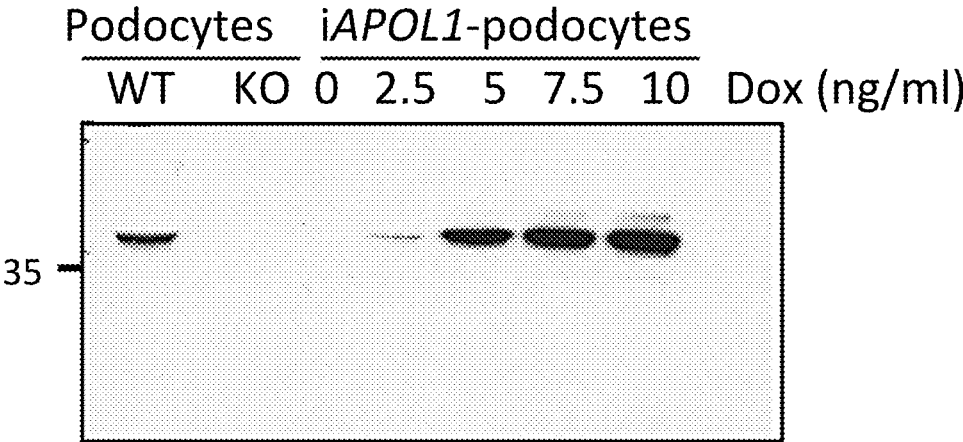
Figure 13B:
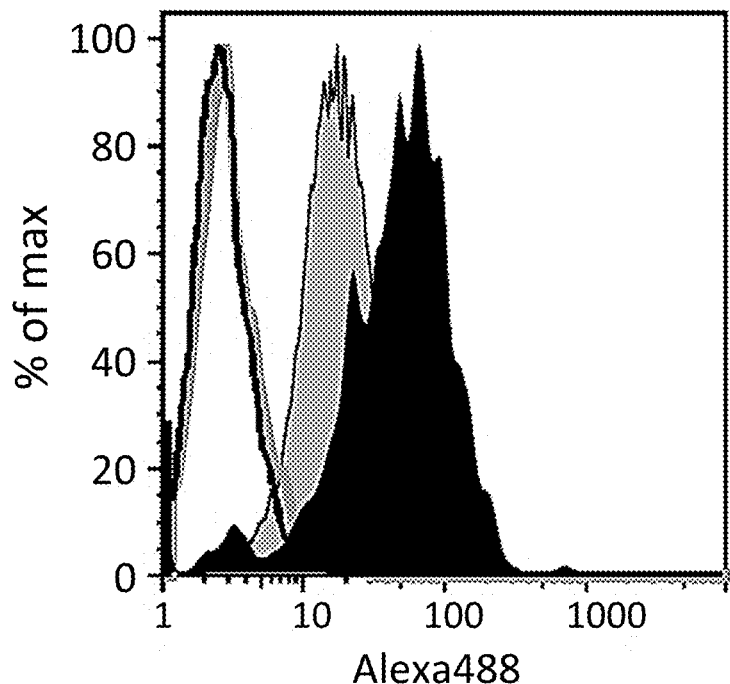
Figure 13C:
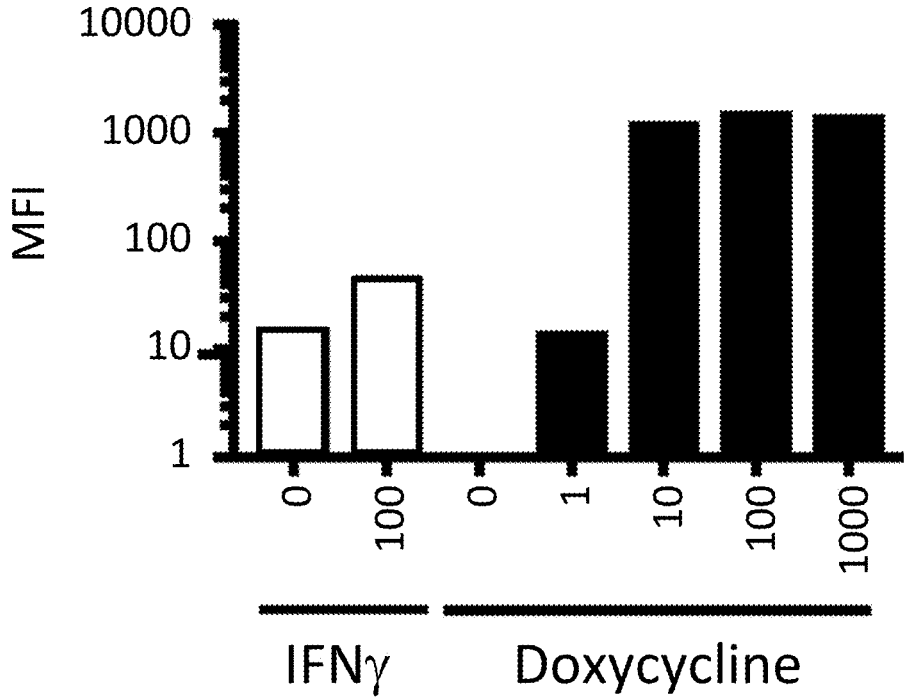

FIGS. 13A-13C show characterization of iAPOL1 podocytes. FIG. 13A shows a Western Blot (with 0.04 μg/ml rabbit 3.1C1 and 3.7D6 mixture) of APOL1 expression in lysates on 4-12% Bis-Tris gels of WT and APOL1 KO podocytes (both after 24 h IFNγ) versus iAPOL1-G0 podocytes±doxycycline stimulation (16 h). 10-fold higher expression than WT+IFNγ is seen after treatment with 10 ng/ml Dox for 16 h.

FIG. 13B shows that surface APOL1 expression by flow cytometry is 10-fold higher in iAPOL1-G0 podocytes (solid black; induced for 24 h with 5 ng/ml dox) than WT (grey; 24 h induced with 100 ng/ml IFNγ) using 1 μg/ml 3.7D6 antibody. APOL1 KO (black line) is completely negative, overlapping with Alexa488 anti-mouse secondary alone (grey line) as expected. A representative histogram from 3-4 experiments is shown.

FIG. 13C shows flow cytometry of surface APOL1 in iAPOL1-G0 podocytes (black bars) at increasing doxycycline concentrations (in ng/ml), showing it saturates at 10 ng/ml of dox, with 1 ng/ml producing levels similar to endogenous non-IFNγ-stimulated podocytes (grey bars). 10 ng/ml dox was selected for future experiments. Representative data from 3 experiments is shown. The y-axis is log MFI.

Figure 14:
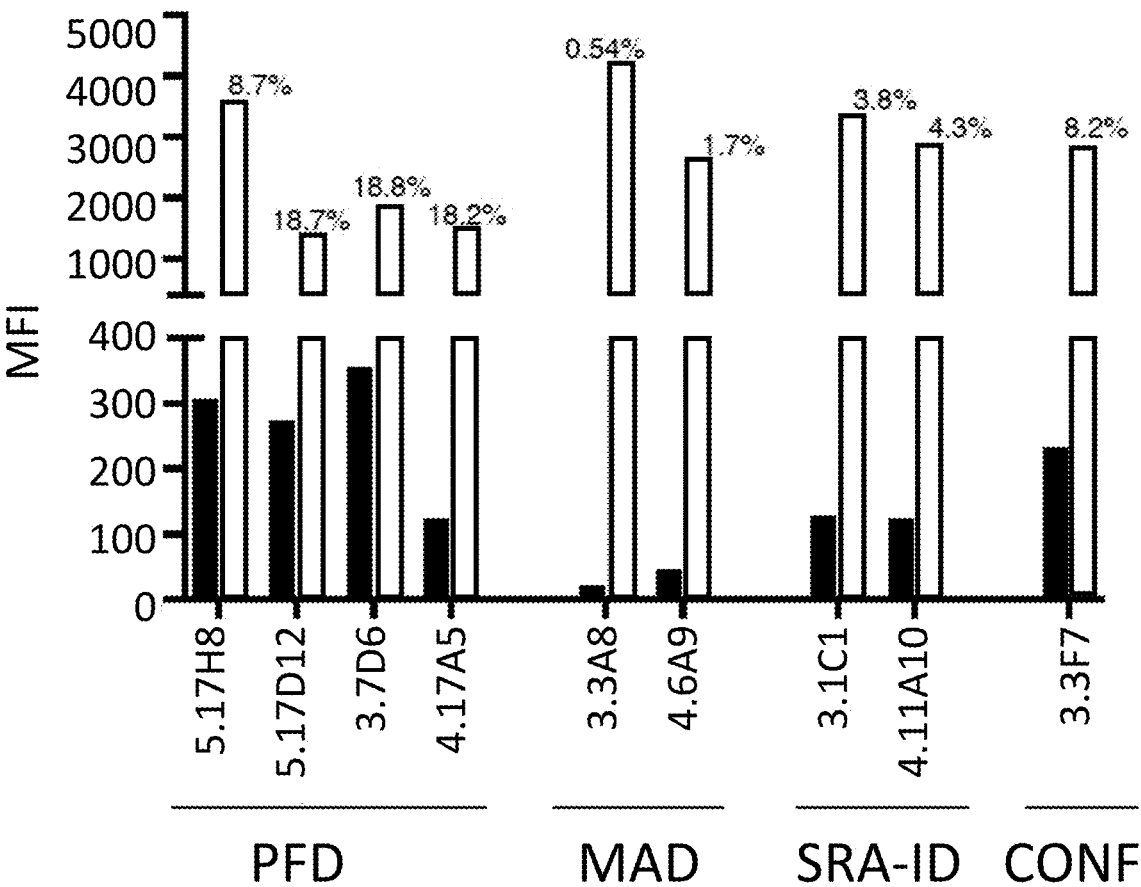

FIG. 14 shows flow cytometry on permeabilized versus intact APOL$_1$-podocytes. Mean fluorescence intensity (MFI) data of fixed and saponin-permeabilized (grey) versus live non-permeabilized (black) APOL1 WT podocytes induced with 100 ng/ml IFNγ for 24 h and stained with 9 representative antibodies is plotted. The numbers on top of bars indicate % of APOL1 on cell surface, calculated by the ratio of cell surface (unpermeabilized) vs total (permeabilized) APOL1 MFI. The MAD antibodies 3.3A8 and 4.6A9 cannot detect surface APOL1 on unpermeabilized podocytes, but can detect intracellular APOL1 on permeabilized podocytes (see also Example 2 below), as well as on live unpermeablized iAPOL1-CHO cells (white triangle in FIG. 2B).

Figure 15:
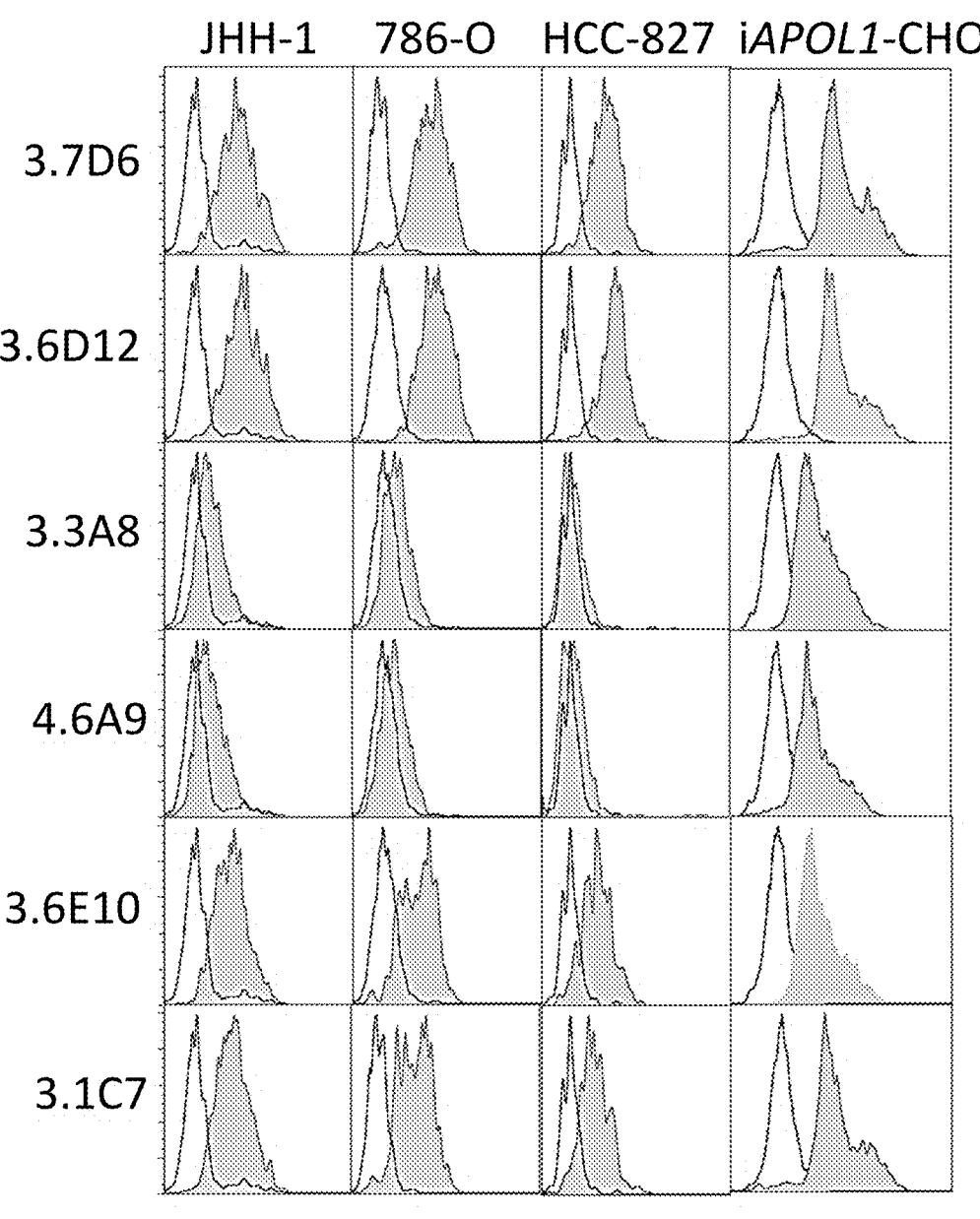

FIG. 15 shows that the MAD is inaccessible in human cell lines. Flow cytometry with antibodies to different domains on JHH-1 (liver), 786-O (kidney) and HCC827 (lung) cells treated with 100 ng/ml IFNγ for 48 h, all show similar patterns of endogenous APOL1 exposure as podocytes (endogenous and stably transfected), whereas iAPOL1-CHO cells treated with 10 μg/ml dox for 48 h, have a more accessible MAD domain (larger shift with antibodies 3.3A8 and 4.6A9).

Figure 16:
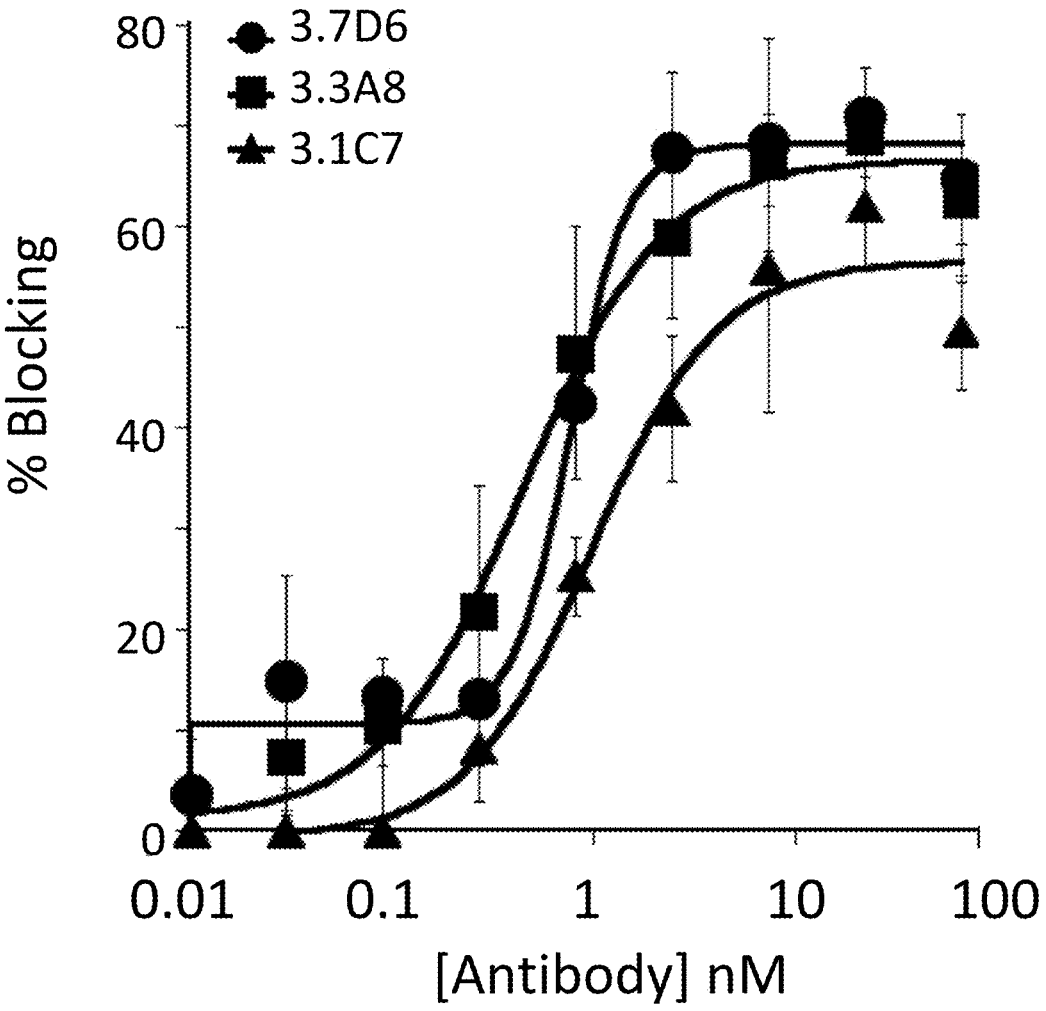

FIG. 16 shows that antibody blockade of trypanolysis is dose-dependent. Anti-APOL1 antibody dose titration was performed in the trypanosome blocking assay with one of the trypanosome blocking antibodies for each domain: PFD antibody 3.7D6 (closed circles; IC$_{50}$ 0.5 nM); MAD antibody 3.3A8 (closed squares; IC$_{50}$ 0.4 nM); and SRA-ID antibody 3.1C7 (closed triangles; IC$_{50}$ 1 nM). Live trypanosomes were measured using the Alamar Blue assay as in FIG. 4C and % blocking calculated by normalizing values to no antibody control sample. The means and SDs of 3 independent experiments are plotted. IC$_{50}$s were calculated in KaleidaGraph v4.1 using the equation $y=m_1/(1+(m_2/m_0)^{\wedge}m_3)$.

FIGS. 17A-17C show immunoprecipitation of APOL1 from NHS with a different set of APOL1 antibodies. FIG. 17A show as in FIG. 5D that all the blocking antibodies could immunoprecipitate APOL1, except the conformational antibody 3.7F5 (SEQ ID NOS: 203-212), which is also a poor blocker. By contrast FIG. 17B shows also as in FIG. 5D that none of the non-blockers pulled down APOL1; the blocking antibody 3.7D6 was included in the last lane as a positive control.

FIG. 17C shows a subset of blocking and non-blocking antibodies to determine if HPR was also co-immunoprecipitated with APOL1; HPR showed the same pattern as APOA1 pull-down by the blocking antibodies.

Figure 18A:
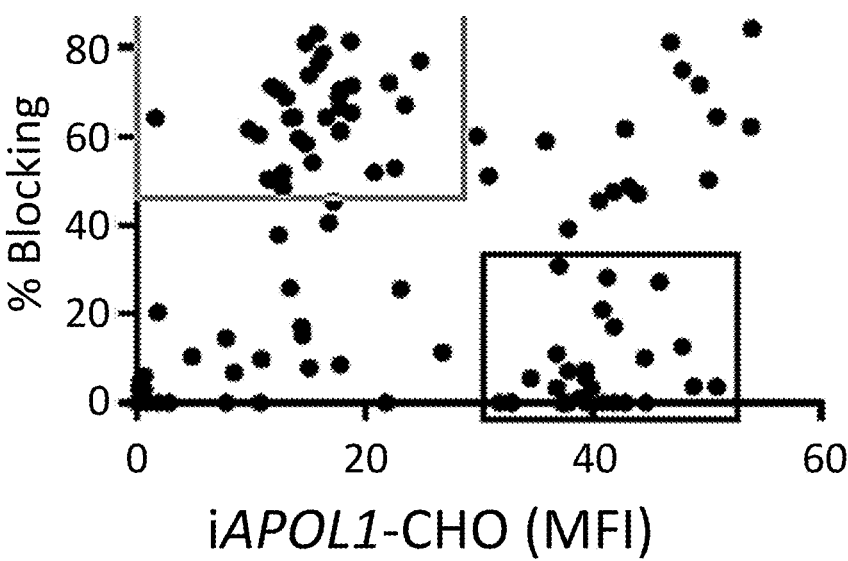
Figure 18B:
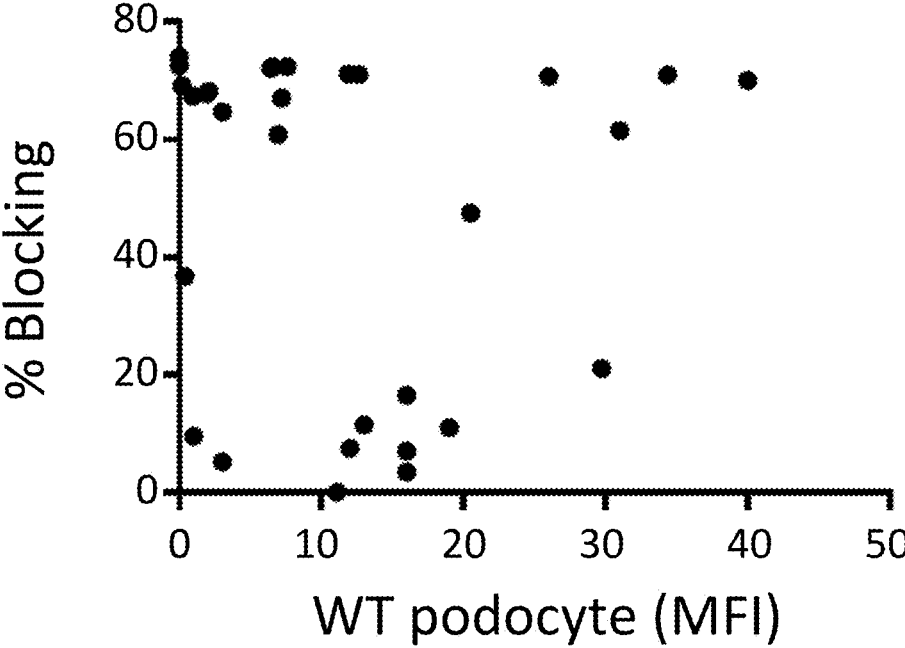

FIGS. 18A-18B show lack of correlation between iAPOL1-CHO recognition and trypanolytic blockade by anti-APOL1 antibodies. The percentage of trypanolysis blocking of each antibody (all 105 hybridomas from method #3) at 1 μg/ml is plotted versus its mean fluorescence intensity (MFI) on iAPOL1-CHO cells (FIG. 18A) or iAPOL1-podocyte cells (FIG. 18B) at the same concentration (construct a of FIG. 1A). Each dot represents an individual antibody. The correlation between surface binding and trypanolysis blockade is poor, since ~20 non-blocking antibodies were able to recognize APOL1 well by FACS (black box) and conversely ~20 strong blockers only weakly recognized APOL1 on CHO cells (MFI <20; grey box). The FACS data is representative of 2 individual experiments and the blocking data is the mean of 2 experiments. FIG. 18B shows MFI on WT podocytes (IFNγ-induced), confirming the lack of correlation of surface binding with trypanolysis in this cell line too. The data represent a replot of that in FIGS. 6A and 6C.

Figure 19A:
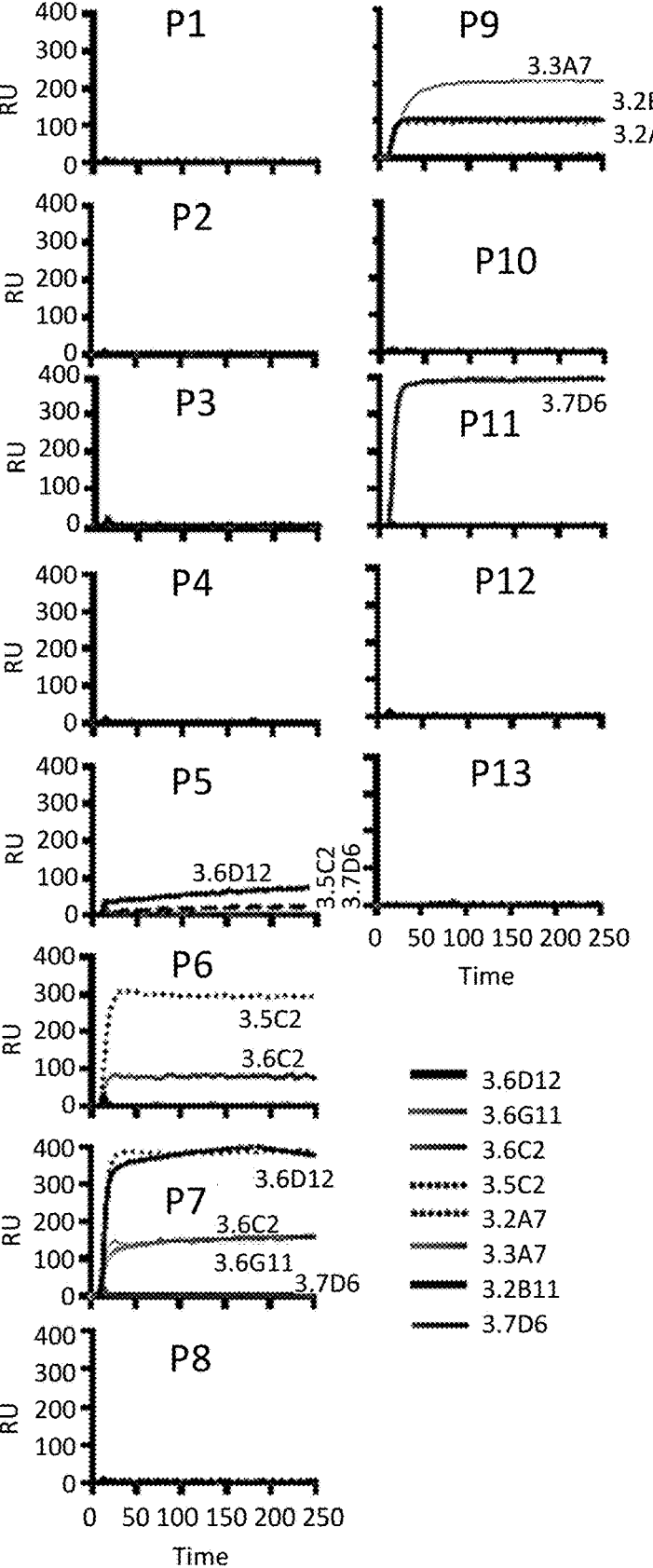
Figure 19B:
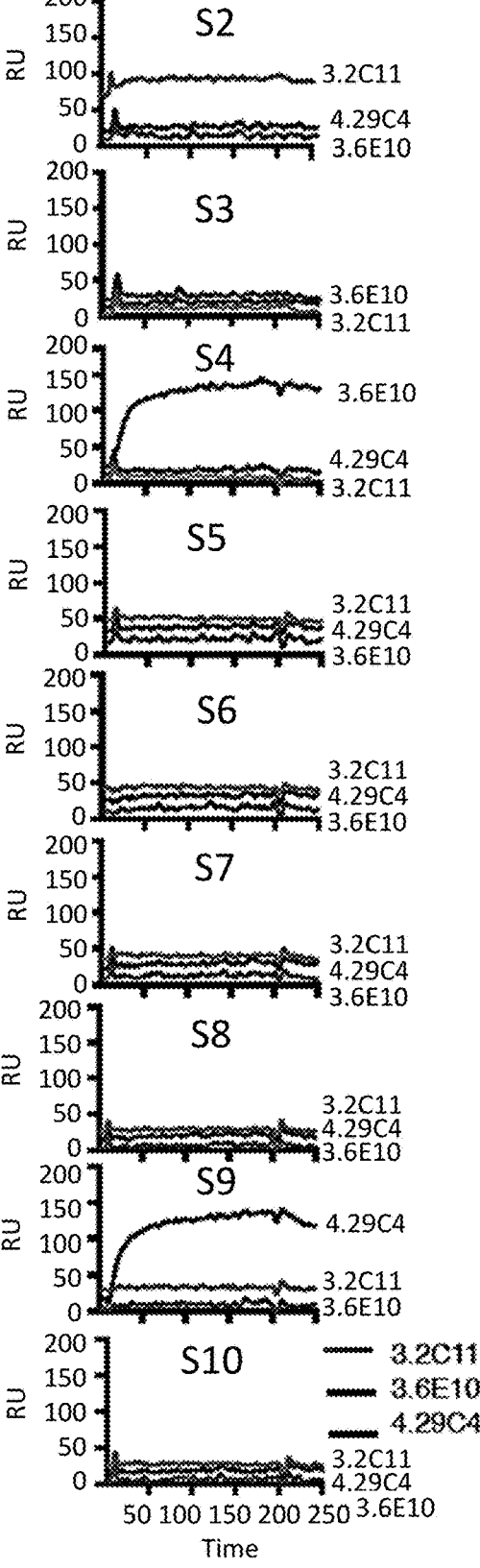

FIGS. 19A-19B show epitope mapping of anti-APOL1 antibodies by surface plasmon resonance. Examples of Wasatch data on 20-mer peptides with anti-APOL1 antibodies is shown for PFD and SRA-ID antibodies on PFD (FIG. 19A) or SRA-ID (FIG. 19B) peptides. The MAD antibodies were all negative by this method and are thus not shown.

Figure 20A:
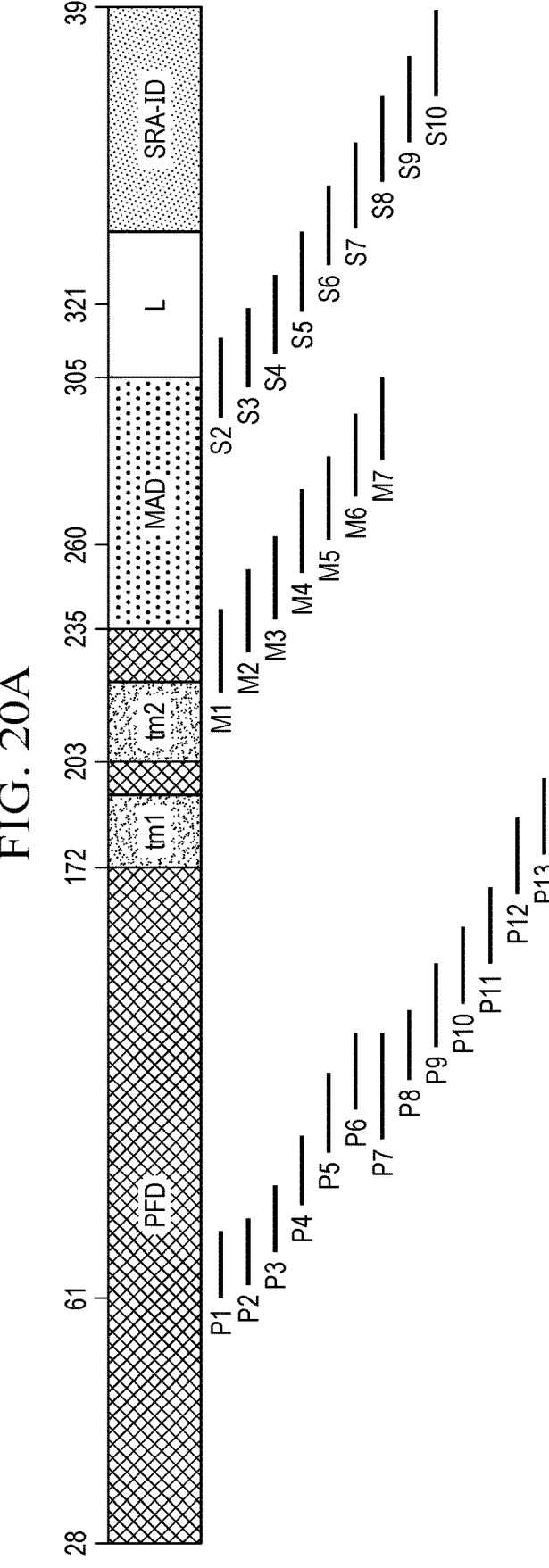

FIGS. 20A-20E show epitope mapping of anti-APOL1 antibodies by western blotting. FIG. 20A shows schematic of APOL1 protein with the overlapping ~20-mer peptides along its length indicated below as black lines. P denotes PFD, M the MAD and S the SRA-ID and peptides were numbered sequentially for each domain. Western blots with Sf9 lysates expressing truncated APOL1 helped determine the broader domain for some of the PFD and MAD antibodies. FLAG, anti-FLAG antibody for FLAG-tagged truncated constructs.

Figure 20B:
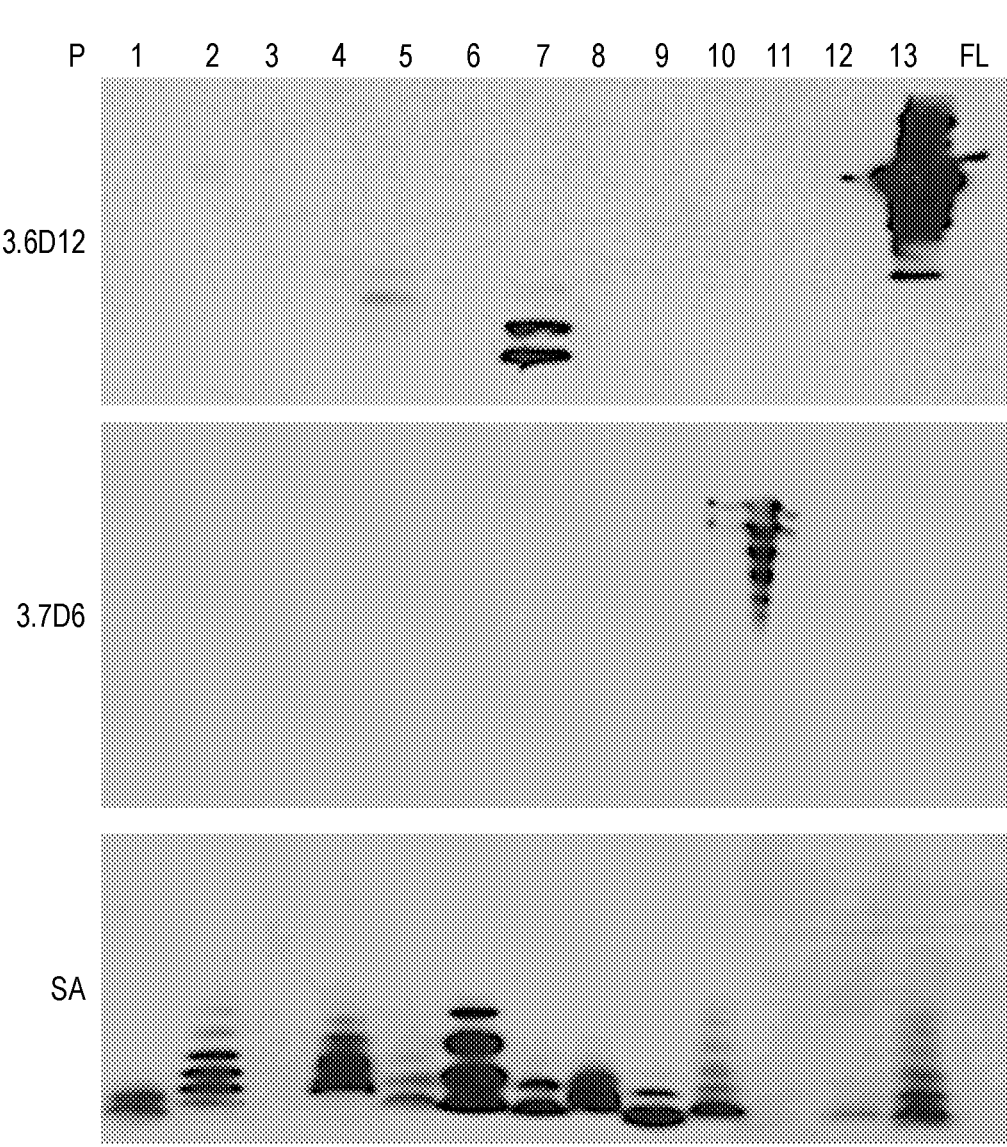
Figures 20C, 20D:
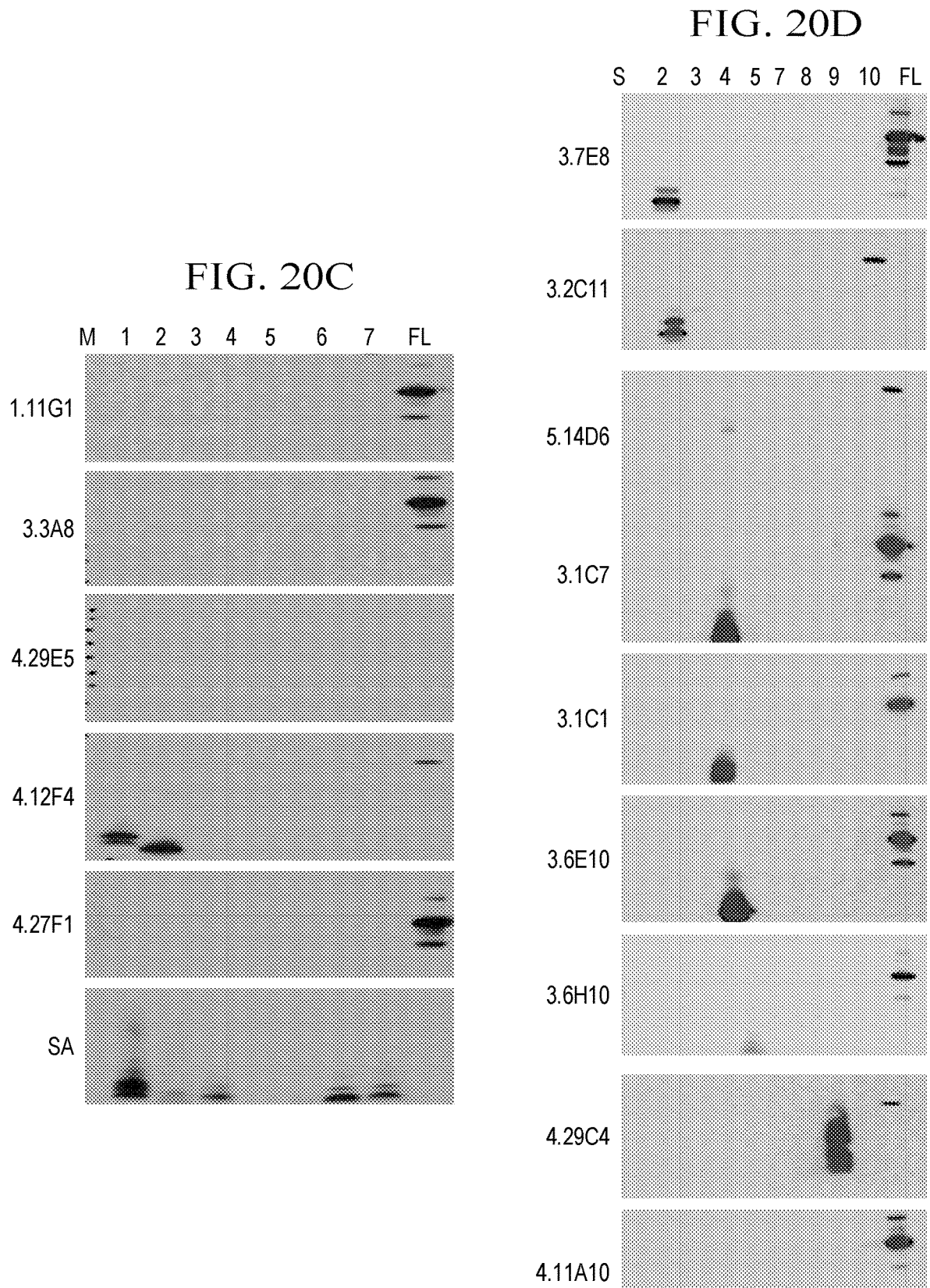

FIG. 20B-D Examples of domain mapping by Western blotting on the above peptides. Most PFD and MAD antibodies were negative on these peptides, which could be due to high oligomerization of these peptides or longer or non-linear epitopes for these antibodies. SRA-ID antibodies (FIG. 20D) bound well to their cognate peptides, indicating linear epitopes; note peptide S6 was not loaded due to insolubility. SA, streptavidin-HRP control to determine which peptides are detectable on the blots. FL, full length recombinant APOL1 control (aa 61-398).

FIG. 20E shows Western blots with Sf9 lysates expressing truncated APOL1 helped determine the broader domain for some of the PFD and MAD antibodies. FLAG, anti-FLAG antibody for FLAG-tagged truncated constructs.

Figure 21A:
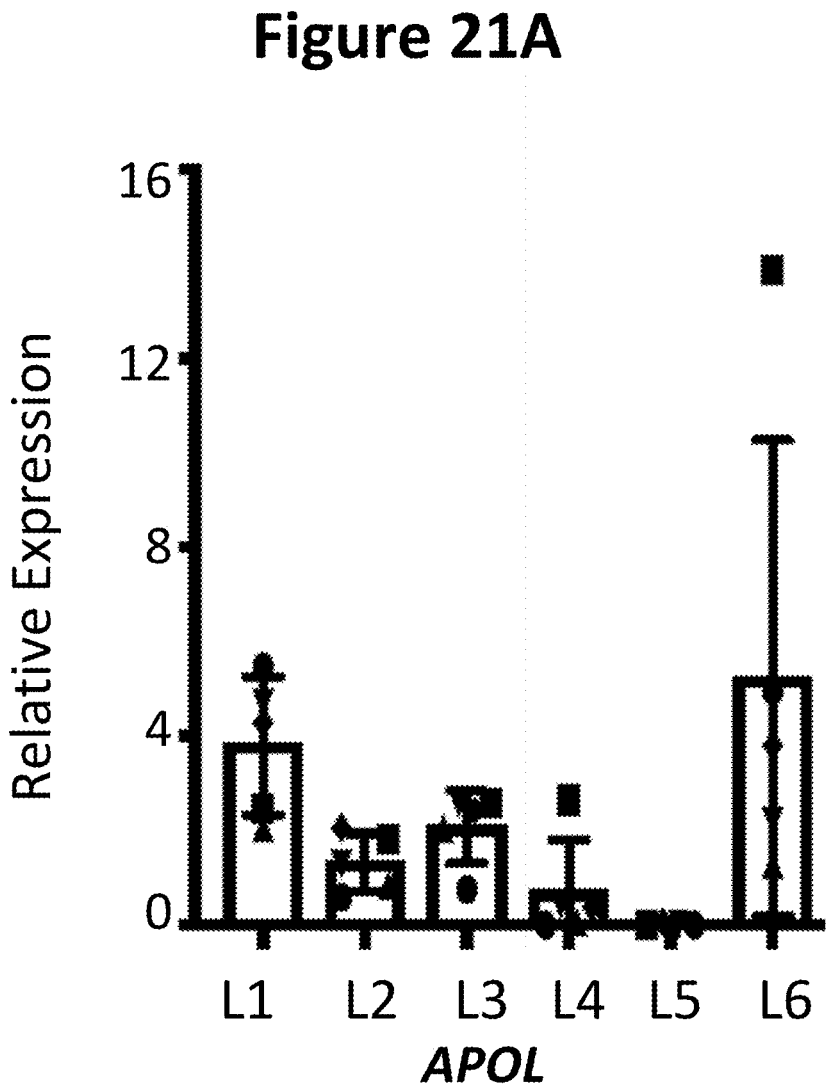

FIG. 21A-21I show expression of APOLs 1, 2 and 6 in kidney podocytes. FIG. 21A shows RT-PCR of 5 normal human kidneys with probes specific for each APOL family member. Data is normalized to RPL19 and the mean and SD of the 5 kidneys is plotted over the individual data points (each kidney is assigned a unique symbol and the mean of the relative expression $(2^{-dcT})$ of up to three independent RT-PCRs is plotted for each sample). See FIG. 30A for APOL probe specificities.

FIGS. 21B-G show dual in situ hybridization (ISH) of normal human kidney from a 59 year old male using probes to APOL1-C2 alone (FIGS. 21B-C), or together with either NPHS2 (podocin, FIGS. 21D-E) or endothelial marker EGFL 7-C1 (Epidermal Growth Factor-Like 7, also known as vascular endothelial statin; FIG. 21F. Evidence that the APOL1 probe does not cross-react with APOL2 is shown in FIG. 30B below. To improve detection of endothelia, we co-stained endothelial PVLAP (plasmalemmal vesicle-associated protein) by IHC (FIG. 21G) and APOL1 mRNA with the ISH C2 probe, which confirmed that APOL1 mRNA is below the detection limit in endothelia. A diffuse pink staining in the proximal tubules is a nonspecific artifact of the red dye, as it is not punctate and was also seen with the negative control probe DAPB (FIG. 30C below). Arrows indicate a subset of cells with APOL1 mRNA only, NPHS2 or EGFL 7 only, or dual positive (which was only the case for APOL1 versus NPHS2). Scale bars are 50 µm in a,c; 20 µm in b, d, e and 10 µm in f. The data is representative of that seen with three other normal kidneys.

Figure 21H:
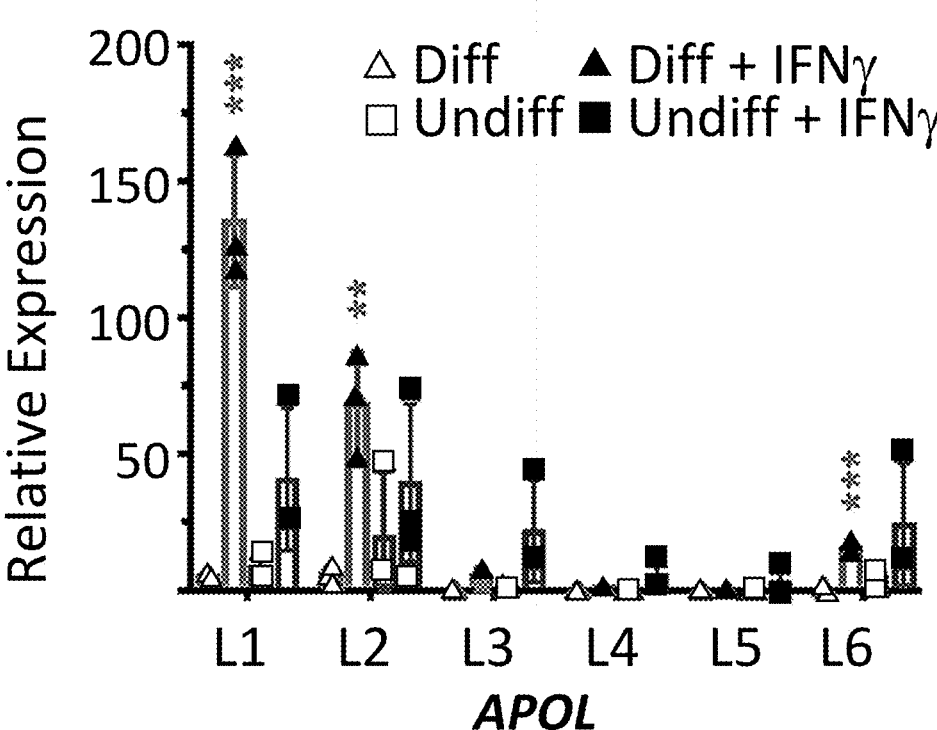

FIG. 21H shows RT-PCR of immortalized differentiated (Diff, upward triangles, grown at 38° C.) or undifferentiated (Undiff, squares, grown at 33° C.) human podocytes (mean±SD of three separate passages, each analyzed in duplicate) using the same probes as in FIG. 21A. The variability is likely attributable to our observation that APOL1 levels decline during passaging. Open triangles or squares, untreated; closed triangles or squares, IFNγ treated (100 ng/ml for 24 h). APOL3 became detectable following IFNγ treatment in undifferentiated, but not differentiated podocytes. Asterisks indicate APOLs whose expression was significantly elevated by IFNγ treatment according to the two-tailed student's unpaired t-test (, p<0.01; *, p<0.001).

Figure 22A:
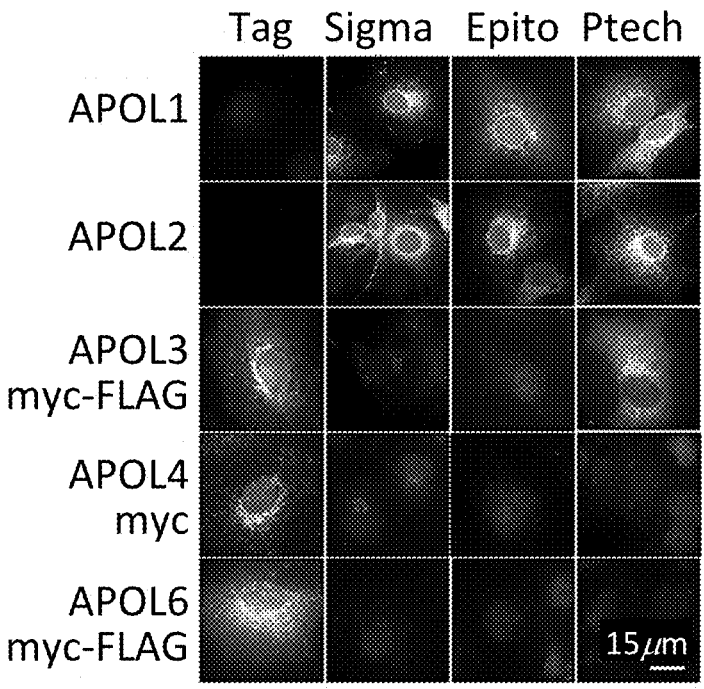
Figure 22B:
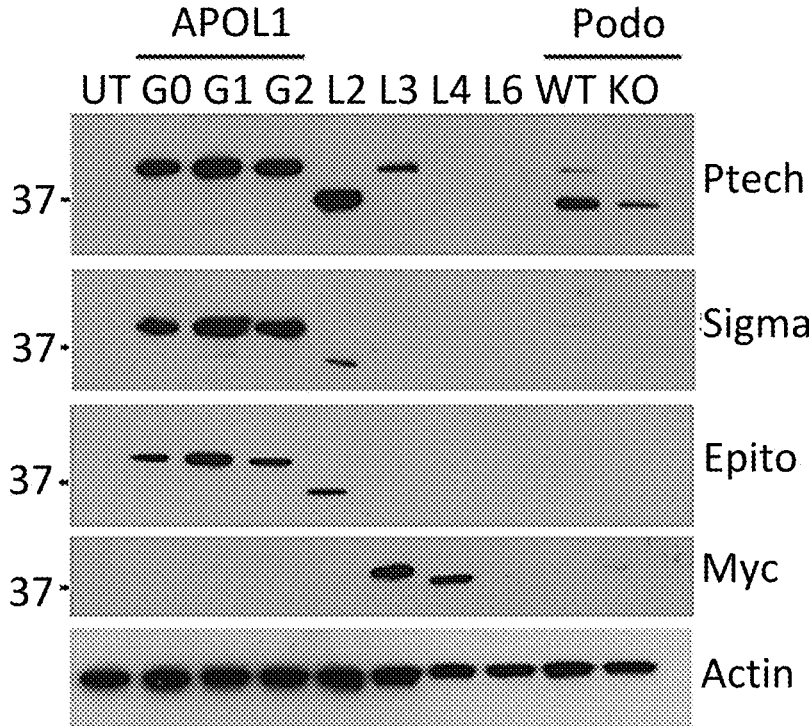

FIG. 21H shows a representative western blot on a 4-12% Bis-Tris gel of immortalized undifferentiated (UD) and differentiated (Diff) podocytes ±IFNγ stimulation using the Proteintech polyclonal that recognizes APOL2 as well as APOL1 (see FIG. 22B). The asterisk denotes a nonspecific band not seen with other anti-APOL1 antibodies. Actin served as the loading control.

FIGS. 22A-22D show that several anti-APOL1 antibodies cross-react with APOL2. FIG. 22A shows APOL-family reactivity of antibodies by immunofluorescence. COS cells were transfected with untagged APOL1-G0, APOL2, APOL3a-myc-FLAG, APOL4-myc or APOL6-myc-FLAG (see Table 3 for cDNAs). After 40-48 h, cells were PFA fixed, Triton X-100 permeabilized and stained with the indicated commercial rabbit polyclonal anti-APOL1 antibodies (at 1 µg/ml; Ptech, Proteintech; Epito, Epitomics) followed by Alexa488 anti-rabbit. Transfection of APOLs 3-6 was confirmed by staining for the epitope tag (with mouse anti-FLAG-M2 or mouse anti-myc 9E10 for APOL4-myc followed by Alexa647 anti-mouse) and any positive signals colocalized with the tag as expected (FIG. 31B). All results were verified in at least one independent experiment.

FIG. 22B shows Western blots of APOL-transfected COS cells or endogenous APOL1 in podocytes after 24 h IFNγ stimulation with 0.44 µg/ml commercial polyclonal antibodies corroborate the IF data. Lysates were run on 4-12% Bis-Tris gels and actin served as the loading control. UT, untransfected COS; G0, G1 (I384M, S342G), G2 (ΔN388, Y389) are the three APOL1 variants; L2, APOL2; L3, APOL3a-myc-FLAG; L4, APOL4-myc, L6: untagged APOL6; WT, wild type podocytes; KO, APOL1 CRISPR knockout podocytes.

Figure 22C:
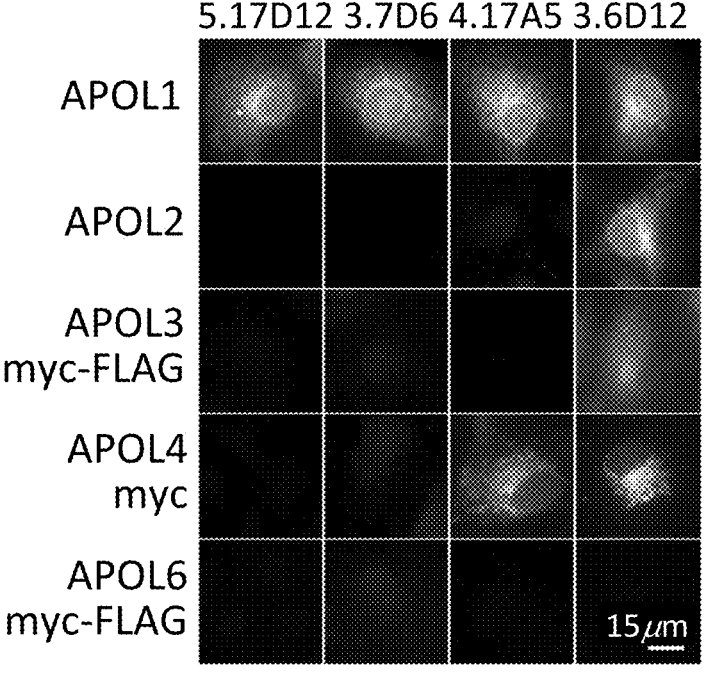

FIG. 22C is as in FIG. 22A except with in-house mouse mAbs at 1 µg/ml. Secondary antibodies were Alexa488 anti-rabbit for 5.17D12 and Alexa488 anti-mouse for the others. 5.17D12 and 3.7D6 are APOL1-specific and although mAb 4.17A5 cross-reacted weakly with APOL4, it could be considered APOL1-specific for the purposes of kidney staining due to lack of APOL4 expression in this tissue (FIGS. 21A and 21H). By contrast, the 3.6D12 mAb cross-reacts with APOLs 2, 3 and 4 by IF.

Figure 22D:
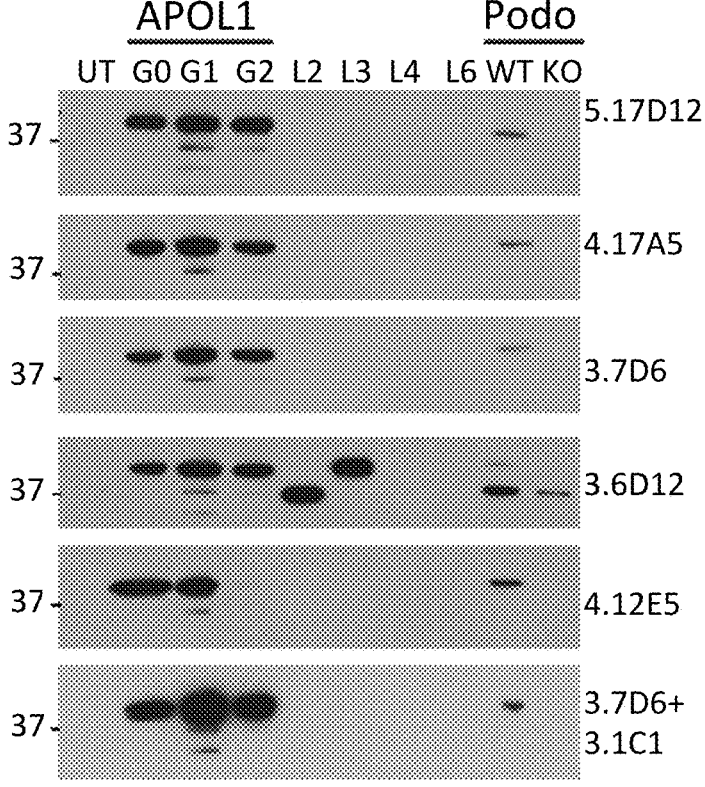

FIG. 22D shows the same lysates as in FIG. 22B probed with the top in-house mouse mAbs at 2 µg/ml, or a mixture of rabbit 3.7D6 and 3.1C1 at 0.05 µg/ml (bottom blot), which covers both ends of APOL1 and is our preferred reagent for western blotting. For comparison, antibody 4.12E5, which maps to the C-terminal APOL1-G2 epitope (Example 1 below), is also included; it barely recognizes APOL1-G2 by western blotting and does not cross-react with APOL2-6 (also by IF, FIG. 31B). The results corroborate the IF cross-reactivities, except for APOL4 cross-reactivity, which appears to be conformationally sensitive. The 3.6D12 antibody continues to recognize APOL2 in the APOL1 KO podocytes (generated as described in Example 1). Note the 4.17A5 western is shown at a longer exposure than the others.

Figure 23:
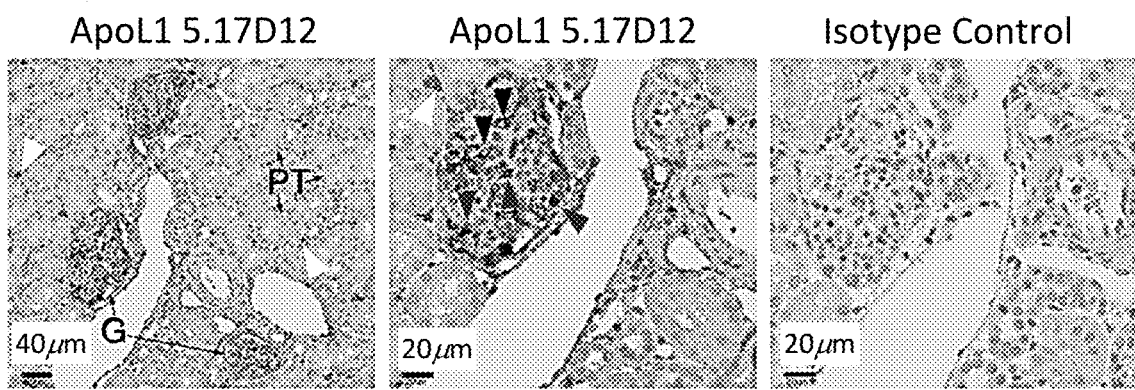

FIG. 23 shows that endogenous APOL1 is found in kidney podocytes and endothelial cells by immunohistochemistry. Immunohistochemistry of formalin-fixed paraffin embedded normal human kidney at 10× (left, 40 µm scale bar) or 20× (center and right, 20 µm scale bars), stained with 0.5 µg/ml APOL1-specific rabbit monoclonal antibody (rabmab) 5.17D12 or rabbit IgG isotype control on an adjacent section (right). Dark arrowheads indicate APOL1 staining in podocytes and glomerular endothelia, respectively. Extraglomerular capillaries were also positive, presumably staining circulating APOL1 (white arrowheads). Unlike a previous report (Example 2, Ref. 73), the staining was not predominantly in proximal tubules. This staining pattern was replicated by two other top anti-APOL1 antibodies to different epitopes and is representative of at least 5 kidneys examined (FIG. 33B and data not shown). G, glomeruli; PT, proximal tubules.

Figures 2B, 24A:
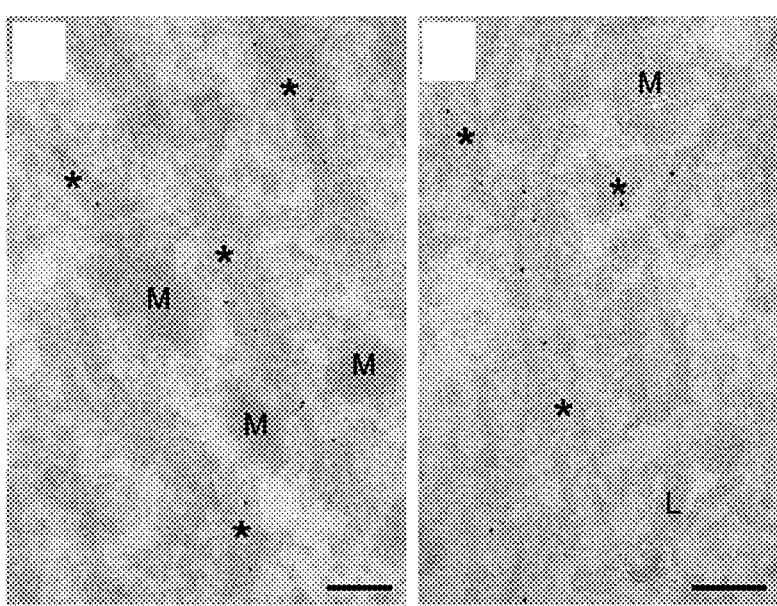
Figure 24C:
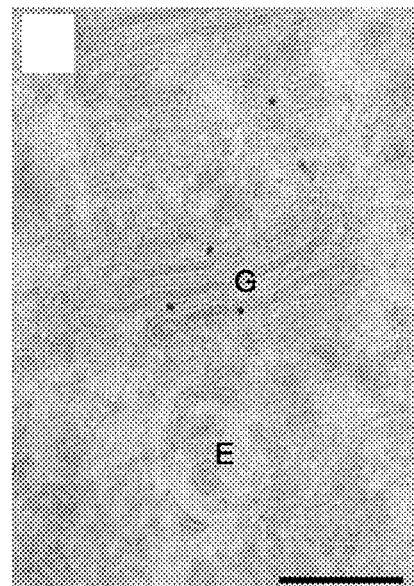

FIGS. 24A-24D show that endogenous and stably transfected APOL1 localizes to the endoplasmic reticulum of cultured podocytes. FIGS. 24A-24C show iEM of iAPOL1-G0 podocytes. APOL1 KO podocytes re-expressing iAPOL1-G0 iAPOL1-G0 (after 48 h 5 ng/ml doxycycline induction) were 4% PFA fixed and immunolabeled with 25 µg/ml rabmab 5.17D12, followed by protein-A gold. Representative staining of APOL1 in the ER (FIGS. 24A-B) and Golgi (FIG. 24C) is shown. All scale bars are 200 nm. *, ER lumen; M, mitochondrion; L, lysosome; E, early endosome; G, Golgi. APOL1 is seen only in the ER and Golgi, not in mitochondria or endolysosomal system. Examples of APOL1 staining in the more perinuclear region of the ER and its absence from the mitochondria and MAM are shown in FIGS. 39A-39D, along with uninduced controls showing that the antibody staining is APOL1-specific (FIGS. 39E-39F).

Figure 24D:
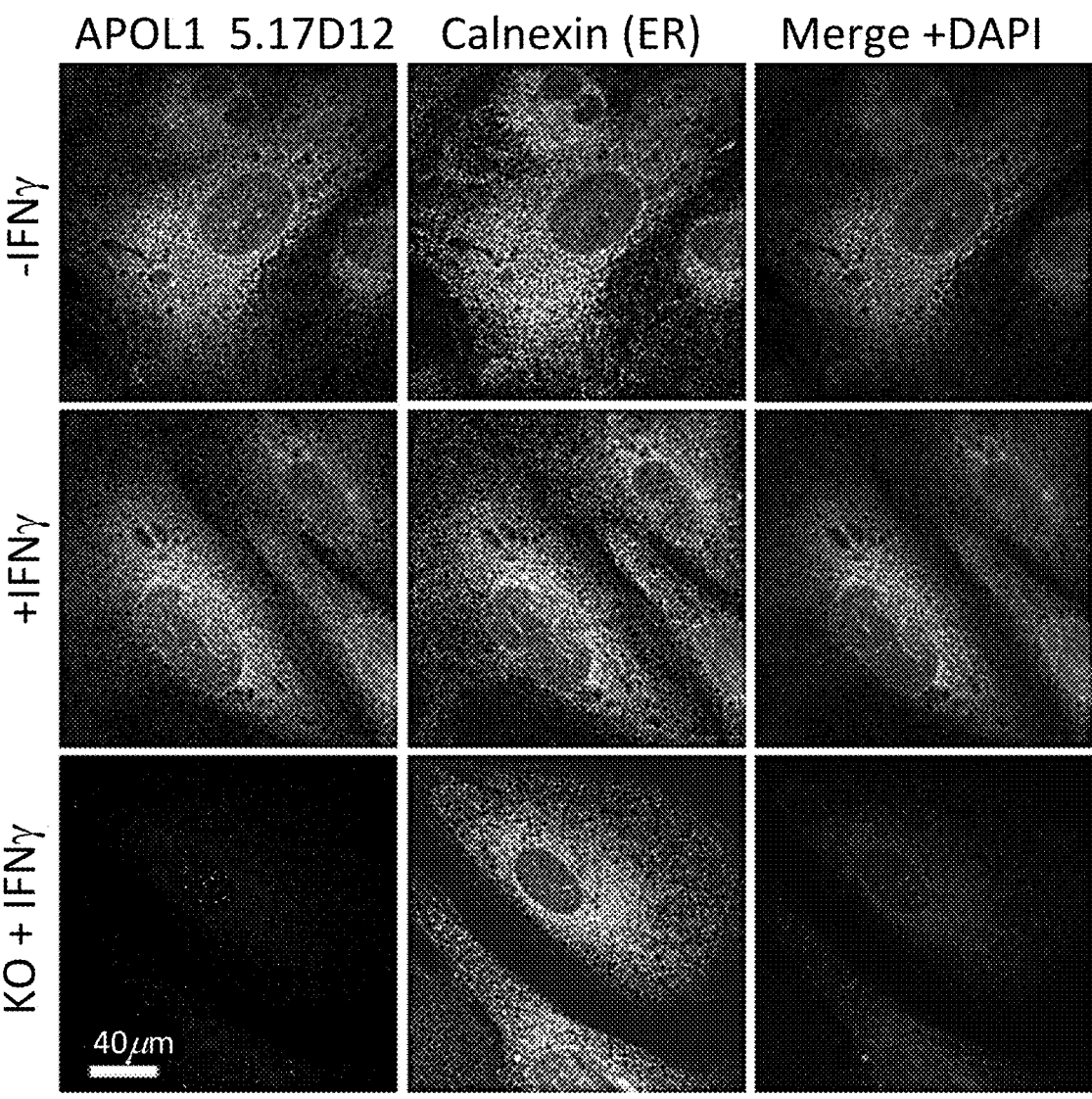

FIG. 24D shows endogenous APOL1 in wild type differentiated podocytes (upper row) is shown in PFA-fixed, saponin permeabilized cells co-stained with 2 µg/ml APOL1 5.17D12 and mouse anti-calnexin; merge with nuclear DAPI is on the right. IFNγ-treated WT cells (middle) show stronger ER APOL1 labeling, while APOL1 knockout (lower) podocytes lacked this. Note that nuclear speckles (overlapping DAPI) are evident in many cells, which are clearly nonspecific (not APOL1) since they are found KO as well as WT cells. Scale bar is 40 µm. APOL1 was similarly ER-localized with 8 other antibodies in both differentiated and undifferentiated podocytes (see FIGS. 41A-B for 4.17A5, and data not shown).

Figure 21I:
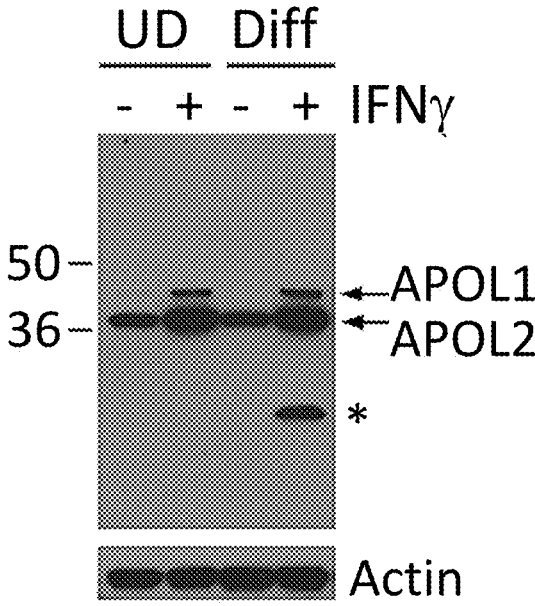
Figure 25A:
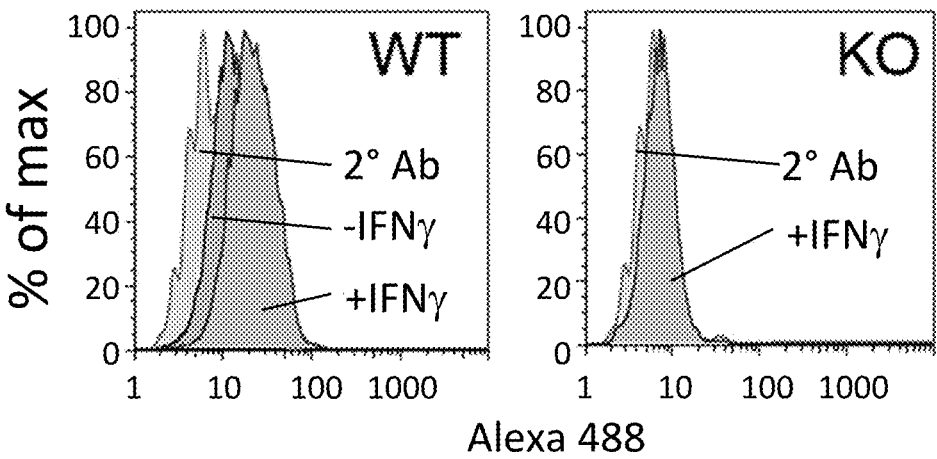
Figure 25B:
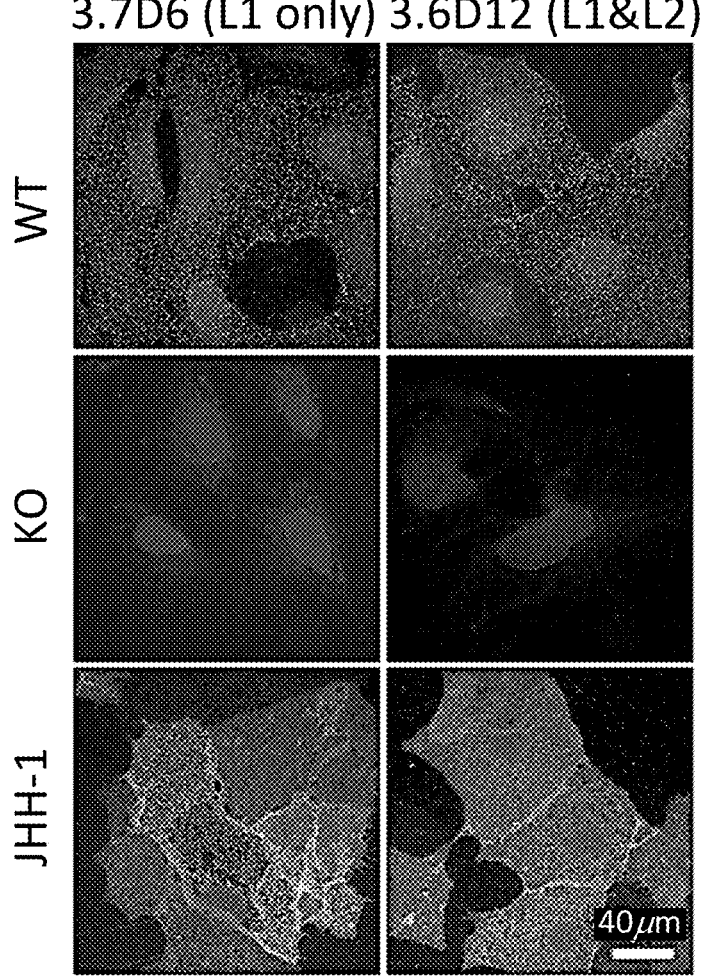
Figure 25C:
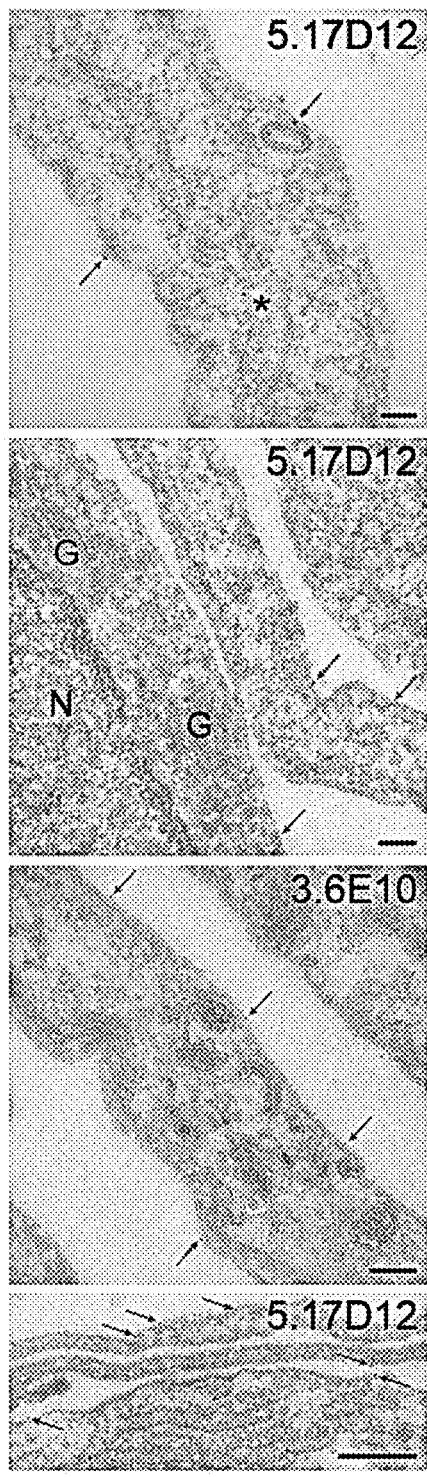
Figure 46A:
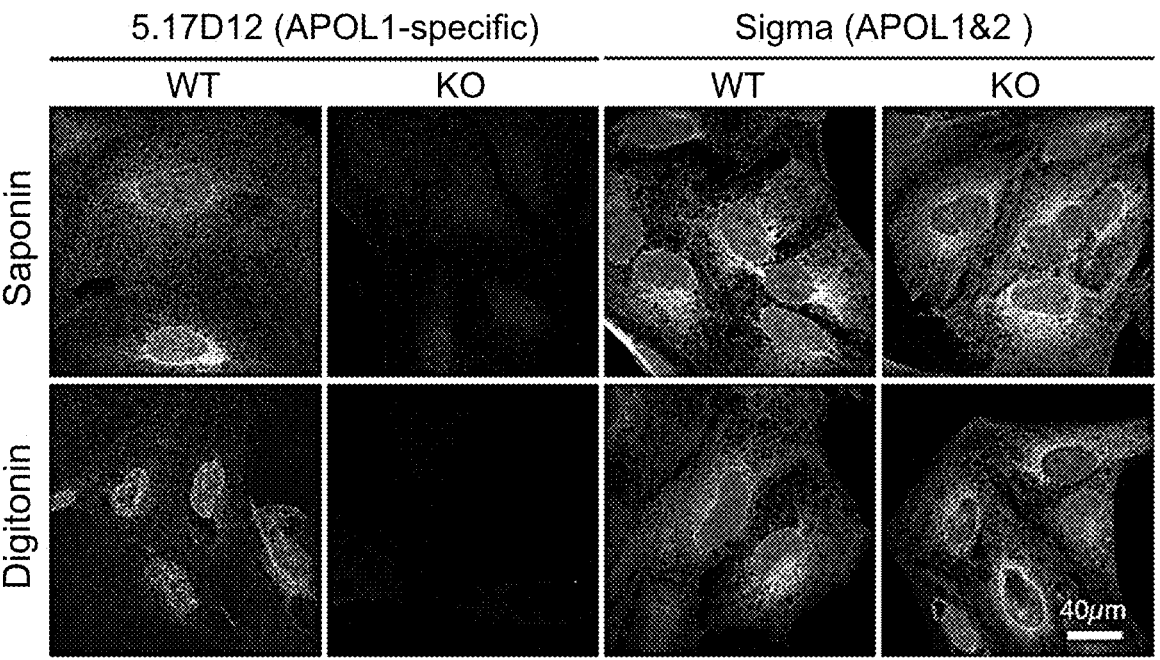

FIGS. 25A-25C show that a small proportion of endogenous podocyte APOL1, but not APOL2, is at the plasma membrane. In FIG. 25A, live WT (left) or APOL1 KO (right) podocytes were incubated on ice for 1 h (without fixation or permeabilization) with 2.5 µg/ml 3.6D12 (an APOL2 cross-reactive mAb). "2° Ab" is Alexa488 anti-mouse secondary antibody alone; "—IFNγ" is untreated; "+IFNγ" is IFNγ-treated cells. There is a shift on WT, but not KO cells (which express APOL2 but not APOL1). The lack of signal on APOL1 KO cells indicates that APOL2 is not on the cell surface, despite being more abundant than APOL1 (FIG. 21I and FIG. 46A). Thus, the shift seen with 3.6D12 in WT cells must represent APOL1, and increases with IFNγ, as expected.

FIG. 25B shows live IFNγ-treated WT podocytes (upper), APOL1 KO podocytes (middle) and liver JHH-1 cells (lower) incubated with 5 µg/ml APOL1-specific 3.7D6 (left) or APOL2 cross-reactive 3.6D12 (right) on ice for 1 h, then washed, PFA fixed and detected (without permeabilization so as to avoid seeing the abundant intracellular ER signal) with Alexa488 anti-mouse (overlaid with nuclear DAPI stain). Punctate signal is seen on the cell surface of WT and JHH-1 but not APOL1 KO podocytes with both APOL1-specific and APOL2-cross-reactive antibodies, indicating that only APOL1 is on the cell surface. Scale bar is 40 µm. Similar results on podocytes were seen with ≥8 other antibodies to different epitopes (data not shown).

FIG. 25C shows iEM of APOL1-G0 podocytes, using the APOL1-specific antibodies 5.17D12 and 3.6E10, showing a small fraction of APOL1 immunogold particles (arrows) dispersed at the cell surface. *, ER lumen. G, Golgi. N, nucleus. Scale bars (top to bottom): 100, 200, 200, and 500 nm.

Figure 26C:
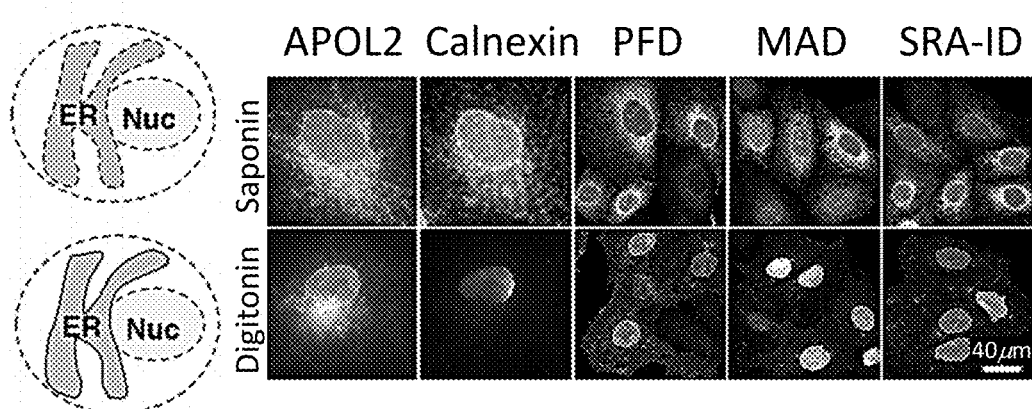

FIGS. 26A-26D show APOL1 is associated with the inner ER membrane face. FIG. 26A shows schematic of PFA-fixed cells permeabilized with saponin (or Triton X-100; upper) with cell surface and ER membranes permeabilized (dashed lines) versus cell surface-specific permeabilization by digitonin (ER membrane is intact, solid line; lower). Note that PFA fixation permeabilizes the nuclei (nuclear envelope) of some cells (Nuc, grey) irrespective of any detergent.

FIG. 26B shows COS cells transiently transfected with APOL2, or doxycycline-induced (5 µg/ml for 20 h) iAPOL1-CHO stables (Example 1 below), PFA fixed and permeabilized with saponin (top) or digitonin (bottom). APOL2 is shown stained with 3.6D12 (a mAb to the N-terminal pore-forming domain (PFD)), although similar results were obtained with the other 43 APOL2-cross reactors (all to the PFD, data not shown). Anti-calnexin luminal domain staining for the APOL2-COS cells is shown adjacent to APOL2 as a control for permeabilization conditions (this antibody does not cross-react with CHO calnexin). APOL1 is shown stained with PFD mAb 3.7D6, membrane-addressing domain (MAD) mAb 3.3A8, or SRA-interacting domain (SRA-ID) mAb 3.1C1, each detected with Alexa488 anti-mouse (see Example 1 below for epitope mapping), although similar results were obtained with all the other APOL1-specific antibodies to all three domains (data not shown). The reticular ER pattern persists in digitonin (plasma membrane only)-permeabilized cells for APOL2, but not APOL1, indicating APOL2 is on the cytoplasmic face of the ER, while APOL1 is inside. The nuclear membrane signal for APOL1 with digitonin is also seen without detergent in some cells since PFA semi-permeabilizes the nuclear membrane (data not shown). With digitonin, some of the more sensitive antibodies, including the PFD (3.7D6) and SRA-ID (3.1C1) antibodies shown here (but not MAD antibody 3.3A8), additionally detected APOL1 on the plasma membrane (arrowhead), which is topologically equivalent to the ER lumen.

FIG. 26C shows representative immunoelectron micrographs of iAPOL1-G0 podocytes (induced for 24 h with 5 ng/ml doxycycline) and immunolabeled with 3.6E10 for APOL1 (left; amplified with rabbit anti-mouse secondary antibody) or the soluble luminal marker anti-KDEL (right), each detected with 10 nm protein A-gold. *, ER lumen; M, mitochondrion. Scale bars are 200 nm. APOL1 appears more closely associated with the inner ER membrane face than does the luminal KDEL.

Figure 26D:
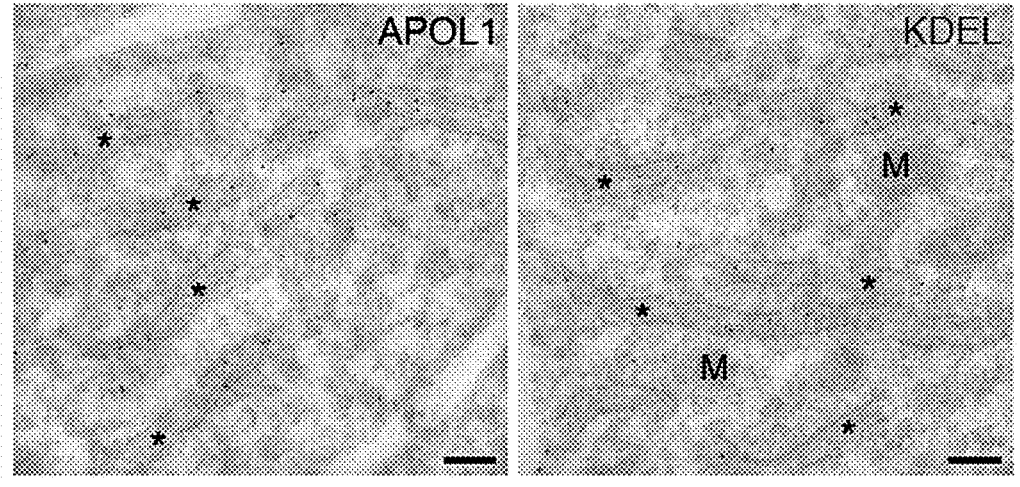

FIG. 26D shows that APOL1 is more associated with the inner ER membrane than KDEL in iAPOL1-G0 podocytes. Quantitation of ER-associated gold particles from 55 images stained as in FIG. 26C, but without rabbit anti-mouse secondary antibody amplification in order to minimize the size of the antibody-protein A-gold complex and render the quantitation more accurate. APOL1 (n=81 gold particles counted) is mainly associated with the inner ER membrane, with a small amount attributed to the outer membrane/cytosol or central lumen by virtue of the large size of the antibody-protein A-gold complex relative to the ER cisternal width (see FIG. 48A for details). By contrast, the luminal KDEL control marker (n=100) appeared equally associated with the ER lumen and within 20 nm of the inner membrane face, and, as expected, was not detected on the outer membrane or in the cytosol.

Figures 27A, 27B:
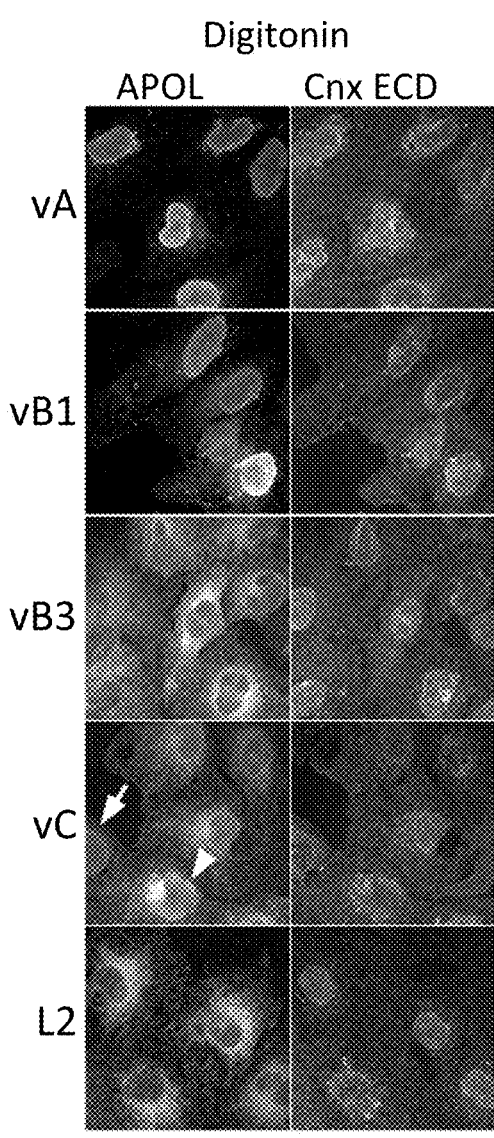
Figure 27C:
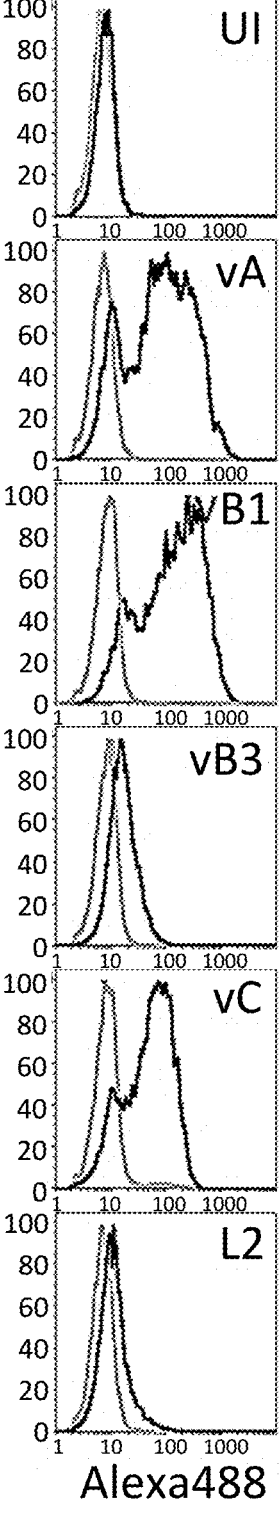

FIGS. 27A-27C show APOL1 isoforms localize to opposite sides of the ER membrane in podocyte stables. FIG. 27A shows stable pools of APOL isoforms PFA fixed and fully permeabilized with Triton X-100 to reveal total APOL distribution, and APOL1/2 was co-stained with rabbit anti-calnexin cytoplasmic tail (intracellular domain, ICD), followed by Alexa488 anti-IgG2a and Dy649 anti-rabbit. All the APOL1 isoforms and APOL2 appear ER-associated and colocalize well with calnexin under these conditions.

FIG. 27B is as in FIG. 27A except with digitonin permeabilization to reveal only cytoplasmic APOLs, and mouse anti-calnexin extracellular (luminal/ECD) domain and isotype-specific secondaries (Alexa488 anti-IgG2a for APOL; Alexa647 anti-IgG1 for calnexin). APOL1.vA, vB1 and a few cells expressing vC exhibit luminal staining (non-cytoplasmic, arrow; arrowhead indicates nuclear envelope (luminal) signal in the same cell as reticular (cytoplasmic) signal)), while vB3, APOL2 and the majority of vC are cytoplasmically oriented since they retain a reticular ER staining pattern with digitonin. Note the calnexin ECD antibody gives similar nuclear membrane staining to the luminal APOL1 isoforms, validating our digitonin method.

FIG. 27C shows flow cytometry of APOL1-G0 isoforms and APOL2 podocyte stable pools (gated on live (PI-negative) cells) stained with 1 μg/ml 3.6D12 and Alexa488 anti-mouse following 22 h induction at 10 ng/ml doxycycline (except UI, uninduced vA control). APOL1.vA and vB1 give a large FACS shift, indicating they are secretory, vC gives a smaller shift (partially secretory) and vB3 and APOL2 (L2) almost no shift (i.e. non-secretory), in accordance with the topologies identified by digitonin IF in FIG. 27B. The y-axis is % maximum and the x-axis is Alexa488 fluorescence intensity. Note that even the secretory isoforms (vA and vB1) were not actually secreted into the media due to being anchored to the cell surface, presumably via their predicted transmembrane domains (Example 2, ref. 90) (data not shown).

Figure 27D:
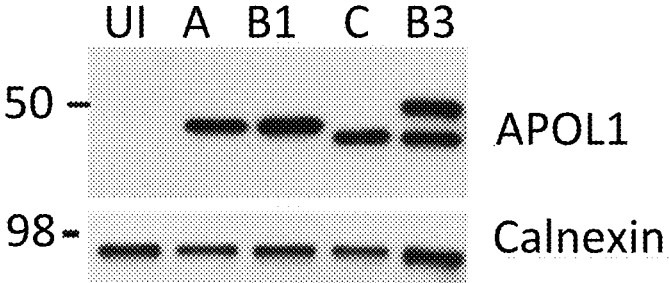

FIG. 27D shows expression of the different APOL1 isoforms at comparable levels in stable podocytes. A portion of the cells used in FIG. 27C were western blotted on a 10% gel with 0.05 μg/ml 3.1C7/3.7D6 (validated in FIG. 22D) and calnexin as a loading control. The similar total expression of the different isoforms implies that the greater FACS shifts with vA and vB1 (FIG. 27C) are due to greater secretory transport to the cell surface rather than higher expression. Furthermore, the similar size of APOL1.vA and vB1 suggests cleavage at the same VRA/EE site and thus that the 43 aa signal sequence of vB1 is functional, in contradiction to the signal sequence program predictions (Table 5). APOL1.vB3 is larger than vA, consistent with lack of signal sequence cleavage, which was confirmed by retention of an N-terminal tag (FIG. 51C), but also has a smaller, potentially cytoplasmically cleaved band. By contrast, vC is smaller than vA, despite predictions that it should be 1 kDa larger since it is mostly non-luminal (Table 5), thus it may also be cytoplasmically clipped; indeed, at high expression levels it appears as a doublet (FIG. 51B).

Figure 28A:
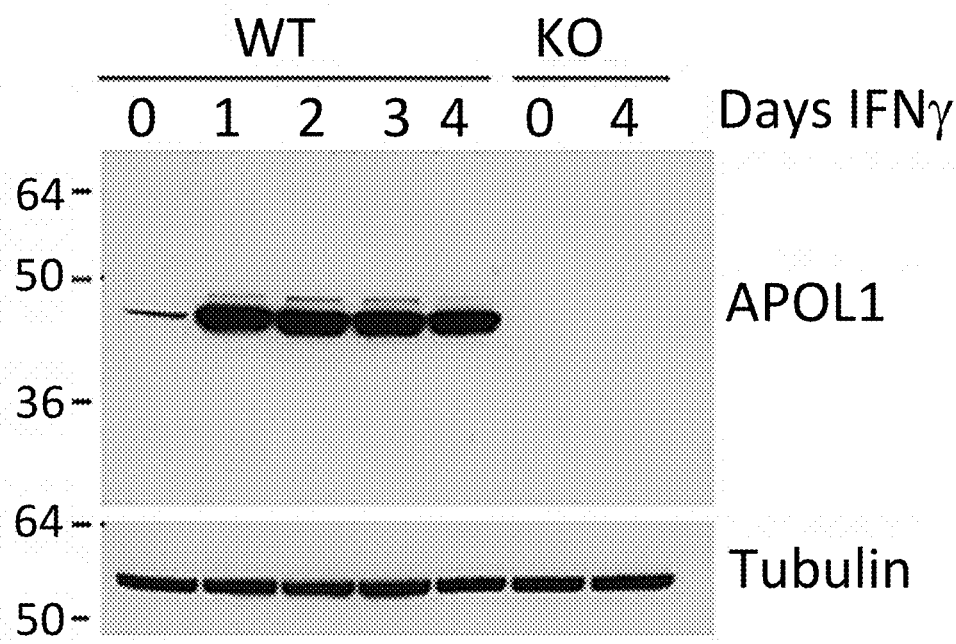
Figure 28B:
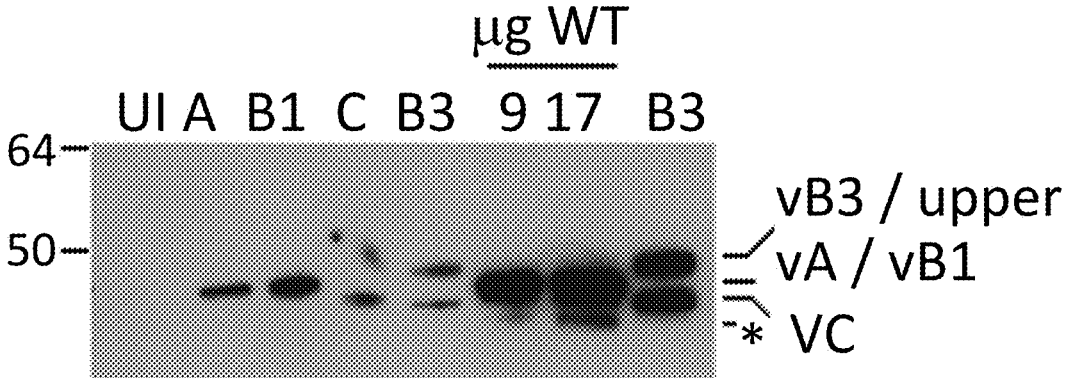

FIGS. 28A-28B show APOL1 isoform expression in podocytes. FIG. 28A shows a Western blot of WT and APOL1 KO podocytes stimulated for 0-4 days with 100 ng/ml IFNγ. Lysates were immunoblotted for APOL1 as in FIG. 27D, then reprobed with 1A2 anti-tubulin as a loading control. IFNγ treatment increases the level of APOL1 and a faint upper band also is reproducibly detected on 10% or 12% Tris-Glycine gels (12% here) at the right loading level. Note there is no band smaller than the major band.

FIG. 28B shows that the upper APOL1 band in IFNγ-stimulated podocytes is the same size as vB3. Western blot of APOL1 isoform stable podocyte lysates from FIG. 27D loaded adjacent to 9 or 17 μg of WT IFNγ-stimulated podocyte lysate and a larger amount of vB3 in the last lane. The upper band of endogenous APOL1 is similar in size to that of APOL1.vB3, although we cannot rule out the possibility that it is a post-translational modification. From the molecular weight predictions (Table 5) it could not represent any of the other isoforms. The band beneath vA in WT podocytes is probably a degradation product, since it is only sporadically detected (compare FIG. 28A).

Figure 29:
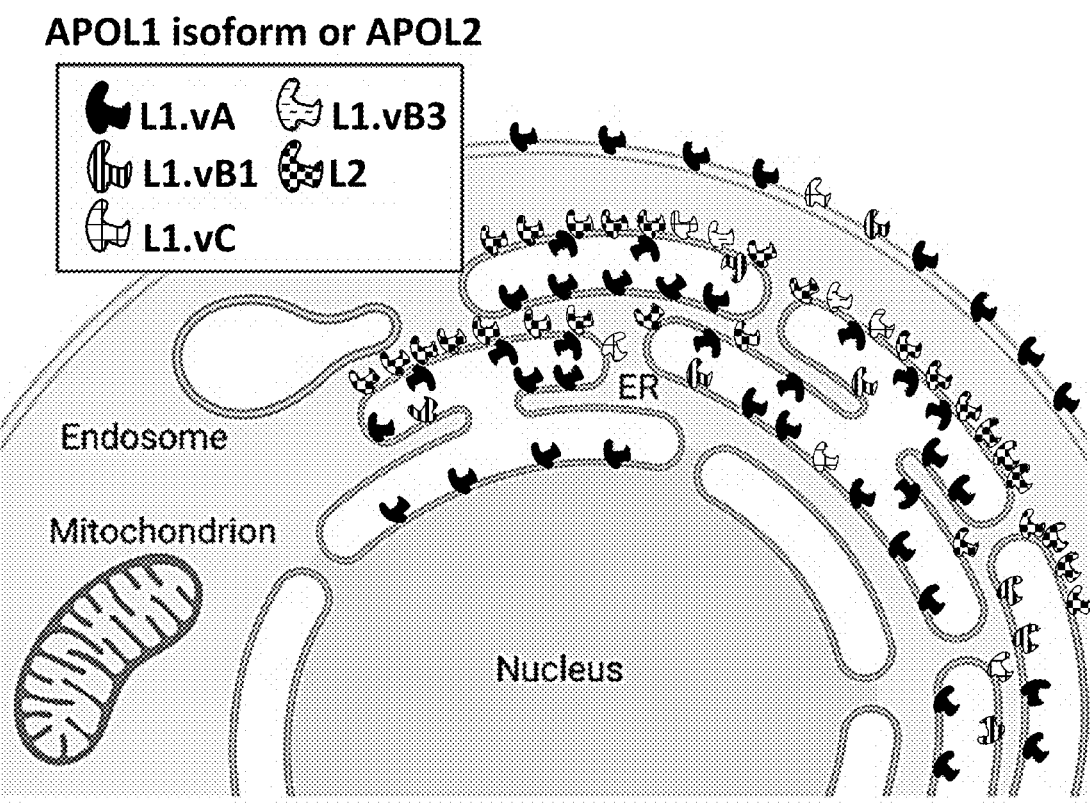

FIG. 29 shows a diagram of a cell to summarize APOL1 isoform and APOL2 subcellular locations. The diagram depicts localization and relative abundance of APOL1 isoforms (note that APOL1 and APOL2 are under-represented compared to the minor variants). APOL1.vA (black), vB1 (striped) and a little of vC (cross-hatched) are within the ER lumen (associated with the inner membrane) and a small proportion of each is transported to the plasma membrane. By contrast, APOL1.vB3 (dashes), APOL2 (checkers) and the majority of APOL1.vC (cross-hatched) are on the cytoplasmic face of the ER and not on the cell surface. This sketch was created with BioRender.

Figure 30A:
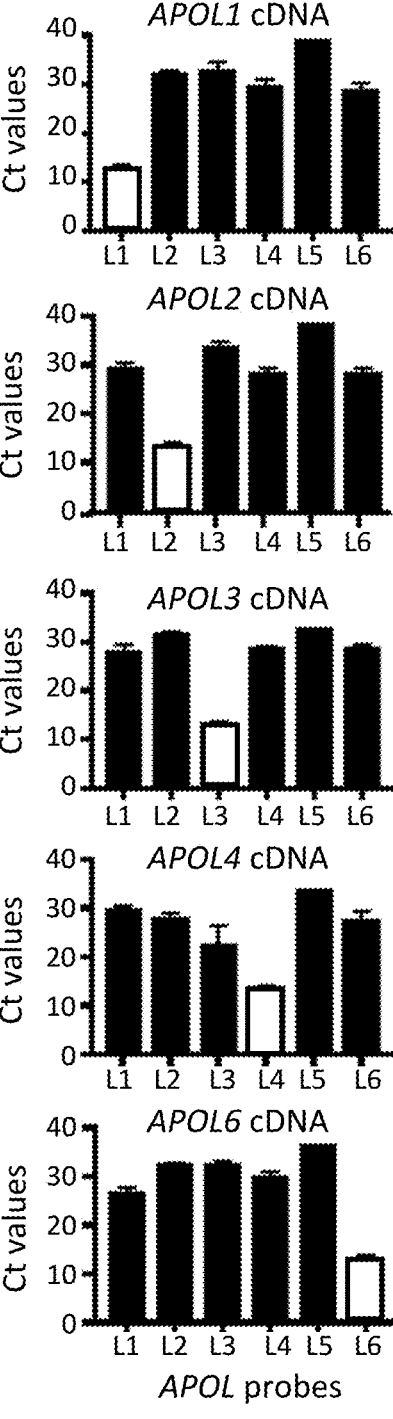
Figure 30B:
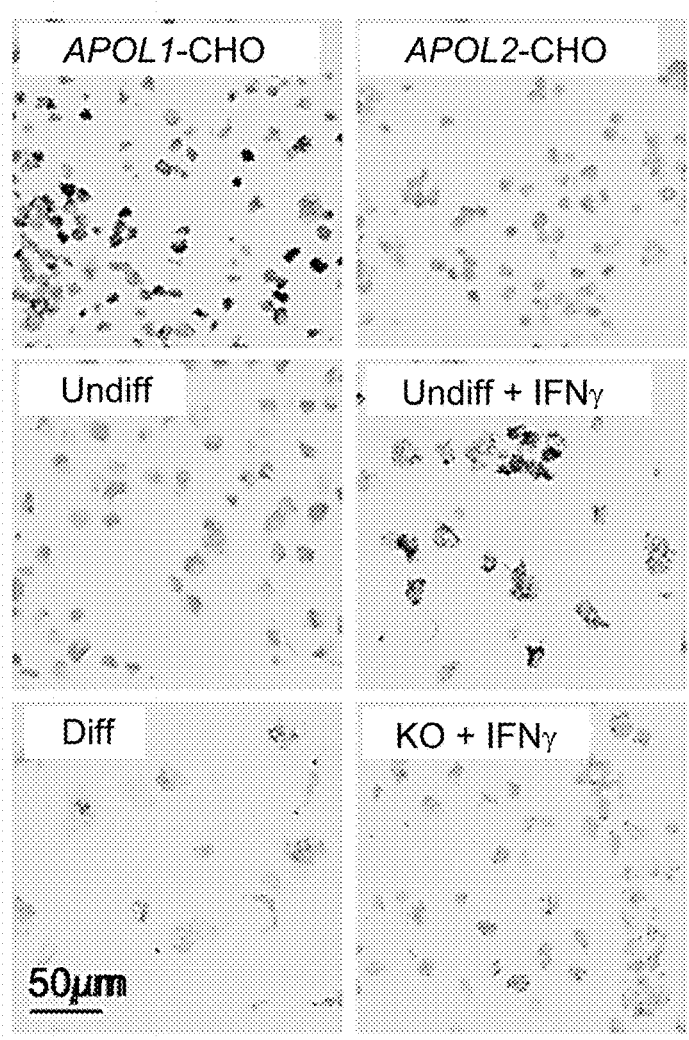
Figure 30C:
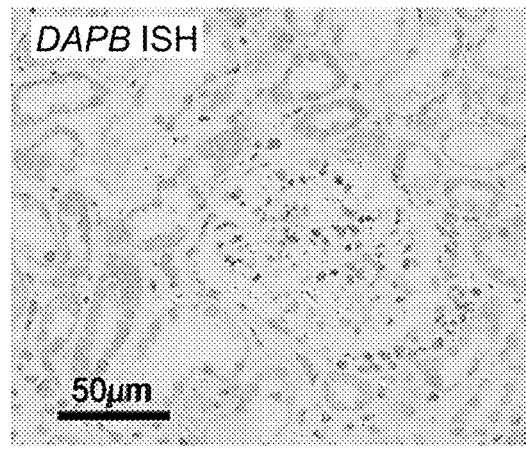

FIGS. 30A-30C show APOL specificities of qRT-PCR and In Situ Hybridization probes. FIG. 30A shows qRT-PCR probes are mostly specific for the designated APOL family member. Validation of the APOL qRT-PCR probes (L1-L6) used in FIGS. 21A and 21C by testing on cDNAs for each available APOL family member (see Table 3 for cDNA details). Red bars indicate the cognate cDNA for each probe. $C_t$ values (cycle thresholds) higher than 22 indicate that the probe is not reactive with that cDNA. Although the L4 probe appears to react a little with APOL3 cDNA, it was completely negative in kidneys and podocytes (FIGS. 21A and 21H), so this cross-reactivity does not matter for this particular purpose. Mean and SD of triplicates from two independent experiments at 1 ng DNA are shown.

FIG. 30B shows that the APOL1 ISH probe does not cross-react with APOL2. Various FFPE cell pellets are stained with the APOL1-C2 probe used in FIG. 21B-G. The probe recognizes APOL1 (APOL1-CHO) but not APOL2 (APOL2-CHO) transfected CHO cells, and gave a weak signal on undifferentiated (Undiff) and differentiated (Diff) human immortalized podocytes, which increased greatly upon IFNγ stimulation (100 ng/ml for 24 h, (Undiff+IFNγ)). There was less (but not no) signal in IFNγ-treated APOL1 KO podocytes (KO+IFNγ), since only one allele is completely deleted, while the other is merely frame-shifted (Example 1 below). The APOL2-CHO cells were confirmed to express APOL2 by IHC (data not shown).

FIG. 30C shows DAPB-C2 negative control ISH probe applied to normal human kidney (in the same experiment as the APOL1-C2 probe in FIGS. 21B-G), showing no discrete puncta. The nonspecific red background staining on proximal tubules is a common artifact of the red dye with this ISH method on kidney tissues and is not probe-specific (it was also seen in FIGS. 21B-H).

Figure 31A:
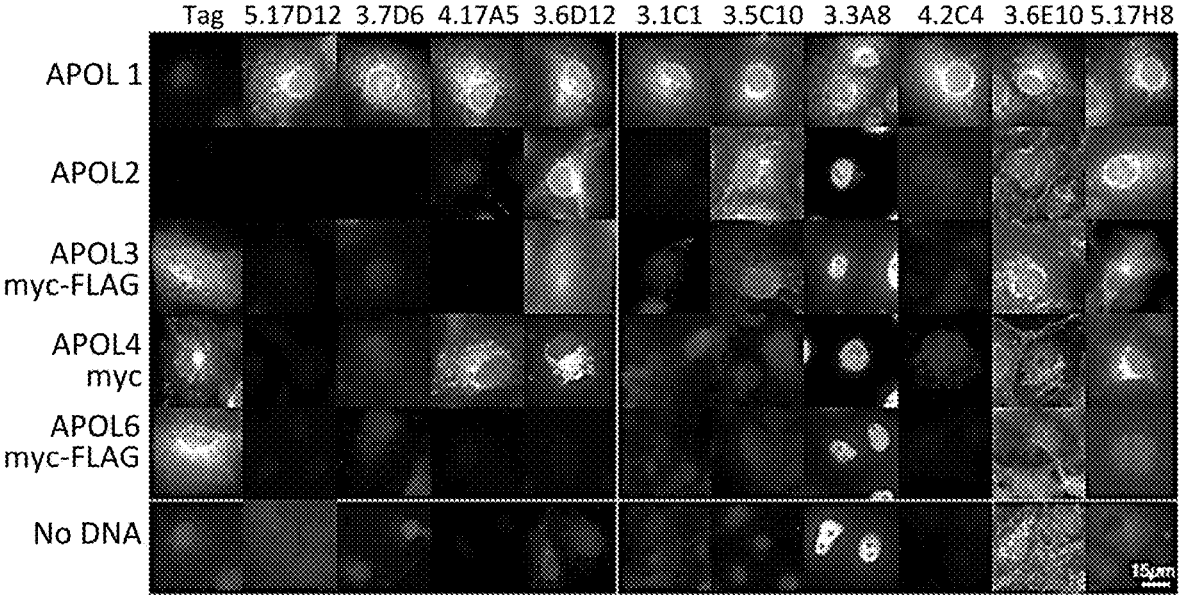
Figure 31B:
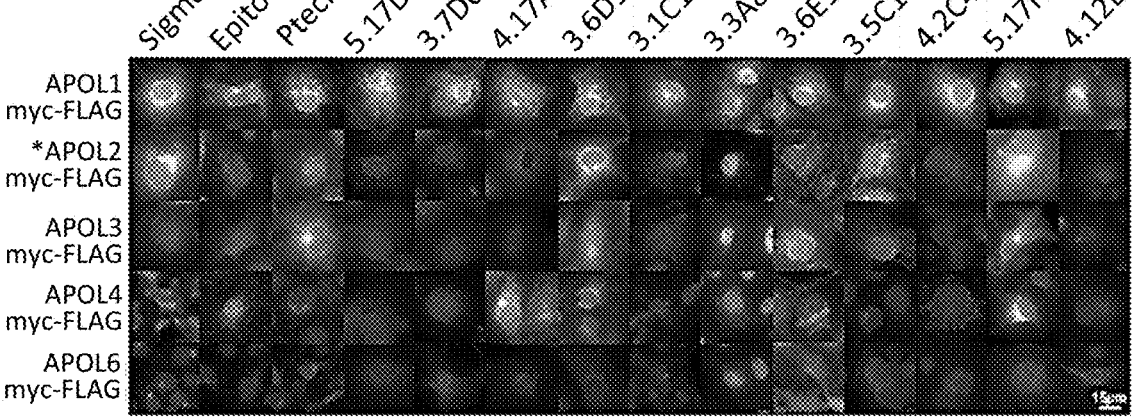

FIGS. 31A-31B show APOL specificities and colocalization with epitope tags of the anti-APOL1 antibodies. In FIG. 31A, to confirm results and demonstrate that the cells in FIGS. 22A-I were actually transfected, untagged APOLs 1 and 2, or C-terminally myc-FLAG tagged APOLs 3 and 6 or APOL4-myc transfected COS cells were stained with the same anti-APOL1 antibodies, as well as all those used elsewhere in this study (Alexa488 anti-mouse or rabbit). Untransfected COS cells are shown in the bottom row, showing nonspecific background staining by 3.3A8 (nuclear) and 3.6E10 (mitochondrial); these two antibodies recognize APOL1, but not other APOLs, and hence are designated APOL1-specific.

FIG. 31B shows APOL staining colocalizes with the epitope tag. COS cells were transfected as in FIG. 31A except APOL1 and APOL2 were also C-terminally myc-FLAG tagged. Overlays of APOL with epitope tags: either mouse anti-FLAG-M2 or mouse anti-myc 9E10 for anti-APOL1 rabmabs; or rabbit anti-Myc 71D10 in conjunction with mouse anti-APOL1. Signals indicate the two antibodies overlap (i.e. anti-APOL1 cross-reacts with that APOL); signals (epitope tag only) indicate no cross-reactivity. Alexa647 anti-rabbit or mouse were used for the tags to rule out the possibility that any colocalization was a bleed-through artifact. Sparsely transfected areas were imaged to permit evaluation of background staining in adjacent untransfected cells—DAPI nuclear staining identifies both untransfected and transfected cell nuclei. APOL1 signal in non-transfected cells indicates nonspecific staining, notably strong nuclear staining for 3.3A8 and mitochondrial staining for 3.6E10. Note that none of the antibodies cross-reacted with the more distantly related APOL6. *, APOL2-myc-FLAG is presumably misfolded, since it is not as cross-reactive as untagged APOL2 (compare FIG. 31A) with several antibodies. Commercial antibodies are Sigma HPA018885, Epitomics EPR2907 (2) (Epito) and Proteintech 11486-2-AP (Ptech). Cross-reactivity results are summarized in Table 4.

Figure 32A:
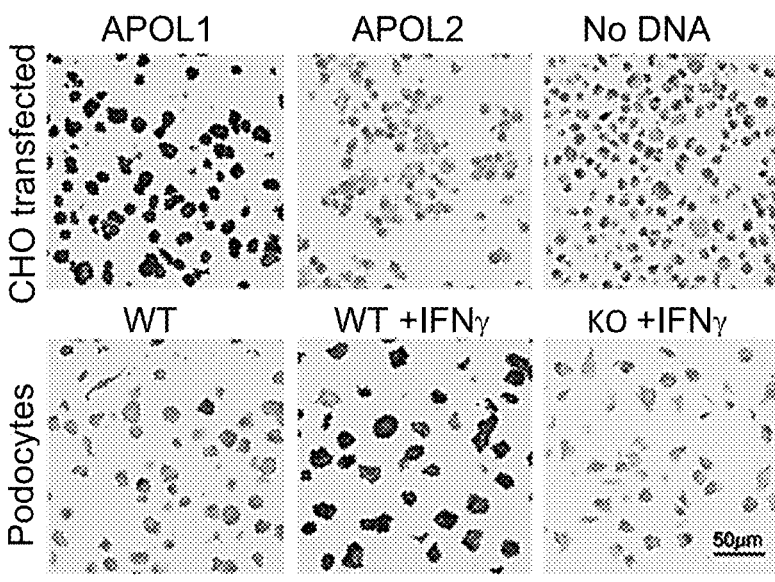
Figure 32B:
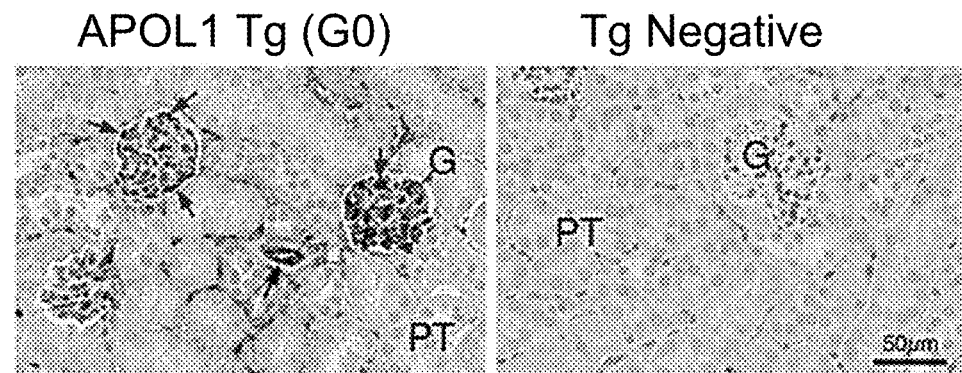
Figure 32C:
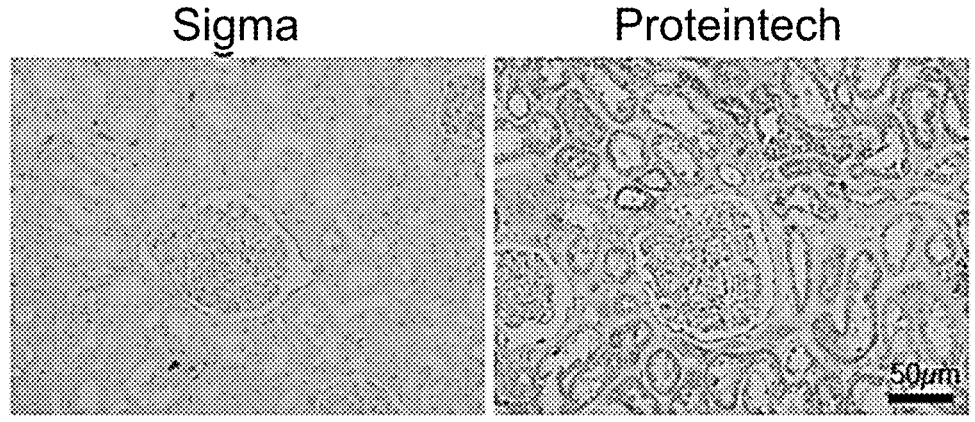

FIGS. 32A-32C show validation of rabmab 5.17D12 for IHC staining and comparison with commercial antibodies. FIG. 32A shows FFPE pellets of CHO cells transfected or not with APOL1 or APOL2 cDNAs (upper row); or untransfected podocytes (lower row), treated or not for 24 h with IFNγ or knocked out for APOL1, stained with 5.17D12 at 0.25 μg/ml. The APOL2 cell pellets were positive with 3.6D12 and the Proteintech polyclonal by IHC (data not shown), verifying successful transfection.

FIG. 32B shows FFPE kidneys of APOL1-G0 transgenic mice expressing APOL1 under its own promoter (left) or a non-transgenic littermate (right) stained with 0.5 μg/ml 5.17D12. Scale bar is 50 μm. Arrows at left and right show podocytes; central, lower black arrow shows glomerular endothelium. G, glomerulus; PT, proximal tubules.

FIG. 32C shows normal human kidney stained with the commercial Sigma (HPA018885) and Proteintech (11486-2-AP) anti-APOL1 polyclonal antibodies at 2 μg/ml. Both antibodies show non-specific binding in proximal tubules, glomeruli and vasculature. Antibody titration assays aimed at improving the signal to noise ratio were unsuccessful (not shown). The Sigma antibody is a recent lot (E105900), which is not as strong or clean as earlier lots. Both images are shown at the same magnification and the scale bar is 50 μm.

Figure 33A:
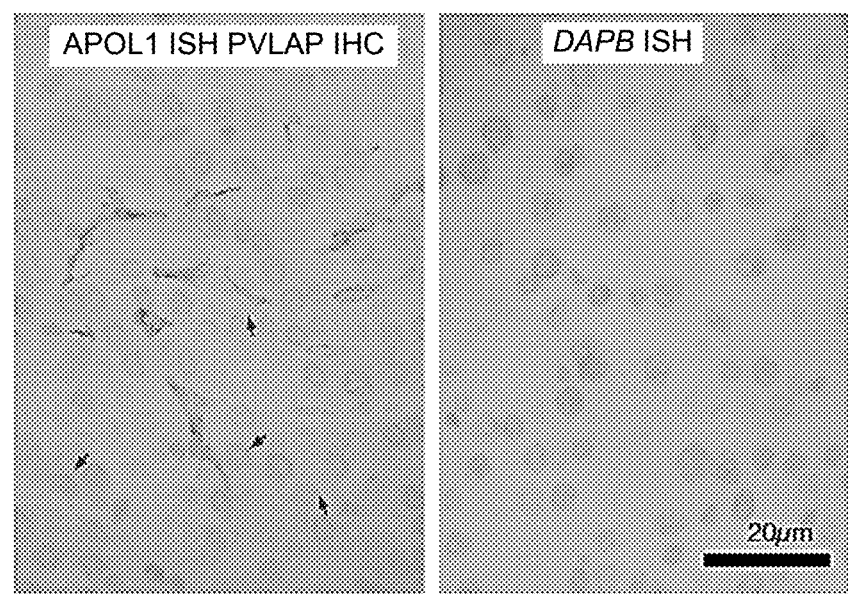
Figure 33B:
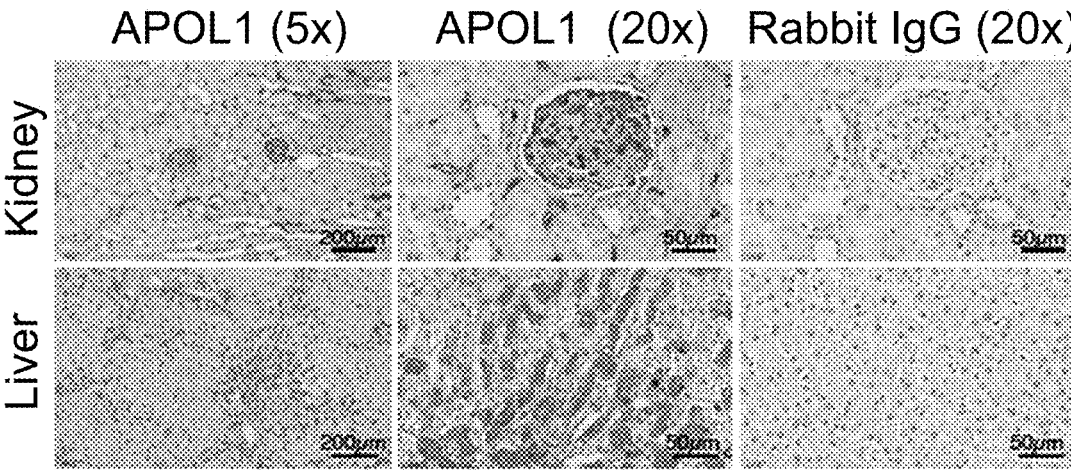

FIGS. 33A-33B shows expression of APOL1 in liver. FIG. 33A in the left panel shows normal human liver co-stained for APOL1 mRNA (arrows) and PVLAP protein in the same experiment as the kidney in FIG. 21B, F. The liver RNA signal is unexpectedly weaker than that in kidney, despite similar signals by RT-PCR (data not shown) and western blotting perhaps because the APOL1-positive hepatocytes (see FIG. 33B) comprise the majority of the liver signal, whereas the glomeruli comprise only about 2% of the total kidney. FIG. 33A in the right panel shows that no signal is seen with negative control DAPB-C2 probe. Scale bar is 20 μm.

FIG. 33B shows normal human kidney (upper) and liver (lower) were stained with 0.5 μg/ml rabbit 5.17D12 anti-APOL1 or isotype control as in FIG. 23. APOL1 is seen in hepatocytes in a central-lobular pattern, wherein the intensity is weaker than that in the kidney glomeruli. Scale bars are 200 μm in 5× panels (left) and 50 μm in 20× panels.

Figure 34:
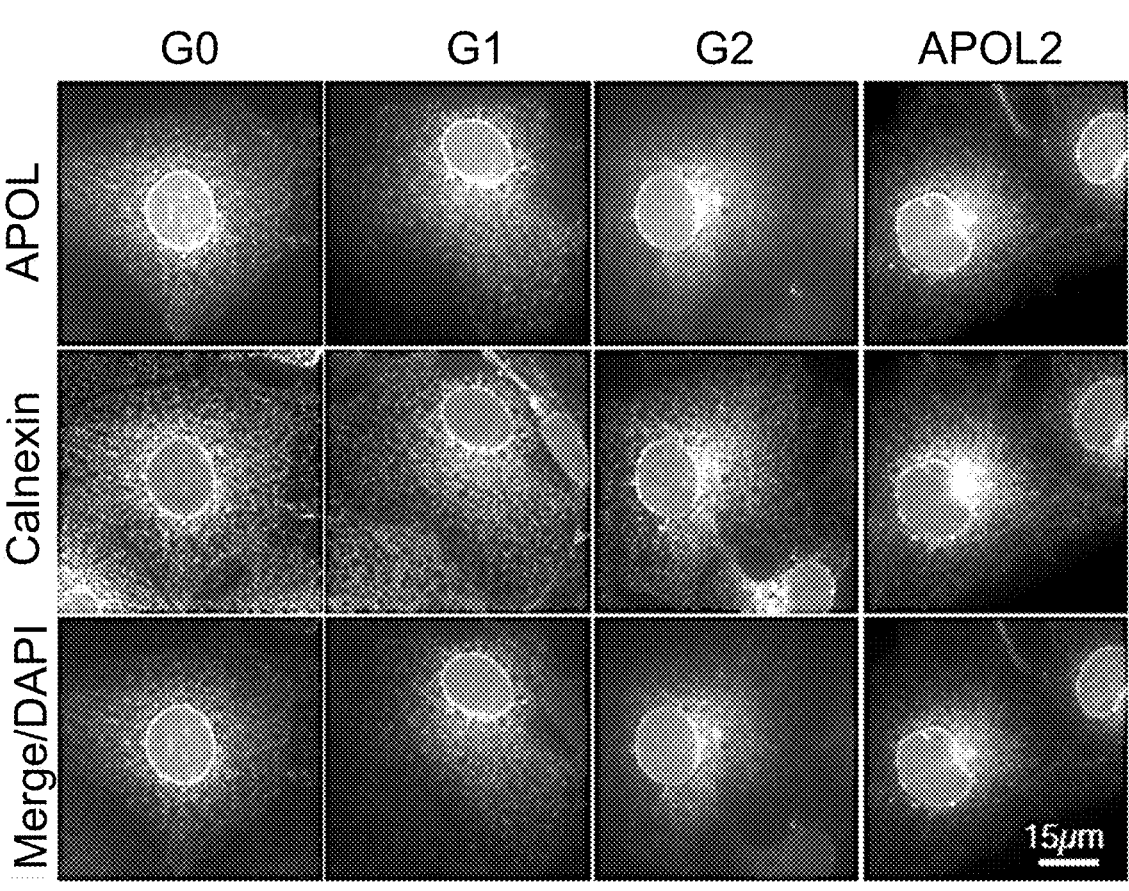

FIG. 34 shows that transiently transfected APOL1-G0, G1 and G2 and APOL2 are all associated with the ER of COS7 cells. COS7 cells were transfected for 43 h, PFA fixed and permeabilized with Triton X-100. APOL1 staining with 1 μg/ml mouse 4.17A5 for APOL1 or 3.6D12 for APOL2 (+Alexa488 anti-mouse) is shown at the top, the ER-specific chaperone rabbit anti-calnexin (+Alexa647 anti-rabbit) in the middle row and overlays at the bottom, where colocalization is shown. DAPI nuclear stain is also shown. Scale bar is 15 μm. Similar APOL1 colocalization was obtained with another ER-specific chaperone, protein disulfide isomerase (data not shown).

Figure 35:
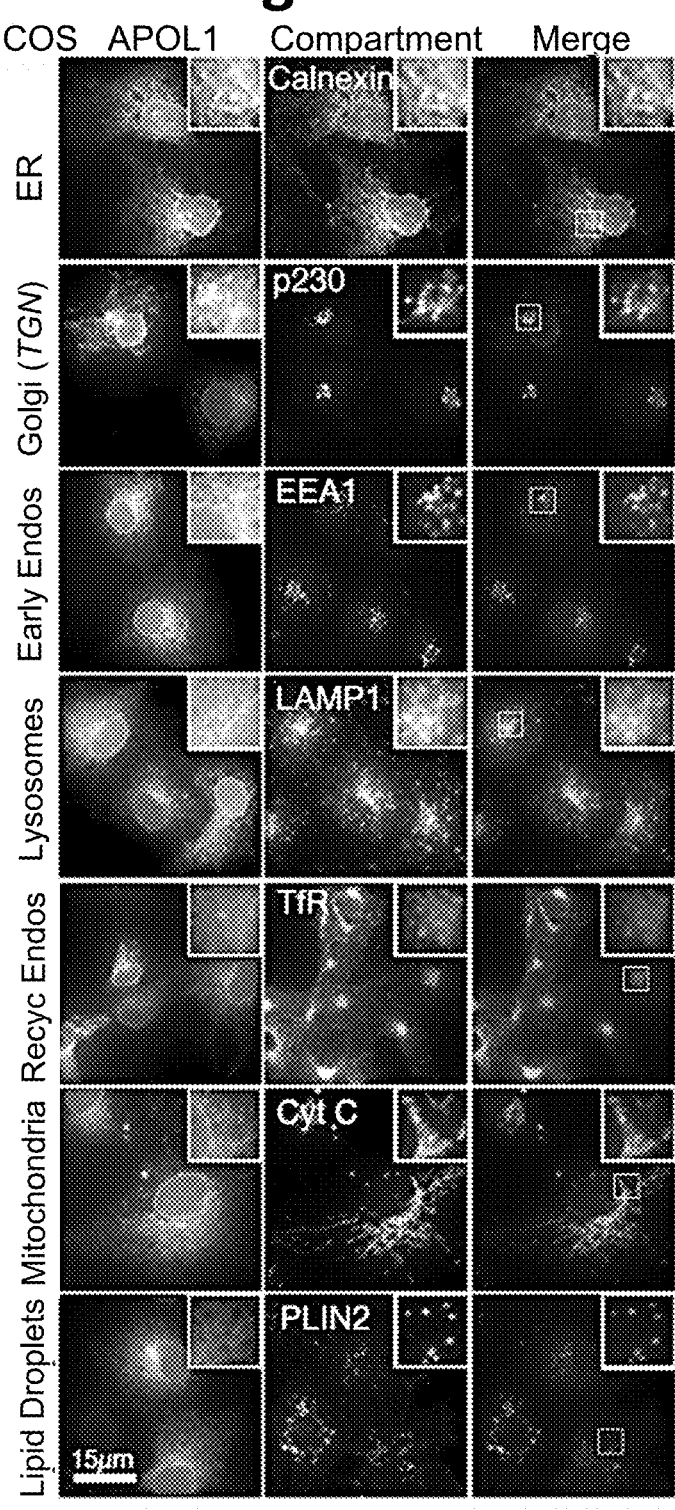

FIG. 35 shows that transiently transfected APOL1 is not detected in other compartments than the ER in COS7 cells by IF. COS7 cells were transfected with APOL1 for 43 h, PFA fixed and permeabilized with saponin, except for the co-staining with cytochrome c, which works better with Triton X-100 permeabilization. APOL1 staining with rabbit 3.7D6 (or murine 4.17A5 for rabbit anti-calnexin and perilipin-2 co-stainings) is on the left, with compartment markers (center) and merges on the right, where any overlap is shown. APOL1 clearly overlaps extensively with the ER antibody to calnexin. There was no or very minimal overlap of APOL1 with the trans-Golgi network marker p230 (Golgin-245); early endosome autoantigen 1 (EEA1); late endosomal and lysosomal marker LAMP1; recycling endosomal marker Transferrin receptor (TfR); mitochondrial intermembrane space marker cytochrome c (Cyt C); or perilipin-2 (PLIN2, Proteintech 15294-1-AP, validated in FIGS. 36A-D). Even with oleic acid treatment to enhance lipid droplets, APOL1 did not relocate to lipid droplets in COS cells, whether the cells expressed high or low levels of APOL1 or perilipin-2 (FIG. 37A). Scale bar is 15 μm and the insets show 3× magnification of the most overlap, generally the perinuclear region, for each antibody pair, confirming lack of meaningful overlap with any compartment except the ER. Occasional apparent partial overlap of APOL1 with mitochondrial tubules is seen, but triple staining reveals "colocalization" of such tubules with calnexin as well (data not shown), suggesting that the ER and mitochondria likely share the same microtubule track at that location and simply cannot be resolved with this epifluorescence microscope (AxioM2). Validation of the other compartment marker antibodies is described in Example 2.

Figure 36A:
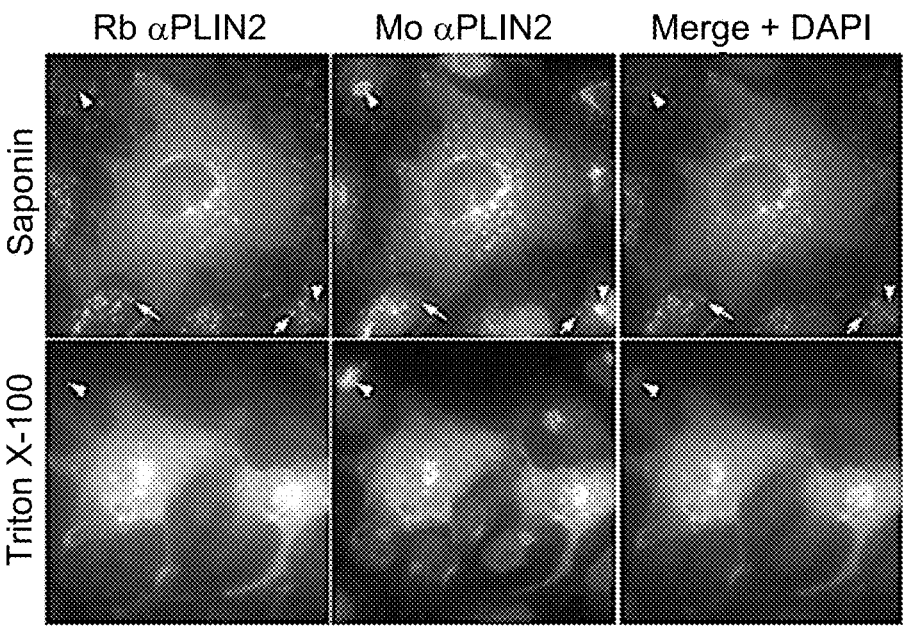
Figure 36B:
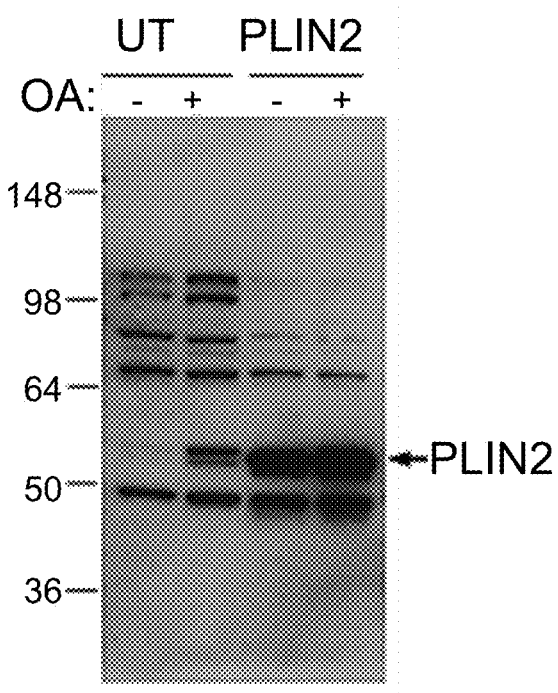

FIGS. 36A-36B show validation of the rabbit anti-perilipin-2 antibody. FIG. 36A shows that two anti-perilipin-2 antibodies recognize transfected perilipin-2 (PLIN2) by immunofluorescence of transfected COS cells. COS cells were transiently transfected for 45 h with human PLIN2, then PFA fixed and permeabilized with saponin (upper) or Triton X-100 (lower). Rabbit anti-perilipin-2 (1.74 μg/ml of Proteintech 15294-1-AP; left) and mouse anti-perilipin-2 mAb ADFP-5 (3.3 μg/ml of Sigma SAB4200452, red; center) both see transfected cytoplasmic perilipin-2 with both permeabilization methods. However, endogenous perilipin-2 on lipid droplets, appearing as small dots or rings (arrows), is detected only with saponin, not Triton X-100 (which extracts the perilipin-2 binding lipids as previously reported).[2] The ADFP-5 antibody additionally stains the Golgi (arrowheads; colocalizing with anti-β4GALT3 (data not shown)), which is not seen with the Proteintech polyclonal. Proteintech anti-perilipin-2 was therefore favored because it was more selective for lipid droplets as well as more sensitive (see FIG. 36C).

FIG. 36B shows that rabbit anti-perilipin-2 recognizes perilipin-2 by western blotting. Untransfected (UT) or perilipin-2 (PLIN2)-transfected COS cells were lysed after 40 h transfection with (+) or without (−) 35 μM oleic acid (OA) in 10% BSA for the last 21 h (−denotes 10% fatty acid-free BSA vehicle). Lysates were western blotted with 0.08 μg/ml rabbit anti-peripilin-2 (Proteintech 15294-1-AP) on 10% Tris-Glycine gels. A faint doublet band (less intense than several background bands) is seen at around 54 kDa in untransfected cells, which becomes more intense following OA treatment, and even more so after PLIN2-transfection, strongly implying it represents perilipin-2.

Figure 36C:
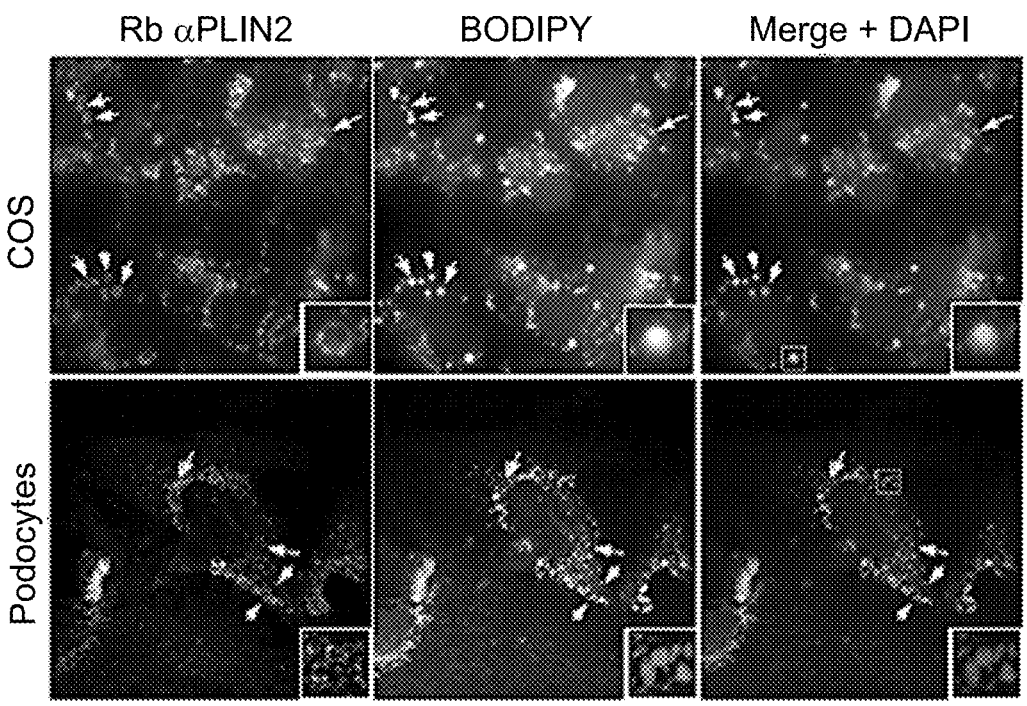
Figure 37A:
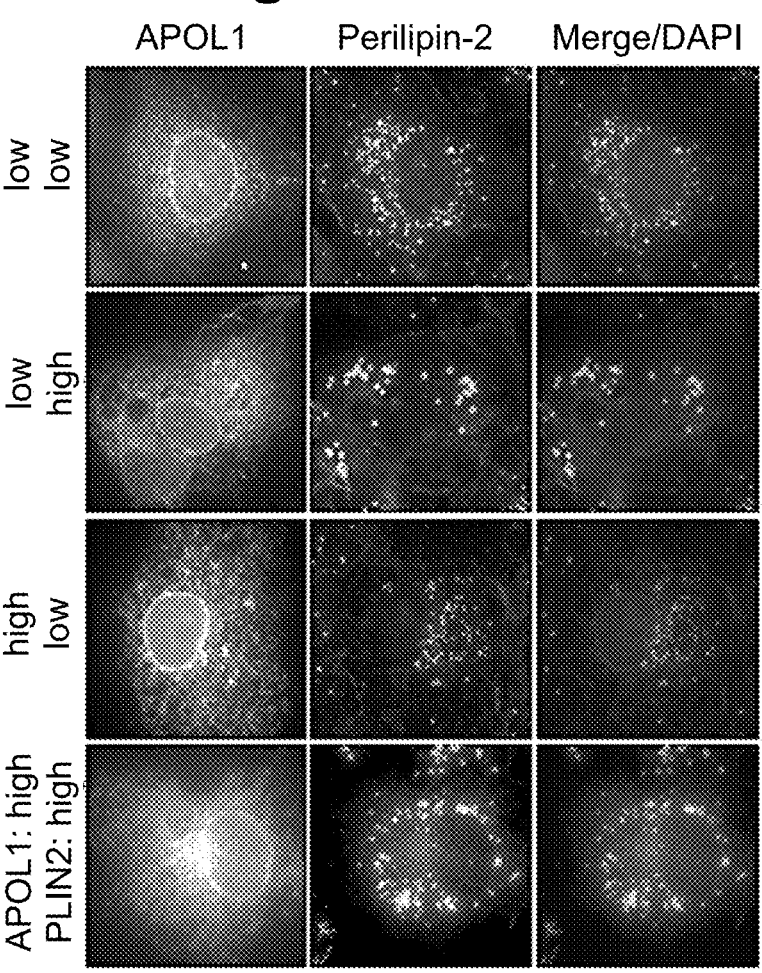

FIG. 36C shows that perilipin-2 staining surrounds lipid droplets in untransfected COS and podocyte cells. To verify that the perilipin-2 rings in untransfected COS (upper) and differentiated podocytes (lower) are lipid droplets, cells were treated for 22 h with 25 μM and 100 μM oleic acid, respectively, then processed for immunofluorescence (PFA/saponin method). After staining for rabbit anti-perilipin-2 (followed by Alexa647-anti-rabbit, red), lipids in the lipid droplets were labeled with 1 µg/ml BODIPY 493/503 (from a 1 mg/ml stock of Molecular Probes D3922 in DMSO) for 30 mins, washed and post-fixed in PFA. Arrows indicate examples of endogenous anti-perilipin-2 surrounding the neutral lipids stained by BODIPY. Insets are 3× magnification of the boxed region.

Figure 36D:
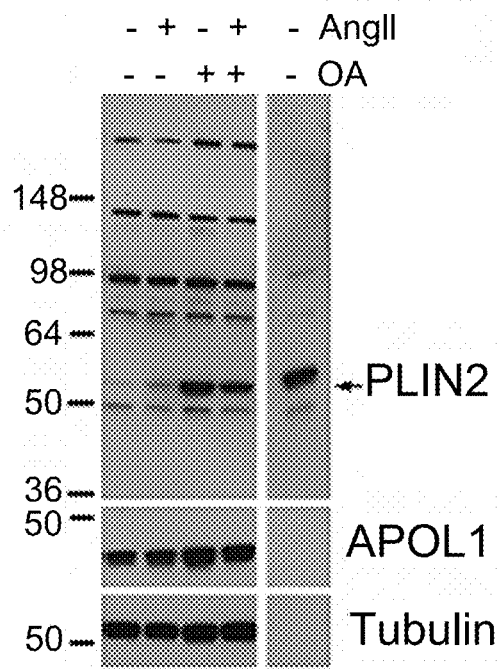

FIG. 36D shows that endogenous perilipin-2 is detected by western blotting of differentiated podocytes. Podocytes were treated with IFNγ for 42 h to upregulate APOL1, with or without 100 nM Angiotensin-II (AngII) and/or 100 µM oleic acid in the last 24 h before lysing and western blotting with rabbit anti-perilipin-2 as in FIG. 36B. The right lane is the PLIN2-COS (non-OA treated) sample from FIG. 36B as a size marker, run on the same gel, but cut and blotted separately to avoid soaking up all the antibody (intervening lanes were removed). The 54 kDa band running at the same size as transfected perilipin-2 increases slightly in intensity following angiotensin-II treatment, as anticipated (Example 2, ref 109), and even more so following oleic acid treatment, suggesting it is indeed perilipin-2. Blots were stripped and reprobed with rabbit 3.1C1/3.7D6 anti-APOL1 to show that APOL1 levels are unaffected by these treatments. Tubulin (mAb 1A2) serves as the loading control.

Figure 37B:
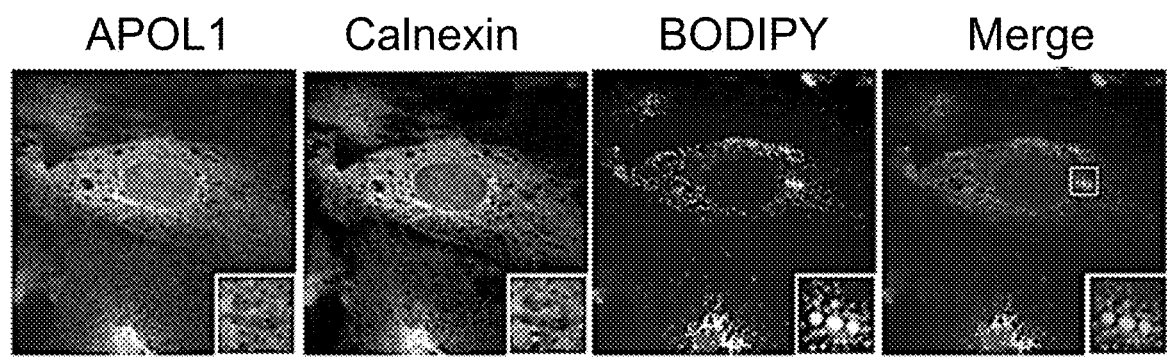

FIGS. 37A-37B show that APOL1 is not seen on lipid droplets in oleic-acid treated cells. FIG. 37A shows COS cells transiently transfected for 45 h with untagged APOL1 and treated with 30 µM oleic acid for the last 16 h. Cells were then processed for PFA/saponin immunofluorescence with 6 µg/ml rat 4.17A5 anti-APOL1 (+Cy3 anti-rat) and mouse anti-perilipin-2 (+Alexa488 anti-mouse). Cells representing high and low levels of APOL1 transfection and high and low levels of perilipin-2 staining are shown; in no case was there colocalization of APOL1 with perilipin-2 on the surface of lipid droplets, unlike a previous study using a C-terminal RFP tag that might affect localization (Example 2, ref 74).

FIG. 37B shows that APOL1 stays in the podocyte ER even when lipid droplets are enlarged with oleic acid. Differentiated WT podocytes were treated with 150 µM oleic acid to enhance lipid droplet formation (and 100 ng/ml IFNγ to stimulate APOL1) for 24 h and processed for immunofluorescence (PFA/TX-100) with 3 µg/ml mouse anti-APOL1 4.17A5 (+Cy3 anti-mouse), rabbit anti-calnexin (+Dy649 anti-rabbit). Lipid droplets were stained for 15 min post permeabilization with 1 µg/ml BODIPY 493/503 (Molecular Probes D-3922). Insets are 3× magnification of the boxed area. APOL1 remains colocalized with calnexin (magenta in the merge) and neither protein is sorted onto the exterior of the BODIPY-positive lipid droplets.

Figure 38A:
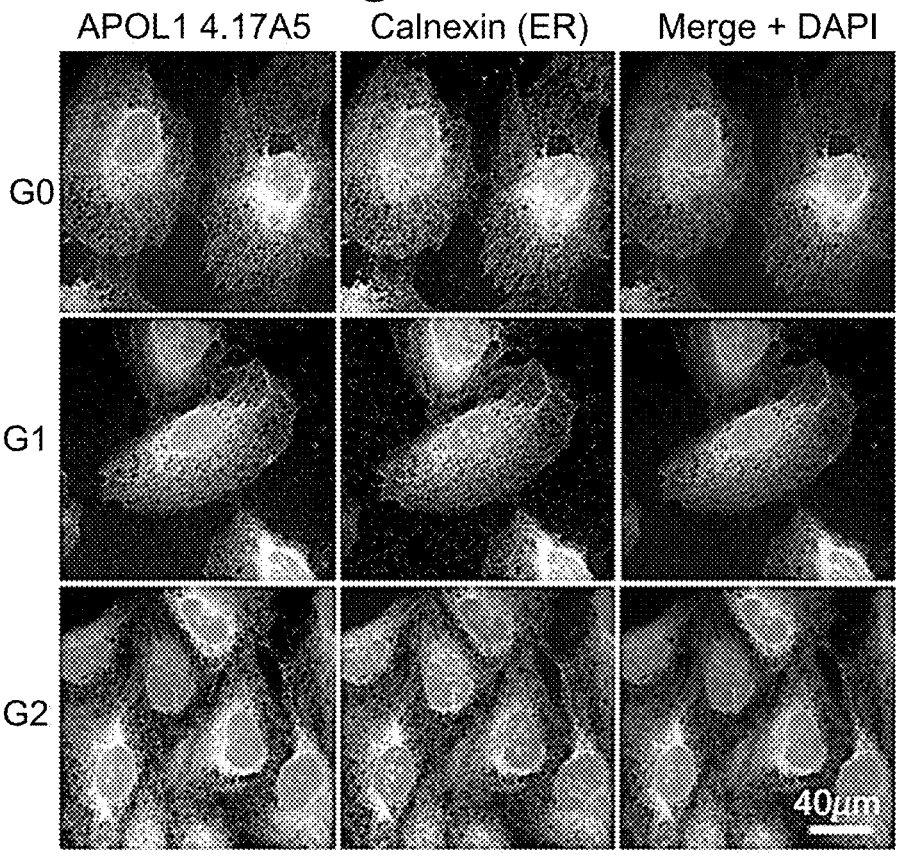
Figure 38B:
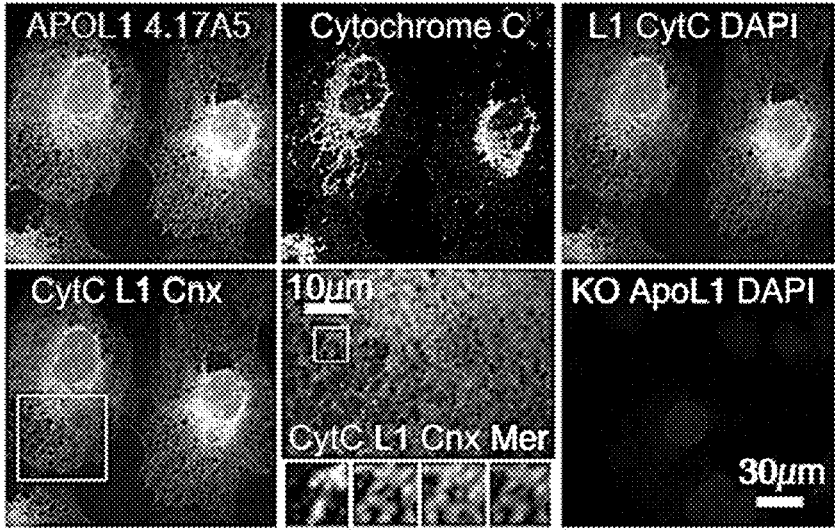

FIGS. 38A-38B show that stably transfected APOL1 G0, G1 and G2 and APOL2 are all associated with the ER in podocytes. In FIG. 38A, stable pools of doxycycline inducible APOL1 podocytes ("iAPOL1" podocytes (made as described in Example 1 below) were induced for 20 h with 10 ng/ml doxycycline, PFA fixed and permeabilized with Triton X-100. APOL1 staining with 1 µg/ml mouse 4.17A5 is shown on the left, with rabbit anti-calnexin (Ab22595, center) and merge on the right, where robust colocalization appears as yellow and nuclear DAPI are shown. Cells were imaged by spinning disk confocal microscopy. Scale bar is 40 µm.

FIG. 38B shows triple labeling of the very same iAPOL1-G0 podocytes as in FIG. 38A with mouse IgG1 anti-cytochrome c in addition to calnexin reveals little colocalization of APOL1 (L1) with mitochondria (lack of staining in upper right merge). Secondary antibodies were Alexa488 anti-IgG2a (for APOL1, "L1"), Alexa555 anti-IgG1 (for cytochrome c, "Cyt C") and Dy649 anti-rabbit (for calnexin, "Cnx"). The triple merge is in the bottom left with the boxed area magnified 3× in the bottom center panel. The predominant signal indicates excellent overlap of APOL1 with calnexin and almost no APOL1/cytochrome c overlap. The few areas of triple overlap are in white, revealing where APOL1 in the ER is in close proximity to mitochondria. Separate channels are shown for the boxed area in the lower center panel (further magnified 2×). Bottom right: uninduced iAPOL1-G0 cells showing absence of 4.17A5 signal in these APOL1 knockout (KO) podocytes; DAPI is shown. Similar lack of mitochondrial overlap was obtained for iAPOL1-G1 and G2 (not shown). Scale bar is 30 µm.

FIGS. 39A-39D show further examples of APOL1 localization to ER but not mitochondria in podocytes by immunoelectron microscopy. Perinuclear region of induced iAPOL1-G0 podocytes stained with 5.17D12 (FIGS. 39A-39C) as in FIG. 24, or 3.6E10 (FIG. 39D) showing that even where the ER and mitochondria are closely apposed, i.e. mitochondria-associated membranes (MAMs), APOL1 remains in the ER and is not detected in mitochondria. Scale bars are 200 nm. FIGS. 39E and 39F show negative control uninduced APOL1 KO podocytes showing lack of APOL1 iEM staining (with 5.17D12 antibody) in any compartment. Arrows, occasional background gold particles. *, ER lumen. L, lysosome. M, mitochondrium. N, nucleus. NE, nuclear envelope. Scale bars are 200 nm.

Figure 40A:
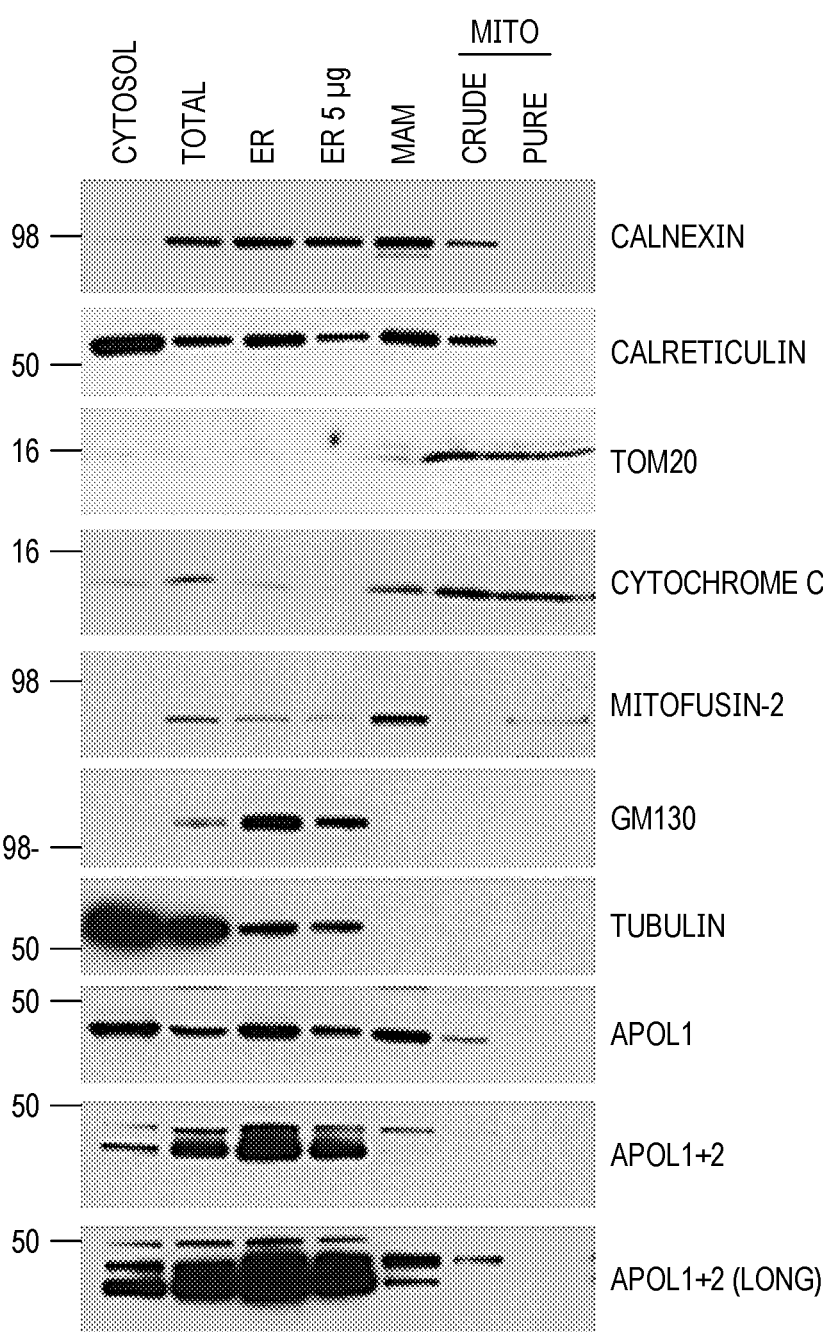

FIGS. 40A-40D show confirmation by fractionation and iEM that APOL1 is in the ER of the MAM and not in mitochondria. FIG. 40A shows a Western blot of 10 µg of each fraction from a Percoll gradient separation of ER, MAM and mitochondria from IFNγ-treated WT podocytes (ER is loaded at 5 µg as well) on 4-20% Tris-Glycine gels. From top to bottom, the markers are: calnexin (ER membrane), calreticulin (ER lumen), TOM20 (mitochondrial outer membrane), cytochrome c (mitochondrial intermembrane space), mitofusin-2 (MAM), GM130 (Golgi matrix), tubulin (cytosol), APOL1 (probed with rabbit 3.1C1/3.7D6) and APOL1+2 (Proteintech; 2 exposures shown). APOL1 is most abundant in the ER fraction, as expected, but was also found in the MAM, and to a lesser extent in crude mitochondria (in agreement with Shah et al.) (Ex. 2, ref 94). However, it was completely absent from purified mitochondria even at long exposures and higher loading (bottom row and data not shown). Some ER membranes may have ruptured during sonication, since soluble calreticulin, but not integral membrane calnexin, is also enriched in the cytosolic fraction. Since some APOL1 is seen in the cytosolic fraction, this potentially supports the notion that inner ER membrane APOL1 may be peripherally attached and become integrated during transit through the acidic Golgi. The plasma membrane was not analyzed since surface APOL1 is completely abolished by the trypsin used to harvest the cells (assessed by FACS, data not shown). Consistent with its localization to the cytosolic face of the ER, APOL2 was most abundant in the ER fraction, but relatively more in the cytosolic and less in the MAM and fraction than APOL1. The MAM fraction was enriched for the MAM marker mitofusin-2, as expected, and also contained the two ER proteins, but not the TOM20 outer membrane mitochondrial marker (Ex. 2, ref 83). Golgi membranes (GM130-positive) were also present in the ER fraction.

FIGS. 40B-40D show iEM of APOL1 at mitochondria-associated membranes (MAMs) in iAPOL1-G0 podocytes (FIG. 40B) and transiently APOL1-transfected HEK293 cells (FIGS. 40C-D) showing mitochondria of the MAM (mitochondria-associated membranes, a subdomain of the ER) are devoid of APOL1, consistent with the fractionation. APOL1 is inside the ER lumen of the MAM, not in the associated mitochondria in both cell types. Immunogold labeling was done using the two strongest APOL1-specific antibodies, 5.17D12 (FIG. 40B) and 3.6E10 (FIGS. 40C-D). *, ER lumen. Arrows, APOL1 gold particles in podocyte. IMM & OMNI, inner and outer mitochondrial membranes. Scale bars: 100 nm (FIG. 40B), 200 nm (FIGS. 40C-D).

Figure 41A:
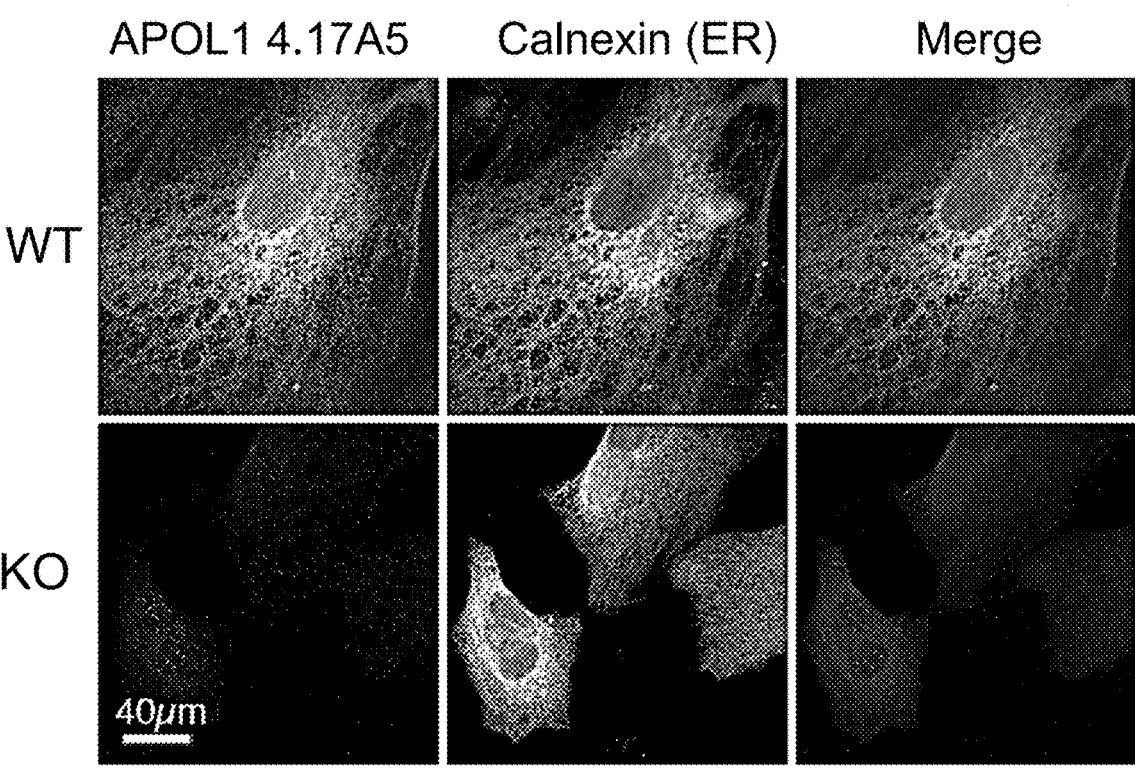
Figure 41B:
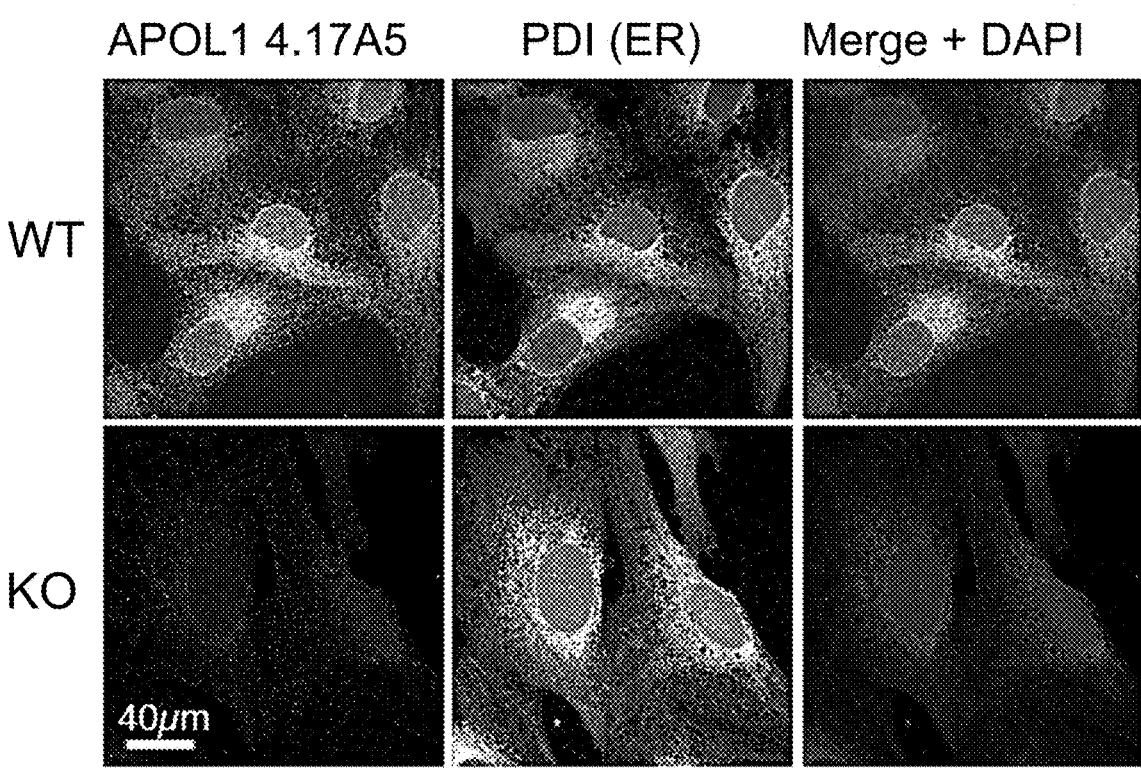

FIGS. 41A-41B show that endogenous APOL1 is also ER-localized in undifferentiated podocytes. FIG. 41A shows differentiated WT (upper) or APOL1 KO (lower) IFNγ-stimulated podocytes PFA fixed, saponin permeabilized and co-stained with an independent anti-APOL1 antibody to that used in FIG. 24D, 2 μg/ml murine 4.17A5 (+Alexa488 anti-mouse) and rabbit anti-calnexin+Cy3 anti-rabbit. Merge reveals good colocalization of the two proteins. Note that 4.17A5 also sees non-specific speckles in some nuclei in APOL1 KO podocytes (and in some WT nuclei, not evident here). Scale bar is 40 μm. FIG. 41B shows similar data as in FIG. 41A except with undifferentiated podocytes and rabbit anti-protein disulfide isomerase (PDI) as the ER marker. Merge (right) indicates colocalization, with DAPI is shown. The ER localization of endogenous APOL1 is not altered upon podocyte differentiation, although the ER generally appears less reticular with all markers in differentiated than undifferentiated cells (compare also with FIG. 43).

Figure 42:
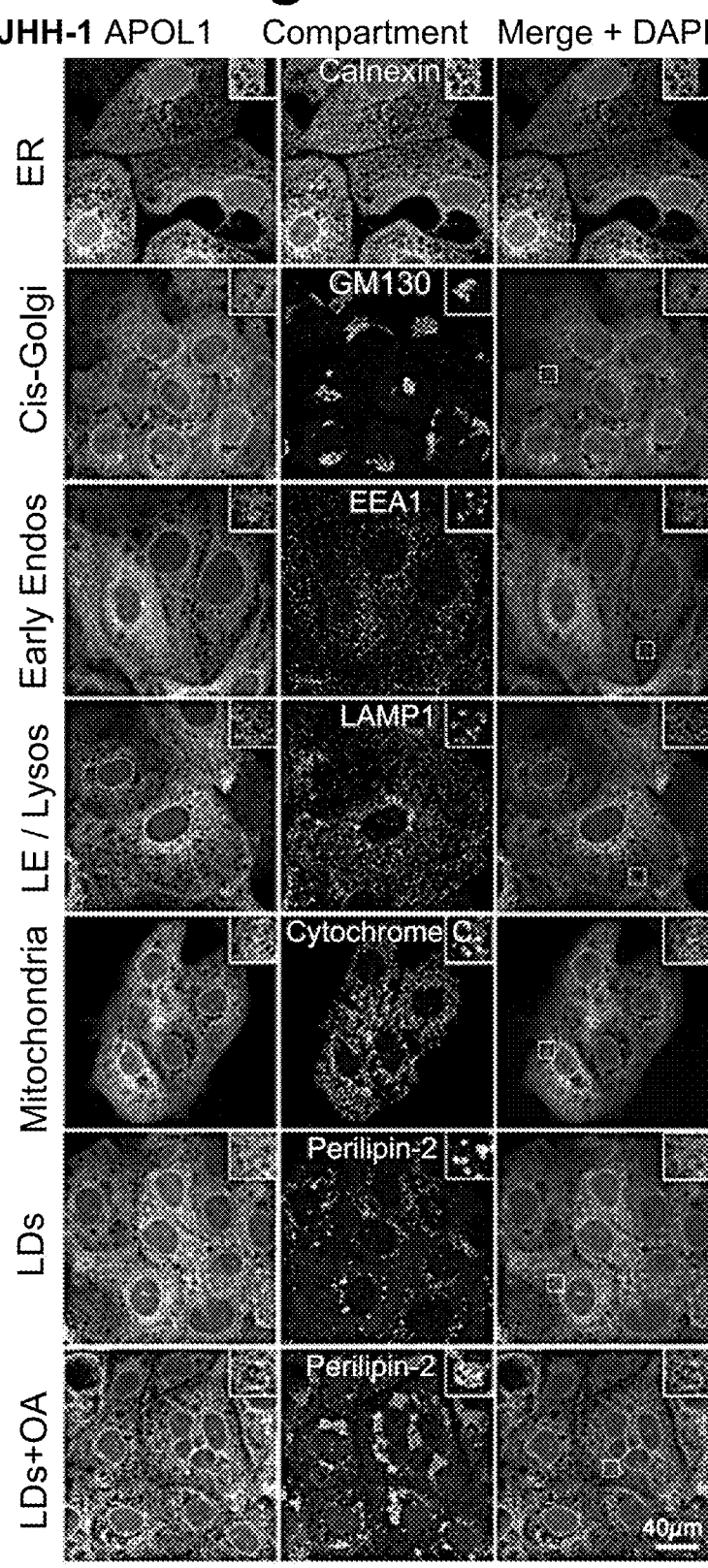

FIG. 42 shows that endogenous liver cell APOL1 is not detected within compartments other than the ER by IF. JHH-1 cells were treated with 100 ng/ml IFNγ for 24 h, PFA-fixed, saponin permeabilized (except for cytochrome c, which works best with Triton X-100) then co-stained with rabbit anti-APOL1 5.17D12 (followed by Alexa488 anti-rabbit) and murine compartment marker antibodies in red (with Cy3 anti-mouse). The same validated compartment markers were used as in FIG. 35, except mouse anti-GM130 was used for the (cis)-Golgi; and mouse anti-calnexin (clone 37) for the ER. Lipid droplets (LDs) were stained with rabbit anti-perilipin-2, so murine 4.17A5 was used for APOL1 in those panels. Endogenous APOL1 is not detected in the mitochondria, Golgi, early, or late endosomes/lysosomes, nor in lipid droplets, even following accumulation of this compartment with 100 μM oleic acid (from NuChekPrep in 10% fatty acid-free BSA) for 21 h (LDs+OA). Scale bar is 40 μm. The only compartment with significant APOL1 overlap (shown in merge) is the ER.

Figure 43:
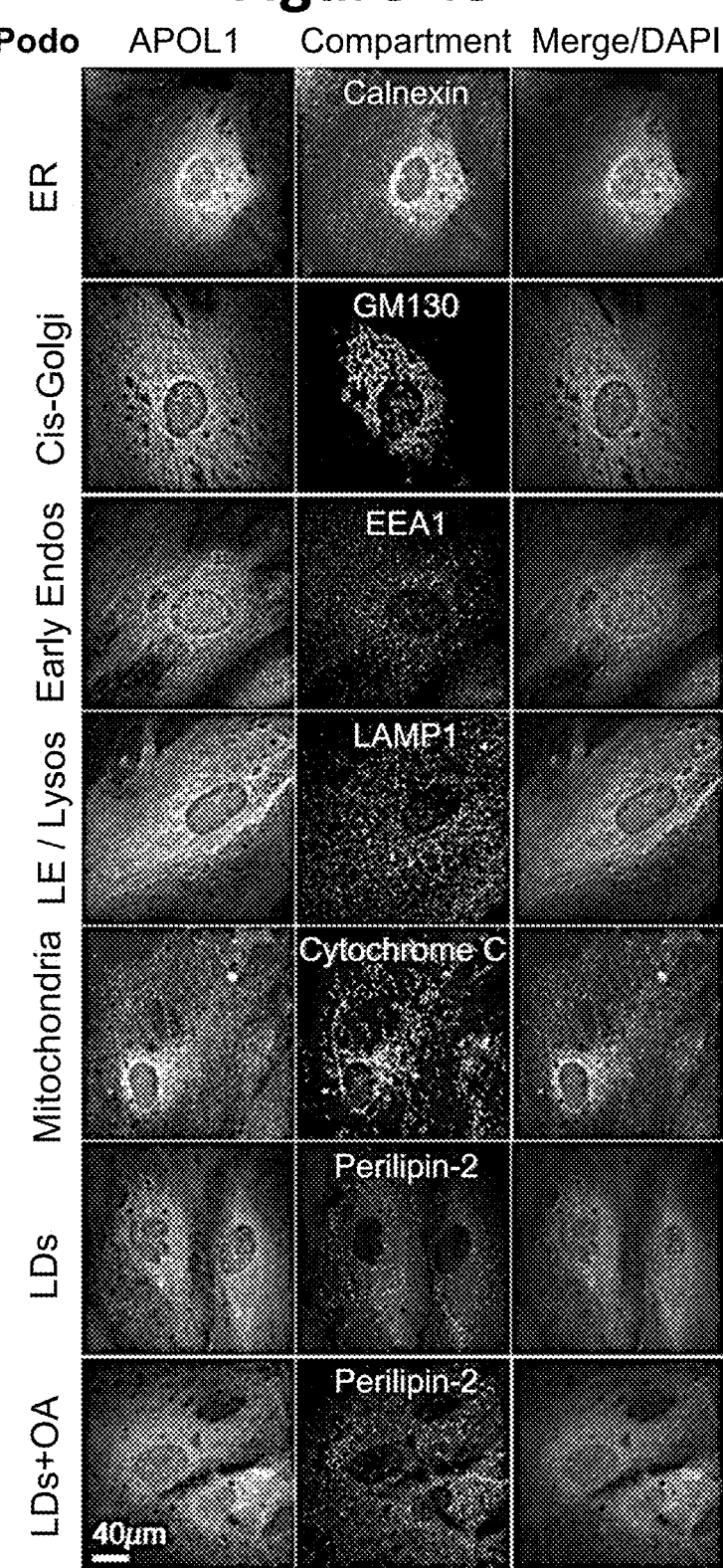

FIG. 43 shows that endogenous podocyte APOL1 is not detected within compartments other than the ER by IF. Differentiated WT podocytes were stained as for the JHH-1 cells in FIG. 42. The lack of association of APOL1 (and calnexin) with lipid droplet results was verified using an independent marker of lipid droplets, BODIPY (FIG. 37B).

Figure 44A:
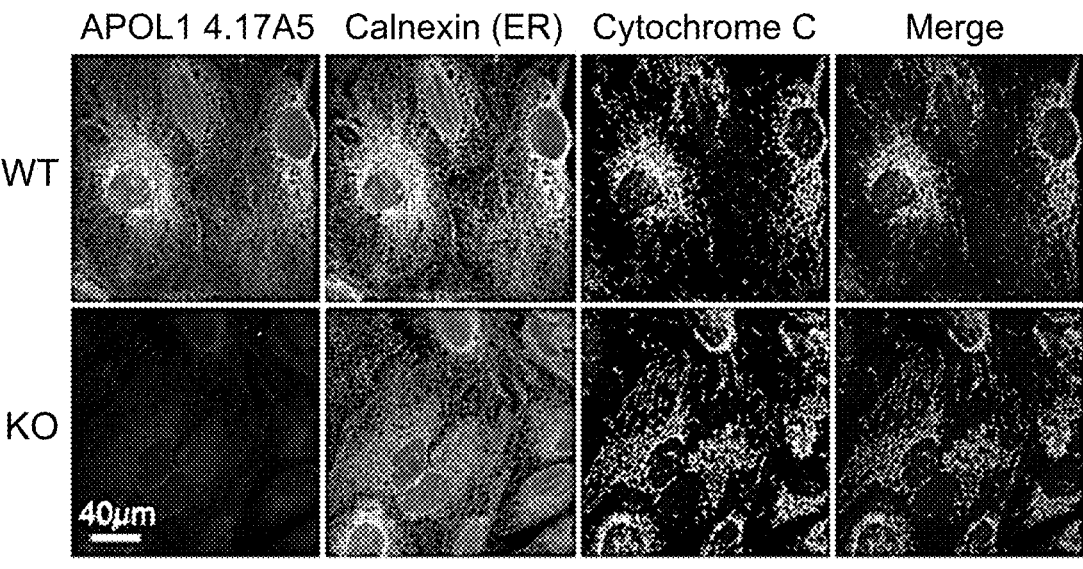
Figure 44B:
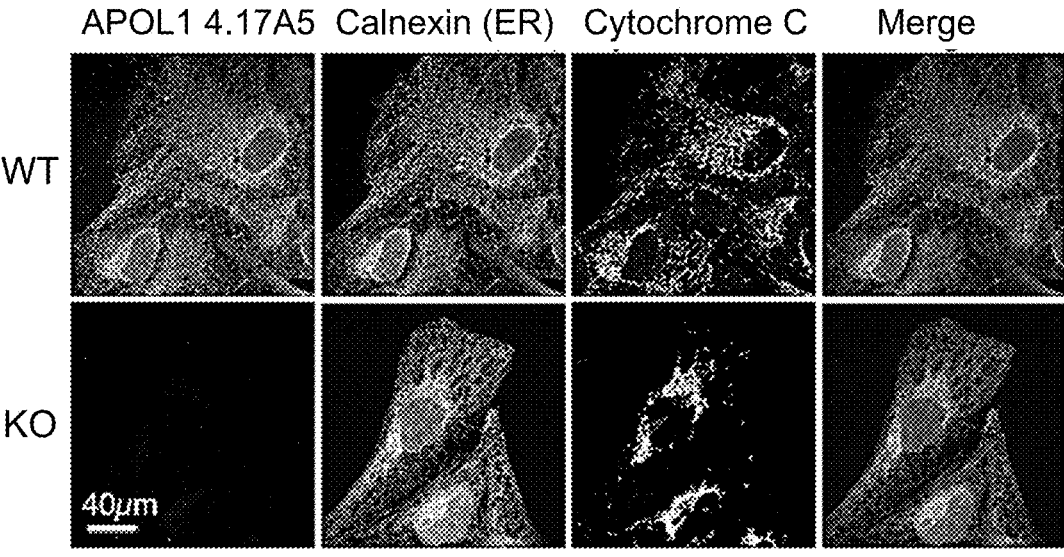

FIGS. 44A-44B show that triple labeling confirms endogenous APOL1 in podocytes is not specifically targeted to mitochondria. FIG. 44A shows IFNγ-stimulated WT (upper) or APOL1 KO (lower) podocytes were PFA fixed, saponin permeabilized and triple stained with rat anti-APOL1 4.17A5 (+Cy3-anti rat highly cross-adsorbed against mouse (Jackson 712-166-153)), rabbit anti-calnexin (+Alexa647 anti-rabbit (Jackson 711-606-152)[[, blue]]) and mouse anti cytochrome c (+Alexa488 anti-mouse, cross-adsorbed against rat (Jackson 711-546-151)). The merge shows magenta staining where APOL1 overlaps with calnexin, and no staining (which would occur if APOL1 overlapped solely with cytochrome c). The limited triple positive areas where the ER and mitochondria appear to overlap are in white. These data indicate APOL1 is not specifically targeted to mitochondria, although it occasionally appears mitochondrial in areas where the mitochondria and ER are too close to resolve. The APOL1 KO cells (lower panel) which lack signal with the 4.17A5 antibody reveal areas of apparent mitochondria and ER overlap (mainly in the membrane-rich perinuclear region). Scale bar is 40 μm.

FIG. 44B is as in FIG. 44A except the secondary antibody fluorophores were switched for calnexin (Alexa488 anti-rabbit (Jackson 711-546-152)) and cytochrome c (Alexa647 anti-mouse (cross-adsorbed against rat; Jackson 715-606-151)) to ensure that the lack of mitochondrial overlap was not merely a color detection bias. In this case, the merge shows abundant signal for APOL1 in the ER (or white triple overlap) rather than magenta (mitochondrial only) overlap. Again, the merge panel of APOL1 KO cells indicates where the ER and mitochondria are closely apposed. Scale bar is 40 μm.

Figure 45A:
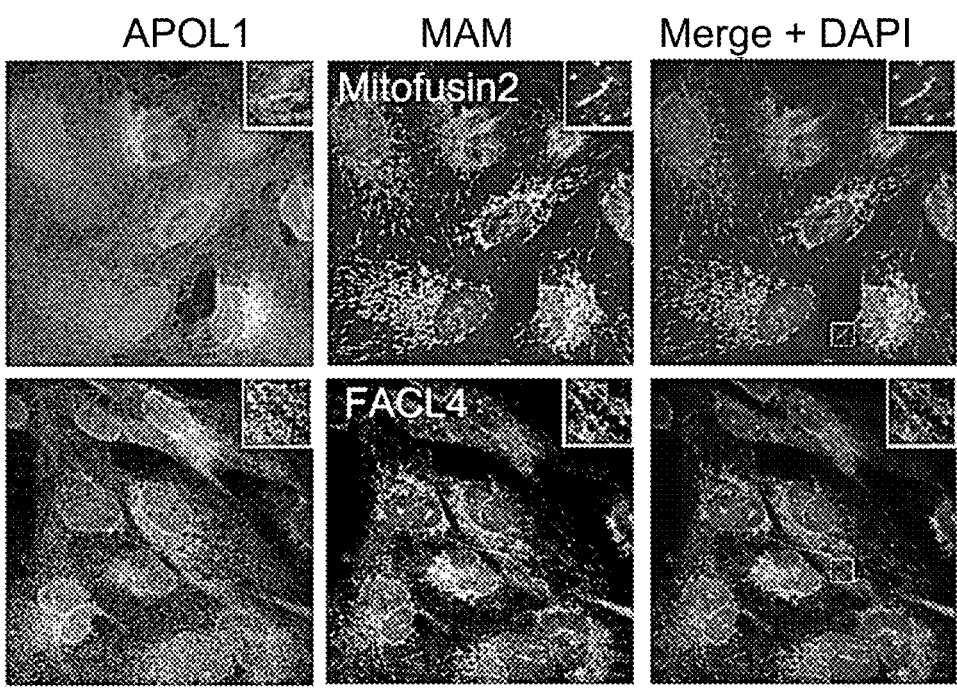
Figure 45B:
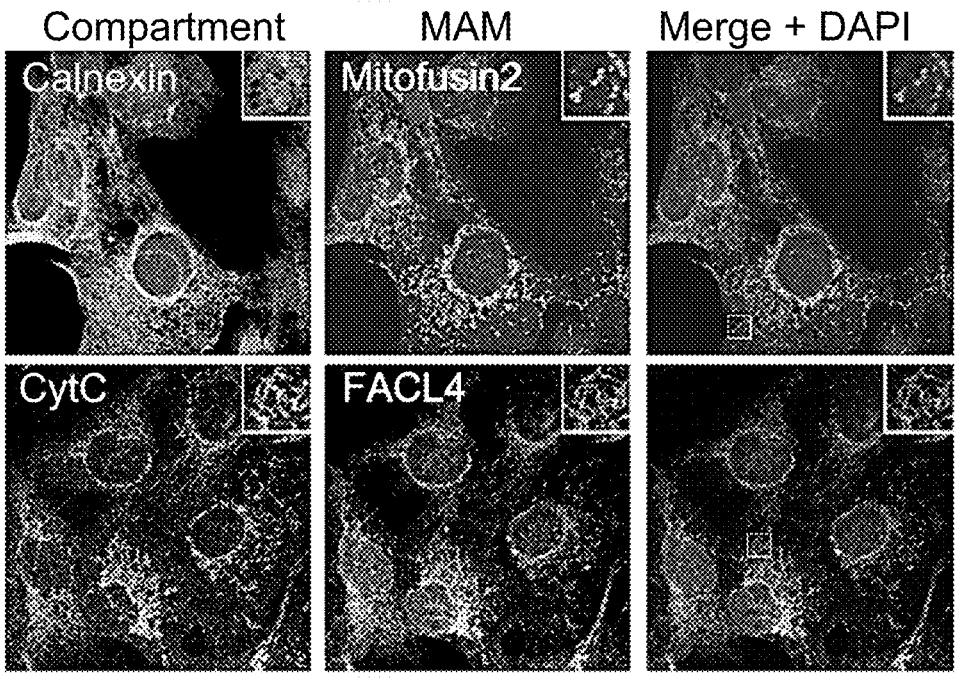

FIGS. 45A-45B show that endogenous podocyte APOL1 is adjacent to the MAM. FIG. 45A shows undifferentiated WT podocytes methanol fixed (at −20° C. for 5 min, the best protocol for the MAM markers but suboptimal for APOL1), and co-stained for APOL1 in red (2 μg/ml 5.17D12 (upper) or 3 μg/ml 4.17A5 (lower)) and MAM markers mouse anti-mitofusin-2 mab 6A8 (Ab56889 at 1 μg/ml; upper) or rabbit anti-FACL4 (Ab137525 at 1 μg/ml; lower). Merge with DAPI is shown on the right and insets are 3× magnification of the respective boxed areas. FIG. 45B shows that the two MAM markers overlap more with mitochondria (cytochrome c; lower) than ER (calnexin; upper). Insets are 3× magnification of the respective boxed areas.

Figure 46B:
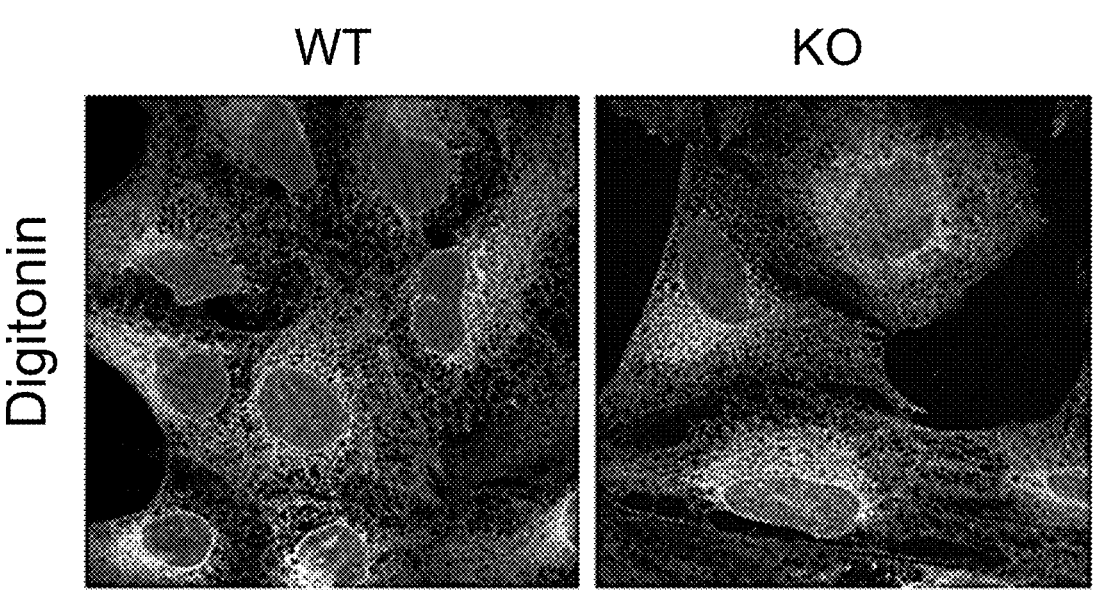

FIGS. 46A-46B show that endogenous APOL1 and APOL2 are on opposite sides of the membrane in podocytes, with APOL2 comprising the majority of the signal. FIG. 46A shows IFNγ-treated WT or APOL1 KO podocytes PFA fixed, permeabilized completely with saponin (upper) or only at the plasma membrane with digitonin (lower; see FIG. 26A) and stained with APOL1-specific 5.17D12 (left two columns) or APOL2-cross reactive Sigma HPA018885 (right two columns), both followed by Alexa488 anti-rabbit. Endogenous APOL1 is on the inside of the ER because the reticular ER signal seen with saponin is replaced with nuclear envelope signal after digitonin permeabilization, representing luminal APOL1 in the ER contiguous with the nuclear membrane; as expected, both signals are APOL1-dependent, being absent in the KO cells. By contrast the reticular ER pattern is evident with both detergents with the Sigma antibody, because it recognizes cytoplasmically oriented APOL2 in addition to luminal APOL1. The Sigma antibody signal in the APOL1 KO podocytes is of course all APOL2. In fact, the vast majority of the Sigma antibody signal in WT podocytes is also APOL2, since firstly the total signal is not much diminished in the APOL1 KO podocytes compared to WT in saponin permeabilized cells; and secondly the nuclear membrane APOL1 signal in digitonin-permeabilized WT cells is far weaker than the APOL2 signal on the outer face of the ER. This agrees with the stronger APOL2 band seen by western blotting (FIGS. 21I, 22B). Note that there was no endosomal or lysosomal staining detected for APOL1 in digitonin-permeabilized podocytes (see FIGS. 52A-B for overlays). FIG. 46B shows APOL2-cross reactive in-house mAb 3.6D12 (detected with Alexa488 anti-mouse) shows similar staining of the cytoplasmic face of the ER to the Sigma antibody after digitonin permeabilization of both WT and APOL1 KO podocytes, confirming that the ER signal in KO cells is APOL2.

Figure 47A:
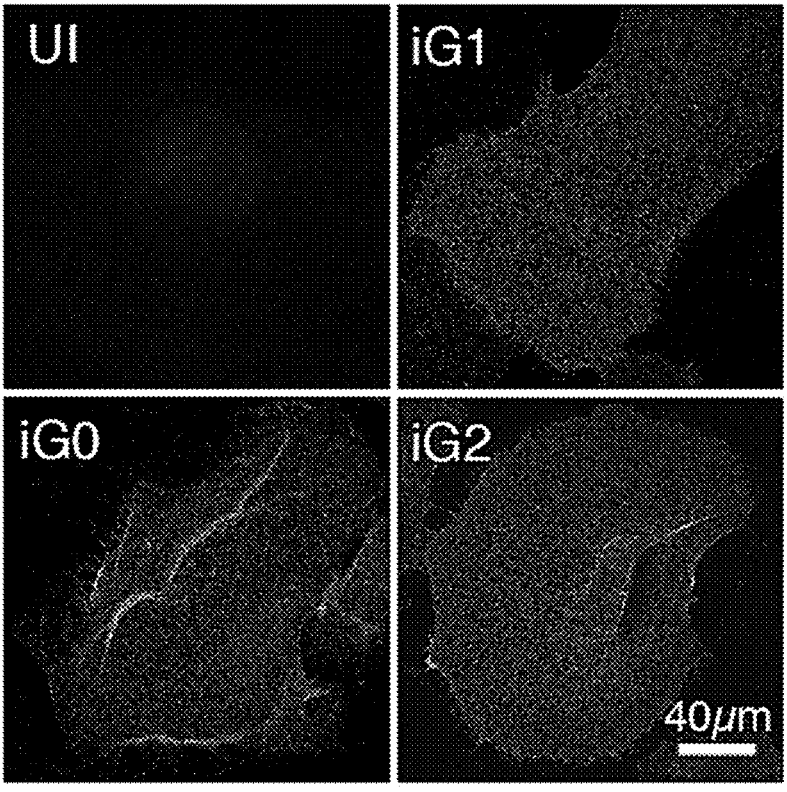
Figure 47B:
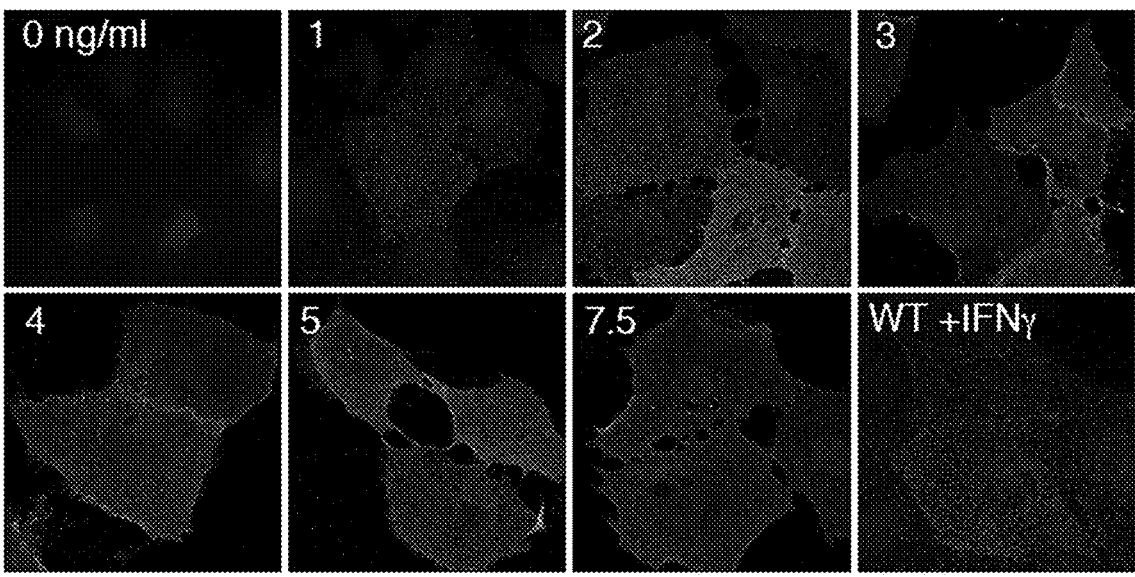

FIGS. 47A-47B show that APOL1 reaches the cell surface in iAPOL1 podocytes and increases with expression level. FIG. 47A shows live iAPOL1-G0, G1 and G2 podocytes induced with 10 ng/ml doxycycline, incubated on ice with antibody 3.6D12 as in FIG. 25B, then fixed and stained with Alexa488 anti-mouse. There was no difference in plasma membrane staining between iAPOL1-G0, G1 and G2. UI is uninduced iAPOL1-G0 (i.e. APOL1 KO) cells, which lack surface APOL1. FIG. 47B is as in FIG. 47A except with a doxycycline dose-response from 0 to 7.5 ng/ml on iAPOL1-G0 podocytes. The last panel shows endogenous APOL1 in IFNγ-stimulated WT podocytes, showing surface signals similar to 1 ng/ml doxycycline in iAPOL1-G0 cells, in agreement with FACS data (see FIG. 13C).

Figure 48A:
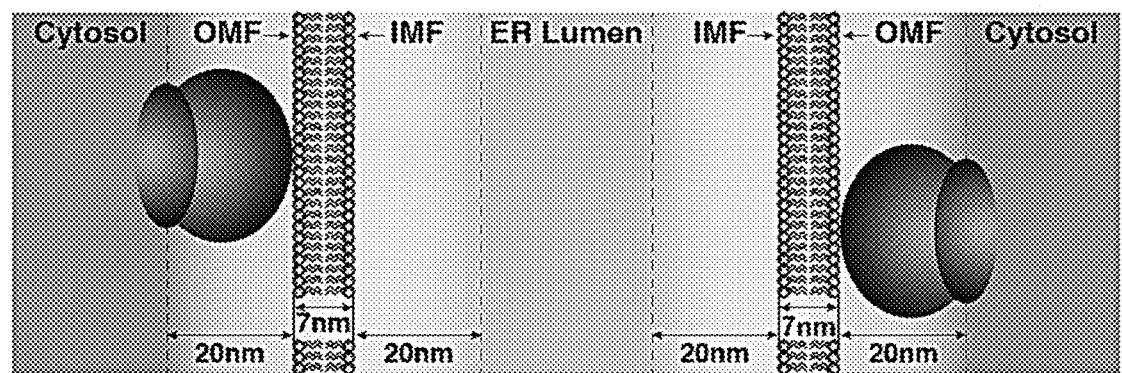
Figure 48B:
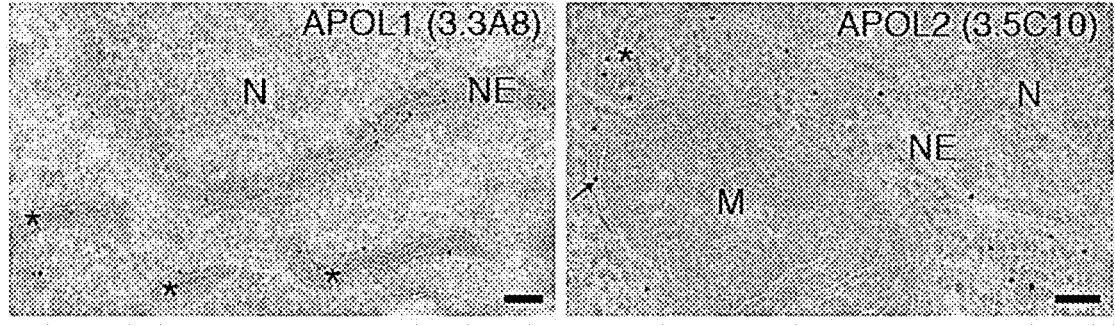
Figure 48C:
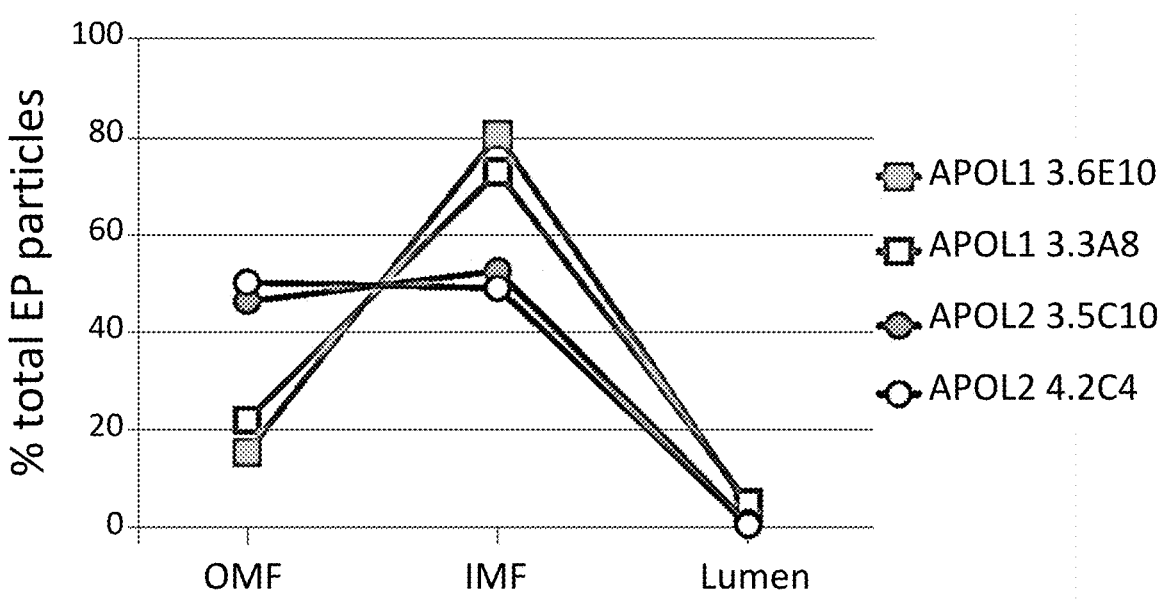

FIGS. 48A-48C show that quantitation of inner versus outer ER membrane face localization of APOL1 and APOL2 by iEM. FIG. 48A shows schematic of gold particle quantitation criteria. The cytosol and the ER lumen are shown. The ER membranes are shown as a 7 nm phospholipid bilayer with indication of their outer (cytosolic) membrane face (OMF) studded with ribosomes (ovals) and inner (luminal) membrane face (IMF). Ten nm gold particles located with their centers in the 20 nm wide, zone, as well as on the outer ER membrane leaflet, were scored as label on the OMF; gold particles located with their centers in the 20 nm wide zone, as well as on the inner ER membrane leaflet, were scored as labeling the IMF. Gold particles located with their centers in the dark area were scored as in the ER lumen. The width of the zones was chosen in accordance as a function of the size of the antibody-Protein-A-10 nm gold particle complex, which is approximately 25 nm long. At the end of an incubation, upon drying of a labeled section, bound gold particles precipitate in a random direction on the section. Only gold particles on perpendicularly cut ER cisterns, hence with sharply visible membranes were quantified. For the quantification of APOL1 in podocytes, only gold particles on stretches of perpendicularly cut ER cisterns with a minimal luminal width of 60 nm were sampled.

FIG. 48B shows representative electron micrographs of paraformaldehyde/glutaraldehyde fixed HEK-293 cells transiently transfected with APOL1 (labeled with 3.3A8, left) or APOL2 (labeled with 3.5C10, right) and detected with 10 nm protein A-gold, showing ER localization of both proteins. *, ER lumen; M, mitochondrion; N, nucleus; NE, nuclear envelope; arrow, ER-associated gold particle in close proximity to mitochondrial membrane. Scale bars are 100 nm.

FIG. 48C shows quantitation of ER-associated gold particles reveals differential distribution for APOL1 and APOL2 within the ER membranes of HEK-293 cells. APOL1-293 cells were labeled with anti-APOL1 mAbs 3.6E10 (to the SRA-ID, closed squares (n=97)) or 3.3A8 (to the MAD, open squares (n=173)). APOL2-293 cells were labeled with anti-APOL2 cross-reactive PFD mAbs 3.5C10 (closed circles (n=254)) or 4.2C4 (open circles (n=264)). Gold particles were quantitated as outlined in (A); n indicates the total number of gold particles counted for each antibody. The majority of APOL1 was associated with the inner membrane face with antibodies to two different domains, with an almost identical distribution to that found in podocytes, despite the podocytes having much wider ER cisternae than HEK-293 cells (compare FIG. 26C). By contrast, both anti-APOL2 antibodies were clearly distributed more towards the outer, cytosolic, face of the ER in agreement with the cytoplasmic accessibility seen by IF (FIG. 26B). See FIGS. 31A-B for validation of antibody cross-reactivities; these four worked the strongest with paraformaldehyde and glutaraldehyde fixation preferred for iEM.

Figure 49A:
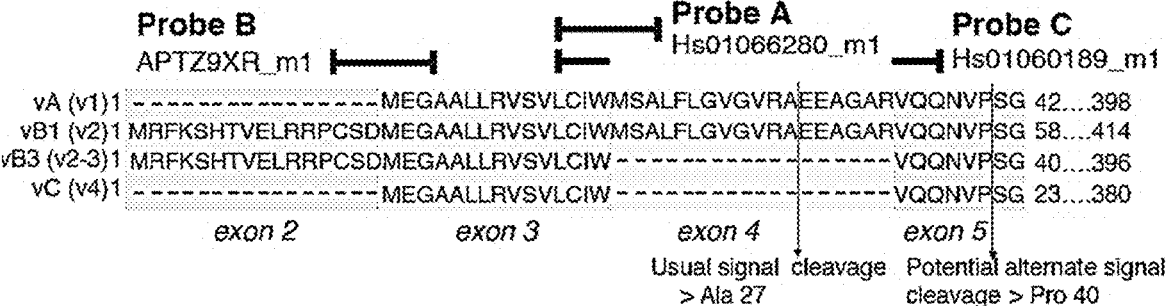
Figure 49B:
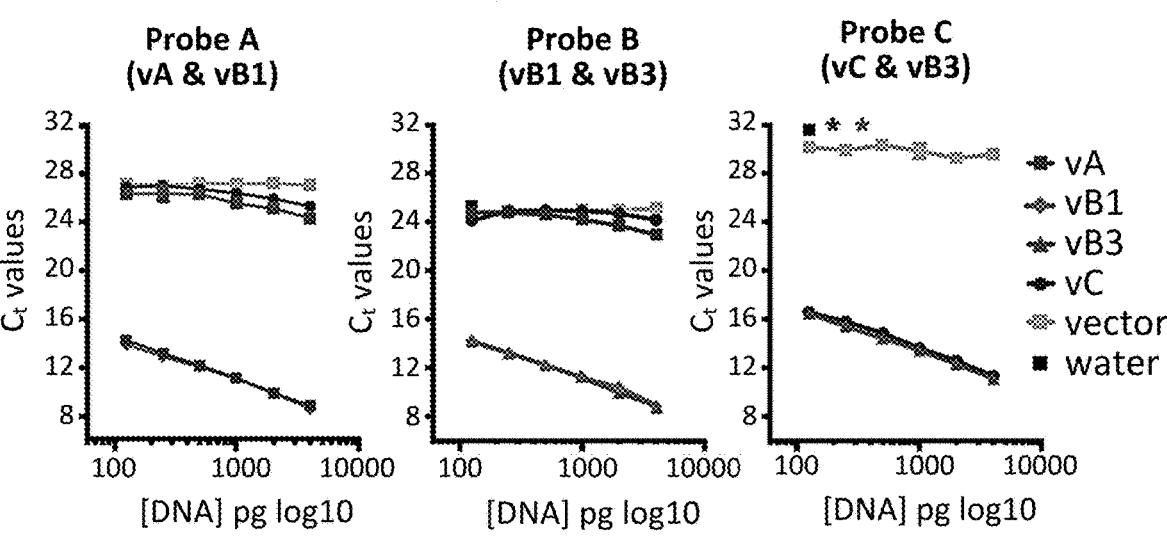
Figure 49C:
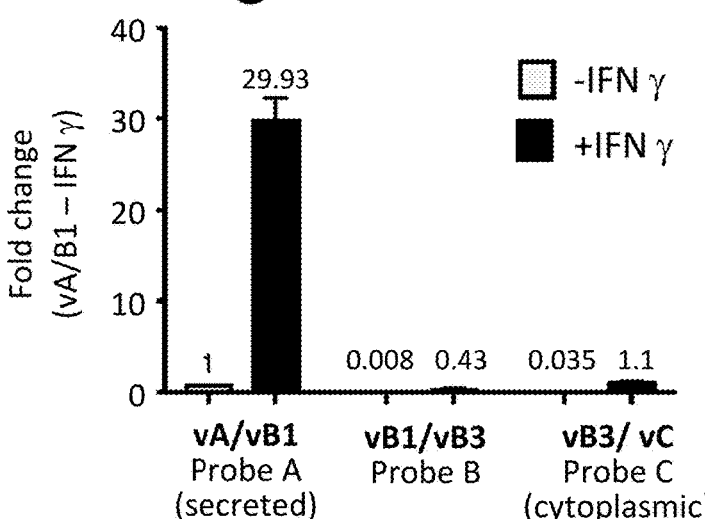

FIGS. 49A-49C show quantitation of relative abundance of APOL1 isoforms in differentiated WT podocytes by RT-PCR. FIG. 49A shows alignment of the different N-terminal splice isoforms of APOL1 and qRT-PCR probe locations. Isoforms APOL1.vA (also known the reference sequence or v1) (SEQ ID NO: 217), vB1 (v2) (SEQ ID NO: 218), vB3 (v2-3) (SEQ ID NO: 219) and vC (v4) (SEQ ID NO: 220) are aligned with different shading highlighting each exon. The major isoform vA (398 aa long) expresses exons 3 and 4 and is thus detected by probe A (Hs01066280_m1) encompassing these two exons. Isoform vB1 (414 aa) has an extra N-terminal 16 aa encoded by exon 2 compared to isoform vA, thus is recognized by probe A, as well as probe B (APTZ9XR_m1), spanning the exon 2-3 boundary. Isoform vB3 (396 aa) expresses the same N-terminal extension as vB1, but lacks exon 4 with the signal sequence cleavage site, hence is recognized by probe B and probe C (Hs_01060189_m1), which spans the exon 3-5 boundary. Isoform vC (380 aa) lacks both exons 2 and 4, thus is only recognized by probe C. The normal signal sequence cleavage site (VRA/EE) encoded by exon 4 (after aa 27 of vA) is thus absent from vB3 and vC, and is predicted instead to be NVP/SG (after aa 40 of vA), encoded by exon 5, should ER import occur.

FIG. 49B shows that the qRT-PCR probes all recognize the intended APOL1 isoforms. The specificities of the TaqMan probes (described in FIG. 49A) were verified by analyzing the qPCR Cycle Threshold values ($C_t$) for APOL1 cDNAs (APOL1 isoforms vA, vB1, vB3, vC and Vector only, with water as a negative control). DNAs were serially diluted two-fold from 4 ng to 125 pg per reaction, each dilution being tested in triplicate. The standard curve was generated as linear regression between $C_t$ and $\log_{10}$ starting concentration of standard DNA (in picograms). APOL1 isoforms (Table 5) and the resulting $C_t$ values are plotted for each DNA concentration. $C_t$ values above 22 indicate lack of probe reactivity; vA and vB1 were completely undetectable by probe C (asterisks) and so could not be plotted. As expected, each specific probe reacted equally well with the expected isoforms, with linear sensitivity over the concentration range tested.

FIG. 49C shows APOL1.vA (the reference sequence) is by far the most abundant APOL1 isoform in podocytes. RNA was reverse transcribed from differentiated human podocytes at passages 23, 24 and 25 with and without 48 h IFNγ stimulation (100 ng/ml) and subjected to qRT-PCR with the three isoform-specific probes. $C_t$ values were normalized to RPL19, and expressed as fold change relative to APOL1.vA/B1 without IFNγ (probe A, Hs01066280_m1). The means and SD of the three passages for each isoform assayed in triplicate are plotted. Under normal conditions, isoforms vA/vB1 (secretory) are expressed, respectively, 125× and 29× higher than vB1/vB3 and vB3/vC (cytoplasmic), which are barely detectable, thus vA must comprise the vast majority of the vA/vB1 signal. IFNγ-treatment upregulates all isoforms around 30×, with secretory isoforms vA/vB1 maintaining 70× and 27× higher expression than vB1/vB3 and cytoplasmic vB3/vC, respectively. Thus, secretory isoform vA is clearly far more abundant than all the others both with and without IFNγ stimulation, hence it is not surprising that cytoplasmic isoforms are undetectable by IF in these cells.

Figure 50A:
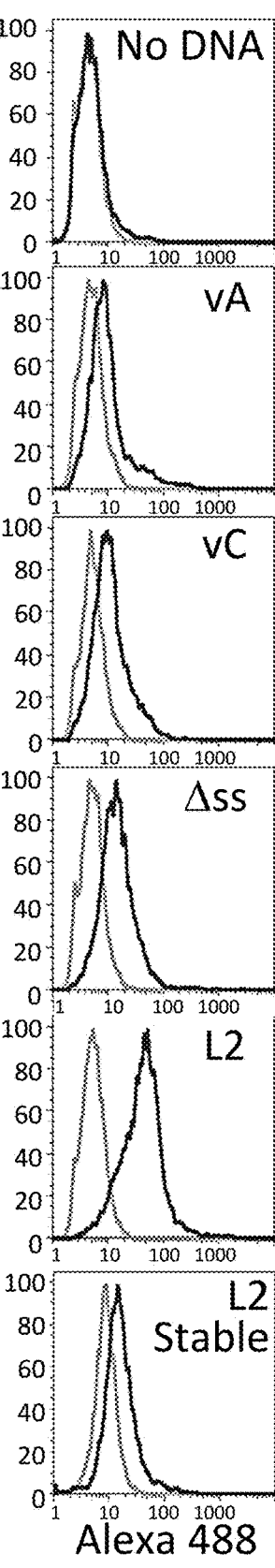
Figure 50B:
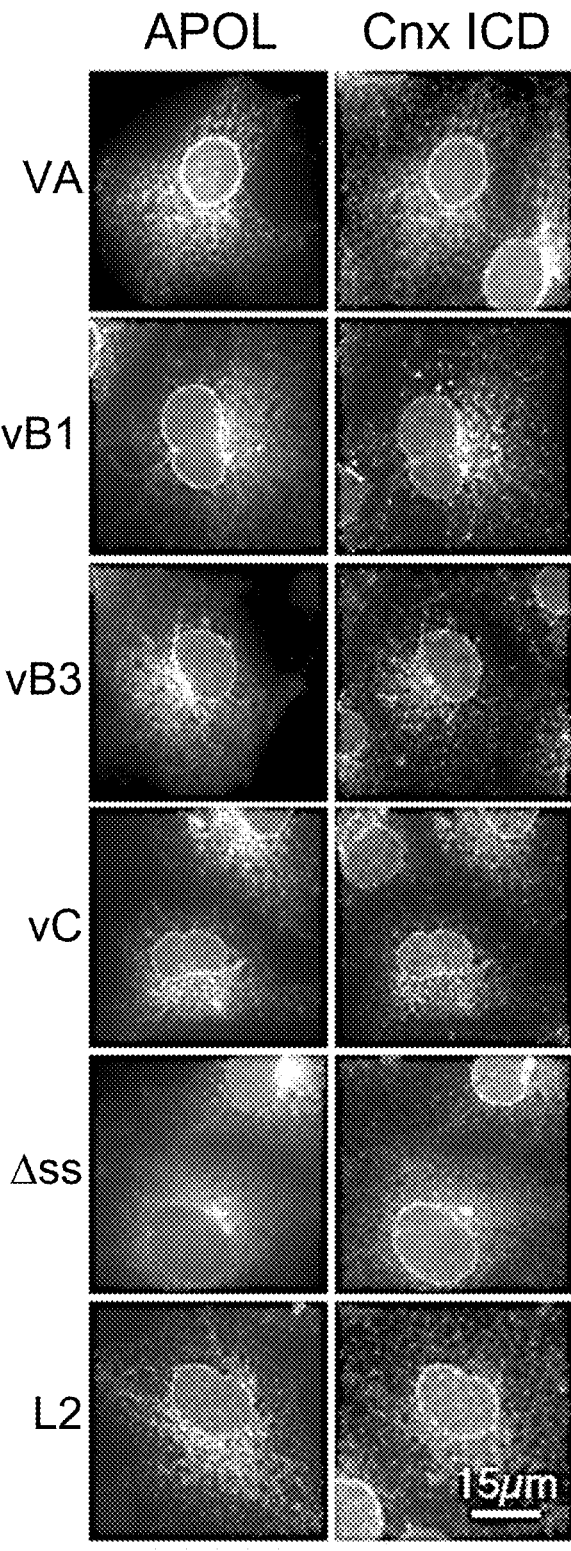
Figure 50C:
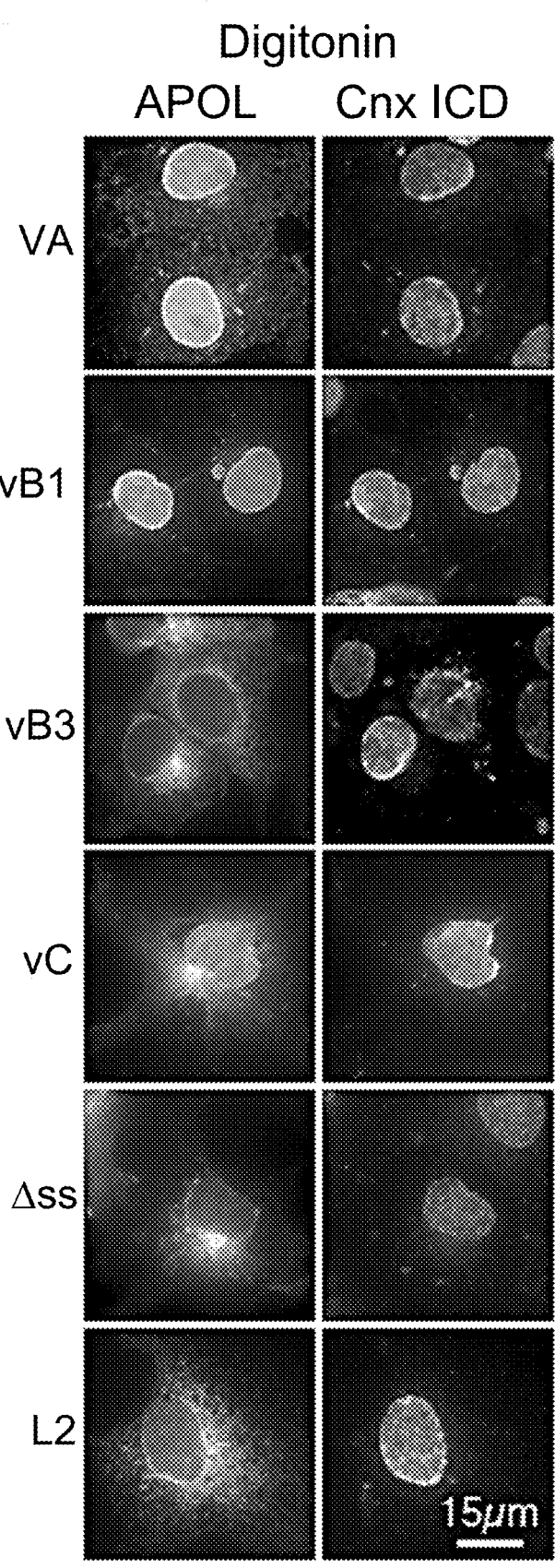

FIGS. 50A-50C show that all APOL1 isoforms and APOL2 appear to reach the cell surface when transiently transfected in COS cells, despite differential ER topology. FIG. 50A shows flow cytometry of live, unpermeabilized transiently transfected COS cells with APOL1 isoforms vA, vC, vA with its 27 aa signal sequence deleted (Δss) or APOL2 (L2). Alexa488 anti-mouse secondary is in grey, 3.6D12 (1 μg/ml) is in red. Unexpectedly, all expressed DNAs gave a shift compared to untransfected (No DNA) cells, including (Δss) and APOL2, suggesting this is an artifact of transient overexpression, as previously seen in HEK-293 cells (Ex. 2, ref. 85). The y-axis is % of maximum. Note that APOL2 was far better transiently transfected than the APOL1 DNAs, hence its greater shift is not necessarily indicative of greater membrane transport, whereas no surface APOL2 was seen when stably expressed in the same cell type (L2 stable, bottom panel).

FIG. 50B shows immunofluorescence of saponin permeabilized COS cells transiently transfected with the indicated APOL1 isoforms or APOL2 (L2). Cells were stained with anti-APOL1/2 3.6D12 and rabbit anti-calnexin intracellular domain (Cnx ICD, cytoplasmic tail (Ab22595)), showing all isoforms localize to the ER. Scale bar is 15 μm.

FIG. 50C shows immunofluorescence of same cDNA transfections as in FIG. 50B except with digitonin permeabilization and co-staining with rabmab 5.17H8 (which cross-reacts with APOL2, FIGS. 31A-31B) and mouse anti-calnexin extracellular (luminal) domain (clone 37). The digitonin data indicate that vA, vB1 and a little of vC are secretory (giving nuclear membrane signal), while vB3, Δss, APOL2 (L2) and most of vC are on the cytoplasmic face of the ER. APOL1.vC was cytoplasmic in most cells, luminal in a few and of mixed topology (as in the cell shown here) in several. Note that the calnexin luminal domain antibody also gives nuclear membrane staining with digitonin, validating our technique.

Figure 51A:
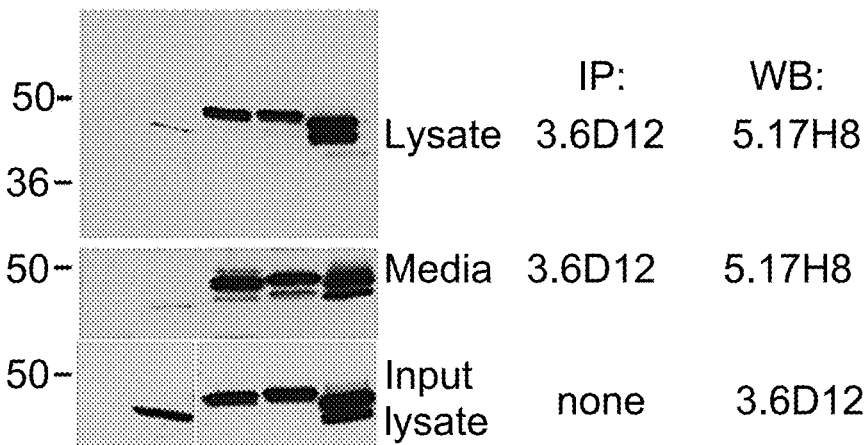
Figure 51B:
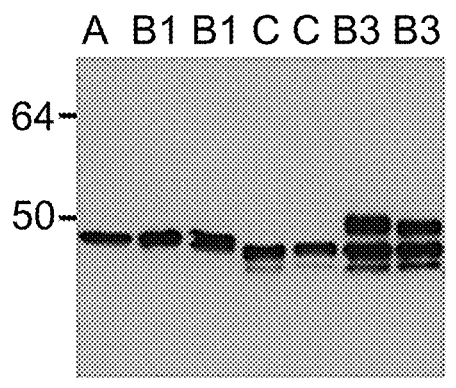
Figure 51C:
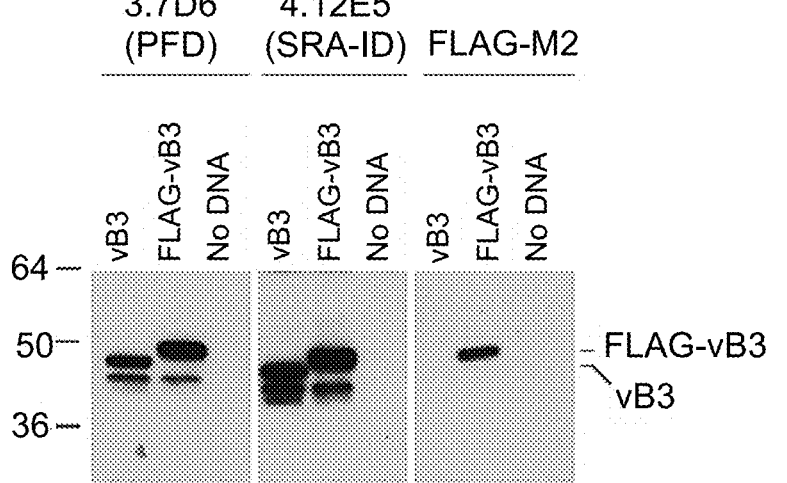

FIGS. 51A-51C show transient transfection artifact in COS cells: APOL2 and signal sequence-free APOL1 isoforms appear in the media despite not being luminal. FIG. 51A shows that secretory and non-secretory APOL1/2 are secreted into the media upon transient overexpression. Transiently transfected COS cells left over from the FACS experiment in FIG. 50A were lysed and immunoprecipitated with 1 μg/ml 3.6D12 using Protein G sepharose beads and immunoblotted on a 12% Tris-Glycine gel with 1 μg/ml rabbit 5.17H8 (top; note this rabmab only cross-reacts weakly with APOL2 by western blotting; APOL2 was in fact far better transfected than the others as assessed by IF). The conditioned cell media were also concentrated and immunoprecipitated in the same way (middle panel). Input lysates are shown in the bottom panel immunolabeled with 1 μg/ml 3.6D12, which recognizes APOL2 better than 5.17H8 (note untransfected and APOL2 were loaded in a different order, but were cut and pasted into the correct order in this figure as indicated by the white line). All proteins were detected in the media at the same relative levels as in the total lysates, irrespective of a functional signal sequence, even though the non-secretory isoforms were correctly localized to the cytoplasmic face of the ER (FIGS. 50A-C), suggesting that the apparent "secretion" is an overexpression artifact. Note that Δss is the same size as vA, suggesting that the 27aa signal sequence is normally cleaved in vA, as predicted (Table 4). UT, untransfected; L2, APOL2; A, APOL1.vA; Δss, APOL1.vA with its 27 aa signal sequence deleted; C, APOL1.vC.

FIG. 51B shows total lysates of COS cells transiently transfected for 46 h with the indicated APOL1 isoforms (with the plasmids used to generate the podocyte stable lines in FIGS. 27A-D) and western blotted on a 10% Tris-Glycine gel with 0.04 μg/ml rabbit anti-APOL1 3.1C7/3.7D6 mixture. Two independent transfections with different DNA preps are shown adjacent to each other for the splice isoforms. The sizes of these APOL1 isoforms in COS cells was the same as in stable podocytes when run on the same blot in a different experiment (data not shown).

FIG. 51C shows that the N-terminus is retained in APOL1-G0.vB3, in agreement with lack of signal cleavage. COS cells transiently transfected with untagged or N-terminally FLAG-tagged APOL1.vB3 were lysed and western blotted on a 10% Tris-Glycine gel with 0.05 μg/ml PFD antibody 3.7D6, 2 μg/ml C-terminal antibody 4.12E5 (G2 domain; Example 1) or 1 μg/ml anti-FLAG-M2. The FLAG tag rendered the construct larger, as expected, and was not cleaved, as evidenced by detection of the upper band with anti-FLAG.

Figure 52A:
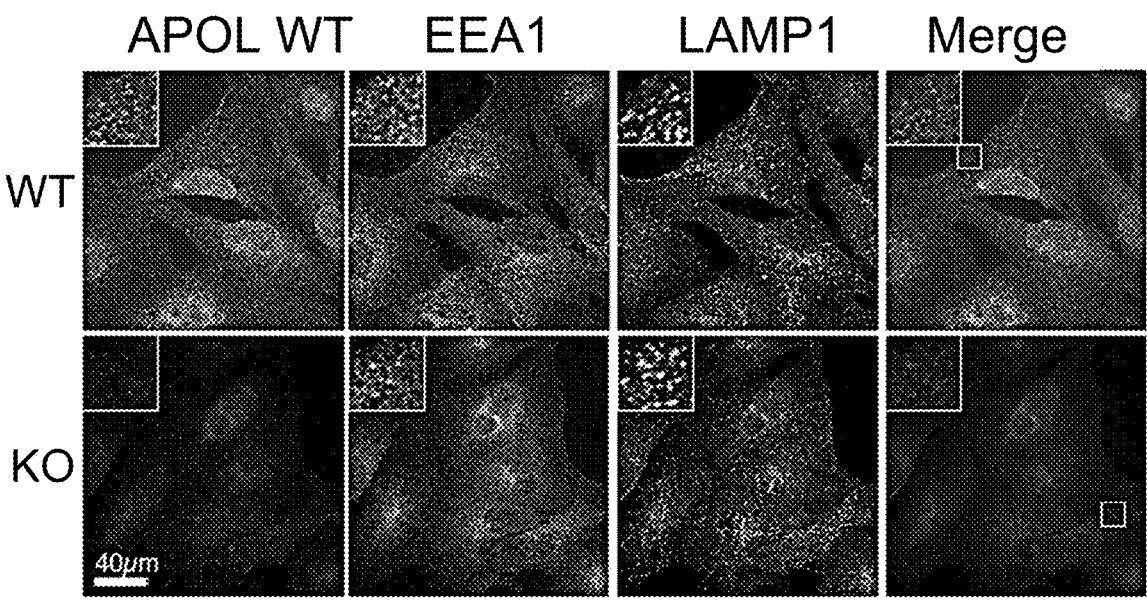
Figure 52B:
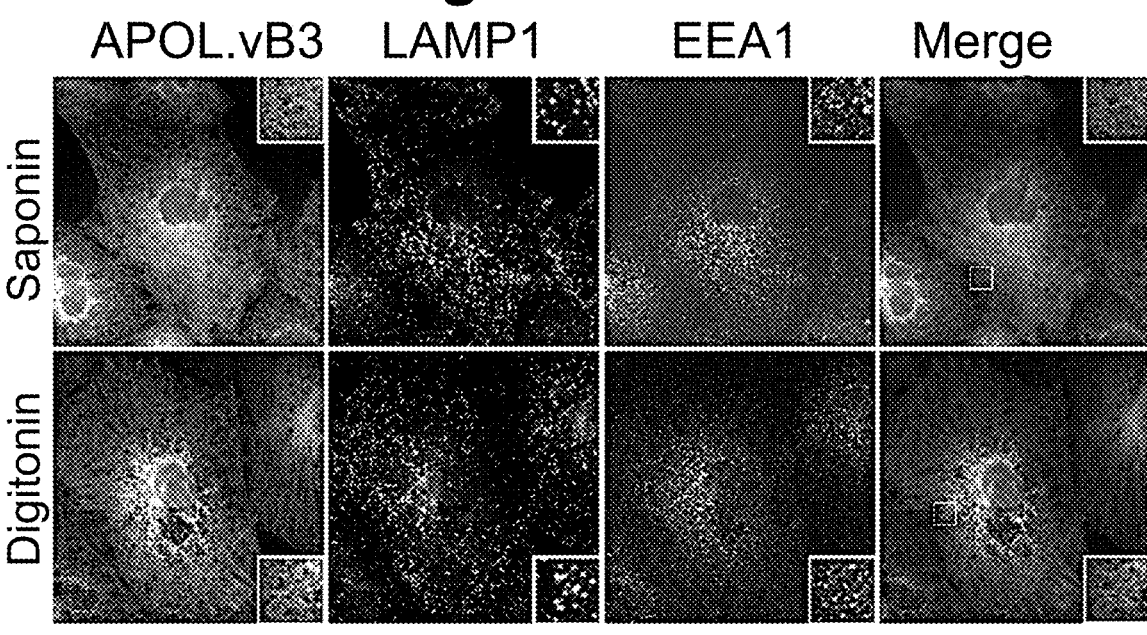

FIGS. 52A-52B show that APOL1 is not associated with endosomes of digitonin-permeabilized podocytes. FIG. 52A shows IFNγ-treated WT (upper) or APOL1 KO (lower) podocytes PFA fixed, digitonin permeabilized and co-stained with 2 μg/ml murine 4.17A5 for endogenous APOL1, 1 μg/ml goat anti-EEA1 for early endosomes; and 1 μg/ml rabbit anti-LAMP1 cytoplasmic domain for late endosomes and lysosomes, followed by Alexa488 anti-mouse, Cy3 anti-goat (Jackson 705-166-147) and Alexa647 anti-rabbit, respectively. Unlike in a previous study with the APOL2-cross reactive Sigma antibody using this digitonin technique (Ex. 2, ref. 19), the punctate extra-nuclear APOL1 signal did not coincide with either early or late endosome and lysosome markers, EEA1 or LAMP1. Using APOL1-specific antibodies is thus critical to interpreting the localization of the protein. The extranuclear membrane signal is likely plasma membrane. Scale bar is 40 μm.

FIG. 52C shows iAPOL1-G0.vB3 podocytes induced for 21 h with 10 ng/ml dox were PFA fixed, permeabilized with saponin (upper) or digitonin (lower) and stained as in (FIG. 52A). Even though APOL1.vB3 is a completely cytoplasmic isoform, it does not stably associate with endosomes or lysosomes. The insets are 3× magnifications of the boxed regions.

DETAILED DESCRIPTION

I. Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

Exemplary techniques used in connection with recombinant DNA, oligonucleotide synthesis, tissue culture and transformation (e.g., electroporation, lipofection), enzymatic reactions, and purification techniques are described, e.g., in Sambrook et al. Molecular Cloning: A Laboratory Manual (2nd ed., Cold Spring Harbor Laboratory Press, Cold Spring Harbor, N.Y. (1989)), among other places.

As utilized in accordance with the present disclosure, the following terms, unless otherwise indicated, shall be understood to have the following meanings:

The terms "APOL1" and "apolipoprotein L1," as used herein, refer to any native human APOL1, including native isoforms and the G0, G1, and G2 variant forms, and forms with and without a signal sequence, unless otherwise indicated. The term encompasses "full-length", unprocessed human APOL1 as well as any form of APOL1 that results from processing in the cell. The term also encompasses naturally occurring isoforms of human APOL1, which includes the vA, vB1, vB3, and vC isoforms, for example, whose accession numbers are provided in Tables 3 and 5 herein, as well as other single nucleotide polymorphisms not explicitly mentioned herein. The amino acid sequence of an exemplary human APOL1 protein in the G0 form, with and without the signal peptide (amino acids 1-27) is shown in SEQ ID NOs: 1 and 2. Other exemplary naturally occurring APOL1 G0 isoforms without the signal sequence are shown in SEQ ID Nos: 213-214. The G1 variant of APOL1 differs from the G0 form in that it contains S342G and I384M substitutions. An exemplary G1 sequence is provided in SEQ ID NO: 215. The G2 variant differs from the G0 form in that amino acids N388 and Y389 are deleted. An exemplary G2 sequence is found in SEQ ID NO: 216 herein.

In the present disclosure, if an amino acid residue or range of residues is provided without explicit reference to an APOL1 sequence, the reference sequence is meant to be that of SEQ ID NO: 2.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary methods for measuring binding affinity are described in the following.

The term "antibody" herein refers to a molecule comprising at least complementarity-determining region (CDR) 1, CDR2, and CDR3 of a heavy chain and at least CDR1, CDR2, and CDR3 of a light chain, wherein the molecule is capable of binding to antigen. The term is used in the broadest sense and encompasses various antibody structures, including but not limited to monoclonal antibodies, polyclonal antibodies, multispecific antibodies (e.g., bispecific antibodies), full length antibodies, single-chain antibodies, and antibody fragments, so long as they exhibit the desired APOL1-specific binding activity.

An "isolated" antibody is one which has been separated from a component of its natural environment. In some aspects, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC) methods. For a review of methods for assessment of antibody purity, see, e.g., Flatman et al., *J. Chromatogr. B* 848:79-87 (2007).

An "antigen" refers to the target of an antibody, i.e., the molecule to which the antibody specifically binds. The term "epitope" denotes the site on an antigen, either proteinaceous or non-proteinaceous, to which an antibody binds. Epitopes on a protein can be formed both from contiguous amino acid stretches (linear epitope) or comprise non-contiguous amino acids (conformational epitope), e.g., coming in spatial proximity due to the folding of the antigen, i.e. by the tertiary folding of a proteinaceous antigen. Linear epitopes are typically still bound by an antibody after exposure of the proteinaceous antigen to denaturing agents, whereas conformational epitopes are typically destroyed upon treatment with denaturing agents. An epitope comprises at least 3, at least 4, at least 5, at least 6, at least 7, or 8-10 amino acids in a unique spatial conformation.

An "anti-APOL1 antibody" or an "APOL1-antibody" or an "antibody that specifically binds APOL1" or an "antibody that binds to APOL1" and similar phrases mean an antibody that specifically binds to APOL1 as defined above. In this disclosure, "specifically binds" or "specific binding" and similar terms means that the binding affinity is sufficiently strong that the interaction between the members of the binding pair cannot be due to random molecular associations (i.e. "nonspecific binding"). Specific binding generally requires a dissociation constant ($K_D$) of 1 μM or less. Specific binding often involves a $K_D$ of 10 nM or less.

The term "heavy chain" refers to a polypeptide comprising at least a heavy chain variable region, with or without a leader sequence. In some embodiments, a heavy chain comprises at least a portion of a heavy chain constant region. The term "full-length heavy chain" refers to a polypeptide comprising a heavy chain variable region and a heavy chain constant region, with or without a leader sequence.

The term "light chain" refers to a polypeptide comprising at least a light chain variable region, with or without a leader sequence. In some embodiments, a light chain comprises at least a portion of a light chain constant region. The term "full-length light chain" refers to a polypeptide comprising a light chain variable region and a light chain constant region, with or without a leader sequence.

The term "hypervariable region" or "HVR" as used herein refers to each of the regions of an antibody variable region which are hypervariable in sequence and which determine antigen binding specificity, for example "complementarity determining regions" ("CDRs"). Generally, antibodies comprise six CDRs: three in the VH (CDR-H1, CDR-H2, CDR-H3), and three in the VL (CDR-L1, CDR-L2, CDR-L3). Unless otherwise indicated, the CDRs are determined according to the sequence table herein. One of skill in the art will understand that the CDR designations can also be determined according to Chothia, supra, McCallum, supra, or any other scientifically accepted nomenclature system. Specifically:

(a) hypervariable loops occurring at amino acid residues 26-32 (L1), 50-52 (L2), 91-96 (L3), 26-32 (H1), 53-55 (H2), and 96-101 (H3) otherwise constitute Chothia CDRs (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) constitute Kabat CDRs (Kabat et al., *Sequences of Proteins of Immunological Interest,* 5th Ed. Public Health Service, National Institutes of Health, Bethesda, MD (1991)); and (c) antigen contacts occurring at amino acid residues 27c-36 (L1), 46-55 (L2), 89-96 (L3), 30-35b (H1), 47-58 (H2), and 93-101 (H3) constitute MacCallum CDRs (MacCallum et al. *J. Mol. Biol.* 262: 732-745 (1996)). If sequences are not provided in the sequence table for CDRs of an antibody herein, and one of the three above types of CDRs is not otherwise stated "e.g. Chothia CDRs or Kabat CDRs," then Kabat CDRs are intended.

"Framework" or "FR" refers to the residues of the variable region residues that are not part of the complementary determining regions (CDRs). The FR of a variable region generally consists of four FRs: FR1, FR2, FR3, and FR4. Accordingly, the CDR and FR sequences generally appear in the following sequence in VH (or VL): FR1-CDR-H1(CDR-L1)-FR2-CDR-H2(CDR-L2)-FR3-CDR-H3(CDR-L3)-FR4.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three complementary determining regions (CDRs). See, e.g., Kindt et al. *Kuby Immunology*, 6*th* ed., W.H. Freeman and Co., page 91 (2007). A variable domain may comprise heavy chain (HC) CDR1-FR2-CDR2-FR3-CDR3 with or without all or a portion of FR1 and/or FR4; and light chain (LC) CDR1-FR2-CDR2-FR3-CDR3 with or without all or a portion of FR1 and/or FR4. That is, a variable domain may lack a portion of FR1 and/or FR4 so long as it retains antigen-binding activity. A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., Nature 352:624-628 (1991).

The light chain and heavy chain "constant regions" of an antibody refer to additional sequence portions outside of the FRs and CDRs and variable regions. Certain antibody fragments may lack all or some of the constant regions. From N- to C-terminus, each heavy chain has a variable domain (VH), also called a variable heavy domain or a heavy chain variable region, followed by three constant heavy domains (CH1, CH2, and CH3). Similarly, from N- to C-terminus, each light chain has a variable domain (VL), also called a variable light domain or a light chain variable region, followed by a constant light (CL) domain.

The term "Fc region" herein is used to define a C-terminal region of an immunoglobulin heavy chain that contains at least a portion of the constant region. The term includes native sequence Fc regions and variant Fc regions. In one aspect, a human IgG heavy chain Fc region extends from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore, an antibody produced by a host cell by expression of a specific nucleic acid molecule encoding a full-length heavy chain may include the full-length heavy chain, or it may include a cleaved variant of the full-length heavy chain. This may be the case where the final two C-terminal amino acids of the heavy chain are glycine (G446) and lysine (K447, numbering according to EU index). Therefore, the C-terminal lysine (Lys447), or the C-terminal glycine (Gly446) and lysine (Lys447), of the Fc region may or may not be present. Thus, a "full-length IgG1" for example, includes an IgG1 with Gly446 and Lys447, or without Lys447, or without both Gly446 and Lys447. Amino acid sequences of heavy chains including an Fc region are denoted herein without C-terminal glycine-lysine dipeptide if not indicated otherwise. In one aspect, a heavy chain including an Fc region as specified herein, comprised in an antibody according to the invention, may comprise Gly446 and Lys447 (numbering according to EU index). In one aspect, a heavy chain including an Fc region as specified herein, comprised in an antibody according to the invention, may comprise Gly446 (numbering according to EU index). Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g., B cell receptor); and B cell activation.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. In certain aspects, the antibody is of the $IgG_1$ isotype. In certain aspects, the antibody is of the $IgG_1$ isotype with the P329G, L234A and L235A mutation to reduce Fc-region effector function. In other aspects, the antibody is of the $IgG_2$ isotype. In certain aspects, the antibody is of the $IgG_4$ isotype with the S228P mutation in the hinge region to improve stability of $IgG_4$ antibody. In some aspects, the antibody may have a non-human IgG constant region, and may be, for example, a murine $IgG_2a$ antibody such as a murine $IgG_2a$ LALAPG antibody. The heavy chain constant domains that correspond to the different classes of immunoglobulins are called $\alpha$, $\delta$, $\varepsilon$, $\gamma$, and $\mu$, respectively. The light chain of an antibody may be assigned to one of two types, called kappa ($\kappa$) and lambda ($\lambda$), based on the amino acid sequence of its constant domain.

An "antibody fragment" refers to a molecule other than an intact antibody that comprises a portion of an intact antibody that binds the antigen (i.e. APOL1) to which the intact antibody binds. Examples of antibody fragments include but are not limited to Fv, Fab, Fab', Fab'-SH, F(ab')₂; diabodies; linear antibodies; single-chain antibody molecules (e.g., scFv, and scFab); single domain antibodies (dAbs); and multispecific antibodies formed from antibody fragments. For a review of certain antibody fragments, see Holliger and Hudson, Nature Biotechnology 23:1126-1136 (2005).

The terms "full length antibody", "intact antibody", and "whole antibody" are used herein interchangeably to refer to an antibody having a structure substantially similar to a native antibody structure or, in the case of an IgG antibody, having heavy chains that contain an Fc region as defined herein.

The term "chimeric" antibody refers to an antibody in which a portion of the heavy and/or light chain is derived from a particular source or species, while the remainder of the heavy and/or light chain is derived from a different source or species.

A "humanized" antibody refers to a chimeric antibody comprising amino acid residues from non-human CDRs and amino acid residues from human FRs. In certain aspects, a humanized antibody will comprise substantially all of at least one, and typically two, variable domains, in which all or substantially all of the CDRs correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human anti-body, refers to an antibody that has undergone humanization.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

An "antibody conjugate" is an antibody conjugated to one or more heterologous molecule(s), including but not limited to a therapeutic agent.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity for the purposes of the alignment. Alignment for purposes of determining percent amino acid sequence identity can be achieved in various ways that are within the skill in the art, for instance, using publicly available computer software such as BLAST, BLAST-2, Clustal W, Megalign (DNAS-TAR) software or the FASTA program package. Those skilled in the art can determine appropriate parameters for aligning sequences, including any algorithms needed to achieve maximal alignment over the full length of the sequences being compared. Alternatively, the percent identity values can be generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087 and is described in WO 2001/007611.

Unless otherwise indicated, for purposes herein, percent amino acid sequence identity values are generated using the ggsearch program of the FASTA package version 36.3.8c or later with a BLOSUM50 comparison matrix. The FASTA program package was authored by W. R. Pearson and D. J. Lipman (1988), "Improved Tools for Biological Sequence Analysis", PNAS 85:2444-2448; W. R. Pearson (1996) "Effective protein sequence comparison" Meth. Enzymol. 266:227-258; and Pearson et. al. (1997) Genomics 46:24-36 and is publicly available from www.fasta.bioch.virginia.edu/ fasta_www2/fasta_down.shtml or www. ebi.ac.uk/Tools/ sss/fasta. Alternatively, a public server accessible at fasta- .bioch.virginia.edu/fasta_www2/index.cgi can be used to compare the sequences, using the ggsearch (global protein: protein) program and default options (BLOSUM50; open: −10; ext: −2; Ktup=2) to ensure a global, rather than local, alignment is performed. Percent amino acid identity is given in the output alignment header.

The term "nucleic acid molecule" or "polynucleotide" includes any compound and/or substance that comprises a polymer of nucleotides. Each nucleotide is composed of a base, specifically a purine- or pyrimidine base (i.e. cytosine (C), guanine (G), adenine (A), thymine (T) or uracil (U)), a sugar (i.e. deoxyribose or ribose), and a phosphate group. Often, the nucleic acid molecule is described by the sequence of bases, whereby said bases represent the primary structure (linear structure) of a nucleic acid molecule. The sequence of bases is typically represented from 5' to 3'. Herein, the term nucleic acid molecule encompasses deoxyribonucleic acid (DNA) including e.g., complementary DNA (cDNA) and genomic DNA, ribonucleic acid (RNA), in particular messenger RNA (mRNA), synthetic forms of DNA or RNA, and mixed polymers comprising two or more of these molecules. The nucleic acid molecule may be linear or circular. In addition, the term nucleic acid molecule includes both sense and antisense strands, as well as single stranded and double stranded forms. Moreover, the herein described nucleic acid molecule can contain naturally occurring or non-naturally occurring nucleotides. Examples of non-naturally occurring nucleotides include modified nucleotide bases with derivatized sugars or phosphate backbone linkages or chemically modified residues. Nucleic acid molecules also encompass DNA and RNA molecules which are suitable as a vector for direct expression of an antibody of the invention in vitro and/or in vivo, e.g., in a host or patient. Such DNA (e.g., cDNA) or RNA (e.g., mRNA) vectors, can be unmodified or modified. For example, mRNA can be chemically modified to enhance the stability of the RNA vector and/or expression of the encoded molecule so that mRNA can be injected into a subject to generate the antibody in vivo (see e.g., Stadler et al, Nature Medicine 2017, published online 12 Jun. 2017, doi:10.1038/ nm.4356 or EP 2 101 823 B1).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-APOL1 antibody" refers to one or more nucleic acid molecules encoding anti-APOL1 antibody heavy and light chains (or fragments thereof), including such nucleic acid molecule(s) in a single vector or separate vectors, and such nucleic acid molecule(s) present at one or more locations in a host cell.

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

The terms "host cell", "host cell line", and "host cell culture" are used interchangeably and refer to cells into which exogenous nucleic acid has been introduced, including the progeny of such cells.

The term "leader sequence" refers to a sequence of amino acid residues located at the N terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached. Nonlimiting exemplary leader sequences also include leader sequences from heterologous proteins. In some embodiments, an antibody lacks a leader sequence. In some embodiments, an antibody comprises at least one leader sequence, which may be selected from native antibody leader sequences and heterologous leader sequences.

II. Compositions and Methods

A. Exemplary Anti-APOL1 Antibodies

In one aspect, the invention provides antibodies that specifically bind to APOL1. In some aspects, the antibodies bind specifically to particular portions of APOL1 that may be exposed on the surface of podocytes but that may be buried in APOL1 found in serum HDL particles. Such antibodies may be useful, for example, in distinguishing between APOL1 on the surface of podocytes from APOL1 found in serum, which is generally found on HDL particles, as described in the Examples herein. As described below in the Examples, the exposed and buried portions of APOL1 differ somewhat between podocyte-localized APOL1 and HDL-localized APOL1, allowing certain antibodies to distinguish between these forms due to differential binding affinities to each type.

The APOL1 protein contains various domains (see FIGS. 7A-B), for example the PFD (pore forming domain) at amino acids 28-235, the transmembrane domains, the MAD (membrane addressing domain) from amino acids 238-305, the L (linker) domain at amino acids 305-338, and the SRA-ID (serum resistance-associated interacting domain) from amino acids 339 to 398. (See SEQ ID Nos: 1, 2, 213, and 214 for reference.)

Certain antibodies herein bind within the PFD (pore forming domain) portion of APOL1, for example, from amino acid 61 to amino acid 172 of APOL1-G0 (amino acids 61-172 of SEQ ID NO: 2). In some aspects, the antibodies bind to the region from amino acid 61 to amino acid 103 of the PFD region (amino acids 61-103 of SEQ ID NO: 2), or they may bind to the region from amino acid 111 to amino acid 150 of the PFD region, either of which may allow the antibodies to recognize APOL1 expressed on podocytes but not APOL1 that circulates as part of HDL particles. This is because those portions of APOL1 may be exposed in podocyte APOL1 but inaccessible in HDL APOL1. In some aspects, the antibodies bind to region from amino acid 103 to amino acid 111 of APOL1 or from amino acid 150 to amino acid 172, which may similarly allow the antibodies to recognize APOL1 expressed on podocytes as well as on HDL particles, as these portions are exposed in both types of APOL1. Such antibodies may also be useful in assays distinguishing podocyte from serum APOL1, for instance by serving as controls.

Some antibodies herein bind within the MAD (membrane-addressing domain) portion of APOL1 from amino acids 260 to 305 (see amino acids 260-305 of SEQ ID NO: 2). In certain aspects, the antibodies bind to the region from amino acid 260 to amino acid 314 of APOL1, which includes portions of the MAD and L (linker) regions of the protein, and which may allow the antibodies to recognize APOL1 found in HDL particles but not APOL1 expressed on podocyte cells.

Other antibodies bind in the L (linker) region of APOL1 between amino acids 314 and 333 (see amino acids 314-333 of SEQ ID NO: 2), which may allow the antibodies to recognize APOL1 on both podocytes and HDL particles. Similarly, some antibodies bind within the SRA-ID (serum resistance-associated interacting domain) portion of APOL1 from amino acid 376 to 398 (amino acids 376-398 of SEQ ID NO: 2), which may allow them to recognize APOL1 on both podocytes and HDL particles.

Binding of antibodies to podocytes may be tested, for example, by in situ hybridization, immuno-histo chemistry (IHC), immunoprecipitation, flow cytometry, or Western blotting. To differentiate binding between podocytes and HDL particles, one may test binding using APOL1 in its native state, for example by flow cytometry or immunoprecipitation. After fixation and/or permeabilization or denaturation on a denaturing western blot, different APOL1 epitopes become exposed.

Binding of antibodies to APOL1 in serum, i.e. on HDL particles, may be tested, for example, by the assay described in the Examples herein that reports ability of the antibodies to block trypanolysis. Accordingly, antibodies that recognize APOL1 on HDL particles may significantly block trypanolysis whereas antibodies that do not significantly recognize APOL1 on HDL particles may not significantly block trypanolysis in the assays described herein.

The trypanolysis assay used herein to text specificity of antibodies for serum APOL1 is as follows. *Trypanosoma brucei brucei* were obtained from ATCC and cultured in HMI-9 media containing IMDM (Genentech), heat-inactivated (56° C. for 30 min) FBS (Seradigm IXL9/06807/GEN), 1% serum plus (Sigma 14008C), HMI-9 (Genentech) and 1% hypoxanthine (Genentech). Trypanosome lysis was performed by treating $1 \times 10^5$ Trypanosomes with serial dilutions of NHS or recombinant APOL1 for 16 h in a total of 100 µl. Live cell read out was done by the Alamar Blue assay as per the manufacturer's protocol, (Thermo Fisher, DAL1100). Briefly 10 µl of Alamar Blue was added to each well, incubated at 37° C. for 4 h. Red fluorescence, indicating live trypanosomes, was measured on a SpectraMax® fluorimeter powered by SoftMAX® PRO with excitation at 530 nm and emission 590 nm. For the antibody blocking assay, 1% normal human serum was preincubated with 1-10 µg/ml of anti-APOL1 antibody or media at room temperature for 20 minutes followed by addition of trypanosomes. After 16 h, the Alamar Blue assay was performed as above and background values for media only were subtracted and % blocking calculated by normalizing to no antibody control. Antibodies that significantly block trypanolysis, as tested in the assay, show at least 25% blocking activity.

The Examples herein describe a number of anti-APOL1 antibodies. The APOL1 binding properties of many of the antibodies are described in the Examples, and, where amino acid sequences of particular antibodies were also determined, those are provided in the Sequence Table that follows the Examples section. In the Examples below, the reference sequence used to generate antibodies herein corresponds to that of SEQ ID NO: 2, representing the "EMR" (E150, M228, R255) APOL1 variant form (the RefSeq). COS cell transient expression experiments herein were performed using the "KIK" variant (K150, 12281, K255), while iAPOL1-podocytes used herein expressed the African variant or "EIK" variant form (E150, I228, K255). (See SEQ ID Nos: 213 and 214, respectively.) The antibodies herein were found to specifically recognize all three of these APOL1 forms.

For example, antibodies 5.17H8, 5.11H2, 3.6D12, 3.6H5, 3.6G11, 3.5A12, 3.6C2, 3.5C2, 3.2A7, 3.3A7, 3.2B11, 3.3B6, 3.7D6, and 4.17A5 specifically bind to the PFD region of APOL1. Of those antibodies, antibodies 5.17H8, 5.17H2 and 3.6C2 as well as 3.5C2, 3.6C2, 3.5A12, 3.2A7, 3.3A7, and 3.2B11 bind preferentially to podocytes compared to serum APOL1 on HDL particles. In contrast, antibodies 4.17A5 and 3.7D6, which also specifically bind to the PFD region bind to podocytes but may also significantly block trypanolysis, indicating that they recognize both APOL1 on podocytes and serum (i.e. HDL) APOL1. Antibodies 3.6D12, 3.6G11, 3.6H5, and 5.17D12 also recognize APOL1 in both podocytes and serum. As a further example, antibodies 4.6A9, 1.11G1, and 3.3A8 bind to the MAD region of the protein at amino acids 260 to 294 and strongly block trypanolysis while showing only low levels of podocyte binding, indicating that they preferentially recognize serum (i.e. HDL) APOL1. Similarly, antibodies 3.2C11, 3.7E8, and 3.7B5 bind to the MAD-L region at amino acids 294-314 and preferentially recognize serum APOL1 over podocyte APOL1. Antibodies 3.1C1, 3.1C7, 3.6E10, 3.6H10, and 3.4G10 bind to the L portion of the protein and recognize APOL1 on both podocytes and serum. Antibody 3.6H10 may preferentially recognize APOL1 on podocytes, however. Antibodies 4.11A10, 4.11H11, and 4.12E5 bind to the SRA-ID part of APOL1 and recognize both podocyte and serum APOL1.

Certain antibodies herein do not significantly bind to other members of the apolipoprotein ligand family, such as APOL2 and/or APOL3 as well as APOL4 and APOL6. Thus, in some aspects, the antibodies do not significantly bind to APOL2. In some aspects the antibodies show no detectable binding to APOL2 or APOL6 according to the detection methods described in the Examples below. In some aspects the antibodies show no detectable binding to APOL2 or APOL6 according to the detection methods described in the Examples below. In some aspects the antibodies show no detectable binding to APOL2 or APOL3 according to the detection methods described in the Examples below. In some aspects, antibodies show no detectable binding to any of APOL2, APOL3, APOL4, or APOL6. For instance, antibodies 5.17D12 and 3.7D6 specifically bind to APOL1 and show little to no binding to other apolipoprotein ligand family members such as APOL2, APOL3, APOL4 and APOL6. By contrast antibody 4.17A5 detects APOL4 as well as APOL1, but not APOL2, APOL3 or APOL6. In contrast, antibody 3.6D12, for example, binds to APOL1 as well as to APOL2 and APOL3. Each of 5.17D12, 4.17A5, and 3.7D6 also specifically recognizes all of the G0, G1, and G2 variants of APOL1.

In some aspects antibodies herein may distinguish between different forms of APOL1, namely the G0, G1, and G2 variants. For example, antibodies 4.11A10, 4.12E5 and 4.11A10 bind specifically to the G0 and G1 forms of APOL1 but do not significantly bind to the G2 form. Thus, those antibodies are able to distinguish G0 and G1 forms from the G2 form.

Accordingly, the different binding characteristics of the antibodies herein may be useful in some aspects for a variety of diagnostic assays and uses in which APOL1 on podocytes needs to be distinguished from APOL1 in serum (i.e. on HDL particles), in which APOL1 needs to be distinguished from APOL2 and/or APOL3 or from all of APOL2, APOL3, APOL4, and APOL6, and/or in which APOL1 G0 and G1 forms need to be distinguished from the G2 form.

Certain antibody clones described in the Examples below were sequenced, and the CDR, variable region, and heavy and light chain sequences of those antibodies are provided in the sub-sections that follow and in the Sequence Table below. In some aspects, antibodies of the disclosure include the following:

1. An isolated antibody that specifically binds to apolipoprotein L1 (APOL1), wherein the antibody comprises:

(a) a heavy chain variable region (VH) comprising a CDR-H1 comprising the amino acid sequence of SEQ ID NO: 3, a CDR-H2 comprising the amino acid sequence of SEQ ID NO: 4, and a CDR-H3 comprising the amino acid sequence of SEQ ID NO: 5; and a light chain variable region (VL) comprising a CDR-L1 comprising the amino acid sequence of SEQ ID NO: 6, a CDR-L2 comprising the amino acid sequence of SEQ ID NO: 7, and a CDR-L3 comprising the amino acid sequence of SEQ ID NO: 8;

(b) a heavy chain variable region (VH) comprising a CDR-H1 comprising the amino acid sequence of SEQ ID NO: 13, a CDR-H2 comprising the amino acid sequence of SEQ ID NO: 14, and a CDR-H3 comprising the amino acid sequence of SEQ ID NO: 15; and a light chain variable region (VL) comprising a CDR-L1 comprising the amino acid sequence of SEQ ID NO: 16, a CDR-L2 comprising the amino acid sequence of SEQ ID NO: 17, and a CDR-L3 comprising the amino acid sequence of SEQ ID NO: 18;

(c) a heavy chain variable region (VH) comprising a CDR-H1 comprising the amino acid sequence of SEQ ID NO: 23, a CDR-H2 comprising the amino acid sequence of SEQ ID NO: 24, and a CDR-H3 comprising the amino acid sequence of SEQ ID NO: 25; and a light chain variable region (VL) comprising a CDR-L1 comprising the amino acid sequence of SEQ ID NO: 26, a CDR-L2 comprising the amino acid sequence of SEQ ID NO: 27, and a CDR-L3 comprising the amino acid sequence of SEQ ID NO: 28;

(d) a heavy chain variable region (VH) comprising a CDR-H1 comprising the amino acid sequence of SEQ ID NO: 33, a CDR-H2 comprising the amino acid sequence of SEQ ID NO: 34, and a CDR-H3 comprising the amino acid sequence of SEQ ID NO: 35; and a light chain variable region (VL) comprising a CDR-L1 comprising the amino acid sequence of SEQ ID NO: 36, a CDR-L2 comprising the amino acid sequence of SEQ ID NO: 37, and a CDR-L3 comprising the amino acid sequence of SEQ ID NO: 38;

(e) a heavy chain variable region (VH) comprising a CDR-H1 comprising the amino acid sequence of SEQ ID NO: 43, a CDR-H2 comprising the amino acid sequence of SEQ ID NO: 44, and a CDR-H3 comprising the amino acid sequence of SEQ ID NO: 45; and a light chain variable region (VL) comprising a CDR-L1 comprising the amino acid sequence of SEQ ID NO: 46, a CDR-L2 comprising the amino acid sequence of SEQ ID NO: 47, and a CDR-L3 comprising the amino acid sequence of SEQ ID NO: 48;

(f) a heavy chain variable region (VH) comprising a CDR-H1 comprising the amino acid sequence of SEQ ID NO: 53, a CDR-H2 comprising the amino acid sequence of SEQ ID NO: 54, and a CDR-H3 comprising the amino acid sequence of SEQ ID NO: 55; and a light chain variable region (VL) comprising a CDR-L1 comprising the amino acid sequence of SEQ ID NO:

56, a CDR-L2 comprising the amino acid sequence of SEQ ID NO: 57, and a CDR-L3 comprising the amino acid sequence of SEQ ID NO: 58;

(g) a heavy chain variable region (VH) comprising a CDR-H1 comprising the amino acid sequence of SEQ ID NO: 63, a CDR-H2 comprising the amino acid sequence of SEQ ID NO: 64, and a CDR-H3 comprising the amino acid sequence of SEQ ID NO: 65; and a light chain variable region (VL) comprising a CDR-L1 comprising the amino acid sequence of SEQ ID NO: 66, a CDR-L2 comprising the amino acid sequence of SEQ ID NO: 67, and a CDR-L3 comprising the amino acid sequence of SEQ ID NO: 68;

(h) a heavy chain variable region (VH) comprising a CDR-H1 comprising the amino acid sequence of SEQ ID NO: 73, a CDR-H2 comprising the amino acid sequence of SEQ ID NO: 74, and a CDR-H3 comprising the amino acid sequence of SEQ ID NO: 75; and a light chain variable region (VL) comprising a CDR-L1 comprising the amino acid sequence of SEQ ID NO: 76, a CDR-L2 comprising the amino acid sequence of SEQ ID NO: 77, and a CDR-L3 comprising the amino acid sequence of SEQ ID NO: 78;

(i) heavy chain variable region (VH) comprising a CDR-H1 comprising the amino acid sequence of SEQ ID NO: 83, a CDR-H2 comprising the amino acid sequence of SEQ ID NO: 84, and a CDR-H3 comprising the amino acid sequence of SEQ ID NO: 85; and a light chain variable region (VL) comprising a CDR-L1 comprising the amino acid sequence of SEQ ID NO: 86, a CDR-L2 comprising the amino acid sequence of SEQ ID NO: 87, and a CDR-L3 comprising the amino acid sequence of SEQ ID NO: 88;

(j) a heavy chain variable region (VH) comprising a CDR-H1 comprising the amino acid sequence of SEQ ID NO: 93, a CDR-H2 comprising the amino acid sequence of SEQ ID NO: 94, and a CDR-H3 comprising the amino acid sequence of SEQ ID NO: 95; and a light chain variable region (VL) comprising a CDR-L1 comprising the amino acid sequence of SEQ ID NO: 96, a CDR-L2 comprising the amino acid sequence of SEQ ID NO: 97, and a CDR-L3 comprising the amino acid sequence of SEQ ID NO: 98;

(k) a heavy chain variable region (VH) comprising a CDR-H1 comprising the amino acid sequence of SEQ ID NO: 103, a CDR-H2 comprising the amino acid sequence of SEQ ID NO: 104, and a CDR-H3 comprising the amino acid sequence of SEQ ID NO: 105; and a light chain variable region (VL) comprising a CDR-L1 comprising the amino acid sequence of SEQ ID NO: 106, a CDR-L2 comprising the amino acid sequence of SEQ ID NO: 107, and a CDR-L3 comprising the amino acid sequence of SEQ ID NO: 108;

(l) a heavy chain variable region (VH) comprising a CDR-H1 comprising the amino acid sequence of SEQ ID NO: 113, a CDR-H2 comprising the amino acid sequence of SEQ ID NO: 114, and a CDR-H3 comprising the amino acid sequence of SEQ ID NO: 115; and a light chain variable region (VL) comprising a CDR-L1 comprising the amino acid sequence of SEQ ID NO: 116, a CDR-L2 comprising the amino acid sequence of SEQ ID NO: 117, and a CDR-L3 comprising the amino acid sequence of SEQ ID NO: 118;

(m) a heavy chain variable region (VH) comprising a CDR-H1 comprising the amino acid sequence of SEQ ID NO: 123, a CDR-H2 comprising the amino acid sequence of SEQ ID NO: 124, and a CDR-H3 comprising the amino acid sequence of SEQ ID NO: 125; and a light chain variable region (VL) comprising a CDR-L1 comprising the amino acid sequence of SEQ ID NO: 126, a CDR-L2 comprising the amino acid sequence of SEQ ID NO: 127, and a CDR-L3 comprising the amino acid sequence of SEQ ID NO: 128;

(n) a heavy chain variable region (VH) comprising a CDR-H1 comprising the amino acid sequence of SEQ ID NO: 133, a CDR-H2 comprising the amino acid sequence of SEQ ID NO: 134, and a CDR-H3 comprising the amino acid sequence of SEQ ID NO: 135; and a light chain variable region (VL) comprising a CDR-L1 comprising the amino acid sequence of SEQ ID NO: 136, a CDR-L2 comprising the amino acid sequence of SEQ ID NO: 137, and a CDR-L3 comprising the amino acid sequence of SEQ ID NO: 138;

(o) a heavy chain variable region (VH) comprising a CDR-H1 comprising the amino acid sequence of SEQ ID NO: 143, a CDR-H2 comprising the amino acid sequence of SEQ ID NO: 144, and a CDR-H3 comprising the amino acid sequence of SEQ ID NO: 145; and a light chain variable region (VL) comprising a CDR-L1 comprising the amino acid sequence of SEQ ID NO: 146, a CDR-L2 comprising the amino acid sequence of SEQ ID NO: 147, and a CDR-L3 comprising the amino acid sequence of SEQ ID NO: 148;

(p) a heavy chain variable region (VH) comprising a CDR-H1 comprising the amino acid sequence of SEQ ID NO: 153, a CDR-H2 comprising the amino acid sequence of SEQ ID NO: 154, and a CDR-H3 comprising the amino acid sequence of SEQ ID NO: 155; and a light chain variable region (VL) comprising a CDR-L1 comprising the amino acid sequence of SEQ ID NO: 156, a CDR-L2 comprising the amino acid sequence of SEQ ID NO: 157, and a CDR-L3 comprising the amino acid sequence of SEQ ID NO: 158;

(q) a heavy chain variable region (VH) comprising a CDR-H1 comprising the amino acid sequence of SEQ ID NO: 163, a CDR-H2 comprising the amino acid sequence of SEQ ID NO: 164, and a CDR-H3 comprising the amino acid sequence of SEQ ID NO: 165; and a light chain variable region (VL) comprising a CDR-L1 comprising the amino acid sequence of SEQ ID NO: 166, a CDR-L2 comprising the amino acid sequence of SEQ ID NO: 167, and a CDR-L3 comprising the amino acid sequence of SEQ ID NO: 168;

(r) a heavy chain variable region (VH) comprising a CDR-H1 comprising the amino acid sequence of SEQ ID NO: 173, a CDR-H2 comprising the amino acid sequence of SEQ ID NO: 174, and a CDR-H3 comprising the amino acid sequence of SEQ ID NO: 175; and a light chain variable region (VL) comprising a CDR-L1 comprising the amino acid sequence of SEQ ID NO: 176, a CDR-L2 comprising the amino acid sequence of SEQ ID NO: 177, and a CDR-L3 comprising the amino acid sequence of SEQ ID NO: 178;

(s) a heavy chain variable region (VH) comprising a CDR-H1 comprising the amino acid sequence of SEQ ID NO: 183, a CDR-H2 comprising the amino acid sequence of SEQ ID NO: 184, and a CDR-H3 comprising the amino acid sequence of SEQ ID NO: 185; and a light chain variable region (VL) comprising a CDR-L1 comprising the amino acid sequence of SEQ ID NO: 186, a CDR-L2 comprising the amino acid sequence of SEQ ID NO: 187, and a CDR-L3 comprising the amino acid sequence of SEQ ID NO: 188;

(t) a heavy chain variable region (VH) comprising a CDR-H1 comprising the amino acid sequence of SEQ ID NO: 193, a CDR-H2 comprising the amino acid sequence of SEQ ID NO: 194, and a CDR-H3 comprising the amino acid sequence of SEQ ID NO: 195; and a light chain variable region (VL) comprising a CDR-L1 comprising the amino acid sequence of SEQ ID NO: 196, a CDR-L2 comprising the amino acid sequence of SEQ ID NO: 197, and a CDR-L3 comprising the amino acid sequence of SEQ ID NO: 198; or (u) a heavy chain variable region (VH) comprising a CDR-H1 comprising the amino acid sequence of SEQ ID NO: 203, a CDR-H2 comprising the amino acid sequence of SEQ ID NO: 204, and a CDR-H3 comprising the amino acid sequence of SEQ ID NO: 205; and a light chain variable region (VL) comprising a CDR-L1 comprising the amino acid sequence of SEQ ID NO: 206, a CDR-L2 comprising the amino acid sequence of SEQ ID NO: 207, and a CDR-L3 comprising the amino acid sequence of SEQ ID NO: 208.

2. The antibody of embodiment 1, wherein the antibody comprises:

the CDRs of embodiment 1(a) and further comprises a VH that is at least 90%, at least 95%, at least 97%, or at least 99% identical to the amino acid sequence of SEQ ID NO: 9 and/or a VL that is at least 90%, at least 95%, at least 97%, or at least 99% identical to the amino acid sequence of SEQ ID NO: 10;

the CDRs of embodiment 1(b) and further comprises a VH that is at least 90%, at least 95%, at least 97%, or at least 99% identical to the amino acid sequence of SEQ ID NO: 19 and/or a VL that is at least 90%, at least 95%, at least 97%, or at least 99% identical to the amino acid sequence of SEQ ID NO: 20;

the CDRs of embodiment 1(c) and further comprises a VH that is at least 90%, at least 95%, at least 97%, or at least 99% identical to the amino acid sequence of SEQ ID NO: 29 and/or a VL that is at least 90%, at least 95%, at least 97%, or at least 99% identical to the amino acid sequence of SEQ ID NO: 30;

the CDRs of embodiment 1(d) and further comprises a VH that is at least 90%, at least 95%, at least 97%, or at least 99% identical to the amino acid sequence of SEQ ID NO: 39 and/or a VL that is at least 90%, at least 95%, at least 97%, or at least 99% identical to the amino acid sequence of SEQ ID NO: 40;

the CDRs of embodiment 1(e) and further comprises a VH that is at least 90%, at least 95%, at least 97%, or at least 99% identical to the amino acid sequence of SEQ ID NO: 49 and/or a VL that is at least 90%, at least 95%, at least 97%, or at least 99% identical to the amino acid sequence of SEQ ID NO: 50;

the CDRs of embodiment 1(f) and further comprises a VH that is at least 90%, at least 95%, at least 97%, or at least 99% identical to the amino acid sequence of SEQ ID NO: 59 and/or a VL that is at least 90%, at least 95%, at least 97%, or at least 99% identical to the amino acid sequence of SEQ ID NO: 60;

the CDRs of embodiment 1(g) and further comprises a VH that is at least 90%, at least 95%, at least 97%, or at least 99% identical to the amino acid sequence of SEQ ID NO: 69 and/or a VL that is at least 90%, at least 95%, at least 97%, or at least 99% identical to the amino acid sequence of SEQ ID NO: 70;

the CDRs of embodiment 1(h) and further comprises a VH that is at least 90%, at least 95%, at least 97%, or at least 99% identical to the amino acid sequence of SEQ ID NO: 79 and/or a VL that is at least 90%, at least 95%, at least 97%, or at least 99% identical to the amino acid sequence of SEQ ID NO: 80;

the CDRs of embodiment 1(i) and further comprises a VH that is at least 90%, at least 95%, at least 97%, or at least 99% identical to the amino acid sequence of SEQ ID NO: 89 and/or a VL that is at least 90%, at least 95%, at least 97%, or at least 99% identical to the amino acid sequence of SEQ ID NO: 90;

the CDRs of embodiment 1(j) and further comprises a VH that is at least 90%, at least 95%, at least 97%, or at least 99% identical to the amino acid sequence of SEQ ID NO: 99 and/or a VL that is at least 90%, at least 95%, at least 97%, or at least 99% identical to the amino acid sequence of SEQ ID NO: 100;

the CDRs of embodiment 1(k) and further comprises a VH that is at least 90%, at least 95%, at least 97%, or at least 99% identical to the amino acid sequence of SEQ ID NO: 109 and/or a VL that is at least 90%, at least 95%, at least 97%, or at least 99% identical to the amino acid sequence of SEQ ID NO: 110;

the CDRs of embodiment 1(l) and further comprises a VH that is at least 90%, at least 95%, at least 97%, or at least 99% identical to the amino acid sequence of SEQ ID NO: 119 and/or a VL that is at least 90%, at least 95%, at least 97%, or at least 99% identical to the amino acid sequence of SEQ ID NO: 120;

the CDRs of embodiment 1(m) and further comprises a VH that is at least 90%, at least 95%, at least 97%, or at least 99% identical to the amino acid sequence of SEQ ID NO: 129 and/or a VL that is at least 90%, at least 95%, at least 97%, or at least 99% identical to the amino acid sequence of SEQ ID NO: 130;

the CDRs of embodiment 1(n) and further comprises a VH that is at least 90%, at least 95%, at least 97%, or at least 99% identical to the amino acid sequence of SEQ ID NO: 139 and/or a VL that is at least 90%, at least 95%, at least 97%, or at least 99% identical to the amino acid sequence of SEQ ID NO: 140;

the CDRs of embodiment 1(o) and further comprises a VH that is at least 90%, at least 95%, at least 97%, or at least 99% identical to the amino acid sequence of SEQ ID NO: 149 and/or a VL that is at least 90%, at least 95%, at least 97%, or at least 99% identical to the amino acid sequence of SEQ ID NO: 150;

the CDRs of embodiment 1(p) and further comprises a VH that is at least 90%, at least 95%, at least 97%, or at least 99% identical to the amino acid sequence of SEQ ID NO: 159 and/or a VL that is at least 90%, at least 95%, at least 97%, or at least 99% identical to the amino acid sequence of SEQ ID NO: 160;

the CDRs of embodiment 1(q) and further comprises a VH that is at least 90%, at least 95%, at least 97%, or at least 99% identical to the amino acid sequence of SEQ ID NO: 169 and/or a VL that is at least 90%, at least 95%, at least 97%, or at least 99% identical to the amino acid sequence of SEQ ID NO: 170;

the CDRs of embodiment 1(r) and further comprises a VH that is at least 90%, at least 95%, at least 97%, or at least 99% identical to the amino acid sequence of SEQ ID NO: 179 and/or a VL that is at least 90%, at least 95%, at least 97%, or at least 99% identical to the amino acid sequence of SEQ ID NO: 180;

the CDRs of embodiment 1(s) and further comprises a VH that is at least 90%, at least 95%, at least 97%, or at least 99% identical to the amino acid sequence of SEQ ID NO: 189 and/or a VL that is at least 90%, at least 95%, at least 97%, or at least 99% identical to the amino acid sequence of SEQ ID NO: 190;

the CDRs of embodiment 1(t) and further comprises a VH that is at least 90%, at least 95%, at least 97%, or at least 99% identical to the amino acid sequence of SEQ ID NO: 199 and/or a VL that is at least 90%, at least 95%, at least 97%, or at least 99% identical to the amino acid sequence of SEQ ID NO: 200; or the CDRs of embodiment 1(u) and further comprises a VH that is at least 90%, at least 95%, at least 97%, or at least 99% identical to the amino acid sequence of SEQ ID NO: 209 and/or a VL that is at least 90%, at least 95%, at least 97%, or at least 99% identical to the amino acid sequence of SEQ ID NO: 210.

3. The antibody of embodiment 1 or 2, wherein the antibody comprises:

the CDRs of embodiment 1(a) and further comprises a VH comprising the amino acid sequence of SEQ ID NO: 9;

the CDRs of embodiment 1(b) and further comprises a VH comprising the amino acid sequence of SEQ ID NO: 19;

the CDRs of embodiment 1(c) and further comprises a VH comprising the amino acid sequence of SEQ ID NO: 29;

the CDRs of embodiment 1(d) and further comprises a VH comprising the amino acid sequence of SEQ ID NO: 39;

the CDRs of embodiment 1(e) and further comprises a VH comprising the amino acid sequence of SEQ ID NO: 49;

the CDRs of embodiment 1(f) and further comprises a VH comprising the amino acid sequence of SEQ ID NO: 59;

the CDRs of embodiment 1(g) and further comprises a VH comprising the amino acid sequence of SEQ ID NO: 69;

the CDRs of embodiment 1(h) and further comprises a VH comprising the amino acid sequence of SEQ ID NO: 79;

the CDRs of embodiment 1(i) and further comprises a VH comprising the amino acid sequence of SEQ ID NO: 89;

the CDRs of embodiment 1(j) and further comprises a VH comprising the amino acid sequence of SEQ ID NO: 99;

the CDRs of embodiment 1(k) and further comprises a VH comprising the amino acid sequence of SEQ ID NO: 109;

the CDRs of embodiment 1(l) and further comprises a VH comprising the amino acid sequence of SEQ ID NO: 119;

the CDRs of embodiment 1(m) and further comprises a VH comprising the amino acid sequence of SEQ ID NO: 129;

the CDRs of embodiment 1(n) and further comprises a VH comprising the amino acid sequence of SEQ ID NO: 139;

the CDRs of embodiment 1(o) and further comprises a VH comprising the amino acid sequence of SEQ ID NO: 149;

the CDRs of embodiment 1(p) and further comprises a VH comprising the amino acid sequence of SEQ ID NO: 159;

the CDRs of embodiment 1(q) and further comprises a VH comprising the amino acid sequence of SEQ ID NO: 169;

the CDRs of embodiment 1(r) and further comprises a VH comprising the amino acid sequence of SEQ ID NO: 179;

the CDRs of embodiment 1(s) and further comprises a VH comprising the amino acid sequence of SEQ ID NO: 189;

the CDRs of embodiment 1(t) and further comprises a VH comprising the amino acid sequence of SEQ ID NO: 199; or the CDRs of embodiment 1(u) and further comprises a VH comprising the amino acid sequence of SEQ ID NO: 209.

4. The antibody of embodiment 1 or 2, wherein the antibody comprises:

the CDRs of embodiment 1(a) and further comprises a VL comprising the amino acid sequence of SEQ ID NO: 10;

the CDRs of embodiment 1(b) and further comprises a VL comprising the amino acid sequence of SEQ ID NO: 20;

the CDRs of embodiment 1(c) and further comprises a VL comprising the amino acid sequence of SEQ ID NO: 30;

the CDRs of embodiment 1(d) and further comprises a VL comprising the amino acid sequence of SEQ ID NO: 40;

the CDRs of embodiment 1(e) and further comprises a VL comprising the amino acid sequence of SEQ ID NO: 50;

the CDRs of embodiment 1(f) and further comprises a VL comprising the amino acid sequence of SEQ ID NO: 60;

the CDRs of embodiment 1(g) and further comprises a VL comprising the amino acid sequence of SEQ ID NO: 70;

the CDRs of embodiment 1(h) and further comprises a VL comprising the amino acid sequence of SEQ ID NO: 80;

the CDRs of embodiment 1(i) and further comprises a VL comprising the amino acid sequence of SEQ ID NO: 90;

the CDRs of embodiment 1(j) and further comprises a VL comprising the amino acid sequence of SEQ ID NO: 100;

the CDRs of embodiment 1(k) and further comprises a VL comprising the amino acid sequence of SEQ ID NO: 110;

the CDRs of embodiment 1(l) and further comprises a VL comprising the amino acid sequence of SEQ ID NO: 120;

the CDRs of embodiment 1(m) and further comprises a VL comprising the amino acid sequence of SEQ ID NO: 130;

the CDRs of embodiment 1(n) and further comprises a VL comprising the amino acid sequence of SEQ ID NO: 140;

the CDRs of embodiment 1(o) and further comprises a VL comprising the amino acid sequence of SEQ ID NO: 150;

the CDRs of embodiment 1(p) and further comprises a VL comprising the amino acid sequence of SEQ ID NO: 160;

the CDRs of embodiment 1(q) and further comprises a VL comprising the amino acid sequence of SEQ ID NO: 170;

the CDRs of embodiment 1(r) and further comprises a VL comprising the amino acid sequence of SEQ ID NO: 180;

the CDRs of embodiment 1(s) and further comprises a VL comprising the amino acid sequence of SEQ ID NO: 190;

the CDRs of embodiment 1(t) and further comprises a VL comprising the amino acid sequence of SEQ ID NO: 200; or the CDRs of embodiment 1(u) and further comprises a VL comprising the amino acid sequence of SEQ ID NO: 210.

5. The antibody of embodiment 1 or 2, wherein the antibody comprises:

a VH comprising the amino acid sequence of SEQ ID NO: 9 and a VL comprising the amino acid sequence of SEQ ID NO: 10;

a VH comprising the amino acid sequence of SEQ ID NO: 19 and a VL comprising the amino acid sequence of SEQ ID NO: 20;

a VH comprising the amino acid sequence of SEQ ID NO: 29 and a VL comprising the amino acid sequence of SEQ ID NO: 30;

a VH comprising the amino acid sequence of SEQ ID NO: 39 and a VL comprising the amino acid sequence of SEQ ID NO: 40;

a VH comprising the amino acid sequence of SEQ ID NO: 49 and a VL comprising the amino acid sequence of SEQ ID NO: 50;

a VH comprising the amino acid sequence of SEQ ID NO: 59 and a VL comprising the amino acid sequence of SEQ ID NO: 60;

a VH comprising the amino acid sequence of SEQ ID NO: 69 and a VL comprising the amino acid sequence of SEQ ID NO: 70;

a VH comprising the amino acid sequence of SEQ ID NO: 79 and a VL comprising the amino acid sequence of SEQ ID NO: 80;

a VH comprising the amino acid sequence of SEQ ID NO: 89 and a VL comprising the amino acid sequence of SEQ ID NO: 90;

a VH comprising the amino acid sequence of SEQ ID NO: 99 and a VL comprising the amino acid sequence of SEQ ID NO: 100;

a VH comprising the amino acid sequence of SEQ ID NO: 109 and a VL comprising the amino acid sequence of SEQ ID NO: 110;

a VH comprising the amino acid sequence of SEQ ID NO: 119 and a VL comprising the amino acid sequence of SEQ ID NO: 120;

a VH comprising the amino acid sequence of SEQ ID NO: 129 and a VL comprising the amino acid sequence of SEQ ID NO: 130;

a VH comprising the amino acid sequence of SEQ ID NO: 139 and a VL comprising the amino acid sequence of SEQ ID NO: 140;

a VH comprising the amino acid sequence of SEQ ID NO: 149 and a VL comprising the amino acid sequence of SEQ ID NO: 150;

a VH comprising the amino acid sequence of SEQ ID NO: 159 and a VL comprising the amino acid sequence of SEQ ID NO: 160;

a VH comprising the amino acid sequence of SEQ ID NO: 169 and a VL comprising the amino acid sequence of SEQ ID NO: 170;

a VH comprising the amino acid sequence of SEQ ID NO: 179 and a VL comprising the amino acid sequence of SEQ ID NO: 180;

a VH comprising the amino acid sequence of SEQ ID NO: 189 and a VL comprising the amino acid sequence of SEQ ID NO: 190;

a VH comprising the amino acid sequence of SEQ ID NO: 199 and a VL comprising the amino acid sequence of SEQ ID NO: 200; or a VH comprising the amino acid sequence of SEQ ID NO: 209 and a VL comprising the amino acid sequence of SEQ ID NO: 210.

6. The antibody of any one of embodiments 1-5, wherein the antibody comprises:

the CDRs of embodiment 1(a) and further comprises a heavy chain (HC) comprising an amino acid sequence at least 90%, at least 95%, at least 97%, or at least 99% identical to the amino acid sequence of SEQ ID NO: 11 and/or a light chain (LC) comprising an amino acid sequence at least 90%, at least 95%, at least 97%, or at least 99% identical to the SEQ ID NO: 12;

the CDRs of embodiment 1(b) and further comprises a heavy chain (HC) comprising an amino acid sequence at least 90%, at least 95%, at least 97%, or at least 99% identical to the SEQ ID NO: 21 and a light chain (LC) comprising an amino acid sequence at least 90%, at least 95%, at least 97%, or at least 99% identical to the SEQ ID NO: 22;

the CDRs of embodiment 1(c) and further comprises a heavy chain (HC) comprising an amino acid sequence at least 90%, at least 95%, at least 97%, or at least 99% identical to the SEQ ID NO: 31 and a light chain (LC) comprising an amino acid sequence at least 90%, at least 95%, at least 97%, or at least 99% identical to the SEQ ID NO: 32;

the CDRs of embodiment 1(d) and further comprises a heavy chain (HC) comprising an amino acid sequence at least 90%, at least 95%, at least 97%, or at least 99% identical to the SEQ ID NO: 41 and a light chain (LC) comprising an amino acid sequence at least 90%, at least 95%, at least 97%, or at least 99% identical to the SEQ ID NO: 42;

the CDRs of embodiment 1(e) and further comprises a heavy chain (HC) comprising an amino acid sequence at least 90%, at least 95%, at least 97%, or at least 99% identical to the SEQ ID NO: 51 and a light chain (LC) comprising an amino acid sequence at least 90%, at least 95%, at least 97%, or at least 99% identical to the SEQ ID NO: 52;

the CDRs of embodiment 1(f) and further comprises a heavy chain (HC) comprising an amino acid sequence at least 90%, at least 95%, at least 97%, or at least 99% identical to the SEQ ID NO: 61 and a light chain (LC) comprising an amino acid sequence at least 90%, at least 95%, at least 97%, or at least 99% identical to the SEQ ID NO: 62;

the CDRs of embodiment 1(g) and further comprises a heavy chain (HC) comprising an amino acid sequence at least 90%, at least 95%, at least 97%, or at least 99% identical to the SEQ ID NO: 71 and a light chain (LC) comprising an amino acid sequence at least 90%, at least 95%, at least 97%, or at least 99% identical to the SEQ ID NO: 72;

the CDRs of embodiment 1(h) and further comprises a heavy chain (HC) comprising an amino acid sequence at least 90%, at least 95%, at least 97%, or at least 99% identical to the SEQ ID NO: 81 and a light chain (LC)

comprising an amino acid sequence at least 90%, at least 95%, at least 97%, or at least 99% identical to the SEQ ID NO: 82;

the CDRs of embodiment 1(i) and further comprises a heavy chain (HC) comprising an amino acid sequence at least 90%, at least 95%, at least 97%, or at least 99% identical to the SEQ ID NO: 91 and a light chain (LC) comprising an amino acid sequence at least 90%, at least 95%, at least 97%, or at least 99% identical to the SEQ ID NO: 92;

the CDRs of embodiment 1(j) and further comprises a heavy chain (HC) comprising an amino acid sequence at least 90%, at least 95%, at least 97%, or at least 99% identical to the SEQ ID NO: 101 and a light chain (LC) comprising an amino acid sequence at least 90%, at least 95%, at least 97%, or at least 99% identical to the SEQ ID NO: 102;

the CDRs of embodiment 1(k) and further comprises a heavy chain (HC) comprising an amino acid sequence at least 90%, at least 95%, at least 97%, or at least 99% identical to the SEQ ID NO: 111 and a light chain (LC) comprising an amino acid sequence at least 90%, at least 95%, at least 97%, or at least 99% identical to the SEQ ID NO: 112;

the CDRs of embodiment 1(l) and further comprises a heavy chain (HC) comprising an amino acid sequence at least 90%, at least 95%, at least 97%, or at least 99% identical to the SEQ ID NO: 121 and a light chain (LC) comprising an amino acid sequence at least 90%, at least 95%, at least 97%, or at least 99% identical to the SEQ ID NO: 122;

the CDRs of embodiment 1(m) and further comprises a heavy chain (HC) comprising an amino acid sequence at least 90%, at least 95%, at least 97%, or at least 99% identical to the SEQ ID NO: 131 and a light chain (LC) comprising an amino acid sequence at least 90%, at least 95%, at least 97%, or at least 99% identical to the SEQ ID NO: 132;

the CDRs of embodiment 1(n) and further comprises a heavy chain (HC) comprising an the SEQ ID NO: 141 and a light chain (LC) comprising an amino acid sequence at least 90%, at least 95%, at least 97%, or at least 99% identical to the SEQ ID NO: 142;

the CDRs of embodiment 1(o) and further comprises a heavy chain (HC) comprising an amino acid sequence at least 90%, at least 95%, at least 97%, or at least 99% identical to the SEQ ID NO: 151 and a light chain (LC) comprising an amino acid sequence at least 90%, at least 95%, at least 97%, or at least 99% identical to the SEQ ID NO: 152;

the CDRs of embodiment 1(p) and further comprises a heavy chain (HC) comprising an amino acid sequence at least 90%, at least 95%, at least 97%, or at least 99% identical to the SEQ ID NO: 161 and a light chain (LC) comprising an amino acid sequence at least 90%, at least 95%, at least 97%, or at least 99% identical to the SEQ ID NO: 162;

the CDRs of embodiment 1(q) and further comprises a heavy chain (HC) comprising an amino acid sequence at least 90%, at least 95%, at least 97%, or at least 99% identical to the SEQ ID NO: 171 and a light chain (LC) comprising an amino acid sequence at least 90%, at least 95%, at least 97%, or at least 99% identical to the SEQ ID NO: 172;

the CDRs of embodiment 1(r) and further comprises a heavy chain (HC) comprising an amino acid sequence at least 90%, at least 95%, at least 97%, or at least 99% identical to the SEQ ID NO: 181 and a light chain (LC) comprising an amino acid sequence at least 90%, at least 95%, at least 97%, or at least 99% identical to the SEQ ID NO: 182;

the CDRs of embodiment 1(s) and further comprises a heavy chain (HC) comprising an amino acid sequence at least 90%, at least 95%, at least 97%, or at least 99% identical to the SEQ ID NO: 191 and a light chain (LC) comprising an amino acid sequence at least 90%, at least 95%, at least 97%, or at least 99% identical to the SEQ ID NO: 192;

the CDRs of embodiment 1(t) and further comprises a heavy chain (HC) comprising an amino acid sequence at least 90%, at least 95%, at least 97%, or at least 99% identical to the SEQ ID NO: 201 and a light chain (LC) comprising an amino acid sequence at least 90%, at least 95%, at least 97%, or at least 99% identical to the SEQ ID NO: 202; or the CDRs of embodiment 1(u) and further comprises a heavy chain (HC) comprising an amino acid sequence at least 90%, at least 95%, at least 97%, or at least 99% identical to the SEQ ID NO: 211 and a light chain (LC) comprising an amino acid sequence at least 90%, at least 95%, at least 97%, or at least 99% identical to the SEQ ID NO: 212.

7. The antibody of embodiment 1, wherein the antibody comprises:

a heavy chain (HC) comprising the amino acid sequence of SEQ ID NO: 11 and a light chain (LC) comprising the amino acid sequence of SEQ ID NO: 12;

a heavy chain (HC) comprising the amino acid sequence of SEQ ID NO: 21 and a light chain (LC) comprising the amino acid sequence of SEQ ID NO: 22;

a heavy chain (HC) comprising the amino acid sequence of SEQ ID NO: 31 and a light chain (LC) comprising the amino acid sequence of SEQ ID NO: 32;

a heavy chain (HC) comprising the amino acid sequence of SEQ ID NO: 41 and a light chain (LC) comprising the amino acid sequence of SEQ ID NO: 42;

a heavy chain (HC) comprising the amino acid sequence of SEQ ID NO: 51 and a light chain (LC) comprising the amino acid sequence of SEQ ID NO: 52;

a heavy chain (HC) comprising the amino acid sequence of SEQ ID NO: 61 and a light chain (LC) comprising the amino acid sequence of SEQ ID NO: 62;

a heavy chain (HC) comprising the amino acid sequence of SEQ ID NO: 71 and a light chain (LC) comprising the amino acid sequence of SEQ ID NO: 72;

a heavy chain (HC) comprising the amino acid sequence of SEQ ID NO: 81 and a light chain (LC) comprising the amino acid sequence of SEQ ID NO: 82;

a heavy chain (HC) comprising the amino acid sequence of SEQ ID NO: 91 and a light chain (LC) comprising the amino acid sequence of SEQ ID NO: 92;

a heavy chain (HC) comprising the amino acid sequence of SEQ ID NO: 101 and a light chain (LC) comprising the amino acid sequence of SEQ ID NO: 102;

a heavy chain (HC) comprising the amino acid sequence of SEQ ID NO: 111 and a light chain (LC) comprising the amino acid sequence of SEQ ID NO: 112;

a heavy chain (HC) comprising the amino acid sequence of SEQ ID NO: 121 and a light chain (LC) comprising the amino acid sequence of SEQ ID NO: 122;

a heavy chain (HC) comprising the amino acid sequence of SEQ ID NO: 131 and a light chain (LC) comprising the amino acid sequence of SEQ ID NO: 132;

a heavy chain (HC) comprising the amino acid sequence of SEQ ID NO: 141 and a light chain (LC) comprising the amino acid sequence of SEQ ID NO: 142;

a heavy chain (HC) comprising the amino acid sequence of SEQ ID NO: 151 and a light chain (LC) comprising the amino acid sequence of SEQ ID NO: 152;

a heavy chain (HC) comprising the amino acid sequence of SEQ ID NO: 161 and a light chain (LC) comprising the amino acid sequence of SEQ ID NO: 162;

a heavy chain (HC) comprising the amino acid sequence of SEQ ID NO: 171 and a light chain (LC) comprising the amino acid sequence of SEQ ID NO: 172;

a heavy chain (HC) comprising the amino acid sequence of SEQ ID NO: 181 and a light chain (LC) comprising the amino acid sequence of SEQ ID NO: 182;

a heavy chain (HC) comprising the amino acid sequence of SEQ ID NO: 191 and a light chain (LC) comprising the amino acid sequence of SEQ ID NO: 192;

a heavy chain (HC) comprising the amino acid sequence of SEQ ID NO: 201 and a light chain (LC) comprising the amino acid sequence of SEQ ID NO: 202; or a heavy chain (HC) comprising the amino acid sequence of SEQ ID NO: 211 and a light chain (LC) comprising the amino acid sequence of SEQ ID NO: 212.

8. An isolated antibody that specifically binds to apolipoprotein L1 (APOL1), wherein the antibody:

specifically binds to a region of APOL1 corresponding to amino acids 61-103 of APOL1 G0 (SEQ ID NO: 2); and/or specifically binds to a region of APOL1 corresponding to amino acids 111-150 of APOL1 G0 (SEQ ID NO: 2); and further wherein the antibody preferentially recognizes APOL1 expressed on podocytes over APOL1 found in serum.

9. The antibody of embodiment 8, wherein the antibody comprises:

(a) a heavy chain variable region (VH) comprising a CDR-H1 comprising the amino acid sequence of SEQ ID NO: 173, a CDR-H2 comprising the amino acid sequence of SEQ ID NO: 174, and a CDR-H3 comprising the amino acid sequence of SEQ ID NO: 175; and a light chain variable region (VL) comprising a CDR-L1 comprising the amino acid sequence of SEQ ID NO: 176, a CDR-L2 comprising the amino acid sequence of SEQ ID NO: 177, and a CDR-L3 comprising the amino acid sequence of SEQ ID NO: 178; or (b) a heavy chain variable region (VH) comprising a CDR-H1 comprising the amino acid sequence of SEQ ID NO: 183, a CDR-H2 comprising the amino acid sequence of SEQ ID NO: 184, and a CDR-H3 comprising the amino acid sequence of SEQ ID NO: 185; and a light chain variable region (VL) comprising a CDR-L1 comprising the amino acid sequence of SEQ ID NO: 186, a CDR-L2 comprising the amino acid sequence of SEQ ID NO: 187, and a CDR-L3 comprising the amino acid sequence of SEQ ID NO: 188.

10. An isolated antibody that specifically binds to apolipoprotein L1 (APOL1), wherein the antibody:

specifically binds to a region of APOL1 corresponding to amino acids 103-111 of APOL1 G0 (SEQ ID NO: 2);

specifically binds to a region of APOL1 corresponding to amino acids 150-172 of APOL1 G0 (SEQ ID NO: 2);

specifically binds to a region of APOL1 corresponding to amino acids 314-333 of APOL1 G0 (SEQ ID NO: 2); and/or specifically binds to a region of APOL1 corresponding to amino acids 376-398 of APOL1 G0 (SEQ ID NO: 2); and further wherein the antibody recognizes both APOL1 expressed on podocytes and APOL1 found in serum.

11. The isolated antibody of embodiment 10, wherein the antibody comprises:

(a) a heavy chain variable region (VH) comprising a CDR-H1 comprising the amino acid sequence of SEQ ID NO: 3, a CDR-H2 comprising the amino acid sequence of SEQ ID NO: 4, and a CDR-H3 comprising the amino acid sequence of SEQ ID NO: 5; and a light chain variable region (VL) comprising a CDR-L1 comprising the amino acid sequence of SEQ ID NO: 6, a CDR-L2 comprising the amino acid sequence of SEQ ID NO: 7, and a CDR-L3 comprising the amino acid sequence of SEQ ID NO: 8;

(b) a heavy chain variable region (VH) comprising a CDR-H1 comprising the amino acid sequence of SEQ ID NO: 53, a CDR-H2 comprising the amino acid sequence of SEQ ID NO: 54, and a CDR-H3 comprising the amino acid sequence of SEQ ID NO: 55; and a light chain variable region (VL) comprising a CDR-L1 comprising the amino acid sequence of SEQ ID NO: 56, a CDR-L2 comprising the amino acid sequence of SEQ ID NO: 57, and a CDR-L3 comprising the amino acid sequence of SEQ ID NO: 58;

(c) a heavy chain variable region (VH) comprising a CDR-H1 comprising the amino acid sequence of SEQ ID NO: 63, a CDR-H2 comprising the amino acid sequence of SEQ ID NO: 64, and a CDR-H3 comprising the amino acid sequence of SEQ ID NO: 65; and a light chain variable region (VL) comprising a CDR-L1 comprising the amino acid sequence of SEQ ID NO: 66, a CDR-L2 comprising the amino acid sequence of SEQ ID NO: 67, and a CDR-L3 comprising the amino acid sequence of SEQ ID NO: 68;

(d) a heavy chain variable region (VH) comprising a CDR-H1 comprising the amino acid sequence of SEQ ID NO: 83, a CDR-H2 comprising the amino acid sequence of SEQ ID NO: 84, and a CDR-H3 comprising the amino acid sequence of SEQ ID NO: 85; and a light chain variable region (VL) comprising a CDR-L1 comprising the amino acid sequence of SEQ ID NO: 86, a CDR-L2 comprising the amino acid sequence of SEQ ID NO: 87, and a CDR-L3 comprising the amino acid sequence of SEQ ID NO: 88;

(e) a heavy chain variable region (VH) comprising a CDR-H1 comprising the amino acid sequence of SEQ ID NO: 73, a CDR-H2 comprising the amino acid sequence of SEQ ID NO: 74, and a CDR-H3 comprising the amino acid sequence of SEQ ID NO: 75; and a light chain variable region (VL) comprising a CDR-L1 comprising the amino acid sequence of SEQ ID NO: 76, a CDR-L2 comprising the amino acid sequence of SEQ ID NO: 77, and a CDR-L3 comprising the amino acid sequence of SEQ ID NO: 78;

(f) a heavy chain variable region (VH) comprising a CDR-H1 comprising the amino acid sequence of SEQ ID NO: 133, a CDR-H2 comprising the amino acid sequence of SEQ ID NO: 134, and a CDR-H3 comprising the amino acid sequence of SEQ ID NO: 135; and a light chain variable region (VL) comprising a CDR-L1 comprising the amino acid sequence of SEQ ID NO: 136, a CDR-L2 comprising the amino acid sequence of SEQ ID NO: 137, and a CDR-L3 comprising the amino acid sequence of SEQ ID NO: 138;

(g) a heavy chain variable region (VH) comprising a CDR-H1 comprising the amino acid sequence of SEQ ID NO: 143, a CDR-H2 comprising the amino acid sequence of SEQ ID NO: 144, and a CDR-H3 comprising the amino acid sequence of SEQ ID NO: 145; and a light chain variable region (VL) comprising a CDR-L1 comprising the amino acid sequence of SEQ ID NO: 146, a CDR-L2 comprising the amino acid sequence of SEQ ID NO: 147, and a CDR-L3 comprising the amino acid sequence of SEQ ID NO: 148; or (h) a heavy chain variable region (VH) comprising a CDR-H1 comprising the amino acid sequence of SEQ ID NO: 123, a CDR-H2 comprising the amino acid sequence of SEQ ID NO: 124, and a CDR-H3 comprising the amino acid sequence of SEQ ID NO: 125; and a light chain variable region (VL) comprising a CDR-L1 comprising the amino acid sequence of SEQ ID NO: 126, a CDR-L2 comprising the amino acid sequence of SEQ ID NO: 127, and a CDR-L3 comprising the amino acid sequence of SEQ ID NO: 128.

12. An isolated antibody that specifically binds to apolipoprotein L1 (APOL1), wherein the antibody:

specifically binds to a region of APOL1 corresponding to amino acids 260-314 of APOL1 G0 (SEQ ID NO: 2); and further wherein the antibody preferentially recognizes APOL1 found in serum over APOL1 expressed on podocytes.

13. The antibody of embodiment 12, wherein the antibody comprises:

(a) a heavy chain variable region (VH) comprising a CDR-H1 comprising the amino acid sequence of SEQ ID NO: 33, a CDR-H2 comprising the amino acid sequence of SEQ ID NO: 34, and a CDR-H3 comprising the amino acid sequence of SEQ ID NO: 35; and a light chain variable region (VL) comprising a CDR-L1 comprising the amino acid sequence of SEQ ID NO: 36, a CDR-L2 comprising the amino acid sequence of SEQ ID NO: 37, and a CDR-L3 comprising the amino acid sequence of SEQ ID NO: 38; or (b) a heavy chain variable region (VH) comprising a CDR-H1 comprising the amino acid sequence of SEQ ID NO: 43, a CDR-H2 comprising the amino acid sequence of SEQ ID NO: 44, and a CDR-H3 comprising the amino acid sequence of SEQ ID NO: 45; and a light chain variable region (VL) comprising a CDR-L1 comprising the amino acid sequence of SEQ ID NO: 46, a CDR-L2 comprising the amino acid sequence of SEQ ID NO: 47, and a CDR-L3 comprising the amino acid sequence of SEQ ID NO: 48.

14. An isolated antibody that specifically binds to apolipoprotein L1 (APOL1), wherein the antibody preferentially binds to the G0 and G1 forms of APOL1 over the G2 form of APOL1.

15. The antibody of embodiment 14, wherein the antibody comprises:

(a) a heavy chain variable region (VH) comprising a CDR-H1 comprising the amino acid sequence of SEQ ID NO: 143, a CDR-H2 comprising the amino acid sequence of SEQ ID NO: 144, and a CDR-H3 comprising the amino acid sequence of SEQ ID NO: 145; and a light chain variable region (VL) comprising a CDR-L1 comprising the amino acid sequence of SEQ ID NO: 146, a CDR-L2 comprising the amino acid sequence of SEQ ID NO: 147, and a CDR-L3 comprising the amino acid sequence of SEQ ID NO: 148;

(b) a heavy chain variable region (VH) comprising a CDR-H1 comprising the amino acid sequence of SEQ ID NO: 123, a CDR-H2 comprising the amino acid sequence of SEQ ID NO: 124, and a CDR-H3 comprising the amino acid sequence of SEQ ID NO: 125; and a light chain variable region (VL) comprising a CDR-L1 comprising the amino acid sequence of SEQ ID NO: 126, a CDR-L2 comprising the amino acid sequence of SEQ ID NO: 127, and a CDR-L3 comprising the amino acid sequence of SEQ ID NO: 128; or (c) a heavy chain variable region (VH) comprising a CDR-H1 comprising the amino acid sequence of SEQ ID NO: 133, a CDR-H2 comprising the amino acid sequence of SEQ ID NO: 134, and a CDR-H3 comprising the amino acid sequence of SEQ ID NO: 135; and a light chain variable region (VL) comprising a CDR-L1 comprising the amino acid sequence of SEQ ID NO: 136, a CDR-L2 comprising the amino acid sequence of SEQ ID NO: 137, and a CDR-L3 comprising the amino acid sequence of SEQ ID NO: 138;

16. An isolated antibody that specifically binds to apolipoprotein L1 (APOL1) and that (a) does not significantly bind to apolipoprotein L2 or L3 (APOL2 or APOL3), and/or (b) does not significantly bind to apolipoprotein L2 or L6 (APOL2 or APOL6), wherein the antibody comprises:

(a) a heavy chain variable region (VH) comprising a CDR-H1 comprising the amino acid sequence of SEQ ID NO: 163, a CDR-H2 comprising the amino acid sequence of SEQ ID NO: 164, and a CDR-H3 comprising the amino acid sequence of SEQ ID NO: 165; and a light chain variable region (VL) comprising a CDR-L1 comprising the amino acid sequence of SEQ ID NO: 166, a CDR-L2 comprising the amino acid sequence of SEQ ID NO: 167, and a CDR-L3 comprising the amino acid sequence of SEQ ID NO: 168;

(b) a heavy chain variable region (VH) comprising a CDR-H1 comprising the amino acid sequence of SEQ ID NO: 103, a CDR-H2 comprising the amino acid sequence of SEQ ID NO: 104, and a CDR-H3 comprising the amino acid sequence of SEQ ID NO: 105; and a light chain variable region (VL) comprising a CDR-L1 comprising the amino acid sequence of SEQ ID NO: 106, a CDR-L2 comprising the amino acid sequence of SEQ ID NO: 107, and a CDR-L3 comprising the amino acid sequence of SEQ ID NO: 108; or (c) a heavy chain variable region (VH) comprising a CDR-H1 comprising the amino acid sequence of SEQ ID NO: 23, a CDR-H2 comprising the amino acid sequence of SEQ ID NO: 24, and a CDR-H3 comprising the amino acid sequence of SEQ ID NO: 25; and a light chain variable region (VL) comprising a CDR-L1 comprising the amino acid sequence of SEQ ID NO: 26, a CDR-L2 comprising the amino acid sequence of SEQ ID NO: 27, and a CDR-L3 comprising the amino acid sequence of SEQ ID NO: 28.

17. The antibody of any one of embodiments 1 to 5 or 8 to 16, wherein the antibody is humanized or chimeric.

18. The antibody of any one of embodiments 1 to 5 or 8 to 16, which is an IgG antibody, such as an $IgG_1$, $IgG_2$, $IgG_3$, or $IgG_4$.

19. The antibody of any one of embodiments 1 to 18, which is a full length antibody.

20. The antibody of any one of embodiments 1 to 5 or 8 to 16, which is an antibody fragment, such as an Fv, single-chain Fv (scFv), Fab, Fab', or $(Fab')_2$.

21. The antibody of any one of embodiments 1 to 20, which is a bispecific or multispecific antibody or wherein the antibody is conjugated covalently or noncovalently to at least one other molecule.

22. The antibody of embodiment 21, wherein the antibody is conjugated covalently or noncovalently to at least one other molecule, wherein the at least one other molecule comprises a detection label and/or a pharmaceutical agent.

23. The antibody of any one of embodiments 1-22, wherein the antibody specifically binds to a polypeptide comprising the amino acid sequence of SEQ ID NO: 2, SEQ ID NO: 213, and/or SEQ ID NO: 214.

In a further aspect, an anti-APOL1 antibody herein may incorporate any of the features, singly or in combination, as described in Sections 1-6 further below. Certain antibodies according to this disclosure are further described in more detail in the sub-sections that directly follow.

Antibody 3.6D12

In some aspects, the disclosure relates to an antibody comprising a heavy chain variable region and a light chain variable region, wherein the heavy chain variable region comprises an amino acid sequence comprising the heavy chain CDRs of the 3.6D12 antibody, comprising SEQ ID NOS: 3, 4, and 5. In some embodiments, the antibody comprises a heavy chain variable region and a light chain variable region, wherein the light chain variable region comprises an amino acid sequence comprising the light chain CDRs of the 3.6D12 antibody, comprising SEQ ID NOS: 6, 7, and 8. In some embodiments, the antibody comprises the heavy chain and the light chain CDRs of 3.6D12, comprising SEQ ID NOS: 3, 4, 5, 6, 7, and 8.

In some embodiments, the antibody comprises heavy chain CDRs of SEQ ID NOS: 3, 4, and 5, and/or the light chain CDRs of SEQ ID NOS: 6, 7, and 8, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 9. In some embodiments, the antibody comprises heavy chain CDRs of SEQ ID NOS: 3, 4, and 5, and/or light chain CDRs of SEQ ID NOS: 6, 7, and 8, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 10. In some embodiments, the antibody comprises heavy chain CDRs of SEQ ID NOS: 3, 4, and 5, and/or light chain CDRs of SEQ ID NOS: 6, 7, and 8, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 9, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 10. In some embodiments, the antibody comprises heavy chain CDRs of SEQ ID NOS: 3, 4, and 5, and/or light chain CDRs of SEQ ID NOS: 6, 7, and 8, and further comprises a heavy chain variable region comprising the amino acid sequence of SEQ ID NO. In some embodiments, the antibody comprises heavy chain CDRs of SEQ ID NOS: 3, 4, and 5, and/or light chain CDRs of SEQ ID NOS: 6, 7, and 8, and further comprises a light chain variable region comprising the amino acid sequence of SEQ ID NO: 10. In some embodiments, the antibody comprises heavy chain CDRs of SEQ ID NOS: 3, 4, and 5, and/or light chain CDRs of SEQ ID NOS: 6, 7, and 8, and further comprises a heavy chain variable region comprising the amino acid sequence of SEQ ID NO: 9, but with up to 5, such as 1, 2, 3, 4, or 5 amino acid substitutions, insertions, or deletions, in the heavy chain framework regions of SEQ ID NO: 9. In some embodiments, the antibody comprises heavy chain CDRs of SEQ ID NOS: 3, 4, and 5, and/or light chain CDRs of SEQ ID NOS: 6, 7, and 8, and further comprises a light chain variable region comprising the amino acid sequence of SEQ ID NO: 10, but with up to 5, such as 1, 2, 3, 4, or 5 amino acid substitutions, insertions, or deletions, in the light chain framework regions of SEQ ID NO: 10. In some embodiments, the antibody comprises a heavy chain variable region comprising the amino acid sequence of SEQ ID NO: 9 and a light chain variable region comprising the amino acid sequence of SEQ ID NO: 10, but with up to 5 amino acid substitutions, insertions, or deletions, such as 1, 2, 3, 4, or 5 amino acid substitutions, insertions, or deletions, in the framework regions of SEQ ID NO: 9 and/or SEQ ID NO: 10.

In some embodiments, the antibody comprises a heavy chain variable region comprising the amino acid sequence of SEQ ID NO: 9 and a light chain variable region comprising the amino acid sequence of SEQ ID NO: 10. In some embodiments, the antibody further comprises a heavy chain and/or a light chain constant region, for instance, as described in the section above. In some embodiments, the antibody comprises a human IgG constant region, such as a human $IgG_1$, $IgG_2$, $IgG_3$, or $IgG_4$. In other embodiments, the antibody comprises heavy chain CDRs of SEQ ID NOS: 3, 4, and 5, and/or the light chain CDRs of SEQ ID NOS: 6, 7, and 8, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 11. In some embodiments, the antibody comprises heavy chain CDRs of SEQ ID NOS: 3, 4, and 5, and/or light chain CDRs of SEQ ID NOS: 6, 7, and 8, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 12. In some embodiments, the antibody comprises heavy chain CDRs of SEQ ID NOS: 3, 4, and 5, and/or light chain CDRs of SEQ ID NOS: 6, 7, and 8, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 11, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 12. In some embodiments, the antibody comprises heavy chain CDRs of SEQ ID NOS: 3, 4, and 5, and/or light chain CDRs of SEQ ID NOS: 6, 7, and 8, and further comprises a heavy chain comprising the amino acid sequence of SEQ ID NO: 11. In some embodiments, the antibody comprises heavy chain CDRs of SEQ ID NOS: 3, 4, and 5, and/or light chain CDRs of SEQ ID NOS: 6, 7, and 8, and further comprises a light chain comprising the amino acid sequence of SEQ ID NO: 12. In some embodiments, the antibody comprises heavy chain CDRs of SEQ ID NOS: 3, 4, and 5, and/or light chain CDRs of SEQ ID NOS: 6, 7, and 8, and further comprises a heavy chain comprising the amino acid sequence of SEQ ID NO: 11, but with up to 5, such as 1, 2, 3, 4, or 5 amino acid substitutions, insertions, or deletions, in the heavy chain framework regions of SEQ ID NO: 11. In some embodiments, the antibody comprises heavy chain CDRs of SEQ ID NOS: 3, 4, and 5, and/or light chain CDRs of SEQ ID NOS: 6, 7, and 8, and further comprises a light chain comprising the amino acid sequence of SEQ ID NO: 12, but with up to 5, such as 1, 2, 3, 4, or 5 amino acid substitutions, insertions, or deletions, in the light chain framework regions of SEQ ID NO: 12. In some embodiments, the antibody comprises a heavy chain comprising the amino acid sequence of SEQ ID NO: 11 and a light chain comprising the amino acid sequence of SEQ ID NO: 12, but with up to 5 amino acid substitutions, insertions, or deletions, such as 1, 2, 3, 4, or 5 amino acid substitutions, insertions, or deletions, in the framework regions of SEQ ID NO: 11 and/or SEQ ID NO: 12.

In some aspects, the antibody recognizes the PFD portion of APOL1. In some aspects, the antibody recognizes the PFD portion from amino acids 103-111. In some aspects, the antibody recognizes both podocyte APOL1 and serum APOL1. In some aspects, the antibody blocks trypanolysis in an assay as described in the Examples herein. For example, in some aspects, the antibody blocks trypanolysis by at least 60% in such an assay. In some aspects, the antibody recognizes APOL1 on wild-type podocytes, for example, as measured by flow cytometry as described in the Examples herein. In some aspects, the antibody both blocks trypanolysis and recognizes APOL1 on wild-type podocytes, for example indicating that it binds to APOL1 located both on podocytes and in serum. In some aspects, the antibody recognizes APOL2, APOL3 and APOL4, but not APOL6 and thus may be used to distinguish APOL6 from the other family members.

Antibody 3.3B6

In some aspects, the disclosure relates to an antibody comprising a heavy chain variable region and a light chain variable region, wherein the heavy chain variable region comprises an amino acid sequence comprising the heavy chain CDRs of the 3.3B6 antibody, comprising SEQ ID NOS: 13, 14, and 15. In some embodiments, the antibody comprises a heavy chain variable region and a light chain variable region, wherein the light chain variable region comprises an amino acid sequence comprising the light chain CDRs of the 3.3B6 antibody, comprising SEQ ID NOS: 16, 17, and 18. In some embodiments, the antibody comprises the heavy chain and the light chain CDRs of 3.3B6, comprising SEQ ID NOS: 13, 14, 15, 16, 17, and 18.

In some embodiments, the antibody comprises heavy chain CDRs of SEQ ID NOS: 13, 14, and 15, and/or the light chain CDRs of SEQ ID NOS: 16, 17, and 18, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 19. In some embodiments, the antibody comprises heavy chain CDRs of SEQ ID NOS: 13, 14, and 15, and/or light chain CDRs of SEQ ID NOS: 16, 17, and 18, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 20. In some embodiments, the antibody comprises heavy chain CDRs of SEQ ID NOS: 13, 14, and 15, and/or light chain CDRs of SEQ ID NOS: 16, 17, and 18, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 19, and a light chain variable region comprising an amino acid sequence that is at least 90%, at least 91%, at least 92%, at least 93%, at least 94%, at least 95%, SEQ ID NO: 20. In some embodiments, the antibody comprises heavy chain CDRs of SEQ ID NOS: 13, 14, and 15, and/or light chain CDRs of SEQ ID NOS: 16, 17, and 18, and further comprises a heavy chain variable region comprising the amino acid sequence of SEQ ID NO: 19. In some embodiments, the antibody comprises heavy chain CDRs of SEQ ID NOS: 13, 14, and 15, and/or light chain CDRs of SEQ ID NOS: 16, 17, and 18, and further comprises a light chain variable region comprising the amino acid sequence of SEQ ID NO: 20. In some embodiments, the antibody comprises heavy chain CDRs of SEQ ID NOS: 13, 14, and 15, and/or light chain CDRs of SEQ ID NOS: 16, 17, and 18, and further comprises a heavy chain variable region comprising the amino acid sequence of SEQ ID NO: 19, but with up to 5, such as 1, 2, 3, 4, or 5 amino acid substitutions, insertions, or deletions, in the heavy chain framework regions of SEQ ID NO: 19. In some embodiments, the antibody comprises heavy chain CDRs of SEQ ID NOS: 13, 14, and 15, and/or light chain CDRs of SEQ ID NOS: 16, 17, and 18, and further comprises a light chain variable region comprising the amino acid sequence of SEQ ID NO: 20, but with up to 5, such as 1, 2, 3, 4, or 5 amino acid substitutions, insertions, or deletions, in the light chain framework regions of SEQ ID NO: 20. In some embodiments, the antibody comprises a heavy chain variable region comprising the amino acid sequence of SEQ ID NO: 19 and a light chain variable region comprising the amino acid sequence of SEQ ID NO: 20, but with up to 5 amino acid substitutions, insertions, or deletions, such as 1, 2, 3, 4, or 5 amino acid substitutions, insertions, or deletions, in the framework regions of SEQ ID NO: 19 and/or SEQ ID NO: 20.

In some embodiments, the antibody comprises a heavy chain variable region comprising the amino acid sequence of SEQ ID NO: 19 and a light chain variable region comprising the amino acid sequence of SEQ ID NO: 20. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 13, 14, and 15, and/or the light chain CDRs of SEQ ID NOS: 16, 17, and 18, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 21. In some embodiments, the antibody comprises heavy chain CDRs of SEQ ID NOS: 13, 14, and 15, and/or light chain CDRs of SEQ ID NOS: 16, 17, and 18, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 22. In some embodiments, the antibody comprises heavy chain CDRs of SEQ ID NOS: 13, 14, and 15, and/or light chain CDRs of SEQ ID NOS: 16, 17, and 18, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 21, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 22. In some embodiments, the antibody comprises heavy chain CDRs of SEQ ID NOS: 13, 14, and 15, and/or light chain CDRs of SEQ ID NOS: 16, 17, and 18, and further comprises a heavy chain comprising the amino acid sequence of SEQ ID NO: 21. In some embodiments, the antibody comprises heavy chain CDRs of SEQ ID NOS: 13, 14, and 15, and/or light chain CDRs of SEQ ID NOS: 16, 17, and 18, and further comprises a light chain comprising the amino acid sequence of SEQ ID NO: 22. In some embodiments, the antibody comprises heavy chain CDRs of SEQ ID NOS: 13, 14, and 15, and/or light chain CDRs of SEQ ID NOS: 16, 17, and 18, and further comprises a heavy chain comprising the amino acid sequence of SEQ ID NO: 21, but with up to 5, such as 1, 2, 3, 4, or 5 amino acid substitutions, insertions, or deletions, in the heavy chain framework regions of SEQ ID NO: 21. In some embodiments, the antibody comprises heavy chain CDRs of SEQ ID NOS: 13, 14, and 15, and/or light chain CDRs of SEQ ID NOS: 16, 17, and 18, and further comprises a light chain comprising the amino acid sequence of SEQ ID NO: 22, but with up to 5, such as 1, 2, 3, 4, or 5 amino acid substitutions, insertions, or deletions, in the light chain framework regions of SEQ ID NO: 22. In some embodiments, the antibody comprises a heavy chain comprising the amino acid sequence of SEQ ID NO: 21 and a light chain comprising the amino acid sequence of SEQ ID NO: 22, but with up to 5 amino acid substitutions, insertions, or deletions, such as 1, 2, 3, 4, or 5 amino acid substitutions, insertions, or deletions, in the framework regions of SEQ ID NO: 21 and/or SEQ ID NO: 22.

In some aspects, the antibody recognizes the PFD portion of APOL1. In some aspects, the antibody recognizes both podocyte APOL1 and serum APOL1. In some aspects, the antibody blocks trypanolysis in an assay as described in the Examples herein. For example, in some aspects, the antibody blocks trypanolysis by at least 60% in such an assay. In some aspects, the antibody recognizes APOL1 on wild-type podocytes, for example, as measured by flow cytometry as described in the Examples herein. In some aspects, the antibody both blocks trypanolysis and recognizes APOL1 on wild-type podocytes, for example indicating that it binds to APOL1 located both on podocytes and in serum.

Antibody 3.7D6

In some aspects, the disclosure relates to an antibody comprising a heavy chain variable region and a light chain variable region, wherein the heavy chain variable region comprises an amino acid sequence comprising the heavy chain CDRs of the 3.7D6 antibody, comprising SEQ ID NOS: 23, 24, and 25. In some embodiments, the antibody comprises a heavy chain variable region and a light chain variable region, wherein the light chain variable region comprises an amino acid sequence comprising the light chain CDRs of the 3.7D6 antibody, comprising SEQ ID NOS: 26, 27, and 28. In some embodiments, the antibody comprises the heavy chain and the light chain CDRs of 3.7D6, comprising SEQ ID NOS: 23, 324, 25, 26, 27, and 28.

In some embodiments, the antibody comprises heavy chain CDRs of SEQ ID NOS: 23, 24, and 25, and/or the light chain CDRs of SEQ ID NOS: 26, 27, and 28, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 29. In some embodiments, the antibody comprises heavy chain CDRs of SEQ ID NOS: 23, 24, and 25, and/or light chain CDRs of SEQ ID NOS: 26, 27, and 28, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 30. In some embodiments, the antibody comprises heavy chain CDRs of SEQ ID NOS: 23, 24, and 25, and/or light chain CDRs of SEQ ID NOS: 26, 27, and 28, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 29, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 30. In some embodiments, the antibody comprises heavy chain CDRs of SEQ ID NOS: 23, 24, and 25, and/or light chain CDRs of SEQ ID NOS: 26, 27, and 28, and further comprises a heavy chain variable region comprising the amino acid sequence of SEQ ID NO: 29. In some embodiments, the antibody comprises heavy chain CDRs of SEQ ID NOS: 23, 24, and 25, and/or light chain CDRs of SEQ ID NOS: 26, 27, and 28, and further comprises a light chain variable region comprising the amino acid sequence of SEQ ID NO: 30. In some embodiments, the antibody comprises heavy chain CDRs of SEQ ID NOS: 23, 24, and 25, and/or light chain CDRs of SEQ ID NOS: 26, 27, and 28, and further comprises a heavy chain variable region comprising the amino acid sequence of SEQ ID NO: 29, but with up to 5, such as 1, 2, 3, 4, or 5 amino acid substitutions, insertions, or deletions, in the heavy chain framework regions of SEQ ID NO: 29. In some embodiments, the antibody comprises heavy chain CDRs of SEQ ID NOS: 23, 24, and 25, and/or light chain CDRs of SEQ ID NOS: 26, 27, and 28, and further comprises a light chain variable region comprising the amino acid sequence of SEQ ID NO: 30, but with up to 5, such as 1, 2, 3, 4, or 5 amino acid substitutions, insertions, or deletions, in the light chain framework regions of SEQ ID NO: 30. In some embodiments, the antibody comprises a heavy chain variable region comprising the amino acid sequence of SEQ ID NO: 29 and a light chain variable region comprising the amino acid sequence of SEQ ID NO: 30, but with up to 5 amino acid substitutions, insertions, or deletions, such as 1, 2, 3, 4, or 5 amino acid substitutions, insertions, or deletions, in the framework regions of SEQ ID NO: 29 and/or SEQ ID NO: 30.

In some embodiments, the antibody comprises a heavy chain variable region comprising the amino acid sequence of SEQ ID NO: 29 and a light chain variable region comprising the amino acid sequence of SEQ ID NO: 30. In some embodiments, the antibody further comprises a heavy chain and/or a light chain constant region, for instance, as described in the section above. In some embodiments, the antibody comprises a human IgG constant region, such as a human $IgG_1$, $IgG_2$, $IgG_3$, or $IgG_4$. In other embodiments, the antibody comprises heavy chain CDRs of SEQ ID NOS: 23, 24, and 25, and/or the light chain CDRs of SEQ ID NOS: 26, 27, and 28, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 31. In some embodiments, the antibody comprises heavy chain CDRs of SEQ ID NOS: 23, 24, and 25, and/or light chain CDRs of SEQ ID NOS: 26, 27, and 28, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 32. In some embodiments, the antibody comprises heavy chain CDRs of SEQ ID NOS: 23, 24, and 25, and/or light chain CDRs of SEQ ID NOS: 26, 27, and 28, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 31, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 32. In some embodiments, the antibody comprises heavy chain CDRs of SEQ ID NOS: 23, 24, and 25, and/or light chain CDRs of SEQ ID NOS: 26, 27, and 28, and further comprises a heavy chain comprising the amino acid sequence of SEQ ID NO: 31. In some embodiments, the antibody comprises heavy chain CDRs of SEQ ID NOS: 23, 24, and 25, and/or light chain CDRs of SEQ ID NOS: 26, 27, and 28, and further comprises a light chain comprising the amino acid sequence of SEQ ID NO: 32. In some embodiments, the antibody comprises heavy chain CDRs of SEQ ID NOS: 23, 24, and 25, and/or light chain CDRs of SEQ ID NOS: 26, 27, and 28, and further comprises a heavy chain comprising the amino acid sequence of SEQ ID NO: 31, but with up to 5, such as 1, 2, 3, 4, or 5 amino acid substitutions, insertions, or deletions, in the heavy chain framework regions of SEQ ID NO: 31. In some embodiments, the antibody comprises heavy chain CDRs of SEQ ID NOS: 23, 24, and 25, and/or light chain CDRs of SEQ ID NOS: 26, 27, and 28, and further comprises a light chain comprising the amino acid sequence of SEQ ID NO: 32, but with up to 5, such as 1, 2, 3, 4, or 5 amino acid substitutions, insertions, or deletions, in the light chain framework regions of SEQ ID NO: 32. In some embodiments, the antibody comprises a heavy chain comprising the amino acid sequence of SEQ ID NO: 31 and a light chain comprising the amino acid sequence of SEQ ID NO: 32, but with up to 5 amino acid substitutions, insertions, or deletions, such as 1, 2, 3, 4, or 5 amino acid substitutions, insertions, or deletions, in the framework regions of SEQ ID NO: 31 and/or SEQ ID NO: 32.

In some aspects, the antibody recognizes the PFD portion of APOL1. In some aspects, the antibody recognizes the PFD portion from amino acids 150-172. In some aspects, the antibody recognizes both podocyte APOL1 and serum APOL1. In some aspects, the antibody blocks trypanolysis in an assay as described in the Examples herein. For example, in some aspects, the antibody blocks trypanolysis by at least 60% in such an assay. In some aspects, the antibody recognizes APOL1 on wild-type podocytes, for example, as measured by flow cytometry as described in the Examples herein. In some aspects, the antibody both blocks trypanolysis and recognizes APOL1 on wild-type podocytes, for example indicating that it binds to APOL1 located both on podocytes and in serum. In some aspects, the antibody does not recognize any of the other APOL family members and is specific to APOL1.

Antibody 3.3A8

In some aspects, the disclosure relates to an antibody comprising a heavy chain variable region and a light chain variable region, wherein the heavy chain variable region comprises an amino acid sequence comprising the heavy chain CDRs of the 3.3A8 antibody, comprising SEQ ID NOS: 33, 34, and 35. In some embodiments, the antibody comprises a heavy chain variable region and a light chain variable region, wherein the light chain variable region comprises an amino acid sequence comprising the light chain CDRs of the 3.3A8 antibody, comprising SEQ ID NOS: 36, 37, and 38. In some embodiments, the antibody comprises the heavy chain and the light chain CDRs of 3.3A8, comprising SEQ ID NOS: 33, 34, 35, 36, 37, and 38.

In some embodiments, the antibody comprises heavy chain CDRs of SEQ ID NOS: 33, 34, and 35, and/or the light chain CDRs of SEQ ID NOS: 36, 37, and 38, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 39. In some embodiments, the antibody comprises heavy chain CDRs of SEQ ID NOS: 33, 34, and 35, and/or light chain CDRs of SEQ ID NOS: 36, 37, and 38, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 40. In some embodiments, the antibody comprises heavy chain CDRs of SEQ ID NOS: 33, 34, and 35, and/or light chain CDRs of SEQ ID NOS: 36, 37, and 38, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 39, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 40. In some embodiments, the antibody comprises heavy chain CDRs of SEQ ID NOS: 33, 34, and 35, and/or light chain CDRs of SEQ ID NOS: 36, 37, and 38, and further comprises a heavy chain variable region comprising the amino acid sequence of SEQ ID NO: 39. In some embodiments, the antibody comprises heavy chain CDRs of SEQ ID NOS: 33, 34, and 35, and/or light chain CDRs of SEQ ID NOS: 36, 37, and 38, and further comprises a light chain variable region comprising the amino acid sequence of SEQ ID NO: 40. In some embodiments, the antibody comprises heavy chain CDRs of SEQ ID NOS: 33, 34, and 35, and/or light chain CDRs of SEQ ID NOS: 36, 37, and 38, and further comprises a heavy chain variable region comprising the amino acid sequence of SEQ ID NO: 39, but with up to 5, such as 1, 2, 3, 4, or 5 amino acid substitutions, insertions, or deletions, in the heavy chain framework regions of SEQ ID NO: 39. In some embodiments, the antibody comprises heavy chain CDRs of SEQ ID NOS: 33, 34, and 35, and/or light chain CDRs of SEQ ID NOS: 36, 37, and 38, and further comprises a light chain variable region comprising the amino acid sequence of SEQ ID NO: 40, but with up to 5, such as 1, 2, 3, 4, or 5 amino acid substitutions, insertions, or deletions, in the light chain framework regions of SEQ ID NO: 40. In some embodiments, the antibody comprises a heavy chain variable region comprising the amino acid sequence of SEQ ID NO: 39 and a light chain variable region comprising the amino acid sequence of SEQ ID NO: 40, but with up to 5 amino acid substitutions, insertions, or deletions, such as 1, 2, 3, 4, or 5 amino acid substitutions, insertions, or deletions, in the framework regions of SEQ ID NO: 39 and/or SEQ ID NO: 40.

In some embodiments, the antibody comprises a heavy chain variable region comprising the amino acid sequence of SEQ ID NO: 39 and a light chain variable region comprising the amino acid sequence of SEQ ID NO: 40. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 33, 34, and 35, and/or the light chain CDRs of SEQ ID NOS: 36, 37, and 38, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 41. In some embodiments, the antibody comprises heavy chain CDRs of SEQ ID NOS: 33, 34, and 35, and/or light chain CDRs of SEQ ID NOS: 36, 37, and 38, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 42. In some embodiments, the antibody comprises heavy chain CDRs of SEQ ID NOS: 33, 34, and 35, and/or light chain CDRs of SEQ ID NOS: 36, 37, and 38, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 41, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 42. In some embodiments, the antibody comprises heavy chain CDRs of SEQ ID NOS: 33, 34, and 35, and/or light chain CDRs of SEQ ID NOS: 36, 37, and 38, and further comprises a heavy chain comprising the amino acid sequence of SEQ ID NO: 41. In some embodiments, the antibody comprises heavy chain CDRs of SEQ ID NOS: 33, 34, and 35, and/or light chain CDRs of SEQ ID NOS: 36, 37, and 38, and further comprises a light chain comprising the amino acid sequence of SEQ ID NO: 42. In some embodiments, the antibody comprises heavy chain CDRs of SEQ ID NOS: 33, 34, and 35, and/or light chain CDRs of SEQ ID NOS: 36, 37, and 38, and further comprises a heavy chain comprising the amino acid sequence of SEQ ID NO: 41, but with up to 5, such as 1, 2, 3, 4, or 5 amino acid substitutions, insertions, or deletions, in the heavy chain framework regions of SEQ ID NO: 41. In some embodiments, the antibody comprises heavy chain CDRs of SEQ ID NOS: 33, 34, and 35, and/or light chain CDRs of SEQ ID NOS: 36, 37, and 38, and further comprises a light chain comprising the amino acid sequence of SEQ ID NO: 42, but with up to 5, such as 1, 2, 3, 4, or 5 amino acid substitutions, insertions, or deletions, in the light chain framework regions of SEQ ID NO: 42. In some embodiments, the antibody comprises a heavy chain comprising the amino acid sequence of SEQ ID NO: 41 and a light chain comprising the amino acid sequence of SEQ ID NO: 42, but with up to 5 amino acid substitutions, insertions, or deletions, such as 1, 2, 3, 4, or 5 amino acid substitutions, insertions, or deletions, in the framework regions of SEQ ID NO: 41 and/or SEQ ID NO: 42.

In some aspects, the 3.3A8 antibody recognizes the MAD portion of APOL1. In some aspects, the antibody recognizes the MAD portion from amino acids 260-294. In some aspects, the antibody preferentially recognizes serum APOL1. In some aspects, the antibody blocks trypanolysis in an assay as described in the Examples herein. For example, in some aspects, the antibody blocks trypanolysis by at least 60% in such an assay. In some aspects, the antibody does not significantly recognize APOL1 on wild-type podocytes, for example, as measured by flow cytometry as described in the Examples herein, but does recognize APOL1 stably expressed in CHO cells. In some aspects, the antibody does not recognize APOL2-6.

Antibody 3.2C11

In some aspects, the disclosure relates to an antibody comprising a heavy chain variable region and a light chain variable region, wherein the heavy chain variable region comprises an amino acid sequence comprising the heavy chain CDRs of the 3.2C11 antibody, comprising SEQ ID NOS: 43, 44, and 45. In some embodiments, the antibody comprises a heavy chain variable region and a light chain variable region, wherein the light chain variable region comprises an amino acid sequence comprising the light chain CDRs of the 3.2C11 antibody, comprising SEQ ID NOS: 46, 47, and 48. In some embodiments, the antibody comprises the heavy chain and the light chain CDRs of 3.2C11, comprising SEQ ID NOS: 43, 44, 45, 46, 47, and 48.

In some embodiments, the antibody comprises heavy chain CDRs of SEQ ID NOS: 43, 44, and 45, and/or the light chain CDRs of SEQ ID NOS: 46, 47, and 48, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 49. In some embodiments, the antibody comprises heavy chain CDRs of SEQ ID NOS: 43, 44, and 45, and/or light chain CDRs of SEQ ID NOS: 46, 47, and 48, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 50. In some embodiments, the antibody comprises heavy chain CDRs of SEQ ID NOS: 43, 44, and 45, and/or light chain CDRs of SEQ ID NOS: 46, 47, and 48, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 49, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 50. In some embodiments, the antibody comprises heavy chain CDRs of SEQ ID NOS: 43, 44, and 45, and/or light chain CDRs of SEQ ID NOS: 46, 47, and 48, and further comprises a heavy chain variable region comprising the amino acid sequence of SEQ ID NO: 49. In some embodiments, the antibody comprises heavy chain CDRs of SEQ ID NOS: 43, 44, and 45, and/or light chain CDRs of SEQ ID NOS: 46, 47, and 48, and further comprises a light chain variable region comprising the amino acid sequence of SEQ ID NO: 50. In some embodiments, the antibody comprises heavy chain CDRs of SEQ ID NOS: 43, 44, and 45, and/or light chain CDRs of SEQ ID NOS: 46, 47, and 48, and further comprises a heavy chain variable region comprising the amino acid sequence of SEQ ID NO: 49, but with up to 5, such as 1, 2, 3, 4, or 5 amino acid substitutions, insertions, or deletions, in the heavy chain framework regions of SEQ ID NO: 49. In some embodiments, the antibody comprises heavy chain CDRs of SEQ ID NOS: 43, 44, and 45, and/or light chain CDRs of SEQ ID NOS: 46, 47, and 48, and further comprises a light chain variable region comprising the amino acid sequence of SEQ ID NO: 50, but with up to 5, such as 1, 2, 3, 4, or 5 amino acid substitutions, insertions, or deletions, in the light chain framework regions of SEQ ID NO: 50. In some embodiments, the antibody comprises a heavy chain variable region comprising the amino acid sequence of SEQ ID NO: 49 and a light chain variable region comprising the amino acid sequence of SEQ ID NO: 50, but with up to 5 amino acid substitutions, insertions, or deletions, such as 1, 2, 3, 4, or 5 amino acid substitutions, insertions, or deletions, in the framework regions of SEQ ID NO: 49 and/or SEQ ID NO: 50.

In some embodiments, the antibody comprises a heavy chain variable region comprising the amino acid sequence of SEQ ID NO: 49 and a light chain variable region comprising the amino acid sequence of SEQ ID NO: 50. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 43, 44, and 45, and/or the light chain CDRs of SEQ ID NOS: 46, 47, and 48, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 51. In some embodiments, the antibody comprises heavy chain CDRs of SEQ ID NOS: 43, 44, and 45, and/or light chain CDRs of SEQ ID NOS: 46, 47, and 48, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 52. In some embodiments, the antibody comprises heavy chain CDRs of SEQ ID NOS: 43, 44, and 45, and/or light chain CDRs of SEQ ID NOS: 46, 47, and 48, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 51, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 52. In some embodiments, the antibody comprises heavy chain CDRs of SEQ ID NOS: 43, 44, and 45, and/or light chain CDRs of SEQ ID NOS: 46, 47, and 48, and further comprises a heavy chain comprising the amino acid sequence of SEQ ID NO: 51. In some embodiments, the antibody comprises heavy chain CDRs of SEQ ID NOS: 43, 44, and 45, and/or light chain CDRs of SEQ ID NOS: 46, 47, and 48, and further comprises a light chain comprising the amino acid sequence of SEQ ID NO: 52. In some embodiments, the antibody comprises heavy chain CDRs of SEQ ID NOS: 43, 44, and 45, and/or light chain CDRs of SEQ ID NOS: 46, 47, and 48, and further comprises a heavy chain comprising the amino acid sequence of SEQ ID NO: 51, but with up to 5, such as 1, 2, 3, 4, or 5 amino acid substitutions, insertions, or deletions, in the heavy chain framework regions of SEQ ID NO: 51. In some embodiments, the antibody comprises heavy chain CDRs of SEQ ID NOS: 43, 44, and 45, and/or light chain CDRs of SEQ ID NOS: 46, 47, and 48, and further comprises a light chain comprising the amino acid sequence of SEQ ID NO: 52, but with up to 5, such as 1, 2, 3, 4, or 5 amino acid substitutions, insertions, or deletions, in the light chain framework regions of SEQ ID NO: 52. In some embodiments, the antibody comprises a heavy chain comprising the amino acid sequence of SEQ ID NO: 51 and a light chain comprising the amino acid sequence of SEQ ID NO: 52, but with up to 5 amino acid substitutions, insertions, or deletions, such as 1, 2, 3, 4, or 5 amino acid substitutions, insertions, or deletions, in the framework regions of SEQ ID NO: 51 and/or SEQ ID NO: 52.

In some aspects, the antibody recognizes the junction between the MAD and Linker (L) portion of APOL1. In some aspects, the antibody recognizes the L portion from amino acids 294-314. In some aspects, the antibody preferentially recognizes serum APOL1. In some aspects, the antibody blocks trypanolysis in an assay as described in the Examples herein. For example, in some aspects, the antibody blocks trypanolysis by at least 60% in such an assay. In some aspects, the antibody blocks trypanolysis in an assay as described in the Examples herein. For example, in some aspects, the antibody blocks trypanolysis by at least 60% in such an assay. In some aspects, the antibody does not significantly recognize APOL1 on wild-type podocytes, for example, as measured by flow cytometry as described in the Examples herein.

Antibody 3.1C1

In some aspects, the disclosure relates to an antibody comprising a heavy chain variable region and a light chain variable region, wherein the heavy chain variable region comprises an amino acid sequence comprising the heavy chain CDRs of the 3.1C1 antibody, comprising SEQ ID NOS: 53, 54, and 55. In some embodiments, the antibody comprises a heavy chain variable region and a light chain variable region, wherein the light chain variable region comprises an amino acid sequence comprising the light chain CDRs of the 3.1C1 antibody, comprising SEQ ID NOS: 56, 57, and 58. In some embodiments, the antibody comprises the heavy chain and the light chain CDRs of 3.1C1, comprising SEQ ID NOS: 53, 54, 55, 56, 57, and 58.

In some embodiments, the antibody comprises heavy chain CDRs of SEQ ID NOS: 53, 54, and 55, and/or the light chain CDRs of SEQ ID NOS: 56, 57, and 58, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 59. In some embodiments, the antibody comprises heavy chain CDRs of SEQ ID NOS: 53, 54, and 55, and/or light chain CDRs of SEQ ID NOS: 56, 57, and 58, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 60. In some embodiments, the antibody comprises heavy chain CDRs of SEQ ID NOS: 53, 54, and 55, and/or light chain CDRs of SEQ ID NOS: 56, 57, and 58, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 59, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 60. In some embodiments, the antibody comprises heavy chain CDRs of SEQ ID NOS: 53, 54, and 55, and/or light chain CDRs of SEQ ID NOS: 56, 57, and 58, and further comprises a heavy chain variable region comprising the amino acid sequence of SEQ ID NO: 59. In some embodiments, the antibody comprises heavy chain CDRs of SEQ ID NOS: 53, 54, and 55, and/or light chain CDRs of SEQ ID NOS: 56, 57, and 58, and further comprises a light chain variable region comprising the amino acid sequence of SEQ ID NO: 60. In some embodiments, the antibody comprises heavy chain CDRs of SEQ ID NOS: 53, 54, and 55, and/or light chain CDRs of SEQ ID NOS: 56, 57, and 58, and further comprises a heavy chain variable region comprising the amino acid sequence of SEQ ID NO: 59, but with up to 5, such as 1, 2, 3, 4, or 5 amino acid substitutions, insertions, or deletions, in the heavy chain framework regions of SEQ ID NO: 59. In some embodiments, the antibody comprises heavy chain CDRs of SEQ ID NOS: 53, 54, and 55, and/or light chain CDRs of SEQ ID NOS: 56, 57, and 58, and further comprises a light chain variable region comprising the amino acid sequence of SEQ ID NO: 60, but with up to 5, such as 1, 2, 3, 4, or 5 amino acid substitutions, insertions, or deletions, in the light chain framework regions of SEQ ID NO: 60. In some embodiments, the antibody comprises a heavy chain variable region comprising the amino acid sequence of SEQ ID NO: 59 and a light chain variable region comprising the amino acid sequence of SEQ ID NO: 60, but with up to 5 amino acid substitutions, insertions, or deletions, such as 1, 2, 3, 4, or 5 amino acid substitutions, insertions, or deletions, in the framework regions of SEQ ID NO: 59 and/or SEQ ID NO: 60.

In some embodiments, the antibody comprises a heavy chain variable region comprising the amino acid sequence of SEQ ID NO: 59 and a light chain variable region comprising the amino acid sequence of SEQ ID NO: 60. In some embodiments, the antibody further comprises a heavy chain and/or a light chain constant region, for instance, as described in the section above. In some embodiments, the antibody comprises a human IgG constant region, such as a human $IgG_1$, $IgG_2$, $IgG_3$, or $IgG_4$. In other embodiments, the antibody comprises heavy chain CDRs of SEQ ID NOS: 53, 54, and 55, and/or the light chain CDRs of SEQ ID NOS: 56, 57, and 58, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 61. In some embodiments, the antibody comprises heavy chain CDRs of SEQ ID NOS: 53, 54, and 55, and/or light chain CDRs of SEQ ID NOS: 56, 57, and 58, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 62. In some embodiments, the antibody comprises heavy chain CDRs of SEQ ID NOS: 53, 54, and 55, and/or light chain CDRs of SEQ ID NOS: 56, 57, and 58, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 61, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 62. In some embodiments, the antibody comprises heavy chain CDRs of SEQ ID NOS: 53, 54, and 55, and/or light chain CDRs of SEQ ID NOS: 56, 57, and 58, and further comprises a heavy chain comprising the amino acid sequence of SEQ ID NO: 61. In some embodiments, the antibody comprises heavy chain CDRs of SEQ ID NOS: 53, 54, and 55, and/or light chain CDRs of SEQ ID NOS: 56, 57, and 58, and further comprises a light chain comprising the amino acid sequence of SEQ ID NO: 62. In some embodiments, the antibody comprises heavy chain CDRs of SEQ ID NOS: 53, 54, and 55, and/or light chain CDRs of SEQ ID NOS: 56, 57, and 58, and further comprises a heavy chain comprising the amino acid sequence of SEQ ID NO: 61, but with up to 5, such as 1, 2, 3, 4, or 5 amino acid substitutions, insertions, or deletions, in the heavy chain framework regions of SEQ ID NO: 61. In some embodiments, the antibody comprises heavy chain CDRs of SEQ ID NOS: 53, 54, and 55, and/or light chain CDRs of SEQ ID NOS: 56, 57, and 58, and further comprises a light chain comprising the amino acid sequence of SEQ ID NO: 62, but with up to 5, such as 1, 2, 3, 4, or 5 amino acid substitutions, insertions, or deletions, in the light chain framework regions of SEQ ID NO: 62. In some embodiments, the antibody comprises a heavy chain comprising the amino acid sequence of SEQ ID NO: 61 and a light chain comprising the amino acid sequence of SEQ ID NO: 62, but with up to 5 amino acid substitutions, insertions, or deletions, such as 1, 2, 3, 4, or 5 amino acid substitutions, insertions, or deletions, in the framework regions of SEQ ID NO: 61 and/or SEQ ID NO: 62.

In some aspects, the antibody recognizes the Linker (L) portion of APOL1. In some aspects, the antibody recognizes the L portion from amino acids 314-333. In some aspects, the antibody preferentially recognizes serum APOL1. In some aspects, the antibody blocks trypanolysis in an assay as described in the Examples herein. For example, in some aspects, the antibody blocks trypanolysis by at least 60% in such an assay. In some aspects, the antibody does not significantly recognize APOL1 on wild-type podocytes, for example, as measured by flow cytometry as described in the Examples herein. In some aspects, the antibody does not recognize APOLs 2, 3, 4, or 6.

Antibody 3.1C7

In some aspects, the disclosure relates to an antibody comprising a heavy chain variable region and a light chain variable region, wherein the heavy chain variable region comprises an amino acid sequence comprising the heavy chain CDRs of the 3.7C1 antibody, comprising SEQ ID NOS: 63, 64, and 65. In some embodiments, the antibody comprises a heavy chain variable region and a light chain variable region, wherein the light chain variable region comprises an amino acid sequence comprising the light chain CDRs of the 3.7C1 antibody, comprising SEQ ID NOS: 66, 67, and 68. In some embodiments, the antibody comprises the heavy chain and the light chain CDRs of 3.7C1, comprising SEQ ID NOS: 63, 64, 65, 66, 67, and 68.

In some embodiments, the antibody comprises heavy chain CDRs of SEQ ID NOS: 63, 64, and 65, and/or the light chain CDRs of SEQ ID NOS: 66, 67, and 68, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 69. In some embodiments, the antibody comprises heavy chain CDRs of SEQ ID NOS: 63, 64, and 65, and/or light chain CDRs of SEQ ID NOS: 66, 67, and 68, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 70. In some embodiments, the antibody comprises heavy chain CDRs of SEQ ID NOS: 63, 64, and 65, and/or light chain CDRs of SEQ ID NOS: 66, 67, and 68, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 69, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 70. In some embodiments, the antibody comprises heavy chain CDRs of SEQ ID NOS: 63, 64, and 65, and/or light chain CDRs of SEQ ID NOS: 66, 67, and 68, and further comprises a heavy chain variable region comprising the amino acid sequence of SEQ ID NO: 69. In some embodiments, the antibody comprises heavy chain CDRs of SEQ ID NOS: 63, 64, and 65, and/or light chain CDRs of SEQ ID NOS: 66, 67, and 68, and further comprises a light chain variable region comprising the amino acid sequence of SEQ ID NO: 70. In some embodiments, the antibody comprises heavy chain CDRs of SEQ ID NOS: 63, 64, and 65, and/or light chain CDRs of SEQ ID NOS: 66, 67, and 68, and further comprises a heavy chain variable region comprising the amino acid sequence of SEQ ID NO: 69, but with up to 5, such as 1, 2, 3, 4, or 5 amino acid substitutions, insertions, or deletions, in the heavy chain framework regions of SEQ ID NO: 69. In some embodiments, the antibody comprises heavy chain CDRs of SEQ ID NOS: 63, 64, and 65, and/or light chain CDRs of SEQ ID NOS: 66, 67, and 68, and further comprises a light chain variable region comprising the amino acid sequence of SEQ ID NO: 70, but with up to 5, such as 1, 2, 3, 4, or 5 amino acid substitutions, insertions, or deletions, in the light chain framework regions of SEQ ID NO: 70. In some embodiments, the antibody comprises a heavy chain variable region comprising the amino acid sequence of SEQ ID NO: 69 and a light chain variable region comprising the amino acid sequence of SEQ ID NO: 70, but with up to 5 amino acid substitutions, insertions, or deletions, such as 1, 2, 3, 4, or 5 amino acid substitutions, insertions, or deletions, in the framework regions of SEQ ID NO: 69 and/or SEQ ID NO: 70.

In some embodiments, the antibody comprises a heavy chain variable region comprising the amino acid sequence of SEQ ID NO: 69 and a light chain variable region comprising the amino acid sequence of SEQ ID NO: 70. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 63, 64, and 65, and/or the light chain CDRs of SEQ ID NOS: 66, 67, and 68, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 71. In some embodiments, the antibody comprises heavy chain CDRs of SEQ ID NOS: 63, 64, and 65, and/or light chain CDRs of SEQ ID NOS: 66, 67, and 68, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 72. In some embodiments, the antibody comprises heavy chain CDRs of SEQ ID NOS: 63, 64, and 65, and/or light chain CDRs of SEQ ID NOS: 66, 67, and 68, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 71, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 72. In some embodiments, the antibody comprises heavy chain CDRs of SEQ ID NOS: 63, 64, and 65, and/or light chain CDRs of SEQ ID NOS: 66, 67, and 68, and further comprises a heavy chain comprising the amino acid sequence of SEQ ID NO: 71. In some embodiments, the antibody comprises heavy chain CDRs of SEQ ID NOS: 63, 64, and 65, and/or light chain CDRs of SEQ ID NOS: 66, 67, and 68, and further comprises a light chain comprising the amino acid sequence of SEQ ID NO: 72. In some embodiments, the antibody comprises heavy chain CDRs of SEQ ID NOS: 63, 64, and 65, and/or light chain CDRs of SEQ ID NOS: 66, 67, and 68, and further comprises a heavy chain comprising the amino acid sequence of SEQ ID NO: 71, but with up to 5, such as 1, 2, 3, 4, or 5 amino acid substitutions, insertions, or deletions, in the heavy chain framework regions of SEQ ID NO: 71. In some embodiments, the antibody comprises heavy chain CDRs of SEQ ID NOS: 63, 64, and 65, and/or light chain CDRs of SEQ ID NOS: 66, 67, and 68, and further comprises a light chain comprising the amino acid sequence of SEQ ID NO: 72, but with up to 5, such as 1, 2, 3, 4, or 5 amino acid substitutions, insertions, or deletions, in the light chain framework regions of SEQ ID NO: 72. In some embodiments, the antibody comprises a heavy chain comprising the amino acid sequence of SEQ ID NO: 71 and a light chain comprising the amino acid sequence of SEQ ID NO: 72, but with up to 5 amino acid substitutions, insertions, or deletions, such as 1, 2, 3, 4, or 5 amino acid substitutions, insertions, or deletions, in the framework regions of SEQ ID NO: 71 and/or SEQ ID NO: 72.

In some aspects, the antibody recognizes the Linker (L) portion of APOL1. In some aspects, the antibody recognizes the L portion from amino acids 314-333. In some aspects, the antibody preferentially recognizes serum APOL1. In some aspects, the antibody blocks trypanolysis in an assay as described in the Examples herein. For example, in some aspects, the antibody blocks trypanolysis by at least 60% in such an assay. In some aspects, the antibody does not significantly recognize APOL1 on wild-type podocytes, for example, as measured by flow cytometry as described in the Examples herein.

Antibody 3.4G10

In some aspects, the disclosure relates to an antibody comprising a heavy chain variable region and a light chain variable region, wherein the heavy chain variable region comprises an amino acid sequence comprising the heavy chain CDRs of the 3.4G10 antibody, comprising SEQ ID NOS: 73, 74, and 75. In some embodiments, the antibody comprises a heavy chain variable region and a light chain variable region, wherein the light chain variable region comprises an amino acid sequence comprising the light chain CDRs of the 3.4G10 antibody, comprising SEQ ID NOS: 76, 77, and 78. In some embodiments, the antibody comprises the heavy chain and the light chain CDRs of 3.4G10, comprising SEQ ID NOS: 73, 74, 75, 76, 77, and 78.

In some embodiments, the antibody comprises heavy chain CDRs of SEQ ID NOS: 73, 74, and 75, and/or the light chain CDRs of SEQ ID NOS: 76, 77, and 78, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 79. In some embodiments, the antibody comprises heavy chain CDRs of SEQ ID NOS: 73, 74, and 75, and/or light chain CDRs of SEQ ID NOS: 76, 77, and 78, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 80. In some embodiments, the antibody comprises heavy chain CDRs of SEQ ID NOS: 73, 74, and 75, and/or light chain CDRs of SEQ ID NOS: 76, 77, and 78, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 79, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 80. In some embodiments, the antibody comprises heavy chain CDRs of SEQ ID NOS: 73, 74, and 75, and/or light chain CDRs of SEQ ID NOS: 76, 77, and 78, and further comprises a heavy chain variable region comprising the amino acid sequence of SEQ ID NO: 79. In some embodiments, the antibody comprises heavy chain CDRs of SEQ ID NOS: 73, 74, and 75, and/or light chain CDRs of SEQ ID NOS: 76, 77, and 78, and further comprises a light chain variable region comprising the amino acid sequence of SEQ ID NO: 80. In some embodiments, the antibody comprises heavy chain CDRs of SEQ ID NOS: 73, 74, and 75, and/or light chain CDRs of SEQ ID NOS: 76, 77, and 78, and further comprises a heavy chain variable region comprising the amino acid sequence of SEQ ID NO: 79, but with up to 5, such as 1, 2, 3, 4, or 5 amino acid substitutions, insertions, or deletions, in the heavy chain framework regions of SEQ ID NO: 79. In some embodiments, the antibody comprises heavy chain CDRs of SEQ ID NOS: 73, 74, and 75, and/or light chain CDRs of SEQ ID NOS: 76, 77, and 78, and further comprises a light chain variable region comprising the amino acid sequence of SEQ ID NO: 80, but with up to 5, such as 1, 2, 3, 4, or 5 amino acid substitutions, insertions, or deletions, in the light chain framework regions of SEQ ID NO: 80. In some embodiments, the antibody comprises a heavy chain variable region comprising the amino acid sequence of SEQ ID NO: 79 and a light chain variable region comprising the amino acid sequence of SEQ ID NO: 80, but with up to 5 amino acid substitutions, insertions, or deletions, such as 1, 2, 3, 4, or 5 amino acid substitutions, insertions, or deletions, in the framework regions of SEQ ID NO: 79 and/or SEQ ID NO: 80.

In some embodiments, the antibody comprises a heavy chain variable region comprising the amino acid sequence of SEQ ID NO: 79 and a light chain variable region comprising the amino acid sequence of SEQ ID NO: 80. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 73, 74, and 75, and/or the light chain CDRs of SEQ ID NOS: 76, 77, and 78, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 81. In some embodiments, the antibody comprises heavy chain CDRs of SEQ ID NOS: 73, 74, and 75, and/or light chain CDRs of SEQ ID NOS: 76, 77, and 78, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 82. In some embodiments, the antibody comprises heavy chain CDRs of SEQ ID NOS: 73, 74, and 75, and/or light chain CDRs of SEQ ID NOS: 76, 77, and 78, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 81, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 82. In some embodiments, the antibody comprises heavy chain CDRs of SEQ ID NOS: 73, 74, and 75, and/or light chain CDRs of SEQ ID NOS: 76, 77, and 78, and further comprises a heavy chain comprising the amino acid sequence of SEQ ID NO: 81. In some embodiments, the antibody comprises heavy chain CDRs of SEQ ID NOS: 73, 74, and 75, and/or light chain CDRs of SEQ ID NOS: 76, 77, and 78, and further comprises a light chain comprising the amino acid sequence of SEQ ID NO: 82. In some embodiments, the antibody comprises heavy chain CDRs of SEQ ID NOS: 73, 74, and 75, and/or light chain CDRs of SEQ ID NOS: 76, 77, and 78, and further comprises a heavy chain comprising the amino acid sequence of SEQ ID NO: 81, but with up to 5, such as 1, 2, 3, 4, or 5 amino acid substitutions, insertions, or deletions, in the heavy chain framework regions of SEQ ID NO: 81. In some embodiments, the antibody comprises heavy chain CDRs of SEQ ID NOS: 73, 74, and 75, and/or light chain CDRs of SEQ ID NOS: 76, 77, and 78, and further comprises a light chain comprising the amino acid sequence of SEQ ID NO: 82, but with up to 5, such as 1, 2, 3, 4, or 5 amino acid substitutions, insertions, or deletions, in the light chain framework regions of SEQ ID NO: 82. In some embodiments, the antibody comprises a heavy chain comprising the amino acid sequence of SEQ ID NO: 81 and a light chain comprising the amino acid sequence of SEQ ID NO: 82, but with up to 5 amino acid substitutions, insertions, or deletions, such as 1, 2, 3, 4, or 5 amino acid substitutions, insertions, or deletions, in the framework regions of SEQ ID NO: 81 and/or SEQ ID NO: 82.

In some aspects, the antibody recognizes the Linker (L) portion of APOL1. In some aspects, the antibody recognizes the L portion from amino acids 324-343. In some aspects, the antibody preferentially recognizes serum APOL1. In some aspects, the antibody blocks trypanolysis in an assay as described in the Examples herein. For example, in some aspects, the antibody blocks trypanolysis by at least 60% in such an assay. In some aspects, the antibody does not significantly recognize APOL1 that is overexpressed on wild-type podocytes, for example, as measured by flow cytometry as described in the Examples herein.

Antibody 3.6E10

In some aspects, the disclosure relates to an antibody comprising a heavy chain variable region and a light chain variable region, wherein the heavy chain variable region comprises an amino acid sequence comprising the heavy chain CDRs of the 3.6E10 antibody, comprising SEQ ID NOS: 83, 84, and 85. In some embodiments, the antibody comprises a heavy chain variable region and a light chain variable region, wherein the light chain variable region comprises an amino acid sequence comprising the light chain CDRs of the 3.6E10 antibody, comprising SEQ ID NOS: 86, 87, and 88. In some embodiments, the antibody comprises the heavy chain and the light chain CDRs of 3.6E10, comprising SEQ ID NOS: 83, 84, 85, 86, 87, and 88.

In some embodiments, the antibody comprises heavy chain CDRs of SEQ ID NOS: 83, 84, and 85, and/or the light chain CDRs of SEQ ID NOS: 86, 87, and 88, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 89. In some embodiments, the antibody comprises heavy chain CDRs of SEQ ID NOS: 83, 84, and 85, and/or light chain CDRs of SEQ ID NOS: 86, 87, and 88, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 90. In some embodiments, the antibody comprises heavy chain CDRs of SEQ ID NOS: 83, 84, and 85, and/or light chain CDRs of SEQ ID NOS: 86, 87, and 88, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 89, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 90. In some embodiments, the antibody comprises heavy chain CDRs of SEQ ID NOS: 83, 84, and 85, and/or light chain CDRs of SEQ ID NOS: 86, 87, and 88, and further comprises a heavy chain variable region comprising the amino acid sequence of SEQ ID NO: 89. In some embodiments, the antibody comprises heavy chain CDRs of SEQ ID NOS: 83, 84, and 85, and/or light chain CDRs of SEQ ID NOS: 86, 87, and 88, and further comprises a light chain variable region comprising the amino acid sequence of SEQ ID NO: 90. In some embodiments, the antibody comprises heavy chain CDRs of SEQ ID NOS: 83, 84, and 85, and/or light chain CDRs of SEQ ID NOS: 86, 87, and 88, and further comprises a heavy chain variable region comprising the amino acid sequence of SEQ ID NO: 89, but with up to 5, such as 1, 2, 3, 4, or 5 amino acid substitutions, insertions, or deletions, in the heavy chain framework regions of SEQ ID NO: 89. In some embodiments, the antibody comprises heavy chain CDRs of SEQ ID NOS: 83, 84, and 85, and/or light chain CDRs of SEQ ID NOS: 86, 87, and 88, and further comprises a light chain variable region comprising the amino acid sequence of SEQ ID NO: 90, but with up to 5, such as 1, 2, 3, 4, or 5 amino acid substitutions, insertions, or deletions, in the light chain framework regions of SEQ ID NO: 90. In some embodiments, the antibody comprises a heavy chain variable region comprising the amino acid sequence of SEQ ID NO: 89 and a light chain variable region comprising the amino acid sequence of SEQ ID NO: 90, but with up to 5 amino acid substitutions, insertions, or deletions, such as 1, 2, 3, 4, or 5 amino acid substitutions, insertions, or deletions, in the framework regions of SEQ ID NO: 89 and/or SEQ ID NO: 90.

In some embodiments, the antibody comprises a heavy chain variable region comprising the amino acid sequence of SEQ ID NO: 89 and a light chain variable region comprising the amino acid sequence of SEQ ID NO: 90. In some embodiments, the antibody further comprises a heavy chain and/or a light chain constant region, for instance, as described in the section above. In some embodiments, the antibody comprises a human IgG constant region, such as a human $IgG_1$, $IgG_2$, $IgG_3$, or $IgG_4$. In other embodiments, the antibody comprises heavy chain CDRs of SEQ ID NOS: 83, 84, and 85, and/or the light chain CDRs of SEQ ID NOS: 86, 87, and 88, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 91. In some embodiments, the antibody comprises heavy chain CDRs of SEQ ID NOS: 83, 84, and 85, and/or light chain CDRs of SEQ ID NOS: 86, 87, and 88, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 92. In some embodiments, the antibody comprises heavy chain CDRs of SEQ ID NOS: 83, 84, and 85, and/or light chain CDRs of SEQ ID NOS: 86, 87, and 88, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 91, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 92. In some embodiments, the antibody comprises heavy chain CDRs of SEQ ID NOS: 83, 84, and 85, and/or light chain CDRs of SEQ ID NOS: 86, 87, and 88, and further comprises a heavy chain comprising the amino acid sequence of SEQ ID NO: 91. In some embodiments, the antibody comprises heavy chain CDRs of SEQ ID NOS: 83, 84, and 85, and/or light chain CDRs of SEQ ID NOS: 86, 87, and 88, and further comprises a light chain comprising the amino acid sequence of SEQ ID NO: 92. In some embodiments, the antibody comprises heavy chain CDRs of SEQ ID NOS: 83, 84, and 85, and/or light chain CDRs of SEQ ID NOS: 86, 87, and 88, and further comprises a heavy chain comprising the amino acid sequence of SEQ ID NO: 91, but with up to 5, such as 1, 2, 3, 4, or 5 amino acid substitutions, insertions, or deletions, in the heavy chain framework regions of SEQ ID NO: 91. In some embodiments, the antibody comprises heavy chain CDRs of SEQ ID NOS: 83, 84, and 85, and/or light chain CDRs of SEQ ID NOS: 86, 87, and 88, and further comprises a light chain comprising the amino acid sequence of SEQ ID NO: 92, but with up to 5, such as 1, 2, 3, 4, or 5 amino acid substitutions, insertions, or deletions, in the light chain framework regions of SEQ ID NO: 92. In some embodiments, the antibody comprises a heavy chain comprising the amino acid sequence of SEQ ID NO: 91 and a light chain comprising the amino acid sequence of SEQ ID NO: 92, but with up to 5 amino acid substitutions, insertions, or deletions, such as 1, 2, 3, 4, or 5 amino acid substitutions, insertions, or deletions, in the framework regions of SEQ ID NO: 91 and/or SEQ ID NO: 92.

In some aspects, the antibody recognizes the Linker (L) portion of APOL1. In some aspects, the antibody recognizes the L portion from amino acids 314-333. In some aspects, the antibody preferentially recognizes serum APOL1. In some aspects, the antibody blocks trypanolysis in an assay as described in the Examples herein. For example, in some aspects, the antibody blocks trypanolysis by at least 60% in such an assay. In some aspects, the antibody does not significantly recognize APOL1 on wild-type podocytes, for example, as measured by flow cytometry as described in the Examples herein.

Antibody 3.3F7

In some aspects, the disclosure relates to an antibody comprising a heavy chain variable region and a light chain variable region, wherein the heavy chain variable region comprises an amino acid sequence comprising the heavy chain CDRs of the 3.3F7 antibody, comprising SEQ ID NOS: 93, 94, and 95. In some embodiments, the antibody comprises a heavy chain variable region and a light chain variable region, wherein the light chain variable region comprises an amino acid sequence comprising the light chain CDRs of the 3.3F7 antibody, comprising SEQ ID NOS: 96, 97, and 98. In some embodiments, the antibody comprises the heavy chain and the light chain CDRs of 3.3F7, comprising SEQ ID NOS: 93, 94, and 95, 96, 97, and 98.

In some embodiments, the antibody comprises heavy chain CDRs of SEQ ID NOS: 93, 94, and 95, and/or the light chain CDRs of SEQ ID NOS: 96, 97, and 98, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 99. In some embodiments, the antibody comprises heavy chain CDRs of SEQ ID NOS: 93, 94, and 95, and/or light chain CDRs of SEQ ID NOS: 96, 97, and 98, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 100. In some embodiments, the antibody comprises heavy chain CDRs of SEQ ID NOS: 93, 94, and 95, and/or light chain CDRs of SEQ ID NOS: 96, 97, and 98, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 99, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 100. In some embodiments, the antibody comprises heavy chain CDRs of SEQ ID NOS: 93, 94, and 95, and/or light chain CDRs of SEQ ID NOS: 96, 97, and 98, and further comprises a heavy chain variable region comprising the amino acid sequence of SEQ ID NO: 99. In some embodiments, the antibody comprises heavy chain CDRs of SEQ ID NOS: 93, 94, and 95, and/or light chain CDRs of SEQ ID NOS: 96, 97, and 98, and further comprises a light chain variable region comprising the amino acid sequence of SEQ ID NO: 100. In some embodiments, the antibody comprises heavy chain CDRs of SEQ ID NOS: 93, 94, and 95, and/or light chain CDRs of SEQ ID NOS: 96, 97, and 98, and further comprises a heavy chain variable region comprising the amino acid sequence of SEQ ID NO: 99, but with up to 5, such as 1, 2, 3, 4, or 5 amino acid substitutions, insertions, or deletions, in the heavy chain framework regions of SEQ ID NO: 99. In some embodiments, the antibody comprises heavy chain CDRs of SEQ ID NOS: 93, 94, and 95, and/or light chain CDRs of SEQ ID NOS: 96, 97, and 98, and further comprises a light chain variable region comprising the amino acid sequence of SEQ ID NO: 100, but with up to 5, such as 1, 2, 3, 4, or 5 amino acid substitutions, insertions, or deletions, in the light chain framework regions of SEQ ID NO: 100. In some embodiments, the antibody comprises a heavy chain variable region comprising the amino acid sequence of SEQ ID NO: 99 and a light chain variable region comprising the amino acid sequence of SEQ ID NO: 100, but with up to 5 amino acid substitutions, insertions, or deletions, such as 1, 2, 3, 4, or 5 amino acid substitutions, insertions, or deletions, in the framework regions of SEQ ID NO: 99 and/or SEQ ID NO: 100.

In some embodiments, the antibody comprises a heavy chain variable region comprising the amino acid sequence of SEQ ID NO: 99 and a light chain variable region comprising the amino acid sequence of SEQ ID NO: 100. In some embodiments, the antibody further comprises a heavy chain and/or a light chain constant region, for instance, as described in the section above. In some embodiments, the antibody comprises a human IgG constant region, such as a human $IgG_1$, $IgG_2$, $IgG_3$, or $IgG_4$. In other embodiments, the antibody comprises heavy chain CDRs of SEQ ID NOS: 93, 94, and 95, and/or the light chain CDRs of SEQ ID NOS: 96, 97, and 98, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 101. In some embodiments, the antibody comprises heavy chain CDRs of SEQ ID NOS: 93, 94, and 95, and/or light chain CDRs of SEQ ID NOS: 96, 97, and 98, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 102. In some embodiments, the antibody comprises heavy chain CDRs of SEQ ID NOS: 93, 94, and 95, and/or light chain CDRs of SEQ ID NOS: 96, 97, and 98, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 101, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 102. In some embodiments, the antibody comprises heavy chain CDRs of SEQ ID NOS: 93, 94, and 95, and/or light chain CDRs of SEQ ID NOS: 96, 97, and 98, and further comprises a heavy chain comprising the amino acid sequence of SEQ ID NO: 101. In some embodiments, the antibody comprises heavy chain CDRs of SEQ ID NOS: 93, 94, and 95, and/or light chain CDRs of SEQ ID NOS: 96, 97, and 98, and further comprises a light chain comprising the amino acid sequence of SEQ ID NO: 102. In some embodiments, the antibody comprises heavy chain CDRs of SEQ ID NOS: 93, 94, and 95, and/or light chain CDRs of SEQ ID NOS: 96, 97, and 98, and further comprises a heavy chain comprising the amino acid sequence of SEQ ID NO: 101, but with up to 5, such as 1, 2, 3, 4, or 5 amino acid substitutions, insertions, or deletions, in the heavy chain framework regions of SEQ ID NO: 101. In some embodiments, the antibody comprises heavy chain CDRs of SEQ ID NOS: 93, 94, and 95, and/or light chain CDRs of SEQ ID NOS: 96, 97, and 98, and further comprises a light chain comprising the amino acid sequence of SEQ ID NO: 102, but with up to 5, such as 1, 2, 3, 4, or 5 amino acid substitutions, insertions, or deletions, in the light chain framework regions of SEQ ID NO: 102. In some embodiments, the antibody comprises a heavy chain comprising the amino acid sequence of SEQ ID NO: 101 and a light chain comprising the amino acid sequence of SEQ ID NO: 102, but with up to 5 amino acid substitutions, insertions, or deletions, such as 1, 2, 3, 4, or 5 amino acid substitutions, insertions, or deletions, in the framework regions of SEQ ID NO: 101 and/or SEQ ID NO: 102.

Figure 1A:
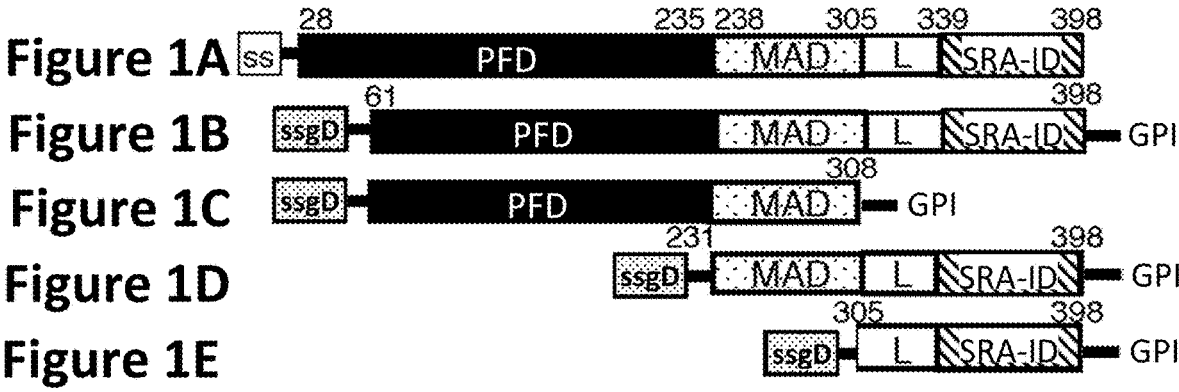
FIGS. 1A-1G show APOL1 constructs and domain specificities of anti-APOL1 antibodies.
Figures 1B, 1C, 1D, 1E, 1F:
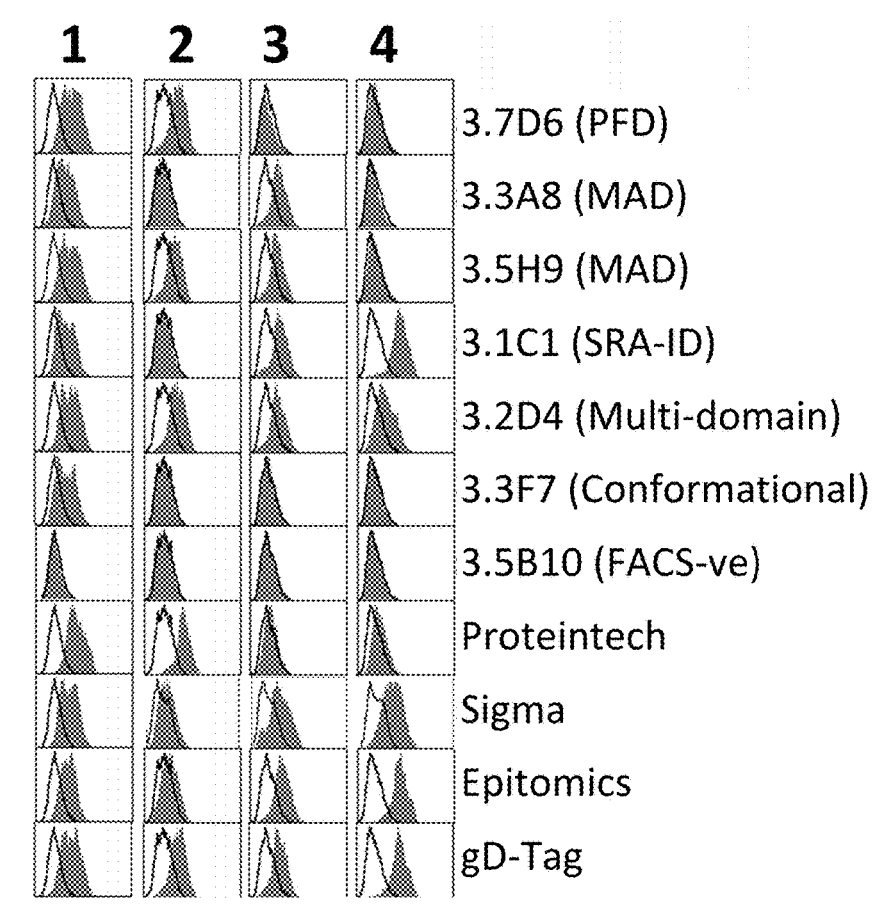
Figure 1G:
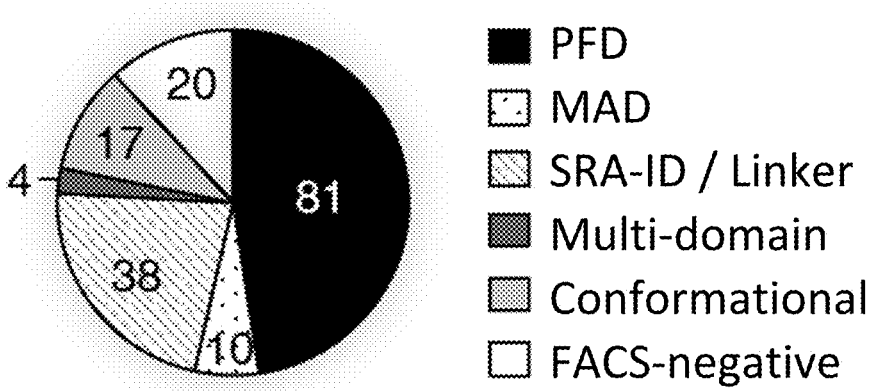

In some aspects, the antibody preferentially recognizes native APOL1, since it recognizes full length (e.g. SEQ ID NO: 2) but not any individual domains by flow cytometry as shown in FIG. 1G and in the Examples. In some aspects, the antibody blocks trypanolysis in an assay as described in the Examples herein. For example, in some aspects, the antibody blocks trypanolysis by at least 60% in such an assay. In some aspects, the antibody recognizes APOL1 on overexpressing podocytes, for example, as measured by flow cytometry as described in the Examples herein.

Antibody 3.7F5

In some aspects, the disclosure relates to an antibody comprising a heavy chain variable region and a light chain variable region, wherein the heavy chain variable region comprises an amino acid sequence comprising the heavy chain CDRs of the 3.7F5 antibody, comprising SEQ ID NOS: 203, 204, and 205. In some embodiments, the antibody comprises a heavy chain variable region and a light chain variable region, wherein the light chain variable region comprises an amino acid sequence comprising the light chain CDRs of the 3.7F5 antibody, comprising SEQ ID NOS: 206, 207, and 208. In some embodiments, the antibody comprises the heavy chain and the light chain CDRs of 3.7F5, comprising SEQ ID NOS: 203, 204, 205, 206, 207, and 208.

In some embodiments, the antibody comprises heavy chain CDRs of SEQ ID NOS: 203, 204, and 205, and/or the light chain CDRs of SEQ ID NOS: 206, 207, and 208, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 209. In some embodiments, the antibody comprises heavy chain CDRs of SEQ ID NOS: 203, 204, and 205, and/or light chain CDRs of SEQ ID NOS: 206, 207, and 208, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 210. In some embodiments, the antibody comprises heavy chain CDRs of SEQ ID NOS: 203, 204, and 205, and/or light chain CDRs of SEQ ID NOS: 206, 207, and 208, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 209, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 210. In some embodiments, the antibody comprises heavy chain CDRs of SEQ ID NOS: 203, 204, and 205, and/or light chain CDRs of SEQ ID NOS: 206, 207, and 208, and further comprises a heavy chain variable region comprising the amino acid sequence of SEQ ID NO: 209. In some embodiments, the antibody comprises heavy chain CDRs of SEQ ID NOS: 203, 204, and 205, and/or light chain CDRs of SEQ ID NOS: 206, 207, and 208, and further comprises a light chain variable region comprising the amino acid sequence of SEQ ID NO: 210. In some embodiments, the antibody comprises heavy chain CDRs of SEQ ID NOS: 203, 204, and 205, and/or light chain CDRs of SEQ ID NOS: 206, 207, and 208, and further comprises a heavy chain variable region comprising the amino acid sequence of SEQ ID NO: 209, but with up to 5, such as 1, 2, 3, 4, or 5 amino acid substitutions, insertions, or deletions, in the heavy chain framework regions of SEQ ID NO: 209. In some embodiments, the antibody comprises heavy chain CDRs of SEQ ID NOS: 203, 204, and 205, and/or light chain CDRs of SEQ ID NOS: 206, 207, and 208, and further comprises a light chain variable region comprising the amino acid sequence of SEQ ID NO: 210, but with up to 5, such as 1, 2, 3, 4, or 5 amino acid substitutions, insertions, or deletions, in the light chain framework regions of SEQ ID NO: 210. In some embodiments, the antibody comprises a heavy chain variable region comprising the amino acid sequence of SEQ ID NO: 209 and a light chain variable region comprising the amino acid sequence of SEQ ID NO: 210, but with up to 5 amino acid substitutions, insertions, or deletions, such as 1, 2, 3, 4, or 5 amino acid substitutions, insertions, or deletions, in the framework regions of SEQ ID NO: 209 and/or SEQ ID NO: 210.

In some embodiments, the antibody comprises a heavy chain variable region comprising the amino acid sequence of SEQ ID NO: 209 and a light chain variable region comprising the amino acid sequence of SEQ ID NO: 210. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 203, 204, and 205, and/or the light chain CDRs of SEQ ID NOS: 206, 207, and 208, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 211. In some embodiments, the antibody comprises heavy chain CDRs of SEQ ID NOS: 203, 204, and 205, and/or light chain CDRs of SEQ ID NOS: 206, 207, and 208, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 212. In some embodiments, the antibody comprises heavy chain CDRs of SEQ ID NOS: 203, 204, and 205, and/or light chain CDRs of SEQ ID NOS: 206, 207, and 208, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 211, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 212. In some embodiments, the antibody comprises heavy chain CDRs of SEQ ID NOS: 203, 204, and 205, and/or light chain CDRs of SEQ ID NOS: 206, 207, and 208, and further comprises a heavy chain comprising the amino acid sequence of SEQ ID NO: 211. In some embodiments, the antibody comprises heavy chain CDRs of SEQ ID NOS: 203, 204, and 205, and/or light chain CDRs of SEQ ID NOS: 206, 207, and 208, and further comprises a light chain comprising the amino acid sequence of SEQ ID NO: 212. In some embodiments, the antibody comprises heavy chain CDRs of SEQ ID NOS: 203, 204, and 205, and/or light chain CDRs of SEQ ID NOS: 206, 207, and 208, and further comprises a heavy chain comprising the amino acid sequence of SEQ ID NO: 211, but with up to 5, such as 1, 2, 3, 4, or 5 amino acid substitutions, insertions, or deletions, in the heavy chain framework regions of SEQ ID NO: 211. In some embodiments, the antibody comprises heavy chain CDRs of SEQ ID NOS: 203, 204, and 205, and/or light chain CDRs of SEQ ID NOS: 206, 207, and 208, and further comprises a light chain comprising the amino acid sequence of SEQ ID NO: 212, but with up to 5, such as 1, 2, 3, 4, or 5 amino acid substitutions, insertions, or deletions, in the light chain framework regions of SEQ ID NO: 212. In some embodiments, the antibody comprises a heavy chain comprising the amino acid sequence of SEQ ID NO: 211 and a light chain comprising the amino acid sequence of SEQ ID NO: 212, but with up to 5 amino acid substitutions, insertions, or deletions, such as 1, 2, 3, 4, or 5 amino acid substitutions, insertions, or deletions, in the framework regions of SEQ ID NO: 211 and/or SEQ ID NO: 212.

In some aspects, the antibody preferentially recognizes native APOL1, since it recognizes full length APOL1 (e.g. SEQ ID NO: 2) but not any individual domains (similar to 3.3F7 shown in FIG. 1G and in the Examples). In some aspects, the antibody blocks trypanolysis in an assay as described in the Examples herein. For example, in some aspects, the antibody blocks trypanolysis by at least 45% in such an assay. In some aspects, the antibody does not significantly recognize APOL1 on overexpressing podocytes, for example, as measured by flow cytometry as described in the Examples herein.

Antibody 4.17A5

In some aspects, the disclosure relates to an antibody comprising a heavy chain variable region and a light chain variable region, wherein the heavy chain variable region comprises an amino acid sequence comprising the heavy chain CDRs of the 4.17A5 antibody, comprising SEQ ID NOS: 103, 104, and 105. In some embodiments, the antibody comprises a heavy chain variable region and a light chain variable region, wherein the light chain variable region comprises an amino acid sequence comprising the light chain CDRs of the 4.17A5 antibody, comprising SEQ ID NOS: 106, 107, and 108. In some embodiments, the antibody comprises the heavy chain and the light chain CDRs of 4.17A5, comprising SEQ ID NOS: 103, 104, 105, 106, 107, and 108.

In some embodiments, the antibody comprises heavy chain CDRs of SEQ ID NOS: 103, 104, and 105, and/or the light chain CDRs of SEQ ID NOS: 106, 107, and 108, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 109. In some embodiments, the antibody comprises heavy chain CDRs of SEQ ID NOS: 103, 104, and 105, and/or light chain CDRs of SEQ ID NOS: 106, 107, and 108, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 110. In some embodiments, the antibody comprises heavy chain CDRs of SEQ ID NOS: 103, 104, and 105, and/or light chain CDRs of SEQ ID NOS: 106, 107, and 108, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 109, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 110. In some embodiments, the antibody comprises heavy chain CDRs of SEQ ID NOS: 103, 104, and 105, and/or light chain CDRs of SEQ ID NOS: 106, 107, and 108, and further comprises a heavy chain variable region comprising the amino acid sequence of SEQ ID NO: 109. In some embodiments, the antibody comprises heavy chain CDRs of SEQ ID NOS: 103, 104, and 105, and/or light chain CDRs of SEQ ID NOS: 106, 107, and 108, and further comprises a light chain variable region comprising the amino acid sequence of SEQ ID NO: 110. In some embodiments, the antibody comprises heavy chain CDRs of SEQ ID NOS: 103, 104, and 105, and/or light chain CDRs of SEQ ID NOS: 106, 107, and 108, and further comprises a heavy chain variable region comprising the amino acid sequence of SEQ ID NO: 109, but with up to 5, such as 1, 2, 3, 4, or 5 amino acid substitutions, insertions, or deletions, in the heavy chain framework regions of SEQ ID NO: 109. In some embodiments, the antibody comprises heavy chain CDRs of SEQ ID NOS: 103, 104, and 105, and/or light chain CDRs of SEQ ID NOS: 106, 107, and 108, and further comprises a light chain variable region comprising the amino acid sequence of SEQ ID NO: 110, but with up to 5, such as 1, 2, 3, 4, or 5 amino acid substitutions, insertions, or deletions, in the light chain framework regions of SEQ ID NO: 110. In some embodiments, the antibody comprises a heavy chain variable region comprising the amino acid sequence of SEQ ID NO: 109 and a light chain variable region comprising the amino acid sequence of SEQ ID NO: 110, but with up to 5 amino acid substitutions, insertions, or deletions, such as 1, 2, 3, 4, or 5 amino acid substitutions, insertions, or deletions, in the framework regions of SEQ ID NO: 109 and/or SEQ ID NO: 110.

In some embodiments, the antibody comprises a heavy chain variable region comprising the amino acid sequence of SEQ ID NO: 109 and a light chain variable region comprising the amino acid sequence of SEQ ID NO: 110. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 103, 104, and 105, and/or the light chain CDRs of SEQ ID NOS: 106, 107, and 108, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 111. In some embodiments, the antibody comprises heavy chain CDRs of SEQ ID NOS: 103, 104, and 105, and/or light chain CDRs of SEQ ID NOS: 106, 107, and 108, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 112. In some embodiments, the antibody comprises heavy chain CDRs of SEQ ID NOS: 103, 104, and 105, and/or light chain CDRs of SEQ ID NOS: 106, 107, and 108, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 111, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 112. In some embodiments, the antibody comprises heavy chain CDRs of SEQ ID NOS: 103, 104, and 105, and/or light chain CDRs of SEQ ID NOS: 106, 107, and 108, and further comprises a heavy chain comprising the amino acid sequence of SEQ ID NO: 111. In some embodiments, the antibody comprises heavy chain CDRs of SEQ ID NOS: 103, 104, and 105, and/or light chain CDRs of SEQ ID NOS: 106, 107, and 108, and further comprises a light chain comprising the amino acid sequence of SEQ ID NO: 112. In some embodiments, the antibody comprises heavy chain CDRs of SEQ ID NOS: 103, 104, and 105, and/or light chain CDRs of SEQ ID NOS: 106, 107, and 108, and further comprises a heavy chain comprising the amino acid sequence of SEQ ID NO: 111, but with up to 5, such as 1, 2, 3, 4, or 5 amino acid substitutions, insertions, or deletions, in the heavy chain framework regions of SEQ ID NO: 111. In some embodiments, the antibody comprises heavy chain CDRs of SEQ ID NOS: 103, 104, and 105, and/or light chain CDRs of SEQ ID NOS: 106, 107, and 108, and further comprises a light chain comprising the amino acid sequence of SEQ ID NO: 112, but with up to 5, such as 1, 2, 3, 4, or 5 amino acid substitutions, insertions, or deletions, in the light chain framework regions of SEQ ID NO: 112. In some embodiments, the antibody comprises a heavy chain comprising the amino acid sequence of SEQ ID NO: 111 and a light chain comprising the amino acid sequence of SEQ ID NO: 112, but with up to 5 amino acid substitutions, insertions, or deletions, such as 1, 2, 3, 4, or 5 amino acid substitutions, insertions, or deletions, in the framework regions of SEQ ID NO: 111 and/or SEQ ID NO: 112.

In some aspects, the antibody recognizes the PFD portion of APOL1. In some aspects, the antibody recognizes the PFD portion from amino acids 150-172. In some aspects, the antibody preferentially recognizes serum APOL1. In some aspects, the antibody blocks trypanolysis in an assay as described in the Examples herein. For example, in some aspects, the antibody blocks trypanolysis by at least 60% in such an assay. In some aspects, the antibody does not significantly recognize APOL1 on wild-type podocytes, for example, as measured by flow cytometry as described in the Examples herein. In some aspects, the antibody does not significantly recognize APOL2. In some aspects, the antibody recognizes APOL4. In some aspects, the antibody does not significantly recognize any of APOL2, APOL3, or APOL6. Thus, in some aspects, the antibody may be used to distinguish APOL1 and/or APOL4 from other related proteins such as APOL2, APOL3, and/or APOL6.

Antibody 4.2C4

In some aspects, the disclosure relates to an antibody comprising a heavy chain variable region and a light chain variable region, wherein the heavy chain variable region comprises an amino acid sequence comprising the heavy chain CDRs of the 4.2C4 antibody, comprising SEQ ID NOS: 113, 114, and 115. In some embodiments, the antibody comprises a heavy chain variable region and a light chain variable region, wherein the light chain variable region comprises an amino acid sequence comprising the light chain CDRs of the 4.2C4 antibody, comprising SEQ ID NOS: 116, 117, and 118. In some embodiments, the antibody comprises the heavy chain and the light chain CDRs of 4.2C4, comprising SEQ ID NOS: 113, 114, 115, 116, 117, and 118.

In some embodiments, the antibody comprises heavy chain CDRs of SEQ ID NOS: 113, 114, and 115, and/or the light chain CDRs of SEQ ID NOS: 116, 117, and 118, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 119. In some embodiments, the antibody comprises heavy chain CDRs of SEQ ID NOS: 113, 114, and 115, and/or light chain CDRs of SEQ ID NOS: 116, 117, and 118, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 120. In some embodiments, the antibody comprises heavy chain CDRs of SEQ ID NOS: 113, 114, and 115, and/or light chain CDRs of SEQ ID NOS: 116, 117, and 118, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 119, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 120. In some embodiments, the antibody comprises heavy chain CDRs of SEQ ID NOS: 113, 114, and 115, and/or light chain CDRs of SEQ ID NOS: 116, 117, and 118, and further comprises a heavy chain variable region comprising the amino acid sequence of SEQ ID NO: 119. In some embodiments, the antibody comprises heavy chain CDRs of SEQ ID NOS: 113, 114, and 115, and/or light chain CDRs of SEQ ID NOS: 116, 117, and 118, and further comprises a light chain variable region comprising the amino acid sequence of SEQ ID NO: 120. In some embodiments, the antibody comprises heavy chain CDRs of SEQ ID NOS: 113, 114, and 115, and/or light chain CDRs of SEQ ID NOS: 116, 117, and 118, and further comprises a heavy chain variable region comprising the amino acid sequence of SEQ ID NO: 119, but with up to 5, such as 1, 2, 3, 4, or 5 amino acid substitutions, insertions, or deletions, in the heavy chain framework regions of SEQ ID NO: 119. In some embodiments, the antibody comprises heavy chain CDRs of SEQ ID NOS: 113, 114, and 115, and/or light chain CDRs of SEQ ID NOS: 116, 117, and 118, and further comprises a light chain variable region comprising the amino acid sequence of SEQ ID NO: 120, but with up to 5, such as 1, 2, 3, 4, or 5 amino acid substitutions, insertions, or deletions, in the light chain framework regions of SEQ ID NO: 120. In some embodiments, the antibody comprises a heavy chain variable region comprising the amino acid sequence of SEQ ID NO: 119 and a light chain variable region comprising the amino acid sequence of SEQ ID NO: 120, but with up to 5 amino acid substitutions, insertions, or deletions, such as 1, 2, 3, 4, or 5 amino acid substitutions, insertions, or deletions, in the framework regions of SEQ ID NO: 119 and/or SEQ ID NO: 120.

In some embodiments, the antibody comprises a heavy chain variable region comprising the amino acid sequence of SEQ ID NO: 119 and a light chain variable region comprising the amino acid sequence of SEQ ID NO: 120. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 113, 114, and 115, and/or the light chain CDRs of SEQ ID NOS: 116, 117, and 118, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 121. In some embodiments, the antibody comprises heavy chain CDRs of SEQ ID NOS: 113, 114, and 115, and/or light chain CDRs of SEQ ID NOS: 116, 117, and 118, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 122. In some embodiments, the antibody comprises heavy chain CDRs of SEQ ID NOS: 113, 114, and 115, and/or light chain CDRs of SEQ ID NOS: 116, 117, and 118, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 121, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 122. In some embodiments, the antibody comprises heavy chain CDRs of SEQ ID NOS: 113, 114, and 115, and/or light chain CDRs of SEQ ID NOS: 116, 117, and 118, and further comprises a heavy chain comprising the amino acid sequence of SEQ ID NO: 121. In some embodiments, the antibody comprises heavy chain CDRs of SEQ ID NOS: 113, 114, and 115, and/or light chain CDRs of SEQ ID NOS: 116, 117, and 118, and further comprises a light chain comprising the amino acid sequence of SEQ ID NO: 122. In some embodiments, the antibody comprises heavy chain CDRs of SEQ ID NOS: 113, 114, and 115, and/or light chain CDRs of SEQ ID NOS: 116, 117, and 118, and further comprises a heavy chain comprising the amino acid sequence of SEQ ID NO: 121, but with up to 5, such as 1, 2, 3, 4, or 5 amino acid substitutions, insertions, or deletions, in the heavy chain framework regions of SEQ ID NO: 121. In some embodiments, the antibody comprises heavy chain CDRs of SEQ ID NOS: 113, 114, and 115, and/or light chain CDRs of SEQ ID NOS: 116, 117, and 118, and further comprises a light chain comprising the amino acid sequence of SEQ ID NO: 122, but with up to 5, such as 1, 2, 3, 4, or 5 amino acid substitutions, insertions, or deletions, in the light chain framework regions of SEQ ID NO: 122. In some embodiments, the antibody comprises a heavy chain comprising the amino acid sequence of SEQ ID NO: 121 and a light chain comprising the amino acid sequence of SEQ ID NO: 122, but with up to 5 amino acid substitutions, insertions, or deletions, such as 1, 2, 3, 4, or 5 amino acid substitutions, insertions, or deletions, in the framework regions of SEQ ID NO: 121 and/or SEQ ID NO: 122.

Antibody 4.12E5

In some aspects, the disclosure relates to an antibody comprising a heavy chain variable region and a light chain variable region, wherein the heavy chain variable region comprises an amino acid sequence comprising the heavy chain CDRs of the 4.12E5 antibody, comprising SEQ ID NOS: 123, 124, and 125. In some embodiments, the antibody comprises a heavy chain variable region and a light chain variable region, wherein the light chain variable region comprises an amino acid sequence comprising the light chain CDRs of the 4.12E5 antibody, comprising SEQ ID NOS: 126, 127, and 128. In some embodiments, the antibody comprises the heavy chain and the light chain CDRs of 4.12E5, comprising SEQ ID NOS: 123, 124, 15, 126, 127, and 128.

In some embodiments, the antibody comprises heavy chain CDRs of SEQ ID NOS: 123, 124, and 125, and/or the light chain CDRs of SEQ ID NOS: 126, 127, and 128, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 129. In some embodiments, the antibody comprises heavy chain CDRs of SEQ ID NOS: 123, 124, and 125, and/or light chain CDRs of SEQ ID NOS: 126, 127, and 128, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 130. In some embodiments, the antibody comprises heavy chain CDRs of SEQ ID NOS: 123, 124, and 125, and/or light chain CDRs of SEQ ID NOS: 126, 127, and 128, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 129, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 130. In some embodiments, the antibody comprises heavy chain CDRs of SEQ ID NOS: 123, 124, and 125, and/or light chain CDRs of SEQ ID NOS: 126, 127, and 128, and further comprises a heavy chain variable region comprising the amino acid sequence of SEQ ID NO: 129. In some embodiments, the antibody comprises heavy chain CDRs of SEQ ID NOS: 123, 124, and 125, and/or light chain CDRs of SEQ ID NOS: 126, 127, and 128, and further comprises a light chain variable region comprising the amino acid sequence of SEQ ID NO: 130. In some embodiments, the antibody comprises heavy chain CDRs of SEQ ID NOS: 123, 124, and 125, and/or light chain CDRs of SEQ ID NOS: 126, 127, and 128, and further comprises a heavy chain variable region comprising the amino acid sequence of SEQ ID NO: 129, but with up to 5, such as 1, 2, 3, 4, or 5 amino acid substitutions, insertions, or deletions, in the heavy chain framework regions of SEQ ID NO: 129. In some embodiments, the antibody comprises heavy chain CDRs of SEQ ID NOS: 123, 124, and 125, and/or light chain CDRs of SEQ ID NOS: 126, 127, and 128, and further comprises a light chain variable region comprising the amino acid sequence of SEQ ID NO: 130, but with up to 5, such as 1, 2, 3, 4, or 5 amino acid substitutions, insertions, or deletions, in the light chain framework regions of SEQ ID NO: 130. In some embodiments, the antibody comprises a heavy chain variable region comprising the amino acid sequence of SEQ ID NO: 129 and a light chain variable region comprising the amino acid sequence of SEQ ID NO: 130, but with up to 5 amino acid substitutions, insertions, or deletions, such as 1, 2, 3, 4, or 5 amino acid substitutions, insertions, or deletions, in the framework regions of SEQ ID NO: 129 and/or SEQ ID NO: 130.

In some embodiments, the antibody comprises a heavy chain variable region comprising the amino acid sequence of SEQ ID NO: 129 and a light chain variable region comprising the amino acid sequence of SEQ ID NO: 130. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 123, 124, and 125, and/or the light chain CDRs of SEQ ID NOS: 126, 127, and 128, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 131. In some embodiments, the antibody comprises heavy chain CDRs of SEQ ID NOS: 123, 124, and 125, and/or light chain CDRs of SEQ ID NOS: 126, 127, and 128, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 132. In some embodiments, the antibody comprises heavy chain CDRs of SEQ ID NOS: 123, 124, and 125, and/or light chain CDRs of SEQ ID NOS: 126, 127, and 128, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 131, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 132. In some embodiments, the antibody comprises heavy chain CDRs of SEQ ID NOS: 123, 124, and 125, and/or light chain CDRs of SEQ ID NOS: 126, 127, and 128, and further comprises a heavy chain comprising the amino acid sequence of SEQ ID NO: 131. In some embodiments, the antibody comprises heavy chain CDRs of SEQ ID NOS: 123, 124, and 125, and/or light chain CDRs of SEQ ID NOS: 126, 127, and 128, and further comprises a light chain comprising the amino acid sequence of SEQ ID NO: 132. In some embodiments, the antibody comprises heavy chain CDRs of SEQ ID NOS: 123, 124, and 125, and/or light chain CDRs of SEQ ID NOS: 126, 127, and 128, and further comprises a heavy chain comprising the amino acid sequence of SEQ ID NO: 131, but with up to 5, such as 1, 2, 3, 4, or 5 amino acid substitutions, insertions, or deletions, in the heavy chain framework regions of SEQ ID NO: 131.

In some embodiments, the antibody comprises heavy chain CDRs of SEQ ID NOS: 123, 124, and 125, and/or light chain CDRs of SEQ ID NOS: 126, 127, and 128, and further comprises a light chain comprising the amino acid sequence of SEQ ID NO: 132, but with up to 5, such as 1, 2, 3, 4, or 5 amino acid substitutions, insertions, or deletions, in the light chain framework regions of SEQ ID NO: 132. In some embodiments, the antibody comprises a heavy chain comprising the amino acid sequence of SEQ ID NO: 131 and a light chain comprising the amino acid sequence of SEQ ID NO: 132, but with up to 5 amino acid substitutions, insertions, or deletions, such as 1, 2, 3, 4, or 5 amino acid substitutions, insertions, or deletions, in the framework regions of SEQ ID NO: 131 and/or SEQ ID NO: 132.

In some aspects, the antibody recognizes the SRA-ID portion of APOL1, such as the portion from amino acids 376-398. In some aspects, the antibody preferentially recognizes serum APOL1. In some aspects, the antibody blocks trypanolysis in an assay as described in the Examples herein. For example, in some aspects, the antibody blocks trypanolysis by at least 60% in such an assay. In some aspects, the antibody preferentially recognizes the G0 and G1 forms of APOL1 over the G2 form. Thus, in some aspects, the antibody can distinguish the G0 and G1 forms from the G2 form.

Antibody 4.11A10

In some aspects, the disclosure relates to an antibody comprising a heavy chain variable region and a light chain variable region, wherein the heavy chain variable region comprises an amino acid sequence comprising the heavy chain CDRs of the 4.11A10 antibody, comprising SEQ ID NOS: 133, 134, and 135. In some embodiments, the antibody comprises a heavy chain variable region and a light chain variable region, wherein the light chain variable region comprises an amino acid sequence comprising the light chain CDRs of the 4.11A10 antibody, comprising SEQ ID NOS: 136, 137, and 138. In some embodiments, the antibody comprises the heavy chain and the light chain CDRs of 4.11A10, comprising SEQ ID NOS: 133, 134, 135, 136, 137, and 138.

In some embodiments, the antibody comprises heavy chain CDRs of SEQ ID NOS: 133, 134, and 135, and/or the light chain CDRs of SEQ ID NOS: 136, 137, and 138, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 139. In some embodiments, the antibody comprises heavy chain CDRs of SEQ ID NOS: 133, 134, and 135, and/or light chain CDRs of SEQ ID NOS: 136, 137, and 138, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 140. In some embodiments, the antibody comprises heavy chain CDRs of SEQ ID NOS: 133, 134, and 135, and/or light chain CDRs of SEQ ID NOS: 136, 137, and 138, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 139, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 140. In some embodiments, the antibody comprises heavy chain CDRs of SEQ ID NOS: 133, 134, and 135, and/or light chain CDRs of SEQ ID NOS: 136, 137, and 138, and further comprises a heavy chain variable region comprising the amino acid sequence of SEQ ID NO: 139. In some embodiments, the antibody comprises heavy chain CDRs of SEQ ID NOS: 133, 134, and 135, and/or light chain CDRs of SEQ ID NOS: 136, 137, and 138, and further comprises a light chain variable region comprising the amino acid sequence of SEQ ID NO: 140. In some embodiments, the antibody comprises heavy chain CDRs of SEQ ID NOS: 133, 134, and 135, and/or light chain CDRs of SEQ ID NOS: 136, 137, and 138, and further comprises a heavy chain variable region comprising the amino acid sequence of SEQ ID NO: 139, but with up to 5, such as 1, 2, 3, 4, or 5 amino acid substitutions, insertions, or deletions, in the heavy chain framework regions of SEQ ID NO: 139. In some embodiments, the antibody comprises heavy chain CDRs of SEQ ID NOS: 133, 134, and 135, and/or light chain CDRs of SEQ ID NOS: 136, 137, and 138, and further comprises a light chain variable region comprising the amino acid sequence of SEQ ID NO: 140, but with up to 5, such as 1, 2, 3, 4, or 5 amino acid substitutions, insertions, or deletions, in the light chain framework regions of SEQ ID NO: 140. In some embodiments, the antibody comprises a heavy chain variable region comprising the amino acid sequence of SEQ ID NO: 139 and a light chain variable region comprising the amino acid sequence of SEQ ID NO: 140, but with up to 5 amino acid substitutions, insertions, or deletions, such as 1, 2, 3, 4, or 5 amino acid substitutions, insertions, or deletions, in the framework regions of SEQ ID NO: 139 and/or SEQ ID NO: 140.

In some embodiments, the antibody comprises a heavy chain variable region comprising the amino acid sequence of SEQ ID NO: 139 and a light chain variable region comprising the amino acid sequence of SEQ ID NO: 140. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 133, 134, and 135, and/or the light chain CDRs of SEQ ID NOS: 136, 137, and 138, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 141. In some embodiments, the antibody comprises heavy chain CDRs of SEQ ID NOS: 133, 134, and 135, and/or light chain CDRs of SEQ ID NOS: 136, 137, and 138, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 142. In some embodiments, the antibody comprises heavy chain CDRs of SEQ ID NOS: 133, 134, and 135, and/or light chain CDRs of SEQ ID NOS: 136, 137, and 138, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 141, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 142. In some embodiments, the antibody comprises heavy chain CDRs of SEQ ID NOS: 133, 134, and 135, and/or light chain CDRs of SEQ ID NOS: 136, 137, and 138, and further comprises a heavy chain comprising the amino acid sequence of SEQ ID NO: 141. In some embodiments, the antibody comprises heavy chain CDRs of SEQ ID NOS: 133, 134, and 135, and/or light chain CDRs of SEQ ID NOS: 136, 137, and 138, and further comprises a light chain comprising the amino acid sequence of SEQ ID NO: 142. In some embodiments, the antibody comprises heavy chain CDRs of SEQ ID NOS: 133, 134, and 135, and/or light chain CDRs of SEQ ID NOS: 136, 137, and 138, and further comprises a heavy chain comprising the amino acid sequence of SEQ ID NO: 141, but with up to 5, such as 1, 2, 3, 4, or 5 amino acid substitutions, insertions, or deletions, in the heavy chain framework regions of SEQ ID NO: 141. In some embodiments, the antibody comprises heavy chain CDRs of SEQ ID NOS: 133, 134, and 135, and/or light chain CDRs of SEQ ID NOS: 136, 137, and 138, and further comprises a light chain comprising the amino acid sequence of SEQ ID NO: 142, but with up to 5, such as 1, 2, 3, 4, or 5 amino acid substitutions, insertions, or deletions, in the light chain framework regions of SEQ ID NO: 142. In some embodiments, the antibody comprises a heavy chain comprising the amino acid sequence of SEQ ID NO: 141 and a light chain comprising the amino acid sequence of SEQ ID NO: 142, but with up to 5 amino acid substitutions, insertions, or deletions, such as 1, 2, 3, 4, or 5 amino acid substitutions, insertions, or deletions, in the framework regions of SEQ ID NO: 141 and/or SEQ ID NO: 142.

In some aspects, the antibody recognizes the SRA-ID portion of APOL1. In some aspects, the antibody recognizes the SRA-ID portion from amino acids 376-398. In some aspects, the antibody preferentially recognizes serum APOL1. In some aspects, the antibody blocks trypanolysis in an assay as described in the Examples herein. For example, in some aspects, the antibody blocks trypanolysis by at least 60% in such an assay. In some aspects, the antibody preferentially recognizes the G0 and G1 forms of APOL1 over the G2 form. Thus, in some aspects, the antibody can distinguish the G0 and G1 forms from the G2 form.

Antibody 4.11H11

In some aspects, the disclosure relates to an antibody comprising a heavy chain variable region and a light chain variable region, wherein the heavy chain variable region comprises an amino acid sequence comprising the heavy chain CDRs of the 4.11H11 antibody, comprising SEQ ID NOS: 143, 144, and 145. In some embodiments, the antibody comprises a heavy chain variable region and a light chain variable region, wherein the light chain variable region comprises an amino acid sequence comprising the light chain CDRs of the 4.11H11 antibody, comprising SEQ ID NOS: 146, 147, and 148. In some embodiments, the antibody comprises the heavy chain and the light chain CDRs of 4.11H11, comprising SEQ ID NOS: 13, 14, 15, 146, 147, and 148.

In some embodiments, the antibody comprises heavy chain CDRs of SEQ ID NOS: 143, 144, and 145, and/or the light chain CDRs of SEQ ID NOS: 146, 147, and 148, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 149. In some embodiments, the antibody comprises heavy chain CDRs of SEQ ID NOS: 143, 144, and 145, and/or light chain CDRs of SEQ ID NOS: 146, 147, and 148, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 150. In some embodiments, the antibody comprises heavy chain CDRs of SEQ ID NOS: 143, 144, and 145, and/or light chain CDRs of SEQ ID NOS: 146, 147, and 148, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 149, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 150. In some embodiments, the antibody comprises heavy chain CDRs of SEQ ID NOS: 143, 144, and 145, and/or light chain CDRs of SEQ ID NOS: 146, 147, and 148, and further comprises a heavy chain variable region comprising the amino acid sequence of SEQ ID NO: 149. In some embodiments, the antibody comprises heavy chain CDRs of SEQ ID NOS: 143, 144, and 145, and/or light chain CDRs of SEQ ID NOS: 146, 147, and 148, and further comprises a light chain variable region comprising the amino acid sequence of SEQ ID NO: 150. In some embodiments, the antibody comprises heavy chain CDRs of SEQ ID NOS: 143, 144, and 145, and/or light chain CDRs of SEQ ID NOS: 146, 147, and 148, and further comprises a heavy chain variable region comprising the amino acid sequence of SEQ ID NO: 149, but with up to 5, such as 1, 2, 3, 4, or 5 amino acid substitutions, insertions, or deletions, in the heavy chain framework regions of SEQ ID NO: 149. In some embodiments, the antibody comprises heavy chain CDRs of SEQ ID NOS: 143, 144, and 145, and/or light chain CDRs of SEQ ID NOS: 146, 147, and 148, and further comprises a light chain variable region comprising the amino acid sequence of SEQ ID NO: 150, but with up to 5, such as 1, 2, 3, 4, or 5 amino acid substitutions, insertions, or deletions, in the light chain framework regions of SEQ ID NO: 150. In some embodiments, the antibody comprises a heavy chain variable region comprising the amino acid sequence of SEQ ID NO: 149 and a light chain variable region comprising the amino acid sequence of SEQ ID NO: 150, but with up to 5 amino acid substitutions, insertions, or deletions, such as 1, 2, 3, 4, or 5 amino acid substitutions, insertions, or deletions, in the framework regions of SEQ ID NO: 149 and/or SEQ ID NO: 150.

In some embodiments, the antibody comprises a heavy chain variable region comprising the amino acid sequence of SEQ ID NO: 149 and a light chain variable region comprising the amino acid sequence of SEQ ID NO: 150. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 143, 144, and 145, and/or the light chain CDRs of SEQ ID NOS: 146, 147, and 148, and further comprises a heavy chain comprising an amino acid sequence that is at least 90%, at least 91%, at least 92%, at least 93%, at least 94%, at least 95%, SEQ ID NO: 151. In some embodiments, the antibody comprises heavy chain CDRs of SEQ ID NOS:

143, 144, and 145, and/or light chain CDRs of SEQ ID NOS: 146, 147, and 148, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 152. In some embodiments, the antibody comprises heavy chain CDRs of SEQ ID NOS: 143, 144, and 145, and/or light chain CDRs of SEQ ID NOS: 146, 147, and 148, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 151, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 152. In some embodiments, the antibody comprises heavy chain CDRs of SEQ ID NOS: 143, 144, and 145, and/or light chain CDRs of SEQ ID NOS: 146, 147, and 148, and further comprises a heavy chain comprising the amino acid sequence of SEQ ID NO: 151. In some embodiments, the antibody comprises heavy chain CDRs of SEQ ID NOS: 143, 144, and 145, and/or light chain CDRs of SEQ ID NOS: 146, 147, and 148, and further comprises a light chain comprising the amino acid sequence of SEQ ID NO: 152. In some embodiments, the antibody comprises heavy chain CDRs of SEQ ID NOS: 143, 144, and 145, and/or light chain CDRs of SEQ ID NOS: 146, 147, and 148, and further comprises a heavy chain comprising the amino acid sequence of SEQ ID NO: 151, but with up to 5, such as 1, 2, 3, 4, or 5 amino acid substitutions, insertions, or deletions, in the heavy chain framework regions of SEQ ID NO: 151. In some embodiments, the antibody comprises heavy chain CDRs of SEQ ID NOS: 143, 144, and 145, and/or light chain CDRs of SEQ ID NOS: 146, 147, and 148, and further comprises a light chain comprising the amino acid sequence of SEQ ID NO: 152, but with up to 5, such as 1, 2, 3, 4, or 5 amino acid substitutions, insertions, or deletions, in the light chain framework regions of SEQ ID NO: 152. In some embodiments, the antibody comprises a heavy chain comprising the amino acid sequence of SEQ ID NO: 151 and a light chain comprising the amino acid sequence of SEQ ID NO: 152, but with up to 5 amino acid substitutions, insertions, or deletions, such as 1, 2, 3, 4, or 5 amino acid substitutions, insertions, or deletions, in the framework regions of SEQ ID NO: 151 and/or SEQ ID NO: 152.

In some aspects, the antibody recognizes the SRA-ID portion of APOL1, such as the portion from amino acids 376-398. In some aspects, the antibody preferentially recognizes the G0 and G1 forms of APOL1 over the G2 form. Thus, in some aspects, the antibody can distinguish the G0 and G1 forms from the G2 form.

Antibody 4.29C4

In some aspects, the disclosure relates to an antibody comprising a heavy chain variable region and a light chain variable region, wherein the heavy chain variable region comprises an amino acid sequence comprising the heavy chain CDRs of the 4.29C4 antibody, comprising SEQ ID NOS: 153, 154, and 155. In some embodiments, the antibody comprises a heavy chain variable region and a light chain variable region, wherein the light chain variable region comprises an amino acid sequence comprising the light chain CDRs of the 4.29C4 antibody, comprising SEQ ID NOS: 156, 157, and 158. In some embodiments, the antibody comprises the heavy chain and the light chain CDRs of 4.29C4, comprising SEQ ID NOS: 153, 154, 155, 156, 157, and 158.

In some embodiments, the antibody comprises heavy chain CDRs of SEQ ID NOS: 153, 154, and 155, and/or the light chain CDRs of SEQ ID NOS: 156, 157, and 158, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 159. In some embodiments, the antibody comprises heavy chain CDRs of SEQ ID NOS: 153, 154, and 155, and/or light chain CDRs of SEQ ID NOS: 156, 157, and 158, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 160. In some embodiments, the antibody comprises heavy chain CDRs of SEQ ID NOS: 153, 154, and 155, and/or light chain CDRs of SEQ ID NOS: 156, 157, and 158, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 159, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 160. In some embodiments, the antibody comprises heavy chain CDRs of SEQ ID NOS: 153, 154, and 155, and/or light chain CDRs of SEQ ID NOS: 156, 157, and 158, and further comprises a heavy chain variable region comprising the amino acid sequence of SEQ ID NO: 159. In some embodiments, the antibody comprises heavy chain CDRs of SEQ ID NOS: 153, 154, and 155, and/or light chain CDRs of SEQ ID NOS: 156, 157, and 158, and further comprises a light chain variable region comprising the amino acid sequence of SEQ ID NO: 160. In some embodiments, the antibody comprises heavy chain CDRs of SEQ ID NOS: 153, 154, and 155, and/or light chain CDRs of SEQ ID NOS: 156, 157, and 158, and further comprises a heavy chain variable region comprising the amino acid sequence of SEQ ID NO: 159, but with up to 5, such as 1, 2, 3, 4, or 5 amino acid substitutions, insertions, or deletions, in the heavy chain framework regions of SEQ ID NO: 159. In some embodiments, the antibody comprises heavy chain CDRs of SEQ ID NOS: 153, 154, and 155, and/or light chain CDRs of SEQ ID NOS: 156, 157, and 158, and further comprises a light chain variable region comprising the amino acid sequence of SEQ ID NO: 160, but with up to 5, such as 1, 2, 3, 4, or 5 amino acid substitutions, insertions, or deletions, in the light chain framework regions of SEQ ID NO: 160. In some embodiments, the antibody comprises a heavy chain variable region comprising the amino acid sequence of SEQ ID NO: 159 and a light chain variable region comprising the amino acid sequence of SEQ ID NO: 160, but with up to 5 amino acid substitutions, insertions, or deletions, such as 1, 2, 3, 4, or 5 amino acid substitutions, insertions, or deletions, in the framework regions of SEQ ID NO: 159 and/or SEQ ID NO: 160.

In some embodiments, the antibody comprises a heavy chain variable region comprising the amino acid sequence of SEQ ID NO: 159 and a light chain variable region comprising the amino acid sequence of SEQ ID NO: 160. In some embodiments, the antibody further comprises a heavy chain and/or a light chain constant region, for instance, as described in the section above. In some embodiments, the antibody comprises a human IgG constant region, such as a human $IgG_1$, $IgG_2$, $IgG_3$, or $IgG_4$. In other embodiments, the antibody comprises heavy chain CDRs of SEQ ID NOS: 153, 154, and 155, and/or the light chain CDRs of SEQ ID NOS: 156, 157, and 158, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 161. In some embodiments, the antibody comprises heavy chain CDRs of SEQ ID NOS: 153, 154, and 155, and/or light chain CDRs of SEQ ID NOS: 156, 157, and 158, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 162. In some embodiments, the antibody comprises heavy chain CDRs of SEQ ID NOS: 153, 154, and 155, and/or light chain CDRs of SEQ ID NOS: 156, 157, and 158, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 161, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 162. In some embodiments, the antibody comprises heavy chain CDRs of SEQ ID NOS: 153, 154, and 155, and/or light chain CDRs of SEQ ID NOS: 156, 157, and 158, and further comprises a heavy chain comprising the amino acid sequence of SEQ ID NO: 161. In some embodiments, the antibody comprises heavy chain CDRs of SEQ ID NOS: 153, 154, and 155, and/or light chain CDRs of SEQ ID NOS: 156, 157, and 158, and further comprises a light chain comprising the amino acid sequence of SEQ ID NO: 162. In some embodiments, the antibody comprises heavy chain CDRs of SEQ ID NOS: 153, 154, and 155, and/or light chain CDRs of SEQ ID NOS: 156, 157, and 158, and further comprises a heavy chain comprising the amino acid sequence of SEQ ID NO: 161, but with up to 5, such as 1, 2, 3, 4, or 5 amino acid substitutions, insertions, or deletions, in the heavy chain framework regions of SEQ ID NO: 161. In some embodiments, the antibody comprises heavy chain CDRs of SEQ ID NOS: 153, 154, and 155, and/or light chain CDRs of SEQ ID NOS: 156, 157, and 158, and further comprises a light chain comprising the amino acid sequence of SEQ ID NO: 162, but with up to 5, such as 1, 2, 3, 4, or 5 amino acid substitutions, insertions, or deletions, in the light chain framework regions of SEQ ID NO: 162. In some embodiments, the antibody comprises a heavy chain comprising the amino acid sequence of SEQ ID NO: 161 and a light chain comprising the amino acid sequence of SEQ ID NO: 162, but with up to 5 amino acid substitutions, insertions, or deletions, such as 1, 2, 3, 4, or 5 amino acid substitutions, insertions, or deletions, in the framework regions of SEQ ID NO: 161 and/or SEQ ID NO: 162.

In some aspects, the antibody recognizes the SRA-ID portion of APOL1. In some aspects, the antibody recognizes the SRA-ID portion from amino acids 364-376. Those amino acids appear to be relatively inaccessible in both podocyte-expressed APOL1 and serum APOL1. Accordingly, in some aspects, the antibody does not significantly recognize either podocyte-expressed APOL1 or serum APOL1.

Antibody 5.17D12

In some aspects, the disclosure relates to an antibody comprising a heavy chain variable region and a light chain variable region, wherein the heavy chain variable region comprises an amino acid sequence comprising the heavy chain CDRs of the 5.17D12 antibody, comprising SEQ ID NOS: 163, 164, and 165. In some embodiments, the antibody comprises a heavy chain variable region and a light chain variable region, wherein the light chain variable region comprises an amino acid sequence comprising the light chain CDRs of the 5.17D12 antibody, comprising SEQ ID NOS: 166, 167, and 168. In some embodiments, the antibody comprises the heavy chain and the light chain CDRs of 5.17D12, comprising SEQ ID NOS: 163, 164, 165, 166, 167, and 168.

In some embodiments, the antibody comprises heavy chain CDRs of SEQ ID NOS: 163, 164, and 165, and/or the light chain CDRs of SEQ ID NOS: 166, 167, and 168, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 169. In some embodiments, the antibody comprises heavy chain CDRs of SEQ ID NOS: 163, 164, and 165, and/or light chain CDRs of SEQ ID NOS: 166, 167, and 168, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 170. In some embodiments, the antibody comprises heavy chain CDRs of SEQ ID NOS: 163, 164, and 165, and/or light chain CDRs of SEQ ID NOS: 166, 167, and 168, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 169, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 170. In some embodiments, the antibody comprises heavy chain CDRs of SEQ ID NOS: 163, 164, and 165, and/or light chain CDRs of SEQ ID NOS: 166, 167, and 168, and further comprises a heavy chain variable region comprising the amino acid sequence of SEQ ID NO: 169. In some embodiments, the antibody comprises heavy chain CDRs of SEQ ID NOS: 163, 164, and 165, and/or light chain CDRs of SEQ ID NOS: 166, 167, and 168, and further comprises a light chain variable region comprising the amino acid sequence of SEQ ID NO: 170. In some embodiments, the antibody comprises heavy chain CDRs of SEQ ID NOS: 163, 164, and 165, and/or light chain CDRs of SEQ ID NOS: 166, 167, and 168, and further comprises a heavy chain variable region comprising the amino acid sequence of SEQ ID NO: 169, but with up to 5, such as 1, 2, 3, 4, or 5 amino acid substitutions, insertions, or deletions, in the heavy chain framework regions of SEQ ID NO: 169. In some embodiments, the antibody comprises heavy chain CDRs of SEQ ID NOS: 163, 164, and 165, and/or light chain CDRs of SEQ ID NOS: 166, 167, and 168, and further comprises a light chain variable region comprising the amino acid sequence of SEQ ID NO: 170, but with up to 5, such as 1, 2, 3, 4, or 5 amino acid substitutions, insertions, or deletions, in the light chain framework regions of SEQ ID NO: 170. In some embodiments, the antibody comprises a heavy chain variable region comprising the amino acid sequence of SEQ ID NO: 169 and a light chain variable region comprising the amino acid sequence of SEQ ID NO: 170, but with up to 5 amino acid substitutions, insertions, or deletions, such as 1, 2, 3, 4, or 5 amino acid substitutions, insertions, or deletions, in the framework regions of SEQ ID NO: 169 and/or SEQ ID NO: 170.

In some embodiments, the antibody comprises a heavy chain variable region comprising the amino acid sequence of SEQ ID NO: 169 and a light chain variable region comprising the amino acid sequence of SEQ ID NO: 170. In some embodiments, the antibody further comprises a heavy chain and/or a light chain constant region, for instance, as described in the section above. In some embodiments, the antibody comprises a human IgG constant region, such as a human $IgG_1$, $IgG_2$, $IgG_3$, or $IgG_4$. In other embodiments, the antibody comprises heavy chain CDRs of SEQ ID NOS: 163, 164, and 165, and/or the light chain CDRs of SEQ ID NOS: 166, 167, and 168, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 171. In some embodiments, the antibody comprises heavy chain CDRs of SEQ ID NOS: 163, 164, and 165, and/or light chain CDRs of SEQ ID NOS: 166, 167, and 168, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 172. In some embodiments, the antibody comprises heavy chain CDRs of SEQ ID NOS: 163, 164, and 165, and/or light chain CDRs of SEQ ID NOS: 166, 167, and 168, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 171, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 172. In some embodiments, the antibody comprises heavy chain CDRs of SEQ ID NOS: 163, 164, and 165, and/or light chain CDRs of SEQ ID NOS: 166, 167, and 168, and further comprises a heavy chain comprising the amino acid sequence of SEQ ID NO: 171. In some embodiments, the antibody comprises heavy chain CDRs of SEQ ID NOS: 163, 164, and 165, and/or light chain CDRs of SEQ ID NOS: 166, 167, and 168, and further comprises a light chain comprising the amino acid sequence of SEQ ID NO: 172. In some embodiments, the antibody comprises heavy chain CDRs of SEQ ID NOS: 163, 164, and 165, and/or light chain CDRs of SEQ ID NOS: 166, 167, and 168, and further comprises a heavy chain comprising the amino acid sequence of SEQ ID NO: 171, but with up to 5, such as 1, 2, 3, 4, or 5 amino acid substitutions, insertions, or deletions, in the heavy chain framework regions of SEQ ID NO: 171. In some embodiments, the antibody comprises heavy chain CDRs of SEQ ID NOS: 163, 164, and 165, and/or light chain CDRs of SEQ ID NOS: 166, 167, and 168, and further comprises a light chain comprising the amino acid sequence of SEQ ID NO: 172, but with up to 5, such as 1, 2, 3, 4, or 5 amino acid substitutions, insertions, or deletions, in the light chain framework regions of SEQ ID NO: 172. In some embodiments, the antibody comprises a heavy chain comprising the amino acid sequence of SEQ ID NO: 171 and a light chain comprising the amino acid sequence of SEQ ID NO: 172, but with up to 5 amino acid substitutions, insertions, or deletions, such as 1, 2, 3, 4, or 5 amino acid substitutions, insertions, or deletions, in the framework regions of SEQ ID NO: 171 and/or SEQ ID NO: 172.

In some aspects, the antibody recognizes the PFD portion of APOL1. In some aspects, the antibody recognizes wild-type APOL1 on the surface of podocytes. In some aspects, the antibody recognizes serum APOL1. In some aspects, the antibody blocks trypanolysis in an assay as described in the Examples herein. For example, in some aspects, the antibody blocks trypanolysis by at least 40% in such an assay. In some aspects, the antibody binds endogenous APOL1 on podocyte cells, such as by flow cytometry. In some aspects, the antibody does not significantly recognize APOL2. In some aspects, the antibody does not significantly recognize any of APOL2, APOL3, APOL4, or APOL6. Thus, in some aspects, the antibody may be used to distinguish APOL1 from other related proteins such as APOL2, APOL3, APOL4, and/or APOL6.

Antibody 5.17H8

In some aspects, the disclosure relates to an antibody comprising a heavy chain variable region and a light chain variable region, wherein the heavy chain variable region comprises an amino acid sequence comprising the heavy chain CDRs of the 5.17H8 antibody, comprising SEQ ID NOS: 173, 174, and 175. In some embodiments, the antibody comprises a heavy chain variable region and a light chain variable region, wherein the light chain variable region comprises an amino acid sequence comprising the light chain CDRs of the 5.17H8 antibody, comprising SEQ ID NOS: 176, 177, and 178. In some embodiments, the antibody comprises the heavy chain and the light chain CDRs of 5.17H8, comprising SEQ ID NOS: 173, 174, 175, 176, 177, and 178.

In some embodiments, the antibody comprises heavy chain CDRs of SEQ ID NOS: 173, 174, and 175, and/or the light chain CDRs of SEQ ID NOS: 176, 177, and 178, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 179. In some embodiments, the antibody comprises heavy chain CDRs of SEQ ID NOS: 173, 174, and 175, and/or light chain CDRs of SEQ ID NOS: 176, 177, and 178, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 180. In some embodiments, the antibody comprises heavy chain CDRs of SEQ ID NOS: 173, 174, and 175, and/or light chain CDRs of SEQ ID NOS: 176, 177, and 178, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 179, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 180. In some embodiments, the antibody comprises heavy chain CDRs of SEQ ID NOS: 173, 174, and 175, and/or light chain CDRs of SEQ ID NOS: 176, 177, and 178, and further comprises a heavy chain variable region comprising the amino acid sequence of SEQ ID NO: 179. In some embodiments, the antibody comprises heavy chain CDRs of SEQ ID NOS: 173, 174, and 175, and/or light chain CDRs of SEQ ID NOS: 176, 177, and 178, and further comprises a light chain variable region comprising the amino acid sequence of SEQ ID NO: 180. In some embodiments, the antibody comprises heavy chain CDRs of SEQ ID NOS: 173, 174, and 175, and/or light chain CDRs of SEQ ID NOS: 176, 177, and 178, and further comprises a heavy chain variable region comprising the amino acid sequence of SEQ ID NO: 179, but with up to 5, such as 1, 2, 3, 4, or 5 amino acid substitutions, insertions, or deletions, in the heavy chain framework regions of SEQ ID NO: 179. In some embodiments, the antibody comprises heavy chain CDRs of SEQ ID NOS: 173, 174, and 175, and/or light chain CDRs of SEQ ID NOS: 176, 177, and 178, and further comprises a light chain variable region comprising the amino acid sequence of SEQ ID NO: 180, but with up to 5, such as 1, 2, 3, 4, or 5 amino acid substitutions, insertions, or deletions, in the light chain framework regions of SEQ ID NO: 180. In some embodiments, the antibody comprises a heavy chain variable region comprising the amino acid sequence of SEQ ID NO: 179 and a light chain variable region comprising the amino acid sequence of SEQ ID NO: 180, but with up to 5 amino acid substitutions, insertions, or deletions, such as 1, 2, 3, 4, or 5 amino acid substitutions, insertions, or deletions, in the framework regions of SEQ ID NO: 179 and/or SEQ ID NO: 180.

In some embodiments, the antibody comprises a heavy chain variable region comprising the amino acid sequence of SEQ ID NO: 179 and a light chain variable region comprising the amino acid sequence of SEQ ID NO: 180. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 173, 174, and 175, and/or the light chain CDRs of SEQ ID NOS: 176, 177, and 178, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 181. In some embodiments, the antibody comprises heavy chain CDRs of SEQ ID NOS: 173, 174, and 175, and/or light chain CDRs of SEQ ID NOS: 176, 177, and 178, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 182. In some embodiments, the antibody comprises heavy chain CDRs of SEQ ID NOS: 173, 174, and 175, and/or light chain CDRs of SEQ ID NOS: 176, 177, and 178, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 181, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 182. In some embodiments, the antibody comprises heavy chain CDRs of SEQ ID NOS: 173, 174, and 175, and/or light chain CDRs of SEQ ID NOS: 176, 177, and 178, and further comprises a heavy chain comprising the amino acid sequence of SEQ ID NO: 181. In some embodiments, the antibody comprises heavy chain CDRs of SEQ ID NOS: 173, 174, and 175, and/or light chain CDRs of SEQ ID NOS: 176, 177, and 178, and further comprises a light chain comprising the amino acid sequence of SEQ ID NO: 182. In some embodiments, the antibody comprises heavy chain CDRs of SEQ ID NOS: 173, 174, and 175, and/or light chain CDRs of SEQ ID NOS: 176, 177, and 178, and further comprises a heavy chain comprising the amino acid sequence of SEQ ID NO: 181, but with up to 5, such as 1, 2, 3, 4, or 5 amino acid substitutions, insertions, or deletions, in the heavy chain framework regions of SEQ ID NO: 181. In some embodiments, the antibody comprises heavy chain CDRs of SEQ ID NOS: 173, 174, and 175, and/or light chain CDRs of SEQ ID NOS: 176, 177, and 178, and further comprises a light chain comprising the amino acid sequence of SEQ ID NO: 182, but with up to 5, such as 1, 2, 3, 4, or 5 amino acid substitutions, insertions, or deletions, in the light chain framework regions of SEQ ID NO: 182. In some embodiments, the antibody comprises a heavy chain comprising the amino acid sequence of SEQ ID NO: 181 and a light chain comprising the amino acid sequence of SEQ ID NO: 182, but with up to 5 amino acid substitutions, insertions, or deletions, such as 1, 2, 3, 4, or 5 amino acid substitutions, insertions, or deletions, in the framework regions of SEQ ID NO: 181 and/or SEQ ID NO: 182.

In some aspects, the antibody recognizes the PFD portion of APOL1. In some aspects, the antibody recognizes the PFD portion from amino acids 61-103. In some aspects, the antibody preferentially recognizes podocyte APOL1, for example by flow cytometry. In some aspects, the antibody specifically binds to wild-type APOL1 expressed on podocyte cells. In some aspects, the antibody does not significantly block trypanolysis in an assay as described in the Examples herein. For example, in some aspects, the antibody blocks trypanolysis by less than 20% in such an assay. Thus, in some aspects, the antibody may be used to distinguish podocyte APOL1 from serum APOL1. Additionally this antibody in some aspects recognizes APOL2, APOL3 and APOL4, but not APOL6 and thus can be used to distinguish APOL6 from the other family members.

Antibody 5.11H2

In some aspects, the disclosure relates to an antibody comprising a heavy chain variable region and a light chain variable region, wherein the heavy chain variable region comprises an amino acid sequence comprising the heavy chain CDRs of the 5.11H12 antibody, comprising SEQ ID NOS: 183, 184, and 185. In some embodiments, the antibody comprises a heavy chain variable region and a light chain variable region, wherein the light chain variable region comprises an amino acid sequence comprising the light chain CDRs of the 5.11H12 antibody, comprising SEQ ID NOS: 186, 187, and 188. In some embodiments, the antibody comprises the heavy chain and the light chain CDRs of 5.11H12, comprising SEQ ID NOS: 183, 184, 185, 186, 187, and 188.

In some embodiments, the antibody comprises heavy chain CDRs of SEQ ID NOS: 183, 184, and 185, and/or the light chain CDRs of SEQ ID NOS: 186, 187, and 188, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 189. In some embodiments, the antibody comprises heavy chain CDRs of SEQ ID NOS: 183, 184, and 185, and/or light chain CDRs of SEQ ID NOS: 186, 187, and 188, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 190. In some embodiments, the antibody comprises heavy chain CDRs of SEQ ID NOS: 183, 184, and 185, and/or light chain CDRs of SEQ ID NOS: 186, 187, and 188, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 189, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 190. In some embodiments, the antibody comprises heavy chain CDRs of SEQ ID NOS: 183, 184, and 185, and/or light chain CDRs of SEQ ID NOS: 186, 187, and 188, and further comprises a heavy chain variable region comprising the amino acid sequence of SEQ ID NO: 189. In some embodiments, the antibody comprises heavy chain CDRs of SEQ ID NOS: 183, 184, and 185, and/or light chain CDRs of SEQ ID NOS: 186, 187, and 188, and further comprises a light chain variable region comprising the amino acid sequence of SEQ ID NO: 190. In some embodiments, the antibody comprises heavy chain CDRs of SEQ ID NOS: 183, 184, and 185, and/or light chain CDRs of SEQ ID NOS: 186, 187, and 188, and further comprises a heavy chain variable region comprising the amino acid sequence of SEQ ID NO: 189, but with up to 5, such as 1, 2, 3, 4, or 5 amino acid substitutions, insertions, or deletions, in the heavy chain framework regions of SEQ ID NO: 189. In some embodiments, the antibody comprises heavy chain CDRs of SEQ ID NOS: 183, 184, and 185, and/or light chain CDRs of SEQ ID NOS: 186, 187, and 188, and further comprises a light chain variable region comprising the amino acid sequence of SEQ ID NO: 190, but with up to 5, such as 1, 2, 3, 4, or 5 amino acid substitutions, insertions, or deletions, in the light chain framework regions of SEQ ID NO: 190. In some embodiments, the antibody comprises a heavy chain variable region comprising the amino acid sequence of SEQ ID NO: 189 and a light chain variable region comprising the amino acid sequence of SEQ ID NO: 190, but with up to 5 amino acid substitutions, insertions, or deletions, such as 1, 2, 3, 4, or 5 amino acid substitutions, insertions, or deletions, in the framework regions of SEQ ID NO: 189 and/or SEQ ID NO: 190.

In some embodiments, the antibody comprises a heavy chain variable region comprising the amino acid sequence of SEQ ID NO: 189 and a light chain variable region comprising the amino acid sequence of SEQ ID NO: 190. In some embodiments, the antibody further comprises a heavy chain and/or a light chain constant region, for instance, as described in the section above. In some embodiments, the antibody comprises a human IgG constant region, such as a human IgG$_1$, IgG$_2$, IgG$_3$, or IgG$_4$. In other embodiments, the antibody comprises heavy chain CDRs of SEQ ID NOS: 183, 184, and 185, and/or the light chain CDRs of SEQ ID NOS: 186, 187, and 188, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 191. In some embodiments, the antibody comprises heavy chain CDRs of SEQ ID NOS: 183, 184, and 185, and/or light chain CDRs of SEQ ID NOS: 186, 187, and 188, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 192. In some embodiments, the antibody comprises heavy chain CDRs of SEQ ID NOS: 183, 184, and 185, and/or light chain CDRs of SEQ ID NOS: 186, 187, and 188, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 191, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 192. In some embodiments, the antibody comprises heavy chain CDRs of SEQ ID NOS: 183, 184, and 185, and/or light chain CDRs of SEQ ID NOS: 186, 187, and 188, and further comprises a heavy chain comprising the amino acid sequence of SEQ ID NO: 191. In some embodiments, the antibody comprises heavy chain CDRs of SEQ ID NOS: 183, 184, and 185, and/or light chain CDRs of SEQ ID NOS: 186, 187, and 188, and further comprises a light chain comprising the amino acid sequence of SEQ ID NO: 192. In some embodiments, the antibody comprises heavy chain CDRs of SEQ ID NOS: 183, 184, and 185, and/or light chain CDRs of SEQ ID NOS: 186, 187, and 188, and further comprises a heavy chain comprising the amino acid sequence of SEQ ID NO: 191, but with up to 5, such as 1, 2, 3, 4, or 5 amino acid substitutions, insertions, or deletions, in the heavy chain framework regions of SEQ ID NO: 191. In some embodiments, the antibody comprises heavy chain CDRs of SEQ ID NOS: 183, 184, and 185, and/or light chain CDRs of SEQ ID NOS: 186, 187, and 188, and further comprises a light chain comprising the amino acid sequence of SEQ ID NO: 192, but with up to 5, such as 1, 2, 3, 4, or 5 amino acid substitutions, insertions, or deletions, in the light chain framework regions of SEQ ID NO: 192. In some embodiments, the antibody comprises a heavy chain comprising the amino acid sequence of SEQ ID NO: 191 and a light chain comprising the amino acid sequence of SEQ ID NO: 192, but with up to 5 amino acid substitutions, insertions, or deletions, such as 1, 2, 3, 4, or 5 amino acid substitutions, insertions, or deletions, in the framework regions of SEQ ID NO: 191 and/or SEQ ID NO: 192.

In some aspects, the antibody recognizes the PFD portion of APOL1. In some aspects, the antibody recognizes the PFD portion from amino acids 61-103. In some aspects, the antibody preferentially recognizes podocyte APOL1. In some aspects, the antibody specifically binds to wild-type APOL1 expressed on podocyte cells. In some aspects, the antibody does not significantly block trypanolysis in an assay as described in the Examples herein. For example, in some aspects, the antibody blocks trypanolysis by less than 20% or less than 10% in such an assay. Thus, in some aspects, the antibody may be used to distinguish podocyte APOL1 from serum APOL1.

5.14D6 Antibody

In some aspects, the disclosure relates to an antibody comprising a heavy chain variable region and a light chain variable region, wherein the heavy chain variable region comprises an amino acid sequence comprising the heavy chain CDRs of the 5.14D6 antibody, comprising SEQ ID NOS: 193, 194, and 195. In some embodiments, the antibody comprises a heavy chain variable region and a light chain variable region, wherein the light chain variable region comprises an amino acid sequence comprising the light chain CDRs of the 5.14D6 antibody, comprising SEQ ID NOS: 196, 197, and 198. In some embodiments, the antibody comprises the heavy chain and the light chain CDRs of 5.14D6, comprising SEQ ID NOS: 193, 194, 195, 196, 197, and 198.

In some embodiments, the antibody comprises heavy chain CDRs of SEQ ID NOS: 193, 194, and 195, and/or the light chain CDRs of SEQ ID NOS: 196, 197, and 198, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 199. In some embodiments, the antibody comprises heavy chain CDRs of SEQ ID NOS: 193, 194, and 195, and/or light chain CDRs of SEQ ID NOS: 196, 197, and 198, and further comprises a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 200. In some embodiments, the antibody comprises heavy chain CDRs of SEQ ID NOS: 193, 194, and 195, and/or light chain CDRs of SEQ ID NOS: 196, 197, and 198, and further comprises a heavy chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 199, and a light chain variable region comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 200. In some embodiments, the antibody comprises heavy chain CDRs of SEQ ID NOS: 193, 194, and 195, and/or light chain CDRs of SEQ ID NOS: 196, 197, and 198, and further comprises a heavy chain variable region comprising the amino acid sequence of SEQ ID NO: 199. In some embodiments, the antibody comprises heavy chain CDRs of SEQ ID NOS: 193, 194, and 195, and/or light chain CDRs of SEQ ID NOS: 196, 197, and 198, and further comprises a light chain variable region comprising the amino acid sequence of SEQ ID NO: 200. In some embodiments, the antibody comprises heavy chain CDRs of SEQ ID NOS: 193, 194, and 195, and/or light chain CDRs of SEQ ID NOS: 196, 197, and 198, and further comprises a heavy chain variable region comprising the amino acid sequence of SEQ ID NO: 199, but with up to 5, such as 1, 2, 3, 4, or 5 amino acid substitutions, insertions, or deletions, in the heavy chain framework regions of SEQ ID NO: 199. In some embodiments, the antibody comprises heavy chain CDRs of SEQ ID NOS: 193, 194, and 195, and/or light chain CDRs of SEQ ID NOS: 196, 197, and 198, and further comprises a light chain variable region comprising the amino acid sequence of SEQ ID NO: 200, but with up to 5, such as 1, 2, 3, 4, or 5 amino acid substitutions, insertions, or deletions, in the light chain framework regions of SEQ ID NO: 200. In some embodiments, the antibody comprises a heavy chain variable region comprising the amino acid sequence of SEQ ID NO: 199 and a light chain variable region comprising the amino acid sequence of SEQ ID NO: 200, but with up to 5 amino acid substitutions, insertions, or deletions, such as 1, 2, 3, 4, or 5 amino acid substitutions, insertions, or deletions, in the framework regions of SEQ ID NO: 199 and/or SEQ ID NO: 200.

In some embodiments, the antibody comprises a heavy chain variable region comprising the amino acid sequence of SEQ ID NO: 199 and a light chain variable region comprising the amino acid sequence of SEQ ID NO: 200. In some embodiments, the antibody further comprises a heavy chain and/or a light chain constant region, for instance, as described in the section above. In some embodiments, the antibody comprises a human IgG constant region, such as a human $IgG_1$, $IgG_2$, $IgG_3$, or $IgG_4$. In other embodiments, the antibody comprises heavy chain CDRs of SEQ ID NOS: 193, 194, and 195, and/or the light chain CDRs of SEQ ID NOS: 196, 197, and 198, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 201. In some embodiments, the antibody comprises heavy chain CDRs of SEQ ID NOS: 193, 194, and 195, and/or light chain CDRs of SEQ ID NOS: 196, 197, and 198, and further comprises a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 202. In some embodiments, the antibody comprises heavy chain CDRs of SEQ ID NOS: 193, 194, and 195, and/or light chain CDRs of SEQ ID NOS: 196, 197, and 198, and further comprises a heavy chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 201, and a light chain comprising an amino acid sequence that is at least 90%, at least 91%, at least 92%, at least 93%, at least 94%, at least 95%, at least 96%, at least 97%, at least 98%, or at least 99% identical to the amino acid sequence of SEQ ID NO: 202. In some embodiments, the antibody comprises heavy chain CDRs of SEQ ID NOS: 193, 194, and 195, and/or light chain CDRs of SEQ ID NOS: 196, 197, and 198, and further comprises a heavy chain comprising the amino acid sequence of SEQ ID NO: 201. In some embodiments, the antibody comprises heavy chain CDRs of SEQ ID NOS: 193, 194, and 195, and/or light chain CDRs of SEQ ID NOS: 196, 197, and 198, and further comprises a light chain comprising the amino acid sequence of SEQ ID NO: 202. In some embodiments, the antibody comprises heavy chain CDRs of SEQ ID NOS: 193, 194, and 195, and/or light chain CDRs of SEQ ID NOS: 196, 197, and 198, and further comprises a heavy chain comprising the amino acid sequence of SEQ ID NO: 201, but with up to 5, such as 1, 2, 3, 4, or 5 amino acid substitutions, insertions, or deletions, in the heavy chain framework regions of SEQ ID NO: 201. In some embodiments, the antibody comprises heavy chain CDRs of SEQ ID NOS: 193, 194, and 195, and/or light chain CDRs of SEQ ID NOS: 196, 197, and 198, and further comprises a light chain comprising the amino acid sequence of SEQ ID NO: 202, but with up to 5, such as 1, 2, 3, 4, or 5 amino acid substitutions, insertions, or deletions, in the light chain framework regions of SEQ ID NO: 202. In some embodiments, the antibody comprises a heavy chain comprising the amino acid sequence of SEQ ID NO: 201 and a light chain comprising the amino acid sequence of SEQ ID NO: 202, but with up to 5 amino acid substitutions, insertions, or deletions, such as 1, 2, 3, 4, or 5 amino acid substitutions, insertions, or deletions, in the framework regions of SEQ ID NO: 201 and/or SEQ ID NO: 202.

In some aspects, the antibody recognizes the linker (L) portion of APOL1. In some aspects, the antibody recognizes APOL1 at residues 304-323. In some aspects, the antibody significantly blocks trypanolysis in an assay as described in the Examples herein. In some aspects, the antibody does not significantly recognize APOL1 on podocyte cells in assays described herein.

1. Antibody Affinity

In certain aspects, an antibody provided herein specifically binds to APOL1, indicating that it has a dissociation constant ($K_D$; affinity) of ≤1 μM for APOL1. In some aspects, the antibody may have an affinity for APOL1 of ≤100 nM or ≤10 nM.

In one aspect, $K_D$ can be measured using surface plasmon resonance. In one aspect, $K_D$ is measured using a BIA-CORE® surface plasmon resonance assay, such as a BIA-core™ T200 or BIAcore™ 8K assay. For example, an assay using a BIAcore™ 8K (BIAcore, Inc., Piscataway, NJ) can be performed at 25° C. or 37° C. with immobilized antibody on a protein A chip at ~300 response units (RU). Ten-fold serial dilutions of antigen are injected in FIBS-P buffer at 37° C. with a flow rate of 100 μL/min. Alternatively, ten-fold serial dilutions of antigen are injected in FIBS-P buffer at 25° C. with a flow rate of 30 μL/min. Association rates (ka) and dissociation rates (kd) are calculated using a 1:1 Langmuir binding model (for example, using BIAcore Insight Evaluation Software version 2.0). The equilibrium dissociation constant (KD) are calculated as the ratio kd/ka.

In an alternative method, $K_D$ is measured by a radiolabeled antigen binding assay (RIA). In one aspect, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 μM or 26 μM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed, and the plate washed eight times with 0.1% polysorbate 20 (TWEEN-20®) in PBS. When the plates have dried, 150 μl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

2. Antibody Fragments

In certain aspects, an antibody provided herein is an antibody fragment.

In one aspect, the antibody fragment is an Fv, single chain Fv, Fab, Fab', Fab'-SH, or $F(ab')_2$ fragment, in particular a Fab fragment. Papain digestion of intact antibodies produces two identical antigen-binding fragments, called "Fab" fragments containing each the heavy- and light-chain variable domains (VH and VL, respectively) and also the constant domain of the light chain (CL) and the first constant domain of the heavy chain (CH1). The term "Fab fragment" thus refers to an antibody fragment comprising a light chain comprising a VL domain and a CL domain, and a heavy chain fragment comprising a VH domain and a CH1 domain. "Fab' fragments" differ from Fab fragments by the addition of residues at the carboxy terminus of the CH1 domain including one or more cysteines from the antibody hinge region. Fab'-SH are Fab' fragments in which the cysteine residue(s) of the constant domains bear a free thiol group. Pepsin treatment yields an $F(ab')_2$ fragment that has two antigen-binding sites (two Fab fragments) and a part of the Fc region. For discussion of Fab and $F(ab')_2$ fragments comprising salvage receptor binding epitope residues and having increased in vivo half-life, see U.S. Pat. No. 5,869,046.

In another aspect, the antibody fragment is a diabody, a triabody or a tetrabody. "Diabodies" are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

In a further aspect, the antibody fragment is a single chain Fab fragment. A "single chain Fab fragment" or "scFab" is a polypeptide consisting of an antibody heavy chain variable domain (VH), an antibody heavy chain constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL. In particular, said linker is a polypeptide of at least 30 amino acids, preferably between 32 and 50 amino acids. Said single chain Fab fragments are stabilized via the natural disulfide bond between the CL domain and the CH1 domain. In addition, these single chain Fab fragments might be further stabilized by generation of interchain disulfide bonds via insertion of cysteine residues (e.g., position 44 in the variable heavy chain and position 100 in the variable light chain according to Kabat numbering).

In another aspect, the antibody fragment is single-chain variable fragment (scFv). A "single-chain variable fragment" or "scFv" is a fusion protein of the variable domains of the heavy (VH) and light chains (VL) of an antibody, connected by a linker. In particular, the linker is a short polypeptide of 10 to 25 amino acids and is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. For a review of scFv fragments, see, e.g., Plückthun, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458.

In another aspect, the antibody fragment is a single-domain antibody. "Single-domain antibodies" are antibody fragments comprising all or a portion of the heavy chain variable domain or all or a portion of the light chain variable domain of an antibody. In certain aspects, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as recombinant production by recombinant host cells (e.g., E. coli), as described herein.

3. Chimeric and Humanized Antibodies

In certain aspects, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain aspects, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which the CDRs (or portions thereof) are derived from a non-human antibody, and FRs (or portions thereof) are derived from human antibody sequences. A humanized antibody optionally will also comprise at least a portion of a human constant region. In some aspects, some FR residues in a humanized antibody are substituted with corresponding residues from a non-human antibody (e.g., the antibody from which the CDR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Multispecific Antibodies

In certain aspects, an antibody provided herein is a multispecific antibody, e.g., a bispecific antibody. "Multispecific antibodies" are monoclonal antibodies that have binding specificities for at least two different sites, i.e., different epitopes on different antigens or different epitopes on the same antigen. In certain aspects, the multispecific antibody has three or more binding specificities. In certain aspects, one of the binding specificities is for APOL1 and the other specificity is for any other antigen. In certain aspects, bispecific antibodies may bind to two (or more) different epitopes of an antigen. Multispecific antibodies may be prepared as full-length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)) and "knob-in-hole" engineering (see, e.g., U.S. Pat. No. 5,731,168, and Atwell et al., J. Mol. Biol. 270:26 (1997)). Nonlimiting exemplary knob-in-hole substitutions include T366W (knob) and T366S/L368A/Y407V (hole). In some embodiments, the knob-in-hole substitutions are in IgG$_1$ constant domains.

Multi-specific antibodies may also be made by engineering electrostatic steering effects for making antibody Fc-heterodimeric molecules. See, e.g., WO 2009/089004; Dillon et al., Mabs 9(2): 213-230 (2017). As a nonlimiting example, in a bispecific antibody comprising two heavy chain variable regions and two light chain variable regions, a first heavy chain variable region may comprise a Q39E substitution (Kabat numbering) and a first light chain variable region may comprise a Q38K substitution (Kabat numbering); and a second heavy chain variable region may comprise a Q39K substitution (Kabat numbering) and a second light chain variable region may comprise a Q38E substitution (Kabat numbering). In some embodiments, the Q39E/Q38K and Q39K/Q38E substitutions reduce mispairing of the heavy and light chains of the bispecific antibody. Similarly, a first heavy chain constant region may comprise a S183K substitution (EU numbering) and a first light chain constant region may comprise a V133E substitution (EU numbering), and the a second heavy chain constant region may comprise a S183E substitution (EU numbering) and a second light chain constant region may comprise a V133K substitution (EU numbering). In some embodiments, the S183K/V133E and S183E/V133K substitutions reduce mispairing of the heavy and light chains of the bispecific antibody.

In some embodiments, a bispecific antibody comprises Q39E/Q38K and Q39K/Q38E substitutions in the binding domains and S183K/V133E and S183E/V133K substitutions in the constant regions. In some embodiments, a bispecific antibody comprises both knob-in-hole substitutions and electrostatic substitutions. See, e.g., WO 2016/172485, which is incorporated by reference here in its entirety for any purpose.

Accordingly, in some embodiments, a multispecific antibody is provided, which comprises a) a first heavy chain/light chain pair binding to a first antigen which comprises a first heavy chain polypeptide (H1) and a first light chain polypeptide (L1), and b) a second heavy chain/light chain pair binding to a second antigen which comprises a second heavy chain polypeptide (H2) and a second light chain polypeptide (L2), wherein each H1 and H2 comprises a heavy chain variable domain (VH) and a heavy chain constant domain (CH1), and each L1 and L2 comprises a light chain variable domain (VL) and a light chain constant domain (CL); wherein the CH1 domain of H1 comprises an amino acid substitution at 5183 (EU numbering) and the CL domain of L1 comprises an amino acid substitution at V133 (EU numbering); and wherein the VH domain of H1 comprises an amino acid substitution at position Q39 and the VL domain of L1 comprises an amino acid substitutions at position Q38 and/or the VH domain of H2 comprises an amino acid substitutions at position Q39 and the VL domain of L2 comprises an amino acid substitution at position Q38 (all Kabat numbering). In some embodiments, the VH domain of H1 comprises an amino acid substitution at Q39 (Kabat numbering) and the VL domain of L1 comprises an amino acid substitution at Q38 (Kabat numbering). In some embodiments, the CH1 domain of H2 comprises an amino acid substitution at 5183 (EU numbering) and the CL domain of L2 comprises an amino acid substitution at V133 (EU numbering). In some embodiments, the VH domain of H2 further comprises an amino acid substitution at position Q39 and the VL domain of L2 further comprises an amino acid substitution at position Q38 (Kabat numbering). In some embodiments, the CH1 domain of H1 comprises a S183K mutation and CL of L1 comprises a V133E mutation, and CH1 of H2 comprises a S183E mutation and the CL domain of L2 comprises the V133K mutation. In some embodiments, the VH domain of H1 comprises a Q39E mutation, the VL domain of L1 comprises a Q38K mutation, the VH domain of H2 comprises a Q39K mutation and the VL domain of L2 comprises a Q38E mutation (all Kabat numbering).

Multi-specific antibodies may also be made by cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992) and WO 2011/034605); using the common light chain technology for circumventing the light chain mispairing problem (see, e.g., WO 98/50431); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g., Gruber et al., *J. Immunol.*, 152:5368 (1994)); and preparing trispecific antibodies as described, e.g., in Tutt et al. *J. Immunol.* 147: 60 (1991).

Engineered antibodies with three or more antigen binding sites, including for example, "Octopus antibodies", or DVD-Ig are also included herein (see, e.g., WO 2001/77342 and WO 2008/024715). Other examples of multispecific antibodies with three or more antigen binding sites can be found in WO 2010/115589, WO 2010/112193, WO 2010/136172, WO 2010/145792, and WO 2013/026831. The bispecific antibody or antigen binding fragment thereof also includes a "Dual Acting FAb" or "DAF" comprising an antigen binding site that binds to APOL1 as well as another different antigen (see, e.g., US 2008/0069820 and WO 2015/095539).

Multi-specific antibodies may also be provided in an asymmetric form with a domain crossover in one or more binding arms of the same antigen specificity, i.e. by exchanging the VH/VL domains (see e.g., WO 2009/080252 and WO 2015/150447), the CH1/CL domains (see e.g., WO 2009/080253) or the complete Fab arms (see e.g., WO 2009/080251, WO 2016/016299, also see Schaefer et al, PNAS, 108 (2011) 1187-1191, and Klein at al., MAbs 8 (2016) 1010-20). In one aspect, the multispecific antibody comprises a cross-Fab fragment. The term "cross-Fab fragment" or "xFab fragment" or "crossover Fab fragment" refers to a Fab fragment, wherein either the variable regions or the constant regions of the heavy and light chain are exchanged. A cross-Fab fragment comprises a polypeptide chain composed of the light chain variable region (VL) and the heavy chain constant region 1 (CH1), and a polypeptide chain composed of the heavy chain variable region (VH) and the light chain constant region (CL). Asymmetrical Fab arms can also be engineered by introducing charged or non-charged amino acid mutations into domain interfaces to direct correct Fab pairing. See e.g., WO 2016/172485.

Various further molecular formats for multispecific antibodies are known in the art and are included herein (see e.g., Spiess et al., Mol Immunol 67 (2015) 95-106).

Examples of bispecific antibody formats that may be useful for this purpose include, but are not limited to, the so-called "BiTE" (bispecific T cell engager) molecules wherein two scFv molecules are fused by a flexible linker (see, e.g., WO 2004/106381, WO 2005/061547, WO 2007/042261, and WO 2008/119567, Nagorsen and Bäuerle, Exp Cell Res 317, 1255-1260 (2011)); diabodies (Holliger et al., Prot Eng 9, 299-305 (1996)) and derivatives thereof, such as tandem diabodies ("TandAb"; Kipriyanov et al., J Mol Biol 293, 41-56 (1999)); "DART" (dual affinity retargeting) molecules which are based on the diabody format but feature a C-terminal disulfide bridge for additional stabilization (Johnson et al., J Mol Biol 399, 436-449 (2010)), and so-called triomabs, which are whole hybrid mouse/rat IgG molecules (reviewed in Seimetz et al., Cancer Treat Rev 36, 458-467 (2010)). Particular T cell bispecific antibody formats included herein are described in WO 2013/026833, WO 2013/026839, WO 2016/020309; Bacac et al., Oncoimmunology 5(8) (2016) e1203498.

5. Antibody Variants

In certain aspects, amino acid sequence variants of the antibodies provided herein are contemplated. For example, it may be desirable to alter the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain aspects, antibody variants having one or more amino acid substitutions are provided. Sites of interest for substitutional mutagenesis include the CDRs and FRs. Conservative substitutions are shown in Table 1 under the heading of "preferred substitutions". More substantial changes are provided in Table 1 under the heading of "exemplary substitutions", and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |

TABLE 1-continued

| Original Residue | Exemplary Substitutions | Preferred Substitutions |
|---|---|---|
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for a member of another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more. CDR residues are mutated and the variant antibodies displayed on phage and screened for a particular biological activity (e.g., binding affinity).

Alterations (e.g., substitutions) may be made in CDRs, e.g., to improve antibody affinity. Such alterations may be made in CDR "hotspots", i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some aspects of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain aspects, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in the CDRs. Such alterations may, for example, be outside of antigen contacting residues in the CDRs. In certain variant VH and VL sequences provided above, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex may be used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT (antibody directed enzyme prodrug therapy)) or a polypeptide which increases the serum half-life of the antibody.

6. Antibody Conjugates

In certain aspects, an antibody provided herein may be modified to contain additional protein or nonproteinaceous moieties. Moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide copolymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The invention also provides conjugates comprising an antibody herein conjugated (chemically bonded) to one or more therapeutic agents such as cytotoxic agents, drugs or radioactive isotopes. In one aspect, a conjugate is an antibody-drug conjugate (ADC) in which an antibody is conjugated to one or more therapeutic agents, for example. The antibody is typically connected to one or more therapeutic agents using linkers. An overview of ADC technology is set forth in Pharmacol Review 68:3-19 (2016).

Conjugates of an antibody and another agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO 94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., Cancer Res. 52:127-131 (1992); U.S. Pat. No. 5,208,020) may be used.

The conjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL, U.S.A).

B. Recombinant Methods and Compositions

Antibodies may be produced using recombinant methods and compositions, e.g., as described in U.S. Pat. No. 4,816,567. For these methods one or more isolated nucleic acid(s) encoding an antibody are provided.

In case of a native antibody or native antibody fragment two nucleic acids are required, one for the light chain or a fragment thereof and one for the heavy chain or a fragment thereof. Such nucleic acid(s) encode an amino acid sequence comprising the VL and/or an amino acid sequence comprising the VH of the antibody (e.g., the light and/or heavy chain(s) of the antibody). These nucleic acids can be on the same expression vector or on different expression vectors.

In case of a bispecific antibody with heterodimeric heavy chains four nucleic acids are required, one for the first light chain, one for the first heavy chain comprising the first heteromonomeric Fc-region polypeptide, one for the second light chain, and one for the second heavy chain comprising the second heteromonomeric Fc-region polypeptide. The four nucleic acids can be comprised in one or more nucleic acid molecules or expression vectors. Such nucleic acid(s) encode an amino acid sequence comprising the first VL and/or an amino acid sequence comprising the first VH including the first heteromonomeric Fc-region and/or an amino acid sequence comprising the second VL and/or an amino acid sequence comprising the second VH including the second heteromonomeric Fc-region of the antibody (e.g., the first and/or second light and/or the first and/or second heavy chains of the antibody). These nucleic acids can be on the same expression vector or on different expression vectors, normally these nucleic acids are located on two or three expression vectors, i.e. one vector can comprise more than one of these nucleic acids. Examples of these bispecific antibodies are CrossMabs (see, e.g., Schaefer, W. et al, PNAS, 108 (2011) 11187-1191). For example, one of the heteromonomeric heavy chain comprises the so-called "knob mutations" (T366W and optionally one of S354C or Y349C) and the other comprises the so-called "hole mutations" (T366S, L368A and Y407V and optionally Y349C or S354C) (see, e.g., Carter, P. et al., Immunotechnol. 2 (1996) 73) according to EU index numbering.

In one aspect, isolated nucleic acids encoding an antibody as used in the methods as reported herein are provided.

In one aspect, a method of making an antibody is provided, wherein the method comprises culturing a host cell comprising nucleic acid(s) encoding the antibody, as provided above, under conditions suitable for expression of the antibody, and optionally recovering the antibody from the host cell (or host cell culture medium).

For recombinant production of an antibody, nucleic acids encoding the antibody, e.g., as described above, are isolated and inserted into one or more vectors for further cloning and/or expression in a host cell. Such nucleic acids may be readily isolated and sequenced using conventional procedures (e.g., by using oligonucleotide probes that are capable of binding specifically to genes encoding the heavy and light chains of the antibody) or produced by recombinant methods or obtained by chemical synthesis.

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, NJ (2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized", resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of (glycosylated) antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells (as described, e.g., in Mather, J. P. et al., Annals N.Y. Acad. Sci. 383 (1982) 44-68); MRC 5 cells; and FS4 cells. Other useful mammalian host cell lines include Chinese hamster ovary (CHO) cells, including DHFR-CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, NJ (2004), pp. 255-268.

In one aspect, the host cell is eukaryotic, e.g., a Chinese Hamster Ovary (CHO) cell or lymphoid cell (e.g., Y0, NS0, Sp20 cell).

C. Assays

Anti-APOL1 antibodies provided herein may be identified, screened for, or characterized for their physical/chemical properties and/or biological activities by various assays.

In one aspect, an antibody of the invention is tested for its antigen binding activity, e.g., by known methods such as ELISA, Western blot, etc. Binding of antibodies to podocytes may be tested, for example, by in situ hybridization, immuno-histo chemistry (IHC), immunoprecipitation, flow cytometry, or Western blotting. To differentiate binding between podocytes and HDL particles, one may test binding using APOL1 in its native state, for example by flow cytometry or immunoprecipitation. After fixation and/or permeabilization or denaturation on a denaturing western blot, different APOL1 epitopes become exposed.

Binding of antibodies to APOL1 in serum, i.e. on HDL particles, may be tested, for example, by the assay described in the Examples herein that reports ability of the antibodies to block trypanolysis. This assay is described in more detail above and in the Examples. This assay can be used in a sample, for instance, to determine the extent to which APOL1 present is exposed on HDL particles.

Any of the above assays may also be combined, depending on the interest of the researcher.

D. Methods and Compositions for Diagnostics and Detection

In certain aspects, any of the antibodies provided herein is useful for detecting the presence of antigen such as APOL1 in a biological sample. The term "detecting" as used herein encompasses quantitative or qualitative detection. In certain aspects, a biological sample comprises a cell or tissue, such as a sample containing podocyte cells.

In certain aspects, the method comprises contacting the biological sample with an anti-APOL1 antibody as described herein under conditions permissive for binding of the antibody to APOL1, and detecting whether a complex is formed between the antibody and the antigen. Such method may be an in vitro or in vivo method. In certain aspects, detection methods involve determining expression of endogenous APOL1 associated with podocyte cells in a sample. For such assays, anti-APOL1 antibodies that distinguish APOL1 from other APOL forms such as one or more of APOL2, APOL3, APOL4, and APOL6 may be used, such as antibodies comprising the CDRs of 5.17D2, 4.17A5, 3.1C1 and 3.7D6. Other antibodies that do not distinguish these proteins, such as one with the CDRs of 3.6D12 or 5.17H8, might also be used in such an assay as controls. In some assays, antibodies that specifically bind to APOL1 on podocytes but do not significantly bind to APOL1 in serum or block trypanolysis as described herein may be used. In some assays, it may be desirable to determine if APOL1 G2 is present on podocytes by using an antibody that can distinguish between the G0 and G1 forms and the G2 form of APOL1, such as one with the CDRs of 4.11A10, 4.12E5, or 4.11H11. Assays used to detect APOL1 on podocytes may include, for example, flow cytometry, in situ hybridization (ISH), immunocytochemistry (IHC), immunoprecipitation, Western blots, and the like. In some aspects, a trypanolysis assay may be used as described herein to detect APOL1 found in serum, e.g. on HDL particles.

In certain aspects, labeled anti-APOL1 antibodies are provided for such assays. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In other aspects, the antibodies herein are not labeled, but are recognized, for example, through secondary antibodies that may incorporate labels or that may induce other molecules to change color or state, thus acting as labels.

E. Articles of Manufacture

In another aspect of the invention, an article of manufacture containing materials useful for diagnostic assays described above is provided. The article of manufacture may be a composition or kit comprising at least one of the antibodies herein stored for future use, e.g. lyophilized or in a liquid formulation comprising other ingredients such as buffers and stabilizers. The article of manufacture may further comprise other reagents useful in performing an assay with the antibody, such as labeling reagents. The article of manufacture may also comprise a container and a label on or associated with the container.

III. Examples

The following are examples of methods and compositions of the invention. It is understood that various other embodiments may be practiced, given the general description provided above.

Example 1: Domain-Specific Antibodies Reveal Differences in the Membrane Topologies of APOL1 in Serum and Podocytes Two variants of circulating APOL1 (Apolipoprotein L1), G1 and G2 protect against subspecies of *Trypanosoma brucei* infection, but concurrently confer a greater risk of chronic kidney disease. Little is known about the topology of APOL1 in HDL particles or on the podocyte cells affected in kidney disease. By generating antibodies along the length of APOL1, we identified which domains are exposed, finding differences between serum and podocyte surface APOL1 topologies. These are the first direct insights into APOL1 conformations in physiological settings and have implications for APOL1-targeted drugs for APOL1 nephropathies.

Circulating Apolipoprotein L1 (APOL1) is the lytic factor for trypanosomes, protecting from human sleeping sickness. Two common African variants of APOL1, G1 and G2, which evolved to protect against species of trypanosomes resistant to wild type, somehow predispose humans to certain chronic kidney diseases (CKD). However, the exact mechanism of APOL1-mediated kidney podocyte damage is still not clear, including its subcellular localization and whether it is related to its role in trypanolysis. 170 APOL1 domain-specific monoclonal antibodies were generated in order to map APOL1 topology in serum (HDL particles) and kidney podocytes by flow cytometry, immunoprecipitation, and trypanolysis assays, and generated APOL1 knockout podocytes to confirm antibody specificity. The results indicate that APOL1 is localized to the cell surface of kidney podocytes, with most of the pore-forming domain (PFD) and C-terminus of the Serum Resistance Associated-interacting domain (SRA-ID), but not the membrane-addressing domain (MAD), being exposed. By contrast, differential trypanolytic blocking activity reveals that the MAD is exposed in serum APOL1, with less of the PFD accessible. The gross topology of APOL1 either in serum or on podocytes was not detectably altered by low pH. The antibodies permitted examination of native APOL1 topology in physiologically relevant membranes, revealing it has a different conformation in serum than on the cell surface. The findings lend credence to the surface ion channel model for APOL1 risk variant-mediated podocyte injury, as well as providing domain accessibility information for designing APOL1-targeted therapeutics.

Apolipoprotein L1 (APOL1) is the component of human serum responsible for trypanolysis (refs. 1-3) and is the only member of APOL1-6 gene cluster (4-5) to have a signal sequence and hence be secreted into the circulation. Circulating APOL1 confers resistance to *Trypanosoma brucei brucei*, thus protecting humans against African sleeping sickness (1). APOL1 exists in two complexes with APOA1 and haptoglobin-related protein (HPR) in human serum: Trypanosome Lytic Factor1 (TLF1) is a lipoprotein particle (HDL3b), whereas TLF2 is lipid-poor but contains IgM (6-8). Upon internalization of TLF1/HDL particles into trypanosomes via the TbHpHb receptor (or of TLF2 independent of this receptor), APOL1 becomes inserted into the lysosomal membrane at low pH, leading to osmotic swelling and eventual trypanosome lysis (6, 9-12). APOL1 has three domains named for putative roles in trypanolysis: a pore forming domain (PFD), membrane addressing domain (MAD) and SRA-interacting domain (1). Two coding variants of APOL1 (G1 and G2) evolved to provide resistance against various sub-species of *T. brucei* (3, 11, 13), but these strongly associate with increased risk of chronic kidney disease in African diaspora (14-15). Kidney disease is thought to be caused by endogenous APOL1 variants in kidney podocytes (the cell type affected in APOL1 nephropathies) rather than circulating APOL1 (16-20). APOL1 is proposed to act as an ion channel in both trypanosomes and mammalian cells, but its location and the nature of the ion are still debated and it is unclear if the same mechanism operates in both species (21-22, 36). Additionally, little is known regarding the topology of APOL1 either in podocyte membranes or HDL particles. Furthermore, it has not been established whether endogenous APOL1 is found on the podocyte cell surface.

To better characterize both podocyte and serum-associated APOL1, we generated 170 antibodies to APOL1. We found different topologies for the two forms of APOL1 and identified regions that might be targetable by APOL1-binding drugs for APOL1 nephropathies.

Materials and Methods

Recombinant APOL1 Generation

His$_6$-APOL1 for immunization: Human APOL1 (NM_003661) aa 61-398 (to ensure all splice isoforms would be recognized) was sub-cloned with an N-terminal his$_6$ tag into a baculovirus intracellular expression vector (pBiNTH, Genentech) and expressed in 101 Sf9 cells. The cell pellet was washed with Tris buffer with protease and proteasome inhibitor MG132 then lysed with 1% Zwittergent 3-14 in Tris buffer with 2× Complete protease inhibitors (Roche 11836153001), plus proteasome inhibitor MG132. It was purified by a 3 ml NiNTA column followed by 5200 column. NiNTA buffer A and B contain 1% Zwittergent 3-14 and Complete protease inhibitors, while 5200 buffer contains 0.1% DDM (n-dodecyl β-D maltoside, Sigma). The 5200 fractions showed three major bands corresponding to full length and degradation products (FIGS. 10A,B), so an improved method with FLAG-APOL1 was used in future preps (see below). The eluted protein from four preps (each fractions B1-C1) was pooled formulated in 200 mM Arginine, 137 mM Succinate, 0.026% DDM, pH 5 and stored in aliquots at −80° C.

FLAG-APOL1 for trypanolysis assays: Human APOL1 (NM_003661) aa 61-398 ("full length") or truncation constructs aa 61-203, 92-321, 61-260 and 88-321 for antibody mapping (see FIGS. 20A-E) were sub-cloned into baculovirus intracellular expression vectors (pBiNTF, Genentech) resulting in N-terminal FLAG tags. The pellet from a 2 liter culture of Sf9 cells was resuspended in 50 mM Tris, 200 mM NaCl pH 7.5 (buffer B) with Complete protease inhibitors (Roche 11836153001) and microfluized. DDM (Anatrace D310 LA) was added to a final concentration of 1% and stirred at 4° C. for 3 h. Cell debris was removed by centrifugation (45 min at 50,000×g). FLAG-APOL1 was purified on a 5 ml anti-FLAG affinity column in buffer B, eluted with 100 mM acetate, 200 mM NaCl, then further purified on an 5200 column (FIG. 10C). The pH was quickly neutralized with 1.5 volume of 1M Tris pH 8.0. All buffers used contained 0.026% DDM and Complete protease inhibitors. The eluted protein fractions (19-21 for full length) were pooled and formulated in 50 mM Tris pH 7.5, 200 mM NaCl, 0.026% DDM. Aliquots were stored at −80° C.

APOL1 Mapping Peptides

Peptides (~20 mers) along the length of APOL1 (FIGS. 20A-E) were synthesized using standard solid-phase Fmoc chemistry and purified by reverse phase HPLC (23).

Antibody Generation

For the HTV (high pressure tail vein injection) DNA delivery method #1, 10 Balb/c mice were each immunized 6 times (50 μg biweekly) with APOL1-G1 or G2 cDNA in a pCAGG vector with mGM-CSF adjuvant (24). Method #2 used 5 Balb/c mice immunized 16 times with the same cDNAs delivered by GeneGun (0.3 μg biweekly) with mGM-CSF and pORFmoFlt3L adjuvant (25). For Method #3, 3 sets of 5 Balb/c mice were each immunized with his$_6$-APOL1-G0 with one of three protocols: a) 16 doses, 10 μg twice a week with RIBI adjuvant (resulting in the highest titers); b) 50 μg biweekly with CFA/IFA adjuvant, 7 doses; c) 10 μg twice a week with TLR cocktail, 16 times. For Method #4, six of the low titer mice from method #3 were boosted 6× with his$_6$-APOL1-G0 SRA-ID (aa 305-398) with RIBI adjuvant to enrich for SRA-ID binding antibodies. Over 15,000 IgG-positive hybridomas (as assessed by CloneDetect) were screened by standard ELISA on his$_6$-APOL1-G0 (data not shown) and the positive antibodies obtained from each immunization were given a prefix 1-4 indicating the immunization strategy used (summarized in Table 2A). Rabbit monoclonal production (Method #5) is described in the accompanying Example below.

Table 2A: Attempts to generate APOL1 variant-specific antibodies using APOL1-G1 and G2 cDNAs injected into mice were not very successful, yielding only four weakly APOL1-binding monoclonals that bound APOL1-G0 in addition to the variants (Method 1 & 2). Injection of protein (Methods 3-5) yielded better results (see above for details). See Example 2 below for details of rabbit monoclonal generation (Method #5). See FIGS. 10A-F for characterization of his$_6$-APOL1-G0. Abbreviations: HTV, hydrodynamic tail vein delivery; I.V., intravenous.

TABLE 2A

| a) | | | |
|---|---|---|---|
| Immunization Method (and Ab prefix) | Antigen | Method (host species) | ELISA-positive Antibodies |
| 1 | APOL1-G1 and G2 DNA | HTV (mouse) | 3 |
| 2 | APOL1-G1 and G2 DNA | GeneGun (mouse) | 1 |
| 3 | His$_6$-APOL1-G0 protein | I.V. (mouse) | 105 |
| 4 | His$_6$-APOL1-G0 protein + SRA-ID-G0 boost | I.V. (mouse) | 26 |
| 5 | His$_6$-APOL1-G0 protein | I.V. (rabbit) | 35 |

Antibody Cloning 35 murine antibodies, selected from each domain for either strong or no FACS signal on iAPOL1-CHO cells and/or ability to block trypanolysis, were selected for DNA cloning and expressed in CHO cells for scale-up and further analysis; the original hybridomas were discarded. The vector was a murine IgG$_2$a backbone with effectorless L234A, L235A, P329G (LALAPG) mutations as previously described (26-27). 22 of the cloned antibodies successfully recognized APOL1 by ELISA. A few of the top cloned murine antibodies were also reformatted with a rabbit or rat backbone. (See Example 2 below.)

Cell Lines

Stably APOL1 expressing CHO cells (iAPOL1-CHO) were generated by lentiviral infection. APOL1 cDNAs encoding sequence for G0 (ref sequence NM_003661) were cloned either as is (iAPOL1-CHO), or with an N-terminal gD epitope tag and a C-terminal GPI anchor sequence (gD-iAPOL1-GPI-CHO or truncation mutants thereof), into the pInducer20 vector and HEK-293 cells were infected to generate lentiviral stocks (28). CHO cells were infected with APOL1-expressing lentivirus and analyzed for expression by Western blotting and FACS.

Human immortal podocytes (AB 8/13) were obtained under license from Prof. Moin Saleem (29). They were grown at 33° C., feeding 2-3× a week with fresh growth medium: RPMI with 10% FBS (Seradigm IXL9/06807/

GEN), 1% glutamine (Genentech), 1% pen/strep (Gibco 15140-122), 1% ITS (insulin, transferrin, selenium; Gibco 41400-045).

To generate the APOL1 KO cell line, using the Zhang lab design tool described at the Website "crispr (dot) mit (dot) edu." (See also Haeussler, M.; Schonig, K.; Eckert, H.; Eschstruth, A.; Mianne, J.; Renaud, J. B.; Schneider-Maunoury, S.; Shkumatava, A.; Teboul, L.; Kent, J.; Joly, J. S.; Concordet, J. P., Evaluation of off-target and on-target scoring algorithms and integration into the guide RNA selection tool CRISPOR. Genome Biol 2016, 17 (1), 148.)

Guide RNAs were designed targeting exon 1 and exon 7 (FIGS. 12A-D) and synthesized by GenScript, since a simple indel strategy with a single gRNA failed. Custom plasmids designed to co-express Cas9-GFP and the paired guides in pUC_AIO_EF1T2cas9 vector were transfected into WT podocytes using Fugene™ 6 (Promega E2691). Transfectants were sorted into single cell clones based on GFP signal. 12 single cell clones, named for the guides used (2-3 clones each) were analyzed for loss of APOL1 protein by Western blotting. Four single cell clones were successfully knocked out, 89401-1, 89401-3, 90109-2 and 90111-1. Clone 89401-3 exhibited growth and morphological qualities similar to the parental podocyte population and was selected for in-depth characterization (data not shown).

For iAPOL1 (dox-inducible APOL1) podocytes, untagged APOL1 isoform A cDNA (Origene SC109941) was recloned into a custom dox-inducible PiggyBac vector (PB indu APOL1 T2 mCherry pgk puro, with mCherry removed) and co-transfected with PiggyBac transposase (pBO, Transposagen Biopharmaceuticals, Inc.) into APOL1 KO clone 89401-3 podocytes using GeneJuice (EMD Millipore 70967). Transfected cells were selected 48 h post transfection with 5 μg/ml puromycin for 2 weeks. Single cell clones were generated from pools of iAPOL1 expressing cells using limiting dilution. All clones were maintained at 33° C. in podocyte media as above except with tetracycline-free FBS (TaKaRa 631101) and 5 μg/ml puromycin (Clontech 631305).

JHH-1 (human hepatocellular carcinoma), 786-0 (human kidney adenocarcinoma) and HCC827 (human lung adenocarcinoma) cells were obtained from a Genentech, Inc. cell repository (which validates lines by STR analysis and checks for absence of *mycoplasma*) and grown in RPMI-1640, with 10% FBS, 1% HEPES and 2 mM glutamine.

Flow Cytometry

Cells were harvested with 5 mM EDTA in PBS, washed once with growth media and twice with PBS. Approximately $0.5 \times 10^6$/ml of cells resuspended in PBS were incubated with anti-APOL1 antibodies for 1 h on ice. Following two PBS washes, 2 μg/ml of Alexa488 anti-mouse or anti-rabbit (Invitrogen A11029 and A21206, respectively) was used for 1 h on ice for detection. Cells were washed twice in PBS and resuspended in PBS with 1 μg/ml propidium iodide. Signals were read in a FACSCalibur3 (Becton Dickinson), with the exception of FIG. 8A and FIG. 14, which used a FACSCelesta, and data was analyzed using FlowJo v8.4.5. Mean fluorescence intensities were plotted in PRISM v7 after subtraction of secondary antibody alone background. For low pH experiments, cells were incubated with the antibodies in the presence of PBS pH 7.0 or PBS pH 5.5 for an hour on ice and detected with secondary antibodies at neutral pH.

Western Blotting

Cell lysates were prepared using native RIPA (NP-40) lysis buffer (150 mM NaCl, 50 mM Tris pH 8, 1% NP-40, 1 mM PMSF and 1× Complete Protease Inhibitors (Roche 11836153001). Protein concentrations were determined using the BCA assay (Pierce 23225). Cell lysates were run on 4-12% Bis-Tris gels (Invitrogen NP03220) in MOPS buffer (Invitrogen NP0001) and transferred to nitrocellulose membranes using an iBLOT2. Precision Plus protein Kaleidoscope markers (BioRad #1610375) was used to determine molecular weights unless otherwise stated. Membranes blocked in 5% Skim Milk in TBST (Tris buffered saline with 0.1% Tween-20) were incubated with 1-2.5 μg/ml primary antibodies overnight at 4° C. Following three TBST washes, anti-mouse (GE Healthcare NA931V, 1:3000) or anti-rabbit HRP (Jackson 711-036-152, 1:8000) was added as secondary antibody. After 1 h, membranes were washed and protein detected using ECL prime (Amersham RPN2232) exposed to MR film (Kodak). Anti-actin HRP-conjugated antibody (clone 13E5, Cell Signaling Technologies 5125S at 1:5000) or calnexin (Abcam Ab22595 at 1:1000) was used as a loading control. For peptide mapping, 2 μl of 1 mM peptides in DMSO were boiled in 5× sample buffer and loaded on 10% Tris-Glycine gel and run using MES buffer. Cell pellets of Sf9 lysates were lysed in native RIPA (NP-40) lysis buffer and run on 10% Tris-Glycine gels.

Immunoprecipitation

Anti-APOL1 antibodies were conjugated to Dynabeads (ThermoFisher 14311D) as per the manufacturer's protocol. Briefly, 10 μg of each antibody was conjugated to 2 mg of Dynabeads overnight at 37° C. with rotation. Next day, unbound antibody was washed off and conjugated antibody was resuspended at a final concentration of 50 μg/ml. 2-5 μg of the conjugated antibody was incubated with 1 μl of undiluted human serum at 4° C. for 16 h in a total volume of 500 μl with PBS. Unbound serum was washed with 150 mM NaCl in PBS. Bound APOL1 was eluted with low pH glycine buffer (this was preferable to direct boiling to avoid elution of non-specifically bound proteins). Eluates were boiled in 5× sample buffer (Invitrogen 39000) and loaded on 4-12% Bis-Tris gels (Invitrogen NP03220). Immunoprecipitated APOL1 was detected by rabbit polyclonal APOL1 antibody (Proteintech 11486-2-AP, 1:1000) and ECL. APOA1 was detected with goat anti-APOA1 (Rockland 600-101-109), HPR was detected with 1 μg/ml rabbit anti-HPR (Millipore ABS 196) and ECL Prime. For low pH experiments, conjugated antibody was incubated with human serum at 4° C. for 1-2 h in presence of PBS pH 7.0 or pH 5.5.

Trypanosome Assay

*Trypanosoma brucei brucei* were obtained under MTA from ATCC and cultured in HMI-9 media containing IMDM (Genentech), heat-inactivated (56° C. for 30 min) FBS (Seradigm IXL9/06807/GEN), 1% serum plus (Sigma 14008C), HMI-9 (Genentech) and 1% hypoxanthine (Genentech). Trypanosome lysis was performed by treating $1 \times 10^5$ Trypanosomes with serial dilutions of NHS or recombinant APOL1 for 16 h in a total of 100 μl. Live cell read out was done by the Alamar Blue assay as per the manufacturer's protocol (30) (Thermo Fisher, DAL1100). Briefly 10 μl of Alamar Blue was added to each well, incubated at 37° C. for 4 h. Red fluorescence, indicating live trypanosomes, was measured on a SpectraMax fluorimeter powered by SoftMAX PRO with excitation at 530 nm and emission 590 nm. For the antibody blocking assay, 1% normal human serum was preincubated with 1-10 μg/ml of anti-APOL1 antibody or media at room temperature for 20 mins followed by addition of trypanosomes. After 16 h, the Alamar Blue assay was performed as above and background values for media only were subtracted and % blocking calculated by normalizing to no antibody control. Data were plotted in Prism v7. Normal Human serum was obtained from healthy volunteers at Genentech. Lipoprotein deficient serum (LPDS, depleted by ultracentrifugation) was commercially obtained from Kalen Biomedical (Cat #780100). KBr-density gradient purified HDL was obtained from Millipore (LP3-5MG).

Surface Plasmon Resonance (SPR) and Wasatch Binning

A 96×96 array-based SPR imaging system (Carterra USA) was used for epitope mapping of anti-ApoL1 monoclonal antibodies. Briefly, purified monoclonal hybridoma antibodies were diluted at 10 μg/ml in 10 mM sodium acetate buffer pH 4.5. Using amine coupling, antibodies were directly immobilized onto a SPR sensorprism CMD 200M chip (XanTec Bioanalytics, Germany) using a Continuous Flow Microspotter (Carterra, USA) to create an array of antibodies. After coupling, the antibodies were blocked with ethanolamine, and primed with running buffer (10 mM HEPES, pH 7.4, 150 mM NaCl, 3 mM EDTA, and 0.005% Tween 20). Epitope mapping was performed by flowing 100 nM of different peptides of APOL1 across the immobilized anti-APOL1 antibodies on the biosensor chip at 25° C. in a running buffer of 10 mM HEPES, pH 7.4, 150 mM NaCl, 3 mM EDTA, and 0.005% Tween 20. After each flow through of the APOL1 peptide, the chip surface was regenerated using 10 mM glycine, pH 2.0. The binding data was processed using the Wasatch binning software tool.

Anti-APOL1 Antibody Generation and Domain Specificity

Several approaches were taken to generate antibodies (Table 2A), the most successful being inoculation of trypanolytically-active his$_6$-tagged APOL1-G0 (wild type; FIGS. 10E-F). This yielded 135 mouse monoclonals (22 of which were successfully cloned) and 35 cloned rabbit monoclonals (see Example 2) that recognized the APOL1 antigen by ELISA (data not shown).

To test if the antibodies could recognize APOL1 expressed in cells, all 170 antibodies were tested by flow cytometry on CHO cells stably expressing doxycycline-inducible GPI-anchored WT-APOL1 (gD-iAPOL1-GPI-CHO; FIG. 1A). 150 (88%) antibodies recognized gD-APOL1-GPI (construct b) and 20 were FACS-negative (FIG. 11). Flow cytometry on CHO cells expressing truncated gD4APOL1-GPI constructs c-e mapped 81 antibodies to the PFD (aa 61-235; FIGS. 1F-G). This construct was further validated by the binding of the Proteintech polyclonal antibody raised specifically to the PFD (FIG. 1F). 10 antibodies mapped to the MAD, and 38 to the SRA-ID or linker (FIGS. 1F-G). The anti-APOL1 Sigma polyclonal and Epitomics rabbit monoclonal also bound the SRA-ID/linker. Four antibodies binding to all three domains were called multi-domain; and (17) that only bound to full length APOL1, but not individual domains, were labeled conformational. Thus, we obtained multiple antibodies to each domain of APOL1 (FIG. 1G).

APOL1 is Present on the Cell Surface

Whether APOL1 forms a chloride channel in the lysosome (12, 21, 32) or a cation channel at the plasma membrane is still debated (24,25). Since our antibodies recognized GPI-anchored gD-APOL1 expressed in CHO cells, we tested by flow cytometry whether non GPI-anchored untagged native full length APOL1 (construct a in iAPOL1-CHO cells) is also localized to the cell surface (FIG. 2A). Native APOL1 was indeed detected on the cell surface by the same 88% (150/170) of antibodies (FIG. 2A) as GPI-anchored gD-APOL1 (FIG. 2B). These antibodies encompassed all domains, suggesting that a significant portion of APOL1 is exposed, unlike typical multi-pass ion channels. Although the antibodies were raised against APOL1-G0, all SRA-ID binders also recognized APOL1-G1 (S342G and I384M) and all but seven recognized G2 (Δ388N/Δ389Y; FIG. 2C, 2D).

Surface expression in CHO cells was not merely a transfection artifact because most of our antibodies also detected endogenous APOL1 (FIG. 3A) on the surface of unpermeabilized immortalized human podocytes (26). Podocytes express low levels of endogenous APOL1, which increases after interferon gamma (IFNγ) treatment (FIG. 3E), as expected (27) but did not achieve the high levels observed in iAPOL1-CHO cells (FIGS. 3F, 3G). Most PFD antibodies detected endogenous APOL1 (FIG. 3B) similarly to in iAPOL1-CHO. However, most MAD and SRA-ID binders recognized podocytes notably less well than the iAPOL1-CHO cells (FIGS. 3C and 3D). Since podocytes are the target cells of APOL1-induced nephropathies, we focused our efforts on understanding APOL1 expression and topology in podocytes using our repertoire of antibodies.

Specificity of Antibodies Towards Podocyte Surface APOL1

To confirm the specificity of the APOL1 signals on the podocyte cell surface, we first knocked out endogenous APOL1 using CRISPR/Cas9 (FIGS. 12A-D). FACS and Western Blotting confirmed total loss of APOL1 (but not APOL2; FIGS. 4A, 4B). Importantly, no surface signal was detected with any of the anti-APOL1 antibodies (data shown for some antibodies only) by FACS (FIG. 4C), confirming that the surface signals in FIGS. 3A-G indeed represented APOL1. The observed lack of WT podocyte binding by several antibodies (FIGS. 3A-D) could have been due to low endogenous expression levels. Therefore, we reintroduced APOL1-G0 into the APOL1-KO podocytes under a doxycycline-inducible promoter (iAPOL1-G0 podocytes) to avoid false negatives. This afforded control of APOL1 protein levels in a doxycycline-dependent manner (FIG. 13C), resulting in a 10 to 100-fold increase in total and surface APOL1 compared to WT podocytes with or without IFNγ, respectively. Flow cytometry with the top antibodies showed overall similar binding patterns on WT podocytes and iAPOL1-G0 podocytes (FIG. 6A, 6B). However, although the PFD and SRA-ID antibodies bound more strongly to the higher expressing iAPOL1 podocytes, the MAD antibodies did not, despite a 100-fold upregulation of surface APOL1, suggesting the MAD may be inaccessible on the podocyte surface in both endogenous and overexpressed APOL1. As a control, permeabilized podocytes did stain with MAD antibodies (FIG. 14). Since most of the MAD antibodies were able to detect APOL1 on iAPOL1-CHO cells but failed to do so effectively in iAPOL1-G0 podocytes (FIG. 3C), this suggests that the MAD may be buried in the podocyte membrane, or perhaps more likely shielded by a human protein, since it is similarly poorly accessible in other human cell lines tested (FIG. 15).

Functional Activity of Anti-APOL1 Antibodies

To determine if there is similarly differential exposure of APOL1 domains in circulating APOL1, we took advantage of the proven functional activity of circulating APOL1 in mediating trypanosome lysis (12, 35, 36). We hypothesized that antibodies binding to accessible parts of serum APOL1 might inhibit APOL1-mediated lysis of *Trypanosoma brucei brucei* (FIG. 5A) and therefore measured the lysis blocking activity of the antibodies in order to determine which APOL1 domains were exposed. We first established a killing curve for normal human serum (NHS) using the Alamar Blue viability assay, achieving ~90%400% killing in 1%-10% NHS (FIG. 5B), which contained ~3.16±0.16 nM APOL1 (n=22) by a sandwich ELISA (data not shown). Lysis in this assay is likely mainly due to HDL-associated APOL1 because purified HDL was similarly active, while lipoprotein-deficient NHS was inactive (FIG. 5B). Trypanolytic blockade for all 170 antibodies was tested at 1 μg/ml with 1% NHS, resulting in 0 to 80% blocking (FIG. 5C). Interestingly, blocking was attained not only by antibodies to the SRA-ID (predicted based on the ability of SRA to inhibit trypanolysis of *T. b. rhodesiense*), but by antibodies to the PFD and MAD as well, agreeing with earlier reports that all three domains are required for trypanolysis or suggesting the antibodies mediate a conformational change in serum APOL1 (12, 29). Antibodies were classified as strong blockers (>60% blocking), medium blockers (26-59%) or non-blockers (<25%; FIG. 5C). The non-blockers presumably either did not recognize circulating APOL1, or bound a non-critical site. Blocking was highly sensitive to antibody concentration, with steep inhibitory curves and IC$_{50}$s of 0.4 nM-1 nM. (FIG. 16). Furthermore, all the blocking antibodies bound circulating APOL1 because they could immunoprecipitate it from NHS, while non-blockers failed to do so (FIGS. 5D and 17A-C). There was a strong correlation between blocking and binding to serum APOL1 (FIG. 5E), suggesting epitope exposure was the key determinant. The presence of blockers and non-blockers within each domain suggests that only certain regions are accessible in the circulation, the others perhaps buried in HDL particles or bound to other proteins. APOA1 as well as HPR co-immunoprecipitated with APOL1 (FIG. 5D and FIG. 17C), confirming that at least some APOL1 is in a complex with TLF1 or TLF2 rather than free (37). Efforts to demonstrate co- 6B), but not circulating APOL1 (as judged by lack of trypanolytic blockade, FIG. 6C) and vice versa. For example, most of the PFD binders (e.g., 5.17H8, 5.11H2, 3.6C2, 3.2A7, 3.2A7 and 3.2B11) recognized podocyte APOL1, but did not block or immunoprecipitate serum APOL1 (FIGS. 6A-C and 17A-C) (10). Conversely, 3.3B6 and 4.17A5 were among the top trypanolytic blockers, but recognized the podocyte surface relatively weakly. More notably, most of the MAD antibodies (4.6A9, 1.11G1 and 3.3A8) were strong blockers, despite low podocyte APOL1 detection (FIG. 6B,C) and strongly immunoprecipitated circulating APOL1 (FIG. 5D). Likewise, most SRA-ID binders (including antibodies against the linker region blocked well while showing little or no podocyte recognition (e.g. 3.7E8, 3.7B5), and the converse was true for 3.6H10. This implies there are distinct regions of APOL1 with differential accessibility on the podocyte surface versus circulating APOL1.

APOL1 Topology

To obtain a more detailed epitope map of the anti-APOL1 antibodies, we determined their binding to a panel of overlapping peptides spanning the entire length of APOL1 by surface plasmon resonance and western blotting, as well as western blotting also using Sf9 lysates expressing truncated APOL1 (examples in FIGS. 19A-B and 20A-E). The results and the resulting topology predictions are summarized in FIGS. 7A-B and rely heavily on the assumption that the three predicted transmembrane domains (22, 36, 38) are correct. (See Table 2B.)

TABLE 2B

| b) Transmembrane prediction program results | | | | | | |
|---|---|---|---|---|---|---|
| Model | # tm* | Tm1 | Tm2 | Tm3 | Tm4 | Fits FACS data? |
| DAS server | 3 | 177-197 | (183-222) | 338-353 | | Only if tm3 is a hairpin loop |
| DAS/cgi | 2 | 184-193 | 341-351 | | | No, MAD is not intracellular[#] and linker is exposed |
| TMHMM | 1 | 177-199 | | | | No, PFD and C-terminus are both exposed |
| TMpred | 2 | 177-196 | 332-353 | | | No, MAD is not intracellular[#] and linker is exposed |
| Tmpred | 4 | 177-196 | (212-230) | (257-276) | 332-353 | No, linker is exposed |
| SPLIT server | 3 | 175-196 | (200-224) | 338-354 | | Only if tm3 is a hairpin loop |

*The N-terminal signal sequence is not counted as a transmembrane domain
Parentheses indicate a weak tm prediction. *
[#]Although the MAD is not exposed in podocytes or other human cell lines, it is in CHO cells, thus we believe it is not intracellular or buried in the membrane, but instead bound to another protein in podocytes and other human cells, since it is unlikely that the transmembrane domains would fundamentally differ between species. See FIG. 9 for working model with 2 full transmembrane domains and hairpin (semi) loop for tm3.

immunoprecipitation of IgM (exclusive to TLF2) (7) failed due to anti-IgM antibody background. In summary, all the antibodies that recognized serum APOL1 were also able to block trypanolysis, irrespective of binding site.

Correlation Between Cell Surface and Circulating APOL1 Accessibility

Since trypanolytic blockade is a useful surrogate for serum APOL1 binding (FIG. 5E), we were effectively able to use the blocking data to compare the topologies of APOL1 in serum versus the cell surface. In iAPOL1-CHO cells there was no correlation of binding with trypanolytic blockade (FIG. 18) (7), suggesting differential domain accessibility in the two sources of APOL1.

More importantly, there were also differential APOL1 accessibilities between serum APOL1 and kidney disease-relevant podocytes (FIG. 18B). Some antibodies bound surface APOL1 in WT and iAPOL1 podocytes (FIG. 6A, In podocytes, the N- and C-termini are both exposed (FIGS. 7A-B), suggesting the presence of an even number of transmembrane domains, or more likely of two full transmembrane domains and one hairpin (i.e. semi-loop; Table 2B). The PFD is extracellular up to the first predicted transmembrane domain, with the two transmembrane domains assumed to be separated by a small intracellular loop (untestable since no antibodies were obtained to that peptide). The MAD is completely inaccessible, but exposed in CHO cells, hence we hypothesize it is obscured by a podocyte or human cell line specific protein (FIG. 15), assuming the transmembrane arrangement does not differ between species. The linker to the 3rd transmembrane domain is exposed, but the SRA-ID is only accessible after aa 376. Most so-called SRA-ID antibodies actually mapped to the linker (aa 306-339); of the nine true SRA-ID binders, eight were at the very C-terminus, seven of which did not bind APOL1-G2 (FIG. 2C). The other mapped to the preceding peptide, which is likely buried, in accordance with a predicted coiled coil (22).

By contrast in serum (presumably in HDL particles), the N-terminus of the PFD is buried up to aa 103 (as is region 111-150) and most of the MAD and start of the linker appear exposed. Assuming that the transmembrane domains are buried (untestable due to lack of antibodies), the remaining topology is similar to podocytes. However, we cannot exclude the possibility that the transmembrane domains could be exposed on the surface of HDL particles.

Low pH does not Affect APOL1 Topology

To further probe the topology of APOL1, we relied on prior knowledge that APOL1 requires a low pH-triggered conformational change to insert into artificial membranes or translocate from HDL to trypanosome lysosome membranes (purportedly via the MAD) (1, 21, 32) and attempted to determine if low pH would alter epitope exposure. iAPOL1-podocytes were therefore incubated with antibodies to each domain at acidic and neutral pH, but revealed no differences in binding (FIG. 8A), suggesting that a gross topology change does not occur on podocytes at acidic pH.

To test whether APOL1 is released from HDL at low pH, we attempted to immunoprecipitate it with non-blocking antibodies to each domain at pH 5.5, but without success (FIG. 8B). Furthermore, the blocking antibodies still pulled down APOA1 along with APOL1 at low pH (FIG. 8B). Both results suggest that APOL1 was not dissociated from HDL particles under these conditions, raising the question as to whether APOL1 dissociation from HDL particles is triggered by acidic pH alone.

Discussion of Results

We generated and characterized 170 monoclonal antibodies against APOL1 to examine the topology of APOL1 on the cell surface and in serum. Our findings demonstrate that APOL1 exhibits different topologies in serum versus on cell lines, implying that different reagents would be required to optimally target the two sources of APOL1.

To determine which domains of APOL1 are exposed in HDL particles, we screened all the antibodies for blockade of serum-mediated trypanolysis as a high-throughput proxy for recognition of serum APOL1. We found that every single antibody that could immunoprecipitate serum APOL1 was a trypanolytic blocker, irrespective of binding site. While it remains to be determined at which step this blockade occurs, the abundance of blocking antibodies suggests that they may simply cause or prevent conformational changes in APOL1. In some aspects, antibodies herein may provide an important tool to study the role of circulating APOL1 in vivo.

Our data reveal differences in the conformation of APOL1 between podocytes and serum, although the topology of APOL1 in the trypanosome lysosome may differ to that in HDL. Other differences between trypanolytic and podocyte APOL1 are that only the risk variants are toxic to mammalian cells (39, 40, 19) and homozygosity increases the risk for development of CKD (14-15, 41). The proposed mechanisms for endogenous APOL1 cytotoxicity are varied and conflicting (33) it being unclear even if cytotoxicity occurs intracellularly or at the cell surface. Our data provide evidence that APOL1 is at the podocyte cell surface, potentially supporting the cell surface cation channel model (32, 39, 42). However, the extensive exposure of APOL1 and predicted low number of transmembrane domains (2-4) clearly differs from typical ion channels with >6 transmembrane domains and few extracellular residues (43).

Our podocyte topology model predicts extracellular exposure of most of APOL1 except the transmembrane domains and adjacent residues and the MAD. The MAD is extracellular in CHO cells but obscured in podocytes, as well other endogenously expressing human cell lines tested, putatively obstructed by a human-specific binding partner (FIG. 9A and FIG. 15). Interestingly, the benign G1 I384M and G2 deletion in the SRA-ID are exposed in APOL1, whereas the pathogenic G1 S342G substitution is predicted to be in the putative 3rd transmembrane domain, although the absence of antibodies to that epitope precludes evaluation of its accessibility. It remains unclear whether the hidden epitopes are truly embedded in the membrane or merely inaccessible due to orientation or other protein binding. The BH3-only domain in the PFD (aa 158-166) bears homology to other BH3-only proteins but its role in apoptosis and autophagy remains disputed (44-45). Since this epitope (3.7D6) is clearly exposed (i.e. luminal) rather than cytoplasmic like BH3-domain interacting proteins, we think it unlikely to play a role in apoptosis or autophagy. In many voltage-gated potassium channels, the ion-conducting pore is comprised of four units of two transmembrane helices with an extracellular loop. For APOL1 we speculate that at least two APOL1 molecules need to oligomerize, perhaps with the PFD transmembrane regions forming the pore, similar to the low pH model proposed by Bruno et al, which predicted a pH and membrane-dependent conformational change in the region 94-169 as regulating the cation selectivity of the channel (21). We agree that this domain is extracellular, but could not detect any pH-dependent changes in overall topology. This might be because APOL1 has already been subjected to a low pH compartment (possibly the Golgi) (46) en route to the plasma membrane, in which it is clearly embedded. However, minor conformational changes that might indicate ion channel closing or opening would not necessarily be detectable.

In serum APOL1, in contrast with podocytes, most of the PFD is inaccessible, potentially buried in the TLF particles or folded onto itself, while the MAD is mainly exposed (FIG. 9B, 9C). Note, however, that not all the blocking antibodies were mappable, thus it is possible that more regions are exposed than currently predicted. The topology differences could be due to differential protein-lipid interactions between bilayered podocytes and monolayered lipoprotein particles. Our data imply that the MAD may not be the HDL-binding region as proposed earlier (1, 12) but rather the PFD and/or initial part of the SRA-ID, quite possibly the three predicted transmembrane domains; however, the absence of antibodies to these hydrophobic regions precludes a definitive answer. The C-terminus of the SRA-ID (376-398) is exposed in HDL, in agreement with its ability to bind SRA and the inability of the G2 variant (ΔN388/Y389) to do so; however we could not determine if S342G in G1 is exposed (15, 47). An important caveat is that we cannot distinguish whether our antibodies block TLF1 (HDL3b) or lipid-poor TLF2 complexes with IgM, which may well have different topologies. Both complexes contain APOA1 and HPR (48), which co-immunoprecipitated with the blocking APOL1 antibodies.

In summary, we have shown that native APOL1 is present on the cell surface of cultured podocytes and stably transfected CHO cells and hence is correctly located to form surface ion channels, albeit with atypical topology. More importantly, APOL1 has different conformations on the cell surface and in the circulation, meaning that not all APOL1-binding agents will bind both sources of APOL1. Testing if the proposed APOL1-suPAR interaction in podocytes (49) is blocked by any of our antibodies might provide clues as to the currently unknown source of APOL1 in this interaction.

While our antibodies could potentially target circulating APOL1, they would probably not cross the glomerular filtration barrier to access podocyte APOL1, at least in IgG format.

Details of Antibody Domain Mapping

Since any one given method was not optimal for all the antibodies tested, data from different approaches were combined to understand antibody domains. For brevity, "binders" refer to podocyte FACS positive antibodies, while "blockers" refer to trypanolysis blockers (i.e. serum APOL1 binders). Because our immunogen lacked the first 60 aa, there were of course no antibodies to this region. In the PFD, two binding non-blockers and weak blocker (5.11H2 and 5.17H8 mapped to aa 61-92 (FIG. 20E), implying that this region is exposed in podocytes but not in serum APOL1 (FIGS. 7A-B). Furthermore, two of the top blockers, 3.6D12 and 3.7D6, also good podocyte binders, mapped to 2 distinct regions, between aa 101-130 and 151-172 (FIGS. 19A and 20B). Most of our other antibodies recognizing region 111-150 were non-blockers and weak binders (FIGS. 18A-B) with the exception of three antibodies. No antibodies mapped to aa 170-240, we speculate perhaps because the two predicted transmembrane domains (aa 177-196 and 204-224) (22) may have been buried in the antigen.

Only 4 MAD binders were successfully cloned: three blocking non-binders mapping to the C-terminal half of the MAD (aa 260-305), indicating that this region is exposed in serum but not on podocytes. By contrast 4.12F4 and 3.5H9 (which could not be cloned) mapped to the N-terminus of the MAD (235-260), but were negative for both binding and blocking, suggesting this domain may be buried in both cases. Thus, the whole MAD is buried in podocytes, but the C-terminal portion is exposed in serum.

Most SRA-ID binders actually mapped to the linker region between the MAD and SRA-ID (aa 306-339), only nine recognizing the SRA-ID proper, seven of which don't recognize APOL1-G2 (FIG. 2C,D) and indeed mapped to the very C-terminal peptide (aa 376-398). 4.29C4, which failed to bind or block, bound to peptide 364-385, suggesting this region is buried, in accordance with a predicted coiled coil there (22). Of the linker domain antibodies, all those adjacent to the MAD (aa 284-313) recognized only serum APOL1. Three antibodies mapping to aa 314-333 were able to bind and block, while 2 weak/non-binding blockers mapped to aa 324-333. Thus, most of the linker (aa 303-330) is exposed in serum APOL1, but aa 306-313 is inaccessible in podocytes. However, the very C-terminus of the SRA-ID is readily accessible in both serum and surface APOL1. Due to lack of antibodies to other regions of APOL1 we cannot confidently predict the complete topology of APOL1, but assuming the three predicted transmembrane domain regions are correct (22). A working model is presented in FIGS. 9A-C.

Amino acid sequences for antibodies whose sequences were obtained are provided in the Sequence Table further below.

References for Example 1

1. Pays, E.; Vanhollebeke, B.; Vanhamme, L.; Paturiaux-Hanocq, F.; Nolan, D. P.; Perez-Morga, D., The trypanolytic factor of human serum. *Nat Rev Microbiol* 2006, 4 (6), 477-86.

2. Samanovic, M.; Molina-Portela, M. P.; Chessler, A. D.; Burleigh, B. A.; Raper, J., Trypanosome lytic factor, an antimicrobial high-density lipoprotein, ameliorates *Leishmania* infection. *PLoS Pathog* 2009, 5 (1), e1000276.

3. Vanhamme, L.; Paturiaux-Hanocq, F.; Poelvoorde, P.; Nolan, D. P.; Lins, L.; Van Den Abbeele, J.; Pays, A.; Tebabi, P.; Van Xong, H.; Jacquet, A.; Moguilevsky, N.; Dieu, M.; Kane, J. P.; De Baetselier, P.; Brasseur, R.; Pays, E., Apolipoprotein L-I is the trypanosome lytic factor of human serum. *Nature* 2003, 422 (6927), 83-7.

4. Duchateau, P. N.; Pullinger, C. R.; Cho, M. H.; Eng, C.; Kane, J. P., Apolipoprotein L gene family: tissue-specific expression, splicing, promoter regions; discovery of a new gene. *J Lipid Res* 2001, 42 (4), 620-30.

5. Page, N. M.; Butlin, D. J.; Lomthaisong, K.; Lowry, P. J., The human apolipoprotein L gene cluster: identification, classification, and sites of distribution. *Genomics* 2001, 74 (1), 71-8.

6. Hajduk, S. L.; Hager, K.; Esko, J. D., High-density lipoprotein-mediated lysis of trypanosomes. *Parasitol Today* 1992, 8 (3), 95-8.

7. Raper, J.; Fung, R.; Ghiso, J.; Nussenzweig, V.; Tomlinson, S., Characterization of a novel trypanosome lytic factor from human serum. *Infect Immun* 1999, 67 (4), 1910-6.

8. Hajduk, S. L.; Moore, D. R.; Vasudevacharya, J.; Siqueira, H.; Torri, A. F.; Tytler, E. M.; Esko, J. D., Lysis of *Trypanosoma brucei* by a toxic subspecies of human high density lipoprotein. *J Biol Chem* 1989, 264 (9), 5210-7.

9. Bishop, J. R.; Shimamura, M.; Hajduk, S. L., Insight into the mechanism of trypanosome lytic factor-1 killing of *Trypanosoma brucei brucei*. *Mol Biochem Parasitol* 2001, 118 (1), 33-40.

10. Drain, J.; Bishop, J. R.; Hajduk, S. L., Haptoglobin-related protein mediates trypanosome lytic factor binding to trypanosomes. *J Biol Chem* 2001, 276 (32), 30254-60.

11. Oli, M. W.; Cotlin, L. F.; Shiflett, A. M.; Hajduk, S. L., Serum resistance-associated protein blocks lysosomal targeting of trypanosome lytic factor in *Trypanosoma brucei*. *Eukaryot Cell* 2006, 5 (1), 132-9.

12. Perez-Morga, D.; Vanhollebeke, B.; Paturiaux-Hanocq, F.; Nolan, D. P.; Lins, L.; Homble, F.; Vanhamme, L.; Tebabi, P.; Pays, A.; Poelvoorde, P.; Jacquet, A.; Brasseur, R.; Pays, E., Apolipoprotein L-I promotes trypanosome lysis by forming pores in lysosomal membranes. *Science* 2005, 309 (5733), 469-72.

13. Cooper, A.; Ilboudo, H.; Alibu, V. P.; Ravel, S.; Enyaru, J.; Weir, W.; Noyes, H.; Capewell, P.; Camara, M.; Milet, J.; Jamonneau, V.; Camara, O.; Matovu, E.; Bucheton, B.; MacLeod, A., APOL1 renal risk variants have contrasting resistance and susceptibility associations with African trypanosomiasis. *Elife* 2017, 6.

14. Tzur, S.; Rosset, S.; Shemer, R.; Yudkovsky, G.; Selig, S.; Tarekegn, A.; Bekele, E.; Bradman, N.; Wasser, W. G.; Behar, D. M.; Skorecki, K., Missense mutations in the APOL1 gene are highly associated with end stage kidney disease risk previously attributed to the MYH9 gene. *Hum Genet* 2010, 128 (3), 345-50.

15. Genovese, G.; Friedman, D. J.; Ross, M. D.; Lecordier, L.; Uzureau, P.; Freedman, B. I.; Bowden, D. W.; Langefeld, C. D.; Oleksyk, T. K.; Uscinski Knob, A. L.; Bernhardy, A. J.; Hicks, P. J.; Nelson, G. W.; Vanhollebeke, B.; Winkler, C. A.; Kopp, J. B.; Pays, E.; Pollak, M. R., Association of trypanolytic ApoL1 variants with kidney disease in African Americans. *Science* 2010, 329 (5993), 841-5.

16. Freedman, B. I.; Limou, S.; Ma, L.; Kopp, J. B., APOL1-Associated Nephropathy: A Key Contributor to Racial Disparities in CKD. *Am J Kidney Dis* 2018, 72 (5S1), S8-S16.

139    140

17. Santoriello, D.; Husain, S. A.; De Serres, S. A.; Bomback, A. S.; Crew, R. J.; Vasilescu, E. R.; Serban, G.; Campenot, E. S.; Kiryluk, K.; Mohan, S.; Hawkins, G. A.; Hicks, P. J.; Cohen, D. J.; Radhakrishnan, J.; Stokes, M. B.; Markowitz, G. S.; Freedman, B. I.; D'Agati, V. D.; Batal, I., Donor APOL1 high-risk genotypes are associated with increased risk and inferior prognosis of de novo collapsing glomerulopathy in renal allografts. *Kidney Int* 2018, 94 (6), 1189-1198.

18. Freedman, B. I.; Pastan, S. O.; Israni, A. K.; Schladt, D.; Julian, B. A.; Gautreaux, M. D.; Hauptfeld, V.; Bray, R. A.; Gebel, H. M.; Kirk, A. D.; Gaston, R. S.; Rogers, J.; Farney, A. C.; Orlando, G.; Stratta, R. J.; Mohan, S.; Ma, L.; Langefeld, C. D.; Bowden, D. W.; Hicks, P. J.; Palmer, N. D.; Palanisamy, A.; Reeves-Daniel, A. M.; Brown, W. M.; Divers, J., APOL1 Genotype and Kidney Transplantation Outcomes From Deceased African American Donors. *Transplantation* 2016, 100 (1), 194-202.

19. Beckerman, P.; Bi-Karchin, J.; Park, A. S.; Qiu, C.; Dummer, P. D.; Soomro, I.; Boustany-Kari, C. M.; Pullen, S. S.; Miner, J. H.; Hu, C. A.; Rohacs, T.; Inoue, K.; Ishibe, S.; Saleem, M. A.; Palmer, M. B.; Cuervo, A. M.; Kopp, J. B.; Susztak, K., Transgenic expression of human APOL1 risk variants in podocytes induces kidney disease in mice. *Nat Med* 2017, 23 (4), 429-438.

20. Aghajan, M.; Booten, S. L.; Althage, M.; Hart, C. E.; Ericsson, A.; Maxvall, I.; Ochaba, J.; Menschik-Lundin, A.; Hartleib, J.; Kuntz, S.; Gattis, D.; Ahlstrom, C.; Watt, A. T.; Engelhardt, J. A.; Monia, B. P.; Magnone, M. C.; Guo, S., Antisense oligonucleotide treatment ameliorates IFN-gamma-induced proteinuria in APOL1-transgenic mice. *JCI Insight* 2019, 4 (12).

21. Bruno, J.; Pozzi, N.; Oliva, J.; Edwards, J. C., Apolipoprotein L1 confers pH-switchable ion permeability to phospholipid vesicles. *J Biol Chem* 2017, 292 (44), 18344-18353.

22. Thomson, R.; Genovese, G.; Canon, C.; Kovacsics, D.; Higgins, M. K.; Carrington, M.; Winkler, C. A.; Kopp, J.; Rotimi, C.; Adeyemo, A.; Doumatey, A.; Ayodo, G.; Alper, S. L.; Pollak, M. R.; Friedman, D. J.; Raper, J., Evolution of the primate trypanolytic factor APOL1. *Proc Natl Acad Sci USA* 2014, 111 (20), E2130-9.

23. Chan, W. C.; White, P. D., *Fmoc solid phase peptide synthesis: a practical approach*. Oxford University Press: New York, 2000; p xxiv, 346 p.

24. Hazen, M.; Bhakta, S.; Vij, R.; Randle, S.; Kallop, D.; Chiang, V.; Hotzel, I.; Jaiswal, B. S.; Ervin, K. E.; Li, B.; Weimer, R. M.; Polakis, P.; Scheller, R. H.; Junutula, J. R.; Hongo, J. A., An improved and robust DNA immunization method to develop antibodies against extracellular loops of multi-transmembrane proteins. *MAbs* 2014, 6 (1), 95-107.

25. Vij, R.; Lin, Z.; Schneider, K.; Seshasayee, D.; Koerber, J. T., Analysis of the effect of promoter type and skin pretreatment on antigen expression and antibody response after gene gun-based immunization. *PLoS One* 2018, 13 (6), e0197962.

26. Lo, M., Kim, H. S., Tong, R. K., Bainbridge, T. W., Vernes, J. M., Zhang, Y., Lin, Y. L., Chung, S., Dennis, M. S., Zuchero, Y. J., Watts, R. J., Couch, J. A., Meng, Y. G., Atwal, J. K., Brerski, R. J., Spiess, C., and Ernst, J. A. (2017) Effector-attenuating Substitutions That Maintain Antibody Stability and Reduce Toxicity in Mice. J Biol Chem 292, 3900-3908.

27. Schlothauer, T., Herter, S., Koller, C. F., Grau-Richards, S., Steinhart, V., Spick, C., Kubbies, M., Klein, C., Umana, P., and Mossner, E. (2016) Novel human IgG$_1$ and IgG$_4$ Fc-engineered antibodies with completely abolished immune effector functions. Protein Eng Des Sel 29, 457-466

28. Meerbrey, K. L.; Hu, G.; Kessler, J. D.; Roarty, K.; Li, M. Z.; Fang, J. E.; Herschkowitz, J. I.; Burrows, A. E.; Ciccia, A.; Sun, T.; Schmitt, E. M.; Bernardi, R. J.; Fu, X.; Bland, C. S.; Cooper, T. A.; Schiff, R.; Rosen, J. M.; Westbrook, T. F.; Elledge, S. J., The pINDUCER lentiviral toolkit for inducible RNA interference in vitro and in vivo. *Proc Natl Acad Sci USA* 2011, 108 (9), 3665-70.

29. Saleem, M. A.; O'Hare, M. J.; Reiser, J.; Coward, R. J.; Inward, C. D.; Farren, T.; Xing, C. Y.; Ni, L.; Mathieson, P. W.; Mundel, P., A conditionally immortalized human podocyte cell line demonstrating nephrin and podocin expression. *J Am Soc Nephrol* 2002, 13 (3), 630-8.

30. Raz, B.; Iten, M.; Grether-Buhler, Y.; Kaminsky, R.; Brun, R., The Alamar Blue assay to determine drug sensitivity of African trypanosomes (*T. b. rhodesiense* and *T. b. gambiense*) in vitro. *Acta Trop* 1997, 68 (2), 139-47.

31. Lan, X.; Jhaveri, A.; Cheng, K.; Wen, H.; Saleem, M. A.; Mathieson, P. W.; Mikulak, J.; Aviram, S.; Malhotra, A.; Skorecki, K.; Singhal, P. C., APOL1 risk variants enhance podocyte necrosis through compromising lysosomal membrane permeability. *Am J Physiol Renal Physiol* 2014, 307 (3), F326-36.

32. Thomson, R.; Finkelstein, A., Human trypanolytic factor APOL1 forms pH-gated cation-selective channels in planar lipid bilayers: relevance to trypanosome lysis. *Proc Natl Acad Sci USA* 2015, 112 (9), 2894-9.

33. Olabisi, O. A.; Heneghan, J. F., APOL1 Nephrotoxicity: What Does Ion Transport Have to Do With It? *Semin Nephrol* 2017, 37 (6), 546-551.

34. Nichols, B.; Jog, P.; Lee, J. H.; Blackler, D.; Wilmot, M.; D'Agati, V.; Markowitz, G.; Kopp, J. B.; Alper, S. L.; Pollak, M. R.; Friedman, D. J., Innate immunity pathways regulate the nephropathy gene Apolipoprotein L1. *Kidney Int* 2015, 87 (2), 332-42.

35. Cooper, A.; Capewell, P.; Clucas, C.; Veitch, N.; Weir, W.; Thomson, R.; Raper, J.; MacLeod, A., A Primate APOL1 Variant That Kills *Trypanosoma brucei* gambiense. *PLoS Negl Trop Dis* 2016, 10 (8), e0004903.

36. Molina Portela, M. P.; Raper, J.; Tomlinson, S., An investigation into the mechanism of trypanosome lysis by human serum factors. *Mol Biochem Parasitol* 2000, 110 (2), 273-82.

37. Shiflett, A. M.; Bishop, J. R.; Pahwa, A.; Hajduk, S. L., Human high density lipoproteins are platforms for the assembly of multi-component innate immune complexes. *J Biol Chem* 2005, 280 (38), 32578-85.

38. Thomson, R.; Samanovic, M.; Raper, J., Activity of trypanosome lytic factor: a novel component of innate immunity. *Future Microbiol* 2009, 4 (7), 789-96.

39 Olabisi, O. A.; Zhang, J. Y.; VerPlank, L.; Zahler, N.; DiBartolo, S., 3rd; Heneghan, J. F.; Schlondorff, J. S.; Suh, J. H.; Yan, P.; Alper, S. L.; Friedman, D. J.; Pollak, M. R., APOL1 kidney disease risk variants cause cytotoxicity by depleting cellular potassium and inducing stress-activated protein kinases. *Proc Natl Acad Sci USA* 2016, 113 (4), 830-7.

40. Ma, L.; Divers, J.; Freedman, B. I., Mechanisms of Injury in APOL1-associated Kidney Disease. *Transplantation* 2019, 103 (3), 487-492.

41. Parsa, A.; Kao, W. H.; Xie, D.; Astor, B. C.; Li, M.; Hsu, C. Y.; Feldman, H. I.; Parekh, R. S.; Kusek, J. W.; Greene, T. H.; Fink, J. C.; Anderson, A. H.; Choi, M. J.; Wright, J. T., Jr.; Lash, J. P.; Freedman, B. I.; Ojo, A.; Winkler, C. A.; Raj, D. S.; Kopp, J. B.; He, J.; Jensvold, N. G.; Tao, K.; Lipkowitz, M. S.; Appel, L. J.; Investigators, A. S.; Investigators, C. S., APOL1 risk variants, race, and progression of chronic kidney disease. *N Engl J Med* 2013, 369 (23), 2183-96.

42. O'Toole, J. F.; Schilling, W.; Kunze, D.; Madhavan, S. M.; Konieczkowski, M.; Gu, Y.; Luo, L.; Wu, Z.; Bruggeman, L. A.; Sedor, J. R., ApoL1 Overexpression Drives Variant-Independent Cytotoxicity. *J Am Soc Nephrol* 2018, 29 (3), 869-879.

43. Benham, C. D., Simple recipe for blocking ion channels. *Nat Biotechnol* 2005, 23 (10), 1234-5.

44. Wan, G.; Zhaorigetu, S.; Liu, Z.; Kaini, R.; Jiang, Z.; Hu, C. A., Apolipoprotein L1, a novel Bcl-2 homology domain 3-only lipid-binding protein, induces autophagic cell death. *J Biol Chem* 2008, 283 (31), 21540-9.

45. Vanhollebeke, B.; Pays, E., The function of apolipoproteins L. *Cell Mol Life Sci* 2006, 63 (17), 1937-44.

46. Paul Paroutis, N. T., and; Grinstein, S., The pH of the Secretory Pathway: Measurement, Determinants, and Regulation. *american physiology society* 2004, 19.

47. Sharma, A. K.; Friedman, D. J.; Pollak, M. R.; Alper, S. L., Structural characterization of the C-terminal coiled-coil domains of wild-type and kidney disease-associated mutants of apolipoprotein L1. *FEBS J* 2016, 283 (10), 1846-62.

48. Vanhollebeke, B.; Nielsen, M. J.; Watanabe, Y.; Truc, P.; Vanhamme, L.; Nakajima, K.; Moestrup, S. K.; Pays, E., Distinct roles of haptoglobin-related protein and apolipoprotein L-I in trypanolysis by human serum. *Proc Natl Acad Sci USA* 2007, 104 (10), 4118-23.

49. Hayek, S. S.; Koh, K. H.; Grams, M. E.; Wei, C.; Ko, Y. A.; Li, J.; Samelko, B.; Lee, H.; Dande, R. R.; Lee, H. W.; Hahm, E.; Peev, V.; Tracy, M.; Tardi, N. J.; Gupta, V.; Altintas, M. M.; Garborcauskas, G.; Stojanovic, N.; Winkler, C. A.; Lipkowitz, M. S.; Tin, A.; Inker, L. A.; Levey, A. S.; Zeier, M.; Freedman, B. I.; Kopp, J. B.; Skorecki, K.; Coresh, J.; Quyyumi, A. A.; Sever, S.; Reiser, J., A tripartite complex of suPAR, APOL1 risk variants and alphavbeta3 integrin on podocytes mediates chronic kidney disease. *Nat Med* 2017, 23 (8), 945-953.

50. Davidson, W. S.; Silva, R. A.; Chantepie, S.; Lagor, W. R.; Chapman, M. J.; Kontush, A., Proteomic analysis of defined HDL subpopulations reveals particle-specific protein clusters: relevance to antioxidative function. *Arterioscler Thromb Vasc Biol* 2009, 29 (6), 870-6.

51. Verdery, R. B.; Benham, D. F.; Baldwin, H. L.; Goldberg, A. P.; Nichols, A. V., Measurement of normative HDL subfraction cholesterol levels by Gaussian summation analysis of gradient gels. *J Lipid Res* 1989, 30 (7), 1085-95.

Example 2: Apolipoprotein L1-Specific Antibodies Detect Endogenous APOL1 Inside the Endoplasmic Reticulum and on the Plasma Membrane of Podocytes APOL1-G1 and G2 variants associate with African American chronic kidney disease. Overexpression of these variants kills cells, with a wide variety of mechanisms proposed, all involving different compartments. The localization of endogenous APOL1 has not been conclusively established because most published antibodies cross-react with APOL2. Here we generated APOL1-specific antibodies and show that endogenous podocyte APOL1 is mainly inside the ER, with a small amount on the cell surface. This potentially supports the ER stress or cell surface cation channel models of cytotoxicity.

Genetic variants G1 and G2 of Apolipoprotein L1 (APOL1) account for the majority of racially disparate chronic kidney diseases in African Americans. Multiple mechanisms of kidney podocyte cytotoxicity by APOL1 variant overexpression have been proposed, each involving different subcellular compartments. It is unclear which compartment endogenous podocyte APOL1 resides in because previous immunolocalization studies either utilized overexpressed protein or commercially available antibodies that we demonstrate cross-react with APOL2. Genetic variants G1 and G2 of Apolipoprotein L1 (APOL1) account for the majority of racially disparate chronic kidney diseases in African Americans. Multiple mechanisms of kidney podocyte cytotoxicity by APOL1 variant overexpression have been proposed, each involving different subcellular compartments. It is unclear which compartment endogenous podocyte APOL1 resides in because previous immunolocalization studies either utilized overexpressed protein or commercially available antibodies that we demonstrate cross-react with APOL2.

APOL1 is found in human kidney podocytes and endothelia. Both endogenous podocyte and transfected APOL1 isoforms vA and vB1 (and a little of isoform vC) localize to the luminal face of the endoplasmic reticulum and to the cell surface, but not to mitochondria, endosomes or lipid droplets. By contrast, APOL2 and isoforms vB3 and vC of APOL1 localize to the cytoplasmic face of the endoplasmic reticulum and are consequently absent from the cell surface. APOL1 knockout podocytes lack staining, attesting to staining specificity. Stable re-transfection of knockout podocytes with inducible APOL1-G0, G1 and G2 showed no differences in localization between variants. APOL1 is found in the ER and plasma membrane, potentially supporting the surface cation channel or ER stress models of APOL1-mediated cytotoxicity.

End-stage renal disease disparately affects African Americans compared to European Americans, in large part due to risk variants G1 and G2 in the APOL1 gene (wild type being designated G0) that are associated with non-diabetic kidney diseases (refs. 52-53). Generation of therapeutics for these APOL1 nephropathies first requires a better understanding of the mechanism of action of APOL1 (refs. 54-55).

Evidence supports that expression of APOL1 in kidney podocytes, rather than circulating APOL1, is likely responsible for kidney disease (54-58). In vitro overexpression of either APOL1 risk variant is usually more cytotoxic than G0 in many cell types, including podocytes (59-62). More compellingly, APOL1 variants induced to high levels specifically in mouse podocytes in vivo leads to proteinuria and glomerular pathology resembling human focal segmental glomerulosclerosis (59).

A variety of putative mechanisms have been proposed to explain APOL1 variant-dependent cytotoxicity, all involving different subcellular compartments (55). These include endoplasmic reticulum (ER) stress; mitochondrial dysfunction (63-64, 72); enhanced cell surface suPAR/integrin binding (65); surface cation efflux channel activity (62, 66); cholesterol accumulation (67) and defects in endosomal maturation, autophagosome flux or lysosomal permeability (59, 60, 62, 68, 69, 70). Accordingly, APOL1 has been variously immunolocalized to the ER (63, 71, 72), mitochondria (63, 64, 73), lipid droplets (74), early and late endosomes (59, 73, 75) and by biochemistry to the plasma membrane (66). However, most studies used overexpressed APOL1, which may not traffic normally, and the antibodies were not characterized for cross-reactivity with related APOL family members. Those antibodies reportedly stained endogenous APOL1 in podocytes, endothelial cells and proximal tubules of human kidneys (76, 77), but we found they also recognize APOL2, thereby calling into question whether APOL1 is truly expressed there.

Here we characterized 80 antibodies specific to APOL1 by immunofluorescence and demonstrate that APOL1 is expressed in endothelial cells and podocytes, specifically in the podocyte ER and plasma membrane, although two N-terminal splice isoforms are cytoplasmic. Our data thus potentially favor the ER stress or surface cation channel models of cytotoxicity.

Methods

Cell Culture

Human immortalized podocytes (AB 8/13) were obtained under license from Moin Saleem (81) and were not genetically confirmed in our laboratory, although we periodically verified that they stained normally by immunofluorescence for podocin and synaptopodin after differentiating at 38° C. for 14-15 days. They were grown at 33° C., feeding 3× a week with fresh growth medium (RPMI with 10% FBS (Seradigm IXL9/06807/GEN), 1% glutamine, 1% pen/strep (Gibco 15140-122), 1% insulin, transferrin, selenium (Gibco 41400-045) and discarded after passage 29 due to loss of APOL1 expression with time. APOL1 CRISPR knockout podocytes and generation of doxycycline-inducible iAPOL1-G0, G1 and G2 podocyte and CHO stables are described in Example 1. The same methods were used to generate iAPOL1 podocytes stably transfected with inducible (non-spliceable) cDNAs for each N-terminal isoform (see Table 5). These podocytes require tetracycline-free FBS and 5 µg/ml puromycin in the medium.

STR-validated COS7 cells were obtained from Genentech, Inc. and maintained in high glucose DMEM, 10% FBS, 1% glutamine, 1% non-essential amino acids (Sigma M7145). Transfection of APOL DNAs (listed in Table 3) was achieved by plating $0.9 \times 10^4$ COS7 cells/well in 8-well LabTekII slides for 24 h, then adding pre-mixed 0.7 µl Fugene HD (Promega E231A) with 0.25 µg DNA per well for 2 days. JHH-1 cells were cultured as in Example 1.

APOL1 cDNA Cloning

All available APOL cDNAs were obtained as summarized in Table 5 below (APOL5 was unavailable). Where indicated, sub-cloning into mammalian expression vectors with C-terminal myc-FLAG tags (Origene; or C-terminal myc only for APOL4) was achieved using EcoRI and XhoI restriction sites. The APOL1 splice isoforms were all untagged. All constructs were verified by Sanger sequencing.

Commercial Antibodies

Commercial anti-APOL1 antibodies were rabbit polyclonals from Sigma (HPA018885, lots E103963 and E105900, used at 0.4 µg/ml for IF and 2 µg/ml for western); and Proteintech (11486-2-AP, lot 00048412, used at 1 µg/ml for IF and 0.44 µg/ml for western); and rabbit monoclonal EPR2907(2) lot GR145110-2 from Epitomics at 2 µg/ml for both IF and western). Compartment marker antibodies were rabbit anti-calnexin (Abcam Ab25595, 0.25 µg/ml [validated in our lab by colocalization with GFP-Calnexin (data not shown) and subsequently shown by Abcam to give no signal in calnexin knockout cells]); rabbit anti-PDI (protein disulfide isomerase; 1:200 Stressgen SPA-890 [validated by colocalization with calnexin]); mouse anti-transferrin receptor H68.4 (1:250 Invitrogen 13-6800 [validated by colocalization with internalized Alexa488-transferrin ligand (data not shown)]); rabbit anti-perilipin-2 (Proteintech 15294-1-AP at 1.74 µg/ml for IF and 0.08 µg/ml for western [validated in FIGS. 36A-D]); mouse anti-perilipin-2 clone ADFP-5 (3.3 µg/ml Sigma SAB4200452 [validated in FIGS. 36A-D]); goat anti-EEA1 (1 µg/ml C15, Sc-6414 lot K1904 for early endosomes [validated by colocalization with mouse anti-EEA1]); rabbit anti-LAMP1 cytoplasmic domain (1 µg/ml Novus NB120-19294 Lot MF159260; [validated by colocalization with mouse anti-LAMP1]); mouse anti-mitofusin 2 clone 6A8 (Abcam Ab56889) at 1 µg/ml; rabbit anti-FACL4 (Abcam Ab137525) at 1 µg/ml (both confirmed by IF to localize to mitochondria (FIG. 45B); and the following mouse monoclonals all from BD Transduction Laboratories: calnexin clone 37 (2.5 µg/ml 610523 [validated by co-localization with rabbit anti-calnexin and Calnexin-GFP]); LAMP1 H4A3 (0.5 µg/ml 555798 [validated by colocalization with GFP-LAMP2a (ref. 101)]); cytochrome c 6H2 (2.5 µg/ml 556432 [validated by its surrounding of mitochondrially targeted GFP by us (101) and by colocalization with MitoTracker by others (ref 102)]); mouse anti-TOM20 (612278 at 1:1000, not validated other than its enrichment in the mitochondrial fraction (FIG. 40A)); GM130 clone 35 (1 µg/ml 610823); p230/Golgin-245 (1 µg/ml 611280 [validated by proximity to GM130]); and EEA1 (early endosome antigen 1) clone 14 (1 µg/ml 610457 [validated by overlap with a 5 min pulse of EGF and transferrin]). Other antibodies were rabmab anti-myc 71D10 (1:200 Cell Signaling Technology 2278), mouse anti-FLAG M2 (1 µg/ml Sigma F3165), mouse anti-myc 9E10 (2 µg/ml, Genentech), β-Actin-HRP 13E5 (1:1000 Cell Signaling Technology 5125), mouse anti-tubulin 1A2 (1:10,000 Sigma T9028) and rabbit anti-calnexin (1:3000 Stressgen SPA-860 for western blot).

Anti-APOL1 Mouse Monoclonal Antibody Generation

Mouse monoclonals were generated to $his_6$-APOL1 (aa 61-398 of NM_003661) as described in Example 1 above. The best 35 mouse monoclonals were sequenced and cloned into a murine $IgG_2a$ expression vector with effectorless L234A, L235A, P329G (LALAPG) mutations as previously described (103-104), with 22 cloned antibodies successfully recognizing APOL1. To enable triple labeling with other species, the Fab regions of some of the best cloned antibodies were sub-cloned into rabbit IgG and/or rat $IgG_2b$ backbones for expression in CHO cells and purification by protein-A affinity chromatography. The unpaired cysteines in the reformatted rabbit antibodies were paired by mutation of residue 80 to cysteine (P80C in rabbit 3.7D6, and A80C in rabbit 3.1C1 and 3.1C7).

Anti-APOL1 Rabbit Monoclonal (Rabmab) Antibody Generation (Method #5)

Two rabbits were immunized 5 times each (at Lampire Biological Laboratories) with 0.5 mg of the above $his_6$-APOL1 antigen, except the 4th and 5th boosts were with fixed antigen in order to maximize immunofluorescence reactivity. For fixation, paraformaldehyde from a 16% stock was diluted into 1 mg of $his_6$-APOL1 to 3% final for 20 min at room temperature and 10 min on ice, then PFA was removed by dialysis in APOL1 buffer (20 mM Tris-Cl pH 7.5, 150 mM NaCl, 0.1% DDM (n-Dodecyl-β-D-maltoside)) in a 10,000 MWCO membrane (Pierce).

Rabbit monoclonals were generated from APOL1-immunized rabbits by the B-cell cloning technology. Peripheral blood mononuclear cells (PBMCs) were isolated from rabbit whole blood after Ficoll density centrifugation. The PBMCs were washed in PBS, then resuspended in FACS buffer (2% FCS in PBS) and stained with FITC-labeled anti-rabbit IgG (AbD Serotec, BioRad). After washing, the cells were resuspended in FACS buffer containing Propidium Iodide. Live single IgG-positive B cells were sorted into 96-well culture plates using a FACSAria sorter (BD Biosciences). After the B cells were cultured in B cell culture medium (Genentech) for a week, the supernatants were screened by ELISA for APOL1 binding. The B cells in each well were lysed in 100 µl RLT buffer (Qiagen, Hilden, Germany) and immediately frozen at −80° C. for storage until molecular cloning. Variable regions (VH and VL) of each ELISA-positive monoclonal antibody were cloned into expression vectors from extracted mRNA as previously described (105). Individual rabbit antibodies were recombinantly expressed in 1 ml Expi293 cells and were subsequently purified with a protein A type resin in a high throughput manner. IF-positive clones were selected for scale up (30 ml) and were purified on a protein A column followed by size exclusion chromatography to remove any protein aggregates.

Antibodies were screened for immunofluorescence by testing at 1 µg/ml on COS cells transiently expressing APOL1 or APOL2 with the methanol protocol and the positives re-tested with PFA/Triton X-100. To rank the antibodies by sensitivity, lower expressing iAPOL1-CHO stables (see Example 1) were stained with the PFA/Saponin method. The strongest few were used to stain endogenous APOL1 in podocytes.

RT-PCR

Flash frozen normal post-mortem human kidneys were obtained under agreement from the University of Michigan (3 females, aged 47, 50 and 62; and two males aged 62 and 63). Total RNA was extracted from tissue or cells using RNeasy mini kit (Qiagen, Valencia, CA). On-column genomic DNA digestion was performed during purification using RNAse-free DNAse set (Qiagen) and cDNA synthesis was done using the High Capacity Reverse Transcription Kit (Applied Biosystems, Foster City, CA) with the provided random hexamer primers. Quantitative PCR reactions were performed by Taqman analysis in triplicate, using APOL-specific probes (ThermoFisher Scientific) on an ABI PRISM sequence detection system (Applied Biosystems). We validated the APOL family probe specificities (catalog numbers: L1 is Hs1066280_m1; L2 is Hs00603146_m1; L3 is Hs00600896_m1; L4 is Hs00540930_m1; L5 is Hs00229052_m1; and L6 is Hs00229051_m1) on cDNAs encoding all the family members (FIG. 30A) and the isoform specificities of the different APOL1 probes are shown in FIG. 49C. Relative mRNA was calculated using 2-Ct method normalized to RPL19. Data was plotted using PRISM.v7 software.

In-Situ Hybridization

FFPE fixed normal post-mortem male (aged 47 and 59) human kidneys were obtained under agreement from the MT group (Van Nuys, CA) with ethics committee approval and informed consent. Kidneys or cell pellets sectioned onto slides at 5 µm were loaded into a Leica BondRx autostainer and baked and dewaxed. Slides were pre-treated with ER2 at 95° C. for 15 min and Leica Enzyme at 40° C. for 15 min. Probes (all RNAScope® LS 2.5 probes from Advanced Cell Diagnostics) were hybridized at 42° C. for 120 min: APOL1 (Hs-APOL1-02-C2, cat #569168-C2, nt 768-1431 of NM_003661.3, 10zz); Hs-NPHS2 (cat #556538, nt 268-1172 of NM_014625.3, 20zz); Hs-EGLF7 (cat #314008, nt 14-1356 of NM_016215.4, 14zz). RNAScope 2.5 LS Duplex Reagent kit (cat #2005835) was used for detecting signal. We verified that the APOL1 probe did not cross-react with APOL2 and was capable of detecting endogenous APOL1 in podocytes (FIGS. 21B-G). Note than earlier version of the APOL1 probe (cat #411578 nt 2-902 of NM_001126541.1) did cross-react with APOL2 (and has thus been discontinued) and this probe did stain glomerular endothelia (data not shown). Sections were counterstained with light Mayer's hematoxylin, dried at 60° C. for 1 h and mounted with Histomount.

Immunohistochemistry

For antibody screening, a mini array of FFPE cell pellets was generated, including untransfected CHO cells, iAPOL1-G0 CHO stables (see Example 1), transiently transfected APOL2 CHO cells, WT podocytes without and with IFNγ stimulation (26 h at 100 ng/ml) and IFNγ-stimulated APOL1 KO podocytes. To generate the cell pellets ten 15 cm dishes of CHO cells were Lipofectamine transfected with 12 µg APOL2 DNA per dish for 48 h; or doxycycline-induced iAPOL1-CHO stable cell lines were used. Cells were detached with 5 mM EDTA in PBS, pelleted, then formalin fixed and paraffin embedded (FFPE) using standard methods. The generation of APOL1-G0 BAC transgenic C57BL/6 mice (under the human APOL1 promoter, which express APOL1 similarly to humans in liver, kidney and lung) will be described elsewhere (see also ref 106). All the murine hybridoma supernatants and cloned rabmabs were screened at 5 µg/ml on the Thermo Fisher AutoStainer with DAKO Target Retrieval solution and ABC-HRP detection.

The optimized protocol for IHC was performed on a Thermo Fisher AutoStainer. After 20 minutes of heat induced antigen retrieval at 99° C. in DAKO Target Retrieval solution, primary anti-APOL1 rabmab 5.17D12 was incubated at 0.5 µg/ml for 60 min at room temperature, followed by a secondary biotinylated donkey anti-rabbit antibody (Jackson ImmunoResearch 711-066-152) at 5 µg/ml for 30 minutes, then Streptavidin-HRP for 30 minutes and a 3 min amplification step with TSA (Perkin Elmer). The chromogen was DAB. FFPE normal human kidneys were obtained under agreement from Folio and Cureline from 2 females and 3 males, aged 64-89.

Immunofluorescence

Cells were plated on LabTekII (Nalge Nunc 154534) slides and fixed at 70-100% confluency. For mAb screening, cells were fixed/permeabilized for 5 min in −20° C. methanol (EMD MX0485-6). For all other experiments, cells were fixed in 3% paraformaldehyde in PBS (EMS 15710) for 20 mins at room temperature, quenched with 50 mM NH₄Cl in PBS for 10 mins, then permeabilized with 0.1% TX-100 in PBS for 4 mins or for 1h in saponin buffer [0.4% saponin (Sigma S7900), 1% bovine serum albumin (BSA; Sigma A2153), 2% fetal bovine serum (Seradigm) in PBS]. First antibodies (stored sterile at 4° C.) were applied for 1 h at room temperature, at 1 µg/ml for screening on transfected cells or at subsequently optimized concentrations for detecting endogenous APOL1. After 3×10 min washes in PBS (for Methanol or TX-100 protocols) or saponin buffer (saponin protocol), secondary antibodies were applied at 1.88 µg/ml for 1 h at room temperature, washed 3× and mounted under No. 1.5 coverslips in ProLong Gold with DAPI (4',6-diamidino-2-phenylindole; Life Technologies P36931). Secondary antibodies (stored at −20° C. in 50% glycerol), all highly cross-adsorbed donkey F(ab')₂ anti H&L from Jackson Immoresearch, included Alexa488 anti-mouse (715-546-150), Alexa488 anti-mouse additionally cross-adsorbed against rat (715-546-151), Alexa488 anti-rabbit (711-546-152), Cy3 anti-mouse (715-166-150), Cy3 anti-rabbit (711-166-152), Cy3 anti-rat (minimally cross-reactive with mouse, 712-166-153), Cy3 anti-goat (705-166-147), Alexa647 anti-rabbit (711-606-152), Dy649 anti-rabbit (712-496-153), Alexa647 anti-mouse (715-606-150 or 715-606-151 for co-staining with rat antibodies). For triple labeling of ER and mitochondria, isotype-specific mouse secondaries were employed: Alexa488 anti-IgG₂a (Invitrogen A21131) for murine 4.17A5 and Alexa555 anti-IgG₁ (Invitrogen A21127) for cytochrome c and Alexa649 anti-rabbit for calnexin. Alternatively rat 4.17A5 and Cy3 anti-rat were used (FIGS. 38A-B).

For selective permeabilization of the plasma membrane the concentration of digitonin was first optimized by ensuring free GFP leached out of the cells pre-fixation, while ER-targeted GFP-Calnexin with luminal GFP (101) was only detectable by GFP fluorescence and not anti-GFP antibodies in the red channel (data not shown). The optimal concentration for COS cells was 0.0025% (20 μM) and was applied for 4 min in place of TX-100 in KHM buffer (110 mM potassium acetate, 20 mM Hepes pH 7.4, 2 mM MgCl₂) (84).

COS cells were imaged on an AxioM2 imaging system (Zeiss) with a 60× PlanAPO NA 1.4 objective, standard DAPI/FITC/Cy3/Cy5 filter sets and a PhotoMetrics HQ2 camera managed by SlideBook (v5.5). Podocyte and CHO cells were imaged by spinning disc confocal microscopy (3i W, Zeiss AxioObserver M1 microscope with Yokogawa W1 spinning disc) with a 63× PlanAPO N.A. 1.4 oil objective and 405, 488, 561 and 640 nm lasers powered by SlideBook (v6). The camera was a Hamamatsu FLASH 4.0 sCMOS.

Electron Microscopy

For iEM, 1.4×10⁶ HEK-293 cells in T25 flasks were reverse transfected with 5.4 μg APOL1 or APOL2 cDNA with 12 μl Fugene 6 (Roche 11814443001) for 50 h or 65 h, respectively. Podocytes and transiently transfected HEK-293 cells were fixed with 4% paraformaldehyde in 0.1M phosphate buffer (PB), pH 7.4, for 2 h at room temperature, then overnight at 4° C., and with 2% paraformaldehyde, 0.2% glutaraldehyde in 0.1 M phosphate buffer (PB), pH 7.4, for 2 h at room temperature, respectively. Fixations were continued in 1% PFA in 0.1 M PB at 4° C. for several days. The cells were scraped, pelleted, embedded in 12% gelatin, cryoprotected with 2.3 M sucrose, mounted on aluminum pins and frozen in liquid nitrogen. Ultrathin cryosections were cut at −120° C. and stained with anti-APOL1 antibodies followed by protein-A gold particles (10 nm). For quantitation, random images of APOL1/2 expressing HEK-293 cells and podocytes were made. The positions of at least 50 gold particles per antibody were scored as either (i) OMF: overlapping on outer ER membrane surface and cytosol, or located in the cytosol at a distance ≤15 nm between outer ER membrane surface and the 10 nm gold particle surface; (ii) IMF: overlapping on inner ER membrane surface and ER lumen, or located in the lumen at a distance ≤15 nm between inner ER membrane surface and gold particle surface; or (iii) Lumen: within the ER lumen, with a distance >15 nm between the 10 nm gold particle surface and the nearest inner ER membrane surface. Two investigators independently performed the quantification procedure. Their percent scores of gold particles on the ER were averaged and the results were plotted as a line chart for each antibody.

Flow Cytometry

Live cells were stained on ice with 1 μg/ml 3.6D12 for 1 h, washed and detected with 1 μg/ml Alexa488 anti-mouse (Invitrogen A11029). Flow cytometry was performed as in Example 1.

Western Blotting

Cells were lysed in native RIPA (1% NP-40 buffer) as in Example 1, except they were run on 10%, 12% or 4-20% Tris-Glycine gels with See Blue Plus 2 molecular weight markers (Invitrogen LC5925); or on 4-12% Bis-Tris gels in MOPS buffer with Precision Plus protein Kaleidoscope markers (BioRad #1610375). The best anti-APOL1 antibody was a mixture of cloned rabbit 3.1C1 and 3.7D6 (at 0.05 μg/ml each).

Podocyte Fractionation

150×15 cm dishes of IFNγ-induced WT podocytes were harvested by trypsinization, manually homogenized in 10 ml (in 5×2 ml batches) IB$_{cells}$-1 buffer (225 mM mannitol, 75 mM sucrose, 30 mM Tris-Cl, 0.1 mM EGTA, pH 7.4) with 50 strokes of a Teflon Potter-Elvehjem #22 tissue grinder, sonicated (3×10 sec at speed 3.5 in Branson 450 sonifier), then fractionated according to the protocol of Wieckowski et al (107). Briefly, the crude mitochondria from the 10,000 g pellet were separated from the MAM by fractionation on a 30% Percoll gradient at 95,000 g for 30 mins; while the ER was collected from the mitochondrial supernatant by centrifugation at 100,000 g. 10 μg of each fraction (judged by the BCA assay, Pierce) was loaded on 4-20% Tris-Glycine gels and probed with suitable compartment markers.

Results

Kidney Podocytes Express APOLs 1, 2, and 6

APOL1 is the only secreted member of the human APOL family, comprising APOL1-APOL6 (78-80), and is most closely related to APOL2 (53% protein identity; Table 3). RT-PCR confirmed that APOLs 1,2,3 and 6, but not APOL4 or 5, mRNAs are expressed in normal human kidneys (FIG. 21A) (78-80). Dual in situ hybridization (ISH) pinpointed APOL1 mRNA to podocytes (FIGS. 21B-G), colocalizing with NPHS2, although some signal was also seen in NPHS2-negative cells morphologically resembling podocytes. Dual ISH of APOL1 and endothelial EGFL 7 mRNA or PVLAP protein showed no colocalization in glomerular endothelial cells, thus APOL1 mRNA is absent or below the detection limit these cells.

TABLE 3 c)
APOL gene homologies and plasmid sources

| APOL gene | C-term Tag | Vector | Source of cDNA | Accession | % ID FLS* | Antigen equivalent aa | % ID with ApoL1 antigen | % similarity with antigen |
|---|---|---|---|---|---|---|---|---|
| APOL1 | none@ | pCMV6-XL5 | Origene SC109941 | NM_003661# NP_003652 | 100 | 61-398 | 100 | 100 |
| APOL2 | none@ | pCMV6-XL4 | Origene SC124549 | NM_145637& NP_663612 | 53 | 1-337 | 61 | 65 |
| APOL3.v2 | Myc-FLAG | pCMV6-Entry | Origene RC208325 | NM_014349 NP_663614 | 40 | 1-331 | 47 | 53 |

TABLE 3-continued c)
APOL gene homologies and plasmid sources

| APOL gene | C-term Tag | Vector | Source of cDNA | Accession | % ID FLS* | Antigen equivalent aa | % ID with ApoL1 antigen | % similarity with antigen |
|---|---|---|---|---|---|---|---|---|
| APOL4.v1 | Myc | pReceiver-M09 | Genecopoeia Z4913 | NM_030643 NP_085146 | 36 | 24-348 | 39 | 43 |
| APOL5 | n/a | n/a | n/a | NP_085145 | 20 | 16-358 (of 433) | 25 | 21 |
| APOL6 | Myc-FLAG | pCMV6-Entry | Origene RC208481 | NM_030641 NP_085144 | 24 | 1-298 (of 343) | 30 | 31 |

*abbreviations: FLS, full length sequence; ID, identity; n/a, DNA clone not available.
[#]The APOL1 (v1) antigen (in a baculovirus vector) comprising amino acids 61-298 of APOL1 G0 isoform A (actual refseq NM_003661) with an N-terminal his$_6$ tag was used for immunization. DNA sequencing of the Origene purported NM_003661 isoform A clone in pCMV6-XL5, on which antibodies were screened by IF, revealed it to actually be sequence BC1430381, containing three common SNPs: E150K (rs2239785), M228I (rs136175) and R255K (rs136176) (refs. 110-112)
[&]The sequenced Origene APOL2 clone has an I245V change (rs132760) from the expected NM_145637 sequence.
[@]We also sub-cloned APOL1 and APOL2 into myc-FLAG/pCMV6-Entry (tagged at C-terminus) in place of APOL3 by PCR using EcoR1 and Xho1 sites.
n/a: No commercially available cDNA was found for APOL5, but it is closely related to APOL6, which was negative with all antibodies tested.

In differentiated immortalized human podocytes (81), only APOL1 and APOL2 mRNAs were detected (FIG. 21H), both increasing >10-fold with interferon gamma (IFNγ) stimulation, as expected (61). APOL6, but not APOLs 3-5, also became detectable after IFNγ treatment. Similar trends were seen in undifferentiated podocytes, although APOL1 induction by IFNγ was less pronounced. By western blotting APOL2 (37 kDa) appeared more abundant than APOL1 (41 kDa), and both increased with IFNγ (FIG. 21I). Thus, specific immunolocalization of APOL1 in podocytes requires antibodies non-cross-reactive with APOL2 or APOL6.

Many Anti-APOL1 Antibodies Cross-React with APOL2

Unfortunately, all three commercial rabbit antibodies used in previous reports (59, 72, 73, 76, 77) do cross-react with APOL2 (FIG. 22A-B), the Proteintech polyclonal additionally recognizing APOL3 (and weakly APOL4, not shown) by immunofluorescence (IF). Therefore, to identify APOL1- specific antibodies, we screened 135 mouse monoclonal antibodies (mAbs) to APOL1 (see Example 1) by IF of APOL1 and APOL2 transfected COS cells. 44 of the 107 mAbs that detected APOL1 cross-reacted with APOL2 (data not shown). To expand epitope coverage, we generated 35 more monoclonals in rabbits (rabmabs), 23 of which immunostained APOL1, and six also APOL2. The high monoclonal cross-reactivity with APOL2 (50/130 IF-positive=38%) was unexpected, since the antigen has only 61% homology (Table 3).

The most sensitive APOL1-specific antibodies for IF were rabmab 5.17D12, and mAbs 4.17A5 and 3.7D6 (FIG. 22C). MAb 3.6D12 was stronger, but cross-reacted with APOLs 2, 3 and 4 (FIG. 22C and Table 4). Western blotting confirmed these APOL specificities, their sensitivities for detecting endogenous podocyte APOL1 (WT) and recognition of APOL1-G1 and G2 (FIG. 22D). The 41 kDa podocyte band was absent in APOL1 knockout (KO) podocytes, confirming antibody specificities.

TABLE 4 d)
Anti-APOL1 antibody crossreactivities by immunofluorescence

| Antibody | Species* | Domain$ | APOL1 | APOL2 | APOL3 | APOL4 | APOL6 |
|---|---|---|---|---|---|---|---|
| 5.17D12 | Rabmab | PFD | +++ | — | — | — | — |
| 3.7D6 | Mouse, rabbit (P80C), rat | PFD | +++ | — | — | — | — |
| 4.17A5 | Mouse, rat | PFD | ++++ | — | — | + | — |
| 3.6D12 | Mouse | PFD | ++++ | +++ | + | + | — |
| 5.17H8 | Rabmab | PFD | ++++ | ++ | ± | ± | — |
| 3.5C10 | Mouse | PFD | ++++ | +++ | + | + | — |
| 3.3A8 | Mouse | MAD | +++ | ++ | — | — | — |
| 4.2C4 | Mouse | PFD | +++ | # | — | — | — |
| 3.6E10 | Mouse | SRA-ID linker | +++ | — | — | — | — |
| 3.1C1 | Mouse, rabbit (A80C) rat | SRA-ID linker | ++ | — | — | — | — |
| 3.1C7 | Mouse, rabbit (A80C) rat | SRA-ID linker | ++ | — | ± | — | — |
| 4.12E5 | Mouse | SRA-ID[&] | ++ | — | — | — | — |
| Sigma HPA018885 | Rabbit | MAD-SRA-ID | ++ | +[^] | — | — | — |

TABLE 4-continued

| | | | | | | | |
|---|---|---|---|---|---|---|---|
| | | | d) Anti-APOL1 antibody crossreactivities by immunofluorescence | | | | |
| Antibody | Species* | Domain$ | APOL1 | APOL2 | APOL3 | APOL4 | APOL6 |
| Epitomics EPR2907(2) | Rabmab | SRA-ID | ++ | ++ | — | — | — |
| Proteintech 11486-2-AP | Rabbit | PFD | ++++ | ++++ | ++ | ± | — |

\* The first listed species is the original; any subsequent ones were sub-cloned. The subcloned rabbit antibodies were mutated to cysteine at residue 80 to avoid unpaired cysteines.
$See Gupta et al. for domain mapping. PFD, pore-forming domain (aa 60-235); MAD, membrane addressing domain (aa 240-303); SRA-ID, SRA-interacting domain (aa 305-398, including MAD-SRA-ID linker).
4.2C4 cross-reacts with APOL2 with PFA/Saponin and by immunoelectron microscopy (but not with PFA/Triton X-100, shown in FIGS. 31A-B).
&4.12E5 does not recognize APOL1-G2 very well by FACS or Western (although it does to a certain extent by IF and IHC (data not shown))
^Sigma antibody only cross-reacts with APOL2 with PFA, not methanol fixation.

++++, very strong; +++ strong; ++ moderate; + weak; ± only cross-reacts with very high over-expressers; n.d., not determined.

APOL1-Specific Antibodies Reveal APOL1 is in Podocytes, Mainly Restricted to the ER Of 170 antibodies screened for APOL1-specificity by immunohistochemistry, 5.17D12 was the best (FIGS. 32A-B). In human and APOL1 transgenic mouse kidneys, 5.17D12 stained podocytes and endothelial cells, but there was no robust staining of proximal tubules (FIG. 23, FIG. 32B), unlike the commercial polyclonals (FIG. 32C) (73, 76). Liver hepatocytes were also positive (FIGS. 33A-B), but weaker than glomeruli; their similar western blot signals (76) presumably reflect the far greater proportion of hepatocytes in liver than glomeruli in kidney.

Subcellularly, APOL1-G0, G1 and G2 expressed transiently in COS cells appeared almost exclusively in the endoplasmic reticulum (ER), including the nuclear envelope, with all 130 IF-positive antibodies, colocalizing with the ER-specific marker calnexin, but not other compartments (FIGS. 34-37A and data not shown). Interestingly, APOL2 also colocalized with calnexin, despite lacking a signal sequence (FIG. 34). All three APOL1 variants likewise localized to the ER and not mitochondria in stably transfected inducible APOL1 ("iAPOL1") podocytes (FIG. 38A), which was confirmed by immunoelectron microscopy (iEM, FIG. 24A, 24B). Although APOL1 occasionally appeared to partially overlap with a few mitochondria by IF in the perinuclear region, this is likely a resolution issue because 5-20% of mitochondria are in close proximity to the ER (82) and triple labeling of APOL1, ER and mitochondria revealed APOL1 was never seen in mitochondria without concomitant ER overlap (FIG. 38B). More convincingly, mitochondria were consistently APOL1-negative by iEM, even when abutting positive ER cisternae (FIGS. 39A-39D). Subcellular fractionation also corroborated that endogenous podocyte APOL1 was enriched in the ER and mitochondrial-associated ER membranes (MAM) (83), but absent from pure mitochondria (FIG. 40A). APOL1 iEM of the MAM confirmed APOL1 is mainly within the ER cisternae (FIGS. 40B-D), not in the mitochondria or space between these organelles. iEM could also detect some APOL1 in the Golgi that was not discernible by IF (FIG. 24C), but not in other intracellular organelles, indicating APOL1 is secretory.

Importantly, ER-localized APOL1 was not merely an overexpression artifact because endogenous APOL1 was similarly ER-localized in both differentiated and undifferentiated podocytes (FIG. 24D and FIGS. 41A-B) and JHH-1 (liver) cells (FIG. 42). Endogenous podocyte APOL1 increased after upregulation by IFNγ and was absent from APOL1 KO podocytes and from other compartments, including Golgi, endosomes, mitochondria and lipid droplets (FIGS. 43-44A-B and 37B) and showed only minor overlap with MAM markers by IF (FIGS. 45A-B). Notably APOL2-cross reactive antibodies stain the ER of APOL1 KO podocytes almost as strongly as WT, indicating that most of the WT signal actually represents APOL2 (FIGS. 46A-B). In summary, endogenous, transiently and stably expressed APOL1 appears ER-restricted in all cell types examined.

APOL1, but not APOL2, is on the Extracellular Face of the Plasma Membrane

Despite not detecting APOL1 at the plasma membrane by IF in any of these (permeabilized) cell lines, most antibodies recognized surface APOL1 by flow cytometry of unpermeabilized WT (but not APOL1-KO) podocytes and stable cell lines (Example 1). APOL2-cross reactive 3.6D12 likewise did not shift on APOL1 KO podocytes (which retain APOL2), indicating that APOL2, is not found on the cell surface (FIG. 25A). Staining of unpermeabilized podocytes showed that surface APOL1 was punctate, with fewer, less bright puncta than in higher expressing JHH-1 cells and iAPOL1-G0, G1 and G2 podocytes (FIG. 25B and FIGS. 47A-B). Surface APOL1 is only a small proportion of the total because in permeabilized cells the far stronger ER signal obscures the surface signal; furthermore, relatively few gold particles were seen on podocyte plasma membranes by iEM (FIG. 25C).

APOL1 and APOL2 Localize to Opposite Faces of the ER Membrane

Since only APOL1 was found on the cell surface, but both APOL1 and APOL2 appeared ER-localized, we examined whether APOL2 localizes to the outer (cytoplasmic) face of the ER by permeabilizing APOL2-transfected COS cells with digitonin, which selectively permeabilizes the plasma membrane, leaving the ER membrane intact (84) (FIG. 26A). All 44 APOL2 cross-reactive mAbs exhibited a similar ER staining pattern with digitonin as with saponin or Triton X-100 (which permeabilize all cell membranes), indicating that APOL2 is indeed on the cytoplasmic face of the ER (FIG. 26B).

By contrast, all 80 APOL1-specific antibodies gave nuclear membrane (plus plasma membrane if high affinity) instead of ER signal with digitonin permeabilization (FIG. 26B), indicating that APOL1 is inaccessible and must therefore be inside the ER lumen (which is contiguous with the nuclear envelope). Thus, all three domains of APOL1 are luminal, with not one single epitope projecting into the cytoplasm. Quantitation of the iEM additionally revealed APOL1 was associated with the inner ER membrane face of iAPOL1 podocytes, not soluble in the ER lumen like the luminal ER marker KDEL (FIG. 26C, 26D). APOL1 was similarly associated with the inner ER membrane of transfected HEK-293 cells (FIGS. 48A-48C), whereas APOL2 was more distributed towards the outer ER membrane, supporting the differential localizations observed with digitonin.

Significantly, endogenous APOL1 and APOL2 were also on the luminal and cytoplasmic faces of the ER, respectively, in digitonin permeabilized podocytes (FIGS. 46A-46B). This suggests that any alternatively spliced cytoplasmic APOL1 isoforms (61, 85) are either luminal or below the detection limit (see below). Thus, APOL1 and APOL2 are on the inner and outer faces of the ER membrane, respectively. APOL1 Isoforms have Different ER Topologies It has been proposed that APOL1 risk variants bind less well than G0 to the vesicle-SNARE VAMPS, resulting in inhibition of endosomal trafficking as a putative mechanism of risk variant pathology (73). However, vesicle-SNAREs are all cytoplasmically oriented, whereas we clearly showed above that APOL1 is not. A caveat is that we likely detected the major reference isoform (vA or v1), whereas IFNγ stimulation of podocytes renders three minor splice variants of APOL1 (isoforms vB1, vB3 and vC) (61, 85) detectable. These differ in their N-termini, so may not all be secreted, meaning they might be cytoplasmic and accessible to VAMPS, thus needed evaluating (FIGS. 49A-49C and Table 5). For clarity, in this Example we call the splice forms "isoforms" and the G1/G2 risk alleles "variants".

FIG. 27B-27D). By contrast, in COS transients vA with its signal sequence deleted (Δss) appeared on the cell surface and in the media equally well as normal vA, despite having the expected opposite ER topology by digitonin IF (FIGS. 50A-51C). Thus, APOLs "secreted" into the media probably at least partially originate from overexpression-induced cell rupture when transiently expressed, as previously suggested (85).

The ER-luminal localization of stable APOL1.vB1 in podocytes agrees with its identical size to vA by western blot (FIG. 27D), which implies their different signal sequences are cleaved at the same site. Conversely, vB3 runs larger, consistent with no signal cleavage (Table 5 and FIG. 51C) and its cytoplasmic location; the lower band may be a cytoplasmic degradation product similar to vC. Intriguingly, APOL1.vC is predominantly cytoplasmic by IF, but also shows a little luminal/cell surface signal, sometimes within the same cell (arrowhead in FIG. 27B).

WT podocytes were western blotted to determine which endogenous APOL1 isoforms are detectable. The major band is the size of vA, as expected, but longer exposures revealed a minor upper band uniquely after IFNγ treatment, which could only represent vB3 if it were a splice isoform, and is indeed similar in size (FIGS. 28A-B and Table 5). RT-PCR confirmed previous reports (61, 85) that the two cytoplasmic isoforms (vB3 and vC) are 30× less abundant than the two luminal ones (vA and vB1; FIG. 49C), hence it is unsurprising that no cytoplasmic endogenous APOL1 could be detected by IF. In summary, APOL1.vA predominates endogenously and is inside the ER, and any minor

TABLE 5 e)
APOL1 isoform information and signal sequence predictions

| APOL1 isoform | Form | Vector/ Source | Accession | FLS* aa | iPSORT score (cutoff = 0.953)[&] | Signal P-4.1 D-score (cutoff = 0.45) [$] | Secretome P2.0[@] | ss (aa) | Predicted mature MW (Da) | Luminal by IF? Ψ |
|---|---|---|---|---|---|---|---|---|---|---|
| vA (v1) | RefSeq | pCMV6-XL5 (Origene SC109941) | NM_003661[#] NP_003652 | 398 | Yes (2.007) | Yes (0.853) | Yes | 27 | 41,111 (Δss) | Yes |
| vV1 (v2) | + Exon2 | pcDNA3.1 (GenScript) | NM_145343 NP_663318 | 414 | No (−0.8) | No (0.36) | Yes | 43 | 41,111 (Δss) | Yes |
| vB3 (v2-3) | + Exon2 ΔExon4 | pcDNA3.1 (GenScript) | KX192151[#] APY18924 | 396 | No (−0.8) | No (0.22) | No | 0 | 44,084 | No |
| vC (v4) | ΔExon4 | pcDNA3.1 (Genscript) | NM_001136541 NP_001130013 | 380 | Yes (1.233) | Yes (0.467) | Yes | 0 or 21 | 42,140 39,831 (Δss) | Yes & No |

*abbreviations: FLS, full length sequence; aa, amino acids; ss, signal sequence; IF, immunofluorescence; MW, molecular weight; Δss, after removal of signal sequence.
[#]DNA contains the three common SNPs E150K (rs2239785), M228I (rs136175) and R255K (rs136176).
[&]iPSORT prediction for presence of N-terminal signal sequence (63). Values above 0.953 are predicted to have a signal sequence (Yes). Note that this algorithm only considers the first 30 aa of the protein, thus APOL1.vB1 is wrongly predicted as non-secreted because its signal sequence is 43 aa.
[$] Signal P-4.1 prediction for N-terminal signal sequence (64). This algorithm evaluates the first 70 aa of the protein.
[@]Secretome P2.0a for non-classical mammalian protein secretion- yes or no refers to a warning given for prediction of a classical signal sequence (65).
Ψ Luminal (right hand column and FIGS. 27A-D) refers to the results of whether the protein is in the ER lumen as deciphered by IF with digitonin (and not on the plasma membrane by FACS) and show that the signal prediction programs were partly correct, but failed to recognize the abnormally long 43aa signal sequence in vB1 and predicted vC as secretory, when in fact only a small proportion is luminal, the majority being cytoplasmic.

It has been shown that all four isoforms are secreted into the media upon transient overexpression in HEK-293 cells (85). However, as the authors suggested (85), this may be an overexpression artifact, since we obtained the same result in transiently transfected COS cells, but not in stable cell lines. In iAPOL1 podocytes individually expressing each of the APOL1 isoforms (all of which localized to the ER, FIG. 27A), only the vA and vB1 isoforms that appeared luminal (with the digitonin technique) gave a large shift at the cell surface by FACS of live cells when induced to comparable levels (i.e. were transported along the secretory pathway;

cytoplasmic variants (vB3 and vC) localize to the outer face of the ER rather than endosomes (FIG. 27B, FIGS. 52A-B).
Discussion of Results We characterized multiple APOL1-specific antibodies to investigate the localization of APOL1. At the tissue level, in agreement with previous reports (59, 73, 76, 77, 86) we found APOL1 mRNA and protein in liver hepatocytes and podocytes of kidneys, but think it is biosynthetic (secretory) rather than endocytic. By contrast, we found no APOL1 protein or mRNA in proximal tubules, suggesting proximal tubule staining with the commercial polyclonals (73, 77)

may be APOL2 cross-reactivity or simply non-specific (FIG. 32C), underscoring the need for specific antibodies. Unlike Ma et al. (76), we could not detect APOL1 mRNA in glomerular endothelial cells, although an earlier version of this probe cross-reactive with APOL2 did (data not shown). It is unclear if the difference is because our shorter probe is less sensitive or if Ma's was not APOL1-specific. Nonetheless, as previously shown (73, 77), APOL1 protein was abundant in glomerular endothelial cells and endothelial capillaries by IHC (FIG. 23), so might be endocytosed from blood in these cell types.

Subcellularly, the major (reference) isoform, APOL1.vA, was consistently (endogenously, transiently and stably expressed) found within the ER, with a small proportion (<20% estimated by comparative FACS of permeabilized and unpermeabilized cells; FIG. 14) transported via the Golgi to the cell surface (FIG. 29). This is not unexpected, since it possesses a definitive signal sequence (79, 85) and is secreted from hepatocytes and associated with circulating HDL particles (71). In immortalized podocytes, however, secretory APOL1 remains attached to the cell surface, perhaps due to lack of transport machinery dedicated to HDL particle production (87). Surface APOL1 appeared punctate all over the cell and was not restricted to focal adhesions, unlike exogenously added APOL1 (65), suggesting it is not complexed with integrins, at least in the absence of integrin stimulation.

Since in trypanosomes (88) and in lipid membranes in vitro (89-90), APOL1 only inserts into membranes at acidic pH, we expected APOL1 to be soluble in the neutral (91) ER lumen. However, quantitative iEM revealed APOL1.vA is on the inner ER membrane, although some was released into the cytosolic fraction by sonication (FIG. 40A), suggesting it might be peripherally associated with phosphatidylinositols (70, 74). We hypothesize that full membrane integration (92) may occur in the Golgi at pH≤6 en route to the cell surface (91). Phosphatidylinositols are abundant in the cytoplasmic leaflet of the ER42 and might explain why nonsecretory APOL1 isoforms (and APOL2) associate with the outer ER membrane instead of being soluble in the neutral cytoplasm.

There was no significant overlap by either IF or iEM of endogenous podocyte APOL1 or transfected APOL1.vA with mitochondria, lipid droplets, or endosomes, organelles reported by others to harbor APOL1 (59, 64, 73, 74). This suggests the more abundant APOL2 and/or inappropriate staining procedures, epitope tags, transfection artifacts or different cell types may have contributed to those results. APOL1 was recently found in crude mitochondrial pellets, dependent on the mitochondrial import machinery (94). We suspect those "mitochondria" may actually be the MAM (a sub-domain of the ER closely apposed to mitochondria (83), since in our hands mitochondria purified away from the MAM contain no detectable APOL1 (FIG. 40A). APOL1 in the MAM actually resides within the ER cisternae (FIGS. 40B-D), a subdomain of the ER associated with lipid synthesis and ER stress signaling (83). Mitochondrial import sequences are recognized in the cytoplasm, not ER (95), so luminal APOL1.vA and vB1 would not be expected to reach mitochondria from the ER lumen. It will thus be important to verify the mitochondrial import findings (94) with endogenous APOL1 to ensure it was not an overexpression artifact. The reported coating of lipid droplets by APOL1-RFP23 likewise does not agree with our data, because they bud from the outer ER membrane (96), whereas untagged APOL1 is on the inner membrane (FIGS. 48A-C), and, like calnexin, was not sorted into lipid droplets (FIG. 37B). Perhaps C-terminal tags alter the distribution of APOL1.

GFP-APOL1 (without a signal sequence (Δss)) previously localized to the ER was interpreted as signal-sequence independent ER targeting (63), but we show that APOL1 Δss (as well as isoforms vB3, vC and APOL2) is topologically distinct, associating with the outer, not inner, ER membrane (FIG. 29). The absence of detectable endogenous cytoplasmic APOL1 in podocytes could be because these podocytes (81) lose APOL1 in culture; cytoplasmic isoforms vB3 and vC could conceivably be expressed at meaningful levels in vivo, particularly if upregulated by inflammatory cytokines (61). However, stably expressed vB3 and vC localize to the outer face of the ER, not to VAMPS-positive early endosomes or secretory granules (97-99). Note the published endosomal staining of podocyte APOL1 was performed with digitonin and the Sigma antibody (59), conditions which would only reveal APOL2 or cytoplasmic variants (FIG. 46A). In any case, APOL1-mediated cytotoxicity is reportedly restricted to the secretory (exon 4-positive) isoforms (vA and vB1) (85), in which the SRA-ID does not cross either the ER (FIG. 26B) or the plasma membrane (Example 1) into the cytoplasm. Thus, we argue that endosome or autophagosome maturation defects via stable VAMP8 binding (59, 70, 73) are likely not a direct mechanism of APOL1-G1 and G2-mediated cytotoxicity, although indirect or transient effects cannot be excluded.

Our localization data favor either the ER stress (72, 100) or cell surface cation channel models (62, 66) for APOL1-variant mediated cytotoxicity. There was no differential localization between variants, in agreement with other studies (63, 64, 73), so the function or magnitude of variant effects presumably differ. Determining where APOL1 resides within podocytes in vivo will be important; for example, whether it colocalizes with basement membrane integrins (65). Studying the subcellular localization of APOL1 in primary podocytes from APOL1 nephropathy patients that have sustained a "second hit" and establishing if APOL1 protein is upregulated in APOL1 risk variant kidneys would also be informative.

In summary, we have generated the first APOL1-specific antibodies sensitive enough to detect endogenous podocyte APOL1. These will be useful tools for future investigations of APOL1 localization and identification of interaction partners without interference from APOL2 binding that has plagued previous studies.

References for Example 2

52. Genovese, G.; Friedman, D. J.; Ross, M. D.; Lecordier, L.; Uzureau, P.; Freedman, B. I.; Bowden, D. W.; Langefeld, C. D.; Oleksyk, T. K.; Uscinski Knob, A. L.; Bernhardy, A. J.; Hicks, P. J.; Nelson, G. W.; Vanhollebeke, B.; Winkler, C. A.; Kopp, J. B.; Pays, E.; Pollak, M. R., Association of trypanolytic ApoL1 variants with kidney disease in African Americans. *Science* 2010, 329 (5993), 841-5.

53. Tzur, S.; Rosset, S.; Shemer, R.; Yudkovsky, G.; Selig, S.; Tarekegn, A.; Bekele, E.; Bradman, N.; Wasser, W. G.; Behar, D. M.; Skorecki, K., Missense mutations in the APOL1 gene are highly associated with end stage kidney disease risk previously attributed to the MYH9 gene. *Hum Genet* 2010, 128 (3), 345-50.

54. Heymann, J.; Winkler, C. A.; Hoek, M.; Susztak, K.; Kopp, J. B., Therapeutics for APOL1 nephropathies: putting out the fire in the podocyte. *Nephrol Dial Transplant* 2017, 32 (suppl_1), i65-i70.

55. Kruzel-Davila, E.; Skorecki, K., Dilemmas and challenges in apolipoprotein L1 nephropathy research. *Curr Opin Nephrol Hypertens* 2019, 28 (1), 77-86.

56. Kopp, J. B.; Heymann, J.; Winkler, C. A., APOL1 Renal Risk Variants: Fertile Soil for HIV-Associated Nephropathy. *Semin Nephrol* 2017, 37 (6), 514-519.

57. Shukha, K.; Mueller, J. L.; Chung, R. T.; Curry, M. P.; Friedman, D. J.; Pollak, M. R.; Berg, A. H., Most ApoL1 Is Secreted by the Liver. *J Am Soc Nephrol* 2017, 28 (4), 1079-1083.

58. Aghajan, M.; Booten, S. L.; Althage, M.; Hart, C. E.; Ericsson, A.; Maxvall, I.; Ochaba, J.; Menschik-Lundin, A.; Hartleib, J.; Kuntz, S.; Gattis, D.; Ahlstrom, C.; Watt, A. T.; Engelhardt, J. A.; Monia, B. P.; Magnone, M. C.; Guo, S., Antisense oligonucleotide treatment ameliorates IFN-gamma-induced proteinuria in APOL1-transgenic mice. *JCI Insight* 2019, 4 (12).

59. Beckerman, P.; Bi-Karchin, J.; Park, A. S.; Qiu, C.; Dummer, P. D.; Soomro, I.; Boustany-Kari, C. M.; Pullen, S. S.; Miner, J. H.; Hu, C. A.; Rohacs, T.; Inoue, K.; Ishibe, S.; Saleem, M. A.; Palmer, M. B.; Cuervo, A. M.; Kopp, J. B.; Susztak, K., Transgenic expression of human APOL1 risk variants in podocytes induces kidney disease in mice. *Nat Med* 2017, 23 (4), 429-438.

60. Lan, X.; Jhaveri, A.; Cheng, K.; Wen, H.; Saleem, M. A.; Mathieson, P. W.; Mikulak, J.; Aviram, S.; Malhotra, A.; Skorecki, K.; Singhal, P. C., APOL1 risk variants enhance podocyte necrosis through compromising lysosomal membrane permeability. *Am J Physiol Renal Physiol* 2014, 307 (3), F326-36.

61. Nichols, B.; Jog, P.; Lee, J. H.; Blackler, D.; Wilmot, M.; D'Agati, V.; Markowitz, G.; Kopp, J. B.; Alper, S. L.; Pollak, M. R.; Friedman, D. J., Innate immunity pathways regulate the nephropathy gene Apolipoprotein L1. *Kidney Int* 2015, 87 (2), 332-42.

62. Olabisi, 0. A.; Zhang, J. Y.; VerPlank, L.; Zahler, N.; DiBartolo, S., 3rd; Heneghan, J. F.; Schlondorff, J. S.; Suh, J. H.; Yan, P.; Alper, S. L.; Friedman, D. J.; Pollak, M. R., APOL1 kidney disease risk variants cause cytotoxicity by depleting cellular potassium and inducing stress-activated protein kinases. *Proc Natl Acad Sci USA* 2016, 113 (4), 830-7.

63. Granado, D.; Muller, D.; Krausel, V.; Kruzel-Davila, E.; Schuberth, C.; Eschborn, M.; Wedlich-Soldner, R.; Skorecki, K.; Pavenstadt, H.; Michgehl, U.; Weide, T., Intracellular APOL1 Risk Variants Cause Cytotoxicity Accompanied by Energy Depletion. *J Am Soc Nephrol* 2017, 28 (11), 3227-3238.

64. Ma, L.; Chou, J. W.; Snipes, J. A.; Bharadwaj, M. S.; Craddock, A. L.; Cheng, D.; Weckerle, A.; Petrovic, S.; Hicks, P. J.; Hemal, A. K.; Hawkins, G. A.; Miller, L. D.; Molina, A. J.; Langefeld, C. D.; Murea, M.; Parks, J. S.; Freedman, B. I., APOL1 Renal-Risk Variants Induce Mitochondrial Dysfunction. *J Am Soc Nephrol* 2017, 28 (4), 1093-1105.

65. Hayek, S. S.; Koh, K. H.; Grams, M. E.; Wei, C.; Ko, Y. A.; Li, J.; Samelko, B.; Lee, H.; Dande, R. R.; Lee, H. W.; Hahm, E.; Peev, V.; Tracy, M.; Tardi, N. J.; Gupta, V.; Altintas, M. M.; Garborcauskas, G.; Stojanovic, N.; Winkler, C. A.; Lipkowitz, M. S.; Tin, A.; Inker, L. A.; Levey, A. S.; Zeier, M.; Freedman, B. I.; Kopp, J. B.; Skorecki, K.; Coresh, J.; Quyyumi, A. A.; Sever, S.; Reiser, J., A tripartite complex of suPAR, APOL1 risk variants and alphavbeta3 integrin on podocytes mediates chronic kidney disease. *Nat Med* 2017, 23 (8), 945-953.

66. O'Toole, J. F.; Schilling, W.; Kunze, D.; Madhavan, S. M.; Konieczkowski, M.; Gu, Y.; Luo, L.; Wu, Z.; Brugge-man, L. A.; Sedor, J. R., ApoL1 Overexpression Drives Variant-Independent Cytotoxicity. *J Am Soc Nephrol* 2018, 29 (3), 869-879.

67. Ryu, J. H.; Ge, M.; Merscher, S.; Rosenberg, A. Z.; Desante, M.; Roshanravan, H.; Okamoto, K.; Shin, M. K.; Hoek, M.; Fornoni, A.; Kopp, J. B., APOL1 renal risk variants promote cholesterol accumulation in tissues and cultured macrophages from APOL1 transgenic mice. *PLoS One* 2019, 14 (4), e0211559.

68. Fu, Y.; Zhu, J. Y.; Richman, A.; Zhang, Y.; Xie, X.; Das, J. R.; Li, J.; Ray, P. E.; Han, Z., APOL1-G1 in Nephrocytes Induces Hypertrophy and Accelerates Cell Death. *J Am Soc Nephrol* 2017, 28 (4), 1106-1116.

69. Kruzel-Davila, E.; Shemer, R.; Ofir, A.; Bavli-Kertselli, I.; Darlyuk-Saadon, I.; Oren-Giladi, P.; Wasser, W. G.; Magen, D.; Zaknoun, E.; Schuldiner, M.; Salzberg, A.; Kornitzer, D.; Marelja, Z.; Simons, M.; Skorecki, K., APOL1-Mediated Cell Injury Involves Disruption of Conserved Trafficking Processes. *J Am Soc Nephrol* 2017, 28 (4), 1117-1130.

70. Wan, G.; Zhaorigetu, S.; Liu, Z.; Kaini, R.; Jiang, Z.; Hu, C. A., Apolipoprotein L1, a novel Bcl-2 homology domain 3-only lipid-binding protein, induces autophagic cell death. *J Biol Chem* 2008, 283 (31), 21540-9.

71. Cheng, D.; Weckerle, A.; Yu, Y.; Ma, L.; Zhu, X.; Murea, M.; Freedman, B. I.; Parks, J. S.; Shelness, G. S., Biogenesis and cytotoxicity of APOL1 renal risk variant proteins in hepatocytes and hepatoma cells. *J Lipid Res* 2015, 56 (8), 1583-93.

72. Wen, H.; Kumar, V.; Lan, X.; Shoshtari, S. S. M.; Eng, J. M.; Zhou, X.; Wang, F.; Wang, H.; Skorecki, K.; Xing, G.; Wu, G.; Luo, H.; Malhotra, A.; Singhal, P. C., APOL1 risk variants cause podocytes injury through enhancing endoplasmic reticulum stress. *Biosci Rep* 2018, 38 (4).

73. Madhavan, S. M.; O'Toole, J. F.; Konieczkowski, M.; Barisoni, L.; Thomas, D. B.; Ganesan, S.; Bruggeman, L. A.; Buck, M.; Sedor, J. R., APOL1 variants change C-terminal conformational dynamics and binding to SNARE protein VAMPS. *JCI Insight* 2017, 2 (14).

74. Chun, J.; Zhang, J. Y.; Wilkins, M. S.; Subramanian, B.; Riella, C.; Magraner, J. M.; Alper, S. L.; Friedman, D. J.; Pollak, M. R., Recruitment of APOL1 kidney disease risk variants to lipid droplets attenuates cell toxicity. *Proc Natl Acad Sci USA* 2019, 116 (9), 3712-3721.

75. Mikulak, J.; Oriolo, F.; Portale, F.; Tentorio, P.; Lan, X.; Saleem, M. A.; Skorecki, K.; Singhal, P. C.; Mavilio, D., Impact of APOL1 polymorphism and IL-1beta priming in the entry and persistence of HIV-1 in human podocytes. *Retrovirology* 2016, 13 (1), 63.

76. Ma, L.; Shelness, G. S.; Snipes, J. A.; Murea, M.; Antinozzi, P. A.; Cheng, D.; Saleem, M. A.; Satchell, S. C.; Banas, B.; Mathieson, P. W.; Kretzler, M.; Hemal, A. K.; Rudel, L. L.; Petrovic, S.; Weckerle, A.; Pollak, M. R.; Ross, M. D.; Parks, J. S.; Freedman, B. I., Localization of APOL1 Protein and mRNA in the Human Kidney: Non-diseased Tissue, Primary Cells, and Immortalized Cell Lines. *Journal of the American Society of Nephrology* 2014, 26 (2), 339-348.

77. Madhavan, S. M.; O'Toole, J. F.; Konieczkowski, M.; Ganesan, S.; Bruggeman, L. A.; Sedor, J. R., APOL1 localization in normal kidney and nondiabetic kidney disease. *J Am Soc Nephrol* 2011, 22 (11), 2119-28.

78. Duchateau, P. N.; Pullinger, C. R.; Cho, M. H.; Eng, C.; Kane, J. P., Apolipoprotein L gene family: tissue-specific expression, splicing, promoter regions; discovery of a new gene. *J Lipid Res* 2001, 42 (4), 620-30.

79. Monajemi, H.; Fontijn, R. D.; Pannekoek, H.; Horrevoets, A. J., The apolipoprotein L gene cluster has emerged recently in evolution and is expressed in human vascular tissue. *Genomics* 2002, 79 (4), 539-46.

80. Page, N. M.; Butlin, D. J.; Lomthaisong, K.; Lowry, P. J., The human apolipoprotein L gene cluster: identification, classification, and sites of distribution. *Genomics* 2001, 74 (1), 71-8.

81. Saleem, M. A.; O'Hare, M. J.; Reiser, J.; Coward, R. J.; Inward, C. D.; Farren, T.; Xing, C. Y.; Ni, L.; Mathieson, P. W.; Mundel, P., A conditionally immortalized human podocyte cell line demonstrating nephrin and podocin expression. *J Am Soc Nephrol* 2002, 13 (3), 630-8.

82. Rizzuto, R.; Pinton, P.; Carrington, W.; Fay, F. S.; Fogarty, K. E.; Lifshitz, L. M.; Tuft, R. A.; Pozzan, T., Close contacts with the endoplasmic reticulum as determinants of mitochondrial Ca2+ responses. *Science* 1998, 280 (5370), 1763-6.

83. van Vliet, A. R.; Verfaillie, T.; Agostinis, P., New functions of mitochondria associated membranes in cellular signaling. *Biochim Biophys Acta* 2014, 1843 (10), 2253-62.

84. Lorenz, H.; Hailey, D. W.; Lippincott-Schwartz, J., Addressing membrane protein topology using the fluorescence protease protection (FPP) assay. *Methods Mol Biol* 2008, 440, 227-33.

85 Khatua, A. K.; Cheatham, A. M.; Kruzel, E. D.; Singhal, P. C.; Skorecki, K.; Popik, W., Exon 4-encoded sequence is a major determinant of cytotoxicity of apolipoprotein L1. Am J Physiol Cell Physiol 2015, 309 (1), C22-37.

86. Kotb, A. M.; Simon, 0.; Blumenthal, A.; Vogelgesang, S.; Dombrowski, F.; Amann, K.; Zimmermann, U.; Endlich, K.; Endlich, N., Knockdown of ApoL1 in Zebrafish Larvae Affects the Glomerular Filtration Barrier and the Expression of Nephrin. *PLoS One* 2016, 11 (5), e0153768.

87. Parks, J. S.; Chung, S.; Shelness, G. S., Hepatic ABC transporters and triglyceride metabolism. *Curr Opin Lipidol* 2012, 23 (3), 196-200.

88. Pays, E.; Vanhollebeke, B.; Vanhamme, L.; Paturiaux-Hanocq, F.; Nolan, D. P.; Perez-Morga, D., The trypanolytic factor of human serum. *Nat Rev Microbiol* 2006, 4 (6), 477-86.

89. Bruno, J.; Pozzi, N.; Oliva, J.; Edwards, J. C., Apolipoprotein L1 confers pH-switchable ion permeability to phospholipid vesicles. *J Biol Chem* 2017, 292 (44), 18344-18353.

90. Thomson, R.; Finkelstein, A., Human trypanolytic factor APOL1 forms pH-gated cation-selective channels in planar lipid bilayers: relevance to trypanosome lysis. *Proc Natl Acad Sci USA* 2015, 112 (9), 2894-9.

91. Paroutis, P.; Touret, N.; Grinstein, S., The pH of the secretory pathway: measurement, determinants, and regulation. *Physiology (Bethesda)* 2004, 19, 207-15.

92. Thomson, R.; Genovese, G.; Canon, C.; Kovacsics, D.; Higgins, M. K.; Carrington, M.; Winkler, C. A.; Kopp, J.; Rotimi, C.; Adeyemo, A.; Doumatey, A.; Ayodo, G.; Alper, S. L.; Pollak, M. R.; Friedman, D. J.; Raper, J., Evolution of the primate trypanolytic factor APOL1. *Proc Natl Acad Sci USA* 2014, 111 (20), E2130-9.

93. Di Paolo, G.; De Camilli, P., Phosphoinositides in cell regulation and membrane dynamics. *Nature* 2006, 443 (7112), 651-7.

94. Shah, S. S.; Lannon, H.; Dias, L.; Zhang, J. Y.; Alper, S. L.; Pollak, M. R.; Friedman, D. J., APOL1 Kidney Risk Variants Induce Cell Death via Mitochondrial Translocation and Opening of the Mitochondrial Permeability Transition Pore. *J Am Soc Nephrol* 2019, 30 (12), 2355-2368.

95. Neupert, W., Protein import into mitochondria. *Annu Rev Biochem* 1997, 66, 863-917.

96. Olzmann, J. A.; Carvalho, P., Dynamics and functions of lipid droplets. *Nat Rev Mol Cell Biol* 2019, 20 (3), 137-155.

97. Advani, R. J.; Bae, H. R.; Bock, J. B.; Chao, D. S.; Doung, Y. C.; Prekeris, R.; Yoo, J. S.; Scheller, R. H., Seven novel mammalian SNARE proteins localize to distinct membrane compartments. *J Biol Chem* 1998, 273 (17), 10317-24.

98. Behrendorff, N.; Dolai, S.; Hong, W.; Gaisano, H. Y.; Thorn, P., Vesicle-associated membrane protein 8 (VAMPS) is a SNARE (soluble N-ethylmaleimide-sensitive factor attachment protein receptor) selectively required for sequential granule-to-granule fusion. *J Biol Chem* 2011, 286 (34), 29627-34.

99. Wong, S. H.; Zhang, T.; Xu, Y.; Subramaniam, V. N.; Griffiths, G.; Hong, W., Endobrevin, a novel synaptobrevin/VAMP-like protein preferentially associated with the early endosome. *Mol Biol Cell* 1998, 9 (6), 1549-63.

100. Hague, S.; Patil, G.; Mishra, A.; Lan, X.; Popik, W.; Malhotra, A.; Skorecki, K.; Singhal, P. C., Effect of APOL1 disease risk variants on APOL1 gene product. *Biosci Rep* 2017, 37 (2).

101. Austin, C. D.; Wen, X.; Gazzard, L.; Nelson, C.; Scheller, R. H.; Scales, S. J., Oxidizing potential of endosomes and lysosomes limits intracellular cleavage of disulfide-based antibody-drug conjugates. *Proc Natl Acad Sci USA* 2005, 102 (50), 17987-92.

102. Chandra, D.; Liu, J. W.; Tang, D. G., Early mitochondrial activation and cytochrome c up-regulation during apoptosis. *J Biol Chem* 2002, 277 (52), 50842-54.

103. Lo, M.; Kim, H. S.; Tong, R. K.; Bainbridge, T. W.; Vernes, J. M.; Zhang, Y.; Lin, Y. L.; Chung, S.; Dennis, M. S.; Zuchero, Y. J.; Watts, R. J.; Couch, J. A.; Meng, Y. G.; Atwal, J. K.; Brerski, R. J.; Spiess, C.; Ernst, J. A., Effector-attenuating Substitutions That Maintain Antibody Stability and Reduce Toxicity in Mice. *J Biol Chem* 2017, 292 (9), 3900-3908.

104. Schlothauer, T.; Herter, S.; Koller, C. F.; Grau-Richards, S.; Steinhart, V.; Spick, C.; Kubbies, M.; Klein, C.; Umana, P.; Mossner, E., Novel human $IgG_1$ and $IgG_4$ Fc-engineered antibodies with completely abolished immune effector functions. *Protein Eng Des Sel* 2016, 29 (10), 457-466.

105. Seeber, S.; Ros, F.; Thorey, I.; Tiefenthaler, G.; Kaluza, K.; Lifke, V.; Fischer, J. A.; Klostermann, S.; Endl, J.; Kopetzki, E.; Pashine, A.; Siewe, B.; Kaluza, B.; Platzer, J.; Offner, S., A robust high throughput platform to generate functional recombinant monoclonal antibodies using rabbit B cells from peripheral blood. *PLoS One* 2014, 9 (2), e86184.

106. Grant Wilson, D.; Foreman, 0.; Peterson, A. S.; Wen, X.; Scales, S. J. Animal model for nephropathy and agents for treating the same. 2014.

107. Wieckowski, M. R.; Giorgi, C.; Lebiedzinska, M.; Duszynski, J.; Pinton, P., Isolation of mitochondria-associated membranes and mitochondria from animal tissues and cells. *Nat Protoc* 2009, 4 (11), 1582-90.

108. Ohsaki, Y.; Maeda, T.; Fujimoto, T., Fixation and permeabilization protocol is critical for the immunolabeling of lipid droplet proteins. *Histochem Cell Biol* 2005, 124 (5), 445-52.

109. Yang, Y.; Yang, Q.; Yang, J.; Ma, Y.; Ding, G., Angiotensin II induces cholesterol accumulation and injury in podocytes. *Sci Rep* 2017, 7 (1), 10672.

110. Bannai, H.; Tamada, Y.; Maruyama, 0.; Nakai, K.; Miyano, S., Extensive feature detection of N-terminal protein sorting signals. *Bioinformatics* 2002, 18 (2), 298-305.

111. Petersen, T. N.; Brunak, S.; von Heijne, G.; Nielsen, H., SignalP 4.0: discriminating signal peptides from transmembrane regions. *Nat Methods* 2011, 8 (10), 785-6.

112. Bendtsen, J. D.; Jensen, L. J.; Blom, N.; Von Heijne, G.; Brunak, S., Feature-based prediction of non-classical and leaderless protein secretion. *Protein Eng Des Sel* 2004, 17 (4), 349-56.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

IV. Table of Certain Sequences

| SEQ ID NO | Description | Sequence |
|---|---|---|
| 1 | Human APOL1 (with leader sequence) G0 form EMR variant Accession no. NP003652 | MEGAALLRVS VLCIWMSALF LGVGVRAEEA GARVQQNVPS GTDTGDPQSK PLGDWAAGTM DRESSIFIED AIKYFKEKVS TQNLLLLLTD NEAWNGFVAA AELPRNEADE LRKALDNLAR QMIMKDKNWH DKGQQYRNWF LKEFPRLKSE LEDNIRRLRA LADGVQKVHK GTTIANVVSG SLSISSGILT LVGMGLAPFT EGGSLVLLEP GMELGITAAL TGITSSTMDY GKKWWTQAQA HDLVIKSLDK LKEVREFLGE NISNFLSLAG NTYQLTRGIG KDIRALRRAR ANLQSVPHAS ASRPRVTEPI SAESGEQVER VNEPSILEMS RGVKLTDVAP VSFFLVLDW YLVYESKHLH EGAKSETAEE LKKVAQELEE KLNILNNNYK ILQADQEL |
| 2 | Human APOL1 without leader sequence - G0 form EMR variant NP003652 | EA GARVQQNVPS GTDTGDPQSK PLGDWAAGTM DRESSIFIED AIKYFKEKVS TQNLLLLLTD NEAWNGFVAA AELPRNEADE LRKALDNLAR QMIMKDKNWH DKGQQYRNWF LKEFPRLKSE LEDNIRRLRA LADGVQKVHK GTTIANVVSG SLSISSGILT LVGMGLAPFT EGGSLVLLEP GMELGITAAL TGITSSTMDY GKKWWTQAQA HDLVIKSLDK LKEVREFLGE NISNFLSLAG NTYQLTRGIG KDIRALRRAR ANLQSVPHAS ASRPRVTEPI SAESGEQVER VNEPSILEMS RGVKLTDVAP VSFFLVLDW YLVYESKHLH EGAKSETAEE LKKVAQELEE KLNILNNNYK ILQADQEL |
| 3 | 3.6D12 VH CDR1 | RCAMS |
| 4 | 3.6D12 VH CDR2 | AISRDSTYTYYSDSVKG |
| 5 | 3.6D12 VH CDR3 | QIDDYYVDALDY |
| 6 | 3.6D12 VL CDR1 | RASKIISKYLA |
| 7 | 3.6D12 VL CDR2 | SGFTLQS |
| 8 | 3.6D12 VL CDR3 | QQHNEYPLT |
| 9 | 3.6D12 VH | EVMLVESGGGLVRPGGSLKLSCTASGFTFSRCAMSWVRQTPEKRLEWVSAISRDSTYTY YSDSVKGRFTVSRDNAKNTLYLQMSSLRSEDTAMYYCARQIDDYYVDALDYWGQGTSV |
| 10 | 3.6D12 VL | DVQITQSPSYLAASPGETITINCRASKIISKYLAWYQEKPGKTIKLLIYSGFTLQSGIP SRFSGSGSGTDFTLTISSLEPEDFAMYYCQQHNEYPLTFGA |
| 11 | 3.6D12 HC LALAPG mIgG2a | MGWSCIILFLVATATGAYAEVMLVESGGGLVRPGGSLKLSCTASGFTFSRCAMSWVRQT PEKRLEWVSAISRDSTYTYYSDSVKGRFTVSRDNAKNTLYLQMSSLRSEDTAMYYCARQ IDDYYVDALDYWGQGTSVTVSSASTKGPSVYPLAPVCGDTTGSSVTLGCLVKGYFPEPV TLTWNSGSLSSGVHTFPAVLQSDLYTLSSSVTVTSSTWPSQSITCNVAHPASSTKVDKK IEPRGPTIKPCPPCKCPAPNAAGGPSVFIFPPKIKDVLMISLSPIVTCVVVDSEDDPD VQISWFVNNVEVHTAQTQTHREDYNSTLRVVSALPIQHQDWMSGKEFKCKVNNKDLGAP IERTISKPKGSVRAPQVYVLPPPEEEMTKKQVTLTCMVTDFMPEDIYVEWTNNGKTELN YKNTEPVLDSDGSYFMYSKLRVEKKNWVERNSYSCSWHEGLHNHHTTKSFSRTPGK |
| 12 | 3.6D12 LC LALAPG mIgG2a | MGWSCIILFLVATATGVHSDVQITQSPSYLAASPGETITINCRASKIISKYLAWYQEKP GKTIKLLIYSGFTLQSGIPSRFSGSGSGTDFTLTISSLEPEDFAMYYCQQHNEYPLTFG AGTKLEIKRADAAPTVSIFPPSSEQLTSGGASVVCFLNNFYPKDINVKWKIDGSERONG VLNSWTDQDSKDSTYSMSSTLTLTKDEYERHNSYTCEATHKTSTSPIVKSFNRNEC |
| 13 | 3.3B6 VH CDR1 | SHWMQ |
| 14 | 3.3B6 VH CDR2 | AIYPGDGDTKFTQKFKD |
| 15 | 3.3B6 VH CDR3 | NLYGYYFDY |
| 16 | 3.3B6 VL CDR1 | RSSTGAVTSGNFAN |
| 17 | 3.3B6 VL CDR2 | GADNRAP |
| 18 | 3.3B6 VL CDR3 | ALWYSDHWV |

IV. Table of Certain Sequences

| SEQ ID NO | Description | Sequence |
| --- | --- | --- |
| 19 | 3.3B6 VH | QVQLQQSGAELARPGASVKLSCKASGYTFTSHWMQWLKQRPGQGLEWIGAIYPGDGDTK<br>FTQKFKDKATLTADKSSTTAYMQLSSLASEDSAVYYCARENLYGYYFDYWGQGTTL |
| 20 | 3.3B6 VL | QAVVTQESALTTSPGETVTLTCRSSTGAVTSGNFANWVQEKPDHLFTGLIGGADNRAPG<br>VPARFSGSLIGDKAALIITGAQTEDEAIYFCALWYSDHWVFGG |
| 21 | 3.3B6 HC<br>LALAPG mIgG2a | MGWSCIILFLVATATGAYAQVQLQQSGAELARPGASVKLSCKASGYTFTSHWMQWLKQR<br>PGQGLEWIGAIYPGDGDTKFTQKFKDKATLTADKSSTTAYMQLSSLASEDSAVYYCARE<br>NLYGYYFDYWGQGTTLTVSSASTKGPSVYPLAPVCGDTTGSSVTLGCLVKGYFPEPVTL<br>TWNSGSLSSGVHTFPAVLQSDLYTLSSSVTVTSSTWPSQSITCNVAHPASSTKVDKKIE<br>PRGPTIKPCPPCKCPAPNAAGGPSVFIFPPKIKDVLMISLSPIVTCVWDVSEDDPDVQ<br>ISWFVNNVEVHTAQTQTHREDYNSTLRWSALPIQHQDWMSGKEFKCKVNNKDLGAPIE<br>RTISKPKGSVRAPQVYVLPPPEEEMTKKQVTLTCMVTDFMPEDIYVEWTNNGKTELNYK<br>NTEPVLDSDGSYFMYSKLRVEKKNWVERNSYSCSVVHEGLHNHHTTKSFSRTPGK |
| 22 | 3.3B6 LC<br>LALAPG mIgG2a | MGWSCIILFLVATATGVHSQAWTQESALTTSPGETVTLTCRSSTGAVTSGNFANWVQE<br>KPDHLFTGLIGGADNRAPGVPARFSGSLIGDKAALIITGAQTEDEAIYFCALWYSDHWV<br>FGGGTKLTVLGQPKSTPTLTVFPPSSEELKENKATLVCLISNFSPSGVTVAWKANGTPI<br>TQGVDTSNPTKEGNKFMASSFLHLTSDQWRSHNSFTCQVTHEGDTVEKSLSRADCL |
| 23 | 3.7D6 VH CDR1 | NYGVN |
| 24 | 3.7D6 VH CDR2 | WINTNTGQTTYAEEFRG |
| 25 | 3.7D6 VH CDR3 | LIYDGDYISSDF |
| 26 | 3.7D6 VL CDR1 | GASENIYGALN |
| 27 | 3.7D6 VL CDR2 | GATNLAD |
| 28 | 3.7D6 VL CDR3 | QNALSMPYT |
| 29 | 3.7D6 VH | QIQLVQSGPDLKKPGETVKISCRTSGYAFTNYGVNWVKQAPGKGLKWMGWINTNTGQTT<br>YAEEFRGRFAISLETSASTAFLTISNLKNEDSATYFCARLIYDGDYISSDFWGQGTTL |
| 30 | 3.7D6 VL | DIQMTQSPDSLSASVGETVTITCGASENIYGALNWYQRKQGKSPQLLIYGATNLADGMS<br>SRFSGSRSGRQYSLKISSLHPDDVATYYCQNALSMPYTFGG |
| 31 | 3.7D6 HC<br>LALAPG mIgG2a | MGWSCIILFLVATATGAYAQIQLVQSGPDLKKPGETVKISCRTSGYAFTNYGVNWVKQA<br>PGKGLKWMGWINTNTGQTTYAEEFRGRFAISLETSASTAFLTISNLKNEDSATYFCARL<br>IYDGDYISSDFWGQGTTLTVSSASTKGPSVYPLAPVCGDTTGSSVTLGCLVKGYFPEPV<br>TLTWNSGSLSSGVHTFPAVLQSDLYTLSSSVTVTSSTWPSQSITCNVAHPASSTKVDKK<br>IEPRGPTIKPCPPCKCPAPNAAGGPSVFIFPPKIKDVLMISLSPIVTCVWDVSEDDPD<br>VQISWFVNNVEVHTAQTQTHREDYNSTLRWSALPIQHQDWMSGKEFKCKVNNKDLGAP<br>IERTISKPKGSVRAPQVYVLPPPEEEMTKKQVTLTCMVTDFMPEDIYVEWTNNGKTELN<br>YKNTEPVLDSDGSYFMYSKLRVEKKNWVERNSYSCSVVHEGLHNHHTTKSFSRTPGK |
| 32 | 3.7D6 LC<br>LALAPG mIgG2a | MGWSCIILFLVATATGVHSDIQMTQSPDSLSASVGETVTITCGASENIYGALNWYQRKQ<br>GKSPQLLIYGATNLADGMSSRFSGSRSGRQYSLKISSLHPDDVATYYCQNALSMPYTFG<br>GGTKLEIKRADAAPTVSIFPPSSEQLTSGGASVVCFLNNFYPKDINVKWKIDGSERQNG<br>VLNSWTDQDSKDSTYSMSSTLTLTKDEYERHNSYTCEATHKTSTSPIVKSFNRNEC |
| 33 | 3.3A8 VH CDR1 | NYEIH |
| 34 | 3.3A8 VH CDR2 | AIHPGNGVTAYNQMFKG |
| 35 | 3.3A8 VH CDR3 | NFDY |
| 36 | 3.3A8 VL CDR1 | RSSQSLTNSYGITYLS |
| 37 | 3.3A8 VL CDR2 | EISNRFS |
| 38 | 3.3A8 VL CDR3 | LQGTHQPFT |
| 39 | 3.3A8 VH | QVQFQQSGAELVRPGASVKVTCKALGYTFSNYEIHWVRQPPVHGLEWIGAIHPGNGVTA<br>YNQMFKGRATLAADKSSSTAYMELSSLTSEDSAVYYCTENFDYWGQGTAL |
| 40 | 3.3A8 VL | DVVVTQTPLSLPVSFGDQVSISCRSSQSLTNSYGITYLSWFLLKPGQSPQLLIYEISNR<br>FSGVPDRFSGSGSGTDFTLKISTIKPEDLGVYFCLQGTHQPFTFGA |
| 41 | 3.3A8 HC<br>LALAPG mIgG2a | MGWSCIILFLVATATGAYAQVQFQQSGAELVRPGASVKVTCKALGYTFSNYEIHWVRQP<br>PVHGLEWIGAIHPGNGVTAYNQMFKGRATLAADKSSSTAYMELSSLTSEDSAVYYCTEN<br>FDYWGQGTALTVSSASTKGPSVYPLAPVCGDTTGSSVTLGCLVKGYFPEPVTLTWNSGS<br>LSSGVHTFPAVLQSDLYTLSSSVTVTSSTWPSQSITCNVAHPASSTKVDKKIEPRGPTI |

| | | IV. Table of Certain Sequences | |
|---|---|---|---|

| SEQ ID NO | Description | Sequence |
|---|---|---|
| | | KPCPPCKCPAPNAAGGPSVFIFPPKIKDVLMISLSPIVTCVWDVSEDDPDVQISWFVN NVEVHTAQTQTHREDYNSTLRWSALPIQHQDWMSGKEFKCKVNNKDLGAPIERTISKP KGSVRAPQVYVLPPPEEEMTKKQVTLTCMVTDFMPEDIYVEWTNNGKTELNYKNTEPVL DSDGSYFMYSKLRVEKKNWVERNSYSCSVVHEGLHNHHTTKSFSRTPGK |
| 42 | 3.3A8 LC LALAPG mIgG2a | MGWSCIILFLVATATGVHSDVWTQTPLSLPVSFGDQVSISCRSSQSLTNSYGITYLSW FLLKPGQSPQLLIYEISNRFSGVPDRFSGSGSGTDFTLKISTIKPEDLGVYFCLQGTHQ PFTFGAGTKLEIKRADAAPTVSIFPPSSEQLTSGGASWCFLNNFYPKDINVKWKIDGS ERQNGVLNSWTDQDSKDSTYSMSSTLTLTKDEYERHNSYTCEATHKTSTSPIVKSFNRN EC |
| 43 | 3.2C11 VH CDR1 | DYEIH |
| 44 | 3.2C11 VH CDR2 | GIHPGNGGTAYNPKFKG |
| 45 | 3.2C11 VH CDR3 | WVDY |
| 46 | 3.2C11 VL CDR1 | RSSQSLVNRHGITYLS |
| 47 | 3.2C11 VL CDR2 | EISNRFS |
| 48 | 3.2C11 VL CDR3 | FQGTHQPFT |
| 49 | 3.2C11 VH | QVQLQQSGAELVRPGASVKLSCKALGYTFTDYEIHWVKQTPVHGLEWIGGIHPGNGGTA YNPKFKGKATLTADTSSSTASMELSSLTSEDSAVYYCTDWVDYWGQGTTL |
| 50 | 3.2C11 VL | DVVVTQTPLSLPVNFGDQVSISCRSSQSLVNRHGITYLSWYLHKPGQSPQLLIYEISNR FSGVPDRFSGSGSGTDFTLKISTIKPEDLGMYYCFQGTHQPFTFGG |
| 51 | 3.2C11 HC LALAPG mIgG2a | MGWSCIILFLVATATGVHSQVQLQQSGAELVRPGASVKLSCKALGYTFTDYEIHWVKQT PVHGLEWIGGIHPGNGGTAYNPKFKGKATLTADTSSSTASMELSSLTSEDSAVYYCTDW VDYWGQGTTLTVSSAKTTAPSVYPLAPVCGDTTGSSVTLGCLVKGYFPEPVTLTWNSGS LSSGVHTFPAVLQSDLYTLSSSVTVTSSTWPSQSITCNVAHPASSTKVDKKIEPRGPTI KPCPPCKCPAPNAAGGPSVFIFPPKIKDVLMISLSPIVTCVWDVSEDDPDVQISWFVN NVEVHTAQTQTHREDYNSTLRWSALPIQHQDWMSGKEFKCKVNNKDLGAPIERTISKP KGSVRAPQVYVLPPPEEEMTKKQVTLTCMVTDFMPEDIYVEWTNNGKTELNYKNTEPVL DSDGSYFMYSKLRVEKKNWVERNSYSCSVVHEGLHNHHTTKSFSRTPGK |
| 52 | 3.2C11 LC LALAPG mIgG2a | MGWSCIILFLVATATGVHSDVVVTQTPLSLPVNFGDQVSISCRSSQSLVNRHGITYLSW YLHKPGQSPQLLIYEISNRFSGVPDRFSGSGSGTDFTLKISTIKPEDLGMYYCFQGTHQ PFTFGGGTKLEIKRADAAPTVSIFPPSSEQLTSGGASWCFLNNFYPKDINVKWKIDGS ERQNGVLNSWTDQDSKDSTYSMSSTLTLTKDEYERHNSYTCEATHKTSTSPIVKSFNRN EC |
| 53 | 3.1C1 VH CDR1 | NYFIH |
| 54 | 3.1C1 VH CDR2 | WINPGNLNTKYTEEFKG |
| 55 | 3.1C1 VH CDR3 | GNPFVY |
| 56 | 3.1C1 VL CDR1 | KSSQSLLNSGNQKKYLT |
| 57 | 3.1C1 VL CDR2 | WTSTRDS |
| 58 | 3.1C1 VL CDR3 | QNDYSYPLT |
| 59 | 3.1C1 VH | QVQLQQSGPELVKPGASVRISCKASGYTFTNYFIHWVKQRPGQGLEWIGWINPGNLNTK YTEEFKGKATLTADKSSSTAYIQLNSLTSEDSAVYFCVNGNPFVYWGQGTLV |
| 60 | 3.1C1 VL | DIVMTQSPSSLTVIAGEKVTLNCKSSQSLLNSGNQKKYLTWLQQKPGQPPKLLIYWTST RDSGVPDRFTGSGSGTDFTLTISSVQAEDLAVYYCQNDYSYPLTFGA |
| 61 | 3.1C1 HC LALAPG mIgG2a | MGWSCIILFLVATATGAYAQVQLQQSGPELVKPGASVRISCKASGYTFTNYFIHWVKQR PGQGLEWIGWINPGNLNTKYTEEFKGKATLTADKSSSTAYIQLNSLTSEDSAVYFCVNG NPFVYWGQGTLVTVSAASTKGPSVYPLAPVCGDTTGSSVTLGCLVKGYFPEPVTLTWNS GSLSSGVHTFPAVLQSDLYTLSSSVTVTSSTWPSQSITCNVAHPASSTKVDKKIEPRGP TIKPCPPCKCPAPNAAGGPSVFIFPPKIKDVLMISLSPIVTCVWDVSEDDPDVQISWF VNNVEVHTAQTQTHREDYNSTLRWSALPIQHQDWMSGKEFKCKVNNKDLGAPIERTIS KPKGSVRAPQVYVLPPPEEEMTKKQVTLTCMVTDFMPEDIYVEWTNNGKTELNYKNTEP VLDSDGSYFMYSKLRVEKKNWVERNSYSCSVVHEGLHNHHTTKSFSRTPGK |

-continued

IV. Table of Certain Sequences

| SEQ ID NO | Description | Sequence |
|---|---|---|
| 62 | 3.1C1 LC LALAPG mIgG2a | MGWSCIILFLVATATGVHSDIVMTQSPSSLTVIAGEKVTLNCKSSQSLLNSGNQKKYLT WLQQKPGQPPKLLIYWTSTRDSGVPDRFTGSGSGTDFTLTISSVQAEDLAVYYCQNDYS YPLTFGAGTKLEIKRADAAPTVSIFPPPSSEQLTSGGASWCFLNNFYPKDINVKWKIDG SERQNGVLNSWTDQDSKDSTYSMSSTLTLTKDEYERHNSYTCEATHKTSTSPIVKSFNR NEC |
| 63 | 3.1C7 VH CDR1 | SYWMH |
| 64 | 3.1C7 VH CDR2 | AIYPGKSDIKYNQKFKD |
| 65 | 3.1C7 VH CDR3 | SIPFVY |
| 66 | 3.1C7 VL CDR1 | KSSQSLLNSENQKKYLT |
| 67 | 3.1C7 VL CDR2 | WTSTRYS |
| 68 | 3.1C7 VL CDR3 | QNDYSYPLT |
| 69 | 3.1C7 VH | EVQLQQSGTVLSRPGASVKMSCKASGYTMTSYWMHWIKQRPGQGLEWIGAIYPGKSDIK YNQKFKDKAKLTAVTATSTAYMEINSLTNEDSAVYYCTNSIPFVYWGQGTLI |
| 70 | 3.1C7 VL | DIVMTQSPSSLTVTAGEKVTMSCKSSQSLLNSENQKKYLTWFQQKPGQPPKLLIYWTST RYSGIPDRFTGSGSGTVFTLTISSVQADDLAVYYCQNDYSYPLTFGG |
| 71 | 3.1C7 HC LALAPG mIgG2a | MGWSCIILFLVATATGAYAEVQLQQSGTVLSRPGASVKMSCKASGYTMTSYWMHWIKQR PGQGLEWIGAIYPGKSDIKYNQKFKDKAKLTAVTATSTAYMEINSLTNEDSAVYYCTNS IPFVYWGQGTLITVSAASTKGPSVYPLAPVCGDTTGSSVTLGCLVKGYFPEPVTLTWNS GSLSSGVHTFPAVLQSDLYTLSSSVTVTSSTWPSQSITCNVAHPASSTKVDKKIEPRGP TIKPCPPCKCPAPNAAGGPSVFIFPPKIKDVLMISLSPIVTCVWDVSEDDPDVQISWF VNNVEVHTAQTQTHREDYNSTLRWSALPIQHQDWMSGKEFKCKVNNKDLGAPIERTIS KPKGSVRAPQVYVLPPPEEEMTKKQVTLTCMVTDFMPEDIYVEWTNNGKTELNYKNTEP VLDSDGSYFMYSKLRVEKKNWVERNSYSCSVVHEGLHNHHTTKSFSRTPGK |
| 72 | 3.1C7 LC mIgG2a | MGWSCIILFLVATATGVHSDIVMTQSPSSLTVTAGEKVTMSCKSSQSLLNSENQKKYLT WFQQKPGQPPKLLIYWTSTRYSGIPDRFTGSGSGTVFTLTISSVQADDLAVYYCQNDYS YPLTFGGGTKLEIKRADAAPTVSIFPPPSSEQLTSGGASVVCFLNNFYPKDINVKWKIDG SERQNGVLNSWTDQDSKDSTYSMSSTLTLTKDEYERHNSYTCEATHKTSTSPIVKSFNR NEC |
| 73 | 3.4G10 VH CDR1 | SGESWH |
| 74 | 3.4G10 VH CDR2 | FIHYSGSANYNPSLKS |
| 75 | 3.4G10 VH CDR3 | SVYNYDGAWFPY |
| 76 | 3.4G10 VL CDR1 | SASSSVSSSYLN |
| 77 | 3.4G10 VL CDR2 | RTSNLAS |
| 78 | 3.4G10 VL CDR3 | HQWSAYPPT |
| 79 | 3.4G10 VH | DVQLQESGPDLVKPSQSLSLTCTVTGYSITSGESWHWIRHFPGNELEWMGFIHYSGSAN YNPSLKSRISITRDTSKNQFFLQLLSVTTDDTATYYCARSVYNYDGAWFPYWGQGTLV |
| 80 | 3.4G10 VL | QIVLTQSPVIMSASPGERVTLTCSASSSVSSSYLNWYQLKPGSSPKVWIYRTSNLASGV PARFSGSGSGTSYSLTISSMEAEDAASYFCHQWSAYPPTFGG |
| 81 | 3.4G10 HC LALAPG mIgG2a | MGWSCIILFLVATATGAYADVQLQESGPDLVKPSQSLSLTCTVTGYSITSGESWHWIRH FPGNELEWMGFIHYSGSANYNPSLKSRISITRDTSKNQFFLQLLSVTTDDTATYYCARS VYNYDGAWFPYWGQGTLVTVSAASTKGPSVYPLAPVCGDTTGSSVTLGCLVKGYFPEPV TLTWNSGSLSSGVHTFPAVLQSDLYTLSSSVTVTSSTWPSQSITCNVAHPASSTKVDKK IEPRGPTIKPCPPCKCPAPNAAGGPSVFIFPPKIKDVLMISLSPIVTCVWDVSEDDPD VQISWFVNNVEVHTAQTQTHREDYNSTLRWSALPIQHQDWMSGKEFKCKVNNKDLGAP IERTISKPKGSVRAPQVYVLPPPEEEMTKKQVTLTCMVTDFMPEDIYVEWTNNGKTELN YKNTEPVLDSDGSYFMYSKLRVEKKNWVERNSYSCSVVHEGLHNHHTTKSFSRTPGK |
| 82 | 3.4G10 LC LALAPG mIgG2a | MGWSCIILFLVATATGVHSQIVLTQSPVIMSASPGERVTLTCSASSSVSSSYLNWYQLK PGSSPKVWIYRTSNLASGVPARFSGSGSGTSYSLTISSMEAEDAASYFCHQWSAYPPTF GGGTKLEIKRADAAPTVSIFPPPSSEQLTSGGASWCFLNNFYPKDINVKWKIDGSERQN GVLNSWTDQDSKDSTYSMSSTLTLTKDEYERHNSYTCEATHKTSTSPIVKSFNRNEC |
| 83 | 3.6E10 VH CDR1 | SYYLH |
| 84 | 3.6E10 VH CDR2 | YINPNTGYTEYTQNFKD |

IV. Table of Certain Sequences

| SEQ ID NO | Description | Sequence |
|---|---|---|
| 85 | 3.6E10 VH CDR3 | GNPFVY |
| 86 | 3.6E10 VL CDR1 | RSSQSLLNSGNQKNYLT |
| 87 | 3.6E10 VL CDR2 | WTSTRYS |
| 88 | 3.6E10 VL CDR3 | QNDYSYPLT |
| 89 | 3.6E10 VH | QVQLQQSGAELAKPGASVKMSCKASGYIFTSYYLHWVKQRPGQGLEWIGYINPNTGYTE YTQNFKDRATLTADKSSSTAYMQLTSLTSEDSAVYFCVNGNPFVYWGQGTLV |
| 90 | 3.6E10 VL | DIVMTQSPSSLTVTTGEKVTMTCRSSQSLLNSGNQKNYLTWFQQKPGQPPKLLIYWTST RYSGVPDRFTGSGSGTDFTLTISSVQAEDLAVYYCQNDYSYPLTFGA |
| 91 | 3.6E10 HC LALAPG mIgG2a | MGWSCIILFLVATATGAYAQVQLQQSGAELAKPGASVKMSCKASGYIFTSYYLHWVKQR PGQGLEWIGYINPNTGYTEYTQNFKDRATLTADKSSSTAYMQLTSLTSEDSAVYFCVNG NPFVYWGQGTLVTVSAASTKGPSVYPLAPVCGDTTGSSVTLGCLVKGYFPEPVTLTWNS GSLSSGVHTFPAVLQSDLYTLSSSVTVTSSTWPSQSITCNVAHPASSTKVDKKIEPRGP TIKPCPPCKCPAPNAAGGPSVFIFPPKIKDVLMISLSPIVTCVWDVSEDDPDVQISWF VNNVEVHTAQTQTHREDYNSTLRWSALPIQHQDWMSGKEFKCKVNNKDLGAPIERTIS KPKGSVRAPQVYVLPPPEEEMTKKQVTLTCMVTDFMPEDIYVEWTNNGKTELNYKNTEP VLDSDGSYFMYSKLRVEKKNWVERNSYSCSVVHEGLHNHHTTKSFSRTPGK |
| 92 | 3.6E10 LC LALAPG mIgG2a | MGWSCIILFLVATATGVHSDIVMTQSPSSLTVTTGEKVTMTCRSSQSLLNSGNQKNYLT WFQQKPGQPPKLLIYWTSTRYSGVPDRFTGSGSGTDFTLTISSVQAEDLAVYYCQNDYS YPLTFGAGTKLEIKRADAAPTVSIFPPSSEQLTSGGASWCFLNNFYPKDINVKWKIDG SERQNGVLNSWTDQDSKDSTYSMSSTLTLTKDEYERHNSYTCEATHKTSTSPIVKSFNR NEC |
| 93 | 3.3F7 VH CDR1 | TYGVH |
| 94 | 3.3F7 VH CDR2 | VIWRGGNTDYNAAFMS |
| 95 | 3.3F7 VH CDR3 | SSYGYHYTMDY |
| 96 | 3.3F7 VL CDR1 | KASQNVGTAVA |
| 97 | 3.3F7 VL CDR2 | WASTRHT |
| 98 | 3.3F7 VL CDR3 | QRYNNFPFT |
| 99 | 3.3F7 VH | QVQLKQSGPSLVQPSQSLSITCTVSGFSLTTYGVHWVRQSPGKGLEWLGVIWRGGNTDY NAAFMSRLSITKDNSQSQVFFKMNSLQADDTAIYYCAKSSYGYHYTMDYWGHGTSV |
| 100 | 3.3F7 VL | DIVVTQSHRFMSTSVGDRVIITCKASQNVGTAVAWYQQKPGQSPKLLIYWASTRHTGVP DRFTGSGSGTDFTLTISNVQSEDLADYFCQRYNNFPFTFGS |
| 101 | 3.3F7 HC LALAPG mIgG2a | MGWSCIILFLVATATGAYAQVQLKQSGPSLVQPSQSLSITCTVSGFSLTTYGVHWVRQS PGKGLEWLGVIWRGGNTDYNAAFMSRLSITKDNSQSQVFFKMNSLQADDTAIYYCAKSS YGYHYTMDYWGHGTSVTVSSASTKGPSVYPLAPVCGDTTGSSVTLGCLVKGYFPEPVTL TWNSGSLSSGVHTFPAVLQSDLYTLSSSVTVTSSTWPSQSITCNVAHPASSTKVDKKIE PRGPTIKPCPPCKCPAPNAAGGPSVFIFPPKIKDVLMISLSPIVTCVWDVSEDDPDVQ ISWFVNNVEVHTAQTQTHREDYNSTLRWSALPIQHQDWMSGKEFKCKVNNKDLGAPIE RTISKPKGSVRAPQVYVLPPPEEEMTKKQVTLTCMVTDFMPEDIYVEWTNNGKTELNYK NTEPVLDSDGSYFMYSKLRVEKKNWVERNSYSCSVVHEGLHNHHTTKSFSRTPGK |
| 102 | 3.3F7 LC LALAPG mIgG2a | MGWSCIILFLVATATGVHSDIWTQSHRFMSTSVGDRVIITCKASQNVGTAVAWYQQKP GQSPKLLIYWASTRHTGVPDRFTGSGSGTDFTLTISNVQSEDLADYFCQRYNNFPFTFG SGTKLEIKRADAAPTVSIFPPSSEQLTSGGASVVCFLNNFYPKDINVKWKIDGSERQNG VLNSWTDQDSKDSTYSMSSTLTLTKDEYERHNSYTCEATHKTSTSPIVKSFNRNEC |
| 103 | 4.17A5 VH CDR1 | NSWIN |
| 104 | 4.17A5 VH CDR2 | RIYPGDGDTKYNGKFKG |
| 105 | 4.17A5 VH CDR3 | FPFGKYEGPGAMDY |
| 106 | 4.17A5 VL CDR1 | RASQDISSYLN |
| 107 | 4.17A5 VL CDR2 | YTSRLHS |
| 108 | 4.17A5 VL CDR3 | QQGNTLPYT |

IV. Table of Certain Sequences

| SEQ ID NO | Description | Sequence |
|---|---|---|
| 109 | 4.17A5 VH | QVQLQQSGPELLKPGASVKISCKGSGYAFSNSWINWVKLRPGQGLEWIGRIYPGDGDTK<br>YNGKFKGKATLTADKSSSTAHMQLRSLTSVDSAVYFCARFPFGKYEGPGAMDYWGQGTS<br>V |
| 110 | 4.17A5 VL | DIQMTQTTSSLSASLGDRVTISCRASQDISSYLNWYQQKPDGTIKLLIYYTSRLHSGVP<br>SRFSGSGSGTDFSLTISNLEQEDIATYFCQQGNTLPYTFGG |
| 111 | 4.17A5 HC<br>LALAPG mIgG2a | MGWSCIILFLVATATGVHSQVQLQQSGPELLKPGASVKISCKGSGYAFSNSWINWVKLR<br>PGQGLEWIGRIYPGDGDTKYNGKFKGKATLTADKSSSTAHMQLRSLTSVDSAVYFCARF<br>PFGKYEGPGAMDYWGQGTSVTVSSAKTTAPSVYPLAPVCGDTTGSSVTLGCLVKGYFPE<br>PVTLTWNSGSLSSGVHTFPAVLQSDLYTLSSSVTVTSSTWPSQSITCNVAHPASSTKVD<br>KKIEPRGPTIKPCPPCKCPAPNAAGGPSVFIFPPKIKDVLMISLSPIVTCVVVDVSEDD<br>PDVQISWFVNNVEVHTAQTQTHREDYNSTLRWSALPIQHQDWMSGKEFKCKVNNKDLG<br>APIERTISKPKGSVRAPQVYVLPPPEEEMTKKQVTLTCMVTDFMPEDIYVEWTNNGKTE<br>LNYKNTEPVLDSDGSYFMYSKLRVEKKNWVERNSYSCSVVHEGLHNHHTTKSFSRTPGK |
| 112 | 4.17A5 LC<br>LALAPG mIgG2a | MGWSCIILFLVATATGVHSDIQMTQTTSSLSASLGDRVTISCRASQDISSYLNWYQQKP<br>DGTIKLLIYYTSRLHSGVPSRFSGSGSGTDFSLTISNLEQEDIATYFCQQGNTLPYTFG<br>GGTKLEIKRADAAPTVSIFPPSSEQLTSGGASVVCFLNNFYPKDINVKWKIDGSERQNG<br>VLNSWTDQDSKDSTYSMSSTLTLTKDEYERHNSYTCEATHKTSTSPIVKSFNRNEC |
| 113 | 4.2C4 VH CDR1 | DYVIS |
| 114 | 4.2C4 VH CDR2 | EMFPGSGTTYYTEKFRG |
| 115 | 4.2C4 VH CDR3 | GTTADY |
| 116 | 4.2C4 VL CDR1 | RASSSVNYMY |
| 117 | 4.2C4 VL CDR2 | YTSNLAP |
| 118 | 4.2C4 VL CDR3 | QQFTSSPYT |
| 119 | 4.2C4 VH | QVQLQQSGPELVKPGASVKMSCKASGYTFTDYVISWVKQRTGQGLEWIGEMFPGSGTTY<br>YTEKFRGKATLTADKSSNTAYMQLSSLTSEDSAVYFCARGTTADYWGQGTTL |
| 120 | 4.2C4 VL | ENVLTQSPAIMSASLGEKVTMSCRASSSVNYMYWYQQKSDASPKLWIYYTSNLAPGVPA<br>RFSGSGSGNSYSLTISSMEGEDAATYYCQQFTSSPYTFGG |
| 121 | 4.2C4 HC<br>LALAPG mIgG2a | MGWSCIILFLVATATGVHSQVQLQQSGPELVKPGASVKMSCKASGYTFTDYVISWVKQR<br>TGQGLEWIGEMFPGSGTTYYTEKFRGKATLTADKSSNTAYMQLSSLTSEDSAVYFCARG<br>TTADYWGQGTTLTVSSAKTTAPSVYPLAPVCGDTTGSSVTLGCLVKGYFPEPVTLTWNS<br>GSLSSGVHTFPAVLQSDLYTLSSSVTVTSSTWPSQSITCNVAHPASSTKVDKKIEPRGP<br>TIKPCPPCKCPAPNAAGGPSVFIFPPKIKDVLMISLSPIVTCVWDVSEDDPDVQISWF<br>VNNVEVHTAQTQTHREDYNSTLRWSALPIQHQDWMSGKEFKCKVNNKDLGAPIERTIS<br>KPKGSVRAPQVYVLPPPEEEMTKKQVTLTCMVTDFMPEDIYVEWTNNGKTELNYKNTEP<br>VLDSDGSYFMYSKLRVEKKNWVERNSYSCSVVHEGLHNHHTTKSFSRTPGK |
| 122 | 4.2C4 LC<br>LALAPG mIgG2a | MGWSCIILFLVATATGVHSENVLTQSPAIMSASLGEKVTMSCRASSSVNYMYWYQQKSD<br>ASPKLWIYYTSNLAPGVPARFSGSGSGNSYSLTISSMEGEDAATYYCQQFTSSPYTFGG<br>GTKLEIKRADAAPTVSIFPPSSEQLTSGGASVVCFLNNFYPKDINVKWKIDGSERQNGV<br>LNSWTDQDSKDSTYSMSSTLTLTKDEYERHNSYTCEATHKTSTSPIVKSFNRNEC |
| 123 | 4.12E5 VH CDR1 | GYFMH |
| 124 | 4.12E5 VH CDR2 | YISCYNGASVYNQRFKG |
| 125 | 4.12E5 VH CDR3 | DVLRYPRYAVDY |
| 126 | 4.12E5 VL CDR1 | KSSQSLLDSDGKTYLN |
| 127 | 4.12E5 VL CDR2 | LVSNLDS |
| 128 | 4.12E5 VL CDR3 | WQGSHFPFT |
| 129 | 4.12E5 VH | EVQLQQSGPELVKTGASVKISCKASGYSFTGYFMHWVKQSHGKSLEWIGYISCYNGASV<br>YNQRFKGKATFTIDTSSSTAYMQFNSLTSEDSAVYYCARDVLRYPRYAVDYWGQGTSV |
| 130 | 4.12E5 VL | DVVMTQTPLTLSVTIGQPASISCKSSQSLLDSDGKTYLNWLLQRPGQSPKRLIYLVSNL<br>DSGVPARFTGSGSGTDFTLKISRVEAEDLGVYYCWQGSHFPFTFGS |

| | | IV. Table of Certain Sequences |
|---|---|---|

| SEQ ID NO | Description | Sequence |
|---|---|---|
| 131 | 4.12E5 HC LALAPG mIgG2a | MGWSCIILFLVATATGVHSEVQLQQSGPELVKTGASVKISCKASGYSFTGYFMHWVKQS HGKSLEWIGYISCYNGASVYNQRFKGKATFTIDTSSSTAYMQFNSLTSEDSAVYYCARD VLRYPRYAVDYWGQGTSVTVSSAKTTAPSVYPLAPVCGDTTGSSVTLGCLVKGYFPEPV TLTWNSGSLSSGVHTFPAVLQSDLYTLSSSVTVTSSTWPSQSITCNVAHPASSTKVDKK IEPRGPTIKPCPPCKCPAPNAAGGPSVFIFPPKIKDVLMISLSPIVTCVVVDVSEDDPD VQISWFVNNVEVHTAQTQTHREDYNSTLRWSALPIQHQDWMSGKEFKCKVNNKDLGAP IERTISKPKGSVRAPQVYVLPPPEEEMTKKQVTLTCMVTDFMPEDIYVEWTNNGKTELN YKNTEPVLDSDGSYFMYSKLRVEKKNWVERNSYSCSVVHEGLHNHHTTKSFSRTPGK |
| 132 | 4.12E5 LC LALAPG mIgG2a | MGWSCIILFLVATATGVHSDVVMTQTPLTLSVTIGQPASISCKSSQSLLDSDGKTYLNW LLQRPGQSPKRLIYLVSNLDSGVPARFTGSGSGTDFTLKISRVEAEDLGVYYCWQGSHF PFTFGSGTKLEIKRADAAPTVSIFPPSSEQLTSGGASWCFLNNFYPKDINVKWKIDGS ERQNGVLNSWTDQDSKDSTYSMSSTLTLTKDEYERHNSYTCEATHKTSTSPIVKSFNRN EC |
| 133 | 4.11A10 VH CDR1 | GYFMH |
| 134 | 4.11A10 VH CDR2 | YISCYNGVSVYNQRFKG |
| 135 | 4.11A10 VH CDR3 | DVLRYPRYAVDY |
| 136 | 4.11A10 VL CDR1 | KSSQSLLDSDGKTYLN |
| 137 | 4.11A10 VL CDR2 | LVSNLDS |
| 138 | 4.11A10 VL CDR3 | WQGSHFPFT |
| 139 | 4.11A10 VH | EVQLQQSGPELVKTGASVKISCKASGYSFTGYFMHWVKQSHGKSLEWIGYISCYNGVSV YNQRFKGKATFTIDTSSSTAYMQFNSLTSEDSAVYYCARDVLRYPRYAVDYWGQGTSV |
| 140 | 4.11A10 VL | DVVMTQTPLTLSVTIGQPASISCKSSQSLLDSDGKTYLNWLLQRPGQSPKRLIYLVSNL DSGVPDRFTGSGSGTDFTLKISRVEAEDLGVYYCWQGSHFPFTFGS |
| 141 | 4.11A10 HC LALAPG mIgG2a | MGWSCIILFLVATATGVHSEVQLQQSGPELVKTGASVKISCKASGYSFTGYFMHWVKQS HGKSLEWIGYISCYNGVSVYNQRFKGKATFTIDTSSSTAYMQFNSLTSEDSAVYYCARD VLRYPRYAVDYWGQGTSVTVSSAKTTAPSVYPLAPVCGDTTGSSVTLGCLVKGYFPEPV TLTWNSGSLSSGVHTFPAVLQSDLYTLSSSVTVTSSTWPSQSITCNVAHPASSTKVDKK IEPRGPTIKPCPPCKCPAPNAAGGPSVFIFPPKIKDVLMISLSPIVTCVWDVSEDDPD VQISWFVNNVEVHTAQTQTHREDYNSTLRWSALPIQHQDWMSGKEFKCKVNNKDLGAP IERTISKPKGSVRAPQVYVLPPPEEEMTKKQVTLTCMVTDFMPEDIYVEWTNNGKTELN YKNTEPVLDSDGSYFMYSKLRVEKKNWVERNSYSCSVVHEGLHNHHTTKSFSRTPGK |
| 142 | 4.11A10 LC LALAPG mIgG2a | MGWSCIILFLVATATGVHSDVVMTQTPLTLSVTIGQPASISCKSSQSLLDSDGKTYLNW LLQRPGQSPKRLIYLVSNLDSGVPDRFTGSGSGTDFTLKISRVEAEDLGVYYCWQGSHF PFTFGSGTKLEIKRADAAPTVSIFPPSSEQLTSGGASWCFLNNFYPKDINVKWKIDGS ERQNGVLNSWTDQDSKDSTYSMSSTLTLTKDEYERHNSYTCEATHKTSTSPIVKSFNRN EC |
| 143 | 4.11H11 VH CDR1 | VYTMN |
| 144 | 4.11H11 VH CDR2 | LINPYNGGTIYNRKFKG |
| 145 | 4.11H11 VH CDR3 | GALYRYEGAMDY |
| 146 | 4.11H11 VL CDR1 | RASSSVIYVH |
| 147 | 4.11H11 VL CDR2 | ATSNLAS |
| 148 | 4.11H11 VL CDR3 | QQWSSNPLT |
| 149 | 4.11H11 VH | EVQVQQSGPELVKPGASMKISCKASGYSFIVYTMNWVKQSHGKNLEWIGLINPYNGGTI YNRKFKGKATLTVDKSSSTAYLELLSLTSEDSAVYYCARGALYRYEGAMDYWGQGTSVI |
| 150 | 4.11H11 VL | QIVLSQFPAILSASPGEKVTMTCRASSSVIYVHWYQQKPGSSPKPWIYATSNLASGVPA RFSGSGSGTSHSLTISRLEAEDTATYYCQQWSSNPLTFGA |
| 151 | 4.11H11 HC LALAPG mIgG2a | MGWSCIILFLVATATGVHSEVQVQQSGPELVKPGASMKISCKASGYSFIVYTMNWVKQS HGKNLEWIGLINPYNGGTIYNRKFKGKATLTVDKSSSTAYLELLSLTSEDSAVYYCARG ALYRYEGAMDYWGQGTSVIVSSAKTTAPSVYPLAPVCGDTTGSSVTLGCLVKGYFPEPV TLTWNSGSLSSGVHTFPAVLQSDLYTLSSSVTVTSSTWPSQSITCNVAHPASSTKVDKK IEPRGPTIKPCPPCKCPAPNAAGGPSVFIFPPKIKDVLMISLSPIVTCVWDVSEDDPD VQISWFVNNVEVHTAQTQTHREDYNSTLRVVSALPIQHQDWMSGKEFKCKVNNKDLGAP IERTISKPKGSVRAPQVYVLPPPEEEMTKKQVTLTCMVTDFMPEDIYVEWTNNGKTELN YKNTEPVLDSDGSYFMYSKLRVEKKNWVERNSYSCSVVHEGLHNHHTTKSFSRTPGK |

IV. Table of Certain Sequences

| SEQ ID NO | Description | Sequence |
|---|---|---|
| 152 | 4.11H11 LC LALAPG mIgG2a | MGWSCIILFLVATATGVHSQIVLSQFPAILSASPGEKVTMTCRASSSVIYVHWYQQKPG SSPKPWIYATSNLASGVPARFSGSGSGTSHSLTISRLEAEDTATYYCQQWSSNPLTFGA GTKLEIKRADAAPTVSIFPPSSEQLTSGGASVVCFLNNFYPKDINVKWKIDGSERQNGV LNSWTDQDSKDSTYSMSSTLTLTKDEYERHNSYTCEATHKTSTSPIVKSFNRNEC |
| 153 | 4.29C4 VH CDR1 | NYWMN |
| 154 | 4.29C4 VH CDR2 | MIHPSDSESRLSQRFKD |
| 155 | 4.29C4 VH CDR3 | LDY |
| 156 | 4.29C4 VL CDR1 | KSSQSLLKSSNQKNYLA |
| 157 | 4.29C4 VL CDR2 | FASTRES |
| 158 | 4.29C4 VL CDR3 | QQHYSAPLT |
| 159 | 4.29C4 VH | QVQLQQPGAELVRPGASVKLSCKASGYSFANYWMNWVKQRPGQGLEWIGMIHPSDSESR LSQRFKDKATLTVDKSSSTAYMQLNSPTSEDSAVYYCARLDYWGQGTSV |
| 160 | 4.29C4 VL | DIVMTQSPSSLAMSVGQKVTMSCKSSQSLLKSSNQKNYLAWYQQKPGQSPKLLVFFAST RESGVPDRFIGSGSGTDFTLTISSVQAEDLADYFCQQHYSAPLTFGA |
| 161 | 4.29C4 HC LALAPG mIgG2a | MGWSCIILFLVATATGVHSQVQLQQPGAELVRPGASVKLSCKASGYSFANYWMNWVKQR PGQGLEWIGMIHPSDSESRLSQRFKDKATLTVDKSSSTAYMQLNSPTSEDSAVYYCARL DYWGQGTSVTVSSAKTTAPSVYPLAPVCGDTTGSSVTLGCLVKGYFPEPVTLTWNSGSL SSGVHTFPAVLQSDLYTLSSSVTVTSSTWPSQSITCNVAHPASSTKVDKKIEPRGPTIK PCPPCKCPAPNAAGGPSVFIFPPPKIKDVLMISLSPIVTCVWDVSEDDPDVQISWFVNN VEVHTAQTQTHREDYNSTLRVVSALPIQHQDWMSGKEFKCKVNNKDLGAPIERTISKPK GSVRAPQVYVLPPPEEEMTKKQVTLTCMVTDFMPEDIYVEWTNNGKTELNYKNTEPVLD SDGSYFMYSKLRVEKKNWVERNSYSCSVVHEGLHNHHTTKSFSRTPGK |
| 162 | 4.29C4 LC LALAPG mIgG2a | MGWSCIILFLVATATGVHSDIVMTQSPSSLAMSVGQKVTMSCKSSQSLLKSSNQKNYLA WYQQKPGQSPKLLVFFASTRESGVPDRFIGSGSGTDFTLTISSVQAEDLADYFCQQHYS APLTFGAGTKLEIKRADAAPTVSIFPPSSEQLTSGGASVVCFLNNFYPKDINVKWKIDG SERQNGVLNSWTDQDSKDSTYSMSSTLTLTKDEYERHNSYTCEATHKTSTSPIVKSFNR NEC |
| 163 | 5.17D12 VH CDR1 | SNYYMC |
| 164 | 5.17D12 VH CDR2 | CVYVGSGGSTYYASWAK |
| 165 | 5.17D12 VH CDR3 | DLSYAGDL |
| 166 | 5.17D12 VL CDR1 | QASESISSYLA |
| 167 | 5.17D12 VL CDR2 | GASNLAS |
| 168 | 5.17D12 VL CDR3 | QSAYYSNSGGHA |
| 169 | 5.17D12 VH | QSLEESGGDLVKPGASLTLTCTASGFSFSSNYYMCWVRQAPGKGLEWIACVYVGSGGST YYASWAKGRFTFSKTSSTTWTLQMTSLTAADTATYFCARDLSYAGDLWGPGTLVTVSS |
| 170 | 5.17D12 VL | DPVMTQTPASVSEPVGGTVTINCQASESISSYLAWYQQKPGQPPKLLIYGASNLASGVP SRFKGSGSGTEYTLTISDLECDDAATYYCQSAYYSNSGGHAFGGGTEVVVK |
| 171 | 5.17D12 HC | METGLRWLLLVAVLKGVQCQSLEESGGDLVKPGASLTLTCTASGFSFSSNYYMCWVRQA PGKGLEWIACVYVGSGGSTYYASWAKGRFTFSKTSSTTWTLQMTSLTAADTATYFCARD LSYAGDLWGPGTLVTVSSGQPKAPSVFPLAPCCGDTPSSTVTLGCLVKGYLPEPVTVTW NSGTLTNGVRTFPSVRQSSGLYSLSSVVSVTSSSQPVTCNVAHPATNTKVDKTVAPSTC SKPTCPPPELLGGPSVFIFPPPKPKDTLMISRTPEVTCVWDVSQDDPEVQFTWYINNEQ VRTARPPLREQQFNSTIRWSTLPIAHQDWLRGKEFKCKVHNKALPAPIEKTISKARGQ PLEPKVYTMGPPREELSSRSVSLTCMINGFYPSDISVEWEKNGKAEDNYKTTPAVLDSD GSYFLYNKLSVPTSEWQRGDVFTCSVMHEALHNHYTQKSISRSPGK |
| 172 | 5.17D12 LC | MDMRAPTQLLGLLLLWLPGVICDPVMTQTPASVSEPVGGTVTINCQASESISSYLAWYQ QKPGQPPKLLIYGASNLASGVPSRFKGSGSGTEYTLTISDLECDDAATYYCQSAYYSNS GGHAFGGGTEVVVKGDPVAPTVLIFPPAADQVATGTVTIVCVANKYFPDVTVTWEVDGT TQTTGIENSKTPQNSADCTYNLSSTLTLTSTQYNSHKEYTCKVTQGTTSVVQSFNRGDC |
| 173 | 5.17H8 VH CDR1 | SYAMG |
| 174 | 5.17H8 VH CDR2 | IISSSGSTHYASWA |

IV. Table of Certain Sequences

| SEQ ID NO | Description | Sequence |
|---|---|---|
| 175 | 5.17H8 VH CDR3 | ARAGSTYYTGYYFNL |
| 176 | 5.17H8 VL CDR1 | QASESIYSNLA |
| 177 | 5.17H8 VL CDR2 | GASTLES |
| 178 | 5.17H8 VL CDR3 | QSGYYGISAINNA |
| 179 | 5.17H8 VH | QSLEESGGRLVTPGTPLTLTCTVSGIDLSSYAMGWVRQAPGKGLEWIGIISSSGSTHYASWAKGRFTISKTSTTVDLKITSPTTEDTATYFCARARAGSTYYTGYYFNLWGQGTLVTVSS |
| 180 | 5.17H8 VL | AIEMTQTASPVSAAVGGTVTINCQASESIYSNLAWYQQKPGQRPKLLIYGASTLESGVPSRFKGSGSGTEYTLTISDLECDDAATYYCQSGYYGISAINNAFGGGTEVVVK |
| 181 | 5.17H8 HC | METGLRWLLLVAVLKGVQCQSLEESGGRLVTPGTPLTLTCTVSGIDLSSYAMGWVRQAPGKGLEWIGIISSSGSTHYASWAKGRFTISKTSTTVDLKITSPTTEDTATYFCARARAGSTYYTGYYFNLWGQGTLVTVSSGQPKAPSVFPLAPCCGDTPSSTVTLGCLVKGYLPEPVTVTWNSGTLTNGVRTFPSVRQSSGLYSLSSVVSVTSSSQPVTCNVAHPATNTKVDKTVAPSTCSKPTCPPPELLGGPSVFIFPPKPKDTLMISRTPEVTCVWDVSQDDPEVQFTWYINNEQVRTARPPLREQQFNSTIRWSTLPIAHQDWLRGKEFKCKVHNKALPAPIEKTISKARGQPLEPKVYTMGPPREELSSRSVSLTCMINGFYPSDISVEWEKNGKAEDNYKTTPAVLDSDGSYFLYNKLSVPTSEWQRGDVFTCSVMHEALHNHYTQKSISRSPGK |
| 182 | 5.17H8 LC | MDMRAPTQLLGLLLLWLPGVTFAIEMTQTASPVSAAVGGTVTINCQASESIYSNLAWYQQKPGQRPKLLIYGASTLESGVPSRFKGSGSGTEYTLTISDLECDDAATYYCQSGYYGISAINNAFGGGTEVVWKGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC |
| 183 | 5.11H2 VH CDR1 | YNYWIY |
| 184 | 5.11H2 VH CDR2 | CINTGNSGITNYANWAK |
| 185 | 5.11H2 VH CDR3 | GGINSGDYMNL |
| 186 | 5.11H2 VL CDR1 | QASENIYRLLA |
| 187 | 5.11H2 VL CDR2 | DASTLAS |
| 188 | 5.11H2 VL CDR3 | QQAYSNSNIDNY |
| 189 | 5.11H2 VH | QSLEESGGDLVKPGASLTLTCTASGFSFSYNYWIYWVRQAPGKGLEWIGCINTGNSGITNYANWAKGRFTISKTSSTTVTLQMTSLTAADTATYFCARGGINSGDYMNLWGPGTLVTVSS |
| 190 | 5.11H2 VL | AYDMTQTPASVEVAVGGTVTIKCQASENIYRLLAWYQQKPGQAPKLLIYDASTLASGVPSRFSGSGSGTQFTLTVSGVQCDDAATYYCQQAYSNSNIDNYFGGGTEVVVK |
| 191 | 5.11H2HC | METGLRWLLLVAVLKGVQCQSLEESGGDLVKPGASLTLTCTASGFSFSYNYWIYWVRQAPGKGLEWIGCINTGNSGITNYANWAKGRFTISKTSSTTVTLQMTSLTAADTATYFCARGGINSGDYMNLWGPGTLVTVSSGQPKAPSVFPLAPCCGDTPSSTVTLGCLVKGYLPEPVTVTWNSGTLTNGVRTFPSVRQSSGLYSLSSVVSVTSSSQPVTCNVAHPATNTKVDKTVAPSTCSKPTCPPPELLGGPSVFIFPPKPKDTLMISRTPEVTCVWDVSQDDPEVQFTWYINNEQVRTARPPLREQQFNSTIRWSTLPIAHQDWLRGKEFKCKVHNKALPAPIEKTISKARGQPLEPKVYTMGPPREELSSRSVSLTCMINGFYPSDISVEWEKNGKAEDNYKTTPAVLDSDGSYFLYNKLSVPTSEWQRGDVFTCSVMHEALHNHYTQKSISRSPGK |
| 192 | 5.11H2LC | MDMRAPTQLLGLLLLWLPGARCAYDMTQTPASVEVAVGGTVTIKCQASENIYRLLAWYQQKPGQAPKLLIYDASTLASGVPSRFSGSGSGTQFTLTVSGVQCDDAATYYCQQAYSNSNIDNYFGGGTEVVVKGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC |
| 193 | 5.14D6 VH CDR1 | SKTIT |
| 194 | 5.14D6 VH CDR2 | FINTDGRAYYASWA |
| 195 | 5.14D6 VH CDR3 | TNL |
| 196 | 5.14D6 VL CDR1 | QASQSVYKNNYLA |
| 197 | 5.14D6 VL CDR2 | SVSTLDS |

IV. Table of Certain Sequences

| SEQ ID NO | Description | Sequence |
|---|---|---|
| 198 | 5.14D6 VL CDR3 | LGSYDCSSADCAA |
| 199 | 5.14D6 VH | QSVEESGGRLVTPGTPLTLTCTVSGFSLSSKTITWVRQAPGKGLEWIGFINTDGRAYYA<br>SWAKGRFTISKTSTTVDLKITSPTTEDTATYFCGRTNLWGQGTLVTVSS |
| 200 | 5.14D6 VL | AQVLTQTSSPVSAAVGSTVTINCQASQSVYKNNYLAWFQQKPGQPPKRLIYSVSTLDSG<br>VPSRFSGSGSGTQFTLTISDVQCDDAATYYCLGSYDCSSADCAAFGGGTEVVVK |
| 201 | 5.14D6 HC | METGLRWLLLVAVLKGVQCQSVEESGGRLVTPGTPLTLTCTVSGFSLSSKTITWVRQAP<br>GKGLEWIGFINTDGRAYYASWAKGRFTISKTSTTVDLKITSPTTEDTATYFCGRTNLWG<br>QGTLVTVSSGQPKAPSVFPLAPCCGDTPSSTVTLGCLVKGYLPEPVTVTWNSGTLTNGV<br>RTFPSVRQSSGLYSLSSVVSVTSSSQPVTCNVAHPATNTKVDKTVAPSTCSKPTCPPPE<br>LLGGPSVFIFPPKPKDTLMISRTPEVTCVVVDVSQDDPEVQFTWYINNEQVRTARPPLR<br>EQQFNSTIRWSTLPIAHQDWLRGKEFKCKVHNKALPAPIEKTISKARGQPLEPKVYTM<br>GPPREELSSRSVSLTCMINGFYPSDISVEWEKNGKAEDNYKTTPAVLDSDGSYFLYNKL<br>SVPTSEWQRGDVFTCSVMHEALHNHYTQKSISRSPGK |
| 202 | 5.14D6 LC | MDMRAPTQLLGLLLLWLPGATFAQVLTQTSSPVSAAVGSTVTINCQASQSVYKNNYLAW<br>FQQKPGQPPKRLIYSVSTLDSGVPSRFSGSGSGTQFTLTISDVQCDDAATYYCLGSYDC<br>SSADCAAFGGGTEVWKGDPVAPTVLIFPPAADQVATGTVTIVCVANKYFPDVTVTWEV<br>DGTTQTTGIENSKTPQNSADCTYNLSSTLTLTSTQYNSHKEYTCKVTQGTTSVVQSFNR<br>GDC |
| 203 | 3.7F5 VH CDR1 | DYNVF |
| 204 | 3.7F5 VH CDR2 | YIDPYNGATSYNQKFKD |
| 205 | 3.7F5 VH CDR3 | GTVRAFFDS |
| 206 | 3.7F5 VL CDR1 | KSSQSLLYRNDQINYLA |
| 207 | 3.7F5 VL CDR2 | WASTRES |
| 208 | 3.7F5 VL CDR3 | QQYYSYPPT |
| 209 | 3.7F5 VH | EIHLQQSGPEVVQPGASLKVSCKASDYSFTDYNVFWVKQSHGKSLEWIAYIDPYNGATS<br>YNQKFKDKATLTVDKSSSTAFMYLNSLTSEDSAVYYCARGTVRAFFDSWGQGTTL |
| 210 | 3.7F5 VL | DIVMSQSPSSLVVSVGEKVSLSCKSSQSLLYRNDQINYLAWYQQKPGQSPKLLIFWAST<br>RESGVPVRFTGSGSGTDFTLNINTVKAEDLAVYYCQQYYSYPPTFGT |
| 211 | 3.7F5 HC<br>LALAPG mIgG2a | MGWSCIILFLVATATGAYAEIHLQQSGPEWQPGASLKVSCKASDYSFTDYNVFWVKQS<br>HGKSLEWIAYIDPYNGATSYNQKFKDKATLTVDKSSSTAFMYLNSLTSEDSAVYYCARG<br>TVRAFFDSWGQGTTLTVSSASTKGPSVYPLAPVCGDTTGSSVTLGCLVKGYFPEPVTLT<br>WNSGSLSSGVHTFPAVLQSDLYTLSSSVTVTSSTWPSQSITCNVAHPASSTKVDKKIEP<br>RGPTIKPCPPCKCPAPNAAGGPSVFIFPPKIKDVLMISLSPIVTCVWDVSEDDPDVQI<br>SWFVNNVEVHTAQTQTHREDYNSTLRWSALPIQHQDWMSGKEFKCKVNNKDLGAPIER<br>TISKPKGSVRAPQVYVLPPPEEEMTKKQVTLTCMVTDFMPEDIYVEWTNNGKTELNYKN<br>TEPVLDSDGSYFMYSKLRVEKKNWVERNSYSCSVVHEGLHNHHTTKSFSRTPGK |
| 212 | 3.7F5 LC<br>LALAPG mIgG2a | MGWSCIILFLVATATGVHSDIVMSQSPSSLWSVGEKVSLSCKSSQSLLYRNDQINYLA<br>WYQQKPGQSPKLLIFWASTRESGVPVRFTGSGSGTDFTLNINTVKAEDLAVYYCQQYYS<br>YPPTFGTGTKLEIKRADAAPTVSIFPPSSEQLTSGGASWCFLNNFYPKDINVKWKIDG<br>SERQNGVLNSWTDQDSKDSTYSMSSTLTLTKDEYERHNSYTCEATHKTSTSPIVKSFNR<br>NEC |
| 213 | Human APOL1<br>KIK isotype<br>G0 form<br>(no signal<br>sequence) |                                       EA GARVQQNVPS GTDTGDPQSK<br>PLGDWAAGTM DRESSIFIED AIKYFKEKVS TQNLLLLLTD NEAWNGFVAA<br>AELPRNEADE LRKALDNLAR QMIMKDKNWH DKGQQYRNWF LKEFPRLKSE<br>LEDNIRRLRA LADGVQKVHK GTTIANVVSG SLSISSGILT LVGMGLAPFT<br>EGGSLVLLEP GMELGITAAL TGITSSTIDY GKKWWTQAQA HDLVIKSLDK<br>LKEVXEFLGE NISNFLSLAG NTYQLTRGIG KDIRALRRAR ANLQSVPHAS<br>ASRPRVTEPI SAESGEQVER VNEPSILEMS RGVKLTDVAP VSFFLVLDW<br>YLVYESKHLH EGAKSETAEE LKKVAQELEE KLNILNNNYK ILQADQEL |
| 214 | Human APOL1<br>EIK isotype<br>G0 form<br>(no signal<br>sequence) |                                       EA GARVQQNVPS GTDTGDPQSK<br>PLGDWAAGTM DRESSIFIED AIKYFKEKVS TQNLLLLLTD NEAWNGFVAA<br>AELPRNEADE LRKALDNLAR QMIMKDKNWH DKGQQYRNWF LKEFPRLKSE<br>LEDNIRRLRA LADGVQKVHK GTTIANVVSG SLSISSGILT LVGMGLAPFT<br>EGGSLVLLEP GMELGITAAL TGITSSTIDY GKKWWTQAQA HDLVIKSLDK<br>LKEVKEFLGE NISNFLSLAG NTYQLTRGIG KDIRALRRAR ANLQSVPHAS<br>ASRPRVTEPI SAESGEQVER VNEPSILEMS RGVKLTDVAP VSFFLVLDW<br>YLVYESKHLH EGAKSETAEE LKKVAQELEE KLNILNNNYK ILQADQEL |

---

IV. Table of Certain Sequences

| SEQ ID NO | Description | Sequence |
|---|---|---|
| 215 | Human APOL1 G1 variant of EMR isotype (no signal sequence) |            EA GARVQQNVPS GTDTGDPQSK PLGDWAAGTM DRESSIFIED AIKYFKEKVS TQNLLLLLTD NEAWNGFVAA AELPRNEADE LRKALDNLAR QMIMKDKNWH DKGQQYRNWF LKEFPRLKSE LEDNIRRLRA LADGVQKVHK GTTIANVVSG SLSISSGILT LVGMGLAPFT EGGSLVLLEP GMELGITAAL TGITSSTIDY GKKWWTQAQA HDLVIKSLDK LKEVKEFLGE NISNFLSLAG NTYQLTRGIG KDIRALRRAR ANLQSVPHAS ASRPRVTEPI SAESGEQVER VNEPSILEMS RGVKLTDVAP VGFFLVLDW YLVYESKHLH EGAKSETAEE LKKVAQELEE KLNMLNNNYK ILQADQEL |
| 216 | Human APOL1 G2 variant of EMR isotype (no signal sequence) |            EA GARVQQNVPS GTDTGDPQSK PLGDWAAGTM DRESSIFIED AIKYFKEKVS TQNLLLLLTD NEAWNGFVAA AELPRNEADE LRKALDNLAR QMIMKDKNWH DKGQQYRNWF LKEFPRLKSE LEDNIRRLRA LADGVQKVHK GTTIANVVSG SLSISSGILT LVGMGLAPFT EGGSLVLLEP GMELGITAAL TGITSSTMDY GKKWWTQAQA HDLVIKSLDK LKEVKEFLGE NISNFLSLAG NTYQLTRGIG KDIRALRRAR ANLQSVPHAS ASRPRVTEPI SAESGEQVER VNEPSILEMS RGVKLTDVAP VSFFLVLDW YLVYESKHLH EGAKSETAEE LKKVAQELEE KLNILNN__K ILQADQEL |

---

What is claimed is:

1. An isolated antibody that specifically binds to apolipoprotein L1 (APOL1), wherein the antibody comprises:

(a) a heavy chain variable region (VH) comprising a CDR-H1 comprising the amino acid sequence of SEQ ID NO: 3, a CDR-H2 comprising the amino acid sequence of SEQ ID NO: 4, and a CDR-H3 comprising the amino acid sequence of SEQ ID NO: 5; and a light chain variable region (VL) comprising a CDR-L1 comprising the amino acid sequence of SEQ ID NO: 6, a CDR-L2 comprising the amino acid sequence of SEQ ID NO: 7, and a CDR-L3 comprising the amino acid sequence of SEQ ID NO: 8;

(b) a heavy chain variable region (VH) comprising a CDR-H1 comprising the amino acid sequence of SEQ ID NO: 13, a CDR-H2 comprising the amino acid sequence of SEQ ID NO: 14, and a CDR-H3 comprising the amino acid sequence of SEQ ID NO: 15; and a light chain variable region (VL) comprising a CDR-L1 comprising the amino acid sequence of SEQ ID NO: 16, a CDR-L2 comprising the amino acid sequence of SEQ ID NO: 17, and a CDR-L3 comprising the amino acid sequence of SEQ ID NO: 18;

(c) a heavy chain variable region (VH) comprising a CDR-H1 comprising the amino acid sequence of SEQ ID NO: 23, a CDR-H2 comprising the amino acid sequence of SEQ ID NO: 24, and a CDR-H3 comprising the amino acid sequence of SEQ ID NO: 25; and a light chain variable region (VL) comprising a CDR-L1 comprising the amino acid sequence of SEQ ID NO: 26, a CDR-L2 comprising the amino acid sequence of SEQ ID NO: 27, and a CDR-L3 comprising the amino acid sequence of SEQ ID NO: 28;

(d) a heavy chain variable region (VH) comprising a CDR-H1 comprising the amino acid sequence of SEQ ID NO: 33, a CDR-H2 comprising the amino acid sequence of SEQ ID NO: 34, and a CDR-H3 comprising the amino acid sequence of SEQ ID NO: 35; and a light chain variable region (VL) comprising a CDR-L1 comprising the amino acid sequence of SEQ ID NO: 36, a CDR-L2 comprising the amino acid sequence of SEQ ID NO: 37, and a CDR-L3 comprising the amino acid sequence of SEQ ID NO: 38;

(e) a heavy chain variable region (VH) comprising a CDR-H1 comprising the amino acid sequence of SEQ ID NO: 43, a CDR-H2 comprising the amino acid sequence of SEQ ID NO: 44, and a CDR-H3 comprising the amino acid sequence of SEQ ID NO: 45; and a light chain variable region (VL) comprising a CDR-L1 comprising the amino acid sequence of SEQ ID NO: 46, a CDR-L2 comprising the amino acid sequence of SEQ ID NO: 47, and a CDR-L3 comprising the amino acid sequence of SEQ ID NO: 48;

(f) a heavy chain variable region (VH) comprising a CDR-H1 comprising the amino acid sequence of SEQ ID NO: 53, a CDR-H2 comprising the amino acid sequence of SEQ ID NO: 54, and a CDR-H3 comprising the amino acid sequence of SEQ ID NO: 55; and a light chain variable region (VL) comprising a CDR-L1 comprising the amino acid sequence of SEQ ID NO: 56, a CDR-L2 comprising the amino acid sequence of SEQ ID NO: 57, and a CDR-L3 comprising the amino acid sequence of SEQ ID NO: 58;

(g) a heavy chain variable region (VH) comprising a CDR-H1 comprising the amino acid sequence of SEQ ID NO: 63, a CDR-H2 comprising the amino acid sequence of SEQ ID NO: 64, and a CDR-H3 comprising the amino acid sequence of SEQ ID NO: 65; and a light chain variable region (VL) comprising a CDR-L1 comprising the amino acid sequence of SEQ ID NO: 66, a CDR-L2 comprising the amino acid sequence of SEQ ID NO: 67, and a CDR-L3 comprising the amino acid sequence of SEQ ID NO: 68;

(h) a heavy chain variable region (VH) comprising a CDR-H1 comprising the amino acid sequence of SEQ ID NO: 73, a CDR-H2 comprising the amino acid sequence of SEQ ID NO: 74, and a CDR-H3 comprising the amino acid sequence of SEQ ID NO: 75; and a light chain variable region (VL) comprising a CDR-L1 comprising the amino acid sequence of SEQ ID NO: 76, a CDR-L2 comprising the amino acid sequence of SEQ ID NO: 77, and a CDR-L3 comprising the amino acid sequence of SEQ ID NO: 78;

(i) heavy chain variable region (VH) comprising a CDR-H1 comprising the amino acid sequence of SEQ ID NO: 83, a CDR-H2 comprising the amino acid sequence of SEQ ID NO: 84, and a CDR-H3 comprising the amino acid sequence of SEQ ID NO: 85; and a light chain variable region (VL) comprising a CDR-L1 comprising the amino acid sequence of SEQ ID NO: 86, a CDR-L2 comprising the amino acid sequence of SEQ ID NO: 87, and a CDR-L3 comprising the amino acid sequence of SEQ ID NO: 88;

(j) a heavy chain variable region (VH) comprising a CDR-H1 comprising the amino acid sequence of SEQ ID NO: 93, a CDR-H2 comprising the amino acid sequence of SEQ ID NO: 94, and a CDR-H3 comprising the amino acid sequence of SEQ ID NO: 95; and a light chain variable region (VL) comprising a CDR-LI comprising the amino acid sequence of SEQ ID NO: 96, a CDR-L2 comprising the amino acid sequence of SEQ ID NO: 97, and a CDR-L3 comprising the amino acid sequence of SEQ ID NO: 98;

(k) a heavy chain variable region (VH) comprising a CDR-H1 comprising the amino acid sequence of SEQ ID NO: 103, a CDR-H2 comprising the amino acid sequence of SEQ ID NO: 104, and a CDR-H3 comprising the amino acid sequence of SEQ ID NO: 105; and a light chain variable region (VL) comprising a CDR-L1 comprising the amino acid sequence of SEQ ID NO: 106, a CDR-L2 comprising the amino acid sequence of SEQ ID NO: 107, and a CDR-L3 comprising the amino acid sequence of SEQ ID NO: 108;

(l) a heavy chain variable region (VH) comprising a CDR-H1 comprising the amino acid sequence of SEQ ID NO: 113, a CDR-H2 comprising the amino acid sequence of SEQ ID NO: 114, and a CDR-H3 comprising the amino acid sequence of SEQ ID NO: 115; and a light chain variable region (VL) comprising a CDR-L1 comprising the amino acid sequence of SEQ ID NO: 116, a CDR-L2 comprising the amino acid sequence of SEQ ID NO: 117, and a CDR-L3 comprising the amino acid sequence of SEQ ID NO: 118;

(m) a heavy chain variable region (VH) comprising a CDR-H1 comprising the amino acid sequence of SEQ ID NO: 123, a CDR-H2 comprising the amino acid sequence of SEQ ID NO: 124, and a CDR-H3 comprising the amino acid sequence of SEQ ID NO: 125; and a light chain variable region (VL) comprising a CDR-L1 comprising the amino acid sequence of SEQ ID NO: 126, a CDR-L2 comprising the amino acid sequence of SEQ ID NO: 127, and a CDR-L3 comprising the amino acid sequence of SEQ ID NO: 128;

(n) a heavy chain variable region (VH) comprising a CDR-H1 comprising the amino acid sequence of SEQ ID NO: 133, a CDR-H2 comprising the amino acid sequence of SEQ ID NO: 134, and a CDR-H3 comprising the amino acid sequence of SEQ ID NO: 135; and a light chain variable region (VL) comprising a CDR-L1 comprising the amino acid sequence of SEQ ID NO: 136, a CDR-L2 comprising the amino acid sequence of SEQ ID NO: 137, and a CDR-L3 comprising the amino acid sequence of SEQ ID NO: 138;

(o) a heavy chain variable region (VH) comprising a CDR-H1 comprising the amino acid sequence of SEQ ID NO: 143, a CDR-H2 comprising the amino acid sequence of SEQ ID NO: 144, and a CDR-H3 comprising the amino acid sequence of SEQ ID NO: 145; and a light chain variable region (VL) comprising a CDR-L1 comprising the amino acid sequence of SEQ ID NO: 146, a CDR-L2 comprising the amino acid sequence of SEQ ID NO: 147, and a CDR-L3 comprising the amino acid sequence of SEQ ID NO: 148;

(p) a heavy chain variable region (VH) comprising a CDR-H1 comprising the amino acid sequence of SEQ ID NO: 153, a CDR-H2 comprising the amino acid sequence of SEQ ID NO: 154, and a CDR-H3 comprising the amino acid sequence of SEQ ID NO: 155; and a light chain variable region (VL) comprising a CDR-L1 comprising the amino acid sequence of SEQ ID NO: 156, a CDR-L2 comprising the amino acid sequence of SEQ ID NO: 157, and a CDR-L3 comprising the amino acid sequence of SEQ ID NO: 158;

(q) a heavy chain variable region (VH) comprising a CDR-H1 comprising the amino acid sequence of SEQ ID NO: 163, a CDR-H2 comprising the amino acid sequence of SEQ ID NO: 164, and a CDR-H3 comprising the amino acid sequence of SEQ ID NO: 165; and a light chain variable region (VL) comprising a CDR-L1 comprising the amino acid sequence of SEQ ID NO: 166, a CDR-L2 comprising the amino acid sequence of SEQ ID NO: 167, and a CDR-L3 comprising the amino acid sequence of SEQ ID NO: 168;

(r) a heavy chain variable region (VH) comprising a CDR-H1 comprising the amino acid sequence of SEQ ID NO: 173, a CDR-H2 comprising the amino acid sequence of SEQ ID NO: 174, and a CDR-H3 comprising the amino acid sequence of SEQ ID NO: 175; and a light chain variable region (VL) comprising a CDR-L1 comprising the amino acid sequence of SEQ ID NO: 176, a CDR-L2 comprising the amino acid sequence of SEQ ID NO: 177, and a CDR-L3 comprising the amino acid sequence of SEQ ID NO: 178;

(s) a heavy chain variable region (VH) comprising a CDR-H1 comprising the amino acid sequence of SEQ ID NO: 183, a CDR-H2 comprising the amino acid sequence of SEQ ID NO: 184, and a CDR-H3 comprising the amino acid sequence of SEQ ID NO: 185; and a light chain variable region (VL) comprising a CDR-L1 comprising the amino acid sequence of SEQ ID NO: 186, a CDR-L2 comprising the amino acid sequence of SEQ ID NO: 187, and a CDR-L3 comprising the amino acid sequence of SEQ ID NO: 188;

(t) a heavy chain variable region (VH) comprising a CDR-H1 comprising the amino acid sequence of SEQ ID NO: 193, a CDR-H2 comprising the amino acid sequence of SEQ ID NO: 194, and a CDR-H3 comprising the amino acid sequence of SEQ ID NO: 195; and a light chain variable region (VL) comprising a CDR-L1 comprising the amino acid sequence of SEQ ID NO: 196, a CDR-L2 comprising the amino acid sequence of SEQ ID NO: 197, and a CDR-L3 comprising the amino acid sequence of SEQ ID NO: 198; or (u) a heavy chain variable region (VH) comprising a CDR-H1 comprising the amino acid sequence of SEQ ID NO: 203, a CDR-H2 comprising the amino acid sequence of SEQ ID NO: 204, and a CDR-H3 comprising the amino acid sequence of SEQ ID NO: 205; and a light chain variable region (VL) comprising a CDR-L1 comprising the amino acid sequence of SEQ ID NO: 206, a CDR-L2 comprising the amino acid sequence of SEQ ID NO: 207, and a CDR-L3 comprising the amino acid sequence of SEQ ID NO: 208.

2. The antibody of claim 1, wherein the antibody:

(a) comprises the CDRs of claim 1(a) and further comprises a VH that is at least 90%, at least 95%, at least 97%, or at least 99% identical to the amino acid sequence of SEQ ID NO: 9 and/or a VL that is at least 90%, at least 95%, at least 97%, or at least 99% identical to the amino acid sequence of SEQ ID NO: 10;

(b) comprises the CDRs of claim 1(b) and further comprises a VH that is at least 90%, at least 95%, at least 97%, or at least 99% identical to the amino acid sequence of SEQ ID NO: 19 and/or a VL that is at least 90%, at least 95%, at least 97%, or at least 99% identical to the amino acid sequence of SEQ ID NO: 20;

(c) comprises the CDRs of claim 1(c) and further comprises a VH that is at least 90%, at least 95%, at least 97%, or at least 99% identical to the amino acid sequence of SEQ ID NO: 29 and/or a VL that is at least 90%, at least 95%, at least 97%, or at least 99% identical to the amino acid sequence of SEQ ID NO: 30;

(d) comprises the CDRs of claim 1(d) and further comprises a VH that is at least 90%, at least 95%, at least 97%, or at least 99% identical to the amino acid sequence of SEQ ID NO: 39 and/or a VL that is at least 90%, at least 95%, at least 97%, or at least 99% identical to the amino acid sequence of SEQ ID NO: 40;

(e) comprises the CDRs of claim 1(e) and further comprises a VH that is at least 90%, at least 95%, at least 97%, or at least 99% identical to the amino acid sequence of SEQ ID NO: 49 and/or a VL that is at least 90%, at least 95%, at least 97%, or at least 99% identical to the amino acid sequence of SEQ ID NO: 50;

(f) comprises the CDRs of claim 1(f) and further comprises a VH that is at least 90%, at least 95%, at least 97%, or at least 99% identical to the amino acid sequence of SEQ ID NO: 59 and/or a VL that is at least 90%, at least 95%, at least 97%, or at least 99% identical to the amino acid sequence of SEQ ID NO: 60;

(g) comprises the CDRs of claim 1(g) and further comprises a VH that is at least 90%, at least 95%, at least 97%, or at least 99% identical to the amino acid sequence of SEQ ID NO: 69 and/or a VL that is at least 90%, at least 95%, at least 97%, or at least 99% identical to the amino acid sequence of SEQ ID NO: 70;

(h) comprises the CDRs of claim 1(h) and further comprises a VH that is at least 90%, at least 95%, at least 97%, or at least 99% identical to the amino acid sequence of SEQ ID NO: 79 and/or a VL that is at least 90%, at least 95%, at least 97%, or at least 99% identical to the amino acid sequence of SEQ ID NO: 80;

(i) comprises the CDRs of claim 1(i) and further comprises a VH that is at least 90%, at least 95%, at least 97%, or at least 99% identical to the amino acid sequence of SEQ ID NO: 89 and/or a VL that is at least 90%, at least 95%, at least 97%, or at least 99% identical to the amino acid sequence of SEQ ID NO: 90;

(j) comprises the CDRs of claim 1(j) and further comprises a VH that is at least 90%, at least 95%, at least 97%, or at least 99% identical to the amino acid sequence of SEQ ID NO: 99 and/or a VL that is at least 90%, at least 95%, at least 97%, or at least 99% identical to the amino acid sequence of SEQ ID NO: 100;

(k) comprises the CDRs of claim 1(k) and further comprises a VH that is at least 90%, at least 95%, at least 97%, or at least 99% identical to the amino acid sequence of SEQ ID NO: 109 and/or a VL that is at least 90%, at least 95%, at least 97%, or at least 99% identical to the amino acid sequence of SEQ ID NO: 110;

(l) comprises the CDRs of claim 1(l) and further comprises a VH that is at least 90%, at least 95%, at least 97%, or at least 99% identical to the amino acid sequence of SEQ ID NO: 119 and/or a VL that is at least 90%, at least 95%, at least 97%, or at least 99% identical to the amino acid sequence of SEQ ID NO: 120;

(m) comprises the CDRs of claim 1(m) and further comprises a VH that is at least 90%, at least 95%, at least 97%, or at least 99% identical to the amino acid sequence of SEQ ID NO: 129 and/or a VL that is at least 90%, at least 95%, at least 97%, or at least 99% identical to the amino acid sequence of SEQ ID NO: 130;

(n) comprises the CDRs of claim 1(n) and further comprises a VH that is at least 90%, at least 95%, at least 97%, or at least 99% identical to the amino acid sequence of SEQ ID NO: 139 and/or a VL that is at least 90%, at least 95%, at least 97%, or at least 99% identical to the amino acid sequence of SEQ ID NO: 140;

(o) comprises the CDRs of claim 1(o) and further comprises a VH that is at least 90%, at least 95%, at least 97%, or at least 99% identical to the amino acid sequence of SEQ ID NO: 149 and/or a VL that is at least 90%, at least 95%, at least 97%, or at least 99% identical to the amino acid sequence of SEQ ID NO: 150;

(p) comprises the CDRs of claim 1(p) and further comprises a VH that is at least 90%, at least 95%, at least 97%, or at least 99% identical to the amino acid sequence of SEQ ID NO: 159 and/or a VL that is at least 90%, at least 95%, at least 97%, or at least 99% identical to the amino acid sequence of SEQ ID NO: 160;

(q) comprises the CDRs of claim 1(q) and further comprises a VH that is at least 90%, at least 95%, at least 97%, or at least 99% identical to the amino acid sequence of SEQ ID NO: 169 and/or a VL that is at least 90%, at least 95%, at least 97%, or at least 99% identical to the amino acid sequence of SEQ ID NO: 170;

(r) comprises the CDRs of claim 1(r) and further comprises a VH that is at least 90%, at least 95%, at least 97%, or at least 99% identical to the amino acid sequence of SEQ ID NO: 179 and/or a VL that is at least 90%, at least 95%, at least 97%, or at least 99% identical to the amino acid sequence of SEQ ID NO: 180;

(s) comprises the CDRs of claim 1(s) and further comprises a VH that is at least 90%, at least 95%, at least 97%, or at least 99% identical to the amino acid sequence of SEQ ID NO: 189 and/or a VL that is at least 90%, at least 95%, at least 97%, or at least 99% identical to the amino acid sequence of SEQ ID NO: 190;

(t) comprises the CDRs of claim 1(t) and further comprises a VH that is at least 90%, at least 95%, at least 97%, or at least 99% identical to the amino acid sequence of SEQ ID NO: 199 and/or a VL that is at least 90%, at least 95%, at least 97%, or at least 99% identical to the amino acid sequence of SEQ ID NO: 200; or (u) comprises the CDRs of claim 1(u) and further comprises a VH that is at least 90%, at least 95%, at least 97%, or at least 99% identical to the amino acid sequence of SEQ ID NO: 209 and/or a VL that is at least 90%, at least 95%, at least 97%, or at least 99% identical to the amino acid sequence of SEQ ID NO: 210.

3. The antibody of claim 1, wherein the antibody comprises:

the CDRs of claim 1(a) and further comprises a VH comprising the amino acid sequence of SEQ ID NO: 9;

the CDRs of claim 1(b) and further comprises a VH comprising the amino acid sequence of SEQ ID NO: 19;

the CDRs of claim 1(c) and further comprises a VH comprising the amino acid sequence of SEQ ID NO: 29;

the CDRs of claim 1(d) and further comprises a VH comprising the amino acid sequence of SEQ ID NO: 39;

the CDRs of claim 1(e) and further comprises a VH comprising the amino acid sequence of SEQ ID NO: 49;

the CDRs of claim 1(f) and further comprises a VH comprising the amino acid sequence of SEQ ID NO: 59;

the CDRs of claim 1(g) and further comprises a VH comprising the amino acid sequence of SEQ ID NO: 69;

the CDRs of claim 1(h) and further comprises a VH comprising the amino acid sequence of SEQ ID NO: 79;

the CDRs of claim 1(i) and further comprises a VH comprising the amino acid sequence of SEQ ID NO: 89;

the CDRs of claim 1(j) and further comprises a VH comprising the amino acid sequence of SEQ ID NO: 99;

the CDRs of claim 1(k) and further comprises a VH comprising the amino acid sequence of SEQ ID NO: 109;

the CDRs of claim 1(l) and further comprises a VH comprising the amino acid sequence of SEQ ID NO: 119;

the CDRs of claim 1(m) and further comprises a VH comprising the amino acid sequence of SEQ ID NO: 129;

the CDRs of claim 1(n) and further comprises a VH comprising the amino acid sequence of SEQ ID NO: 139;

the CDRs of claim 1(o) and further comprises a VH comprising the amino acid sequence of SEQ ID NO: 149;

the CDRs of claim 1(p) and further comprises a VH comprising the amino acid sequence of SEQ ID NO: 159;

the CDRs of claim 1(q) and further comprises a VH comprising the amino acid sequence of SEQ ID NO: 169;

the CDRs of claim 1(r) and further comprises a VH comprising the amino acid sequence of SEQ ID NO: 179;

the CDRs of claim 1(s) and further comprises a VH comprising the amino acid sequence of SEQ ID NO: 189;

the CDRs of claim 1(t) and further comprises a VH comprising the amino acid sequence of SEQ ID NO: 199; or the CDRs of claim 1(u) and further comprises a VH comprising the amino acid sequence of SEQ ID NO: 209.

4. The antibody of claim 1, wherein the antibody comprises:

the CDRs of claim 1(a) and further comprises a VL comprising the amino acid sequence of SEQ ID NO: 10;

the CDRs of claim 1(b) and further comprises a VL comprising the amino acid sequence of SEQ ID NO: 20;

the CDRs of claim 1(c) and further comprises a VL comprising the amino acid sequence of SEQ ID NO: 30;

the CDRs of claim 1(d) and further comprises a VL comprising the amino acid sequence of SEQ ID NO: 40;

the CDRs of claim 1(e) and further comprises a VL comprising the amino acid sequence of SEQ ID NO: 50;

the CDRs of claim 1(f) and further comprises a VL comprising the amino acid sequence of SEQ ID NO: 60;

the CDRs of claim 1(g) and further comprises a VL comprising the amino acid sequence of SEQ ID NO: 70;

the CDRs of claim 1(h) and further comprises a VL comprising the amino acid sequence of SEQ ID NO: 80;

the CDRs of claim 1(i) and further comprises a VL comprising the amino acid sequence of SEQ ID NO: 90;

the CDRs of claim 1(j) and further comprises a VL comprising the amino acid sequence of SEQ ID NO: 100;

the CDRs of claim 1(k) and further comprises a VL comprising the amino acid sequence of SEQ ID NO: 110;

the CDRs of claim 1(l) and further comprises a VL comprising the amino acid sequence of SEQ ID NO: 120;

the CDRs of claim 1(m) and further comprises a VL comprising the amino acid sequence of SEQ ID NO: 130;

the CDRs of claim 1(n) and further comprises a VL comprising the amino acid sequence of SEQ ID NO: 140;

the CDRs of claim 1(o) and further comprises a VL comprising the amino acid sequence of SEQ ID NO: 150;

the CDRs of claim 1(p) and further comprises a VL comprising the amino acid sequence of SEQ ID NO: 160;

the CDRs of claim 1(q) and further comprises a VL comprising the amino acid sequence of SEQ ID NO: 170;

the CDRs of claim 1(r) and further comprises a VL comprising the amino acid sequence of SEQ ID NO: 180;

the CDRs of claim 1(s) and further comprises a VL comprising the amino acid sequence of SEQ ID NO: 190;

the CDRs of claim 1(t) and further comprises a VL comprising the amino acid sequence of SEQ ID NO: 200; or the CDRs of claim 1(u) and further comprises a VL comprising the amino acid sequence of SEQ ID NO: 210.

5. The antibody of claim 1, wherein the antibody comprises:

a VH comprising the amino acid sequence of SEQ ID NO: 9 and a VL comprising the amino acid sequence of SEQ ID NO: 10;

a VH comprising the amino acid sequence of SEQ ID NO: 19 and a VL comprising the amino acid sequence of SEQ ID NO: 20;

a VH comprising the amino acid sequence of SEQ ID NO: 29 and a VL comprising the amino acid sequence of SEQ ID NO: 30;

a VH comprising the amino acid sequence of SEQ ID NO: 39 and a VL comprising the amino acid sequence of SEQ ID NO: 40;

a VH comprising the amino acid sequence of SEQ ID NO: 49 and a VL comprising the amino acid sequence of SEQ ID NO: 50;

a VH comprising the amino acid sequence of SEQ ID NO: 59 and a VL comprising the amino acid sequence of SEQ ID NO: 60;

a VH comprising the amino acid sequence of SEQ ID NO: 69 and a VL comprising the amino acid sequence of SEQ ID NO: 70;

a VH comprising the amino acid sequence of SEQ ID NO: 79 and a VL comprising the amino acid sequence of SEQ ID NO: 80;

a VH comprising the amino acid sequence of SEQ ID NO: 89 and a VL comprising the amino acid sequence of SEQ ID NO: 90;

a VH comprising the amino acid sequence of SEQ ID NO: 99 and a VL comprising the amino acid sequence of SEQ ID NO: 100;

a VH comprising the amino acid sequence of SEQ ID NO: 109 and a VL comprising the amino acid sequence of SEQ ID NO: 110;

a VH comprising the amino acid sequence of SEQ ID NO: 119 and a VL comprising the amino acid sequence of SEQ ID NO: 120;

a VH comprising the amino acid sequence of SEQ ID NO: 129 and a VL comprising the amino acid sequence of SEQ ID NO: 130;

a VH comprising the amino acid sequence of SEQ ID NO: 139 and a VL comprising the amino acid sequence of SEQ ID NO: 140;

a VH comprising the amino acid sequence of SEQ ID NO: 149 and a VL comprising the amino acid sequence of SEQ ID NO: 150;

a VH comprising the amino acid sequence of SEQ ID NO: 159 and a VL comprising the amino acid sequence of SEQ ID NO: 160;

a VH comprising the amino acid sequence of SEQ ID NO: 169 and a VL comprising the amino acid sequence of SEQ ID NO: 170;

a VH comprising the amino acid sequence of SEQ ID NO: 179 and a VL comprising the amino acid sequence of SEQ ID NO: 180;

a VH comprising the amino acid sequence of SEQ ID NO: 189 and a VL comprising the amino acid sequence of SEQ ID NO: 190;

a VH comprising the amino acid sequence of SEQ ID NO: 199 and a VL comprising the amino acid sequence of SEQ ID NO: 200; or a VH comprising the amino acid sequence of SEQ ID NO: 209 and a VL comprising the amino acid sequence of SEQ ID NO: 210.

6. The antibody of claim 1, wherein the antibody comprises:

the CDRs of claim 1(a) and further comprises a heavy chain (HC) comprising an amino acid sequence at least 90%, at least 95%, at least 97%, or at least 99% identical to the amino acid sequence of SEQ ID NO: 11 and/or a light chain (LC) comprising an amino acid sequence at least 90%, at least 95%, at least 97%, or at least 99% identical to the SEQ ID NO: 12;

the CDRs of claim 1(b) and further comprises a heavy chain (HC) comprising an amino acid sequence at least 90%, at least 95%, at least 97%, or at least 99% identical to the SEQ ID NO: 21 and a light chain (LC) comprising an amino acid sequence at least 90%, at least 95%, at least 97%, or at least 99% identical to the SEQ ID NO: 22;

the CDRs of claim 1(c) and further comprises a heavy chain (HC) comprising an amino acid sequence at least 90%, at least 95%, at least 97%, or at least 99% identical to the SEQ ID NO: 31 and a light chain (LC) comprising an amino acid sequence at least 90%, at least 95%, at least 97%, or at least 99% identical to the SEQ ID NO: 32;

the CDRs of claim 1(d) and further comprises a heavy chain (HC) comprising an amino acid sequence at least 90%, at least 95%, at least 97%, or at least 99% identical to the SEQ ID NO: 41 and a light chain (LC) comprising an amino acid sequence at least 90%, at least 95%, at least 97%, or at least 99% identical to the SEQ ID NO: 42;

the CDRs of claim 1(e) and further comprises a heavy chain (HC) comprising an amino acid sequence at least 90%, at least 95%, at least 97%, or at least 99% identical to the SEQ ID NO: 51 and a light chain (LC) comprising an amino acid sequence at least 90%, at least 95%, at least 97%, or at least 99% identical to the SEQ ID NO: 52;

the CDRs of claim 1(f) and further comprises a heavy chain (HC) comprising an amino acid sequence at least 90%, at least 95%, at least 97%, or at least 99% identical to the SEQ ID NO: 61 and a light chain (LC) comprising an amino acid sequence at least 90%, at least 95%, at least 97%, or at least 99% identical to the SEQ ID NO: 62;

the CDRs of claim 1(g) and further comprises a heavy chain (HC) comprising an amino acid sequence at least 90%, at least 95%, at least 97%, or at least 99% identical to the SEQ ID NO: 71 and a light chain (LC) comprising an amino acid sequence at least 90%, at least 95%, at least 97%, or at least 99% identical to the SEQ ID NO: 72;

the CDRs of claim 1(h) and further comprises a heavy chain (HC) comprising an amino acid sequence at least 90%, at least 95%, at least 97%, or at least 99% identical to the SEQ ID NO: 81 and a light chain (LC) comprising an amino acid sequence at least 90%, at least 95%, at least 97%, or at least 99% identical to the SEQ ID NO: 82;

the CDRs of claim 1(i) and further comprises a heavy chain (HC) comprising an amino acid sequence at least 90%, at least 95%, at least 97%, or at least 99% identical to the SEQ ID NO: 91 and a light chain (LC) comprising an amino acid sequence at least 90%, at least 95%, at least 97%, or at least 99% identical to the SEQ ID NO: 92;

the CDRs of claim 1(j) and further comprises a heavy chain (HC) comprising an amino acid sequence at least 90%, at least 95%, at least 97%, or at least 99% identical to the SEQ ID NO: 101 and a light chain (LC) comprising an amino acid sequence at least 90%, at least 95%, at least 97%, or at least 99% identical to the SEQ ID NO: 102;

the CDRs of claim 1(k) and further comprises a heavy chain (HC) comprising an amino acid sequence at least 90%, at least 95%, at least 97%, or at least 99% identical to the SEQ ID NO: 111 and a light chain (LC) comprising an amino acid sequence at least 90%, at least 95%, at least 97%, or at least 99% identical to the SEQ ID NO: 112;

the CDRs of claim 1(l) and further comprises a heavy chain (HC) comprising an amino acid sequence at least 90%, at least 95%, at least 97%, or at least 99% identical to the SEQ ID NO: 121 and a light chain (LC) comprising an amino acid sequence at least 90%, at least 95%, at least 97%, or at least 99% identical to the SEQ ID NO: 122;

the CDRs of claim 1(m) and further comprises a heavy chain (HC) comprising an amino acid sequence at least 90%, at least 95%, at least 97%, or at least 99% identical to the SEQ ID NO: 131 and a light chain (LC) comprising an amino acid sequence at least 90%, at least 95%, at least 97%, or at least 99% identical to the SEQ ID NO: 132;

the CDRs of claim 1(n) and further comprises a heavy chain (HC) comprising an amino acid sequence at least 90%, at least 95%, at least 97%, or at least 99% identical to the SEQ ID NO: 141 and a light chain (LC) comprising an amino acid sequence at least 90%, at least 95%, at least 97%, or at least 99% identical to the SEQ ID NO: 142;

the CDRs of claim 1(o) and further comprises a heavy chain (HC) comprising an amino acid sequence at least 90%, at least 95%, at least 97%, or at least 99% identical to the SEQ ID NO: 151 and a light chain (LC) comprising an amino acid sequence at least 90%, at least 95%, at least 97%, or at least 99% identical to the SEQ ID NO: 152;

the CDRs of claim 1(p) and further comprises a heavy chain (HC) comprising an amino acid sequence at least 90%, at least 95%, at least 97%, or at least 99% identical to the SEQ ID NO: 161 and a light chain (LC) comprising an amino acid sequence at least 90%, at least 95%, at least 97%, or at least 99% identical to the SEQ ID NO: 162;

the CDRs of claim 1(q) and further comprises a heavy chain (HC) comprising an amino acid sequence at least 90%, at least 95%, at least 97%, or at least 99% identical to the SEQ ID NO: 171 and a light chain (LC) comprising an amino acid sequence at least 90%, at least 95%, at least 97%, or at least 99% identical to the SEQ ID NO: 172;

the CDRs of claim 1(r) and further comprises a heavy chain (HC) comprising an amino acid sequence at least 90%, at least 95%, at least 97%, or at least 99% identical to the SEQ ID NO: 181 and a light chain (LC) comprising an amino acid sequence at least 90%, at least 95%, at least 97%, or at least 99% identical to the SEQ ID NO: 182;

the CDRs of claim 1(s) and further comprises a heavy chain (HC) comprising an amino acid sequence at least 90%, at least 95%, at least 97%, or at least 99% identical to the SEQ ID NO: 191 and a light chain (LC) comprising an amino acid sequence at least 90%, at least 95%, at least 97%, or at least 99% identical to the SEQ ID NO: 192;

the CDRs of claim 1(t) and further comprises a heavy chain (HC) comprising an amino acid sequence at least 90%, at least 95%, at least 97%, or at least 99% identical to the SEQ ID NO: 201 and a light chain (LC) comprising an amino acid sequence at least 90%, at least 95%, at least 97%, or at least 99% identical to the SEQ ID NO: 202; or the CDRs of claim 1(u) and further comprises a heavy chain (HC) comprising an amino acid sequence at least 90%, at least 95%, at least 97%, or at least 99% identical to the SEQ ID NO: 211 and a light chain (LC) comprising an amino acid sequence at least 90%, at least 95%, at least 97%, or at least 99% identical to the SEQ ID NO: 212.

7. The antibody of claim 1, wherein the antibody comprises:

a heavy chain (HC) comprising the amino acid sequence of SEQ ID NO: 11 and a light chain (LC) comprising the amino acid sequence of SEQ ID NO: 12;

a heavy chain (HC) comprising the amino acid sequence of SEQ ID NO: 21 and a light chain (LC) comprising the amino acid sequence of SEQ ID NO: 22;

a heavy chain (HC) comprising the amino acid sequence of SEQ ID NO: 31 and a light chain (LC) comprising the amino acid sequence of SEQ ID NO: 32;

a heavy chain (HC) comprising the amino acid sequence of SEQ ID NO: 41 and a light chain (LC) comprising the amino acid sequence of SEQ ID NO: 42;

a heavy chain (HC) comprising the amino acid sequence of SEQ ID NO: 51 and a light chain (LC) comprising the amino acid sequence of SEQ ID NO: 52;

a heavy chain (HC) comprising the amino acid sequence of SEQ ID NO: 61 and a light chain (LC) comprising the amino acid sequence of SEQ ID NO: 62;

a heavy chain (HC) comprising the amino acid sequence of SEQ ID NO: 71 and a light chain (LC) comprising the amino acid sequence of SEQ ID NO: 72;

a heavy chain (HC) comprising the amino acid sequence of SEQ ID NO: 81 and a light chain (LC) comprising the amino acid sequence of SEQ ID NO: 82;

a heavy chain (HC) comprising the amino acid sequence of SEQ ID NO: 91 and a light chain (LC) comprising the amino acid sequence of SEQ ID NO: 92;

a heavy chain (HC) comprising the amino acid sequence of SEQ ID NO: 101 and a light chain (LC) comprising the amino acid sequence of SEQ ID NO: 102;

a heavy chain (HC) comprising the amino acid sequence of SEQ ID NO: 111 and a light chain (LC) comprising the amino acid sequence of SEQ ID NO: 112;

a heavy chain (HC) comprising the amino acid sequence of SEQ ID NO: 121 and a light chain (LC) comprising the amino acid sequence of SEQ ID NO: 122;

a heavy chain (HC) comprising the amino acid sequence of SEQ ID NO: 131 and a light chain (LC) comprising the amino acid sequence of SEQ ID NO: 132;

a heavy chain (HC) comprising the amino acid sequence of SEQ ID NO: 141 and a light chain (LC) comprising the amino acid sequence of SEQ ID NO: 142;

a heavy chain (HC) comprising the amino acid sequence of SEQ ID NO: 151 and a light chain (LC) comprising the amino acid sequence of SEQ ID NO: 152;

a heavy chain (HC) comprising the amino acid sequence of SEQ ID NO: 161 and a light chain (LC) comprising the amino acid sequence of SEQ ID NO: 162;

a heavy chain (HC) comprising the amino acid sequence of SEQ ID NO: 171 and a light chain (LC) comprising the amino acid sequence of SEQ ID NO: 172;

a heavy chain (HC) comprising the amino acid sequence of SEQ ID NO: 181 and a light chain (LC) comprising the amino acid sequence of SEQ ID NO: 182;

a heavy chain (HC) comprising the amino acid sequence of SEQ ID NO: 191 and a light chain (LC) comprising the amino acid sequence of SEQ ID NO: 192;

a heavy chain (HC) comprising the amino acid sequence of SEQ ID NO: 201 and a light chain (LC) comprising the amino acid sequence of SEQ ID NO: 202; or a heavy chain (HC) comprising the amino acid sequence of SEQ ID NO: 211 and a light chain (LC) comprising the amino acid sequence of SEQ ID NO: 212.

8. An isolated antibody that specifically binds to apolipoprotein L1 (APOL1), wherein the antibody:

a) specifically binds to a region of APOL1 corresponding to amino acids 61-103 of APOL1 G0 (SEQ ID NO: 2); and/or b) specifically binds to a region of APOL1 corresponding to amino acids 111-150 of APOL1 G0 (SEQ ID NO: 2);

wherein the antibody preferentially recognizes APOL1 expressed on podocytes over APOL1 found in serum; and further wherein the antibody comprises:

(a) a heavy chain variable region (VH) comprising a CDR-H1 comprising the amino acid sequence of SEQ ID NO: 173, a CDR-H2 comprising the amino acid sequence of SEQ ID NO: 174, and a CDR-H3 comprising the amino acid sequence of SEQ ID NO: 175; and a light chain variable region (VL) comprising a CDR-L1 comprising the amino acid sequence of SEQ ID NO: 176, a CDR-L2 comprising the amino acid sequence of SEQ ID NO: 177, and a CDR-L3 comprising the amino acid sequence of SEQ ID NO: 178; or (b) a heavy chain variable region (VH) comprising a CDR-H1 comprising the amino acid sequence of SEQ ID NO: 183, a CDR-H2 comprising the amino acid sequence of SEQ ID NO: 184, and a CDR-H3 comprising the amino acid sequence of SEQ ID NO: 185; and a light chain variable region (VL) comprising a CDR-L1 comprising the amino acid sequence of SEQ ID NO: 186, a CDR-L2 comprising the amino acid sequence of SEQ ID NO: 187, and a CDR-L3 comprising the amino acid sequence of SEQ ID NO: 188.

9. An isolated antibody that specifically binds to apolipoprotein L1 (APOL1), wherein the antibody:

a) specifically binds to a region of APOL1 corresponding to amino acids 103-111 of APOL1 G0 (SEQ ID NO: 2);

b) specifically binds to a region of APOL1 corresponding to amino acids 150-172 of APOL1 G0 (SEQ ID NO: 2);

c) specifically binds to a region of APOL1 corresponding to amino acids 314-333 of APOL1 G0 (SEQ ID NO: 2); and/or d) specifically binds to a region of APOL1 corresponding to amino acids 376-398 of APOL1 G0 (SEQ ID NO: 2);

wherein the antibody recognizes both APOL1 expressed on podocytes and APOL1 found in serum; and further wherein the antibody comprises:

(a) a heavy chain variable region (VH) comprising a CDR-H1 comprising the amino acid sequence of SEQ ID NO: 3, a CDR-H2 comprising the amino acid sequence of SEQ ID NO: 4, and a CDR-H3 comprising the amino acid sequence of SEQ ID NO: 5; and a light chain variable region (VL) comprising a CDR-L1 comprising the amino acid sequence of SEQ ID NO: 6, a CDR-L2 comprising the amino acid sequence of SEQ ID NO: 7, and a CDR-L3 comprising the amino acid sequence of SEQ ID NO: 8;

(b) a heavy chain variable region (VH) comprising a CDR-H1 comprising the amino acid sequence of SEQ ID NO: 53, a CDR-H2 comprising the amino acid sequence of SEQ ID NO: 54, and a CDR-H3 comprising the amino acid sequence of SEQ ID NO: 55; and a light chain variable region (VL) comprising a CDR-L1 comprising the amino acid sequence of SEQ ID NO: 56, a CDR-L2 comprising the amino acid sequence of SEQ ID NO: 57, and a CDR-L3 comprising the amino acid sequence of SEQ ID NO: 58;

(c) a heavy chain variable region (VH) comprising a CDR-H1 comprising the amino acid sequence of SEQ ID NO: 63, a CDR-H2 comprising the amino acid sequence of SEQ ID NO: 64, and a CDR-H3 comprising the amino acid sequence of SEQ ID NO: 65; and a light chain variable region (VL) comprising a CDR-L1 comprising the amino acid sequence of SEQ ID NO: 66, a CDR-L2 comprising the amino acid sequence of SEQ ID NO: 67, and a CDR-L3 comprising the amino acid sequence of SEQ ID NO: 68;

(d) a heavy chain variable region (VH) comprising a CDR-H1 comprising the amino acid sequence of SEQ ID NO: 83, a CDR-H2 comprising the amino acid sequence of SEQ ID NO: 84, and a CDR-H3 comprising the amino acid sequence of SEQ ID NO: 85; and a light chain variable region (VL) comprising a CDR-L1 comprising the amino acid sequence of SEQ ID NO: 86, a CDR-L2 comprising the amino acid sequence of SEQ ID NO: 87, and a CDR-L3 comprising the amino acid sequence of SEQ ID NO: 88;

(e) a heavy chain variable region (VH) comprising a CDR-H1 comprising the amino acid sequence of SEQ ID NO: 73, a CDR-H2 comprising the amino acid sequence of SEQ ID NO: 74, and a CDR-H3 comprising the amino acid sequence of SEQ ID NO: 75; and a light chain variable region (VL) comprising a CDR-L1 comprising the amino acid sequence of SEQ ID NO: 76, a CDR-L2 comprising the amino acid sequence of SEQ ID NO: 77, and a CDR-L3 comprising the amino acid sequence of SEQ ID NO: 78;

(f) a heavy chain variable region (VH) comprising a CDR-H1 comprising the amino acid sequence of SEQ ID NO: 133, a CDR-H2 comprising the amino acid sequence of SEQ ID NO: 134, and a CDR-H3 comprising the amino acid sequence of SEQ ID NO: 135; and a light chain variable region (VL) comprising a CDR-L1 comprising the amino acid sequence of SEQ ID NO: 136, a CDR-L2 comprising the amino acid sequence of SEQ ID NO: 137, and a CDR-L3 comprising the amino acid sequence of SEQ ID NO: 138;

(g) a heavy chain variable region (VH) comprising a CDR-H1 comprising the amino acid sequence of SEQ ID NO: 143, a CDR-H2 comprising the amino acid sequence of SEQ ID NO: 144, and a CDR-H3 comprising the amino acid sequence of SEQ ID NO: 145; and a light chain variable region (VL) comprising a CDR-L1 comprising the amino acid sequence of SEQ ID NO: 146, a CDR-L2 comprising the amino acid sequence of SEQ ID NO: 147, and a CDR-L3 comprising the amino acid sequence of SEQ ID NO: 148; or (h) a heavy chain variable region (VH) comprising a CDR-H1 comprising the amino acid sequence of SEQ ID NO: 123, a CDR-H2 comprising the amino acid sequence of SEQ ID NO: 124, and a CDR-H3 comprising the amino acid sequence of SEQ ID NO: 125; and a light chain variable region (VL) comprising a CDR-L1 comprising the amino acid sequence of SEQ ID NO: 126, a CDR-L2 comprising the amino acid sequence of SEQ ID NO: 127, and a CDR-L3 comprising the amino acid sequence of SEQ ID NO: 128.

10. The antibody of claim 1, wherein the antibody is humanized or chimeric.

11. The antibody of claim 1, which is an IgG antibody.

12. The antibody of claim 1, which is a full-length antibody or an antibody fragment, wherein the antibody fragment is chosen from Fv, single-chain Fv (scFv), Fab, Fab', and (Fab')$_2$.

13. The antibody of claim 1, which is a bispecific or multispecific antibody or wherein the antibody is conjugated covalently or noncovalently to at least one other molecule, wherein the at least one other molecule comprises a detection label and/or a pharmaceutical agent.

14. An isolated nucleic acid, wherein the isolated nucleic acid encodes for the antibody of claim 1, or the isolated nucleic acid is an isolated vector comprising one or more nucleic acids encoding a heavy chain and a light chain of the antibody of claim 1.

15. An isolated host cell comprising the nucleic acid of claim 14.

16. A method of producing an antibody that binds to APOL1 comprising culturing the host cell of claim 15 under conditions suitable for the expression of the antibody.

17. The method of claim 16, further comprising recovering the antibody from the host cell.

18. An antibody produced by the method of claim 17.

19. A method of detecting apolipoprotein L1 (APOL1) in a sample, comprising:

providing a sample comprising at least one of APOL1, APOL2, APOL3, APOL4, or APOL6;

contacting the sample with an anti-APOL1 antibody of claim 1; and detecting the presence of the APOL1 protein in the sample based on recognition of the protein by the anti-APOL1 antibody;

wherein the sample comprises human kidney cells, human podocyte cells, human endothelial cells or wherein the sample is a human serum or blood sample.

20. A method of specifically detecting podocyte cells expressing apolipoprotein L1 (APOL1), comprising providing a sample comprising podocyte cells, contacting the sample with an anti-APOL1 antibody of claim 1, and detecting binding of the antibody to the sample, wherein the antibody (a) preferentially binds to APOL1 found on podocyte cells over APOL1 found in serum, (b) the antibody does not significantly bind to APOL2, and/or (c) the antibody does not significantly bind to APOL6.

\* \* \* \* \*